US011884948B2

(12) United States Patent
Hutagalung et al.

(10) Patent No.: US 11,884,948 B2
(45) Date of Patent: *Jan. 30, 2024

(54) GENETICALLY MODIFIED ORGANISMS FOR PRODUCTION OF POLYKETIDES

(71) Applicant: PYRONE SYSTEMS, INC., San Diego, CA (US)

(72) Inventors: Alexander Hutagalung, San Diego, CA (US); Jose Miguel Laplaza, San Diego, CA (US)

(73) Assignee: PYRONE SYSTEMS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/449,847

(22) Filed: Oct. 4, 2021

(65) Prior Publication Data
US 2022/0119853 A1 Apr. 21, 2022

Related U.S. Application Data

(63) Continuation of application No. 16/783,122, filed on Feb. 5, 2020, now Pat. No. 11,136,605, which is a continuation of application No. PCT/US2019/051357, filed on Sep. 16, 2019.

(60) Provisional application No. 62/731,978, filed on Sep. 17, 2018, provisional application No. 62/731,980, filed on Sep. 17, 2018.

(51) Int. Cl.
C12P 17/06 (2006.01)
C12N 1/16 (2006.01)
C12P 7/42 (2006.01)

(52) U.S. Cl.
CPC ............. C12P 17/06 (2013.01); C12N 1/16 (2013.01); C12P 7/42 (2013.01); C12Y 103/03006 (2013.01); C12Y 203/01206 (2015.07); C12Y 404/01026 (2015.07)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,965,188 A | 10/1990 | Mullis |
| 5,232,841 A | 8/1993 | Hashimoto |
| 5,268,273 A | 12/1993 | Buckholz |
| 5,389,529 A | 2/1995 | Panayotatos |
| 5,470,719 A | 11/1995 | Meng |
| 5,648,247 A | 7/1997 | Picataggio |
| 5,656,493 A | 8/1997 | Mullis |
| 5,712,114 A | 1/1998 | Mankovich |
| 5,766,891 A | 6/1998 | Shuman |
| 5,846,818 A | 12/1998 | Robinson |
| 5,888,732 A | 3/1999 | Hartley |
| 5,932,474 A | 8/1999 | Tsien |
| 6,008,378 A | 12/1999 | Tsien |
| 6,054,271 A | 4/2000 | Tsien |
| 6,143,557 A | 11/2000 | Hartley |
| 6,171,861 B1 | 1/2001 | Hartley |
| 6,270,969 B1 | 8/2001 | Hartley |
| 6,277,608 B1 | 8/2001 | Hartley |
| 6,288,302 B1 | 9/2001 | Yu |
| 6,451,569 B1 | 9/2002 | Tsien |
| 6,518,488 B1 | 2/2003 | Agarwal |
| 6,720,140 B1 | 4/2004 | Hartley |
| 7,851,199 B2 | 12/2010 | Bailey et al. |
| 8,884,100 B2 | 11/2014 | Page et al. |
| 9,546,362 B2 | 1/2017 | Page et al. |
| 9,611,460 B2 | 4/2017 | Page et al. |
| 9,765,308 B2 | 9/2017 | Page et al. |
| 9,822,384 B2 | 11/2017 | Poulos et al. |
| 10,059,971 B2 | 8/2018 | Page et al. |
| 10,287,557 B2 | 5/2019 | Geysens et al. |
| 11,136,605 B2 * | 10/2021 | Hutagalung ........... C12N 9/001 |
| 2002/0007051 A1 | 1/2002 | Cheo |
| 2003/0083373 A1 | 5/2003 | Tsien |
| 2005/0032176 A1 | 2/2005 | Khosla |
| 2005/0112590 A1 | 5/2005 | Boom |
| 2005/0287592 A1 | 12/2005 | Kless |
| 2006/0057689 A1 | 3/2006 | Otto et al. |
| 2008/0026421 A1 | 1/2008 | Sagt et al. |
| 2012/0077252 A1 | 3/2012 | Picataggio |

(Continued)

FOREIGN PATENT DOCUMENTS

| | | |
|---|---|---|
| JP | 2000-078979 | 3/2000 |
| JP | 2001-029082 | 2/2001 |

(Continued)

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession Q33DR0. Dec. 6, 2005 (Year: 2005).
Agarwal et al. 2001 "Gene isolation and characterization of two acyl CoA oxidases from soybean with broad substrate specificities and enhanced expression in the growing seedling axis." Plant Mol Biol. Nov. 2001;47(4):519-31.
Aizpurua-Olaizola et al. "Identification and quantification of cannabinoids in Cannabis sativa L. plants by high performance liquid chromatography-mass spectrometry." Anal Bioanal Chem. Nov. 2014;406(29):7549-60.

(Continued)

Primary Examiner — Christian L Fronda
(74) Attorney, Agent, or Firm — KNOBBE, MARTENS, OLSON & BEAR LLP

(57) ABSTRACT

Strains of yeasts are provided containing the genes for the production of cannabinoids from fatty acids. The enzymes that mediate cannabinoid production are localized to the cytosol, peroxisome or different compartments within the secretory pathway (e.g., endoplasmic reticulum, Golgi, vacuole) to ensure efficient production. The engineered microorganisms produce cannabinoids in a controlled fermentation process.

20 Claims, 31 Drawing Sheets
Specification includes a Sequence Listing.

(56) References Cited

U.S. PATENT DOCUMENTS

| | | | |
|---|---|---|---|
| 2012/0122180 | A1 | 5/2012 | Austin |
| 2014/0004598 | A1 | 1/2014 | Picataggio et al. |
| 2014/0228586 | A1 | 8/2014 | Beardslee et al. |
| 2016/0010126 | A1 | 1/2016 | Poulos et al. |
| 2016/0298151 | A1 | 10/2016 | Butt et al. |
| 2017/0211049 | A1 | 7/2017 | Page et al. |
| 2017/0233779 | A1 | 9/2017 | Page et al. |
| 2018/0030486 | A1 | 2/2018 | Beardslee et al. |
| 2018/0073043 | A1 | 3/2018 | Poulos et al. |
| 2018/0155748 | A1 | 6/2018 | Butt et al. |
| 2018/0334692 | A1 | 11/2018 | Barr et al. |
| 2019/0078098 | A1 | 3/2019 | Alper |
| 2019/0169661 | A1 | 6/2019 | Page |

FOREIGN PATENT DOCUMENTS

| | | | |
|---|---|---|---|
| WO | WO 1996/019497 | A1 | 6/1996 |
| WO | WO 1998/056943 | A1 | 12/1998 |
| WO | WO 1999/021013 | A1 | 4/1999 |
| WO | WO 2017/139496 | A1 | 9/2017 |
| WO | WO 2017/160801 | A1 | 9/2017 |
| WO | WO 2018/148848 | A1 | 8/2018 |
| WO | WO 2018/148849 | A1 | 8/2018 |
| WO | WO 2018/200888 | A1 | 11/2018 |
| WO | WO 2018/219995 | A1 | 12/2018 |
| WO | WO 2019/071000 | A1 | 4/2019 |

OTHER PUBLICATIONS

Akbergenov et al., ARC-1, a sequence element complementary to an internal 18S rRNA segment, enhances translation efficiency in plants when present in the leader or intercistronic region of mRNAs Nucleic Acids Research 32:1, 239-247 (2004).
Alani et al., "A method for gene disruption that allows repeated use of URA3 selection in the construction of multiply disrupted yeast strains", Genetics 116(4):541-545 Aug. 1987.
Alconado and Juarez 2006. "Acyl-CoA oxidase activity from Beauveria bassiana, an entomopathgenic fungus". J Basic Microbiol. 2006;46(6):435-43.
Arie et al., "Phylogenetic identification of n-alkane assimilating Candida yeasts based on nucleotide divergence in the 5 end of LSU rDNA gene" J. Gen. Appl. Microbiol., 46, 257-262 (2000).
Austin, M. B. and J. P. Noel., "The chalcone synthase superfamily of type III polyketide synthases", Natural Product Reports, 2002. 20(1): p. 79-110.
Backer et al. "Innovative development and validation of an HPLC/DAD method for the qualitative and quantitative determination of major cannabinoids in cannabis plant material." J Chromatogr B Analyt Technol Biomed Life Sci. Dec. 15, 2009;877(32):4115-24.
Bakke et al. "N-ethylmaleimide-resistant acyl-coenzyme A oxidase from Arthrobacter ureafaciens NBRC 12140: molecular cloning, gene expression and characterization of the recombinant enzyme." Biochim Biophys Acta. Jan. 2007;1774(1):65-71.
Barth and Gaillardin. "Physiology and genetics of the dimorphic fungus Yarrowia lipolytica." FEMS Microbiol Rev. Apr. 1997;19(4):219-37.
Beggah et al. "Intra-and intermolecular events direct the propeptide-mediated maturation of the Candida albicans secreted aspartic proteinase Sap1p." Microbiology. Nov. 2000;146 ( Pt 11):2765-73.
Brocard and Hartig. "Peroxisome targeting signal 1: is it really a simple tripeptide?" Biochim Biophys Acta. Dec. 2006;1763(12):1565-73.
Brown et al. Aspergillus has distinct fatty acid synthases for primary and secondary metabolism.: Proc Natl Acad Sci U S A. Dec. 10, 1996;93(25):14873-7.
Capone et al., "Amber, ochre and opal suppressor tRNA genes derived from a human serine tRNA gene", EMBO J. 4:213, 1985.
Carvalho et al. "Designing microorganisms for heterologous biosynthesis of cannabinoids." FEMS Yeast Res. Jun. 1, 2017;17(4).
Chica et al. Curr Opin Biotechnol. Aug. 2005; 16(4):378-84. (Year: 2005).

Current Protocols in Molecular Biology, John Wiley & Sons, N.Y., 6.3.1-6.3.6 (1989).
Deshpande, Mukund V., Appl. Biochem. Biotechnol., 36:227 (1992).
Eggertsson, et al., "Transfer ribonucleic acid-mediated suppression of termination codons in *Escherichia coli*.", (1988) Microbiological Review 52(3):354-374.
Engleerg-Kukla, et al. (1996) in *Escherichia coli* and *Salmonella* Cellular and Molecular Biology, Chapter 60, pp. 909-921, Neidhardt, et al. eds., ASM Press, Washington, D.C.
Gagne et al. "Identification of olivetolic acid cyclase from Cannabis sativa reveals a unique catalytic route to plant polyketides." Proc Natl Acad Sci U S A. Jul. 31, 2012;109(31):12811-6.
Gajewski et al. "Engineering fungal de novo fatty acid synthesis for short chain fatty acid production." Nat Commun. Mar. 10, 2017;8:14650.
Gallie et al., "The 5'-leader sequence of tobacco mosaic virus RNA enhances the expression of foreign gene transcripts in vitro and in vivo", Nucleic Acids Research 15: 3257-3273 (1987).
Gallie, The 5'-leader of tobacco mosaic virus promotes translation through enhanced recruitment of eIF4F Nucleic Acids Research 30: 3401-3411 (2002).
Gao et al. "Iterative integration of multiple-copy pathway genes in Yarrowia lipolytica for heterologous β-carotene production". Metab Eng. May 2017;41:192-201.
Ghaedi et al. Journal of Sciences, Islamic Republic of Iran (2009), 20(3), 205-211. Abstract. (Year: 2009).
Gietz and Woods "Transformation of Yeast by Lithium Acetate/Single-Stranded Carrier DNA/Polyethylene Glycol Method". Methods Enzymol. 2002;350:87-96.
Hiltunen et al. (JBC, vol. 267, No. 10, Apr. 5, 1992, pp. 6646-6653).
Hong et al. "Engineering Yarrowia lipolytica to express secretory invertase with strong FBA1IN promoter". Yeast. Feb. 2012;29(2):59-72.
Hooks et al. "Long-chain acyl-CoA oxidases of *Arabidopsis*." Plant J. Oct. 1999;20(1):1-13.
Hooks et al., Biochem J., 320:607-614 (1996).
Hunkova and Fenci. "Toxic effects of fatty acids on yeast cells: dependence of inhibitory effects on fatty acid concentration." Biotechnol Bioeng. Nov. 1977;19(11):1623-41.
Kistler and Broz "Cellular compartmentalization of secondary metabolism" Front. Microbiology Feb. 2015.
Kizer et al. Appl Environ Microbial. May 2008;74(10):3229-41. (Year: 2008).
Klionsky et al. "Intracellular sorting and processing of a yeast vacuolar hydrolase: proteinase A propeptide contains vacuolar targeting information." Mol Cell Biol. May 1988;8(5):2105-16.
Krink-Koutsoubelis et al."Engineered Production of Short-Chain Acyl-Coenzyme A Esters in *Saccharomyces cerevisiae*." ACS Synth Biol. Apr. 20, 2018;7(4):1105-1115.
Lametschwandtner et al. "The difference in recognition of terminal tripeptides as peroxisomal targeting signal 1 between yeast and human is due to different affinities of their receptor Pex5p to the cognate signal and to residues adjacent to it." J Biol Chem. Dec. 11, 1998;273(50):33635-43.
Landy, Curr. Opin. Biotech. 3:699-707 (1993).
Ledesma-Amaro and Nicaud. "Yarrowia lipolytica as a biotechnological chassis to produce usual and unusual fatty acids." Prog Lipid Res. Jan. 2016;61:40-50.
Liang et al. "Structure, mechanism and function of prenyltransferase." Eur J Biochem. Jul. 2002;269(14):3339-54.
Lim et al., "Exploiting the Biosynthetic Potential of Type III Polyketide Synthases", Molecules, 2016.21(6): p. 806.
Lui et al. "Membrane stress caused by octanoic acid in *Saccharomyces cerevisiae*" Appl Microbiol Biotechnol. Apr. 2013;97(7):3239-51.
Luo et al 2019 "Complete biosynthesis of cannabinoids and their unnatural analogues in yeast." Nature. Mar. 2019;567(7746):123-126.
Luo et. al 2002 "The acyl-CoA oxidases from the yeast Yarrowia lipolytica: characterization of Aox2p." Arch Biochem Biophys. Nov 1;407(1):32-8.
Marks M D, et al. (2009) Identification of candidate genes affecting Delta9-tetrahydrocannabinol biosynthesis in Cannabis sativa. J Exp Bot. 60, 3715-3726.

(56) References Cited

OTHER PUBLICATIONS

Meyers & Miller, Cabios 4: 11-17 (1988).
Mignone et al., "Untranslated regions of mRNAs", Genome Biology 3(3): reviews 0004.1-0001.10 (2002).
Mignone et al., "UTRdb and UTRsite: a collection of sequences and regulatory motifs of the untranslated regions of eukaryotic mRNAs", Nucleic Acids Research 33: D141-D146 (2005).
Morimoto et al. (1998) Purification and characterization of cannabichromenic acid synthase from Cannabis sativa. Phytochemistry. 49: 1525-1529.
Needleman & Wunsch, J. Mol. Biol. 48: 444-453 (1970).
Nelson Biochemistry Jun. 25, 1996; 35(25):8429-38.
Page and Nagel, "Biosynthesis of terpenophenolics in hop and cannabis", In J T Romeo, ed, Integrative Plant Biochemistry, vol. 40. Elsevier, Oxford, pp. 179-210, 2006.
Pamplaniyi "Identification, isolation, and functional characterization of prenyltransferases in cannabis sativa "Dissertation Dortmund 2016.
Papanikolaou S., and Aggelis G., Bioresour. Technol. 82(1):43-9 (2002).
Paulous et al., "Comparison of the capacity of different viral internal ribosome entry segments to direct translation initiation in poly(A)-dependent reticulocyte lysates", Nucleic Acids Research 31: 722-733 (2003).
Reiser et. al 2009 "AoxA is a major peroxisomal long chain fattyacyl-CoA oxidase required for beta-oxidation in A. nidulans". Curr Genet. Apr. 2010;56(2):139-50.
Sauer, B., Curr. Opin. Biotech. 5:521-527 (1994).
Sekiguchi and Shuman, Nucl. Acids Res. 22:5360-5365, 1994.
Setoyama et. al 1995 "Functional expression of two forms of rat acyl-CoA oxidase and their substrate specificities" Dec. 14;217(2):482-7.
Shimiu et al. Type III Polyketide Synthases: Functional Classification and Phylogenomics. Chembiochem. Jan. 3, 2017;18(1):50-65.
Shuman, "Site-specific Interaction of Vaccinia Virus Topoisomerase I with Duplex DNA", J. Biol. Chem. 266:11372-11379, 1991.
Singh et al. Curr Protein Pept Sci. 2017, 18, 1-11 (Year: 2017).
Sirikantaramas S. et al. (2005) Tetrahydrocannabinolic acid synthase, the enzyme controlling marijuana psychoactivity, is secreted into the storage cavity of the glandular trichomes. Plant Cell Physiol. 46: 1578-1582.
Stout et al. "The hexanoyl-CoA precursor for cannabinoid biosynthesis is formed by an acyl-activating enzyme in Cannabis sativa trichomes." Plant J. Aug. 2012;71(3):353-65.
Tan et al. "Synthetic Pathway for the Production of Olivetolic Acid in *Escherichia coli*," ACS Synthetic Biology, Jul. 5, 2018, vol. 7, No. 8, pp. 1886-1896.
Taura et al. "Characterization of olivetol synthase, a polyketide synthase putatively involved in cannabinoid biosynthetic pathway." FEBS Lett. Jun. 18, 2009;583(12):2061-6.
Taura F. et al. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. 271: 17411-17416.
Taura F. et al. (2007) Cannabidiolic-acid synthase, the chemotype-determining enzyme in the fiber-type Cannabis sativa. FEBS Lett. 581: 2929-2934.
Taura F. et al.(1995) First direct evidence for the mechanism of 1-tetrahydrocannabinolic acid biosynthesis. J Am Chem Soc. 117: 9766-9767.
Tjalsma et al., "Signal Peptide-Dependent Protein Transport in Bacillus subtilis: a Genome-Based Survey of the Secretome", Microbiol. Molec. Biol. Rev. 64: 515-547 (2000).
Vincent et al., "Helicase-dependent isothermal DNA amplification". EMBO reports 5 (8): 795-800 (2004).
Yang et al "Structural basis for olivetolic acid formation by a polyketide cyclase from Cannabis sativa." FEBS J. Mar. 2016;283(6):1088-106.
Yu et al. "Type III Polyketide Synthases in Natural Product Biosynthesis", IUBMB Life, 2012. 64(4): p. 285-295.
Zirpel "Recombinant Expression and Functional Characterization of Cannabinoid Producing Enzymes in Komagataella phaffii" Dissertation Dortmund 2018.
Zirpel et al. "Optimization of Δ9-tetrahydrocannabinolic acid synthase production in Komagataella phaffii via post-translational bottleneck identification." J Biotechnol. Apr. 20, 2018;272-273:40-47.
Zirpel et al. "Production of Δ9-tetrahydrocannabinolic acid from cannabigerolic acid by whole cells of Pichia (Komagataella) pastoris expressing Δ9-tetrahydrocannabinolic acid synthase from *Cannabis sativa* L." Biotechnol Lett. Sep. 2015;37(9):1869-75.

\* cited by examiner

Map of pLD1

Map of pLD10

Map of pLD12

Map of pLD14

Map of pLD16

Map of pLD20

Map of pLD22

Map of pLD24

Map of pLD56

Map of pLD87

Map of pLD101

Map of pLD102

Map of pLD111

Map of pLD112

Map of pLD113

Map of pLD125

Map of pLD127

Map of pLD131

Map of pLD132

Map of pLD135

Map of pLD137

Map of pLD138

Map of pLD139

Map of pLD19

Map of pLD26

SEQUENCE LISTING

```
<160> NUMBER OF SEQ ID NOS: 182

<210> SEQ ID NO 1
<211> LENGTH: 22
<212> TYPE: PRT
<213> ORGANISM: Saccharomyces cerevisiae

<400> SEQUENCE: 1

Met Phe Ser Leu Lys Ala Leu Leu Pro Leu Ala Leu Leu Leu Val Ser
1               5                   10                  15

Ala Asn Gln Val Ala Ala
            20

<210> SEQ ID NO 2
<211> LENGTH: 54
<212> TYPE: PRT
<213> ORGANISM: Saccharomyces cerevisiae

<400> SEQUENCE: 2

Lys Val His Lys Ala Lys Ile Tyr Lys His Glu Leu Ser Asp Glu Met
1               5                   10                  15

Lys Glu Val Thr Phe Glu Gln His Leu Ala His Leu Gly Gln Lys Tyr
            20                  25                  30

Leu Thr Gln Phe Glu Lys Ala Asn Pro Glu Val Val Phe Ser Arg Glu
        35                  40                  45

His Pro Phe Phe Thr Glu
    50

<210> SEQ ID NO 3
<211> LENGTH: 18
<212> TYPE: PRT
<213> ORGANISM: Homo sapiens
```

-continued

<400> SEQUENCE: 3

Met Val Arg Met Val Pro Val Leu Leu Ser Leu Leu Leu Leu Leu Gly
1               5                   10                  15

Pro Ala

<210> SEQ ID NO 4
<211> LENGTH: 19
<212> TYPE: PRT
<213> ORGANISM: Kluyveromyces marxianus

<400> SEQUENCE: 4

Met Leu Phe Ser Asn Thr Leu Leu Ile Ala Ala Ala Ser Ala Leu Leu
1               5                   10                  15

Ala Glu Ala

<210> SEQ ID NO 5
<211> LENGTH: 19
<212> TYPE: PRT
<213> ORGANISM: Saccharomycopsis fibuligera

<400> SEQUENCE: 5

Met Lys Phe Gly Val Leu Phe Ser Val Phe Ala Ala Ile Val Ser Ala
1               5                   10                  15

Leu Pro Ala

<210> SEQ ID NO 6
<211> LENGTH: 6
<212> TYPE: PRT
<213> ORGANISM: Saccharomyces cerevisiae

<400> SEQUENCE: 6

Gly Arg Arg Ala Lys Leu
1               5

<210> SEQ ID NO 7
<211> LENGTH: 3
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa = Ser, Ala, His, Cys, Glu, Pro, Gln, or Val
<220> FEATURE:
<221> NAME/KEY: VARIANT
<222> LOCATION: (2)...(2)
<223> OTHER INFORMATION: Xaa = Lys, Arg, His, or Gln
<220> FEATURE:
<221> NAME/KEY: VARIANT
<222> LOCATION: (3)...(3)
<223> OTHER INFORMATION: Xaa = Leu or Phe
<220> FEATURE:
<223> OTHER INFORMATION: PTS sequence
<220> FEATURE:
<221> NAME/KEY: VARIANT
<222> LOCATION: 1, 2, 3
<223> OTHER INFORMATION: Xaa = Any Amino Acid

<400> SEQUENCE: 7

Xaa Xaa Xaa
1

<210> SEQ ID NO 8
<211> LENGTH: 9
<212> TYPE: PRT
<213> ORGANISM: Artificial Sequence

```
<220> FEATURE:
<221> NAME/KEY: VARIANT
<222> LOCATION: (1)...(1)
<223> OTHER INFORMATION: Xaa = Arg or Lys
<220> FEATURE:
<221> NAME/KEY: VARIANT
<222> LOCATION: (2)...(2)
<223> OTHER INFORMATION: Xaa = Leu, Val, Ile, or Gln
<220> FEATURE:
<221> NAME/KEY: VARIANT
<222> LOCATION: (3)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (5)...(5)
<223> OTHER INFORMATION: Xaa = Leu, Val, Ile, His, or Gln
<220> FEATURE:
<221> NAME/KEY: VARIANT
<222> LOCATION: (6)...(6)
<223> OTHER INFORMATION: Xaa = Leu, Ser, Gly, Ala, or Lys
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (8)...(8)
<223> OTHER INFORMATION: Xaa = His or Gln
<220> FEATURE:
<221> NAME/KEY: VARIANT
<222> LOCATION: (9)...(9)
<223> OTHER INFORMATION: Xaa = Leu, Ala, or Phe
<223> OTHER INFORMATION: PTS2 Sequence

<400> SEQUENCE: 8

Xaa Xaa Xaa Xaa Xaa Xaa Xaa Xaa Xaa
1               5

<210> SEQ ID NO 9
<211> LENGTH: 9
<212> TYPE: PRT
<213> ORGANISM: Saccharomyces cerevisiae

<400> SEQUENCE: 9

Arg Arg Met Leu Ser Ser Lys Gln Leu
1               5

<210> SEQ ID NO 10
<211> LENGTH: 709
<212> TYPE: PRT
<213> ORGANISM: Artificial Sequence
<220> FEATURE:
<223> OTHER INFORMATION: Arthrobacter

<400> SEQUENCE: 10

Met Thr Glu Val Val Asp Arg Ala Ser Ser Pro Ala Ser Pro Gly Ser
1               5                   10                  15

Thr Thr Ala Ala Ala Asp Gly Ala Lys Val Ala Val Glu Pro Arg Val
                20                  25                  30

Asp Val Ala Ala Leu Gly Glu Gln Leu Leu Gly Arg Trp Ala Asp Ile
            35                  40                  45

Arg Leu His Ala Arg Asp Leu Ala Gly Arg Glu Val Val Gln Lys Val
        50                  55                  60

Glu Gly Leu Thr His Thr Glu His Arg Ser Arg Val Phe Gly Gln Leu
65                  70                  75                  80
```

```
Lys Tyr Leu Val Asp Asn Asn Ala Val His Arg Ala Phe Pro Ser Arg
                85                  90                  95
Leu Gly Gly Ser Asp Asp His Gly Gly Asn Ile Ala Gly Phe Glu Glu
            100                 105                 110
Leu Val Thr Ala Asp Pro Ser Leu Gln Ile Lys Ala Gly Val Gln Trp
        115                 120                 125
Gly Leu Phe Gly Ser Ala Val Met His Leu Gly Thr Arg Glu His His
130                 135                 140
Asp Lys Trp Leu Pro Gly Ile Met Ser Leu Ile Pro Gly Cys Phe
145                 150                 155                 160
Ala Met Thr Glu Thr Gly His Gly Ser Asp Val Ala Ser Ile Ala Thr
                165                 170                 175
Thr Ala Thr Tyr Asp Glu Glu Thr Gln Glu Phe Val Ile Asp Thr Pro
            180                 185                 190
Phe Arg Ala Ala Trp Lys Asp Tyr Ile Gly Asn Ala Ala Asn Asp Gly
        195                 200                 205
Leu Ala Ala Val Val Phe Ala Gln Leu Ile Thr Arg Lys Val Asn His
210                 215                 220
Gly Val His Ala Phe Tyr Val Asp Leu Arg Asp Pro Ala Thr Gly Asp
225                 230                 235                 240
Phe Leu Pro Gly Ile Gly Gly Glu Asp Asp Gly Ile Lys Gly Gly Leu
                245                 250                 255
Asn Gly Ile Asp Asn Gly Arg Leu His Phe Thr Asn Val Arg Ile Pro
            260                 265                 270
Arg Thr Asn Leu Leu Asn Arg Tyr Gly Asp Val Ala Val Asp Gly Thr
        275                 280                 285
Tyr Ser Ser Thr Ile Glu Ser Pro Gly Arg Arg Phe Phe Thr Met Leu
290                 295                 300
Gly Thr Leu Val Gln Gly Arg Val Ser Leu Asp Gly Ala Ala Val Ala
305                 310                 315                 320
Ala Ser Lys Val Ala Leu Gln Ser Ala Ile His Tyr Ala Ala Glu Arg
                325                 330                 335
Arg Gln Phe Asn Ala Thr Ser Pro Thr Glu Glu Val Leu Leu Asp
            340                 345                 350
Tyr Gln Arg His Gln Arg Leu Phe Thr Arg Leu Ala Thr Thr Tyr
        355                 360                 365
Ala Ala Ser Phe Ala His Glu Gln Leu Leu Gln Lys Phe Asp Asp Val
        370                 375                 380
Phe Ser Gly Ala His Asp Thr Asp Ala Asp Arg Gln Asp Leu Glu Thr
385                 390                 395                 400
Leu Ala Ala Ala Leu Lys Pro Leu Ser Thr Trp His Ala Leu Asp Thr
                405                 410                 415
Leu Gln Glu Cys Arg Glu Ala Cys Gly Gly Ala Gly Phe Leu Ile Glu
            420                 425                 430
Asn Arg Phe Ala Ser Leu Arg Ala Asp Leu Asp Val Tyr Val Thr Phe
        435                 440                 445
Glu Gly Asp Asn Thr Val Leu Leu Gln Leu Val Ala Lys Arg Leu Leu
    450                 455                 460
Ala Asp Tyr Ala Lys Glu Phe Arg Gly Ala Asn Phe Gly Val Leu Ala
465                 470                 475                 480
Arg Tyr Val Val Asp Gln Ala Ala Gly Val Ala Leu His Arg Thr Gly
                485                 490                 495
Leu Arg Gln Val Ala Gln Phe Val Ala Asp Ser Gly Ser Val Gln Lys
```

```
                        500                 505                 510
Ser Ala Leu Ala Leu Arg Asp Glu Glu Gly Gln Arg Thr Leu Leu Thr
            515                 520                 525

Asp Arg Val Gln Ser Met Val Ala Glu Val Gly Ala Ala Leu Lys Gly
            530                 535                 540

Ala Gly Lys Leu Pro Gln His Gln Ala Ala Ala Leu Phe Asn Gln His
545                 550                 555                 560

Gln Asn Glu Leu Ile Glu Ala Ala Gln Ala His Ala Glu Leu Leu Gln
                565                 570                 575

Trp Glu Ala Phe Thr Glu Ala Leu Ala Lys Val Asp Asp Ala Gly Thr
            580                 585                 590

Lys Glu Val Leu Thr Arg Leu Arg Asp Leu Phe Gly Leu Ser Leu Ile
            595                 600                 605

Glu Lys His Leu Ser Trp Tyr Leu Met Asn Gly Arg Leu Ser Met Gln
            610                 615                 620

Arg Gly Arg Thr Val Gly Thr Tyr Ile Asn Arg Leu Leu Val Lys Ile
625                 630                 635                 640

Arg Pro His Ala Leu Asp Leu Val Asp Ala Phe Gly Tyr Gly Ala Glu
                645                 650                 655

His Leu Arg Ala Ala Ile Ala Thr Gly Ala Glu Ala Thr Arg Gln Asp
            660                 665                 670

Glu Ala Arg Thr Tyr Phe Arg Gln Gln Arg Ala Ser Gly Ser Ala Pro
            675                 680                 685

Ala Asp Glu Lys Thr Leu Leu Ala Ile Lys Ala Gly Lys Ser Arg Gly
690                 695                 700

Arg Arg Ala Lys Leu
705

<210> SEQ ID NO 11
<211> LENGTH: 700
<212> TYPE: PRT
<213> ORGANISM: Yarrowia lipolytica

<400> SEQUENCE: 11

Met Asn Pro Asn Asn Thr Gly Thr Ile Glu Ile Asn Gly Lys Glu Tyr
1               5                   10                  15

Asn Thr Phe Thr Glu Pro Pro Val Ala Met Ala Gln Glu Arg Ala Lys
            20                  25                  30

Thr Ser Phe Pro Val Arg Glu Met Thr Tyr Phe Leu Asp Gly Gly Glu
        35                  40                  45

Lys Asn Thr Leu Lys Asn Glu Gln Ile Met Glu Glu Ile Glu Arg Asp
    50                  55                  60

Pro Leu Phe Asn Asn Asp Asn Tyr Tyr Asp Leu Asn Lys Glu Gln Ile
65                  70                  75                  80

Arg Glu Leu Thr Met Glu Arg Val Ala Lys Leu Ser Leu Phe Val Arg
                85                  90                  95

Asp Gln Pro Glu Asp Ile Lys Lys Arg Phe Ala Leu Ile Gly Ile
            100                 105                 110

Ala Asp Met Gly Thr Tyr Thr Arg Leu Gly Val His Tyr Gly Leu Phe
        115                 120                 125

Phe Gly Ala Val Arg Gly Thr Gly Thr Ala Glu Gln Phe Gly His Trp
    130                 135                 140

Ile Ser Lys Gly Ala Gly Asp Leu Arg Lys Phe Tyr Gly Cys Phe Ser
145                 150                 155                 160
```

```
Met Thr Glu Leu Gly His Gly Ser Asn Leu Ala Gly Leu Glu Thr Thr
            165                 170                 175
Ala Ile Tyr Asp Glu Glu Thr Asp Glu Phe Ile Ile Asn Thr Pro His
            180                 185                 190
Ile Ala Ala Thr Lys Trp Trp Ile Gly Gly Ala Ala His Thr Ala Thr
            195                 200                 205
His Thr Val Val Phe Ala Arg Leu Ile Val Lys Gly Lys Asp Tyr Gly
            210                 215                 220
Val Lys Thr Phe Val Val Gln Leu Arg Asn Ile Asn Asp His Ser Leu
225                 230                 235                 240
Lys Val Gly Ile Ser Ile Gly Asp Ile Gly Lys Lys Met Gly Arg Asp
            245                 250                 255
Gly Ile Asp Asn Gly Trp Ile Gln Phe Thr Asn Val Arg Ile Pro Arg
            260                 265                 270
Gln Asn Leu Leu Met Lys Tyr Thr Lys Val Asp Arg Glu Gly Asn Val
            275                 280                 285
Thr Gln Pro Pro Leu Ala Gln Leu Thr Tyr Gly Ser Leu Ile Thr Gly
            290                 295                 300
Arg Val Ser Met Ala Ser Asp Ser His Gln Val Gly Lys Arg Phe Ile
305                 310                 315                 320
Thr Ile Ala Leu Arg Tyr Ala Cys Ile Arg Arg Gln Phe Ser Thr Thr
            325                 330                 335
Pro Gly Gln Pro Glu Thr Lys Ile Ile Asp Tyr Pro Tyr His Gln Arg
            340                 345                 350
Arg Leu Leu Pro Leu Leu Ala Tyr Val Tyr Ala Leu Lys Met Thr Ala
            355                 360                 365
Asp Glu Val Gly Ala Leu Phe Ser Arg Thr Met Leu Lys Met Asp Asp
            370                 375                 380
Leu Lys Pro Asp Asp Lys Ala Gly Leu Asn Glu Val Val Ser Asp Val
385                 390                 395                 400
Lys Glu Leu Phe Ser Val Ser Ala Gly Leu Lys Ala Phe Ser Thr Trp
            405                 410                 415
Ala Cys Ala Asp Val Ile Asp Lys Thr Arg Gln Ala Cys Gly Gly His
            420                 425                 430
Gly Tyr Ser Gly Tyr Asn Gly Phe Gly Gln Ala Tyr Ala Asp Trp Val
            435                 440                 445
Val Gln Cys Thr Trp Glu Gly Asp Asn Asn Ile Leu Thr Leu Ser Ala
            450                 455                 460
Gly Arg Ala Leu Ile Gln Ser Ala Val Ala Leu Arg Lys Gly Glu Pro
465                 470                 475                 480
Val Gly Asn Ala Val Ser Tyr Leu Lys Arg Tyr Lys Asp Leu Ala Asn
            485                 490                 495
Ala Lys Leu Asn Gly Arg Ser Leu Thr Asp Pro Lys Val Leu Val Glu
            500                 505                 510
Ala Trp Glu Val Ala Ala Gly Asn Ile Ile Asn Arg Ala Thr Asp Gln
            515                 520                 525
Tyr Glu Lys Leu Ile Gly Glu Gly Leu Asn Ala Asp Gln Ala Phe Glu
            530                 535                 540
Val Leu Ser Gln Gln Arg Phe Gln Ala Ala Lys Val His Thr Arg Arg
545                 550                 555                 560
His Leu Ile Ala Ala Phe Phe Ser Arg Ile Asp Thr Glu Ala Gly Glu
            565                 570                 575
Ala Ile Lys Gln Pro Leu Leu Asn Leu Ala Leu Leu Phe Ala Leu Trp
```

```
                580             585             590
Ser Ile Glu Glu Asp Ser Gly Leu Phe Leu Arg Glu Gly Phe Leu Glu
            595                 600                 605

Pro Lys Asp Ile Asp Thr Val Thr Glu Leu Val Asn Lys Tyr Cys Thr
610                 615                 620

Thr Val Arg Glu Glu Val Ile Gly Tyr Thr Asp Ala Phe Asn Leu Ser
625                 630                 635                 640

Asp Tyr Phe Ile Asn Ala Pro Ile Gly Cys Tyr Asp Gly Asp Ala Tyr
                645                 650                 655

Arg His Tyr Phe Gln Lys Val Asn Glu Gln Asn Pro Ala Arg Asp Pro
                660                 665                 670

Arg Pro Pro Tyr Tyr Ala Ser Thr Leu Lys Pro Phe Leu Phe Arg Glu
            675                 680                 685

Glu Glu Asp Asp Asp Ile Cys Glu Leu Asp Glu Glu
            690                 695                 700

<210> SEQ ID NO 12
<211> LENGTH: 661
<212> TYPE: PRT
<213> ORGANISM: Rattus norvegicus

<400> SEQUENCE: 12

Met Asn Pro Asp Leu Arg Lys Glu Arg Ala Ser Ala Thr Phe Asn Pro
1               5                   10                  15

Glu Leu Ile Thr His Ile Leu Asp Gly Ser Pro Glu Asn Thr Arg Arg
            20                  25                  30

Arg Arg Glu Ile Glu Asn Leu Ile Leu Asn Asp Pro Asp Phe Gln His
        35                  40                  45

Glu Asp Tyr Asn Phe Leu Thr Arg Ser Gln Arg Tyr Glu Val Ala Val
    50                  55                  60

Lys Lys Ser Ala Thr Met Val Lys Lys Met Arg Glu Tyr Gly Ile Ser
65                  70                  75                  80

Asp Pro Glu Glu Ile Met Trp Phe Lys Lys Leu Tyr Leu Ala Asn Phe
                85                  90                  95

Val Glu Pro Val Gly Leu Asn Tyr Ser Met Phe Ile Pro Thr Leu Leu
            100                 105                 110

Asn Gln Gly Thr Thr Ala Gln Gln Glu Lys Trp Met Arg Pro Ser Gln
        115                 120                 125

Glu Leu Gln Ile Ile Gly Thr Tyr Ala Gln Thr Glu Met Gly His Gly
    130                 135                 140

Thr His Leu Arg Gly Leu Glu Thr Thr Ala Thr Tyr Asp Pro Lys Thr
145                 150                 155                 160

Gln Glu Phe Ile Leu Asn Ser Pro Thr Val Thr Ser Ile Lys Trp Trp
                165                 170                 175

Pro Gly Gly Leu Gly Lys Thr Ser Asn His Ala Ile Val Leu Ala Gln
            180                 185                 190

Leu Ile Thr Gln Gly Glu Cys Tyr Gly Leu His Ala Phe Val Val Pro
        195                 200                 205

Ile Arg Glu Ile Gly Thr His Lys Pro Leu Pro Gly Ile Thr Val Gly
    210                 215                 220

Asp Ile Gly Pro Lys Phe Gly Tyr Glu Glu Met Asp Asn Gly Tyr Leu
225                 230                 235                 240

Lys Met Asp Asn Tyr Arg Ile Pro Arg Glu Asn Met Leu Met Lys Tyr
                245                 250                 255
```

```
Ala Gln Val Lys Pro Asp Gly Thr Tyr Val Lys Pro Leu Ser Asn Lys
            260                 265                 270

Leu Thr Tyr Gly Thr Met Val Phe Val Arg Ser Phe Leu Val Gly Asn
        275                 280                 285

Ala Ala Gln Ser Leu Ser Lys Ala Cys Thr Ile Ala Ile Arg Tyr Ser
    290                 295                 300

Ala Val Arg Arg Gln Ser Glu Ile Lys Gln Ser Glu Pro Glu Pro Gln
305                 310                 315                 320

Ile Leu Asp Phe Gln Thr Gln Tyr Lys Leu Phe Pro Leu Leu Ala
                325                 330                 335

Thr Ala Tyr Ala Phe His Phe Val Gly Arg Tyr Met Lys Glu Thr Tyr
            340                 345                 350

Leu Arg Ile Asn Glu Ser Ile Gly Gln Gly Asp Leu Ser Glu Leu Pro
                355                 360                 365

Glu Leu His Ala Leu Thr Ala Gly Leu Lys Ala Phe Thr Thr Trp Thr
        370                 375                 380

Ala Asn Ala Gly Ile Glu Glu Cys Arg Met Ala Cys Gly Gly His Gly
385                 390                 395                 400

Tyr Ser His Ser Ser Gly Ile Pro Asn Ile Tyr Val Thr Phe Thr Pro
                405                 410                 415

Ala Cys Thr Phe Glu Gly Glu Asn Thr Val Met Met Leu Gln Thr Ala
            420                 425                 430

Arg Phe Leu Met Lys Ile Tyr Asp Gln Val Arg Ser Gly Lys Leu Val
        435                 440                 445

Gly Gly Met Val Ser Tyr Leu Asn Asp Leu Pro Ser Gln Arg Ile Gln
    450                 455                 460

Pro Gln Gln Val Ala Val Trp Pro Thr Met Val Asp Ile Asn Ser Leu
465                 470                 475                 480

Glu Gly Leu Thr Glu Ala Tyr Lys Leu Arg Ala Ala Arg Leu Val Glu
                485                 490                 495

Ile Ala Ala Lys Asn Leu Gln Thr His Val Ser His Arg Lys Ser Lys
            500                 505                 510

Glu Val Ala Trp Asn Leu Thr Ser Val Asp Leu Val Arg Ala Ser Glu
        515                 520                 525

Ala His Cys His Tyr Val Val Lys Val Phe Ser Asp Lys Leu Pro
    530                 535                 540

Lys Ile Gln Asp Lys Ala Val Gln Ala Val Leu Arg Asn Leu Cys Leu
545                 550                 555                 560

Leu Tyr Ser Leu Tyr Gly Ile Ser Gln Lys Gly Gly Asp Phe Leu Glu
                565                 570                 575

Gly Ser Ile Ile Thr Gly Ala Gln Leu Ser Gln Val Asn Ala Arg Ile
            580                 585                 590

Leu Glu Leu Leu Thr Leu Ile Arg Pro Asn Ala Val Ala Leu Val Asp
        595                 600                 605

Ala Phe Asp Phe Lys Asp Met Thr Leu Gly Ser Val Leu Gly Arg Tyr
    610                 615                 620

Asp Gly Asn Val Tyr Glu Asn Leu Phe Glu Trp Ala Lys Lys Ser Pro
625                 630                 635                 640

Leu Asn Lys Thr Glu Val His Glu Ser Tyr His Lys His Leu Lys Pro
                645                 650                 655

Leu Gln Ser Lys Leu
            660
```

```
<210> SEQ ID NO 13
<211> LENGTH: 661
<212> TYPE: PRT
<213> ORGANISM: Rattus norvegicus

<400> SEQUENCE: 13

Met Asn Pro Asp Leu Arg Lys Glu Arg Ala Ser Ala Thr Phe Asn Pro
1               5                   10                  15

Glu Leu Ile Thr His Ile Leu Asp Gly Ser Pro Glu Asn Thr Arg Arg
            20                  25                  30

Arg Arg Glu Ile Glu Asn Leu Ile Leu Asn Asp Pro Asp Phe Gln His
        35                  40                  45

Glu Asp Tyr Asn Phe Leu Thr Arg Ser Gln Arg Tyr Glu Val Ala Val
    50                  55                  60

Lys Lys Ser Ala Thr Met Val Lys Lys Met Arg Glu Tyr Gly Ile Ser
65                  70                  75                  80

Asp Pro Glu Glu Ile Met Trp Phe Lys Asn Ser Val His Arg Gly His
                85                  90                  95

Pro Glu Pro Leu Asp Leu His Leu Gly Met Phe Leu Pro Thr Leu Leu
            100                 105                 110

His Gln Ala Thr Ala Glu Gln Gln Glu Arg Phe Phe Met Pro Ala Trp
        115                 120                 125

Asn Leu Glu Ile Thr Gly Thr Tyr Ala Gln Thr Glu Met Gly His Gly
    130                 135                 140

Thr His Leu Arg Gly Leu Glu Thr Thr Ala Thr Tyr Asp Pro Lys Thr
145                 150                 155                 160

Gln Glu Phe Ile Leu Asn Ser Pro Thr Val Thr Ser Ile Lys Trp Trp
                165                 170                 175

Pro Gly Gly Leu Gly Lys Thr Ser Asn His Ala Ile Val Leu Ala Gln
            180                 185                 190

Leu Ile Thr Gln Gly Glu Cys Tyr Gly Leu His Ala Phe Val Val Pro
        195                 200                 205

Ile Arg Glu Ile Gly Thr His Lys Pro Leu Pro Gly Ile Thr Val Gly
    210                 215                 220

Asp Ile Gly Pro Lys Phe Gly Tyr Glu Glu Met Asp Asn Gly Tyr Leu
225                 230                 235                 240

Lys Met Asp Asn Tyr Arg Ile Pro Arg Glu Asn Met Leu Met Lys Tyr
                245                 250                 255

Ala Gln Val Lys Pro Asp Gly Thr Tyr Val Lys Pro Leu Ser Asn Lys
            260                 265                 270

Leu Thr Tyr Gly Thr Met Val Phe Val Arg Ser Phe Leu Val Gly Asn
        275                 280                 285

Ala Ala Gln Ser Leu Ser Lys Ala Cys Thr Ile Ala Ile Arg Tyr Ser
    290                 295                 300

Ala Val Arg Arg Gln Ser Glu Ile Lys Gln Ser Glu Pro Glu Pro Gln
305                 310                 315                 320

Ile Leu Asp Phe Gln Thr Gln Gln Tyr Lys Leu Phe Pro Leu Leu Ala
                325                 330                 335

Thr Ala Tyr Ala Phe His Phe Val Gly Arg Tyr Met Lys Glu Thr Tyr
            340                 345                 350

Leu Arg Ile Asn Glu Ser Ile Gly Gln Gly Asp Leu Ser Glu Leu Pro
        355                 360                 365

Glu Leu His Ala Leu Thr Ala Gly Leu Lys Ala Phe Thr Thr Trp Thr
    370                 375                 380
```

-continued

Ala Asn Ala Gly Ile Glu Glu Cys Arg Met Ala Cys Gly Gly His Gly
385                 390                 395                 400

Tyr Ser His Ser Ser Gly Ile Pro Asn Ile Tyr Val Thr Phe Thr Pro
            405                 410                 415

Ala Cys Thr Phe Glu Gly Glu Asn Thr Val Met Met Leu Gln Thr Ala
        420                 425                 430

Arg Phe Leu Met Lys Ile Tyr Asp Gln Val Arg Ser Gly Lys Leu Val
    435                 440                 445

Gly Gly Met Val Ser Tyr Leu Asn Asp Leu Pro Ser Gln Arg Ile Gln
450                 455                 460

Pro Gln Gln Val Ala Val Trp Pro Thr Met Val Asp Ile Asn Ser Leu
465                 470                 475                 480

Glu Gly Leu Thr Glu Ala Tyr Lys Leu Arg Ala Ala Arg Leu Val Glu
            485                 490                 495

Ile Ala Ala Lys Asn Leu Gln Thr His Val Ser His Arg Lys Ser Lys
        500                 505                 510

Glu Val Ala Trp Asn Leu Thr Ser Val Asp Leu Val Arg Ala Ser Glu
    515                 520                 525

Ala His Cys His Tyr Val Val Val Lys Val Phe Ser Asp Lys Leu Pro
530                 535                 540

Lys Ile Gln Asp Lys Ala Val Gln Ala Val Leu Arg Asn Leu Cys Leu
545                 550                 555                 560

Leu Tyr Ser Leu Tyr Gly Ile Ser Gln Lys Gly Gly Asp Phe Leu Glu
            565                 570                 575

Gly Ser Ile Ile Thr Gly Ala Gln Leu Ser Gln Val Asn Ala Arg Ile
        580                 585                 590

Leu Glu Leu Leu Thr Leu Ile Arg Pro Asn Ala Val Ala Leu Val Asp
    595                 600                 605

Ala Phe Asp Phe Lys Asp Met Thr Leu Gly Ser Val Leu Gly Arg Tyr
610                 615                 620

Asp Gly Asn Val Tyr Glu Asn Leu Phe Glu Trp Ala Lys Lys Ser Pro
625                 630                 635                 640

Leu Asn Lys Thr Glu Val His Glu Ser Tyr His Lys His Leu Lys Pro
            645                 650                 655

Leu Gln Ser Lys Leu
        660

<210> SEQ ID NO 14
<211> LENGTH: 664
<212> TYPE: PRT
<213> ORGANISM: Glycine max

<400> SEQUENCE: 14

Met Glu Asp Gly Val Asp His Leu Ala Phe Glu Arg Asn Lys Ala Gln
1               5                   10                  15

Phe Asp Val Glu Asp Met Lys Ile Ile Trp Ala Gly Ser Arg Gln Asp
            20                  25                  30

Phe Glu Leu Ser Asp Arg Ile Ser Arg Leu Val Ala Ser Asp Pro Ala
        35                  40                  45

Phe Arg Lys Asp Asp Arg Thr Arg Leu Ile Gly Arg Leu Phe Lys Asn
    50                  55                  60

Thr Leu Arg Lys Ala Ala Tyr Ala Trp Lys Arg Ile Asn Glu Leu Arg
65                  70                  75                  80

Leu Asn Glu Gln Glu Ala Tyr Lys Leu Arg Ser Phe Val Asp Gln Pro
            85                  90                  95

-continued

```
Ala Phe Thr Asp Leu His Trp Gly Met Phe Val Pro Ala Ile Gln Gly
            100                 105                 110

Gln Gly Thr Asp Glu Gln Gln Lys Trp Leu Pro Leu Ala Tyr Gly
        115                 120                 125

Met Gln Ile Ile Gly Cys Tyr Ala Gln Thr Glu Leu Gly His Gly Ser
    130                 135                 140

Asn Val Gln Gly Leu Glu Thr Thr Ala Thr Phe Asp Pro Lys Thr Asp
145                 150                 155                 160

Glu Phe Val Ile His Ser Pro Thr Leu Thr Ser Ser Lys Trp Trp Pro
                165                 170                 175

Gly Gly Leu Gly Lys Ile Ser Thr His Ala Val Ala Tyr Ala Arg Leu
            180                 185                 190

Ile Ile Gly Gly Glu Asp His Gly Val His Gly Phe Ile Val Gln Leu
        195                 200                 205

Arg Ser Leu Asp Asp His Leu Pro Leu Pro Gly Ile Thr Ile Gly Asp
    210                 215                 220

Ile Gly Met Lys Phe Gly Asn Ala Ala Tyr Asn Thr Met Asp Asn Gly
225                 230                 235                 240

Val Leu Arg Phe Asp His Val Arg Ile Pro Arg Asn Gln Met Leu Met
                245                 250                 255

Arg Val Ser Gln Val Thr Arg Glu Gly Arg Tyr Val Ser Ser Asn Val
            260                 265                 270

Pro Arg Gln Leu Val Tyr Gly Thr Met Val Asn Val Arg Gln Lys Ile
        275                 280                 285

Val Ala Asp Ala Ser Val Ala Leu Ser Arg Ala Val Cys Ile Ala Thr
    290                 295                 300

Arg Tyr Ser Ala Val Arg Arg Gln Phe Gly Ser His Asn Gly Gly Leu
305                 310                 315                 320

Glu Thr Gln Val Ile Asp Tyr Lys Thr Gln Gln Ala Arg Leu Phe Pro
                325                 330                 335

Leu Leu Ala Ser Ala Tyr Ala Phe Arg Phe Val Gly Gly Trp Leu Lys
            340                 345                 350

Trp Leu Tyr Met Asp Val Thr Glu Arg Leu Gln Ala Asn Asp Phe Ser
        355                 360                 365

Thr Leu Pro Glu Ala His Ala Cys Thr Ala Gly Leu Lys Ser Leu Thr
    370                 375                 380

Thr Thr Ala Thr Ala Asp Gly Ile Glu Glu Cys Arg Lys Leu Cys Gly
385                 390                 395                 400

Gly His Gly Tyr Leu Cys Ser Ser Gly Leu Pro Glu Leu Phe Ala Val
                405                 410                 415

Tyr Val Pro Ala Cys Thr Tyr Glu Gly Asp Asn Val Val Leu Leu Leu
            420                 425                 430

Gln Val Ala Arg His Leu Met Lys Thr Val Ser Gln Leu Gly Ser Gly
        435                 440                 445

Asn Lys Pro Val Gly Thr Thr Ala Tyr Met Ala Arg Val Glu Gln Leu
    450                 455                 460

Met Gln Tyr His Ser Asp Val Glu Lys Ala Glu Asp Trp Leu Lys Pro
465                 470                 475                 480

Asn Val Val Leu Glu Ala Phe Glu Ala Arg Ala Ser Arg Met Ser Val
                485                 490                 495

Ala Cys Ala Gln Asn Leu Ser Lys Phe Ala Asn Pro Glu Glu Gly Phe
            500                 505                 510
```

```
Gln Glu Leu Ala Ala Asp Leu Val Asp Ala Val Ala His Cys Gln
            515                 520                 525

Leu Ile Val Val Ser Lys Phe Ile Glu Lys Leu Gln Gln Asp Ile Pro
530                 535                 540

Gly Lys Gly Val Lys Gln Leu Glu Val Leu Cys Ser Ile Tyr Ala
545                 550                 555                 560

Leu Phe Leu Leu His Lys His Leu Gly Asp Phe Leu Ser Thr Gly Cys
                565                 570                 575

Ile Asn Pro Lys Gln Gly Ser Leu Ala Ser Glu Gln Leu Arg Asn Leu
                580                 585                 590

Tyr Ser Gln Val Arg Pro Asn Ala Ile Ala Leu Val Asp Ala Phe Asn
        595                 600                 605

Tyr Thr Asp His Tyr Leu Gly Ser Ile Leu Gly Arg Tyr Asp Gly Asn
    610                 615                 620

Val Tyr Pro Lys Met Asn Glu Glu Ala Trp Lys Asp Pro Leu Asn Asp
625                 630                 635                 640

Ser Val Val Pro Asp Gly Phe Lys Glu Tyr Ile Gln Pro Met Leu Lys
                645                 650                 655

Gln Gln Leu Arg Asn Ala Arg Leu
                660

<210> SEQ ID NO 15
<211> LENGTH: 665
<212> TYPE: PRT
<213> ORGANISM: Glycine max

<400> SEQUENCE: 15

Met Glu Gly Met Val Asp His Leu Ala Phe Glu Arg Asn Asn Ser Gln
1               5                   10                  15

Phe Asp Val Asp Glu Met Lys Ile Val Trp Ala Gly Ser Arg His Ala
            20                  25                  30

Phe Glu Val Ser Asp Lys Met Ala Arg Leu Val Ala Ser Asp Pro Ala
        35                  40                  45

Phe Arg Lys Asp Asp Arg Val Val Leu Asp Arg Lys Ala Leu Phe Lys
    50                  55                  60

Asn Thr Leu Arg Lys Ala Ala Tyr Ala Trp Lys Arg Ile Ile Glu Leu
65                  70                  75                  80

Arg Leu Ser Glu Glu Glu Ala Ala Met Leu Arg Ser Phe Val Asp Gln
                85                  90                  95

Pro Ala Phe Thr Asp Leu His Trp Gly Met Phe Val Pro Ala Ile Lys
            100                 105                 110

Gly Gln Gly Thr Glu Glu Gln Lys Lys Trp Leu Pro Leu Ala His
        115                 120                 125

Lys Met Gln Ile Ile Gly Cys Tyr Ala Gln Thr Glu Leu Gly His Gly
    130                 135                 140

Ser Asn Val Gln Gly Leu Glu Thr Thr Ala Thr Phe Asp Pro Arg Thr
145                 150                 155                 160

Asp Glu Phe Val Ile His Ser Pro Thr Leu Thr Ser Ser Lys Trp Trp
                165                 170                 175

Pro Gly Gly Leu Gly Lys Val Ser Thr His Ala Val Val Tyr Ala Arg
            180                 185                 190

Leu Ile Thr Asp Gly Gln Asp His Gly Val His Gly Phe Ile Val Gln
        195                 200                 205

Leu Arg Ser Leu Asp Asp His Leu Pro Leu Pro Gly Ile Thr Val Gly
    210                 215                 220
```

-continued

Asp Ile Gly Met Lys Phe Gly Asn Gly Ala Tyr Asn Ser Met Asp Asn
225                 230                 235                 240

Gly Met Leu Arg Phe Asp His Val Arg Ile Pro Arg Asn Gln Met Leu
            245                 250                 255

Met Arg Val Ser Gln Val Thr Arg Glu Gly Lys Tyr Val Gln Ser Ser
        260                 265                 270

Val Pro Arg Gln Leu Val Tyr Gly Thr Met Val Tyr Val Arg Gln Thr
    275                 280                 285

Ile Val Ser Asp Ala Ser Val Ala Leu Ser Arg Ala Val Cys Ile Ala
290                 295                 300

Thr Arg Tyr Ser Ala Val Arg Arg Gln Phe Gly Ser Lys Glu Gly Gly
305                 310                 315                 320

Leu Glu Thr Gln Val Ile Asp Tyr Lys Thr Gln Gln Ala Arg Leu Phe
            325                 330                 335

Pro Leu Leu Ala Ser Ala Tyr Ala Phe Arg Phe Val Gly Glu Trp Leu
            340                 345                 350

Lys Trp Leu Tyr Met Asp Val Met Lys Arg Leu Gln Ala Ser Asp Phe
            355                 360                 365

Ser Thr Leu Pro Glu Ala His Ala Cys Thr Ala Gly Leu Lys Ser Leu
370                 375                 380

Thr Thr Ser Ala Thr Ala Asp Gly Ile Glu Glu Cys Arg Lys Leu Cys
385                 390                 395                 400

Gly Gly His Gly Tyr Leu Cys Ser Ser Gly Leu Pro Glu Leu Phe Ala
            405                 410                 415

Val Tyr Ile Pro Thr Cys Thr Tyr Glu Gly Asp Asn Thr Val Leu Leu
            420                 425                 430

Leu Gln Val Ala Arg His Leu Ile Lys Thr Ile Ser Gln Leu Gly Ser
            435                 440                 445

Arg Asn Lys Pro Val Gly Thr Thr Ser Tyr Ile Gly Arg Val Glu Gln
450                 455                 460

Leu Met Gln Tyr Arg Ser Asp Val Gln Lys Val Glu Asp Trp Leu Lys
465                 470                 475                 480

Pro Asn Ala Val Leu Gly Ala Phe Glu Ala Arg Ala Ala Lys Lys Val
            485                 490                 495

Val Ala Cys Ala Gln Asn Leu Ser Lys Phe Thr Asn Pro Glu Glu Gly
        500                 505                 510

Phe Gln Glu Leu Ser Val Asp Leu Val Glu Ala Ala Val Ala His Cys
            515                 520                 525

Gln Leu Ile Val Val Ser Lys Phe Ile Glu Lys Leu Gln Gln Asp Ile
        530                 535                 540

Pro Gly Lys Gly Val Lys Gln Gln Leu Glu Leu Leu Cys Ser Ile Tyr
545                 550                 555                 560

Ala Leu Phe Leu Leu His Lys His Leu Gly Asp Phe Leu Ala Thr Gly
            565                 570                 575

Cys Ile Thr Pro Lys Gln Gly Ser Leu Ala Asn Glu Leu Leu Arg Ser
            580                 585                 590

Leu Tyr Ser Gln Val Arg Pro Asn Ala Ile Ala Leu Val Asp Ala Phe
        595                 600                 605

Asn Tyr Thr Asp His Tyr Leu Gly Ser Val Leu Gly Arg Tyr Asp Gly
            610                 615                 620

Asp Val Tyr Pro Lys Leu Tyr Glu Glu Ala Trp Lys Asp Pro Leu Asn
625                 630                 635                 640

Asp Ser Val Val Pro Asp Gly Phe Gln Glu Tyr Ile Arg Pro Met Leu
                645                 650                 655

Lys Gln Gln Leu Arg Asn Ala Arg Leu
            660                 665

<210> SEQ ID NO 16
<211> LENGTH: 684
<212> TYPE: PRT
<213> ORGANISM: Beuvaria bassiana

<400> SEQUENCE: 16

Met Ser Phe Pro Asp Asn Leu Lys Pro Lys Glu Pro Ser Gly Ser Ser
1               5                   10                  15

Leu Leu Glu Lys Glu Arg Arg Gln Ser Pro Val Asp Val Asp Ala Leu
            20                  25                  30

Gly Lys His Ile Phe Ala Gly Thr Ser Phe Leu Glu Arg Gln Ala Arg
        35                  40                  45

Val Leu Arg Ala Ile Glu Gln Glu Pro Leu Phe Asp Lys Ser Arg Gln
50                  55                  60

Gln Gln Leu Ser Arg Val Glu Arg Val Lys Leu Gly Leu Ala Arg Gly
65                  70                  75                  80

Lys Leu Met Arg Arg Leu Gln Asp Arg His Gly Trp Asp Met Asp Asp
                85                  90                  95

Tyr His Met Ala Ala Tyr Leu Val Gly Glu Gln Ser Pro Tyr Arg Leu
            100                 105                 110

His Val Gly Met Phe Arg Thr Thr Val Glu Glu Gln Ser Ser Asp Ala
        115                 120                 125

Gln Arg Ala Tyr Trp Met Pro Arg Val Asn Gly Trp Glu Val Ser Gly
130                 135                 140

Ala Tyr Ser Gln Thr Glu Leu Gly His Gly Ser Asn Val Arg Gly Val
145                 150                 155                 160

Glu Leu Glu Ala Arg Trp Asp Pro Ala Ala Arg Glu Phe Val Val His
                165                 170                 175

Ser Pro Thr Leu Thr Ala Ala Lys Trp Trp Asn Gly Ser Leu Gly Arg
            180                 185                 190

Thr Ala Asn His Ala Ile Leu Met Ala Gln Leu Met Val Pro Asp Pro
        195                 200                 205

Lys Arg Glu Gly Gln Tyr Ile Ser His Gly Pro Gln Ala Phe Ile Ala
210                 215                 220

Gln Ile Arg Asp Leu Lys Thr Asn Leu Pro Leu Glu Gly Val Val Ile
225                 230                 235                 240

Gly Asp Ile Gly Val Lys Ile Gly Phe Thr Ser Met Asp Asn Gly Tyr
                245                 250                 255

Met Leu Phe Asn Gln Phe Arg Ile Pro His Ser Ala Leu Leu Ser Arg
            260                 265                 270

Tyr Val Gln Leu Asp Pro Glu Thr Gly Val Phe Ser Lys Ser Pro Asn
        275                 280                 285

Pro Ala Leu Ala Tyr Gly Thr Met Thr Ser Ile Arg Thr Met Leu Val
290                 295                 300

Glu Glu Ala Gly Thr His Leu Ala Arg Ala Val Thr Ile Ala Ile Arg
305                 310                 315                 320

Tyr Thr Ala Ile Arg Gln Gln Phe Arg Asp Lys Asp Ser Gln Asp Pro
                325                 330                 335

Ser Ser Ala Glu Leu Gln Val Leu Asp Tyr Pro Thr Val Gln Val Arg
            340                 345                 350

Leu Phe Pro Leu Leu Ala Ala Phe Ala Leu Gln Tyr Thr Gly Lys
        355                 360                 365

Val Met Arg Gln Asp Tyr Ala Lys Thr Arg Gly Glu Val Glu Lys Gly
        370                 375                 380

Asn Leu Glu Gly Leu Ala Val Met His Ser Asn Ser Ser Gly Leu Lys
385                 390                 395                 400

Ser Leu Ser Thr Glu Ile Thr Asn Ala Gly Ile Glu Thr Cys Arg Arg
                405                 410                 415

Ala Met Gly Gly His Gly Tyr Gly Ser Gly Ser Gly Leu Val Glu Met
                420                 425                 430

Gln Lys Asp Tyr Gln Ala Lys Pro Ile Leu Glu Gly Asp Asn Trp Met
        435                 440                 445

Ile Thr Gln Gln Thr Ser Ser Phe Leu Ile Lys Arg Met Thr Ala Ala
        450                 455                 460

Ala Lys Thr Arg Asn Glu Pro Pro Lys Asp Gln Ile Asp Ala Gln Leu
465                 470                 475                 480

Lys Thr Phe Leu His Gln Lys Asp Lys Gly Arg Thr Phe Asp Ile Leu
                485                 490                 495

Asn Ser Asp Ser Asp Ile Glu Glu Ser Phe Lys Trp Arg Ala Ser
                500                 505                 510

Met Thr Tyr Asp Ala Tyr Glu Ala Arg Val Ile Lys Lys Lys Arg His
        515                 520                 525

Asn Asp Leu Leu Ile Gln Phe His Lys Leu Ser His Ala His Ser Gln
        530                 535                 540

Ser Ile Met Val Ser Ser Phe Leu Thr Thr Leu Thr Ser Ser Asn Asp
545                 550                 555                 560

Leu Ala His Glu Thr Lys Glu Ile Val Phe Asp Leu Tyr Arg Leu Phe
                565                 570                 575

Ala Tyr Thr Thr Ile Gln Ala Glu Ser Tyr Glu Phe Leu Arg Cys Gly
                580                 585                 590

Ala Ala Ser Ser Lys Asp Leu Asp Ala Leu Pro Glu Arg Ile Gln Ala
        595                 600                 605

Leu Leu Thr Arg Ile Arg Pro His Ala Val Lys Leu Val Asp Ala Trp
        610                 615                 620

Lys Ile Pro Asp Tyr Leu Leu Asp Ser Ala Leu Gly Arg Tyr Asp Gly
625                 630                 635                 640

Asn Val Tyr Glu Asp Leu Phe Asn Arg Ala His Arg Leu Asn Pro Leu
                645                 650                 655

Asn Asp Ile Val Phe Asn Pro Asp Tyr Lys Asp Glu Ile Val Lys
                660                 665                 670

Gly Ser Gly Glu Arg Lys Pro Leu Ser Pro Lys Leu
        675                 680

<210> SEQ ID NO 17
<211> LENGTH: 696
<212> TYPE: PRT
<213> ORGANISM: Aspergillus nidulans

<400> SEQUENCE: 17

Met Pro Asn Pro Pro Ala Trp Val Gln Ala Leu Lys Pro Ala Ser
1               5                   10                  15

Pro Gln Gly Thr Glu Leu Leu Thr Gln Glu Arg Ala Gln Ser Asn Ile
                20                  25                  30

Asp Val Asp Thr Leu Gly Asp Leu Leu His Thr Lys Glu Ala Leu Lys

```
            35                  40                  45
Lys Gln Asp Glu Ile Leu Ser Val Leu Lys Ser Glu Lys Val Phe Asp
 50                  55                  60
Lys Ser Arg Asn His Val Leu Gly Arg Thr Glu Lys Ile Gln Leu Ala
 65                  70                  75                  80
Leu Ala Arg Gly Lys Arg Leu Gln Gln Leu Lys Lys Ala His Asn Trp
                     85                  90                  95
Ser Asp Glu Asp Val His Val Ala Asn Asp Leu Val Ser Glu Pro Thr
                    100                 105                 110
Pro Tyr Gly Leu His Ala Ser Met Phe Leu Val Thr Leu Arg Glu Gln
                    115                 120                 125
Gly Thr Pro Glu Gln His Lys Leu Phe Tyr Glu Arg Ala Arg Asn Tyr
                    130                 135                 140
Glu Ile Ile Gly Cys Tyr Ala Gln Thr Glu Leu Gly His Gly Ser Asn
145                 150                 155                 160
Val Arg Gly Leu Glu Thr Thr Ala Thr Trp Asp Pro Ser Asp Gln Thr
                    165                 170                 175
Phe Ile Ile His Ser Pro Thr Leu Thr Ala Ser Lys Trp Trp Ile Gly
                    180                 185                 190
Ser Leu Gly Arg Thr Ala Asn His Ala Val Val Met Ala Gln Leu Tyr
                    195                 200                 205
Ile Gly Gly Lys Asn Tyr Gly Pro His Pro Phe Val Val Gln Ile Arg
                    210                 215                 220
Asp Met Glu Thr His Gln Pro Leu Glu Asn Val Tyr Val Gly Asp Ile
225                 230                 235                 240
Gly Pro Lys Phe Gly Tyr Asn Thr Met Asp Asn Gly Phe Leu Leu Phe
                    245                 250                 255
Asn Lys Leu Lys Ile Pro His Val Asn Met Leu Ala Arg Phe Ala Gln
                    260                 265                 270
Val Asp Lys Ala Thr Asn Lys Tyr Ile Arg Pro Ala Ser Pro Ser Leu
                    275                 280                 285
Met Tyr Gly Thr Met Thr Trp Val Arg Ser Asn Ile Val Leu Gln Ala
                    290                 295                 300
Gly Gly Val Leu Ala Arg Gly Val Thr Ile Ala Val Arg Tyr Cys Ala
305                 310                 315                 320
Val Arg Arg Gln Phe Gln Asp Arg Asp Ala Lys Ala Asn Ala Glu Glu
                    325                 330                 335
Asn Gln Val Leu Asn Tyr Lys Met Val Gln Ile Arg Leu Leu Pro Leu
                    340                 345                 350
Leu Ala Ala Met Tyr Ala Leu His Phe Thr Gly Arg Gly Met Met Arg
                    355                 360                 365
Leu Tyr Glu Glu Asn Gln Glu Arg Met Lys Ala Ala Gln Ala Asp
                    370                 375                 380
Gln Glu Lys Arg Gly Ala Gly Pro Glu Gln Leu Arg Ala Gly Ser Asp
385                 390                 395                 400
Leu Leu Ala Asp Leu His Ala Thr Ser Cys Gly Leu Lys Ala Leu Ala
                    405                 410                 415
Ser Thr Thr Ala Gly Glu Gly Leu Glu Val Cys Arg Arg Ala Cys Gly
                    420                 425                 430
Gly His Gly Tyr Ser Asn Tyr Ser Gly Ile Gly Pro Trp Tyr Ala Asp
                    435                 440                 445
Tyr Leu Pro Thr Leu Thr Trp Glu Gly Asp Asn Tyr Met Leu Thr Gln
                    450                 455                 460
```

```
Gln Val Ala Arg Tyr Leu Leu Lys Ser Ala Arg Ala Val Leu Ala Gly
465                 470                 475                 480

Lys Gly Thr Ala Asn Asp Thr Ser Arg Ile Leu Gln Ala Tyr Leu Ala
                485                 490                 495

Arg Arg Asp Lys Gly Ala Ser Phe Asp Ile Leu Gly Asn Asp Ala Asp
            500                 505                 510

Ile Val Ala Ala Phe Ala Trp Arg Thr Ala His Leu Thr Phe Glu Thr
        515                 520                 525

Leu Lys Tyr Arg Asp Val Glu Lys Arg Ser Trp Asn Ser Leu Leu Ile
    530                 535                 540

Asn Phe Trp Arg Leu Ser Thr Ala Leu Ser Gln Tyr Leu Val Val Lys
545                 550                 555                 560

Asn Phe Tyr Glu Ala Val Asn Ser Pro Glu Ile Arg Ser Ser Leu Asp
                565                 570                 575

Lys Asp Thr Ala Ser Thr Leu Arg Ser Leu Phe Arg Leu His Ala Leu
            580                 585                 590

His Thr Leu Asp Arg Glu Ala Ser Glu Phe Phe Ser Ser Ala Ala Val
        595                 600                 605

Thr Val Arg Gln Ile Gly Leu Thr Gln Thr Ser Glu Val Pro Lys Leu
    610                 615                 620

Leu Asp Glu Ile Arg Pro His Ala Val Arg Leu Val Asp Ser Trp Lys
625                 630                 635                 640

Ile Pro Asp Trp Gln Leu Asp Ser Ala Leu Gly Arg Ser Asp Gly Asp
                645                 650                 655

Val Tyr Pro Asp Leu Phe Lys Arg Ala Ser Met Gln Asn Pro Val Asn
            660                 665                 670

Asp Leu Val Phe Asp Pro Tyr Pro Trp Asn Glu Asn Val Leu Lys Asn
        675                 680                 685

Ala Gly Glu Ile Lys Ser Lys Leu
    690                 695

<210> SEQ ID NO 18
<211> LENGTH: 646
<212> TYPE: PRT
<213> ORGANISM: Arabidopsis thaliana

<400> SEQUENCE: 18

Met Glu Ser Arg Arg Glu Lys Asn Pro Met Thr Glu Glu Glu Ser Asp
1               5                   10                  15

Gly Leu Ile Ala Ala Arg Arg Ile Gln Arg Leu Ser Leu His Leu Ser
            20                  25                  30

Pro Ser Leu Thr Pro Ser Pro Ser Leu Pro Leu Val Gln Thr Glu Thr
        35                  40                  45

Cys Ser Ala Arg Ser Lys Lys Leu Asp Val Asn Gly Glu Ala Leu Ser
    50                  55                  60

Leu Tyr Met Arg Gly Lys His Ile Asp Ile Gln Glu Lys Ile Phe Asp
65                  70                  75                  80

Phe Phe Asn Ser Arg Pro Asp Leu Gln Thr Pro Ile Glu Ile Ser Lys
                85                  90                  95

Asp Asp His Arg Glu Leu Cys Met Asn Gln Leu Ile Gly Leu Val Arg
            100                 105                 110

Glu Ala Gly Val Arg Pro Phe Arg Tyr Val Ala Asp Asp Pro Glu Lys
        115                 120                 125

Tyr Phe Ala Ile Met Glu Ala Val Gly Ser Val Asp Met Ser Leu Gly
```

-continued

```
            130                 135                 140
Ile Lys Met Gly Val Gln Tyr Ser Leu Trp Gly Ser Val Ile Asn
145                 150                 155                 160

Leu Gly Thr Lys Lys His Arg Asp Lys Tyr Phe Asp Gly Ile Asp Asn
            165                 170                 175

Leu Asp Tyr Thr Gly Cys Phe Ala Met Thr Glu Leu His His Gly Ser
                180                 185                 190

Asn Val Gln Gly Leu Gln Thr Thr Ala Thr Phe Asp Pro Leu Lys Asp
            195                 200                 205

Glu Phe Val Ile Asp Thr Pro Asn Asp Gly Ala Ile Lys Trp Trp Ile
210                 215                 220

Gly Asn Ala Ala Val His Gly Lys Phe Ala Thr Val Phe Ala Arg Leu
225                 230                 235                 240

Ile Leu Pro Thr His Asp Ser Lys Gly Val Ser Asp Met Gly Val His
                245                 250                 255

Ala Phe Ile Val Pro Ile Arg Asp Met Lys Thr His Gln Thr Leu Pro
                260                 265                 270

Gly Val Glu Ile Gln Asp Cys Gly His Lys Val Gly Leu Asn Gly Val
            275                 280                 285

Asp Asn Gly Ala Leu Arg Phe Arg Ser Val Arg Ile Pro Arg Asp Asn
            290                 295                 300

Leu Leu Asn Arg Phe Gly Asp Val Ser Arg Asp Gly Thr Tyr Thr Ser
305                 310                 315                 320

Ser Leu Pro Thr Ile Asn Lys Arg Phe Gly Ala Thr Leu Gly Glu Leu
                325                 330                 335

Val Gly Gly Arg Val Gly Leu Ala Tyr Ala Ser Val Gly Val Leu Lys
            340                 345                 350

Ile Ser Ala Thr Ile Ala Ile Arg Tyr Ser Leu Leu Arg Gln Gln Phe
            355                 360                 365

Gly Pro Pro Lys Gln Pro Glu Val Ser Ile Leu Asp Tyr Gln Ser Gln
370                 375                 380

Gln His Lys Leu Met Pro Met Leu Ala Ser Thr Tyr Ala Tyr His Phe
385                 390                 395                 400

Ala Thr Val Tyr Leu Val Glu Lys Tyr Ser Glu Met Lys Lys Thr His
                405                 410                 415

Asp Glu Gln Leu Val Ala Asp Val His Ala Leu Ser Ala Gly Leu Lys
            420                 425                 430

Ser Tyr Val Thr Ser Tyr Thr Ala Lys Ala Leu Ser Val Cys Arg Glu
            435                 440                 445

Ala Cys Gly Gly His Gly Tyr Ala Ala Val Asn Arg Phe Gly Ser Leu
450                 455                 460

Arg Asn Asp His Asp Ile Phe Gln Thr Phe Glu Gly Asp Asn Thr Val
465                 470                 475                 480

Leu Leu Gln Gln Val Ala Ala Asp Leu Leu Lys Arg Tyr Lys Glu Lys
                485                 490                 495

Phe Gln Gly Gly Thr Leu Thr Val Thr Trp Ser Tyr Leu Arg Glu Ser
            500                 505                 510

Met Asn Thr Tyr Leu Ser Gln Pro Asn Pro Val Thr Ala Arg Trp Glu
            515                 520                 525

Gly Glu Asp His Leu Arg Asp Pro Lys Phe Gln Leu Asp Ala Phe Arg
530                 535                 540

Tyr Arg Thr Ser Arg Leu Leu Gln Asn Val Ala Ala Arg Leu Gln Lys
545                 550                 555                 560
```

His Ser Lys Thr Leu Gly Gly Phe Gly Ala Trp Asn Arg Cys Leu Asn
            565                 570                 575

His Leu Leu Thr Leu Ala Glu Ser His Ile Glu Thr Val Ile Leu Ala
        580                 585                 590

Lys Phe Ile Glu Ala Val Lys Asn Cys Pro Asp Pro Ser Ala Lys Ala
            595                 600                 605

Ala Leu Lys Leu Ala Cys Asp Leu Tyr Ala Leu Asp Arg Ile Trp Lys
        610                 615                 620

Asp Ile Gly Thr Tyr Arg Asn Val Asp Tyr Val Ala Pro Asn Lys Ala
625                 630                 635                 640

Lys Val Cys Phe Leu Val
            645

<210> SEQ ID NO 19
<211> LENGTH: 692
<212> TYPE: PRT
<213> ORGANISM: Arabidopsis thaliana

<400> SEQUENCE: 19

Met Glu Ser Arg Arg Glu Lys Asn Pro Met Thr Glu Glu Ser Asp
1               5                   10                  15

Gly Leu Ile Ala Ala Arg Arg Ile Gln Arg Leu Ser Leu His Leu Ser
            20                  25                  30

Pro Ser Leu Thr Pro Ser Pro Ser Leu Pro Leu Val Gln Thr Glu Thr
        35                  40                  45

Cys Ser Ala Arg Ser Lys Lys Leu Asp Val Asn Gly Glu Ala Leu Ser
    50                  55                  60

Leu Tyr Met Arg Gly Lys His Ile Asp Ile Gln Glu Lys Ile Phe Asp
65                  70                  75                  80

Phe Phe Asn Ser Arg Pro Asp Leu Gln Thr Pro Ile Glu Ile Ser Lys
                85                  90                  95

Asp Asp His Arg Glu Leu Cys Met Asn Gln Leu Ile Gly Leu Val Arg
            100                 105                 110

Glu Ala Gly Val Arg Pro Phe Arg Tyr Val Ala Asp Asp Pro Glu Lys
        115                 120                 125

Tyr Phe Ala Ile Met Glu Ala Val Gly Ser Val Asp Met Ser Leu Gly
    130                 135                 140

Ile Lys Met Gly Val Gln Tyr Ser Leu Trp Gly Gly Ser Val Ile Asn
145                 150                 155                 160

Leu Gly Thr Lys Lys His Arg Asp Lys Tyr Phe Asp Gly Ile Asp Asn
                165                 170                 175

Leu Asp Tyr Thr Gly Cys Phe Ala Met Thr Glu Leu His His Gly Ser
            180                 185                 190

Asn Val Gln Gly Leu Gln Thr Thr Ala Thr Phe Asp Pro Leu Lys Asp
        195                 200                 205

Glu Phe Val Ile Asp Thr Pro Asn Asp Gly Ala Ile Lys Trp Trp Ile
    210                 215                 220

Gly Asn Ala Ala Val His Gly Lys Phe Ala Thr Val Phe Ala Arg Leu
225                 230                 235                 240

Ile Leu Pro Thr His Asp Ser Lys Gly Val Ser Asp Met Gly Val His
                245                 250                 255

Ala Phe Ile Val Pro Ile Arg Asp Met Lys Thr His Gln Thr Leu Pro
            260                 265                 270

Gly Val Glu Ile Gln Asp Cys Gly His Lys Val Gly Leu Asn Gly Val

```
            275                 280                 285
Asp Asn Gly Ala Leu Arg Phe Arg Ser Val Arg Ile Pro Arg Asp Asn
    290                 295                 300
Leu Leu Asn Arg Phe Gly Asp Val Ser Arg Asp Gly Thr Tyr Thr Ser
305                 310                 315                 320
Ser Leu Pro Thr Ile Asn Lys Arg Phe Gly Ala Thr Leu Gly Glu Leu
                325                 330                 335
Val Gly Gly Arg Val Gly Leu Ala Tyr Ala Ser Val Gly Val Leu Lys
            340                 345                 350
Ile Ser Ala Thr Ile Ala Ile Arg Tyr Ser Leu Leu Arg Gln Gln Phe
            355                 360                 365
Gly Pro Pro Lys Gln Pro Glu Val Ser Ile Leu Asp Tyr Gln Ser Gln
            370                 375                 380
Gln His Lys Leu Met Pro Met Leu Ala Ser Thr Tyr Ala Tyr His Phe
385                 390                 395                 400
Ala Thr Val Tyr Leu Val Glu Lys Tyr Ser Glu Met Lys Lys Thr His
                405                 410                 415
Asp Glu Gln Leu Val Ala Asp Val His Ala Leu Ser Ala Gly Leu Lys
            420                 425                 430
Ser Tyr Val Thr Ser Tyr Thr Ala Lys Ala Leu Ser Val Cys Arg Glu
            435                 440                 445
Ala Cys Gly Gly His Gly Tyr Ala Ala Val Asn Arg Phe Gly Ser Leu
450                 455                 460
Arg Asn Asp His Asp Ile Phe Gln Thr Phe Glu Gly Asp Asn Thr Val
465                 470                 475                 480
Leu Leu Gln Gln Val Ala Ala Asp Leu Leu Lys Arg Tyr Lys Glu Lys
                485                 490                 495
Phe Gln Gly Gly Thr Leu Thr Val Thr Trp Ser Tyr Leu Arg Glu Ser
            500                 505                 510
Met Asn Thr Tyr Leu Ser Gln Pro Asn Pro Val Thr Ala Arg Trp Glu
            515                 520                 525
Gly Glu Asp His Leu Arg Asp Pro Lys Phe Gln Leu Asp Ala Phe Arg
            530                 535                 540
Tyr Arg Thr Ser Arg Leu Leu Gln Asn Val Ala Ala Arg Leu Gln Lys
545                 550                 555                 560
His Ser Lys Thr Leu Gly Gly Phe Gly Ala Trp Asn Arg Cys Leu Asn
                565                 570                 575
His Leu Leu Thr Leu Ala Glu Ser His Ile Glu Thr Val Ile Leu Ala
            580                 585                 590
Lys Phe Ile Glu Ala Val Lys Asn Cys Pro Asp Pro Ser Ala Lys Ala
            595                 600                 605
Ala Leu Lys Leu Ala Cys Asp Leu Tyr Ala Leu Asp Arg Ile Trp Lys
            610                 615                 620
Asp Ile Gly Thr Tyr Arg Asn Val Asp Tyr Val Ala Pro Asn Lys Ala
625                 630                 635                 640
Lys Ala Ile His Lys Leu Thr Glu Tyr Leu Ser Phe Gln Val Arg Asn
                645                 650                 655
Val Ala Lys Glu Leu Val Asp Ala Phe Glu Leu Pro Asp His Val Thr
            660                 665                 670
Arg Ala Pro Ile Ala Met Gln Ser Asp Ala Tyr Ser Gln Tyr Thr Gln
            675                 680                 685
Val Val Gly Phe
    690
```

```
<210> SEQ ID NO 20
<211> LENGTH: 711
<212> TYPE: PRT
<213> ORGANISM: Candida viswanathii
<220> FEATURE:
<221> NAME/KEY: VARIANT
<222> LOCATION: 711
<223> OTHER INFORMATION: Xaa = Any Amino Acid
<220> FEATURE:
<221> NAME/KEY: VARIANT
<222> LOCATION: 711
<223> OTHER INFORMATION: Xaa = Any Amino Acid

<400> SEQUENCE: 20

Met Thr Phe Thr Lys Lys Asn Val Ser Val Ser Gln Gly Pro Asp Pro
1               5                   10                  15

Arg Thr Ser Ile Gln Thr Glu Arg Ala Asn Ser Lys Phe Asp Pro Val
            20                  25                  30

Thr Met Asn Tyr Phe Leu Glu Gly Ser Lys Glu Arg Ser Glu Leu Met
        35                  40                  45

Lys Ser Leu Ala Gln Gln Ile Glu Arg Asp Pro Ile Leu Phe Thr Asp
    50                  55                  60

Gly Ser Tyr Tyr Asp Leu Thr Lys Asp Gln Gln Arg Glu Leu Thr Val
65                  70                  75                  80

Leu Lys Ile Asn Arg Leu Ser Arg Tyr Arg Glu Gly Asp Ser Val Asp
                85                  90                  95

Thr Phe Asn Lys Arg Leu Ser Ile Met Gly Val Val Asp Pro Gln Val
            100                 105                 110

Ala Thr Arg Ile Gly Val Asn Leu Gly Leu Phe Leu Ser Cys Ile Ser
        115                 120                 125

Gly Asn Gly Thr Ala Glu Gln Phe Lys Tyr Trp Ala Ile Asp Lys Gly
130                 135                 140

Thr His Asn Ile Gln Gly Leu Tyr Gly Cys Phe Gly Met Thr Glu Leu
145                 150                 155                 160

Gly His Gly Ser Asn Val Ala Gly Val Glu Thr Thr Ala Thr Phe Asp
                165                 170                 175

Lys Glu Thr Asp Glu Phe Val Ile Asn Thr Pro His Ile Gly Ala Thr
            180                 185                 190

Lys Trp Trp Ile Gly Gly Ala Ala His Ser Ala Thr His Cys Ser Val
        195                 200                 205

Tyr Ala Arg Leu Val Val Asp Gly Lys Asp Tyr Gly Val Lys Thr Phe
    210                 215                 220

Val Val Pro Leu Arg Asp Ser Asn His Asp Leu Met Pro Gly Val Thr
225                 230                 235                 240

Val Gly Asp Ile Gly Ala Lys Met Gly Arg Asp Gly Ile Asp Asn Gly
                245                 250                 255

Trp Ile Gln Phe Ser Asn Val Arg Ile Pro Arg Phe Phe Met Leu Gln
            260                 265                 270

Lys Phe Cys Lys Val Ser Ala Glu Gly Glu Val Val Leu Pro Pro Leu
        275                 280                 285

Glu Gln Leu Ser Tyr Ser Ala Leu Leu Gly Gly Arg Val Met Met Val
    290                 295                 300

Leu Asp Ser Tyr Arg Met Leu Ala Arg Val Ser Thr Ile Ala Leu Arg
305                 310                 315                 320

Tyr Ala Ile Gly Arg Arg Gln Phe Lys Gly Asp Asn Val Asp Gln Asn
                325                 330                 335
```

```
Asp Pro Asn Ala Leu Glu Thr Gln Leu Ile Asp Tyr Pro Leu His Gln
            340                 345                 350

Lys Arg Leu Phe Pro Tyr Leu Ala Ala Tyr Val Val Ser Thr Gly
            355                 360                 365

Ala Leu Lys Val Glu His Thr Ile Gln Ser Thr Leu Ala Thr Leu Asp
370                 375                 380

Ala Ala Val Glu Asn Asn Asp Thr Thr Ala Ile Phe Lys Ser Ile Asp
385                 390                 395                 400

Asp Met Lys Ser Leu Phe Ile Asp Ser Gly Ser Leu Lys Ala Thr Thr
                405                 410                 415

Thr Trp Leu Ala Ala Glu Ala Ile Asp Gln Cys Arg Gln Ala Cys Gly
            420                 425                 430

Gly His Gly Tyr Ser Ser Tyr Asn Gly Phe Ala Lys Ala Phe Asn Asp
            435                 440                 445

Trp Val Val Gln Cys Thr Trp Glu Gly Asp Asn Asn Val Leu Ser Leu
            450                 455                 460

Ser Val Gly Lys Pro Ile Ile Lys Gln Ile Ile Gly Ile Glu Asp Asn
465                 470                 475                 480

Gly Lys Thr Val Arg Gly Ser Thr Ala Phe Leu Asn Gln Val Lys Asp
                485                 490                 495

Phe Thr Gly Ser Asn Ala Ser Lys Val Val Leu Asn Asn Thr Ser Asp
            500                 505                 510

Leu Asn Asp Ile Asn Lys Val Ile Lys Ser Ile Glu Val Ala Ile Ile
                515                 520                 525

Arg Leu Ala His Glu Ala Ala Ile Ser Val Arg Lys Glu Ser Leu Asp
            530                 535                 540

Phe Ala Gly Ala Glu Leu Val Gln Ile Ser Lys Leu Lys Ala His His
545                 550                 555                 560

Tyr Leu Leu Thr Glu Phe Val Lys Arg Val Gly Glu Phe Glu His Lys
                565                 570                 575

Glu Leu Val Pro Phe Leu Asn Thr Ile Gly Arg Leu Tyr Ser Ala Thr
            580                 585                 590

Val Val Leu Asp Lys Phe Ala Gly Val Phe Leu Thr Phe Asn Val Ala
            595                 600                 605

Ser Pro Gln Ala Ile Thr Asp Leu Ala Ser Thr Gln Ile Pro Lys Leu
            610                 615                 620

Cys Ala Glu Val Arg Pro Asn Val Val Ala Tyr Thr Asp Ser Phe Gln
625                 630                 635                 640

Gln Ser Asp Met Val Ile Asn Ser Ala Ile Gly Lys Tyr Asp Gly Asp
                645                 650                 655

Val Tyr Glu Asn Tyr Phe Asp Leu Val Lys Gln Leu Asn Pro Pro Lys
            660                 665                 670

Asn Thr Lys Ala Pro Tyr Thr Ala Ala Leu Glu Gly Met Leu Asn Arg
            675                 680                 685

Pro Ser Leu Glu Ala Arg Glu Arg Tyr Glu Lys Ser Asp Glu Thr Ala
            690                 695                 700

Ala Ile Leu Ser Lys Pro Xaa
705                 710

<210> SEQ ID NO 21
<211> LENGTH: 662
<212> TYPE: PRT
<213> ORGANISM: Candida viswanathii
```

<400> SEQUENCE: 21

```
Met Pro Thr Glu Leu Gln Lys Glu Arg Glu Leu Thr Lys Phe Asn Pro
1               5                   10                  15
Lys Glu Leu Asn Tyr Phe Leu Glu Gly Ser Gln Glu Arg Ser Glu Ile
            20                  25                  30
Ile Ser Asn Met Val Glu Gln Met Gln Lys Asp Pro Ile Leu Lys Val
        35                  40                  45
Asp Ala Ser Tyr Tyr Asn Leu Thr Lys Asp Gln Gln Arg Glu Val Thr
    50                  55                  60
Ala Lys Lys Ile Ala Arg Leu Ser Arg Tyr Phe Glu His Glu Tyr Pro
65                  70                  75                  80
Asp Gln Gln Ala Gln Arg Leu Ser Ile Leu Gly Val Phe Asp Pro Gln
                85                  90                  95
Val Phe Thr Arg Ile Gly Val Asn Leu Gly Leu Phe Val Ser Cys Val
            100                 105                 110
Arg Gly Asn Gly Thr Asn Ser Gln Phe Phe Tyr Trp Thr Ile Asn Lys
        115                 120                 125
Gly Ile Asp Lys Leu Arg Gly Ile Tyr Gly Cys Phe Gly Met Thr Glu
    130                 135                 140
Leu Ala His Gly Ser Asn Val Gln Gly Ile Glu Thr Thr Ala Thr Phe
145                 150                 155                 160
Asp Glu Asp Thr Asp Glu Phe Val Ile Asn Thr Pro His Ile Gly Ala
                165                 170                 175
Thr Lys Trp Trp Ile Gly Gly Ala Ala His Ser Ala Thr His Cys Ser
            180                 185                 190
Val Tyr Ala Arg Leu Lys Val Lys Gly Lys Asp Tyr Gly Val Lys Thr
        195                 200                 205
Phe Val Val Pro Leu Arg Asp Ser Asn His Asp Leu Glu Pro Gly Val
    210                 215                 220
Thr Val Gly Asp Ile Gly Ala Lys Met Gly Arg Asp Gly Ile Asp Asn
225                 230                 235                 240
Gly Trp Ile Gln Phe Ser Asn Val Arg Ile Pro Arg Phe Phe Met Leu
                245                 250                 255
Gln Lys Tyr Cys Lys Val Ser Arg Ser Gly Glu Val Thr Met Pro Pro
            260                 265                 270
Ser Glu Gln Leu Ser Tyr Ser Ala Leu Ile Gly Gly Arg Val Thr Met
        275                 280                 285
Met Met Asp Ser Tyr Arg Met Thr Ser Arg Phe Ile Thr Ile Ala Leu
    290                 295                 300
Arg Tyr Ala Ile His Arg Arg Gln Phe Lys Lys Lys Asp Thr Asp Thr
305                 310                 315                 320
Ile Glu Thr Lys Leu Ile Asp Tyr Pro Leu His Gln Lys Arg Leu Phe
                325                 330                 335
Pro Phe Leu Ala Ala Ala Tyr Leu Phe Ser Gln Gly Ala Leu Tyr Leu
            340                 345                 350
Glu Gln Thr Met Asn Ala Thr Asn Asp Lys Leu Asp Glu Ala Val Ser
        355                 360                 365
Ala Gly Glu Lys Glu Ala Ile Asp Ala Ala Ile Val Glu Ser Lys Lys
    370                 375                 380
Leu Phe Val Ala Ser Gly Cys Leu Lys Ser Thr Cys Thr Trp Leu Thr
385                 390                 395                 400
Ala Glu Ala Ile Asp Glu Ala Arg Gln Ala Cys Gly Gly His Gly Tyr
                405                 410                 415
```

```
Ser Ser Tyr Asn Gly Phe Gly Lys Ala Tyr Ser Asp Trp Val Val Gln
            420                 425                 430

Cys Thr Trp Glu Gly Asp Asn Asn Ile Leu Ala Met Asn Val Ala Lys
            435                 440                 445

Pro Met Val Arg Asp Leu Leu Lys Glu Pro Glu Gln Lys Gly Leu Val
450                 455                 460

Leu Ser Ser Val Ala Asp Leu Asp Pro Ala Lys Leu Val Lys Ala
465                 470                 475                 480

Phe Asp His Ala Leu Ser Gly Leu Ala Arg Asp Ile Gly Ala Val Ala
                485                 490                 495

Glu Asp Lys Gly Phe Asp Ile Thr Gly Pro Ser Leu Val Leu Val Ser
            500                 505                 510

Lys Leu Asn Ala His Arg Phe Leu Ile Asp Gly Phe Phe Lys Arg Ile
            515                 520                 525

Thr Pro Glu Trp Ser Glu Val Leu Arg Pro Leu Gly Phe Leu Tyr Ala
            530                 535                 540

Asp Trp Ile Leu Thr Asn Phe Gly Ala Thr Phe Leu Gln Tyr Gly Ile
545                 550                 555                 560

Ile Thr Pro Asp Val Ser Arg Lys Ile Ser Ser Glu His Phe Pro Ala
                565                 570                 575

Leu Cys Ala Lys Val Arg Pro Asn Val Val Gly Leu Thr Asp Gly Phe
            580                 585                 590

Asn Leu Thr Asp Met Met Thr Asn Ala Ala Ile Gly Arg Tyr Asp Gly
            595                 600                 605

Asn Val Tyr Glu His Tyr Phe Glu Thr Val Lys Ala Leu Asn Pro Pro
            610                 615                 620

Glu Asn Thr Lys Ala Pro Tyr Ser Lys Ala Leu Glu Asp Met Leu Asn
625                 630                 635                 640

Arg Pro Asp Leu Glu Val Arg Glu Arg Gly Lys Ser Glu Glu Ala
                645                 650                 655

Ala Glu Ile Leu Ser Ser
            660

<210> SEQ ID NO 22
<211> LENGTH: 689
<212> TYPE: PRT
<213> ORGANISM: Yarrowia lipolytica

<400> SEQUENCE: 22

Met Thr Thr Asn Thr Phe Thr Asp Pro Pro Val Glu Met Ala Lys Glu
1               5                   10                  15

Arg Gly Lys Thr Gln Phe Thr Val Arg Asp Val Thr Asn Phe Leu Asn
            20                  25                  30

Gly Gly Glu Glu Thr Gln Ile Val Glu Lys Ile Met Ser Ser Ile
            35                  40                  45

Glu Arg Asp Pro Val Leu Ser Val Thr Ala Asp Tyr Asp Cys Asn Leu
        50                  55                  60

Gln Gln Ala Arg Lys Gln Thr Met Glu Arg Val Ala Ala Leu Ser Pro
65                  70                  75                  80

Tyr Leu Val Thr Asp Thr Glu Lys Leu Ser Leu Trp Arg Ala Gln Leu
                85                  90                  95

His Gly Met Val Asp Met Ser Arg Thr Arg Leu Ser Ile His Asn
            100                 105                 110

Asn Leu Phe Ile Gly Ser Ile Arg Gly Ser Gly Thr Pro Glu Gln Phe
```

```
            115                 120                 125
Lys Tyr Trp Val Lys Lys Gly Ala Val Ala Val Lys Gln Phe Tyr Gly
130                 135                 140

Cys Phe Ala Met Thr Glu Leu Gly His Gly Ser Asn Leu Lys Gly Leu
145                 150                 155                 160

Glu Thr Thr Ala Thr Tyr Asp Gln Asp Ser Asp Gln Phe Ile Ile Asn
                165                 170                 175

Thr Pro His Ile Gly Ala Thr Lys Trp Trp Ile Gly Ala Ala His
            180                 185                 190

Thr Ser Thr His Cys Val Cys Phe Ala Lys Leu Ile Val His Gly Lys
            195                 200                 205

Asp Tyr Gly Thr Arg Asn Phe Val Pro Leu Arg Asn Val His Asp
210                 215                 220

His Ser Leu Lys Val Gly Val Ser Ile Gly Asp Ile Gly Lys Lys Met
225                 230                 235                 240

Gly Arg Asp Gly Val Asp Asn Gly Trp Ile Gln Phe Thr Asn Val Arg
                245                 250                 255

Ile Pro Arg Gln Asn Met Leu Met Arg Tyr Ala Lys Val Ser Asp Thr
            260                 265                 270

Gly Val Val Thr Lys Pro Ala Leu Asp Gln Leu Thr Tyr Gly Ala Leu
            275                 280                 285

Ile Arg Gly Arg Val Ser Met Ile Ala Asp Ser Phe His Val Ser Lys
290                 295                 300

Arg Phe Leu Thr Ile Ala Leu Arg Tyr Ala Cys Val Arg Arg Gln Phe
305                 310                 315                 320

Gly Thr Ser Gly Asp Thr Lys Glu Thr Lys Ile Ile Asp Tyr Pro Tyr
                325                 330                 335

His Gln Arg Arg Leu Leu Pro Leu Leu Ala Tyr Cys Tyr Ala Met Lys
            340                 345                 350

Met Gly Ala Asp Glu Ala Gln Lys Thr Trp Ile Glu Thr Thr Asp Arg
            355                 360                 365

Ile Leu Ala Leu Asn Pro Asn Asp Pro Ala Gln Lys Asn Asp Leu Glu
370                 375                 380

Lys Ala Val Thr Asp Thr Lys Glu Leu Phe Ala Ala Ser Ala Gly Met
385                 390                 395                 400

Lys Ala Phe Thr Thr Trp Gly Cys Ala Lys Ile Ile Asp Glu Cys Arg
                405                 410                 415

Gln Ala Cys Gly Gly His Gly Tyr Ser Gly Tyr Asn Gly Phe Gly Gln
            420                 425                 430

Gly Tyr Ala Asp Trp Val Val Gln Cys Thr Trp Glu Gly Asp Asn Asn
            435                 440                 445

Val Leu Cys Leu Ser Met Gly Arg Gly Leu Val Gln Ser Ala Leu Gln
450                 455                 460

Ile Leu Ala Gly Lys His Val Gly Ala Ser Ile Gln Tyr Val Gly Asp
465                 470                 475                 480

Lys Ser Lys Ile Ser Gln Asn Gly Gln Gly Thr Pro Arg Glu Gln Leu
                485                 490                 495

Leu Ser Pro Glu Phe Leu Val Glu Ala Phe Arg Thr Ala Ser Arg Asn
            500                 505                 510

Asn Ile Leu Arg Thr Thr Asp Lys Tyr Gln Glu Leu Val Lys Thr Leu
            515                 520                 525

Asn Pro Asp Gln Ala Phe Glu Glu Leu Ser Gln Gln Arg Phe Gln Cys
530                 535                 540
```

```
Ala Arg Ile His Thr Arg Gln His Leu Ile Ser Ser Phe Tyr Ala Arg
545                 550                 555                 560

Ile Ala Thr Ala Lys Asp Asp Ile Lys Pro His Leu Leu Lys Leu Ala
            565                 570                 575

Asn Leu Phe Ala Leu Trp Ser Ile Glu Glu Asp Thr Gly Ile Phe Leu
        580                 585                 590

Arg Glu Asn Ile Leu Thr Pro Gly Asp Ile Asp Leu Ile Asn Ser Leu
    595                 600                 605

Val Asp Glu Leu Cys Val Ala Val Arg Asp Gln Val Ile Gly Leu Thr
610                 615                 620

Asp Ala Phe Gly Leu Ser Asp Phe Phe Ile Asn Ala Pro Ile Gly Ser
625                 630                 635                 640

Tyr Asp Gly Asn Val Tyr Glu Lys Tyr Phe Ala Lys Val Asn Gln Gln
            645                 650                 655

Asn Pro Ala Thr Asn Pro Arg Pro Tyr Tyr Glu Ser Thr Leu Lys
        660                 665                 670

Pro Phe Leu Phe Arg Glu Glu Asp Asp Glu Ile Cys Asp Leu Asp
    675                 680                 685

Glu

<210> SEQ ID NO 23
<211> LENGTH: 700
<212> TYPE: PRT
<213> ORGANISM: Yarrowia lipolytica

<400> SEQUENCE: 23

Met Asn Pro Asn Asn Thr Gly Thr Ile Glu Ile Asn Gly Lys Glu Tyr
1               5                   10                  15

Asn Thr Phe Thr Glu Pro Pro Val Ala Met Ala Gln Glu Arg Ala Lys
            20                  25                  30

Thr Ser Phe Pro Val Arg Glu Met Thr Tyr Phe Leu Asp Gly Gly Glu
        35                  40                  45

Lys Asn Thr Leu Lys Asn Glu Gln Ile Met Glu Glu Ile Glu Arg Asp
    50                  55                  60

Pro Leu Phe Asn Asn Asp Asn Tyr Tyr Asp Leu Asn Lys Glu Gln Ile
65                  70                  75                  80

Arg Glu Leu Thr Met Glu Arg Val Ala Lys Leu Ser Leu Phe Val Arg
                85                  90                  95

Asp Gln Pro Glu Asp Asp Ile Lys Lys Arg Phe Ala Leu Ile Gly Ile
            100                 105                 110

Ala Asp Met Gly Thr Tyr Thr Arg Leu Gly Val His Tyr Gly Leu Phe
        115                 120                 125

Phe Gly Ala Val Arg Gly Thr Gly Thr Ala Glu Gln Phe Gly His Trp
    130                 135                 140

Ile Ser Lys Gly Ala Gly Asp Leu Arg Lys Phe Tyr Gly Cys Phe Ser
145                 150                 155                 160

Met Thr Glu Leu Gly His Gly Ser Asn Leu Ala Gly Leu Glu Thr Thr
                165                 170                 175

Ala Ile Tyr Asp Glu Glu Thr Asp Glu Phe Ile Ile Asn Thr Pro His
            180                 185                 190

Ile Ala Ala Thr Lys Trp Trp Ile Gly Gly Ala Ala His Thr Ala Thr
        195                 200                 205

His Thr Val Val Phe Ala Arg Leu Ile Val Lys Gly Lys Asp Tyr Gly
    210                 215                 220
```

```
Val Lys Thr Phe Val Val Gln Leu Arg Asn Ile Asn Asp His Ser Leu
225                 230                 235                 240

Lys Val Gly Ile Ser Ile Gly Asp Ile Gly Lys Lys Met Gly Arg Asp
                245                 250                 255

Gly Ile Asp Asn Gly Trp Ile Gln Phe Thr Asn Val Arg Ile Pro Arg
                260                 265                 270

Gln Asn Leu Leu Met Lys Tyr Thr Lys Val Asp Arg Glu Gly Asn Val
            275                 280                 285

Thr Gln Pro Pro Leu Ala Gln Leu Thr Tyr Gly Ser Leu Ile Thr Gly
        290                 295                 300

Arg Val Ser Met Ala Ser Asp Ser His Gln Val Gly Lys Arg Phe Ile
305                 310                 315                 320

Thr Ile Ala Leu Arg Tyr Ala Cys Ile Arg Arg Gln Phe Ser Thr Thr
                325                 330                 335

Pro Gly Gln Pro Glu Thr Lys Ile Ile Asp Tyr Pro Tyr His Gln Arg
                340                 345                 350

Arg Leu Leu Pro Leu Leu Ala Tyr Val Tyr Ala Leu Lys Met Thr Ala
            355                 360                 365

Asp Glu Val Gly Ala Leu Phe Ser Arg Thr Met Leu Lys Met Asp Asp
370                 375                 380

Leu Lys Pro Asp Asp Lys Ala Gly Leu Asn Glu Val Val Ser Asp Val
385                 390                 395                 400

Lys Glu Leu Phe Ser Val Ser Ala Gly Leu Lys Ala Phe Ser Thr Trp
                405                 410                 415

Ala Cys Ala Asp Val Ile Asp Lys Thr Arg Gln Ala Cys Gly Gly His
                420                 425                 430

Gly Tyr Ser Gly Tyr Asn Gly Phe Gly Gln Ala Tyr Ala Asp Trp Val
            435                 440                 445

Val Gln Cys Thr Trp Glu Gly Asp Asn Asn Ile Leu Thr Leu Ser Ala
        450                 455                 460

Gly Arg Ala Leu Ile Gln Ser Ala Val Ala Leu Arg Lys Gly Glu Pro
465                 470                 475                 480

Val Gly Asn Ala Val Ser Tyr Leu Lys Arg Tyr Lys Asp Leu Ala Asn
                485                 490                 495

Ala Lys Leu Asn Gly Arg Ser Leu Thr Asp Pro Lys Val Leu Val Glu
            500                 505                 510

Ala Trp Glu Val Ala Ala Gly Asn Ile Ile Asn Arg Ala Thr Asp Gln
        515                 520                 525

Tyr Glu Lys Leu Ile Gly Glu Gly Leu Asn Ala Asp Gln Ala Phe Glu
            530                 535                 540

Val Leu Ser Gln Gln Arg Phe Gln Ala Ala Lys Val His Thr Arg Arg
545                 550                 555                 560

His Leu Ile Ala Ala Phe Phe Ser Arg Ile Asp Thr Glu Ala Gly Glu
                565                 570                 575

Ala Ile Lys Gln Pro Leu Leu Asn Leu Ala Leu Leu Phe Ala Leu Trp
            580                 585                 590

Ser Ile Glu Glu Asp Ser Gly Leu Phe Leu Arg Glu Gly Phe Leu Glu
        595                 600                 605

Pro Lys Asp Ile Asp Thr Val Thr Glu Leu Val Asn Lys Tyr Cys Thr
        610                 615                 620

Thr Val Arg Glu Glu Val Ile Gly Tyr Thr Asp Ala Phe Asn Leu Ser
625                 630                 635                 640
```

Asp Tyr Phe Ile Asn Ala Pro Ile Gly Cys Tyr Asp Gly Asp Ala Tyr
              645                 650                 655

Arg His Tyr Phe Gln Lys Val Asn Glu Gln Asn Pro Ala Arg Asp Pro
          660                 665                 670

Arg Pro Pro Tyr Tyr Ala Ser Thr Leu Lys Pro Phe Leu Phe Arg Glu
      675                 680                 685

Glu Glu Asp Asp Asp Ile Cys Glu Leu Asp Glu Glu
  690                 695                 700

<210> SEQ ID NO 24
<211> LENGTH: 700
<212> TYPE: PRT
<213> ORGANISM: Yarrowia lipolytica

<400> SEQUENCE: 24

Met Ile Ser Pro Asn Leu Thr Ala Asn Val Glu Ile Asp Gly Lys Gln
1               5                   10                  15

Tyr Asn Thr Phe Thr Glu Pro Pro Lys Ala Leu Ala Gly Glu Arg Ala
            20                  25                  30

Lys Val Lys Phe Pro Ile Lys Asp Met Thr Glu Phe Leu His Gly Gly
        35                  40                  45

Glu Glu Asn Val Thr Met Ile Glu Arg Leu Met Thr Glu Leu Glu Arg
    50                  55                  60

Asp Pro Val Leu Asn Val Ser Gly Asp Tyr Asp Met Pro Lys Glu Gln
65                  70                  75                  80

Leu Arg Glu Thr Ala Val Ala Arg Ile Ala Ala Leu Ser Gly His Trp
                85                  90                  95

Lys Lys Asp Thr Glu Lys Glu Ala Leu Leu Arg Ser Gln Leu His Gly
            100                 105                 110

Ile Val Asp Met Gly Thr Arg Ile Arg Leu Gly Val His Thr Gly Leu
        115                 120                 125

Phe Met Gly Ala Ile Arg Gly Ser Gly Thr Lys Glu Gln Tyr Asp Tyr
    130                 135                 140

Trp Val Arg Lys Gly Ala Ala Asp Val Lys Gly Phe Tyr Gly Cys Phe
145                 150                 155                 160

Ala Met Thr Glu Leu Gly His Gly Ser Asn Val Ala Gly Leu Glu Thr
                165                 170                 175

Thr Ala Thr Tyr Ile Gln Asp Thr Asp Glu Phe Ile Ile Asn Thr Pro
            180                 185                 190

Asn Thr Gly Ala Thr Lys Trp Trp Ile Gly Gly Ala Ala His Ser Ala
        195                 200                 205

Thr His Thr Ala Cys Phe Ala Arg Leu Leu Val Asp Gly Lys Asp Tyr
    210                 215                 220

Gly Val Lys Ile Phe Val Val Gln Leu Arg Asp Val Ser Ser His Ser
225                 230                 235                 240

Leu Met Pro Gly Ile Ala Leu Gly Asp Ile Gly Lys Lys Met Gly Arg
                245                 250                 255

Asp Ala Ile Asp Asn Gly Trp Ile Gln Phe Thr Asn Val Arg Ile Pro
            260                 265                 270

Arg Gln Asn Met Leu Met Lys Tyr Ala Lys Val Ser Ser Thr Gly Lys
        275                 280                 285

Val Ser Gln Pro Pro Leu Ala Gln Leu Thr Tyr Gly Ala Leu Ile Gly
    290                 295                 300

Gly Arg Val Thr Met Ile Ala Asp Ser Phe Phe Val Ser Gln Arg Phe
305                 310                 315                 320

```
Ile Thr Ile Ala Leu Arg Tyr Ala Cys Val Arg Arg Gln Phe Gly Thr
            325                 330                 335

Thr Pro Gly Gln Pro Glu Thr Lys Ile Ile Asp Tyr Pro Tyr His Gln
            340                 345                 350

Arg Arg Leu Leu Pro Leu Leu Ala Phe Thr Tyr Ala Met Lys Met Ala
            355                 360                 365

Ala Asp Gln Ser Gln Ile Gln Tyr Asp Gln Thr Thr Asp Leu Leu Gln
            370                 375                 380

Thr Ile Asp Pro Lys Asp Lys Gly Ala Leu Gly Lys Ala Ile Val Asp
385                 390                 395                 400

Leu Lys Glu Leu Phe Ala Ser Ser Ala Gly Leu Lys Ala Phe Thr Thr
            405                 410                 415

Trp Thr Cys Ala Asn Ile Ile Asp Gln Cys Arg Gln Ala Cys Gly Gly
            420                 425                 430

His Gly Tyr Ser Gly Tyr Asn Gly Phe Gly Gln Ala Tyr Ala Asp Trp
            435                 440                 445

Val Val Gln Cys Thr Trp Glu Gly Asp Asn Asn Val Leu Cys Leu Ser
            450                 455                 460

Met Gly Arg Gly Leu Ile Gln Ser Cys Leu Gly His Arg Lys Gly Lys
465                 470                 475                 480

Pro Leu Gly Ser Ser Val Gly Tyr Leu Ala Asn Lys Gly Leu Glu Gln
            485                 490                 495

Ala Thr Leu Ser Gly Arg Asp Leu Lys Asp Pro Lys Val Leu Ile Glu
            500                 505                 510

Ala Trp Glu Lys Val Ala Asn Gly Ala Ile Gln Arg Ala Thr Asp Lys
            515                 520                 525

Phe Val Glu Leu Thr Lys Gly Gly Leu Ser Pro Asp Gln Ala Phe Glu
            530                 535                 540

Glu Leu Ser Gln Gln Arg Phe Gln Cys Ala Lys Ile His Thr Arg Lys
545                 550                 555                 560

His Leu Val Thr Ala Phe Tyr Glu Arg Ile Asn Ala Ser Ala Lys Ala
            565                 570                 575

Asp Val Lys Pro Tyr Leu Ile Asn Leu Ala Asn Leu Phe Thr Leu Trp
            580                 585                 590

Ser Ile Glu Glu Asp Ser Gly Leu Phe Leu Arg Glu Gly Phe Leu Gln
            595                 600                 605

Pro Lys Asp Ile Asp Gln Val Thr Glu Leu Val Asn His Tyr Cys Lys
            610                 615                 620

Glu Val Arg Asp Gln Val Ala Gly Tyr Thr Asp Ala Phe Gly Leu Ser
625                 630                 635                 640

Asp Trp Phe Ile Asn Ala Pro Ile Gly Asn Tyr Asp Gly Asp Val Tyr
            645                 650                 655

Lys His Tyr Phe Ala Lys Val Asn Gln Gln Asn Pro Ala Gln Asn Pro
            660                 665                 670

Arg Pro Pro Tyr Tyr Glu Ser Thr Leu Arg Pro Phe Leu Phe Arg Glu
            675                 680                 685

Asp Glu Asp Asp Asp Ile Cys Glu Leu Asp Glu Glu
            690                 695                 700

<210> SEQ ID NO 25
<211> LENGTH: 701
<212> TYPE: PRT
<213> ORGANISM: Yarrowia lipolytica
```

<400> SEQUENCE: 25

```
Met Ile Thr Pro Asn Pro Ala Asn Asp Ile Val His Asp Gly Lys Leu
1               5                   10                  15

Tyr Asp Thr Phe Thr Glu Pro Pro Lys Leu Met Ala Gln Glu Arg Ala
            20                  25                  30

Gln Leu Asp Phe Asp Pro Arg Asp Ile Thr Tyr Phe Leu Asp Gly Ser
        35                  40                  45

Lys Glu Glu Thr Glu Leu Leu Glu Ser Leu Met Leu Met Tyr Glu Arg
    50                  55                  60

Asp Pro Leu Phe Asn Asn Gln Asn Glu Tyr Asp Glu Ser Phe Glu Thr
65                  70                  75                  80

Leu Arg Glu Arg Ser Val Lys Arg Ile Phe Gln Leu Ser Lys Ser Ile
                85                  90                  95

Ala Met Asp Pro Glu Pro Met Ser Phe Arg Lys Ile Gly Phe Leu Gly
            100                 105                 110

Ile Leu Asp Met Gly Thr Tyr Ala Arg Leu Gly Val His Tyr Ala Leu
        115                 120                 125

Phe Cys Asn Ser Ile Arg Gly Gln Gly Thr Pro Asp Gln Leu Met Tyr
    130                 135                 140

Trp Leu Asp Gln Gly Ala Met Val Ile Lys Gly Phe Tyr Gly Cys Phe
145                 150                 155                 160

Ala Met Thr Glu Met Gly His Gly Ser Asn Leu Ser Arg Leu Glu Thr
                165                 170                 175

Ile Ala Thr Phe Asp Lys Glu Thr Asp Glu Phe Ile Ile Asn Thr Pro
            180                 185                 190

His Val Gly Ala Thr Lys Trp Trp Ile Gly Gly Ala Ala His Thr Ala
        195                 200                 205

Thr His Thr Leu Ala Phe Ala Arg Leu Gln Val Asp Gly Lys Asp Tyr
    210                 215                 220

Gly Val Lys Ser Phe Val Val Pro Leu Arg Asn Leu Asp Asp His Ser
225                 230                 235                 240

Leu Arg Pro Gly Ile Ala Thr Gly Asp Ile Gly Lys Lys Met Gly Arg
                245                 250                 255

Asp Ala Val Asp Asn Gly Trp Ile Gln Phe Thr Asn Val Arg Val Pro
            260                 265                 270

Arg Asn Tyr Met Leu Met Lys His Thr Lys Val Leu Arg Asp Gly Thr
        275                 280                 285

Val Lys Gln Pro Pro Leu Ala Gln Leu Thr Tyr Gly Ser Leu Ile Thr
    290                 295                 300

Gly Arg Val Gln Met Thr Thr Asp Ser His Asn Val Ser Lys Lys Phe
305                 310                 315                 320

Leu Thr Ile Ala Leu Arg Tyr Ala Thr Ile Arg Arg Gln Phe Ser Ser
                325                 330                 335

Thr Pro Gly Glu Pro Glu Thr Arg Leu Ile Asp Tyr Leu Tyr His Gln
            340                 345                 350

Arg Arg Leu Leu Pro Leu Met Ala Tyr Ser Tyr Ala Met Lys Leu Ala
        355                 360                 365

Gly Asp His Val Arg Glu Leu Phe Phe Ala Ser Gln Glu Lys Ala Glu
    370                 375                 380

Ser Leu Lys Glu Asp Asp Lys Ala Gly Val Glu Ser Tyr Val Gln Asp
385                 390                 395                 400

Ile Lys Glu Leu Phe Ser Val Ser Ala Gly Leu Lys Ala Ala Thr Thr
                405                 410                 415
```

```
Trp Ala Cys Ala Asp Ile Ile Asp Lys Ala Arg Gln Ala Cys Gly Gly
                420                 425                 430

His Gly Tyr Ser Ala Tyr Asn Gly Phe Gly Gln Ala Phe Gln Asp Trp
            435                 440                 445

Val Val Gln Cys Thr Trp Glu Gly Asp Asn Thr Val Leu Thr Leu Ser
    450                 455                 460

Ala Gly Arg Ala Leu Ile Gln Ser Ala Leu Val Tyr Arg Lys Glu Gly
465                 470                 475                 480

Lys Leu Gly Asn Ala Thr Lys Tyr Leu Ser Arg Ser Lys Glu Leu Ala
                485                 490                 495

Asn Ala Lys Arg Asn Gly Arg Ser Leu Glu Asp Pro Lys Leu Leu Val
            500                 505                 510

Glu Ala Trp Glu Ala Val Ser Ala Gly Ala Ile Asn Ala Ala Thr Asp
    515                 520                 525

Ala Tyr Glu Glu Leu Ser Lys Gln Gly Val Ser Val Asp Glu Cys Phe
530                 535                 540

Glu Gln Val Ser Gln Glu Arg Phe Gln Ala Ala Arg Ile His Thr Arg
545                 550                 555                 560

Arg Ala Leu Ile Glu Ala Phe Tyr Ser Arg Ile Ala Thr Ala Asp Glu
                565                 570                 575

Lys Val Lys Pro His Leu Ile Pro Leu Ala Asn Leu Phe Ala Leu Trp
            580                 585                 590

Ser Ile Glu Glu Asp Ser Ala Leu Phe Leu Ala Glu Gly Tyr Phe Glu
    595                 600                 605

Pro Glu Asp Ile Ile Glu Val Thr Ser Leu Val Asn Lys Tyr Cys Gly
610                 615                 620

Ile Val Arg Lys Asn Val Ile Gly Tyr Thr Asp Ala Phe Asn Leu Ser
625                 630                 635                 640

Asp Tyr Phe Ile Asn Ala Ala Ile Gly Arg Tyr Asp Gly Asp Val Tyr
                645                 650                 655

Lys Asn Tyr Phe Glu Lys Val Lys Gln Gln Tyr Pro Pro Glu Gly Gly
            660                 665                 670

Lys Pro His Tyr Tyr Glu Asp Val Met Lys Pro Phe Leu His Arg Glu
    675                 680                 685

Arg Ile Pro Asp Val Pro Met Glu Pro Glu Asp Ile Gln
690                 695                 700

<210> SEQ ID NO 26
<211> LENGTH: 699
<212> TYPE: PRT
<213> ORGANISM: Yarrowia lipolytica

<400> SEQUENCE: 26

Met Asn Asn Asn Pro Thr Asn Val Ile Leu Gly Gly Lys Glu Tyr Asp
1               5                   10                  15

Thr Phe Thr Glu Pro Pro Ala Gln Met Glu Leu Glu Arg Ala Lys Thr
            20                  25                  30

Gln Phe Lys Val Arg Asp Val Thr Asn Phe Leu Thr Gly Ser Glu Gln
        35                  40                  45

Glu Thr Leu Leu Thr Glu Arg Ile Met Arg Glu Ile Glu Arg Asp Pro
    50                  55                  60

Val Leu Asn Val Ala Gly Asp Tyr Asp Ala Asp Leu Pro Thr Lys Arg
65                  70                  75                  80

Arg Gln Ala Val Glu Arg Ile Gly Ala Leu Ala Arg Tyr Leu Pro Lys
```

```
                    85              90              95
Asp Ser Glu Lys Glu Ala Ile Leu Arg Gly Gln Leu His Gly Ile Val
                100             105             110
Asp Met Gly Thr Arg Thr Arg Ile Ala Val His Tyr Gly Leu Phe Met
                115             120             125
Gly Ala Ile Arg Gly Ser Gly Thr Lys Glu Gln Tyr Asp Tyr Trp Val
                130             135             140
Ala Lys Gly Ala Ala Thr Leu His Lys Phe Tyr Gly Cys Phe Ala Met
145             150             155             160
Thr Glu Leu Gly His Gly Ser Asn Val Ala Gly Leu Glu Thr Thr Ala
                165             170             175
Thr Leu Asp Lys Asp Thr Asp Glu Phe Ile Ile Asn Thr Pro Asn Ser
                180             185             190
Gly Ala Thr Lys Trp Trp Ile Gly Gly Ala Ala His Ser Ala Thr His
                195             200             205
Thr Ala Cys Leu Ala Arg Leu Ile Val Asp Gly Lys Asp Tyr Gly Val
                210             215             220
Lys Ile Phe Ile Val Gln Leu Arg Asp Leu Asn Ser His Ser Leu Leu
225             230             235             240
Asn Gly Ile Ala Ile Gly Asp Ile Gly Lys Lys Met Gly Arg Asp Ala
                245             250             255
Ile Asp Asn Gly Trp Ile Gln Phe Thr Asp Val Arg Ile Pro Arg Gln
                260             265             270
Asn Met Leu Met Arg Tyr Asp Arg Val Ser Arg Asp Gly Glu Val Thr
                275             280             285
Thr Ser Glu Leu Ala Gln Leu Thr Tyr Gly Ala Leu Leu Ser Gly Arg
                290             295             300
Val Thr Met Ile Ala Glu Ser His Leu Leu Ser Ala Arg Phe Leu Thr
305             310             315             320
Ile Ala Leu Arg Tyr Ala Cys Ile Arg Arg Gln Phe Gly Ala Val Pro
                325             330             335
Asp Lys Pro Glu Thr Lys Leu Ile Asp Tyr Pro Tyr His Gln Arg Arg
                340             345             350
Leu Leu Pro Leu Leu Ala Tyr Thr Tyr Ala Met Lys Met Gly Ala Asp
                355             360             365
Glu Ala Gln Gln Gln Tyr Asn Ser Ser Phe Gly Ala Leu Leu Lys Leu
                370             375             380
Asn Pro Val Lys Asp Ala Glu Lys Phe Ala Val Ala Thr Ala Asp Leu
385             390             395             400
Lys Ala Leu Phe Ala Ser Ser Ala Gly Met Lys Ala Phe Thr Thr Trp
                405             410             415
Ala Ala Ala Lys Ile Ile Asp Glu Cys Arg Gln Ala Cys Gly Gly His
                420             425             430
Gly Tyr Ser Gly Tyr Asn Gly Phe Gly Gln Ala Tyr Ala Asp Trp Val
                435             440             445
Val Gln Cys Thr Trp Glu Gly Asp Asn Asn Val Leu Cys Leu Ser Met
                450             455             460
Gly Arg Ser Leu Ile Gln Ser Cys Ile Ala Met Arg Lys Lys Lys Gly
465             470             475             480
His Val Gly Lys Ser Val Glu Tyr Leu Gln Arg Arg Asp Glu Leu Gln
                485             490             495
Asn Ala Arg Val Asp Asn Lys Pro Leu Thr Asp Pro Ala Val Leu Ile
                500             505             510
```

```
Thr Ala Trp Glu Lys Val Ala Cys Glu Ala Ile Asn Arg Ala Thr Asp
            515                 520                 525

Ser Phe Ile Lys Leu Thr Gln Glu Gly Leu Ser Pro Asp Gln Ala Phe
        530                 535                 540

Glu Glu Leu Ser Gln Gln Arg Phe Glu Cys Ala Arg Ile His Thr Arg
545                 550                 555                 560

Lys His Leu Ile Thr Ser Phe Tyr Ala Arg Ile Ser Lys Ala Lys Ala
                565                 570                 575

Arg Val Lys Pro His Leu Thr Val Leu Ala Asn Leu Phe Ala Val Trp
            580                 585                 590

Ser Ile Glu Glu Asp Ser Gly Leu Phe Leu Arg Glu Gly Cys Phe Glu
        595                 600                 605

Pro Ala Glu Met Asp Glu Ile Thr Ala Leu Val Asp Glu Leu Cys Cys
    610                 615                 620

Glu Ala Arg Glu Gln Val Ile Gly Phe Thr Asp Ala Phe Asn Leu Ser
625                 630                 635                 640

Asp Phe Phe Ile Asn Ala Pro Ile Gly Arg Phe Asp Gly Asp Ala Tyr
                645                 650                 655

Lys His Tyr Met Asp Glu Val Lys Ala Ala Asn Asn Pro Arg Asn Thr
            660                 665                 670

His Ala Pro Tyr Tyr Glu Thr Lys Leu Arg Pro Phe Leu Phe Arg Pro
        675                 680                 685

Asp Glu Asp Glu Glu Ile Cys Asp Leu Asp Glu
    690                 695

<210> SEQ ID NO 27
<211> LENGTH: 689
<212> TYPE: PRT
<213> ORGANISM: Yarrowia lipolytica

<400> SEQUENCE: 27

Met Leu Ser Gln Gln Ser Leu Asn Thr Phe Thr Glu Pro Pro Val Glu
1               5                   10                  15

Met Ala Arg Glu Arg Asn Gln Thr Ser Phe Asn Pro Arg Leu Leu Thr
            20                  25                  30

Tyr Phe Leu Asp Gly Gly Glu Lys Asn Thr Leu Leu Met Asp Arg Leu
        35                  40                  45

Met Gln Glu Tyr Glu Arg Asp Pro Val Phe Arg Asn Glu Gly Asp Tyr
    50                  55                  60

Asp Ile Thr Asp Val Ala Gln Ser Arg Glu Leu Ala Phe Lys Arg Ile
65                  70                  75                  80

Ala Lys Leu Ile Glu Tyr Val His Thr Asp Asp Glu Glu Thr Tyr Leu
                85                  90                  95

Tyr Arg Cys Met Leu Leu Gly Gln Ile Asp Met Gly Ala Phe Ala Arg
            100                 105                 110

Tyr Ala Ile His His Gly Val Trp Gly Ala Ile Arg Gly Ala Gly
        115                 120                 125

Thr Pro Glu Gln Tyr Glu Phe Trp Val Lys Gly Ser Leu Ser Val
    130                 135                 140

Lys Lys Phe Tyr Gly Ser Phe Ser Met Thr Glu Leu Gly His Gly Ser
145                 150                 155                 160

Asn Leu Val Gly Leu Glu Thr Thr Ala Thr Leu Asp Lys Asn Ala Asp
                165                 170                 175

Glu Phe Val Ile Asn Thr Pro Asn Val Ala Ala Thr Lys Trp Trp Ile
```

-continued

```
            180                 185                 190
Gly Gly Ala Ala Asp Thr Ala Thr His Thr Ala Val Phe Ala Arg Leu
            195                 200                 205
Ile Val Asp Gly Glu Asp His Gly Val Lys Thr Phe Val Val Gln Leu
        210                 215                 220
Arg Asp Val Glu Thr His Asn Leu Met Pro Gly Ile Ala Ile Gly Asp
225                 230                 235                 240
Cys Gly Lys Lys Met Gly Arg Gln Gly Thr Asp Asn Gly Trp Ile Gln
                245                 250                 255
Phe Thr His Val Arg Ile Pro Arg Gln Asn Met Leu Met Arg Tyr Cys
            260                 265                 270
His Val Asp Ser Asp Gly Asn Val Thr Glu Pro Met Met Ala Gln Met
        275                 280                 285
Ala Tyr Gly Ala Leu Leu Ala Gly Arg Val Gly Met Ala Met Asp Ser
    290                 295                 300
Tyr Phe Thr Ser Arg Lys Phe Leu Thr Ile Ala Leu Arg Tyr Ala Thr
305                 310                 315                 320
Ile Arg Arg Ala Phe Ala Ala Gly Gly Gln Glu Thr Lys Leu Ile
                325                 330                 335
Asp Tyr Pro Tyr His Gln Arg Arg Leu Leu Pro Leu Met Ala Gln Thr
            340                 345                 350
Tyr Ala Ile Lys Cys Thr Ala Asp Lys Val Arg Asp Gln Phe Val Lys
        355                 360                 365
Val Thr Asp Met Leu Leu Asn Leu Asp Val Ser Asp Gln Glu Ala Val
    370                 375                 380
Pro Lys Ala Ile Ala Glu Ala Lys Glu Leu Phe Ser Val Ser Ala Gly
385                 390                 395                 400
Val Lys Ala Thr Thr Thr Trp Ala Cys Ala His Thr Ile Asp Gln Cys
                405                 410                 415
Arg Gln Ala Cys Gly Gly His Gly Tyr Ser Ala Tyr Asn Gly Phe Gly
            420                 425                 430
Arg Ala Tyr Ser Asp Trp Val Ile Gln Cys Thr Trp Glu Gly Asp Asn
        435                 440                 445
Asn Ile Leu Cys Leu Ser Ala Gly Arg Ala Leu Val Gln Ser Asn Arg
    450                 455                 460
Ala Val Arg Ala Gly Lys Pro Ile Gly Pro Thr Ala Tyr Leu Ala
465                 470                 475                 480
Ala Pro Ala Gly Ser Pro Lys Leu Ala Gly Arg Asn Leu Tyr Asp Pro
                485                 490                 495
Lys Val Met Ile Gly Ala Trp Glu Thr Val Ser Arg Ala Leu Ile Asn
            500                 505                 510
Arg Thr Thr Asp Glu Phe Glu Val Leu Ala Lys Lys Gly Leu Ser Thr
        515                 520                 525
Ala Gln Ala Tyr Glu Glu Leu Ser Gln Arg Phe Leu Cys Thr Arg
    530                 535                 540
Ile His Thr Arg Leu Tyr Met Val Lys Asn Phe Tyr Glu Arg Ile Ala
545                 550                 555                 560
Glu Glu Gly Thr Glu Phe Thr Lys Glu Pro Leu Thr Arg Leu Ala Asn
                565                 570                 575
Leu Tyr Ala Phe Trp Ser Val Glu Glu Ala Gly Ile Phe Leu Arg
            580                 585                 590
Glu Gly Tyr Ile Thr Pro Gln Glu Leu Lys Tyr Ile Ser Ala Glu Ile
        595                 600                 605
```

Arg Lys Gln Leu Leu Glu Val Arg Lys Asp Val Ile Gly Tyr Thr Asp
610                 615                 620

Ala Phe Asn Val Pro Asp Phe Phe Leu Asn Ser Ala Ile Gly Arg Ala
625                 630                 635                 640

Asp Gly Asp Val Tyr Lys Asn Tyr Phe Lys Val Val Asn Thr Gln Asn
            645                 650                 655

Pro Pro Gln Asp Pro Arg Pro Pro Tyr Tyr Glu Ser Val Ile Arg Pro
            660                 665                 670

Phe Leu Phe Arg Lys Asp Glu Asp Glu Ile Cys Ser Leu Glu Asp
            675                 680                 685

Glu

<210> SEQ ID NO 28
<211> LENGTH: 906
<212> TYPE: PRT
<213> ORGANISM: Candida viswanathii

<400> SEQUENCE: 28

Met Ser Pro Val Asp Phe Lys Asp Lys Val Ile Ile Thr Gly Ala
1               5                   10                  15

Gly Gly Gly Leu Gly Lys Tyr Tyr Ser Leu Glu Phe Ala Lys Leu Gly
                20                  25                  30

Ala Lys Val Val Asn Asp Leu Gly Ala Leu Asn Gly Gln Gly
            35                  40                  45

Gly Asn Ser Lys Ala Ala Asp Val Val Asp Glu Ile Val Lys Asn
        50                  55                  60

Gly Gly Val Ala Val Ala Asp Tyr Asn Asn Val Leu Asp Gly Asp Lys
65                  70                  75                  80

Ile Val Glu Thr Ala Val Lys Asn Phe Gly Thr Val His Val Ile Ile
                85                  90                  95

Asn Asn Ala Gly Ile Leu Arg Asp Ala Ser Met Lys Lys Met Thr Glu
                100                 105                 110

Lys Asp Tyr Lys Leu Val Ile Asp Val His Leu Asn Gly Ala Phe Ala
            115                 120                 125

Val Thr Lys Ala Ala Trp Pro Tyr Phe Gln Lys Gln Lys Tyr Gly Arg
        130                 135                 140

Ile Val Asn Thr Ser Ser Pro Ala Gly Leu Tyr Gly Asn Phe Gly Gln
145                 150                 155                 160

Ala Asn Tyr Ala Ser Ala Lys Ser Ala Leu Leu Gly Phe Ala Glu Thr
                165                 170                 175

Leu Ala Lys Glu Gly Ala Lys Tyr Asn Ile Lys Ala Asn Ala Ile Ala
            180                 185                 190

Pro Leu Ala Arg Ser Arg Met Thr Glu Ser Ile Leu Pro Pro Met
        195                 200                 205

Leu Glu Lys Leu Gly Pro Glu Lys Val Ala Pro Leu Val Leu Tyr Leu
        210                 215                 220

Ser Ser Ala Glu Asn Glu Leu Thr Gly Gln Phe Phe Glu Val Ala Ala
225                 230                 235                 240

Gly Phe Tyr Ala Gln Ile Arg Trp Glu Arg Ser Gly Gly Val Leu Phe
                245                 250                 255

Lys Pro Asp Gln Ser Phe Thr Ala Glu Val Val Ala Lys Arg Phe Ser
            260                 265                 270

Glu Ile Leu Asp Tyr Asp Asp Ser Arg Lys Pro Glu Tyr Leu Lys Asn
            275                 280                 285

```
Gln Tyr Pro Phe Met Leu Asn Asp Tyr Ala Thr Leu Thr Asn Glu Ala
    290                 295                 300

Arg Lys Leu Pro Ala Asn Asp Ala Ser Gly Ala Pro Thr Val Ser Leu
305                 310                 315                 320

Lys Asp Lys Val Val Leu Ile Thr Gly Ala Gly Ala Gly Leu Gly Lys
                325                 330                 335

Glu Tyr Ala Lys Trp Phe Ala Lys Tyr Gly Ala Lys Val Val Val Asn
            340                 345                 350

Asp Phe Lys Asp Ala Thr Lys Thr Val Asp Glu Ile Lys Ala Ala Gly
        355                 360                 365

Gly Glu Ala Trp Pro Asp Gln His Asp Val Ala Lys Asp Ser Glu Ala
    370                 375                 380

Ile Ile Lys Asn Val Ile Asp Lys Tyr Gly Thr Ile Asp Ile Leu Val
385                 390                 395                 400

Asn Asn Ala Gly Ile Leu Arg Asp Arg Ser Phe Ala Lys Met Ser Lys
                405                 410                 415

Gln Glu Trp Asp Ser Val Gln Val His Leu Ile Gly Thr Phe Asn
            420                 425                 430

Leu Ser Arg Leu Ala Trp Pro Tyr Phe Val Glu Lys Gln Phe Gly Arg
        435                 440                 445

Ile Ile Asn Ile Thr Ser Thr Ser Gly Ile Tyr Gly Asn Phe Gly Gln
450                 455                 460

Ala Asn Tyr Ser Ser Ser Lys Ala Gly Ile Leu Gly Leu Ser Lys Thr
465                 470                 475                 480

Met Ala Ile Glu Gly Ala Lys Asn Asn Ile Lys Val Asn Ile Val Ala
                485                 490                 495

Pro His Ala Glu Thr Ala Met Thr Leu Thr Ile Phe Arg Glu Gln Asp
            500                 505                 510

Lys Asn Leu Tyr His Ala Asp Gln Val Ala Pro Leu Leu Val Tyr Leu
        515                 520                 525

Gly Thr Asp Asp Val Pro Val Thr Gly Glu Thr Phe Glu Ile Gly Gly
    530                 535                 540

Gly Trp Ile Gly Asn Thr Arg Trp Gln Arg Ala Lys Gly Ala Val Ser
545                 550                 555                 560

His Asp Glu His Thr Thr Val Glu Phe Ile Lys Glu His Leu Asn Glu
                565                 570                 575

Ile Thr Asp Phe Thr Thr Asp Thr Glu Asn Pro Lys Ser Thr Thr Glu
            580                 585                 590

Ser Ser Met Ala Ile Leu Ser Ala Val Gly Gly Asp Asp Asp Asp Asp
        595                 600                 605

Asp Glu Asp Glu Glu Glu Asp Glu Gly Asp Glu Glu Asp Glu Glu
    610                 615                 620

Asp Glu Glu Glu Asp Asp Pro Val Trp Arg Phe Asp Arg Asp Val
625                 630                 635                 640

Ile Leu Tyr Asn Ile Ala Leu Gly Ala Thr Thr Lys Gln Leu Lys Tyr
                645                 650                 655

Val Tyr Glu Asn Asp Ser Asp Phe Gln Val Ile Pro Thr Phe Gly His
            660                 665                 670

Leu Ile Thr Phe Asn Ser Gly Lys Ser Gln Asn Ser Phe Ala Lys Leu
        675                 680                 685

Leu Arg Asn Phe Asn Pro Met Leu Leu Leu His Gly Glu His Tyr Leu
    690                 695                 700
```

-continued

```
Lys Val His Ser Trp Pro Pro Thr Glu Gly Glu Ile Lys Thr Thr
705                 710                 715                 720

Phe Glu Pro Ile Ala Thr Thr Pro Lys Gly Thr Asn Val Val Ile Val
            725                 730                 735

His Gly Ser Lys Ser Val Asp Asn Lys Ser Gly Glu Leu Ile Tyr Ser
            740                 745                 750

Asn Glu Ala Thr Tyr Phe Ile Arg Asn Cys Gln Ala Asp Asn Lys Val
            755                 760                 765

Tyr Ala Asp Arg Pro Ala Phe Ala Thr Asn Gln Phe Leu Ala Pro Lys
            770                 775                 780

Arg Ala Pro Asp Tyr Gln Val Asp Val Pro Val Ser Glu Asp Leu Ala
785                 790                 795                 800

Ala Leu Tyr Arg Leu Ser Gly Asp Arg Asn Pro Leu His Ile Asp Pro
            805                 810                 815

Asn Phe Ala Lys Gly Ala Lys Phe Pro Lys Pro Ile Leu His Gly Met
            820                 825                 830

Cys Thr Tyr Gly Leu Ser Ala Lys Ala Leu Ile Asp Lys Phe Gly Met
            835                 840                 845

Phe Asn Glu Ile Lys Ala Arg Phe Thr Gly Ile Val Phe Pro Gly Glu
            850                 855                 860

Thr Leu Arg Val Leu Ala Trp Lys Glu Ser Asp Asp Thr Ile Val Phe
865                 870                 875                 880

Gln Thr His Val Val Asp Arg Gly Thr Ile Ala Ile Asn Asn Ala Ala
            885                 890                 895

Ile Lys Leu Val Gly Asp Lys Ala Lys Ile
            900                 905

<210> SEQ ID NO 29
<211> LENGTH: 472
<212> TYPE: PRT
<213> ORGANISM: Candida viswanathii

<400> SEQUENCE: 29

Met Met Trp Lys Phe Leu Ile Ala Ile Gly Leu Ile Phe Ser Tyr Cys
1               5                   10                  15

Cys Asn Ala Gln Leu Leu Asp Ser Leu Ser Phe Asp Asn Asn Trp Val
            20                  25                  30

Asn Thr His Tyr Ile Arg Thr Ile Asp Leu Ser Lys Gly Phe Val Lys
            35                  40                  45

Glu Thr Asp Leu Ile Gln Ile Lys Asn Ile Asn Asp Lys Pro Gln Asp
        50                  55                  60

Glu Tyr Tyr Phe Val Val Asn Asp Gly Phe Ser Ile Asp Glu Leu
65              70                  75                  80

Ser Ile Phe Ser Ala Phe Val Gly Asp Gln Ala Leu Glu Val Glu Val
                85                  90                  95

Asp Glu Val Val Pro Asp Lys Val Phe Lys Leu Lys Leu Pro Val Pro
            100                 105                 110

Ile Ala Pro Asn Ser Asp Leu Glu Leu Arg Ile Asn Phe Val Tyr Ile
            115                 120                 125

Asp Ser Leu Val Ser Val Pro Ser Lys Ile Ala Met Asp Ala Thr Gln
        130                 135                 140

Gln Leu Leu Tyr Lys Thr Asn Lys Phe Pro Phe Ser Pro Tyr Val Thr
145                 150                 155                 160

Gln Glu Tyr Thr Leu Ala Leu Ser Gly Met Ser Lys Gly Gln Glu Met
                165                 170                 175
```

```
Asp Leu His Ile Asp Val Glu Asp Thr Pro Gly Leu Pro Asp Leu Lys
                180                 185                 190

Pro Arg Val Glu Ser Gln Val Leu Lys Tyr Gly Pro Ile Ala Glu Asp
            195                 200                 205

Ile Pro Ala Phe Ala Leu Lys Pro Met Gly Leu Met Tyr Asp His Asn
210                 215                 220

Arg Pro Leu Thr Lys Ala Val Ser Leu Asn Arg Ser Ile Trp Leu Pro
225                 230                 235                 240

Ala Ser Asp Ile Asn Lys Val Ser Ile Glu Glu Tyr Glu Leu Thr
                245                 250                 255

Asn Thr Gly Ala Glu Leu Asp Lys Gly Phe Ser Arg Val Asp Trp Met
            260                 265                 270

Lys Gly Arg Phe Glu Ser Thr Arg Asn His Trp Ala Leu Ser His Leu
            275                 280                 285

Glu Ile Pro Leu Leu Glu Arg Gly Phe Asp Asp Tyr Tyr Tyr Thr Asp
            290                 295                 300

Lys Val Gly Val Val Ser Thr His Lys Ile Phe Lys Asn His Leu Leu
305                 310                 315                 320

Leu Gln Pro Arg Tyr Pro Val Phe Gly Gly Trp Lys Tyr Asn Phe Thr
            325                 330                 335

Leu Gly Trp Ser Glu Glu Leu Ser Lys Phe Leu His Lys Leu His Asp
            340                 345                 350

Asn Gln Asp Glu Tyr Ile Ile Lys Phe Pro Ile Leu Asn Ser Leu Arg
            355                 360                 365

Asp Val Thr Tyr Gln Asp Val Tyr Leu Glu Phe Tyr Leu Pro Glu Asn
            370                 375                 380

Ala Glu Phe Gln Asn Ile Ser Ser Pro Ile Ala Phe Glu Ser Ile Ser
385                 390                 395                 400

Ile Glu Asn Glu Leu Ser Tyr Leu Asp Val Ser Lys Gly His Thr Lys
                405                 410                 415

Ile Thr Val His Tyr Thr Asn Leu Phe Asp Asp Leu His Lys Leu Asp
                420                 425                 430

Val Phe Val Lys Tyr Gln Tyr Thr Gln Val Ala Phe Ile Tyr Lys Ile
            435                 440                 445

Ala Lys Ile Ser Gly Phe Val Phe Leu Gly Leu Val Ser Tyr Tyr Leu
450                 455                 460

Leu Gly Leu Leu Asp Leu Ser Ile
465                 470

<210> SEQ ID NO 30
<211> LENGTH: 519
<212> TYPE: PRT
<213> ORGANISM: Saccharomyces fibuligera

<400> SEQUENCE: 30

Met Lys Phe Gly Val Leu Phe Ser Val Phe Ala Ala Ile Val Ser Ala
1               5                   10                  15

Leu Pro Leu Gln Glu Gly Pro Leu Asn Lys Arg Ala Tyr Pro Ser Phe
                20                  25                  30

Glu Ala Tyr Ser Asn Tyr Lys Val Asp Arg Thr Asp Leu Glu Thr Phe
            35                  40                  45

Leu Asp Lys Gln Lys Glu Val Ser Leu Tyr Tyr Leu Leu Gln Asn Ile
50                  55                  60

Ala Tyr Pro Glu Gly Gln Phe Asn Asn Gly Val Pro Gly Thr Val Ile
```

-continued

```
            65                  70                  75                  80
Ala Ser Pro Ser Thr Ser Asn Pro Asp Tyr Tyr Gln Trp Thr Arg
                    85                  90                  95

Asp Ser Ala Ile Thr Phe Leu Thr Val Leu Ser Glu Leu Glu Asp Asn
                100                 105                 110

Asn Phe Asn Thr Thr Leu Ala Lys Ala Val Glu Tyr Tyr Ile Asn Thr
                115                 120                 125

Ser Tyr Asn Leu Gln Arg Thr Ser Asn Pro Ser Gly Ser Phe Asp Asp
            130                 135                 140

Glu Asn His Lys Gly Leu Gly Glu Pro Lys Phe Asn Thr Asp Gly Ser
145                 150                 155                 160

Ala Tyr Thr Gly Ala Trp Gly Arg Pro Gln Asn Asp Gly Pro Ala Leu
                165                 170                 175

Arg Ala Tyr Ala Ile Ser Arg Tyr Leu Asn Asp Val Asn Ser Leu Asn
                180                 185                 190

Glu Gly Lys Leu Val Leu Thr Asp Ser Gly Asp Ile Asn Phe Ser Ser
            195                 200                 205

Thr Glu Asp Ile Tyr Lys Asn Ile Ile Lys Pro Asp Leu Glu Tyr Val
            210                 215                 220

Ile Gly Tyr Trp Asp Ser Thr Gly Phe Asp Leu Trp Glu Glu Asn Gln
225                 230                 235                 240

Gly Arg His Phe Phe Thr Ser Leu Val Gln Gln Lys Ala Leu Ala Tyr
                245                 250                 255

Ala Val Asp Ile Ala Lys Ser Phe Asp Asp Gly Asp Phe Ala Asn Thr
                260                 265                 270

Leu Ser Ser Thr Ala Ser Thr Leu Glu Ser Tyr Leu Ser Gly Ser Asp
            275                 280                 285

Gly Gly Phe Val Asn Thr Asp Val Asn His Ile Val Glu Asn Pro Asp
            290                 295                 300

Leu Leu Gln Gln Asn Ser Arg Gln Gly Leu Asp Ser Ala Thr Tyr Ile
305                 310                 315                 320

Gly Pro Leu Leu Thr His Asp Ile Gly Glu Ser Ser Thr Pro Phe
                325                 330                 335

Asp Val Asp Asn Glu Tyr Val Leu Gln Ser Tyr Tyr Leu Leu Leu Glu
            340                 345                 350

Asp Asn Lys Asp Arg Tyr Ser Val Asn Ser Ala Tyr Ser Ala Gly Ala
            355                 360                 365

Ala Ile Gly Arg Tyr Pro Glu Asp Val Tyr Asn Gly Asp Gly Ser Ser
370                 375                 380

Glu Gly Asn Pro Trp Phe Leu Ala Thr Ala Tyr Ala Ala Gln Val Pro
385                 390                 395                 400

Tyr Lys Leu Ala Tyr Asp Ala Lys Ser Ala Ser Asn Asp Ile Thr Ile
                405                 410                 415

Asn Lys Ile Asn Tyr Asp Phe Phe Asn Lys Tyr Ile Val Asp Leu Ser
                420                 425                 430

Thr Ile Asn Ser Ala Tyr Gln Ser Ser Asp Ser Val Thr Ile Lys Ser
            435                 440                 445

Gly Ser Asp Glu Phe Asn Thr Val Ala Asp Asn Leu Val Thr Phe Gly
            450                 455                 460

Asp Ser Phe Leu Gln Val Ile Leu Asp His Ile Asn Asp Asp Gly Ser
465                 470                 475                 480

Leu Asn Glu Gln Leu Asn Arg Tyr Thr Gly Tyr Ser Thr Gly Ala Tyr
                485                 490                 495
```

-continued

Ser Leu Thr Trp Ser Ser Gly Ala Leu Leu Glu Ala Ile Arg Leu Arg
                500                 505                 510

Asn Lys Val Lys Ala Leu Ala
        515

<210> SEQ ID NO 31
<211> LENGTH: 403
<212> TYPE: PRT
<213> ORGANISM: Rattus norvegicus

<400> SEQUENCE: 31

Met Ile His Thr Asn Leu Lys Lys Phe Ser Leu Phe Ile Leu Val
1               5                   10                  15

Phe Leu Leu Phe Ala Val Ile Cys Val Trp Lys Lys Gly Ser Asp Tyr
                20                  25                  30

Glu Ala Leu Thr Leu Gln Ala Lys Glu Phe Gln Met Pro Lys Ser Gln
            35                  40                  45

Glu Lys Val Ala Met Gly Ser Ala Ser Gln Val Val Phe Ser Asn Ser
    50                  55                  60

Lys Gln Asp Pro Lys Glu Asp Ile Pro Ile Leu Ser Tyr His Arg Val
65                  70                  75                  80

Thr Ala Lys Val Lys Pro Gln Pro Ser Phe Gln Val Trp Asp Lys Asp
                85                  90                  95

Ser Thr Tyr Ser Lys Leu Asn Pro Arg Leu Leu Lys Ile Trp Arg Asn
                100                 105                 110

Tyr Leu Asn Met Asn Lys Tyr Lys Val Ser Tyr Lys Gly Pro Gly Pro
            115                 120                 125

Gly Val Lys Phe Ser Val Glu Ala Leu Arg Cys His Leu Arg Asp His
    130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Val Gly
                165                 170                 175

Pro Trp Gln Arg Cys Ala Val Val Ser Ser Ala Gly Ser Leu Lys Asn
            180                 185                 190

Ser Gln Leu Gly Arg Glu Ile Asp Asn His Asp Ala Val Leu Arg Phe
    195                 200                 205

Asn Gly Ala Pro Thr Asp Asn Phe Gln Gln Asp Val Gly Ser Lys Thr
210                 215                 220

Thr Ile Arg Leu Met Asn Ser Gln Leu Val Thr Thr Glu Lys Arg Phe
225                 230                 235                 240

Leu Lys Asp Ser Leu Tyr Thr Glu Gly Ile Leu Ile Val Trp Asp Pro
                245                 250                 255

Ser Val Tyr His Ala Asp Ile Pro Lys Trp Tyr Gln Lys Pro Asp Tyr
            260                 265                 270

Asn Phe Phe Glu Thr Tyr Lys Ser Tyr Arg Arg Leu Asn Pro Ser Gln
    275                 280                 285

Pro Phe Tyr Ile Leu Lys Pro Gln Met Pro Trp Glu Leu Trp Asp Ile
290                 295                 300

Ile Gln Glu Ile Ser Ala Asp Leu Ile Gln Pro Asn Pro Pro Ser Ser
305                 310                 315                 320

Gly Met Leu Gly Ile Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr

```
                   340                 345                 350
His Gln Lys Phe Phe Asp Ser Ala Cys Thr Met Gly Ala Tyr Asp Pro
            355                 360                 365

Leu Leu Phe Glu Lys Asn Met Val Lys His Leu Asn Glu Gly Thr Asp
    370                 375                 380

Glu Asp Ile Tyr Leu Phe Gly Lys Ala Thr Leu Ser Gly Phe Arg Asn
385                 390                 395                 400

Ile Arg Cys

<210> SEQ ID NO 32
<211> LENGTH: 219
<212> TYPE: PRT
<213> ORGANISM: Homo sapiens

<400> SEQUENCE: 32

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ile Ser Phe
    210                 215

<210> SEQ ID NO 33
<211> LENGTH: 815
<212> TYPE: PRT
<213> ORGANISM: Candida viswanathii

<400> SEQUENCE: 33

Met Thr Leu Leu Leu Lys Pro Thr Ser Glu Leu Asp Ala Thr Ser Arg
1               5                   10                  15

Lys Ile Ile Glu Arg Ile Gln Ser Asn Ser Pro Thr Phe Gln His Leu
            20                  25                  30

Phe Asp Leu Leu Leu Asn Leu Leu Pro Phe Phe Asp Lys Thr Val Ser
        35                  40                  45
```

```
Leu Leu Gly Ser Ile Gly Tyr Cys Asp Tyr Glu Val Ala Tyr Val Thr
 50                  55                  60

Tyr Gln Thr Cys Ile Gln Val Val Gly Leu Met Lys Pro Lys Thr Asn
 65                  70                  75                  80

Ser Leu Asn Gln Asp Ile Phe Lys Gly Val Gln Leu Gln Thr Arg Lys
                 85                  90                  95

Arg Ala Ser Thr Phe Lys Ala Ile Leu Ser Tyr Phe Ala Glu Pro Glu
                100                 105                 110

Thr Gln Glu Glu Asp Pro Leu Leu Asn Arg Phe Lys Ser Leu Ser Gly
                115                 120                 125

Gly Gly Ser Lys Thr Lys Ser Ser Gln Asp Glu Val Phe His Glu Trp
                130                 135                 140

Ile Thr Ser Ser Glu Leu Gln Arg Glu Leu Ser Ser Lys Lys Val Leu
145                 150                 155                 160

Leu Ile Asp Phe Arg Pro Arg Lys Asp Tyr Leu Asn Asn His Ile Lys
                165                 170                 175

Tyr Lys Asp Leu Val His Ile Glu Pro Thr Gln Leu Glu Thr Leu Leu
                180                 185                 190

Asp Ser Ala Ser Asp Gln Asp Leu Glu Thr Leu Val Lys Lys Ser Ala
                195                 200                 205

Pro Tyr Asp Gln Tyr His Ile Phe Leu Glu Arg His Lys Tyr Asp Leu
                210                 215                 220

Ile Val Val Tyr Asn Tyr Asn Tyr Gly Ser Glu Ser Thr Asp Arg Leu
225                 230                 235                 240

Leu Gly Ile Ile Asp Val Val Ser Lys Pro Asn Pro Phe Thr Lys Leu
                245                 250                 255

Ile Thr Ile Leu Met Asn Asn Lys Tyr Ile Ser Ser Arg Leu Lys Val
                260                 265                 270

Lys Pro Leu Phe Leu Ser Gly Gly Val Leu Asn Trp Tyr Lys Thr Phe
                275                 280                 285

Gly Ile Glu Tyr Leu Glu Arg Thr Leu Val Gln Asn Gly Val Ala His
                290                 295                 300

Thr Ser Asp Asn Gln Tyr Leu Lys Ser Phe Asn Asp Tyr Val Ser Thr
305                 310                 315                 320

Ser Lys Glu Thr Pro Lys Thr Gln Val Lys Thr Gln Asn Gly Asp Tyr
                325                 330                 335

Ile Arg Pro Ser Gln Arg Lys Val Asn Gln Phe Asp Pro Val Pro Val
                340                 345                 350

Lys Ser Gly Pro Thr Val Phe Ala Ser Ala Lys Val Asp Leu Pro Pro
                355                 360                 365

Thr Pro Gly Ser Pro Ala Val Ser Thr Pro Ser Pro Arg Ala Pro
370                 375                 380

Ala Pro Pro Thr Lys Thr Thr Ser Leu Thr His Val Pro Glu Lys Glu
385                 390                 395                 400

Ala Lys Ser Pro Ser Pro Val Thr Lys Glu Val Thr Val Ser Ser Lys
                405                 410                 415

Lys Ser Gln Phe Leu Glu Leu Tyr Thr Thr Gly Leu Val Asn Leu Gly
                420                 425                 430

Asn Ser Cys Tyr Met Asn Cys Val Val Gln Cys Leu Ala Ala Ala Pro
                435                 440                 445

Gln Leu Thr Ser Phe Phe Pro Thr Ile Thr Glu Ser Phe Ser Asp
450                 455                 460
```

His Ser Tyr Arg Gln His Ile Asn Ser Asn Asn Lys Leu Gly Thr Lys
465                 470                 475                 480

Gly Glu Leu Thr Thr Ser Phe Val Glu Leu Ile Leu Asn Met Leu Asn
            485                 490                 495

Asn Asn Gly Lys Ala Phe Ser Pro Thr Lys Phe Lys Arg Thr Met Gly
        500                 505                 510

Ser Leu Ser Pro Ser Gln Gln Phe Leu Thr Tyr Asp Gln Gln Asp Cys
    515                 520                 525

Ile Glu Phe Leu Asn Phe Leu Leu Asp Ala Leu His Glu Asp Leu Asn
530                 535                 540

Asn Val Thr Ile Thr Asp Pro Ser Glu Arg Lys Leu Ile Thr Asp Leu
545                 550                 555                 560

Ser Pro Glu Gln Glu Lys Ser Arg Glu Thr Leu Pro Val Arg Leu Ala
            565                 570                 575

Ser Thr Ile Glu Trp Glu Arg Tyr Leu Lys Leu Asn Phe Ser Val Ile
        580                 585                 590

Val Asp Tyr Phe Gln Gly Gln His Leu Ser Gln Leu Lys Cys Leu Glu
    595                 600                 605

Cys Gly Phe Thr Ser Thr Thr Tyr Asn Ala Phe Ser Ile Leu Ser Leu
610                 615                 620

Pro Ile Pro Gln Lys Leu Asn Asn Leu Gly Lys Val Leu Leu Lys Asp
625                 630                 635                 640

Cys Leu Glu Glu Phe Val Thr Thr Glu Leu Leu Asp Asp Asn Asn Lys
            645                 650                 655

Trp Tyr Cys Pro Gln Cys Lys Arg Phe Thr Arg Leu Thr Lys Lys Ile
        660                 665                 670

Ala Ile Thr Arg Leu Pro Gln Val Leu Ile Val Asn Phe Asn Arg Phe
    675                 680                 685

Lys Met Thr Asn Thr Gly Gly Phe Asn Lys Leu Glu Thr Phe Val Thr
690                 695                 700

Tyr Pro Val Asn Glu Glu Leu Asp Met Thr Pro Tyr Trp Pro Asp Val
705                 710                 715                 720

Gly Ser Arg Ile Asn Glu Asn Ser Thr Met Ser Ile Glu Met Glu Gln
            725                 730                 735

Asp Leu Leu Gln Ser Phe Pro Ile Arg Asn Gln Thr Pro Pro Phe Lys
        740                 745                 750

Tyr Lys Leu Phe Gly Val Ala Asn His Phe Gly Asn Leu Thr Thr Gly
    755                 760                 765

His Tyr Thr Ser Tyr Val Tyr Lys His Ser Asp Ser Lys Lys Thr Arg
770                 775                 780

Asn Trp Cys Tyr Phe Asp Asp Ser Lys Ile Thr Tyr Asn Val Ser Pro
785                 790                 795                 800

Ser Gln Val Val Asn Lys Asn Ala Tyr Cys Leu Phe Phe Gln Arg
            805                 810                 815

<210> SEQ ID NO 34
<211> LENGTH: 421
<212> TYPE: PRT
<213> ORGANISM: Candida viswanathii

<400> SEQUENCE: 34

Met Gln Leu Ser Leu Ser Val Leu Ser Thr Val Ala Thr Ala Leu Leu
1               5                   10                  15

Ser Leu Thr Thr Ala Val Asp Ala Lys Ser His Asn Ile Lys Leu Ser
            20                  25                  30

```
Lys Leu Ser Asn Glu Glu Thr Leu Asp Ala Ser Thr Phe Gln Glu Tyr
            35                  40                  45

Thr Ser Ser Leu Ala Asn Lys Tyr Met Asn Leu Phe Asn Ala Ala His
    50                  55                  60

Gly Asn Pro Thr Ser Phe Gly Leu Gln His Val Leu Ser Asn Gln Glu
65                  70                  75                  80

Ala Glu Val Pro Phe Val Thr Pro Gln Lys Gly Gly Lys Tyr Asp Ala
                85                  90                  95

Pro Leu Thr Asn Tyr Leu Asn Ala Gln Tyr Phe Thr Glu Ile Glu Ile
                100                 105                 110

Gly Thr Pro Gly Gln Pro Phe Lys Val Ile Leu Asp Thr Gly Ser Ser
            115                 120                 125

Asn Leu Trp Val Pro Ser Gln Asp Cys Thr Ser Leu Ala Cys Phe Leu
130                 135                 140

His Ser Lys Tyr Asp His Asp Ala Ser Ser Thr Tyr Lys Ala Asn Gly
145                 150                 155                 160

Ser Glu Phe Ser Ile Gln Tyr Gly Ser Gly Ser Met Glu Gly Tyr Ile
                165                 170                 175

Ser Gln Asp Ile Leu Thr Ile Gly Asp Leu Val Ile Pro Lys Gln Asp
            180                 185                 190

Phe Ala Glu Ala Thr Ser Glu Pro Gly Leu Ala Phe Ala Phe Gly Lys
            195                 200                 205

Phe Asp Gly Ile Leu Gly Leu Ala Tyr Asp Ser Ile Ser Val Asn His
210                 215                 220

Ile Val Pro Pro Val Tyr Asn Ala Ile Asn Gln Gly Leu Leu Asp Lys
225                 230                 235                 240

Pro Gln Val Ser Phe Tyr Leu Gly Asn Thr Glu Lys Asp Glu Asn Asp
                245                 250                 255

Gly Gly Leu Ala Thr Phe Gly Gly Tyr Asp Ala Ser Leu Phe Gln Gly
            260                 265                 270

Lys Ile Thr Trp Leu Pro Val Arg Arg Lys Ala Tyr Trp Glu Val Ser
            275                 280                 285

Phe Glu Gly Ile Gly Leu Gly Asp Glu Tyr Ala Glu Leu Gln Lys Thr
            290                 295                 300

Gly Ala Ala Ile Asp Thr Gly Thr Ser Leu Ile Thr Leu Pro Ser Ser
305                 310                 315                 320

Leu Ala Glu Ile Ile Asn Ala Lys Ile Gly Ala Thr Lys Ser Trp Ser
                325                 330                 335

Gly Gln Tyr Gln Ile Asp Cys Ala Lys Arg Asp Glu Leu Pro Asp Leu
            340                 345                 350

Thr Leu Thr Phe Ala Gly His Asn Phe Thr Leu Thr Ala His Asp Tyr
            355                 360                 365

Ile Leu Glu Val Ser Gly Ser Cys Ile Ser Val Phe Thr Pro Met Asp
370                 375                 380

Phe Pro Lys Pro Ile Gly Asp Leu Ala Ile Ile Gly Asp Ala Phe Leu
385                 390                 395                 400

Arg Lys Tyr Tyr Ser Ile Tyr Asp Leu Asp Lys Asn Ala Val Gly Leu
                405                 410                 415

Ala Pro Ser Lys Ala
            420

<210> SEQ ID NO 35
<211> LENGTH: 551
```

<212> TYPE: PRT
<213> ORGANISM: Candida viswanathii

<400> SEQUENCE: 35

```
Met Gly Ile Thr Asn Glu Thr Gln Ala Leu Leu Gly Gly Asp Ser Leu
1               5                   10                  15

Ser Cys Leu Asn Lys Lys Ser Asn Thr Lys Arg Asn Leu Ser Tyr
            20                  25                  30

Leu Leu Asn Ile Ile Thr Val Ser Ile Ala Tyr Leu Cys Phe Phe
            35                  40                  45

Ala Thr His Asn His Asn Asp Ser Gly Ile Pro Lys Val Asp Pro
        50                  55                  60

His Lys Lys Lys Asn Ile Ile Met Met Val Thr Asp Gly Met Gly Pro
65                  70                  75                  80

Ala Ser Leu Ser Ala Ala Arg Ser Phe Arg Gln Phe Arg Asp Lys Leu
                85                  90                  95

Ala Ile Asn Asp Ile Leu Thr Leu Asp Gln Tyr Leu Ile Gly Ser Ser
                100                 105                 110

Arg Thr Arg Ser Ser Ser Ser Leu Val Thr Asp Ser Ala Ala Gly Ala
        115                 120                 125

Thr Ala Phe Ser Cys Ala Leu Lys Ser Tyr Asn Gly Ala Ile Gly Val
130                 135                 140

Ser Pro Asp Lys Ser Pro Cys Gly Thr Ile Leu Glu Ala Leu Lys Leu
145                 150                 155                 160

Gln Gly Tyr Tyr Thr Gly Leu Val Val Thr Arg Ile Thr Asp Ala
                165                 170                 175

Thr Pro Ala Ala Phe Ser Ala His Val Asp Tyr Arg Phe Gln Glu Asp
        180                 185                 190

Leu Ile Ala Glu His Gln Leu Gly Glu Tyr Pro Phe Gly Arg Ala Val
                195                 200                 205

Asp Leu Ile Leu Gly Gly Gly Arg Cys His Phe Leu Pro Thr Ala Gln
        210                 215                 220

Gly Gly Cys Arg Ala Asp Asp Arg Asn Leu Ile Lys Glu Ser Ser Asp
225                 230                 235                 240

Thr Trp Gln Tyr Val Gly Asp Arg Gln Gln Phe Asp Gln Leu Lys Gly
                245                 250                 255

Gly Lys Asn Val Ser Leu Pro Leu Leu Gly Leu Leu Ala Asn Thr Asp
            260                 265                 270

Ile Pro Tyr Ala Ile Asp Arg Asp Glu Lys Glu Tyr Pro Ser Leu Ala
            275                 280                 285

Glu Gln Val Lys Val Ala Leu Thr Ala Leu Ser Asp Ala Thr Lys Asp
290                 295                 300

Ser Asp Gln Gly Phe Phe Leu Leu Ile Glu Gly Ser Arg Ile Asp His
305                 310                 315                 320

Ala Gly His His Asn Asp Pro Thr Ala Gln Val Arg Glu Val Leu Ala
                325                 330                 335

Tyr Asp Glu Ala Phe Gly Glu Val Ile Lys Phe Ile Asp Ser Thr Asp
                340                 345                 350

Val Glu Thr Val Ala Ile Ser Ser Asp His Glu Thr Gly Gly Leu
        355                 360                 365

Val Val Ser Arg Gln Val Thr Pro Glu Tyr Asp Tyr Ile Trp Tyr
        370                 375                 380

Pro Glu Val Leu Leu Asn Ser Thr His Ser Gly Asp Tyr Leu Ala His
385                 390                 395                 400
```

```
Lys Ile Ala Asp Tyr Lys Asn Lys Asp Asp Thr Ala Lys Leu Thr Lys
                405                 410                 415

Phe Ile Lys His Glu Ile Leu Glu Thr Asp Leu Gly Val Thr Asp Tyr
            420                 425                 430

Thr Asp Lys Asp Val Gln Ala Ile Leu Asp Lys Val Asn Asp Pro Ala
        435                 440                 445

Asn Leu Leu Tyr Val Leu Asn Asp Ile Val Ser Phe Arg Ala Gln Ile
    450                 455                 460

Gly Trp Thr Thr His Gly His Ser Ala Val Asp Val Asn Ile Tyr Ala
465                 470                 475                 480

His Thr Asn Ser Pro Ala Ile Arg Ala Lys Leu Ala Ser Ala Lys Ala
                485                 490                 495

Tyr His Gly Leu Ser Gly Asn His Glu Asn Ile Glu Ile Gly Ala Phe
                500                 505                 510

Met Glu Glu Ile Thr Gly Ser Asn Leu Ser Arg Val Thr Glu Leu Ile
            515                 520                 525

Lys Lys Thr Ala His Ser Pro Ser Leu Ser Lys Lys Glu Phe Ser Val
        530                 535                 540

Asp Glu Phe His Gly Asn Val
545                 550

<210> SEQ ID NO 36
<211> LENGTH: 140
<212> TYPE: PRT
<213> ORGANISM: Saccharomyces cerevisiae

<400> SEQUENCE: 36

Met Cys Cys Tyr Cys Val Cys Cys Thr Val Ser Asp Phe Ile Leu Tyr
1               5                   10                  15

Ile Val Ala Phe Phe Pro Pro Ala Ala Val Leu Leu Arg Ser Gly
            20                  25                  30

Pro Cys Ser Ser Asp Phe Leu Leu Asn Val Leu Leu Thr Leu Leu Gly
        35                  40                  45

Phe Leu Pro Gly Met Leu His Ala Phe Tyr Tyr Ile Thr Ile Thr Ser
    50                  55                  60

Pro Leu Arg Asn Ala Glu Tyr Val Tyr Tyr Gln Gln Gly Trp Val
65                  70                  75                  80

Asp Ser Glu Arg Asn Val Pro Ser Asn Arg Pro Gln Asn Ser Gln Thr
                85                  90                  95

Pro Gln Asn Arg Pro Gln Gln Gly Ser Ser Ala Arg Asn Val Tyr Pro
            100                 105                 110

Ser Val Glu Thr Pro Leu Leu Gln Gly Ala Ala Pro His Asp Asn Lys
        115                 120                 125

Gln Ser Leu Val Glu Ser Pro Pro Tyr Val Pro
    130                 135                 140

<210> SEQ ID NO 37
<211> LENGTH: 377
<212> TYPE: PRT
<213> ORGANISM: Candida viswanathii

<400> SEQUENCE: 37

Met Arg Leu Lys Asp Ile Lys Leu Ile Leu Ile Gly Ile Leu Thr Ile
1               5                   10                  15

Ser Val Thr Tyr Phe Leu Ile Ser Ser Phe Ser Gly Pro Arg Ala Tyr
            20                  25                  30
```

```
Thr Thr Ser Asp Pro Asn Ser Ser Lys Met Gln Phe Leu Arg Ala Leu
        35                  40                  45

Glu Ser His Pro Asn Trp Lys Glu Thr Gly Leu Asn Phe Gln Pro Thr
 50                  55                  60

Lys Lys Leu Glu Val Asp Asp Ser Ser Thr Pro Val Arg Gln Gln Leu
 65                  70                  75                  80

Ala Ala Arg Phe Pro Tyr Asp Pro Thr Gln Pro Phe Pro Lys Asn Ile
                85                  90                  95

Trp Gln Thr Trp Lys Val Gly Ile Glu Asp Glu Thr Phe Pro Lys Arg
                100                 105                 110

Tyr Leu Lys Phe Gln Leu Ser Trp Asp Thr Lys Asn Pro Glu Tyr Lys
            115                 120                 125

His His Val Ile Pro Asp Asp Gln Cys Asp Glu Leu Val Ala Gln Leu
        130                 135                 140

Phe Glu Asp Val Pro Asp Val Ala Arg Ala Tyr Lys Val Met Pro Lys
145                 150                 155                 160

Ser Ile Leu Lys Ala Asp Phe Phe Arg Tyr Leu Ile Leu Phe Ala Arg
                165                 170                 175

Gly Gly Val Tyr Thr Asp Ile Asp Thr Val Gly Leu Lys Pro Ile Asp
                180                 185                 190

Thr Trp Met Ser Asn Met Glu Leu Leu Trp Gly Glu Pro Asn Arg Ala
                195                 200                 205

Gly Leu Val Val Gly Ile Glu Ala Asp Pro Asp Arg Pro Asp Trp Ala
    210                 215                 220

Asp Trp Tyr Ala Arg Arg Ile Gln Phe Cys Gln Trp Thr Ile Gln Leu
225                 230                 235                 240

Lys Lys Gly His Pro Met Leu Arg Glu Leu Ile Thr Lys Ile Thr Asp
                245                 250                 255

Ile Thr Leu Thr Arg Glu Lys Arg Asn Glu Leu Lys Lys Val Leu Gly
            260                 265                 270

Lys Asp Glu Gly Gly Asp Ile Met Asn Trp Thr Gly Pro Gly Ile Phe
        275                 280                 285

Thr Asp Thr Val Phe Ser Tyr Met Asn Ala Ile Leu Gln Ala Pro Glu
    290                 295                 300

Val Ile Thr Gly Lys Tyr Lys Trp Asp Asn Ile Val Asp Trp Lys Val
305                 310                 315                 320

Phe Thr Gly Met Gln Met Pro Ile Ala Ile Asp Asp Val Leu Val Leu
                325                 330                 335

Pro Ile Thr Ser Phe Ser Pro Asp Val Ser Gln Met Gly Ser Lys Ser
            340                 345                 350

Ser Thr Asp Pro Met Ala Tyr Ala Lys His Met Phe Leu Gly Ser Trp
        355                 360                 365

Lys Asp Asp Gly Met Pro Glu Met Glu
    370                 375

<210> SEQ ID NO 38
<211> LENGTH: 720
<212> TYPE: PRT
<213> ORGANISM: Cannabis sativa

<400> SEQUENCE: 38

Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
```

```
            20                  25                  30
Leu Ala Glu Ile Val Cys Asn Tyr Gly Ala Thr Pro Gln Thr Trp
            35                  40                  45
Ile Asn Ile Ala Asn His Ile Leu Ser Pro Asp Leu Pro Phe Ser Leu
50                  55                  60
His Gln Met Leu Phe Tyr Gly Cys Tyr Lys Asp Phe Gly Pro Ala Pro
65                  70                  75                  80
Pro Ala Trp Ile Pro Asp Pro Glu Lys Val Lys Ser Thr Asn Leu Gly
                    85                  90                  95
Ala Leu Leu Glu Lys Arg Gly Lys Glu Phe Leu Gly Val Lys Tyr Lys
                100                 105                 110
Asp Pro Ile Ser Ser Phe Ser His Phe Gln Glu Phe Ser Val Arg Asn
                115                 120                 125
Pro Glu Val Tyr Trp Arg Thr Val Leu Met Asp Glu Met Lys Ile Ser
                130                 135                 140
Phe Ser Lys Asp Pro Glu Cys Ile Leu Arg Arg Asp Asp Ile Asn Asn
145                 150                 155                 160
Pro Gly Gly Ser Glu Trp Leu Pro Gly Gly Tyr Leu Asn Ser Ala Lys
                    165                 170                 175
Asn Cys Leu Asn Val Asn Ser Asn Lys Lys Leu Asn Asp Thr Met Ile
                180                 185                 190
Val Trp Arg Asp Glu Gly Asn Asp Asp Leu Pro Leu Asn Lys Leu Thr
                195                 200                 205
Leu Asp Gln Leu Arg Lys Arg Val Trp Leu Val Gly Tyr Ala Leu Glu
                210                 215                 220
Glu Met Gly Leu Glu Lys Gly Cys Ala Ile Ala Ile Asp Met Pro Met
225                 230                 235                 240
His Val Asp Ala Val Val Ile Tyr Leu Ala Ile Val Leu Ala Gly Tyr
                    245                 250                 255
Val Val Val Ser Ile Ala Asp Ser Phe Ser Ala Pro Glu Ile Ser Thr
                260                 265                 270
Arg Leu Arg Leu Ser Lys Ala Lys Ala Ile Phe Thr Gln Asp His Ile
                275                 280                 285
Ile Arg Gly Lys Lys Arg Ile Pro Leu Tyr Ser Arg Val Val Glu Ala
                290                 295                 300
Lys Ser Pro Met Ala Ile Val Ile Pro Cys Ser Gly Ser Asn Ile Gly
305                 310                 315                 320
Ala Glu Leu Arg Asp Gly Asp Ile Ser Trp Asp Tyr Phe Leu Glu Arg
                    325                 330                 335
Ala Lys Glu Phe Lys Asn Cys Glu Phe Thr Ala Arg Glu Gln Pro Val
                340                 345                 350
Asp Ala Tyr Thr Asn Ile Leu Phe Ser Ser Gly Thr Thr Gly Glu Pro
                355                 360                 365
Lys Ala Ile Pro Trp Thr Gln Ala Thr Pro Leu Lys Ala Ala Ala Asp
                370                 375                 380
Gly Trp Ser His Leu Asp Ile Arg Lys Gly Asp Val Ile Val Trp Pro
385                 390                 395                 400
Thr Asn Leu Gly Trp Met Met Gly Pro Trp Leu Val Tyr Ala Ser Leu
                    405                 410                 415
Leu Asn Gly Ala Ser Ile Ala Leu Tyr Asn Gly Ser Pro Leu Val Ser
                420                 425                 430
Gly Phe Ala Lys Phe Val Gln Asp Ala Lys Val Thr Met Leu Gly Val
                435                 440                 445
```

```
Val Pro Ser Ile Val Arg Ser Trp Lys Ser Thr Asn Cys Val Ser Gly
    450                 455                 460

Tyr Asp Trp Ser Thr Ile Arg Cys Phe Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720

<210> SEQ ID NO 39
<211> LENGTH: 385
<212> TYPE: PRT
<213> ORGANISM: Cannabis sativa

<400> SEQUENCE: 39

Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
```

```
                100                 105                 110
Pro Lys Ser Lys Ile Thr His Leu Ile Phe Thr Ser Ala Ser Thr Thr
            115                 120                 125

Asp Met Pro Gly Ala Asp Tyr His Cys Ala Lys Leu Leu Gly Leu Ser
        130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Asp Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
290                 295                 300

Asp Lys Val Glu Glu Lys Leu Asp Leu Lys Lys Glu Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
370                 375                 380

Tyr
385

<210> SEQ ID NO 40
<211> LENGTH: 391
<212> TYPE: PRT
<213> ORGANISM: Artificial Sequence
<220> FEATURE:
<223> OTHER INFORMATION: Cannabis sativa

<400> SEQUENCE: 40

Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
```

```
                65                  70                  75                  80
Met Gln Thr Leu Asp Ala Arg Gln Asp Met Leu Val Glu Val Pro
                    85                  90                  95

Lys Leu Gly Lys Asp Ala Cys Ala Lys Ala Ile Lys Glu Trp Gly Gln
                100                 105                 110

Pro Lys Ser Lys Ile Thr His Leu Ile Phe Thr Ser Ala Ser Thr Thr
                115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                    165                 170                 175

Ala Arg Val Leu Ala Val Cys Cys Asp Ile Met Ala Cys Leu Phe Arg
                180                 185                 190

Gly Pro Ser Asp Ser Asp Leu Glu Leu Leu Val Gly Gln Ala Ile Phe
                195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                    245                 250                 255

Leu Ile Phe Asp Leu His Lys Asp Val Pro Met Leu Ile Ser Asn Asn
                260                 265                 270

Ile Glu Lys Cys Leu Ile Glu Ala Phe Thr Pro Ile Gly Ile Ser Asp
                275                 280                 285

Trp Asn Ser Ile Phe Trp Ile Thr His Pro Gly Gly Lys Ala Ile Leu
    290                 295                 300

Asp Lys Val Glu Glu Lys Leu Asp Leu Lys Lys Glu Lys Phe Val Asp
305                 310                 315                 320

Ser Arg His Val Leu Ser Glu His Gly Asn Met Ser Ser Ser Thr Val
                    325                 330                 335

Leu Phe Val Met Asp Glu Leu Arg Lys Arg Ser Leu Glu Glu Gly Lys
                340                 345                 350

Ser Thr Thr Gly Asp Gly Phe Glu Trp Gly Val Leu Phe Gly Phe Gly
                355                 360                 365

Pro Gly Leu Thr Val Glu Arg Val Val Arg Ser Val Pro Ile Lys
    370                 375                 380

Tyr Gly Arg Arg Ala Lys Leu
385                 390

<210> SEQ ID NO 41
<211> LENGTH: 105
<212> TYPE: PRT
<213> ORGANISM: Cannabis sativa

<400> SEQUENCE: 41

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
                20                  25                  30

Ile Ile Pro Ala Met Lys Asp Val Tyr Trp Gly Lys Asp Val Thr Gln
                35                  40                  45
```

```
Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
 65                  70                  75                  80

Phe Gly Asp Val Tyr Arg Ser Phe Trp Glu Lys Leu Leu Ile Phe Asp
                 85                  90                  95

Tyr Thr Pro Arg Lys Leu Lys Pro Lys
                100                 105

<210> SEQ ID NO 42
<211> LENGTH: 111
<212> TYPE: PRT
<213> ORGANISM: Artificial Sequence
<220> FEATURE:
<223> OTHER INFORMATION: Cannabis sativa

<400> SEQUENCE: 42

Met Ala Val Lys His Leu Ile Val Leu Lys Phe Lys Asp Glu Ile Thr
  1               5                  10                  15

Glu Ala Gln Lys Glu Glu Phe Phe Lys Thr Tyr Val Asn Leu Val Asn
                 20                  25                  30

Ile Ile Pro Ala Met Lys Asp Val Tyr Trp Gly Lys Asp Val Thr Gln
             35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
 65                  70                  75                  80

Phe Gly Asp Val Tyr Arg Ser Phe Trp Glu Lys Leu Leu Ile Phe Asp
                 85                  90                  95

Tyr Thr Pro Arg Lys Leu Lys Pro Lys Gly Arg Arg Ala Lys Leu
                100                 105                 110

<210> SEQ ID NO 43
<211> LENGTH: 393
<212> TYPE: PRT
<213> ORGANISM: Cannabis sativa

<400> SEQUENCE: 43

Met Gly Leu Ser Ser Val Cys Thr Phe Ser Phe Gln Thr Asn Tyr His
  1               5                  10                  15

Thr Leu Leu Asn Pro His Asn Asn Pro Lys Thr Ser Leu Leu Cys
                 20                  25                  30

Tyr Arg His Pro Lys Thr Pro Ile Lys Tyr Ser Tyr Asn Asn Phe Pro
             35                  40                  45

Ser Lys His Thr Lys Ser Phe His Leu Gln Asn Lys Cys Ser Glu Ser
    50                  55                  60

Leu Ser Ile Ala Lys Asn Ser Ile Arg Ala Ala Thr Thr Asn Gln Thr
 65                  70                  75                  80

Glu Pro Pro Glu Ser Asp Asn His Ser Val Ala Thr Lys Ile Leu Asn
                 85                  90                  95

Phe Gly Lys Ala Cys Trp Lys Leu Gln Arg Pro Tyr Thr Ile Ile Ala
                100                 105                 110

Phe Thr Ser Cys Ala Cys Gly Leu Phe Gly Lys Glu Leu His Asn
            115                 120                 125

Thr Asn Leu Ile Ser Trp Ser Leu Met Phe Lys Ala Phe Phe Phe Leu
    130                 135                 140

Val Ala Ile Leu Cys Ile Ala Ser Phe Thr Thr Thr Ile Asn Gln Ile
```

```
                145                 150                 155                 160
Tyr Asp Leu His Ile Asp Arg Ile Asn Lys Pro Asp Leu Pro Leu Ala
                165                 170                 175

Ser Gly Glu Ile Ser Val Asn Thr Ala Trp Ile Met Ser Ile Ile Val
            180                 185                 190

Ala Leu Phe Gly Leu Ile Ile Thr Ile Lys Met Lys Gly Gly Pro Leu
        195                 200                 205

Tyr Ile Phe Gly Tyr Cys Phe Gly Ile Phe Gly Gly Ile Val Tyr Ser
    210                 215                 220

Val Pro Pro Phe Arg Trp Lys Gln Asn Pro Ser Thr Ala Phe Leu Leu
225                 230                 235                 240

Asn Phe Leu Ala His Ile Ile Thr Asn Phe Thr Phe Tyr Tyr Ala Ser
                245                 250                 255

Arg Ala Ala Leu Gly Leu Pro Phe Glu Leu Arg Pro Ser Phe Thr Phe
            260                 265                 270

Leu Leu Ala Phe Met Lys Ser Met Gly Ser Ala Leu Ala Leu Ile Lys
        275                 280                 285

Asp Ala Ser Asp Val Glu Gly Asp Thr Lys Phe Gly Ile Ser Thr Leu
    290                 295                 300

Ala Ser Lys Tyr Gly Ser Arg Asn Leu Thr Leu Phe Cys Ser Gly Ile
305                 310                 315                 320

Val Leu Leu Ser Tyr Val Ala Ala Ile Leu Ala Gly Ile Ile Trp Pro
                325                 330                 335

Gln Ala Phe Asn Ser Asn Val Met Leu Leu Ser His Ala Ile Leu Ala
            340                 345                 350

Phe Trp Leu Ile Leu Gln Thr Arg Asp Phe Ala Leu Thr Asn Tyr Asp
        355                 360                 365

Pro Glu Ala Gly Arg Arg Phe Tyr Glu Phe Met Trp Lys Leu Tyr Tyr
    370                 375                 380

Ala Glu Tyr Leu Val Tyr Val Phe Ile
385                 390

<210> SEQ ID NO 44
<211> LENGTH: 321
<212> TYPE: PRT
<213> ORGANISM: Artificial Sequence
<220> FEATURE:
<223> OTHER INFORMATION: Cannabis sativa

<400> SEQUENCE: 44

Met Ala Ala Thr Thr Asn Gln Thr Glu Pro Pro Glu Ser Asp Asn His
1               5                   10                  15

Ser Val Ala Thr Lys Ile Leu Asn Phe Gly Lys Ala Cys Trp Lys Leu
            20                  25                  30

Gln Arg Pro Tyr Thr Ile Ile Ala Phe Thr Ser Cys Ala Cys Gly Leu
        35                  40                  45

Phe Gly Lys Glu Leu Leu His Asn Thr Asn Leu Ile Ser Trp Ser Leu
    50                  55                  60

Met Phe Lys Ala Phe Phe Phe Leu Val Ala Ile Leu Cys Ile Ala Ser
65                  70                  75                  80

Phe Thr Thr Thr Ile Asn Gln Ile Tyr Asp Leu His Ile Asp Arg Ile
                85                  90                  95

Asn Lys Pro Asp Leu Pro Leu Ala Ser Gly Glu Ile Ser Val Asn Thr
            100                 105                 110

Ala Trp Ile Met Ser Ile Ile Val Ala Leu Phe Gly Leu Ile Ile Thr
```

```
            115                 120                 125
Ile Lys Met Lys Gly Gly Pro Leu Tyr Ile Phe Gly Tyr Cys Phe Gly
        130                 135                 140

Ile Phe Gly Gly Ile Val Tyr Ser Val Pro Phe Arg Trp Lys Gln
145                 150                 155                 160

Asn Pro Ser Thr Ala Phe Leu Leu Asn Phe Leu Ala His Ile Ile Thr
                    165                 170                 175

Asn Phe Thr Phe Tyr Tyr Ala Ser Arg Ala Ala Leu Gly Leu Pro Phe
                180                 185                 190

Glu Leu Arg Pro Ser Phe Thr Phe Leu Leu Ala Phe Met Lys Ser Met
            195                 200                 205

Gly Ser Ala Leu Ala Leu Ile Lys Asp Ala Ser Asp Val Glu Gly Asp
        210                 215                 220

Thr Lys Phe Gly Ile Ser Thr Leu Ala Ser Lys Tyr Gly Ser Arg Asn
225                 230                 235                 240

Leu Thr Leu Phe Cys Ser Gly Ile Val Leu Leu Ser Tyr Val Ala Ala
                    245                 250                 255

Ile Leu Ala Gly Ile Ile Trp Pro Gln Ala Phe Asn Ser Asn Val Met
                260                 265                 270

Leu Leu Ser His Ala Ile Leu Ala Phe Trp Leu Ile Leu Gln Thr Arg
            275                 280                 285

Asp Phe Ala Leu Thr Asn Tyr Asp Pro Glu Ala Gly Arg Arg Phe Tyr
        290                 295                 300

Glu Phe Met Trp Lys Leu Tyr Tyr Ala Glu Tyr Leu Val Tyr Val Phe
305                 310                 315                 320

Ile

<210> SEQ ID NO 45
<211> LENGTH: 398
<212> TYPE: PRT
<213> ORGANISM: Cannabis sativa

<400> SEQUENCE: 45

Met Gly Leu Ser Leu Val Cys Thr Phe Ser Phe Gln Thr Asn Tyr His
1               5                   10                  15

Thr Leu Leu Asn Pro His Asn Lys Asn Pro Lys Asn Ser Leu Leu Ser
                20                  25                  30

Tyr Gln His Pro Lys Thr Pro Ile Ile Lys Ser Ser Tyr Asp Asn Phe
            35                  40                  45

Pro Ser Lys Tyr Cys Leu Thr Lys Asn Phe His Leu Leu Gly Leu Asn
        50                  55                  60

Ser His Asn Arg Ile Ser Ser Gln Ser Arg Ser Ile Arg Ala Gly Ser
65                  70                  75                  80

Asp Gln Ile Glu Gly Ser Pro His His Glu Ser Asp Asn Ser Ile Ala
                85                  90                  95

Thr Lys Ile Leu Asn Phe Gly His Thr Cys Trp Lys Leu Gln Arg Pro
            100                 105                 110

Tyr Val Val Lys Gly Met Ile Ser Ile Ala Cys Gly Leu Phe Gly Arg
        115                 120                 125

Glu Leu Phe Asn Asn Arg His Leu Phe Ser Trp Gly Leu Met Trp Lys
    130                 135                 140

Ala Phe Phe Ala Leu Val Pro Ile Leu Ser Phe Asn Phe Phe Ala Ala
145                 150                 155                 160

Ile Met Asn Gln Ile Tyr Asp Val Asp Ile Asp Arg Ile Asn Lys Pro
```

-continued

```
                165                 170                 175

Asp Leu Pro Leu Val Ser Gly Glu Met Ser Ile Glu Thr Ala Trp Ile
            180                 185                 190

Leu Ser Ile Ile Val Ala Leu Thr Gly Leu Ile Val Thr Ile Lys Leu
            195                 200                 205

Lys Ser Ala Pro Leu Phe Val Phe Ile Tyr Ile Phe Gly Ile Phe Ala
            210                 215                 220

Gly Phe Ala Tyr Ser Val Pro Pro Ile Arg Trp Lys Gln Tyr Pro Phe
225                 230                 235                 240

Thr Asn Phe Leu Ile Thr Ile Ser Ser His Val Gly Leu Ala Phe Thr
            245                 250                 255

Ser Tyr Ser Ala Thr Thr Ser Ala Leu Gly Leu Pro Phe Val Trp Arg
            260                 265                 270

Pro Ala Phe Ser Phe Ile Ile Ala Phe Met Thr Val Met Gly Met Thr
            275                 280                 285

Ile Ala Phe Ala Lys Asp Ile Ser Asp Ile Glu Gly Asp Ala Lys Tyr
            290                 295                 300

Gly Val Ser Thr Val Ala Thr Lys Leu Gly Ala Arg Asn Met Thr Phe
305                 310                 315                 320

Val Val Ser Gly Val Leu Leu Leu Asn Tyr Leu Val Ser Ile Ser Ile
            325                 330                 335

Gly Ile Ile Trp Pro Gln Val Phe Lys Ser Asn Ile Met Ile Leu Ser
            340                 345                 350

His Ala Ile Leu Ala Phe Cys Leu Ile Phe Gln Thr Arg Glu Leu Ala
            355                 360                 365

Leu Ala Asn Tyr Ala Ser Ala Pro Ser Arg Gln Phe Phe Glu Phe Ile
            370                 375                 380

Trp Leu Leu Tyr Tyr Ala Glu Tyr Phe Val Tyr Val Phe Ile
385                 390                 395

<210> SEQ ID NO 46
<211> LENGTH: 394
<212> TYPE: PRT
<213> ORGANISM: Cannabis sativa

<400> SEQUENCE: 46

Met Gly Leu Ser Ser Val Cys Thr Phe Ser Phe Gln Thr Asn Tyr His
1               5                   10                  15

Thr Leu Leu Asn Pro His Asn Asn Pro Lys Thr Ser Leu Leu Tyr
            20                  25                  30

Arg His Pro Lys Thr Pro Ile Lys Tyr Ser Tyr Asn Asn Phe Pro Ser
            35                  40                  45

Lys His Cys Ser Thr Lys Ser Phe His Leu Gln Asn Lys Cys Ser Glu
50                  55                  60

Ser Leu Ser Ile Ala Lys Asn Ser Ile Arg Ala Ala Thr Thr Asn Gln
65                  70                  75                  80

Thr Glu Pro Pro Glu Ser Asp Asn His Ser Val Ala Thr Lys Ile Leu
            85                  90                  95

Asn Phe Gly Lys Ala Cys Trp Lys Leu Gln Arg Pro Tyr Thr Ile Ile
            100                 105                 110

Ala Phe Thr Ser Cys Ala Cys Gly Leu Phe Gly Lys Glu Leu Leu His
            115                 120                 125

Asn Thr Asn Leu Ile Ser Trp Ser Leu Met Phe Lys Ala Phe Phe Phe
            130                 135                 140
```

```
Leu Val Ala Val Leu Cys Ile Ala Ser Phe Thr Thr Thr Ile Asn Gln
145                 150                 155                 160

Ile Tyr Asp Leu His Ile Asp Arg Ile Asn Lys Pro Asp Leu Pro Leu
                165                 170                 175

Ala Ser Gly Glu Ile Ser Val Asn Thr Ala Trp Ile Met Ser Ile Ile
            180                 185                 190

Val Ala Leu Phe Gly Leu Ile Ile Thr Ile Lys Met Lys Gly Gly Pro
        195                 200                 205

Leu Tyr Ile Phe Gly Tyr Cys Phe Gly Ile Phe Gly Gly Thr Val Tyr
    210                 215                 220

Ser Val Pro Pro Phe Arg Trp Lys Gln Asn Pro Ser Thr Ala Phe Leu
225                 230                 235                 240

Leu Asn Phe Leu Ala His Ile Ile Thr Asn Phe Thr Phe Tyr His Ala
                245                 250                 255

Ser Arg Ala Ala Leu Gly Leu Pro Phe Glu Leu Arg Pro Ser Phe Thr
                260                 265                 270

Phe Leu Leu Ala Phe Met Lys Ser Met Gly Ser Ala Leu Ala Leu Ile
            275                 280                 285

Lys Asp Ala Ser Asp Val Glu Gly Asp Thr Lys Phe Gly Ile Ser Thr
290                 295                 300

Leu Ala Ser Lys Tyr Gly Ser Arg Asn Leu Thr Leu Phe Cys Ser Gly
305                 310                 315                 320

Ile Val Leu Leu Ser Tyr Val Ala Ala Ile Leu Ala Gly Ile Ile Trp
                325                 330                 335

Pro Gln Ala Phe Asn Ser Asn Val Met Leu Leu Ser His Ala Ile Leu
            340                 345                 350

Ala Phe Trp Leu Ile Leu Gln Thr Arg Asp Phe Ala Leu Thr Asn Tyr
        355                 360                 365

Asp Pro Glu Ala Gly Arg Arg Phe Tyr Glu Phe Met Trp Lys Leu Tyr
    370                 375                 380

Tyr Ala Glu Tyr Leu Val Tyr Val Phe Ile
385                 390

<210> SEQ ID NO 47
<211> LENGTH: 397
<212> TYPE: PRT
<213> ORGANISM: Cannabis sativa

<400> SEQUENCE: 47

Met Glu Leu Ser Ser Ile Cys Asn Phe Ser Phe Gln Thr Asn Tyr His
1               5                   10                  15

Thr Leu Leu Asn Pro His Asn Lys Asn Pro Lys Ser Ser Leu Leu Ser
                20                  25                  30

His Gln His Pro Lys Thr Pro Ile Ile Thr Ser Ser Tyr Asn Asn Phe
            35                  40                  45

Pro Ser Asn Tyr Cys Ser Asn Lys Asn Phe His Leu Gln Asn Arg Cys
        50                  55                  60

Ser Lys Ser Leu Leu Ile Ala Lys Asn Ser Ile Arg Thr Asp Thr Ala
65                  70                  75                  80

Asn Gln Thr Glu Pro Pro Glu Ser Asn Thr Lys Tyr Ser Val Val Thr
                85                  90                  95

Lys Ile Leu Ser Phe Gly His Thr Cys Trp Lys Leu Gln Arg Pro Tyr
            100                 105                 110

Thr Phe Ile Gly Val Ile Ser Cys Ala Cys Gly Leu Phe Gly Arg Glu
        115                 120                 125
```

Leu Phe His Asn Thr Asn Leu Leu Ser Trp Ser Leu Met Leu Lys Ala
            130                 135                 140

Phe Ser Ser Leu Met Val Ile Leu Ser Val Asn Leu Cys Thr Asn Ile
145                 150                 155                 160

Ile Asn Gln Ile Thr Asp Leu Asp Ile Asp Arg Ile Asn Lys Pro Asp
                165                 170                 175

Leu Pro Leu Ala Ser Gly Glu Met Ser Ile Glu Thr Ala Trp Ile Met
            180                 185                 190

Ser Ile Ile Val Ala Leu Thr Gly Leu Ile Leu Thr Ile Lys Leu Asn
        195                 200                 205

Cys Gly Pro Leu Phe Ile Ser Leu Tyr Cys Val Ser Ile Leu Val Gly
210                 215                 220

Ala Leu Tyr Ser Val Pro Pro Phe Arg Trp Lys Gln Asn Pro Asn Thr
225                 230                 235                 240

Ala Phe Ser Ser Tyr Phe Met Gly Leu Val Ile Val Asn Phe Thr Cys
                245                 250                 255

Tyr Tyr Ala Ser Arg Ala Ala Phe Gly Leu Pro Phe Glu Met Ser Pro
            260                 265                 270

Pro Phe Thr Phe Ile Leu Ala Phe Val Lys Ser Met Gly Ser Ala Leu
        275                 280                 285

Phe Leu Cys Lys Asp Val Ser Asp Ile Glu Gly Asp Ser Lys His Gly
290                 295                 300

Ile Ser Thr Leu Ala Thr Arg Tyr Gly Ala Lys Asn Ile Thr Phe Leu
305                 310                 315                 320

Cys Ser Gly Ile Val Leu Leu Thr Tyr Val Ser Ala Ile Leu Ala Ala
                325                 330                 335

Ile Ile Trp Pro Gln Ala Phe Lys Ser Asn Val Met Leu Leu Ser His
            340                 345                 350

Ala Thr Leu Ala Phe Trp Leu Ile Phe Gln Thr Arg Glu Phe Ala Leu
        355                 360                 365

Thr Asn Tyr Asn Pro Glu Ala Gly Arg Lys Phe Tyr Glu Phe Met Trp
370                 375                 380

Lys Leu His Tyr Ala Glu Tyr Leu Val Tyr Val Phe Ile
385                 390                 395

<210> SEQ ID NO 48
<211> LENGTH: 400
<212> TYPE: PRT
<213> ORGANISM: Cannabis sativa

<400> SEQUENCE: 48

Met Val Phe Ser Ser Val Cys Ser Phe Pro Ser Ser Leu Gly Thr Asn
1               5                   10                  15

Phe Lys Leu Val Pro Arg Ser Asn Phe Lys Ala Ser Ser Ser His Tyr
            20                  25                  30

His Glu Ile Asn Asn Phe Ile Asn Asn Lys Pro Ile Lys Phe Ser Tyr
        35                  40                  45

Phe Ser Ser Arg Leu Tyr Cys Ser Ala Lys Pro Ile Val His Arg Glu
50                  55                  60

Asn Lys Phe Thr Lys Ser Phe Ser Leu Ser His Leu Gln Arg Lys Ser
65                  70                  75                  80

Ser Ile Lys Ala His Gly Glu Ile Glu Ala Asp Gly Ser Asn Gly Thr
                85                  90                  95

Ser Glu Phe Asn Val Met Lys Ser Gly Asn Ala Ile Trp Arg Phe Val

```
            100                 105                 110
Arg Pro Tyr Ala Ala Lys Gly Val Leu Phe Asn Ser Ala Ala Met Phe
        115                 120                 125

Ala Lys Glu Leu Val Gly Asn Leu Asn Leu Phe Ser Trp Pro Leu Met
130                 135                 140

Phe Lys Ile Leu Ser Phe Thr Leu Val Ile Leu Cys Ile Phe Val Ser
145                 150                 155                 160

Thr Ser Gly Ile Asn Gln Ile Tyr Asp Leu Asp Ile Asp Arg Leu Asn
                165                 170                 175

Lys Pro Asn Leu Pro Val Ala Ser Gly Glu Ile Ser Val Glu Leu Ala
            180                 185                 190

Trp Leu Leu Thr Ile Val Cys Thr Ile Ser Gly Leu Thr Leu Thr Ile
        195                 200                 205

Ile Thr Asn Ser Gly Pro Phe Phe Pro Phe Leu Tyr Ser Ala Ser Ile
    210                 215                 220

Phe Phe Gly Phe Leu Tyr Ser Ala Pro Pro Phe Arg Trp Lys Lys Asn
225                 230                 235                 240

Pro Phe Thr Ala Cys Phe Cys Asn Val Met Leu Tyr Val Gly Thr Ser
                245                 250                 255

Val Gly Val Tyr Tyr Ala Cys Lys Ala Ser Leu Gly Leu Pro Ala Asn
            260                 265                 270

Trp Ser Pro Ala Phe Cys Leu Leu Phe Trp Phe Ile Ser Leu Leu Ser
        275                 280                 285

Ile Pro Ile Ser Ile Ala Lys Asp Leu Ser Asp Ile Glu Gly Asp Arg
    290                 295                 300

Lys Phe Gly Ile Ile Thr Phe Ser Thr Lys Phe Gly Ala Lys Pro Ile
305                 310                 315                 320

Ala Tyr Ile Cys His Gly Leu Met Leu Leu Asn Tyr Val Ser Val Met
                325                 330                 335

Ala Ala Ala Ile Ile Trp Pro Gln Phe Phe Asn Ser Ser Val Ile Leu
            340                 345                 350

Leu Ser His Ala Phe Met Ala Ile Trp Val Leu Tyr Gln Ala Trp Ile
        355                 360                 365

Leu Glu Lys Ser Asn Tyr Ala Thr Glu Thr Cys Gln Lys Tyr Tyr Ile
    370                 375                 380

Phe Leu Trp Ile Ile Phe Ser Leu Glu His Ala Phe Tyr Leu Phe Met
385                 390                 395                 400

<210> SEQ ID NO 49
<211> LENGTH: 384
<212> TYPE: PRT
<213> ORGANISM: Cannabis sativa

<400> SEQUENCE: 49

Met Glu Leu Ser Leu Ser Leu Gly Gly Pro Thr Ile Phe Pro Arg Tyr
1               5                   10                  15

Arg Ala Ser Tyr Thr Ser Thr Lys Leu Thr Thr His Phe Ser Asn Phe
                20                  25                  30

Pro Ser Lys Phe Ser Thr Lys Asn Phe His Gln Thr Leu Ser Phe Tyr
            35                  40                  45

Gly Pro Thr Arg Gly Ser Lys Ser Leu Leu Asn Thr His Gln Trp Arg
        50                  55                  60

Asn Ser Ile Arg Ala Cys Ala Glu Ala Gly Ala Ala Gly Ser Asn Pro
65                  70                  75                  80
```

```
Val Leu Asn Lys Val Ser Asp Phe Arg Asp Ala Cys Trp Arg Phe Leu
                85                  90                  95

Arg Pro His Thr Ile Arg Gly Thr Thr Leu Gly Ser Ile Ala Leu Val
            100                 105                 110

Ala Arg Ala Leu Ile Glu Asn Pro Asn Leu Ile Lys Trp Ser Leu Leu
        115                 120                 125

Leu Lys Ala Phe Ser Gly Leu Leu Ala Leu Ile Cys Gly Asn Gly Tyr
    130                 135                 140

Ile Val Gly Ile Asn Gln Ile Tyr Asp Ile Gly Ile Asp Lys Val Asn
145                 150                 155                 160

Lys Pro Tyr Leu Pro Ile Ala Ala Gly Asp Leu Ser Val Gln Ser Ala
                165                 170                 175

Trp Tyr Leu Val Ile Leu Phe Ala Val Ala Gly Leu Leu Thr Val Gly
            180                 185                 190

Phe Asn Phe Gly Pro Phe Ile Thr Ser Leu Tyr Cys Leu Gly Leu Val
        195                 200                 205

Leu Gly Thr Ile Tyr Ser Val Pro Pro Phe Arg Met Lys Arg Phe Pro
    210                 215                 220

Val Ala Ala Phe Leu Ile Ile Ala Thr Val Arg Gly Phe Leu Leu Asn
225                 230                 235                 240

Phe Gly Val Tyr Tyr Ala Thr Arg Ala Ala Leu Gly Leu Thr Phe Glu
                245                 250                 255

Trp Ser Ser Ala Val Ala Phe Ile Thr Thr Phe Val Thr Leu Phe Ala
            260                 265                 270

Leu Val Ile Ala Ile Thr Lys Asp Leu Pro Asp Val Glu Gly Asp Arg
    275                 280                 285

Lys Phe Gln Ile Ser Thr Phe Ala Thr Lys Leu Gly Val Arg Asn Ile
290                 295                 300

Ala Tyr Leu Gly Ser Gly Leu Leu Leu Leu Asn Tyr Ile Gly Ala Ile
305                 310                 315                 320

Ala Ala Ala Ile Tyr Met Pro Gln Ala Phe Lys Arg Asn Leu Met Leu
                325                 330                 335

Pro Ile His Thr Ile Leu Ala Leu Ser Leu Val Phe Gln Ala Trp Val
            340                 345                 350

Leu Glu Gln Ala Asn Tyr Thr Lys Glu Ala Ile Ala Gly Phe Tyr Arg
    355                 360                 365

Phe Ile Trp Asn Leu Phe Tyr Val Glu Tyr Ile Ile Phe Pro Phe Ile
    370                 375                 380

<210> SEQ ID NO 50
<211> LENGTH: 387
<212> TYPE: PRT
<213> ORGANISM: Cannabis sativa

<400> SEQUENCE: 50

Met Ala Ile Ala Leu Trp Leu Pro Arg Ile Ser Arg Ser Thr Thr Arg
1               5                   10                  15

Arg Phe Leu Lys Pro Ser Ser Ser Leu Thr Leu Phe Ser Val Ser His
            20                  25                  30

Ser His Asn Tyr Ile Val Thr Ser Asn Arg Ser Pro Ile Pro Arg Leu
        35                  40                  45

Phe Thr Val Pro Asn Gln Ser His Gly Arg Glu Trp Val Ser Val Ser
    50                  55                  60

Glu Val Arg Leu Gly Tyr Val Ser His Ile Ser Thr Ala Gly Lys Ser
65                  70                  75                  80
```

```
Asp Glu Asn Arg Ser Arg Asp Ala Gln Val Ala Asp Val Ser Trp Ile
                85                  90                  95

Asp Leu Tyr Leu Pro Arg Gln Ile His Pro Tyr Val Arg Leu Ala Arg
            100                 105                 110

Leu Asp Lys Pro Ile Gly Thr Trp Leu Leu Ala Trp Pro Cys Met Trp
        115                 120                 125

Ser Ile Ser Leu Ala Ala Asn Pro Gly His Leu Pro Asp Ile Lys Met
    130                 135                 140

Met Thr Leu Phe Gly Cys Gly Ala Leu Leu Arg Gly Ala Gly Cys
145                 150                 155                 160

Thr Ile Asn Asp Leu Leu Asp Arg Asp Ile Asp Thr Met Val Glu Arg
                165                 170                 175

Thr Lys Leu Arg Pro Val Ala Ser Gly Ile Ile Thr Pro Phe Gln Gly
            180                 185                 190

Ile Cys Phe Leu Gly Phe Gln Leu Leu Gly Leu Gly Ile Leu Leu
        195                 200                 205

Gln Leu Asn Asn Tyr Ser Arg Ile Leu Gly Ala Ser Ser Leu Leu Leu
    210                 215                 220

Val Phe Ser Tyr Pro Leu Met Lys Arg Leu Thr Phe Trp Pro Gln Ala
225                 230                 235                 240

Tyr Leu Gly Leu Thr Phe Asn Trp Gly Ala Leu Leu Gly Trp Ala Ala
                245                 250                 255

Val Lys Gly Asn Ile Asp Pro Ala Ile Val Leu Pro Leu Tyr Ala Ser
            260                 265                 270

Gly Val Phe Trp Thr Leu Val Tyr Asp Thr Ile Tyr Ala His Gln Asp
        275                 280                 285

Lys Glu Asp Asp Val Arg Val Gly Ile Lys Ser Thr Ala Leu Arg Phe
    290                 295                 300

Gly Asp Leu Thr Lys Gln Trp Asn Met Gly Phe Gly Ala Ala Cys Ile
305                 310                 315                 320

Ser Ser Leu Ala Leu Ser Gly Tyr Asn Ala Glu Ile Gly Trp Pro Phe
                325                 330                 335

Tyr Ala Ser Leu Val Ala Ala Ser Gly Gln Leu Ala Trp Gln Ile Ser
            340                 345                 350

Thr Val Asp Leu Ser Ser Arg Asp Asp Cys Asn Lys Lys Phe Val Ser
        355                 360                 365

Asn Lys Trp Phe Gly Ala Ile Ile Phe Ser Gly Ile Val Leu Ala Arg
    370                 375                 380

Ile Ser Ser
385

<210> SEQ ID NO 51
<211> LENGTH: 308
<212> TYPE: PRT
<213> ORGANISM: Cannabis sativa

<400> SEQUENCE: 51

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
```

```
            50                  55                  60
Ile Ser Val Pro Thr Ser His Gly Asp Pro Tyr Ala Thr Val Val Glu
 65                  70                  75                  80

Lys Gly Leu Phe Pro Ala Thr Gly His Pro Val Asp Leu Leu Ala
                 85                  90                  95

Asp Thr Gln Lys His Leu Pro Val Ser Met Phe Ala Ile Asp Gly Glu
                100                 105                 110

Val Thr Gly Gly Phe Lys Lys Thr Tyr Ala Phe Phe Pro Thr Asp Asn
                115                 120                 125

Met Pro Gly Val Ala Glu Leu Ser Ala Ile Pro Ser Met Pro Pro Ala
                130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
                180                 185                 190

Val Arg Glu Leu Gly Leu His Val Pro Asn Glu Leu Gly Leu Lys Phe
                195                 200                 205

Cys Lys Arg Ser Phe Ser Val Tyr Pro Thr Leu Asn Trp Glu Thr Gly
210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
                260                 265                 270

Gly Leu Thr Leu Ser Pro Lys Glu Glu Tyr Tyr Lys Leu Gly Ala Tyr
                275                 280                 285

Tyr His Ile Thr Asp Val Gln Arg Gly Leu Leu Lys Ala Phe Asp Ser
                290                 295                 300

Leu Glu Asp Gly
305

<210> SEQ ID NO 52
<211> LENGTH: 852
<212> TYPE: PRT
<213> ORGANISM: Streptomyces

<400> SEQUENCE: 52

Met Ser Glu Ala Ala Asp Val Glu Arg Val Tyr Ala Ala Met Glu Glu
  1               5                  10                  15

Ala Ala Gly Leu Leu Gly Val Ala Cys Ala Arg Asp Lys Ile Tyr Pro
                 20                  25                  30

Leu Leu Ser Thr Phe Gln Asp Thr Leu Val Glu Gly Gly Ser Val Val
                 35                  40                  45

Val Phe Ser Met Ala Ser Gly Arg His Ser Thr Glu Leu Asp Phe Ser
 50                  55                  60

Ile Ser Val Pro Thr Ser His Gly Asp Pro Tyr Ala Thr Val Val Glu
 65                  70                  75                  80

Lys Gly Leu Phe Pro Ala Thr Gly His Pro Val Asp Leu Leu Ala
                 85                  90                  95

Asp Thr Gln Lys His Leu Pro Val Ser Met Phe Ala Ile Asp Gly Glu
                100                 105                 110
```

-continued

```
Val Thr Gly Gly Phe Lys Lys Thr Tyr Ala Phe Phe Pro Thr Asp Asn
            115                 120                 125

Met Pro Gly Val Ala Glu Leu Ser Ala Ile Pro Ser Met Pro Pro Ala
130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Gln Arg Gly Leu Leu Lys Ala Phe Asp Ser
    290                 295                 300

Leu Glu Asp Gly Met Lys Cys Ser Thr Phe Ser Phe Trp Phe Val Cys
305                 310                 315                 320

Lys Ile Ile Phe Phe Phe Ser Phe Asn Ile Gln Thr Ser Ile Ala
                325                 330                 335

Asn Pro Arg Glu Asn Phe Leu Lys Cys Phe Ser Gln Tyr Ile Pro Asn
            340                 345                 350

Asn Ala Thr Asn Leu Lys Leu Val Tyr Thr Gln Asn Asn Pro Leu Tyr
        355                 360                 365

Met Ser Val Leu Asn Ser Thr Ile His Asn Leu Arg Phe Thr Ser Asp
    370                 375                 380

Thr Thr Pro Lys Pro Leu Val Ile Val Thr Pro Ser His Val Ser His
385                 390                 395                 400

Ile Gln Gly Thr Ile Leu Cys Ser Lys Lys Val Gly Leu Gln Ile Arg
                405                 410                 415

Thr Arg Ser Gly Gly His Asp Ser Glu Gly Met Ser Tyr Ile Ser Gln
            420                 425                 430

Val Pro Phe Val Ile Val Asp Leu Arg Asn Met Arg Ser Ile Lys Ile
        435                 440                 445

Asp Val His Ser Gln Thr Ala Trp Val Glu Ala Gly Ala Thr Leu Gly
    450                 455                 460

Glu Val Tyr Tyr Trp Val Asn Glu Lys Asn Glu Asn Leu Ser Leu Ala
465                 470                 475                 480

Ala Gly Tyr Cys Pro Thr Val Cys Ala Gly Gly His Phe Gly Gly Gly
                485                 490                 495

Gly Tyr Gly Pro Leu Met Arg Asn Tyr Gly Leu Ala Ala Asp Asn Ile
            500                 505                 510

Ile Asp Ala His Leu Val Asn Val His Gly Lys Val Leu Asp Arg Lys
        515                 520                 525

Ser Met Gly Glu Asp Leu Phe Trp Ala Leu Arg Gly Gly Gly Ala Glu
```

```
            530             535             540
Ser Phe Gly Ile Ile Val Ala Trp Lys Ile Arg Leu Val Ala Val Pro
545                 550             555                 560

Lys Ser Thr Met Phe Ser Val Lys Lys Ile Met Glu Ile His Glu Leu
                565             570             575

Val Lys Leu Val Asn Lys Trp Gln Asn Ile Ala Tyr Lys Tyr Asp Lys
            580             585             590

Asp Leu Leu Leu Met Thr His Phe Ile Thr Arg Asn Ile Thr Asp Asn
                595             600             605

Gln Gly Lys Asn Lys Thr Ala Ile His Thr Tyr Phe Ser Ser Val Phe
            610             615             620

Leu Gly Gly Val Asp Ser Leu Val Asp Leu Met Asn Lys Ser Phe Pro
625                 630             635                 640

Glu Leu Gly Ile Lys Lys Thr Asp Cys Arg Gln Leu Ser Trp Ile Asp
                645             650             655

Thr Ile Ile Phe Tyr Ser Gly Val Val Asn Tyr Asp Thr Asp Asn Phe
                660             665             670

Asn Lys Glu Ile Leu Leu Asp Arg Ser Ala Gly Gln Asn Gly Ala Phe
            675             680             685

Lys Ile Lys Leu Asp Tyr Val Lys Lys Pro Ile Pro Glu Ser Val Phe
690                 695             700

Val Gln Ile Leu Glu Lys Leu Tyr Glu Glu Asp Ile Gly Ala Gly Met
705                 710             715                 720

Tyr Ala Leu Tyr Pro Tyr Gly Gly Ile Met Asp Glu Ile Ser Glu Ser
                725             730             735

Ala Ile Pro Phe Pro His Arg Ala Gly Ile Leu Tyr Glu Leu Trp Tyr
                740             745             750

Ile Cys Ser Trp Glu Lys Gln Glu Asp Asn Lys His Leu Asn Trp
            755             760             765

Ile Arg Asn Ile Tyr Asn Phe Met Thr Pro Tyr Val Ser Lys Asn Pro
            770             775             780

Arg Leu Ala Tyr Leu Asn Tyr Arg Asp Leu Asp Ile Gly Ile Asn Asp
785                 790             795             800

Pro Lys Asn Pro Asn Asn Tyr Thr Gln Ala Arg Ile Trp Gly Glu Lys
                805             810             815

Tyr Phe Gly Lys Asn Phe Asp Arg Leu Val Lys Val Lys Thr Leu Val
                820             825             830

Asp Pro Asn Asn Phe Phe Arg Asn Glu Gln Ser Ile Pro Pro Leu Pro
                835             840             845

Arg His Arg His
        850

<210> SEQ ID NO 53
<211> LENGTH: 573
<212> TYPE: PRT
<213> ORGANISM: Artificial Sequence
<220> FEATURE:
<223> OTHER INFORMATION: Cannabis sativa

<400> SEQUENCE: 53

Met Phe Leu Lys His Ile Phe Val Ala Leu Ala Phe Ala Leu Leu Ala
1               5               10              15

Asp Ala Thr Pro Ala Gln Lys Arg Ser Pro Gly Phe Val Ala Leu Asp
                20              25              30

Phe Asp Ile Val Lys Val Gln Lys Asn Val Thr Ala Asn Asp Asp Ala
```

-continued

```
                35                  40                  45
Ala Ala Ile Val Ala Lys Arg Gln Thr Asn Pro Arg Glu Asn Phe Leu
 50                  55                  60

Lys Cys Phe Ser Gln Tyr Ile Pro Asn Asn Ala Thr Asn Leu Lys Leu
 65                  70                  75                  80

Val Tyr Thr Gln Asn Asn Pro Leu Tyr Met Ser Val Leu Asn Ser Thr
                 85                  90                  95

Ile His Asn Leu Arg Phe Thr Ser Asp Thr Thr Pro Lys Pro Leu Val
                100                 105                 110

Ile Val Thr Pro Ser His Val Ser His Ile Gln Gly Thr Ile Leu Cys
            115                 120                 125

Ser Lys Lys Val Gly Leu Gln Ile Arg Thr Arg Ser Gly Gly His Asp
130                 135                 140

Ser Glu Gly Met Ser Tyr Ile Ser Gln Val Pro Phe Val Ile Val Asp
145                 150                 155                 160

Leu Arg Asn Met Arg Ser Ile Lys Ile Asp Val His Ser Gln Thr Ala
                165                 170                 175

Trp Val Glu Ala Gly Ala Thr Leu Gly Glu Val Tyr Tyr Trp Val Asn
            180                 185                 190

Glu Lys Asn Glu Asn Leu Ser Leu Ala Ala Gly Tyr Cys Pro Thr Val
        195                 200                 205

Cys Ala Gly Gly His Phe Gly Gly Gly Tyr Gly Pro Leu Met Arg
210                 215                 220

Asn Tyr Gly Leu Ala Ala Asp Asn Ile Ile Asp Ala His Leu Val Asn
225                 230                 235                 240

Val His Gly Lys Val Leu Asp Arg Lys Ser Met Gly Glu Asp Leu Phe
                245                 250                 255

Trp Ala Leu Arg Gly Gly Gly Ala Glu Ser Phe Gly Ile Ile Val Ala
            260                 265                 270

Trp Lys Ile Arg Leu Val Ala Val Pro Lys Ser Thr Met Phe Ser Val
        275                 280                 285

Lys Lys Ile Met Glu Ile His Glu Leu Val Lys Leu Val Asn Lys Trp
    290                 295                 300

Gln Asn Ile Ala Tyr Lys Tyr Asp Lys Asp Leu Leu Leu Met Thr His
305                 310                 315                 320

Phe Ile Thr Arg Asn Ile Thr Asp Asn Gln Gly Lys Asn Lys Thr Ala
                325                 330                 335

Ile His Thr Tyr Phe Ser Ser Val Phe Leu Gly Gly Val Asp Ser Leu
            340                 345                 350

Val Asp Leu Met Asn Lys Ser Phe Pro Glu Leu Gly Ile Lys Lys Thr
        355                 360                 365

Asp Cys Arg Gln Leu Ser Trp Ile Asp Thr Ile Ile Phe Tyr Ser Gly
    370                 375                 380

Val Val Asn Tyr Asp Thr Asp Asn Phe Asn Lys Glu Ile Leu Leu Asp
385                 390                 395                 400

Arg Ser Ala Gly Gln Asn Gly Ala Phe Lys Ile Lys Leu Asp Tyr Val
                405                 410                 415

Lys Lys Pro Ile Pro Glu Ser Val Phe Val Gln Ile Leu Glu Lys Leu
            420                 425                 430

Tyr Glu Glu Asp Ile Gly Ala Gly Met Tyr Ala Leu Tyr Pro Tyr Gly
        435                 440                 445

Gly Ile Met Asp Glu Ile Ser Glu Ser Ala Ile Pro Phe Pro His Arg
    450                 455                 460
```

Ala Gly Ile Leu Tyr Glu Leu Trp Tyr Ile Cys Ser Trp Glu Lys Gln
465                 470                 475                 480

Glu Asp Asn Glu Lys His Leu Asn Trp Ile Arg Asn Ile Tyr Asn Phe
            485                 490                 495

Met Thr Pro Tyr Val Ser Lys Asn Pro Arg Leu Ala Tyr Leu Asn Tyr
            500                 505                 510

Arg Asp Leu Asp Ile Gly Ile Asn Asp Pro Lys Asn Pro Asn Asn Tyr
            515                 520                 525

Thr Gln Ala Arg Ile Trp Gly Glu Lys Tyr Phe Gly Lys Asn Phe Asp
            530                 535                 540

Arg Leu Val Lys Val Lys Thr Leu Val Asp Pro Asn Asn Phe Phe Arg
545                 550                 555                 560

Asn Glu Gln Ser Ile Pro Pro Leu Pro Arg His Arg His
            565                 570

<210> SEQ ID NO 54
<211> LENGTH: 543
<212> TYPE: PRT
<213> ORGANISM: Artificial Sequence
<220> FEATURE:
<223> OTHER INFORMATION: Cannabis sativa

<400> SEQUENCE: 54

Met Gln Leu Ser Leu Ser Val Leu Ser Thr Val Ala Thr Ala Leu Leu
1               5                   10                  15

Ser Leu Thr Thr Ala Val Asp Ala Lys Ser His Asn Pro Arg Glu Asn
            20                  25                  30

Phe Leu Lys Cys Phe Ser Gln Tyr Ile Pro Asn Asn Ala Thr Asn Leu
        35                  40                  45

Lys Leu Val Tyr Thr Gln Asn Asn Pro Leu Tyr Met Ser Val Leu Asn
50                  55                  60

Ser Thr Ile His Asn Leu Arg Phe Thr Ser Asp Thr Thr Pro Lys Pro
65                  70                  75                  80

Leu Val Ile Val Thr Pro Ser His Val Ser His Ile Gln Gly Thr Ile
                85                  90                  95

Leu Cys Ser Lys Lys Val Gly Leu Gln Ile Arg Thr Arg Ser Gly Gly
            100                 105                 110

His Asp Ser Glu Gly Met Ser Tyr Ile Ser Gln Val Pro Phe Val Ile
        115                 120                 125

Val Asp Leu Arg Asn Met Arg Ser Ile Lys Ile Asp Val His Ser Gln
130                 135                 140

Thr Ala Trp Val Glu Ala Gly Ala Thr Leu Gly Glu Val Tyr Tyr Trp
145                 150                 155                 160

Val Asn Glu Lys Asn Glu Asn Leu Ser Leu Ala Ala Gly Tyr Cys Pro
                165                 170                 175

Thr Val Cys Ala Gly Gly His Phe Gly Gly Gly Gly Tyr Gly Pro Leu
            180                 185                 190

Met Arg Asn Tyr Gly Leu Ala Ala Asp Asn Ile Ile Asp Ala His Leu
        195                 200                 205

Val Asn Val His Gly Lys Val Leu Asp Arg Lys Ser Met Gly Glu Asp
210                 215                 220

Leu Phe Trp Ala Leu Arg Gly Gly Gly Ala Glu Ser Phe Gly Ile Ile
225                 230                 235                 240

Val Ala Trp Lys Ile Arg Leu Val Ala Val Pro Lys Ser Thr Met Phe
                245                 250                 255

```
Ser Val Lys Lys Ile Met Glu Ile His Glu Leu Val Lys Leu Val Asn
            260                 265                 270

Lys Trp Gln Asn Ile Ala Tyr Lys Tyr Asp Lys Asp Leu Leu Met
            275                 280                 285

Thr His Phe Ile Thr Arg Asn Ile Thr Asp Asn Gln Gly Lys Asn Lys
290                 295                 300

Thr Ala Ile His Thr Tyr Phe Ser Ser Val Phe Leu Gly Gly Val Asp
305                 310                 315                 320

Ser Leu Val Asp Leu Met Asn Lys Ser Phe Pro Glu Leu Gly Ile Lys
                325                 330                 335

Lys Thr Asp Cys Arg Gln Leu Ser Trp Ile Asp Thr Ile Ile Phe Tyr
            340                 345                 350

Ser Gly Val Val Asn Tyr Asp Thr Asp Asn Phe Asn Lys Glu Ile Leu
            355                 360                 365

Leu Asp Arg Ser Ala Gly Gln Asn Gly Ala Phe Lys Ile Lys Leu Asp
            370                 375                 380

Tyr Val Lys Lys Pro Ile Pro Glu Ser Val Phe Val Gln Ile Leu Glu
385                 390                 395                 400

Lys Leu Tyr Glu Glu Asp Ile Gly Ala Gly Met Tyr Ala Leu Tyr Pro
                405                 410                 415

Tyr Gly Gly Ile Met Asp Glu Ile Ser Glu Ser Ala Ile Pro Phe Pro
            420                 425                 430

His Arg Ala Gly Ile Leu Tyr Glu Leu Trp Tyr Ile Cys Ser Trp Glu
            435                 440                 445

Lys Gln Glu Asp Asn Glu Lys His Leu Asn Trp Ile Arg Asn Ile Tyr
            450                 455                 460

Asn Phe Met Thr Pro Tyr Val Ser Lys Asn Pro Arg Leu Ala Tyr Leu
465                 470                 475                 480

Asn Tyr Arg Asp Leu Asp Ile Gly Ile Asn Asp Pro Lys Asn Pro Asn
                485                 490                 495

Asn Tyr Thr Gln Ala Arg Ile Trp Gly Glu Lys Tyr Phe Gly Lys Asn
            500                 505                 510

Phe Asp Arg Leu Val Lys Val Lys Thr Leu Val Asp Pro Asn Asn Phe
            515                 520                 525

Phe Arg Asn Glu Gln Ser Ile Pro Pro Leu Pro Arg His Arg His
            530                 535                 540
```

<210> SEQ ID NO 55
<211> LENGTH: 608
<212> TYPE: PRT
<213> ORGANISM: Artificial Sequence
<220> FEATURE:
<223> OTHER INFORMATION: Cannabis sativa

<400> SEQUENCE: 55

```
Met Gln Leu Ser Leu Ser Val Leu Ser Thr Val Ala Thr Ala Leu Leu
1               5                   10                  15

Ser Leu Thr Thr Ala Val Asp Ala Lys Ser His Asn Ile Lys Leu Ser
            20                  25                  30

Lys Leu Ser Asn Glu Glu Thr Leu Asp Ala Ser Thr Phe Gln Glu Tyr
        35                  40                  45

Thr Ser Ser Leu Ala Asn Lys Tyr Met Asn Leu Phe Asn Ala Ala His
    50                  55                  60

Gly Asn Pro Thr Ser Phe Gly Leu Gln His Val Leu Ser Asn Gln Glu
65                  70                  75                  80
```

-continued

```
Ala Glu Val Pro Phe Val Thr Pro Gln Lys Gly Gly Asn Pro Arg Glu
                 85                  90                  95

Asn Phe Leu Lys Cys Phe Ser Gln Tyr Ile Pro Asn Asn Ala Thr Asn
            100                 105                 110

Leu Lys Leu Val Tyr Thr Gln Asn Asn Pro Leu Tyr Met Ser Val Leu
        115                 120                 125

Asn Ser Thr Ile His Asn Leu Arg Phe Thr Ser Asp Thr Thr Pro Lys
130                 135                 140

Pro Leu Val Ile Val Thr Pro Ser His Val Ser His Ile Gln Gly Thr
145                 150                 155                 160

Ile Leu Cys Ser Lys Lys Val Gly Leu Gln Ile Arg Thr Arg Ser Gly
                165                 170                 175

Gly His Asp Ser Glu Gly Met Ser Tyr Ile Ser Gln Val Pro Phe Val
            180                 185                 190

Ile Val Asp Leu Arg Asn Met Arg Ser Ile Lys Ile Asp Val His Ser
        195                 200                 205

Gln Thr Ala Trp Val Glu Ala Gly Ala Thr Leu Gly Glu Val Tyr Tyr
210                 215                 220

Trp Val Asn Glu Lys Asn Glu Asn Leu Ser Leu Ala Ala Gly Tyr Cys
225                 230                 235                 240

Pro Thr Val Cys Ala Gly Gly His Phe Gly Gly Gly Tyr Gly Pro
                245                 250                 255

Leu Met Arg Asn Tyr Gly Leu Ala Ala Asp Asn Ile Ile Asp Ala His
            260                 265                 270

Leu Val Asn Val His Gly Lys Val Leu Asp Arg Lys Ser Met Gly Glu
        275                 280                 285

Asp Leu Phe Trp Ala Leu Arg Gly Gly Gly Ala Glu Ser Phe Gly Ile
290                 295                 300

Ile Val Ala Trp Lys Ile Arg Leu Val Ala Val Pro Lys Ser Thr Met
305                 310                 315                 320

Phe Ser Val Lys Lys Ile Met Glu Ile His Glu Leu Val Lys Leu Val
                325                 330                 335

Asn Lys Trp Gln Asn Ile Ala Tyr Lys Tyr Asp Lys Asp Leu Leu Leu
            340                 345                 350

Met Thr His Phe Ile Thr Arg Asn Ile Thr Asp Asn Gln Gly Lys Asn
        355                 360                 365

Lys Thr Ala Ile His Thr Tyr Phe Ser Ser Val Phe Leu Gly Gly Val
370                 375                 380

Asp Ser Leu Val Asp Leu Met Asn Lys Ser Phe Pro Glu Leu Gly Ile
385                 390                 395                 400

Lys Lys Thr Asp Cys Arg Gln Leu Ser Trp Ile Asp Thr Ile Ile Phe
                405                 410                 415

Tyr Ser Gly Val Val Asn Tyr Asp Thr Asp Asn Phe Asn Lys Glu Ile
            420                 425                 430

Leu Leu Asp Arg Ser Ala Gly Gln Asn Gly Ala Phe Lys Ile Lys Leu
        435                 440                 445

Asp Tyr Val Lys Lys Pro Ile Pro Glu Ser Val Phe Val Gln Ile Leu
450                 455                 460

Glu Lys Leu Tyr Glu Glu Asp Ile Gly Ala Gly Met Tyr Ala Leu Tyr
465                 470                 475                 480

Pro Tyr Gly Gly Ile Met Asp Glu Ile Ser Glu Ser Ala Ile Pro Phe
                485                 490                 495
```

```
Pro His Arg Ala Gly Ile Leu Tyr Glu Leu Trp Tyr Ile Cys Ser Trp
                500                 505                 510

Glu Lys Gln Glu Asp Asn Glu Lys His Leu Asn Trp Ile Arg Asn Ile
            515                 520                 525

Tyr Asn Phe Met Thr Pro Tyr Val Ser Lys Asn Pro Arg Leu Ala Tyr
        530                 535                 540

Leu Asn Tyr Arg Asp Leu Asp Ile Gly Ile Asn Asp Pro Lys Asn Pro
545                 550                 555                 560

Asn Asn Tyr Thr Gln Ala Arg Ile Trp Gly Lys Tyr Phe Gly Lys
                565                 570                 575

Asn Phe Asp Arg Leu Val Lys Val Lys Thr Leu Val Asp Pro Asn Asn
            580                 585                 590

Phe Phe Arg Asn Glu Gln Ser Ile Pro Pro Leu Pro Arg His Arg His
        595                 600                 605

<210> SEQ ID NO 56
<211> LENGTH: 523
<212> TYPE: PRT
<213> ORGANISM: Artificial Sequence
<220> FEATURE:
<223> OTHER INFORMATION: Cannabis sativa

<400> SEQUENCE: 56

Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255
```

```
Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365

Phe Val Gln Ile Leu Glu Lys Leu Tyr Glu Glu Asp Ile Gly Ala Gly
    370                 375                 380

Met Tyr Ala Leu Tyr Pro Tyr Gly Gly Ile Met Asp Glu Ile Ser Glu
385                 390                 395                 400

Ser Ala Ile Pro Phe Pro His Arg Ala Gly Ile Leu Tyr Glu Leu Trp
                405                 410                 415

Tyr Ile Cys Ser Trp Glu Lys Gln Glu Asp Asn Glu Lys His Leu Asn
            420                 425                 430

Trp Ile Arg Asn Ile Tyr Asn Phe Met Thr Pro Tyr Val Ser Lys Asn
        435                 440                 445

Pro Arg Leu Ala Tyr Leu Asn Tyr Arg Asp Leu Asp Ile Gly Ile Asn
    450                 455                 460

Asp Pro Lys Asn Pro Asn Asn Tyr Thr Gln Ala Arg Ile Trp Gly Glu
465                 470                 475                 480

Lys Tyr Phe Gly Lys Asn Phe Asp Arg Leu Val Lys Val Lys Thr Leu
                485                 490                 495

Val Asp Pro Asn Asn Phe Phe Arg Asn Glu Gln Ser Ile Pro Pro Leu
            500                 505                 510

Pro Arg His Arg His Gly Arg Arg Ala Lys Leu
        515                 520

<210> SEQ ID NO 57
<211> LENGTH: 545
<212> TYPE: PRT
<213> ORGANISM: Cannabis sativa

<400> SEQUENCE: 57

Met Asn Cys Ser Ala Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110
```

-continued

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Phe Ser Phe Pro Gly Gly Tyr Cys
                165                 170                 175

Pro Thr Val Gly Val Gly Gly His Phe Ser Gly Gly Tyr Gly Ala
                180                 185                 190

Leu Met Arg Asn Tyr Gly Leu Ala Ala Asp Asn Ile Ile Asp Ala His
                195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
                260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
        290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
                340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
        370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Val Gly Met Tyr Val Leu
                405                 410                 415

Tyr Pro Tyr Gly Gly Ile Met Glu Glu Ile Ser Glu Ser Ala Ile Pro
                420                 425                 430

Phe Pro His Arg Ala Gly Ile Met Tyr Glu Leu Trp Tyr Thr Ala Ser
        435                 440                 445

Trp Glu Lys Gln Glu Asp Asn Glu Lys His Ile Asn Trp Val Arg Ser
        450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
                500                 505                 510

Lys Asn Phe Asn Arg Leu Val Lys Val Lys Thr Lys Ala Asp Pro Asn
        515                 520                 525

-continued

```
Asn Phe Phe Arg Asn Glu Gln Ser Ile Pro Pro Leu Pro His His
            530                 535                 540
His
545

<210> SEQ ID NO 58
<211> LENGTH: 574
<212> TYPE: PRT
<213> ORGANISM: Artificial Sequence
<220> FEATURE:
<223> OTHER INFORMATION: Cannabis sativa

<400> SEQUENCE: 58

Met Phe Leu Lys His Ile Phe Val Ala Leu Ala Phe Ala Leu Leu Ala
1               5                   10                  15

Asp Ala Thr Pro Ala Gln Lys Arg Ser Pro Gly Phe Val Ala Leu Asp
            20                  25                  30

Phe Asp Ile Val Lys Val Gln Lys Asn Val Thr Ala Asn Asp Asp Ala
            35                  40                  45

Ala Ala Ile Val Ala Lys Arg Gln Thr Asn Pro Gln Glu Asn Phe Leu
    50                  55                  60

Lys Cys Phe Ser Glu Tyr Ile Pro Asn Asn Pro Ala Asn Pro Lys Phe
65                  70                  75                  80

Ile Tyr Thr Gln His Asp Gln Leu Tyr Met Ser Val Leu Asn Ser Thr
                85                  90                  95

Ile Gln Asn Leu Arg Phe Thr Ser Asp Thr Thr Pro Lys Pro Leu Val
            100                 105                 110

Ile Val Thr Pro Ser Asn Val Ser His Ile Gln Ala Ser Ile Leu Cys
            115                 120                 125

Ser Lys Lys Val Gly Leu Gln Ile Arg Thr Arg Ser Gly Gly His Asp
    130                 135                 140

Ala Glu Gly Met Ser Tyr Ile Ser Gln Val Pro Phe Val Val Val Asp
145                 150                 155                 160

Leu Arg Asn Met His Ser Ile Lys Ile Asp Val His Ser Gln Thr Ala
                165                 170                 175

Trp Val Glu Ala Gly Ala Thr Leu Gly Glu Val Tyr Tyr Trp Ile Asn
            180                 185                 190

Glu Lys Asn Glu Asn Phe Ser Phe Pro Gly Gly Tyr Cys Pro Thr Val
            195                 200                 205

Gly Val Gly Gly His Phe Ser Gly Gly Gly Tyr Gly Ala Leu Met Arg
    210                 215                 220

Asn Tyr Gly Leu Ala Ala Asp Asn Ile Ile Asp Ala His Leu Val Asn
225                 230                 235                 240

Val Asp Gly Lys Val Leu Asp Arg Lys Ser Met Gly Glu Asp Leu Phe
                245                 250                 255

Trp Ala Ile Arg Gly Gly Gly Gly Glu Asn Phe Gly Ile Ile Ala Ala
            260                 265                 270

Trp Lys Ile Lys Leu Val Ala Val Pro Ser Lys Ser Thr Ile Phe Ser
            275                 280                 285

Val Lys Lys Asn Met Glu Ile His Gly Leu Val Lys Leu Phe Asn Lys
    290                 295                 300

Trp Gln Asn Ile Ala Tyr Lys Tyr Asp Lys Asp Leu Val Leu Met Thr
305                 310                 315                 320

His Phe Ile Thr Lys Asn Ile Thr Asp Asn His Gly Lys Asn Lys Thr
                325                 330                 335
```

-continued

```
Thr Val His Gly Tyr Phe Ser Ser Ile Phe His Gly Val Asp Ser
            340                 345                 350

Leu Val Asp Leu Met Asn Lys Ser Phe Pro Glu Leu Gly Ile Lys Lys
        355                 360                 365

Thr Asp Cys Lys Glu Phe Ser Trp Ile Asp Thr Thr Ile Phe Tyr Ser
    370                 375                 380

Gly Val Val Asn Phe Asn Thr Ala Asn Phe Lys Lys Glu Ile Leu Leu
385                 390                 395                 400

Asp Arg Ser Ala Gly Lys Lys Thr Ala Phe Ser Ile Lys Leu Asp Tyr
                405                 410                 415

Val Lys Lys Pro Ile Pro Glu Thr Ala Met Val Lys Ile Leu Glu Lys
            420                 425                 430

Leu Tyr Glu Glu Asp Val Gly Val Gly Met Tyr Val Leu Tyr Pro Tyr
        435                 440                 445

Gly Gly Ile Met Glu Glu Ile Ser Glu Ser Ala Ile Pro Phe Pro His
    450                 455                 460

Arg Ala Gly Ile Met Tyr Glu Leu Trp Tyr Thr Ala Ser Trp Glu Lys
465                 470                 475                 480

Gln Glu Asp Asn Glu Lys His Ile Asn Trp Val Arg Ser Val Tyr Asn
                485                 490                 495

Phe Thr Thr Pro Tyr Val Ser Gln Asn Pro Arg Leu Ala Tyr Leu Asn
            500                 505                 510

Tyr Arg Asp Leu Asp Leu Gly Lys Thr Asn Pro Glu Ser Pro Asn Asn
        515                 520                 525

Tyr Thr Gln Ala Arg Ile Trp Gly Glu Lys Tyr Phe Gly Lys Asn Phe
    530                 535                 540

Asn Arg Leu Val Lys Val Lys Thr Lys Ala Asp Pro Asn Asn Phe Phe
545                 550                 555                 560

Arg Asn Glu Gln Ser Ile Pro Pro Leu Pro Pro His His His
                565                 570

<210> SEQ ID NO 59
<211> LENGTH: 544
<212> TYPE: PRT
<213> ORGANISM: Artificial Sequence
<220> FEATURE:
<223> OTHER INFORMATION: Cannabis sativa

<400> SEQUENCE: 59

Met Gln Leu Ser Leu Ser Val Leu Ser Thr Val Ala Thr Ala Leu Leu
1               5                   10                  15

Ser Leu Thr Thr Ala Val Asp Ala Lys Ser His Asn Pro Gln Glu Asn
            20                  25                  30

Phe Leu Lys Cys Phe Ser Glu Tyr Ile Pro Asn Asn Pro Ala Asn Pro
        35                  40                  45

Lys Phe Ile Tyr Thr Gln His Asp Gln Leu Tyr Met Ser Val Leu Asn
    50                  55                  60

Ser Thr Ile Gln Asn Leu Arg Phe Thr Ser Asp Thr Thr Pro Lys Pro
65                  70                  75                  80

Leu Val Ile Val Thr Pro Ser Asn Val Ser His Ile Gln Ala Ser Ile
                85                  90                  95

Leu Cys Ser Lys Lys Val Gly Leu Gln Ile Arg Thr Arg Ser Gly Gly
            100                 105                 110

His Asp Ala Glu Gly Met Ser Tyr Ile Ser Gln Val Pro Phe Val Val
        115                 120                 125
```

```
Val Asp Leu Arg Asn Met His Ser Ile Lys Ile Asp Val His Ser Gln
130                 135                 140

Thr Ala Trp Val Glu Ala Gly Ala Thr Leu Gly Glu Val Tyr Tyr Trp
145                 150                 155                 160

Ile Asn Glu Lys Asn Glu Asn Phe Ser Phe Pro Gly Gly Tyr Cys Pro
                165                 170                 175

Thr Val Gly Val Gly Gly His Phe Ser Gly Gly Tyr Gly Ala Leu
        180                 185                 190

Met Arg Asn Tyr Gly Leu Ala Ala Asp Asn Ile Ile Asp Ala His Leu
        195                 200                 205

Val Asn Val Asp Gly Lys Val Leu Asp Arg Lys Ser Met Gly Glu Asp
210                 215                 220

Leu Phe Trp Ala Ile Arg Gly Gly Gly Glu Asn Phe Gly Ile Ile
225                 230                 235                 240

Ala Ala Trp Lys Ile Lys Leu Val Ala Val Pro Ser Lys Ser Thr Ile
                245                 250                 255

Phe Ser Val Lys Lys Asn Met Glu Ile His Gly Leu Val Lys Leu Phe
            260                 265                 270

Asn Lys Trp Gln Asn Ile Ala Tyr Lys Tyr Asp Lys Asp Leu Val Leu
        275                 280                 285

Met Thr His Phe Ile Thr Lys Asn Ile Thr Asp Asn His Gly Lys Asn
290                 295                 300

Lys Thr Thr Val His Gly Tyr Phe Ser Ser Ile Phe His Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Lys Glu Phe Ser Trp Ile Asp Thr Thr Ile Phe
            340                 345                 350

Tyr Ser Gly Val Val Asn Phe Asn Thr Ala Asn Phe Lys Lys Glu Ile
        355                 360                 365

Leu Leu Asp Arg Ser Ala Gly Lys Lys Thr Ala Phe Ser Ile Lys Leu
370                 375                 380

Asp Tyr Val Lys Lys Pro Ile Pro Glu Thr Ala Met Val Lys Ile Leu
385                 390                 395                 400

Glu Lys Leu Tyr Glu Glu Asp Val Gly Val Gly Met Tyr Val Leu Tyr
                405                 410                 415

Pro Tyr Gly Gly Ile Met Glu Glu Ile Ser Glu Ser Ala Ile Pro Phe
            420                 425                 430

Pro His Arg Ala Gly Ile Met Tyr Glu Leu Trp Tyr Thr Ala Ser Trp
        435                 440                 445

Glu Lys Gln Glu Asp Asn Glu Lys His Ile Asn Trp Val Arg Ser Val
450                 455                 460

Tyr Asn Phe Thr Thr Pro Tyr Val Ser Gln Asn Pro Arg Leu Ala Tyr
465                 470                 475                 480

Leu Asn Tyr Arg Asp Leu Asp Leu Gly Lys Thr Asn Pro Glu Ser Pro
                485                 490                 495

Asn Asn Tyr Thr Gln Ala Arg Ile Trp Gly Glu Lys Tyr Phe Gly Lys
            500                 505                 510

Asn Phe Asn Arg Leu Val Lys Val Lys Thr Lys Ala Asp Pro Asn Asn
        515                 520                 525

Phe Phe Arg Asn Glu Gln Ser Ile Pro Pro Leu Pro Pro His His His
530                 535                 540
```

-continued

```
<210> SEQ ID NO 60
<211> LENGTH: 609
<212> TYPE: PRT
<213> ORGANISM: Artificial Sequence
<220> FEATURE:
<223> OTHER INFORMATION: Cannabis sativa

<400> SEQUENCE: 60

Met Gln Leu Ser Leu Ser Val Leu Ser Thr Val Ala Thr Ala Leu Leu
1               5                   10                  15

Ser Leu Thr Thr Ala Val Asp Ala Lys Ser His Asn Ile Lys Leu Ser
            20                  25                  30

Lys Leu Ser Asn Glu Glu Thr Leu Asp Ala Ser Thr Phe Gln Glu Tyr
        35                  40                  45

Thr Ser Ser Leu Ala Asn Lys Tyr Met Asn Leu Phe Asn Ala Ala His
    50                  55                  60

Gly Asn Pro Thr Ser Phe Gly Leu Gln His Val Leu Ser Asn Gln Glu
65                  70                  75                  80

Ala Glu Val Pro Phe Val Thr Pro Gln Lys Gly Gly Asn Pro Gln Glu
                85                  90                  95

Asn Phe Leu Lys Cys Phe Ser Glu Tyr Ile Pro Asn Asn Pro Ala Asn
            100                 105                 110

Pro Lys Phe Ile Tyr Thr Gln His Asp Gln Leu Tyr Met Ser Val Leu
        115                 120                 125

Asn Ser Thr Ile Gln Asn Leu Arg Phe Thr Ser Asp Thr Thr Pro Lys
    130                 135                 140

Pro Leu Val Ile Val Thr Pro Ser Asn Val Ser His Ile Gln Ala Ser
145                 150                 155                 160

Ile Leu Cys Ser Lys Lys Val Gly Leu Gln Ile Arg Thr Arg Ser Gly
                165                 170                 175

Gly His Asp Ala Glu Gly Met Ser Tyr Ile Ser Gln Val Pro Phe Val
            180                 185                 190

Val Val Asp Leu Arg Asn Met His Ser Ile Lys Ile Asp Val His Ser
        195                 200                 205

Gln Thr Ala Trp Val Glu Ala Gly Ala Thr Leu Gly Glu Val Tyr Tyr
    210                 215                 220

Trp Ile Asn Glu Lys Asn Glu Asn Phe Ser Phe Pro Gly Gly Tyr Cys
225                 230                 235                 240

Pro Thr Val Gly Val Gly Gly His Phe Ser Gly Gly Gly Tyr Gly Ala
                245                 250                 255

Leu Met Arg Asn Tyr Gly Leu Ala Ala Asp Asn Ile Ile Asp Ala His
            260                 265                 270

Leu Val Asn Val Asp Gly Lys Val Leu Asp Arg Lys Ser Met Gly Glu
        275                 280                 285

Asp Leu Phe Trp Ala Ile Arg Gly Gly Gly Gly Glu Asn Phe Gly Ile
    290                 295                 300

Ile Ala Ala Trp Lys Ile Lys Leu Val Ala Val Pro Ser Lys Ser Thr
305                 310                 315                 320

Ile Phe Ser Val Lys Lys Asn Met Glu Ile His Gly Leu Val Lys Leu
                325                 330                 335

Phe Asn Lys Trp Gln Asn Ile Ala Tyr Lys Tyr Asp Lys Asp Leu Val
            340                 345                 350

Leu Met Thr His Phe Ile Thr Lys Asn Ile Thr Asp Asn His Gly Lys
        355                 360                 365

Asn Lys Thr Thr Val His Gly Tyr Phe Ser Ser Ile Phe His Gly Gly
```

-continued

```
                370                 375                 380
Val Asp Ser Leu Val Asp Leu Met Asn Lys Ser Phe Pro Glu Leu Gly
385                 390                 395                 400

Ile Lys Lys Thr Asp Cys Lys Glu Phe Ser Trp Ile Asp Thr Thr Ile
            405                 410                 415

Phe Tyr Ser Gly Val Val Asn Phe Asn Thr Ala Asn Phe Lys Lys Glu
            420                 425                 430

Ile Leu Leu Asp Arg Ser Ala Gly Lys Lys Thr Ala Phe Ser Ile Lys
            435                 440                 445

Leu Asp Tyr Val Lys Lys Pro Ile Pro Glu Thr Ala Met Val Lys Ile
            450                 455                 460

Leu Glu Lys Leu Tyr Glu Glu Asp Val Gly Val Gly Met Tyr Val Leu
465                 470                 475                 480

Tyr Pro Tyr Gly Gly Ile Met Glu Glu Ile Ser Glu Ser Ala Ile Pro
            485                 490                 495

Phe Pro His Arg Ala Gly Ile Met Tyr Glu Leu Trp Tyr Thr Ala Ser
            500                 505                 510

Trp Glu Lys Gln Glu Asp Asn Glu Lys His Ile Asn Trp Val Arg Ser
            515                 520                 525

Val Tyr Asn Phe Thr Thr Pro Tyr Val Ser Gln Asn Pro Arg Leu Ala
530                 535                 540

Tyr Leu Asn Tyr Arg Asp Leu Asp Leu Gly Lys Thr Asn Pro Glu Ser
545                 550                 555                 560

Pro Asn Asn Tyr Thr Gln Ala Arg Ile Trp Gly Glu Lys Tyr Phe Gly
            565                 570                 575

Lys Asn Phe Asn Arg Leu Val Lys Val Lys Thr Lys Ala Asp Pro Asn
            580                 585                 590

Asn Phe Phe Arg Asn Glu Gln Ser Ile Pro Pro Leu Pro Pro His His
            595                 600                 605

His

<210> SEQ ID NO 61
<211> LENGTH: 525
<212> TYPE: PRT
<213> ORGANISM: Artificial Sequence
<220> FEATURE:
<223> OTHER INFORMATION: Cannabis sativa

<400> SEQUENCE: 61

Met Ser Asn Pro Gln Glu Asn Phe Leu Lys Cys Phe Ser Glu Tyr Ile
1               5                   10                  15

Pro Asn Asn Pro Ala Asn Pro Lys Phe Ile Tyr Thr Gln His Asp Gln
            20                  25                  30

Leu Tyr Met Ser Val Leu Asn Ser Thr Ile Gln Asn Leu Arg Phe Thr
        35                  40                  45

Ser Asp Thr Thr Pro Lys Pro Leu Val Ile Val Thr Pro Ser Asn Val
    50                  55                  60

Ser His Ile Gln Ala Ser Ile Leu Cys Ser Lys Lys Val Gly Leu Gln
65                  70                  75                  80

Ile Arg Thr Arg Ser Gly Gly His Asp Ala Glu Gly Met Ser Tyr Ile
                85                  90                  95

Ser Gln Val Pro Phe Val Val Val Asp Leu Arg Asn Met His Ser Ile
            100                 105                 110

Lys Ile Asp Val His Ser Gln Thr Ala Trp Val Glu Ala Gly Ala Thr
        115                 120                 125
```

```
Leu Gly Glu Val Tyr Tyr Trp Ile Asn Glu Lys Asn Glu Asn Phe Ser
130                 135                 140

Phe Pro Gly Gly Tyr Cys Pro Thr Val Gly Val Gly Gly His Phe Ser
145                 150                 155                 160

Gly Gly Gly Tyr Gly Ala Leu Met Arg Asn Tyr Gly Leu Ala Ala Asp
                165                 170                 175

Asn Ile Ile Asp Ala His Leu Val Asn Val Asp Gly Lys Val Leu Asp
            180                 185                 190

Arg Lys Ser Met Gly Glu Asp Leu Phe Trp Ala Ile Arg Gly Gly Gly
        195                 200                 205

Gly Glu Asn Phe Gly Ile Ile Ala Ala Trp Lys Ile Lys Leu Val Ala
210                 215                 220

Val Pro Ser Lys Ser Thr Ile Phe Ser Val Lys Lys Asn Met Glu Ile
225                 230                 235                 240

His Gly Leu Val Lys Leu Phe Asn Lys Trp Gln Asn Ile Ala Tyr Lys
                245                 250                 255

Tyr Asp Lys Asp Leu Val Leu Met Thr His Phe Ile Thr Lys Asn Ile
                260                 265                 270

Thr Asp Asn His Gly Lys Asn Lys Thr Val His Gly Tyr Phe Ser
            275                 280                 285

Ser Ile Phe His Gly Val Asp Ser Leu Val Asp Leu Met Asn Lys
290                 295                 300

Ser Phe Pro Glu Leu Gly Ile Lys Lys Thr Asp Cys Lys Glu Phe Ser
305                 310                 315                 320

Trp Ile Asp Thr Thr Ile Phe Tyr Ser Gly Val Val Asn Phe Asn Thr
                325                 330                 335

Ala Asn Phe Lys Lys Glu Ile Leu Leu Asp Arg Ser Ala Gly Lys Lys
            340                 345                 350

Thr Ala Phe Ser Ile Lys Leu Asp Tyr Val Lys Lys Pro Ile Pro Glu
        355                 360                 365

Thr Ala Met Val Lys Ile Leu Glu Lys Leu Tyr Glu Glu Asp Val Gly
370                 375                 380

Val Gly Met Tyr Val Leu Tyr Pro Tyr Gly Gly Ile Met Glu Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Ser Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445

Gln Asn Pro Arg Leu Ala Tyr Leu Asn Tyr Arg Asp Leu Asp Leu Gly
450                 455                 460

Lys Thr Asn Pro Glu Ser Pro Asn Asn Tyr Thr Gln Ala Arg Ile Trp
465                 470                 475                 480

Gly Glu Lys Tyr Phe Gly Lys Asn Phe Asn Arg Leu Val Lys Val Lys
                485                 490                 495

Thr Lys Ala Asp Pro Asn Asn Phe Phe Arg Asn Glu Gln Ser Ile Pro
            500                 505                 510

Pro Leu Pro Pro His His His Gly Arg Arg Ala Lys Leu
        515                 520                 525

<210> SEQ ID NO 62
<211> LENGTH: 545
```

```
<212> TYPE: PRT
<213> ORGANISM: Cannabis sativa

<400> SEQUENCE: 62
```

| | | | | | | | | | | | | | | |
|---|---|---|---|---|---|---|---|---|---|---|---|---|---|---|
|Met|Asn|Cys|Ser|Thr|Phe|Ser|Phe|Trp|Phe|Val|Cys|Lys|Ile|Ile|Phe|
|1| | | |5| | | |10| | | | |15| |

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Cys Lys Ile Lys Leu Val Val Val Pro Ser Lys Ala Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Met
        275                 280                 285

Leu Thr Thr His Phe Arg Thr Arg Asn Ile Thr Asp Asn His Gly Lys
290                 295                 300

Asn Lys Thr Thr Val His Gly Tyr Phe Ser Ser Ile Phe Leu Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Leu Ser Trp Ile Asp Thr Thr Ile
            340                 345                 350

Phe Tyr Ser Gly Val Val Asn Tyr Asn Thr Ala Asn Phe Lys Lys Glu
        355                 360                 365

Ile Leu Leu Asp Arg Ser Ala Gly Lys Lys Thr Ala Phe Ser Ile Lys
370                 375                 380

Leu Asp Tyr Val Lys Lys Leu Ile Pro Glu Thr Ala Met Val Lys Ile
385                 390                 395                 400

```
Leu Glu Lys Leu Tyr Glu Glu Val Gly Val Gly Met Tyr Val Leu
            405                 410                 415

Tyr Pro Tyr Gly Gly Ile Met Asp Glu Ile Ser Glu Ser Ala Ile Pro
        420                 425                 430

Phe Pro His Arg Ala Gly Ile Met Tyr Glu Leu Trp Tyr Thr Ala Thr
            435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
            485                 490                 495

Pro Asn Asn Tyr Thr Gln Ala Arg Ile Trp Gly Glu Lys Tyr Phe Gly
        500                 505                 510

Lys Asn Phe Asn Arg Leu Val Lys Val Lys Thr Lys Ala Asp Pro Asn
            515                 520                 525

Asn Phe Phe Arg Asn Glu Gln Ser Ile Pro Pro Leu Pro Pro Arg His
    530                 535                 540

His
545

<210> SEQ ID NO 63
<211> LENGTH: 567
<212> TYPE: DNA
<213> ORGANISM: Candida viswanathii

<400> SEQUENCE: 63
gaggatgaag aagacgaaga cgaattggat gaagatgaag cgtatgagta ttatgagtac      60
tgtcggacgt tggaaggtgg cagagttaag cccgagaaag caaggaagga gtgggagatg     120
atgagtgatg cggccaagag gatgtgaagg ctgcgtatct gttttttgata gctggtggta     180 gccgaataga ggaaggcaag cttgttcata ttggatgatg atggtagatg gtggctgcca     240
aagtggttgt aaatagaaaa aagtgggttt gggtctgttg atagttagtg gtggcggctg     300
tctgtgatta cgtcagcaag tagcacctcg gcagttaaaa cagcagcaac agaaaaaaaa     360
tgtgtgaaag tttgattccc ccacagtcta ccacacccag agttccattt atccataata     420
tcacaagcaa tagaaaaata aaaaattatc aacaaatcac aacgaaaaga ttctgcaaaa     480
ttattttcac ttcttctttt gacttcctct tcttcttgtt aggttctttc catattttcc     540
ccttaaaccc atacacaacg cagccat                                        567

<210> SEQ ID NO 64
<211> LENGTH: 529
<212> TYPE: DNA
<213> ORGANISM: Artificial Sequence
<220> FEATURE:
<223> OTHER INFORMATION: PoX4_Promoter_CV

<400> SEQUENCE: 64
gagctccaat tgtaatattt cgggagaaat atcgttgggg taaaacaaca gagagagaga      60
gggagagatg gttctggtag aattataatc tggttgttgc aaatgctact gatcgactct     120
ggcaatgtct gtagctcgct agttgtatgc aacttaggtg ttatgcatac acacggttat     180
tcggttgaat tgtggagtaa aaattgtctg agttgtgtct tagctactgg ctggcccccc     240
gcgaaagata atcaaaatta cacttgtgaa ttttgcaca cacaccgatt aacatttccc     300
```

```
ttttttgtcc accgatacac gcttgcctct tcttattttc tctgtgcttc ccctcctgt    360
gacttttcc accattgata taaaatcaac tccatttccc taaaatctcc ccagattcta    420
aaaacaactt cttctcttct gcttttcctt attttgtta tatttattta ccatcccttta   480
ttttgaatag ttattcccca ctaacattgt tcaaatcttc acgacataa                529

<210> SEQ ID NO 65
<211> LENGTH: 861
<212> TYPE: DNA
<213> ORGANISM: Candida viswanathii

<400> SEQUENCE: 65
gtgccgacgg agtaacaaaa atgttacagt gcgcactact tatcccgcta aggtgataaa    60
ctgcaaaaac acaccgtcaa ggagaagtcg acgttttgcc gccacttgtg aagggaagaa   120
gagtcgttga gttgatgtaa ttaagctggc acgtagatac cagaaggttc tagagtagag   180
cttgggtggt gtttggccct gtttggacca cggatagaga tggagaatcc cttggttaga   240
gcggagagga aaaaattgaa actttgcata tcccacttca ttatccttga tgtaaccgtt   300
ttatggggta attaaagtgt ggaaaaataa tcagggagac atattcccga tcaattgggt   360
ggtggtcgct caatttctgt gagtagtagg ctcagtggtg tgtattggga ttggtagtag   420
tctgtataag cagtgttata taacccattg cttgttgatt cctattttgc tggcaaaagt   480
gacaactgta gttgtgagat aatcctcggt tattacgcct ggggggggcag acagccaaag   540
ttgtgcccgt gcgacaatgg catcagaaga aacagaaaaa aaaaacacag gcatttttat   600
ccacatgcac actaccccca ctattcctgt ctgcagtgtg cttgtgtgtg gccccccgca   660
gaatcaacag ggcaaactct ggagcctgaa tctttatata aacttcaggc attggcccc    720
cttttcacaa ttcttcacat ccaccatttt tttttcttctt tcctaccata ttagttttt    780
tttattcttt tcctacctat ctgattatta tcaaacatct ggtcatcctc aaaagaaaga   840
aagaaactat aacaatcaat c                                            861

<210> SEQ ID NO 66
<211> LENGTH: 599
<212> TYPE: DNA
<213> ORGANISM: Candida viswanathii

<400> SEQUENCE: 66
tggattatgt aatcacaggc tgtttctcca ttcctgcatg taggctggcc cgcggtatca    60
accatcgtcc cgcttcttct ggttttttt tttttccgc tatgatattt ttgatctctt    120
gggggatttg gtgggtctgc cccccccgct actacaagct caaacacccg aaaccttaca   180
acacacacac acacatcccg cttagttgcg ggttgaagaa cgtgtattcc cgtagggtta   240
atggtgtgtc cccccctagt caccgcttc tgccattctg ggtttgcctt caaagctggc   300
ataaatgacg aaaaaaagc acagcatcct gcacacaacc ctgctcagtg tgacaggtgg   360
tggtgtaata gaaaaacctcg gcttaaaacc tctggtcaga gcatcaactg caatcttgtc   420
tttttctgct gccctcacat tctccccaca cattcccacc ctcaagattt cacaggcaaa   480
aactgcaaat atatataaat ctacaaccaa ttctttcccc agatggaaaa tctaatttt    540
gttcacccctt tttctttctc ctgctatcac tgctactgca catattcaac accacaacc   599

<210> SEQ ID NO 67
<211> LENGTH: 502
<212> TYPE: DNA
<213> ORGANISM: Artificial Sequence
```

<220> FEATURE:
<223> OTHER INFORMATION: TEF1_promoter_CV

<400> SEQUENCE: 67

```
gactgggaga acagaccaag gatgcccata caccattaat aacaagcaca ccttgataaa    60
tctctagtgt tgacaaattg gtgatttgaa catgactgta gagagagaga caagtaacca   120
ctgatggatt ggtggtggca ataaccact ttaaataaag accaactcac acacaaagac    180
agcaggtcgt gttcctattt ccaattttca caaggagaaa ataaaaatt tttcaatgag    240
attaactaaa gaaacagaca ggcagcccac aagaagaaga agaagaagag gaagaggaag   300
aagaagaaga agaagaagaa gaagagaaaa aaaatttttc cctctgcgtt gcgttgggct   360
tgggttgcca gcacccacca tatataactc tcatcaaata cccagtagag aaaaattttt   420
cctccctctt tttctttctt tcttctcctt cttttgctac tctttctgtt tttcatcaaa   480
aagatatata taatcaatca tg                                             502
```

<210> SEQ ID NO 68
<211> LENGTH: 502
<212> TYPE: DNA
<213> ORGANISM: Candida viswanathii

<400> SEQUENCE: 68

```
accaaacgtt acttttttt tgcaatcgga tggtatgggt ctggggttca cctgttttgt    60
aaagctacag aaggtggcat atttctctga tcaggtgttt tttttttcgg ctgctgctgc   120
tcgtggtggt gtagtggtag tggtgtgtgt gtgtgtgtgt gcgtgcgtgt ggaaggacgc   180
tttttgctct ctgactcctc ccaatcagaa gttgctatag tggtgaaaca acaatggatg   240
ataatgcccc gggcggtgcg tgtccgacac aaaccactac attttttagc tgggagccta   300
ctgccactac gacccaccca cccatggtca acaaaaaaat tctgacaaat tataaaataa   360
cccttgaatt cccccttgga aaaattttg gtatttctct ctctctttc ctttccctct    420
tctttttctc tccatcaatc aattgacgtt cagtaactca attaattaca tcacatccct   480
caattaaaga atttaaacaa tg                                             502
```

<210> SEQ ID NO 69
<211> LENGTH: 1006
<212> TYPE: DNA
<213> ORGANISM: Artificial Sequence
<220> FEATURE:
<223> OTHER INFORMATION: POX2_Promoter_Yl

<400> SEQUENCE: 69

```
acgattccgc caagtgagac tggcgatcgg gagaagggtt ggtggtcatg ggggatagaa    60
tttgtacaag tggaaaaacc actacgagta gcggatttga taccacaagt agcagagata   120
tacagcaatg gtgggagtgc aagtatcgga atgtactgta cctcctgtac tcgtactcgt   180
acggcactcg tagaaacggg gcaatacggg ggagaagcga tcgcccgtct gttcaatcgc   240
cacaagtccg agtaatgctt gagtatcgaa gtcttgtacc tccctgtcaa tcatggcacc   300
actggtcttg acttgtctat tcatactgga caagcgccag agttaagctt gtagcgaatt   360
tcgccctcgg acatcacccc atacgacgga cacacatgcc cgacaaacag cctctcttat   420
tgtagctgaa agtatattga atgtgaacgt gtacaatatc aggtaccagc ggggaggttac   480
ggccaaggtg ataccggaat aaccctggct tggagatggt cggtccattg tactgaagtg   540
tccgtgtcgt ttccgtcact gccccaattg gacatgtttg ttttccgat ctttcgggcg    600
```

```
cctctcctt  gtctccttgt  ctgtctcctg  gactgttgct  accccatttc  tttggcctcc      660
attggttcct  ccccgtcttt  cacgtcgtct  atggttgcat  ggtttccctt  atacttttcc      720
ccacagtcac  atgttatgga  ggggtctaga  tggaggccta  attttgacgt  gcaaggggcg      780
aattggggcg  agaaacacgt  cgtggacatg  gtgcaaggcc  cgcagggttg  attcgacgct      840
tttccgcgaa  aaaaacaagt  ccaaataccc  ccgtttattc  tccctcggct  ctcggtattt      900
cacatgaaaa  ctataaccta  gactacacgg  gcaaccttaa  ccccagagta  tacttatata      960
ccaaagggat  gggtcctcaa  aaatcacaca  agcaacgacg  ccatga                    1006
```

<210> SEQ ID NO 70
<211> LENGTH: 1004
<212> TYPE: DNA
<213> ORGANISM: Yarrowia lipolytica

<400> SEQUENCE: 70

```
aaacttctcc  gagtctgtgc  cttcaggtgg  gcatagttga  tgggtgtttt  gaagttaata       60
gtggggaaga  actatggcaa  acaagcagat  gcaggcacct  tgtaactgca  gaccggttct      120
tgtctaccga  ctccgctgca  cctgtgccgc  ggtacatgtc  gtcacaggct  gcggggttcg      180
gaggccccct  tgcaacctcc  tttgatagtt  gctatggccc  caaagagtta  tacgagatag      240
acccacagat  ctacttgact  gttgtcacag  aacctgctag  gtttgcttat  tgtacccgct      300
ttgtagctac  tgtacaacga  caacgtcaaa  aattgagacg  cgaacaaact  ccagatgcag      360
aacccaaacc  tctctctcag  agtttcgagt  gcttctacct  cacagtaaag  tggaggtgga      420
cctgcaaggg  aattcagtca  caaggccccg  aatgtctccg  aaactccaat  cggaccgttt      480
aaacagacta  atatcacgtc  attgattgat  attagcatcc  ggcaagagcc  gcaaggttat      540
ctcctcacca  atgagcctgt  tgtacggctc  attccgcatc  tgcggctgat  tcagtttcga      600
gtggggatgg  tagacttcat  tgcagcattc  ctaaccttct  acttggtccg  tggagatgtc      660
atggacatcg  attttgggct  gagaagcctt  ttgacgatgt  tgatatcact  gaccgctaat      720
ttactctggc  agtttctccg  gctctcgagg  catcgtcgat  caccaaacac  tatctgctag      780
tctaaatgtc  cgacacgaca  gcttttgatc  gccgtgaacg  gcgcagacct  catgcaccat      840
gcaccagggc  caaatcaatt  acgggtcgct  tagcgttgca  gtcggggcat  tatggtggaa      900
gttccgatac  ggcacagaca  cattccatag  tgggggggatt  ggattataaa  agggccatag      960
aaagccctca  attgataccc  aagtaccagc  tctcctcact  atga                      1004
```

<210> SEQ ID NO 71
<211> LENGTH: 1367
<212> TYPE: DNA
<213> ORGANISM: Artificial Sequence
<220> FEATURE:
<223> OTHER INFORMATION: ICL1_Promoter_Yk

<400> SEQUENCE: 71

```
gaccccctcc  ttttgccagt  atatccaccg  caacacccac  catgagcgac  atctgatacc       60
gtgccgcgac  cactaccccca  aataagctcc  aactaatatg  ccgaggcagg  tgggaaacta      120
tgcactccag  acgacgctgt  agaagcacat  ggaaggtgcg  gaggcggtgg  caacgagggg      180
catgagccat  caacgagtaa  ccacagacaa  ggcaaggggg  gaaacgcgac  cggaatctct      240
cgcggtcacg  tgacccgccc  gggttccact  cgtccatgtt  gtgtctctgg  tgtcttcggc      300
cgactcgcat  tggttaaact  tccaccaccg  caatcacgtc  ccactggcca  aacttttttct      360 gctttctctg  acttttttctg  gccaaaaggc  aacgtcggaa  agggtcggga  ggattcggaa      420
```

```
ccgacgaaaa tcggccggct ccagcggggg tagttcggca gtcctggtgg gagctctagg      480
ggagctgtgg tctgtgtagg gcgcgggtcc gggtttgttg ggtgtcaaat cacgtgtttt      540 tgccccccg  ctgagccgga ctccgacaac cgtgtctcca acggcctgac taagctgctc      600
ccagcactct gccgtagcgt tggtctgtcc tgtcgcactc tgttcaaaga cagaagaaag      660
aaaaagctaa cctccacgtc agagacaatg gtagaaggct tgttccttgc aaccgaggag      720
agtgagtgtt ctcggcacga gcatcatggg cgatctggag ggtattttg  agggaaaaa       780 acgggatcag gacaaacaga ggccacagac cgggaatctg gccccaaaa  cggccttttc      840 ccgtcgcaaa accggtctac atacacccct tcggcccgcc acaggccggt gtgaaaaacc      900
ctaaagcttg cttcaaacca gacggacgca cagcaagaca catcatgaag agtcacctgc      960
agtatatata gatctgggga ttcccagtag actgaccaag catacaaaag tgagtatcca     1020
acagcgacac gtgagatggc agagacacag agacgtgtct acatggttgg acaagtctcc     1080
acattcgcca gagacgtatc cacatacaaa cacaatctca cagctgatct gctcctgtga     1140
cagcacagta catgttagtg gatgaggtgt tgtgtagtgg gttaaatggg tggactgatt     1200
cagtggcatc ggtggcgaca ccctctactc ttcatgtcgt cacctaccgt tcggaatccc     1260
aattatctga tgaactaaac gatttctggc caaaacacaa ttttgccaaa gaagtcgttc     1320
tcaccaatgc aagtgtcaca tcaaacatct gtcccgtact aacccag                  1367

<210> SEQ ID NO 72
<211> LENGTH: 1004
<212> TYPE: DNA
<213> ORGANISM: Artificial Sequence
<220> FEATURE:
<223> OTHER INFORMATION: POT1_Promoter+Y1

<400> SEQUENCE: 72
ccacaatacc ccacagtgtg catatcaaac ctaccggttg ttgctctctc cagccttact       60
aagaaggagg cgacgtggca gtggctcgcg ggaggatcgg cgggaaactc cgggatatcc      120
gtcgagagtt tacacgtgaa tgggcagcgc aatccgttga cgacgatacg actggcaaag      180
tagcgacgat acctgccaga caggtgacat gtgcaggccg cactaacaag gaaacgggcg      240 ctggggggg  cgggcttcta gactttgccc ttgaacagga atctagtggg ggcttgtctt      300
tccgccaatg ggggagcgcc tgttgagcga ccgtgcatgc tggaacgcca agtgtatgta      360
cagctggtgt tctcgcagcg gtatgtgacg ggacttacat ctctcgtttt ttcatgacca      420
cgttttcaca ggctcggagg tacgttaaag ttttgaaggc tgcatctgaa ccgaggtatg      480
ggggagtttg aggagcaaca gtgttgggc  tgaggggcc  aagatcgggg caagcagagg      540
tcttagatca attgtgggaa tcccaaaggg ctcgttatcc cctttttcca cccaattcgg      600
gtcccaattg atccactact ggcttgccca agttacccca gaaatgccgc cccggatttc      660
tccaaaaacc taataagctt catgaacttt ggtggaagtg actttctaca gagtggagag      720
aaccgtggac acgtggcaat ggcgctgacc gtgtccccga gccgaatcga cgtgagggga      780
gaacggagta tctgcggtca tgtgaccttc cagagcggcg tcgccagtgt gcacgcggtg      840
acccccagtt tggttctctg tcacacgcat actacctcgg ctctccacat gctgaacttt      900
atctttcgtg gggatcatac cgaaagttgc aactaccagg tgtatataaa gcctggtaga      960
ctccccccac tttggacctc atccaaccaa gacacacaaa aatg                     1004

<210> SEQ ID NO 73
```

```
<211> LENGTH: 174
<212> TYPE: DNA
<213> ORGANISM: Candida viswanathii

<400> SEQUENCE: 73
gagtgactct tttgataaga gtcgcaaatt tgatttcata agtatatatt cattatgtaa      60
agtagtaaat ggaaaattca ttaaaaaaaa agcaaatttc cgttgtatgc atactccgaa     120
cacaaaacta gccccggaaa aacccttagt tgatagttgc gaatttaggt cgac           174

<210> SEQ ID NO 74
<211> LENGTH: 200
<212> TYPE: DNA
<213> ORGANISM: Candida viswanathii

<400> SEQUENCE: 74
agctccaggc ttgttatgac tctagagaga agtgtgtgtg tttgcgtttg ttttactata     60
cattcaacat gttcttttc tttttgata tttattccaa ctataattat acacagattc      120
gtatatactt tactttaccc tctttcgtag ttttttaatt tgatgatttt tgagtttcat    180
atccaaggtc aaaacccgac                                                200

<210> SEQ ID NO 75
<211> LENGTH: 251
<212> TYPE: DNA
<213> ORGANISM: Yarrowia lipolytica

<400> SEQUENCE: 75
taggcaatta acagatagtt tgccggtgat aattctctta acctcccaca ctcctttgac      60
ataacgattt atgtaacgaa actgaaattt gaccagatat tgttgtaaat agaaaatctg    120
gcttgtaggt ggcaaaatgc ggcgtctttg ttcatcaatt ccctctgtga ctactcgtca    180
tccctttatg ttcgactgtc gtatttctta ttttccatac atatgcaagt gagatgcccg    240
tgtccgaatt c                                                         251

<210> SEQ ID NO 76
<211> LENGTH: 308
<212> TYPE: DNA
<213> ORGANISM: Artificial Sequence
<220> FEATURE:
<223> OTHER INFORMATION: TDH3_terminator_YL

<400> SEQUENCE: 76
cttccgagta gctatccgaa gatcaagagc gaagcaagtt gtaagtccag gacatgtttc      60
ccgcccacgc gagtgattta taacacctct ctttttttgac acccgctcgc cttgaaattc    120
atgtcacata aattatagtc aacgacgttt gaataacttg tcttgtagtt cgatgatgat    180
catatgatta cattaatagt aattactgta tttgatatat atactaatta caatagtaca    240
tattagaaca tacaatagtt agtgccgtga agtggcttaa ataccgcga gtcgattacg     300 taatatta                                                             308

<210> SEQ ID NO 77
<211> LENGTH: 2133
<212> TYPE: DNA
<213> ORGANISM: Artificial Sequence
<220> FEATURE:
<223> OTHER INFORMATION: LEU2_Marker_Yl

<400> SEQUENCE: 77
aacgtaccac tgtcctccac tacaaacaca cccaatctgc ttcttctagt caaggttgct      60
```

```
acaccggtaa attataaatc atcatttcat tagcagggct gggcccttttt tatagagtct      120
tatacactag cggaccctgc cggtagacca acccgcaggc gcgtcagttt gctccttcca      180
tcaatgcgtc gtagaaacga cttactcctt cttgagcagc tccttgacct tgttggcaac      240
aaagtctccg acctcggagg tggaggagga gcctccgata tcggcggtag tgataccagc      300
ctcgacggac tccttgacgg cagcctcaac agcgtcaccg gcgggcttca tgttaagaga      360
gaacttgagc atcatggcgg cagacagaat ggtggcaatg ggttgaccct tctgcttgcc      420
gagatcgggg gcagatccgt gacagggctc gtacagaccg aacgcctcgt tggtgtcggg      480
cagagaagcc agagaggcgg agggcagcag acccagagaa ccggggatga cggaggcctc      540
gtcggagatg atatcgccaa acatgttggt ggtgatgatg ataccattca tcttggaggg      600
ctgcttgatg aggatcatgg cggccgagtc gatcagctgg tggttgagct ccagctgggg      660
gaattcgtcc ttgaggactc gggtgacggt cttttcgcca agtcgagagg aggccagcac      720
gttggccttg tcaagggacc acacgggaag aggggggttg tgctgaaggg ccaggaaggc      780
ggccattcgg gcaattcgct caacctcagg aacggagtaa gtctcagtgt cggaagcgac      840
gccagatccg tcatcctcct ttcgctctcc aaagtagata cctccgacga gctctcggac      900
aatgatgaag tcggtgccct caacgtttcg gatggggag agatcggcga gcttgggcga      960
cagcagctgg cagggtcgca ggttggcgta caggttcagg tcctttcgca gcttgagaag      1020
accctgctcg ggtcgcacgt cggttcgtcc gtcgggagtg gtccatacgg tgttggcagc      1080
gcctccgaca gcaccgagca taatagagtc agcctttcgg cagatgtcga gagtagcgtc      1140
ggtgatgggc tcgccctcct tctcaatggc agctcctcca atgagtcggt cctcaaacac      1200
aaactcggtg ccggaggcct cagcaacaga cttgagcacc ttgacggcct cggcaatcac      1260
ctcggggcca cagaagtcgc cgccgagaag aacaatcttc ttggagtcag tcttggtctt      1320
cttagtttcg ggttccattg tggatgtgtg tggttgtatg tgtgatgtgg tgtgtggagt      1380
gaaaatctgt ggctggcaaa cgctcttgta tatatacgca cttttgcccg tgctatgtgg      1440
aagactaaac ctccgaagat tgtgactcag gtagtgcggt atcggctagg gacccaaacc      1500
ttgtcgatgc cgatagcgct atcgaacgta ccccagccgg ccgggagtat gtcggagggg      1560
acatacgaga tcgtcaaggg tttgtggcca actggtaaat aaatgatgac tcaggcgacg      1620
acggaattcg acagcaacta ctcctttcac caaccatgtg catttagct cgaataacat      1680
tcacaggctt ggtgatctac atccatggtg tctggccgat taccgtggtg ttttggcagt      1740
aacgagaata ttgagtgaac tcttcccatc accaataaag actcatacta caatcacgag      1800
cgcttcagct gccactatag tgttggtgac acaatacccc tcgatgctgg gcattactgt      1860
agcaagagat attatttcat ggcgcatttt ccagtctacc tgactttta gtgtgatttc      1920
ttctccacat tttatgctca gtgtgaaaag ttggagtgca cacttaatta tcgccggttt      1980
tcggaaagta ctatgtgctc aaggttcac cccacgttac gtatgcagca cattgagcag      2040
cctttggacc gtggagataa cggtgtggag atagcaacgg gtagtcttcg tattaattca      2100
atgcattgtt agtttatat gatatggtgt cga                                    2133
```

<210> SEQ ID NO 78
<211> LENGTH: 1142
<212> TYPE: DNA
<213> ORGANISM: Artificial Sequence
<220> FEATURE:
<223> OTHER INFORMATION: URA3_Marker_Yl

```
<400> SEQUENCE: 78
tttctaattt ggaccgatag ccgtatagtc cagtctatct ataagttcaa ctaactcgta      60
actattacca taacatatac ttcactgccc cagataaggt tccgataaaa agttgtgcag     120
actaaattta tttcagtctc ctcttcacca ccaaaatgcc ctcctacgaa gcgcgagcta     180
acgtccacaa gtccgccttt gccgcccgag tgctcaagct cgtggcagcc aagaaaacca     240
acctgtgtgc ttctctggat gttaccacca ccaaggagtc cattgagctt gccgataagg     300
tcggacctta tgtgtgcatg atcaagaccc atatcgacat cattgacgac ttcacctacg     360
ccggaactgt gctccccctc aaggaacttg ctcttaagca cggtttcttc ctgttcgagg     420
acagaaagtt cgcagatatt ggcaacactg tcaagcacca gtacaagaac ggtgtctacc     480
gaatcgccga gtggtccgat atcaccaacg cccacggtgt accggaaccc ggaatcattg     540
ctggcctgcg agctggtgcc gaggaaactg tctctgaaca agaaggag gatgtctctg        600 actacgagaa ctcccagtac aaggagttcc tggtcccctc tcccaacgag aagctggcca     660
gaggtctgct catgctggcc gagctgtctt gcaagggctc tctggccact ggcgagtact     720
ccaagcagac cattgagctt gcccgatccg accccgagtt tgtggttggc ttcattgccc     780
agaaccgacc taagggcgac tctgaggact ggcttattct gaccccgggg gtgggtcttg     840
acgacaaggg agatgctctc ggacagcagt accgaactgt tgaggatgtc atgtctaccg     900
gaacggatat cataattgtc ggccgaggtc tgtacggcca gaaccgagat cctattgagg     960
aggccaagcg ataccagaag gctggctggg aggcttacca gaagattaac tgttagaggt    1020
tagactatgg atatgtcatt taactgtgta tatagagagc gtgcaagtat ggagcgcttg    1080
ttcagcttgt atgatggtca gacgacctgt ctgatcgagt atgtatgata ctgcacaacc    1140
tg                                                                   1142

<210> SEQ ID NO 79
<211> LENGTH: 9
<212> TYPE: PRT
<213> ORGANISM: Artificial Sequence
<220> FEATURE:
<223> OTHER INFORMATION: FLAG

<400> SEQUENCE: 79

Asp Tyr Lys Asp Asp Asp Asp Lys Gly
1               5

<210> SEQ ID NO 80
<211> LENGTH: 14
<212> TYPE: PRT
<213> ORGANISM: paramyxovirus simian parainfluenza virus 5

<400> SEQUENCE: 80

Gly Lys Pro Ile Pro Asn Pro Leu Leu Gly Leu Asp Ser Thr
1               5                   10

<210> SEQ ID NO 81
<211> LENGTH: 10
<212> TYPE: PRT
<213> ORGANISM: Homo sapiens

<400> SEQUENCE: 81

Glu Gln Lys Leu Ile Ser Glu Glu Asp Leu
1               5                   10

<210> SEQ ID NO 82
```

```
<211> LENGTH: 11
<212> TYPE: PRT
<213> ORGANISM: Herpes simplex virus

<400> SEQUENCE: 82

Gln Pro Glu Leu Ala Pro Glu Asp Pro Glu Asp
1               5                   10

<210> SEQ ID NO 83
<211> LENGTH: 9
<212> TYPE: PRT
<213> ORGANISM: Vesicular stomatitis virus

<400> SEQUENCE: 83

Tyr Pro Tyr Asp Val Pro Asp Tyr Ala
1               5

<210> SEQ ID NO 84
<211> LENGTH: 261
<212> TYPE: PRT
<213> ORGANISM: Influenza

<400> SEQUENCE: 84

Met Thr Lys Phe Ile Gly Cys Ile Asp Leu His Asn Gly Glu Val Lys
1               5                   10                  15

Gln Ile Val Gly Gly Thr Leu Thr Ser Lys Lys Glu Asp Val Pro Lys
            20                  25                  30

Thr Asn Phe Val Ser Gln His Pro Ser Ser Tyr Tyr Ala Lys Leu Tyr
        35                  40                  45

Lys Asp Arg Asp Val Gln Gly Cys His Val Ile Lys Leu Gly Pro Asn
    50                  55                  60

Asn Asp Asp Ala Ala Arg Glu Ala Leu Gln Glu Ser Pro Gln Phe Leu
65                  70                  75                  80

Gln Val Gly Gly Gly Ile Asn Asp Thr Asn Cys Leu Glu Trp Leu Lys
                85                  90                  95

Trp Ala Ser Lys Val Ile Val Thr Ser Trp Leu Phe Thr Lys Glu Gly
            100                 105                 110

His Phe Gln Leu Lys Arg Leu Glu Arg Leu Thr Glu Leu Cys Gly Lys
        115                 120                 125

Asp Arg Ile Val Val Asp Leu Ser Cys Arg Lys Thr Gln Asp Gly Arg
    130                 135                 140

Trp Ile Val Ala Met Asn Lys Trp Gln Thr Leu Thr Asp Leu Glu Leu
145                 150                 155                 160

Asn Ala Asp Thr Phe Arg Glu Leu Arg Lys Tyr Thr Asn Glu Phe Leu
                165                 170                 175

Ile His Ala Ala Asp Val Glu Gly Leu Cys Gly Gly Ile Asp Glu Leu
            180                 185                 190

Leu Val Ser Lys Leu Phe Glu Trp Thr Lys Asp Tyr Asp Asp Leu Lys
        195                 200                 205

Ile Val Tyr Ala Gly Gly Ala Lys Ser Val Asp Asp Leu Lys Leu Val
    210                 215                 220

Asp Glu Leu Ser His Gly Lys Val Asp Leu Thr Phe Gly Ser Ser Leu
225                 230                 235                 240

Asp Ile Phe Gly Gly Asn Leu Val Lys Phe Glu Asp Cys Cys Arg Trp
                245                 250                 255

Asn Glu Lys Gln Gly
            260
```

```
<210> SEQ ID NO 85
<211> LENGTH: 5
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = Any Amino Acid
<220> FEATURE:
<223> OTHER INFORMATION: Cysteine-rich tag

<400> SEQUENCE: 85

Cys Cys Xaa Cys Cys
1               5

<210> SEQ ID NO 86
<211> LENGTH: 6
<212> TYPE: PRT
<213> ORGANISM: Artificial Sequence
<220> FEATURE:
<223> OTHER INFORMATION: VSV-G

<400> SEQUENCE: 86

Cys Cys Pro Gly Cys Cys
1               5

<210> SEQ ID NO 87
<211> LENGTH: 6
<212> TYPE: PRT
<213> ORGANISM: Artificial Sequence
<220> FEATURE:
<223> OTHER INFORMATION: polyhistidine element

<400> SEQUENCE: 87

Cys Cys Pro Gly Cys Cys
1               5

<210> SEQ ID NO 88
<211> LENGTH: 261
<212> TYPE: PRT
<213> ORGANISM: Saccharomyces cerevisiae

<400> SEQUENCE: 88

Met Thr Lys Phe Ile Gly Cys Ile Asp Leu His Asn Gly Glu Val Lys
1               5                   10                  15

Gln Ile Val Gly Gly Thr Leu Thr Ser Lys Lys Glu Asp Val Pro Lys
                20                  25                  30

Thr Asn Phe Val Ser Gln His Pro Ser Ser Tyr Tyr Ala Lys Leu Tyr
            35                  40                  45

Lys Asp Arg Asp Val Gln Gly Cys His Val Ile Lys Leu Gly Pro Asn
        50                  55                  60

Asn Asp Asp Ala Ala Arg Glu Ala Leu Gln Glu Ser Pro Gln Phe Leu
65                  70                  75                  80

Gln Val Gly Gly Gly Ile Asn Asp Thr Asn Cys Leu Glu Trp Leu Lys
                85                  90                  95

Trp Ala Ser Lys Val Ile Val Thr Ser Trp Leu Phe Thr Lys Glu Gly
                100                 105                 110

His Phe Gln Leu Lys Arg Leu Glu Arg Leu Thr Glu Leu Cys Gly Lys
            115                 120                 125

Asp Arg Ile Val Val Asp Leu Ser Cys Arg Lys Thr Gln Asp Gly Arg
        130                 135                 140

Trp Ile Val Ala Met Asn Lys Trp Gln Thr Leu Thr Asp Leu Glu Leu
```

```
             145                 150                 155                 160
Asn Ala Asp Thr Phe Arg Glu Leu Arg Lys Tyr Thr Asn Glu Phe Leu
                165                 170                 175

Ile His Ala Ala Asp Val Glu Gly Leu Cys Gly Gly Ile Asp Glu Leu
            180                 185                 190

Leu Val Ser Lys Leu Phe Glu Trp Thr Lys Asp Tyr Asp Asp Leu Lys
            195                 200                 205

Ile Val Tyr Ala Gly Gly Ala Lys Ser Val Asp Leu Lys Leu Val
210                 215                 220

Asp Glu Leu Ser His Gly Lys Val Asp Leu Thr Phe Gly Ser Ser Leu
225                 230                 235                 240

Asp Ile Phe Gly Gly Asn Leu Val Lys Phe Glu Asp Cys Cys Arg Trp
                245                 250                 255

Asn Glu Lys Gln Gly
            260

<210> SEQ ID NO 89
<211> LENGTH: 6
<212> TYPE: PRT
<213> ORGANISM: Cricetulus griseus

<400> SEQUENCE: 89

Leu Val Pro Arg Gly Ser
1               5

<210> SEQ ID NO 90
<211> LENGTH: 5
<212> TYPE: PRT
<213> ORGANISM: Artificial Sequence
<220> FEATURE:
<223> OTHER INFORMATION: enterokinase

<400> SEQUENCE: 90

Asp Asp Asp Asp Lys
1               5

<210> SEQ ID NO 91
<211> LENGTH: 7
<212> TYPE: PRT
<213> ORGANISM: Artificial Sequence
<220> FEATURE:
<223> OTHER INFORMATION: TEV protease

<400> SEQUENCE: 91

Glu Asn Leu Tyr Phe Gln Gly
1               5

<210> SEQ ID NO 92
<211> LENGTH: 8
<212> TYPE: PRT
<213> ORGANISM: Artificial Sequence
<220> FEATURE:
<223> OTHER INFORMATION: PreScission protease

<400> SEQUENCE: 92

Leu Glu Val Leu Phe Gln Gly Pro
1               5

<210> SEQ ID NO 93
<211> LENGTH: 2130
<212> TYPE: DNA
<213> ORGANISM: Artificial Sequence
<220> FEATURE:
```

<223> OTHER INFORMATION: CvACO1P Gene

<400> SEQUENCE: 93

```
atgacagaag tagtagatag agcaagttcc ccagcaagtc caggatctac gaccgccgcc        60
gcagacggtg ctaaggtggc ggtggagcca cgcgtagatg tagcggccct tggcgagcag       120
ttgctagggc gatgggctga catcagattg cacgcacgag acttagcagg ccgcgaagtg       180
gtccaaaagg ttgaaggact tacgcacact gagcatcgga gtagagtctt tggacagttg       240
aagtacttgg tagacaacaa tgctgttcac agagcttttc cctccaggct aggtggatca       300
gatgaccatg gcggtaatat agctggattc gaggaattag ttactgctga tccatcattg       360
caaataaagg ccggcgttca gtggggtttg tttggttctg cagtgatgca cttgggaacc       420
cgtgaacatc atgacaagtg gttgccaggt attatgtcgt tagaaatacc ggggtgtttc       480
gcgatgacag aaaccgggca cggtagcgac gtggcctcta ttgctacaac agcaacttat       540
gatgaggaaa cccaagagtt tgttattgat accccgttca gagccgcttg gaaagattat       600
atcggtaatg cagcgaacga tggtttggcg gcagttgttt tcgcacaatt aatcacgagg       660
aaagtgaacc atggtgtaca cgccttttac gtggatctca gagatcctgc gactggagac       720
ttcctacccg gaataggagg agaggacgat ggaatcaagg ggggattgaa tggcattgac       780
aacggtagac tacattttac gaacgtacgc attcctagaa ctaatcttct taacagatat       840
ggcgatgtgg cggtcgacgg cacataccctg tcgaccatcg aatcaccagg cgccggttc       900
tttacgatgc ttggtactct agtccagggt agagttagtc tcgatggagc agctgtcgct       960
gcactgaagg tcgcattgca aagtgcaatt cactacgctg cggagaggag acaatttaat      1020
gcgacttcac ctactgaaga gaggtccttc cttgattatc agaggcatca aaggagactc      1080
tttacacgac ttgcaacgac gtacgccgca tctttcgccc acgagcagct attgcaaaag      1140
ttcgatgatg tcttttcagg ggcacatgat accgacgccg accggcagga cttggaaacc      1200
ctagccgccg ctttgaagcc attgagcaca tggcatgcac ttgacacgtt acaagaatgc      1260
agagaggcct gtgggggggc cggattttttg atagaaaacc gtttcgcgag cttgcgtgct      1320
gacttggacg tttacgtcac attcgagggt gataacacag ttttattgca attggttgct      1380
aaacggctct tggcagacta cgcaaaagag ttcagagggg ccaacttcgg cgttcttgcc      1440
aggtatgtgg ttgaccaagc cgcgggagtg gcgctccacc gaacaggact aaggcaagtc      1500
gctcaatttg ttgcagacag cgggtccgtt cagaagtcgg ctcttgcgct tcgcgatgaa      1560
gagggtcaac gaacattgtt aacggacaga gtacagagca tggttgccga agtggggct      1620
gccttgaaag gcgcaggcaa attaccccaa catcaagcag ctgcattgtt caaccaacac      1680
cagaacgaac ttattgaggc tgcccaggcc catgcagaac tcctccaatg ggaggcattt      1740
acagaagctc tcgctaaagt cgacgatgct ggtacaaagg aagtgcttac tcgattgcga      1800
gatctctttg gtttgtcctt gattgaaaaa cacttgctgt ggtatcttat gaatggacgt      1860
ttgtccatgc aaagaggcag acagttgga acttacatta atcgtttact tgtcaagatc      1920
cgtccacacg cactagactt ggttgatgcc ttcggttacg gcgcggagca tttgcgtgct      1980
gctatcgcca ccgagcgga agcaacccga caggatgaag cccgaacgta ttttagacaa      2040
caacgggcat cgggactggc cccggccgat gaaaagacct actcgctat caaagctggt      2100
aaatcaagag ggcgaagggc aaagctatga                                       2130
```

<210> SEQ ID NO 94
<211> LENGTH: 2163

<212> TYPE: DNA
<213> ORGANISM: Artificial Sequence
<220> FEATURE:
<223> OTHER INFORMATION: CvHXS1 Gene

<400> SEQUENCE: 94

```
atgggaaaaa attataaatc tttggactca gttgtggcta gtgacttcat tgcacttggg    60
atcacatcag aagttgctga gacattgcac ggacgcttgg cagagatagt ttgcaactac   120
ggcgccgcaa cacctcagac ctggattaac atcgcaaacc atattctaag tccagatctt   180
ccatttagtc tccatcagat gttgttctac ggttgttata aggactttgg tccagcaccc   240
ccagcttgga taccagaccc cgaaaaagta aagtccacga acttaggtgc cttgttagaa   300
aagcggggaa aggagtttct aggcgttaag tataaggacc aataagtct gttttctcac   360
ttccaggagt ttagcgttcg aaatccggaa gtctactggc ggacggtact tatggatgaa   420
atgaagatac tgttcagcaa agatcccgaa tgtatcctca gacgcgacga cattaacaac   480
ccaggggct ctgagtggct accaggtgga tatctcaacc tggccaagaa ctgtttgaat   540
gtaaatagta acaaaaaact taacgacact atgatagtgt ggagagatga aggaaatgac   600
gatctcccat tgaataaatt gactcttgat caattacgaa aacgagtctg gttggttgga   660
tacgccctag aagagatggg ccttgagaag ggatgtgcga ttgcaattga catgcccatg   720
cacgtagatg cggttgtgat ctatttagct atcgtcttgg caggctacgt cgttgtctcc   780
attgcagatt cattctcagc accggaaatt tccacaagat tgcgtctatc aaaggctaag   840
gctattttta cacaagatca tatcatccga gggaaaaagc gtataccttt gtacctgcgt   900
gtcgtcgagg ccaagtctcc gatggcaata gttatcccgt gttcgggttc aaatattggt   960
gcggaattgc gggatggtga tattctgtgg gattacttct agaacgcgc aaaggaattt  1020
aagaactgcg aatttacagc ccgtgaacag ccagtggacg cgtacacaaa tattttgttc  1080
tcatcgggaa ccaccggaga gccaaaggcg ataccatgga ctcaagctac gcctctcaag  1140
gcggctgctg atggttggtc acacttggac attagaaagg gtgacgtaat tgtatggcct  1200
accaatttgg ggtggatgat ggggccttgg ttggtctatg cttcactcct taacggggca  1260
agcatcgcat tgtataacgg atctccacta gtgtccggct ttgccaaatt cgttcaagat  1320
gcgaaagtta ctatgctagg agttgtcccc tccatcgtac gaagctggaa aagcactaat  1380
tgcgttagtg ggtacgattg tctacaatc agatgcttct cctcatcggg tgaggcatcg  1440
aatgtcgatg aatacttatg gctaatggga agggctaact acaaaccggt catcgaaatg  1500
tgcggtggca cagagatcgg gggtgccttc agcgccggtt cgtttttaca agcccaatct  1560
ttgagtagct tctcatccca atgtatggga tgcaccttgt acattctcga caagaatggc  1620
tacccgatgc caagaacaa gccgggtata ggtgaattgg ccttgggacc cgtgatgttc  1680
ggtgcttcca agactttact taacggaaac catcatgacg tttatttcaa aggcatgccc  1740
accttgaacg gagaagtctt gaggagacac ggagatatct cgaactcac ttcgaacggc  1800
tattatcacg ctcatggtag agcagatgac acgatgaata tcggggggat taaaatttcc  1860
tcaatcgaga ttgaaagggt gtgtaatgaa gttgacgata gagtgtttga gactacggcc  1920
attggagtgc ctccattggg cggaggtcca gagcagctcg ttatctttt tgttcttaag  1980
gacagcaatg atacgaccat cgacctaaac caattgcgac ttagttttaa tcttgggtta  2040
caaaagaaat tgaacccact ttttaaggtg acgaggggttg tgccactttc gctgttgcct  2100
aggacagcca ccaacaaaat aatgagaaga gtgcttagac agcaatttag tcatttcgag  2160
```

| | |
|---|---:|
| tga | 2163 |

<210> SEQ ID NO 95
<211> LENGTH: 1158
<212> TYPE: DNA
<213> ORGANISM: Artificial Sequence
<220> FEATURE:
<223> OTHER INFORMATION: CvTKS1 Gene

<400> SEQUENCE: 95

| | |
|---|---:|
| atgaatcatt taagagcaga aggacccgca tcagtgttag cgataggtac agctaaccca | 60 |
| gagaatatct taatccaaga tgaatttcct gactactatt tccgtgttac taaatcggaa | 120 |
| catatgactc aacttaaaga gaagttccgg aaaatctgcg ataaatccat gatccgaaag | 180 |
| agaaactgtt tccttaacga gaacatctc aagcaaaacc cgaggttggt agagcacgaa | 240 |
| atgcagacct ggatgctag gcaggacatg ttggtggtcg aagtgccaaa actcggcaag | 300 |
| gacgcgtgcg ctaaggcaat caaggagtgg ggtcaaccga agtctaaaat cacgcatcta | 360 |
| atatttacat ctgcactgac aaccgacatg ccgggtgccg attatcactg cgccaagcta | 420 |
| cttggattga gtccactggt taagagagtt atgatgtatc aattggggtg ttacggaggg | 480 |
| ggcacagtcc tcagaattgc taaggatatt gcggaaaata caagggcgc gagggtcctt | 540 |
| gctgtatgtt gtgatattat ggcctgtttg tttcgcgggc cctcggattc agatttggaa | 600 |
| ttgcttgtcg gacaggcaat ttttggtgac ggggccgcag cagtcatagt gggagccgaa | 660 |
| ccagacgaaa gcgtgggtga agaccaatc tttgagttgg ttctgaccgg acaaacgatc | 720 |
| ttacctaact cggaaggtac gattggagga catattagaa agccggcct aattttcgat | 780 |
| cttcacaaag acgttccaat gttaatctcc aataacatag aaaagtgctt gatagaagca | 840 |
| tttactccca ttggtattag tgactggaac agcattttct ggatcaccca ccctggagga | 900 |
| aaagctatac tcgataaggt tgaagagaaa ctcgacttga aaaaggagaa attcgttgac | 960 |
| tcacgacatg tgttatcaga gcacgggaat atgagttcat ccacagtctt gttcgtaatg | 1020 |
| gatgaattgc gaaaacgctc tcttgaggag ggaaagagca caaccggtga cgggtttgag | 1080 |
| tggggcgtgc tattcggttt tggcccaggt ttgactgtcg agcgggttgt tgttcgtagt | 1140 |
| gtaccaatta agtactga | 1158 |

<210> SEQ ID NO 96
<211> LENGTH: 1176
<212> TYPE: DNA
<213> ORGANISM: Artificial Sequence
<220> FEATURE:
<223> OTHER INFORMATION: CvTKS1P Gene

<400> SEQUENCE: 96

| | |
|---|---:|
| atgaatcatt taagagcaga aggacccgca tcagtgttag cgataggtac agctaaccca | 60 |
| gagaatatct taatccaaga tgaatttcct gactactatt tccgtgttac taaatcggaa | 120 |
| catatgactc aacttaaaga gaagttccgg aaaatctgcg ataaatccat gatccgaaag | 180 |
| agaaactgtt tccttaacga gaacatctc aagcaaaacc cgaggttggt agagcacgaa | 240 |
| atgcagacct ggatgctag gcaggacatg ttggtggtcg aagtgccaaa actcggcaag | 300 |
| gacgcgtgcg ctaaggcaat caaggagtgg ggtcaaccga agtctaaaat cacgcatcta | 360 |
| atatttacat ctgcactgac aaccgacatg ccgggtgccg attatcactg cgccaagcta | 420 |
| cttggattga gtccactggt taagagagtt atgatgtatc aattggggtg ttacggaggg | 480 |
| ggcacagtcc tcagaattgc taaggatatt gcggaaaata caagggcgc gagggtcctt | 540 |

```
gctgtatgtt gtgatattat ggcctgtttg tttcgcgggc cctcggattc agatttggaa      600
ttgcttgtcg gacaggcaat ttttggtgac ggggccgcag cagtcatagt gggagccgaa      660
ccagacgaaa gcgtgggtga aagaccaatc tttgagttgg ttctgaccgg acaaacgatc      720
ttacctaact cggaaggtac gattggagga catattagag aagccggcct aattttcgat      780
cttcacaaag acgttccaat gttaatctcc aataacatag aaaagtgctt gatagaagca      840
tttactccca ttggtattag tgactggaac agcattttct ggatcaccca ccctggagga      900
aaagctatac tcgataaggt tgaagagaaa ctcgacttga aaaggagaa attcgttgac       960 tcacgacatg tgttatcaga gcacgggaat atgagttcat ccacagtctt gttcgtaatg     1020
gatgaattgc gaaaacgctc tcttgaggag ggaaagagca caaccggtga cgggtttgag     1080
tggggcgtgc tattcggttt tggcccaggt ttgactgtcg agcgggttgt tgttcgtagt     1140
gtaccaatta agtacggaag aagggcaaag ttgtga                              1176

<210> SEQ ID NO 97
<211> LENGTH: 318
<212> TYPE: DNA
<213> ORGANISM: Artificial Sequence
<220> FEATURE:
<223> OTHER INFORMATION: CvOAC1 Gene

<400> SEQUENCE: 97
atggcagtca acacctaat agttctcaaa tttaaagacg agattactga agctcagaag        60
gaagagttct ttaagacata tgttaactta gtcaacatca tccccgcgat gaaggacgtc      120
tactggggca aggatgtgac gcaaaaaaat aaggaagaag gatacacaca tatcgttgag      180
gtgacctttg agagtgtgga aactattcaa gattatatta ttcacccagc ccatgtaggg      240
ttcggtgacg tttatcgatc attctgggaa aagttgctta tatttgatta caccccaaga      300
aaattgaagc ctaagtga                                                   318

<210> SEQ ID NO 98
<211> LENGTH: 336
<212> TYPE: DNA
<213> ORGANISM: Artificial Sequence
<220> FEATURE:
<223> OTHER INFORMATION: CvOACP1 Gene

<400> SEQUENCE: 98
atggcagtca acacctaat agttctcaaa tttaaagacg agattactga agctcagaag        60
gaagagttct ttaagacata tgttaactta gtcaacatca tccccgcgat gaaggacgtc      120
tactggggca aggatgtgac gcaaaaaaat aaggaagaag gatacacaca tatcgttgag      180
gtgacctttg agagtgtgga aactattcaa gattatatta ttcacccagc ccatgtaggg      240
ttcggtgacg tttatcgatc attctgggaa aagttgctta tatttgatta caccccaaga      300
aaattgaagc ctaagggaag acgagctaag ttgtga                                336

<210> SEQ ID NO 99
<211> LENGTH: 1188
<212> TYPE: DNA
<213> ORGANISM: Artificial Sequence
<220> FEATURE:
<223> OTHER INFORMATION: CvPTS1 Gene

<400> SEQUENCE: 99
atgggtttat cgtcagtgtg cacttttct tttcaaacaa actaccacac cctcctaaac         60
```

| | |
|---|---|
| cctcacaata taacccaaa aacctccttg ctatgttaca gacatccaaa gacaccgatc | 120 |
| aagtattcat acaacaattt tcccagtaaa cattgctcaa cgaagtcctt ccacttgcaa | 180 |
| aacaaatgca gcgaatcatt gtcgatagct aaaaactcga tacgtgcggc aaccactaac | 240 |
| caaactgagc caccagagag cgataatcat tcagtcgcca ccaagatttt gaactttgga | 300 |
| aaagcctgtt ggaaacttca aaggccttac accattatcg catttaccag ttgcgcatgt | 360 |
| ggtttgttcg ggaaggaatt attacacaac acaaatttga tcagctggag cctaatgttt | 420 |
| aaggcatttt tcttcttagt tgcaattttg tgtatagctt cgtttacaac gaccattaat | 480 |
| cagatttacg accttcacat cgatcggatc aataaaccag acttgcccct tgcctctggg | 540 |
| gaaatctctg taaatactgc atggatcatg ctgataatcg tggctttgtt tggattgatt | 600 |
| attacaatta agatgaaggg gggtccatta tatatattcg ggtactgctt cggcattttc | 660 |
| ggtggtatcg tttactccgt cccacccttt agatggaaac agaaccccag tacggccttt | 720 |
| ctactcaatt tcttggctca tatcatcaca aacttcacat tctattatgc aagccgagcg | 780 |
| gcgcttggtt tgccgttcga actcagaccg agttttacat ttctccttgc cttcatgaaa | 840 |
| ctgatgggac tggcccttgc attgatcaag gatgcgtcag atgtcgaagg cgacactaag | 900 |
| ttcggcattc tgacgcttgc ttccaagtat ggaagtagaa atctaacgct tttttgttca | 960 |
| ggaatagtgc tacttagtta tgttgctgct atactcgctg gcattatttg gcctcaggcc | 1020 |
| ttcaactcta acgtaatgtt gttatcccat gctattttgg cgttctggtt gatcttgcaa | 1080 |
| acgcgagatt ttgcactcac taactacgac ccagaggcag gaaggcgctt ttacgagttt | 1140 |
| atgtggaagt tgtattatgc cgaatacttg gtttatgttt tcatttga | 1188 |

<210> SEQ ID NO 100
<211> LENGTH: 966
<212> TYPE: DNA
<213> ORGANISM: Artificial Sequence
<220> FEATURE:
<223> OTHER INFORMATION: CVPTS1dN Gene

<400> SEQUENCE: 100

| | |
|---|---|
| atggcggcaa ccactaacca aactgagcca ccagagagcg ataatcattc agtcgccacc | 60 |
| aagattttga actttggaaa agcctgttgg aaacttcaaa ggccttacac cattatcgca | 120 |
| tttaccagtt gcgcatgtgg tttgttcggg aaggaattat tacacaacac aaatttgatc | 180 |
| agctggagcc taatgtttaa ggcattttc ttcttagttg caattttgtg tatagcttcg | 240 |
| tttacaacga ccattaatca gatttacgac cttcacatcg atcggatcaa taaaccagac | 300 |
| ttgccccttg cctctgggga atctctgta aatactgcat ggatcatgct gataatcgtg | 360 |
| gctttgtttg gattgattat acaattaag atgaaggggg gtccattata tatattcggg | 420 |
| tactgcttcg gcattttcgg tggtatcgtt tactccgtcc cacccttag atggaaacag | 480 |
| aaccccagta cggcctttct actcaatttc ttggctcata tcatcacaaa cttcacattc | 540 |
| tattatgcaa gccgagcggc gcttggtttg ccgttcgaac tcagaccgag ttttacattt | 600 |
| ctccttgcct tcatgaaact gatgggactg gcccttgcat tgatcaagga tgcgtcagat | 660 |
| gtcgaaggcg acactaagtt cggcattctg acgcttgctt ccaagtatgg aagtagaaat | 720 |
| ctaacgcttt tttgttcagg aatagtgcta cttagttatg ttgctgctat actcgctggc | 780 |
| attatttggc ctcaggcctt caactctaac gtaatgttgt tatcccatgc tattttggcg | 840 |
| ttctggttga tcttgcaaac gcgagatttt gcactcacta actacgaccc agaggcagga | 900 |
| aggcgctttt acgagtttat gtggaagttg tattatgccg aatacttggt ttatgttttc | 960 | atttga                                                                  966

<210> SEQ ID NO 101
<211> LENGTH: 1197
<212> TYPE: DNA
<213> ORGANISM: Artificial Sequence
<220> FEATURE:
<223> OTHER INFORMATION: CvPTS2 Gene

<400> SEQUENCE: 101
atggggttgt ccttagtttg tacgttcagt ttccaaacta actaccacac actactaaat      60
ccgcacaaca aaaacccgaa aaattcattg ctctcctatc agcacccaaa acacccatt      120
atcaagtcta gttacgacaa cttttccatca aaatactgtc taacgaaaaa ctttcatttg    180
ttgggcttaa attctcataa tcgtatttcc agtcagtccc gatcgatcag ggccgggagt     240
gaccaaattg aaggttctcc acatcatgaa agtgacaatt caattgctac gaagatttta    300
aactttgggc atacatgctg aagctacag cgaccgtatg tagttaaggg gatgatcagc     360
attgcctgcg gcctattcgg aagggaactc ttcaataata gacatctttt tccttggggt    420
ttaatgtgga aagcttttttt cgctttggtt cctatcctta gttttaactt cttcgccgct   480
attatgaatc aaatttacga tgttgacatc gaccgtatta acaaacccga tctcccccctt   540
gtttcaggcg agatgtccat tgaaacggca tggattttgt ccatcattgt tgcgcttact    600
ggcttgattg ttaccattaa gcttaaaagc gctcccttgt tcgtttttat atacattttc   660
ggcattttg ccggattcgc atacagtgtc ccgcctatac gttggaaaca atatccattc    720
acgaacttct tgatcacgat ctcatcacat gttggattgg cctttacgtc ctacagtgct  780
accacatctg cccttggatt gccttttcgtt tggaggcctg ccttctcgtt tatcattgca  840
tttatgacag tgatgggaat gactatcgca tttgctaaag atatcagcga catagagggc  900
gatgcaaaat atggggtgag tactgttgcg acgaagttgg gcgcccgaaa tatgaccttc  960
gttgtttccg gcgttctttt acttaactat ttagtatcga ttagcatcgg gatcatctgg 1020
ccacaggtgt ttaaatcaaa tattatgatc ttgtcgcatg ccatcctagc tttctgtctt 1080
atatttcaaa caagagaatt agccctagcg aactacgcct cagcaccaag tcgtcagttc 1140
ttcgaattta tatggctact ctactacgcc gaatacttcg tctatgtctt catttag    1197

<210> SEQ ID NO 102
<211> LENGTH: 1635
<212> TYPE: DNA
<213> ORGANISM: Artificial Sequence
<220> FEATURE:
<223> OTHER INFORMATION: CvCBD1 Gene

<400> SEQUENCE: 102
atgaagtgtt ctacgtttag ttttttggttt gtttgtaaaa ttatattctt cttttttttcc    60
ttcaacattc agacatcaat cgccaaccca agggaaaact tccttaagtg ttttctgcag    120
tacatcccta acaatgcaac aaacctcaag ttggtgtaca ctcaaaacaa tccactctat   180
atgagcgtgc ttaatagcac aatccacaac ttgcgcttca cgtcagatac tacgcctaag  240
ccactagtga tcgttacacc atcacacgtc agccatattc aaggaacgat cctatgtctg  300
aaaaaggtcg ggttgcaaat caggactcga tcaggagggc acgatagtga gggaatgagt  360
tacatctcgc aagtacccctt cgtgatagtt gacttgcgaa atatgcggtc tattaaaatt  420
gacgtacata gccagaccgc ctgggttgaa gcaggggcaa ccttgggtga agtttattac  480

| | |
|---|---|
| tgggtcaatg aaaaaaacga aaacctaagt cttgctgctg atattgccc caccgtttgc | 540 |
| gcgggtggtc attttggagg cggcggatat ggtccgttga tgagaaatta tggacttgca | 600 |
| gcagacaata ttatagatgc ccacttggtg aacgttcatg gaaaggtctt ggaccgtaag | 660 |
| tccatggggt aagatctttt ctgggccttg agaggtggtg gagcggaatc gtttggcatc | 720 |
| atcgttgcct ggaaaattag gttggttgcg gtcccgaaga gtacaatgtt ctccgtgaag | 780 |
| aagattatgg aaatacatga gcttgtcaag ttagttaaca agtggcaaaa tatcgcttat | 840 |
| aagtatgata aagacttgct tttgatgact cattttatta cgcgaaacat aaccgataac | 900 |
| cagggcaaga acaagactgc tattcacacg tacttctcct ctgtatttct tggaggagta | 960 |
| gactccttag ttgacttgat gaacaagagt ttcccagaat tggggattaa aagacagat | 1020 |
| tgcagacaat tatcgtggat agatacaatc atattctata gcggtgtcgt caattacgat | 1080 |
| actgataatt ttaataaaga aatcctccta gatcgttcag ctgggcaaaa cggggcattc | 1140 |
| aaaattaaat tggattatgt gaagaaacca attccagagc tggtgtttgt tcagatattg | 1200 |
| gaaaaacttt acgaagaaga cattggcgca ggtatgtacg ctttgtatcc atatggaggc | 1260 |
| attatggacg agatctcaga gctggcgatc cccttcccgc acagagctgg gatactctac | 1320 |
| gagctatggt acatctgctc ttgggagaaa caagaagaca cgagaaaca tctcaattgg | 1380 |
| attcggaaca tatacaactt tatgaccca tacgtatcaa aaacccgcg cttagcatac | 1440 |
| ttgaattaca gagacttaga tatccggtatc aatgatccta agaatcctaa caattacacc | 1500 |
| caagcccgta tttggggtga gaaatatttc ggcaagaatt ttgacagatt agttaaggtc | 1560 |
| aaaacactcg tggaccccaa caactttttc cgaaacgagc agtcgattcc accactaccc | 1620 |
| aggcatagac actga | 1635 |

<210> SEQ ID NO 103
<211> LENGTH: 1722
<212> TYPE: DNA
<213> ORGANISM: Artificial Sequence
<220> FEATURE:
<223> OTHER INFORMATION: CBD1dNS1

<400> SEQUENCE: 103

| | |
|---|---|
| atgttcttga acacattttt tgttgctctc gcttttgcct tgttagctga cgctacccca | 60 |
| gcccagaaga gatctcccgg cttcgttgct ttagactttg acatcgtcaa ggttcaaaag | 120 |
| aacgtgactg ccaacgacga cgccgctgcc attgttgcca agagacagac caacccaagg | 180 |
| gaaaacttcc ttaagtgttt tctgcagtac atccctaaca tgcaacaaa cctcaagttg | 240 |
| gtgtacactc aaaacaatcc actctatatg agcgtgctta atagcacaat ccacaacttg | 300 |
| cgcttcacgt cagatactac gcctaagcca ctagtgatcg ttacaccatc acacgtcagc | 360 |
| catattcaag gaacgatcct atgtctgaaa aaggtcgggt gcaaatcag gactcgatca | 420 |
| ggagggcacg atagtgaggg aatgagttac atctcgcaag tacccttcgt gatagttgac | 480 |
| ttgcgaaata tgcggtctat taaaattgac gtacatagcc agaccgcctg ggttgaagca | 540 |
| ggggcaacct tgggtgaagt ttattactgg gtcaatgaaa aaaacgaaaa cctaagtctt | 600 |
| gctgctggat attgccccac cgtttgcgcg ggtggtcatt ttggaggcgg cggatatggt | 660 |
| ccgttgatga gaaattatgg acttgcagca gacaatatta gatgcccca cttggtgaac | 720 |
| gttcatggaa aggtcttgga ccgtaagtcc atgggtgaag atcttttctg ggccttgaga | 780 |
| ggtggtggag cggaatcgtt tggcatcatc gttgcctgga aaattaggtt ggttgcggtc | 840 |
| ccgaagagta caatgttctc cgtgaagaag attatggaaa tacatgagct tgtcaagtta | 900 |

```
gttaacaagt ggcaaaatat cgcttataag tatgataaag acttgctttt gatgactcat      960
tttattacgc gaaacataac cgataaccag ggcaagaaca agactgctat tcacacgtac     1020
ttctcctctg tatttcttgg aggagtagac tccttagttg acttgatgaa caagagtttc     1080
ccagaattgg ggattaagaa gacagattgc agacaattat cgtggataga tacaatcata     1140
ttctatagcg gtgtcgtcaa ttacgatact gataatttta ataaagaaat cctcctagat     1200
cgttcagctg gcaaaacgg  ggcattcaaa attaaattgg attatgtgaa gaaaccaatt     1260
ccagagctgg tgtttgttca gatattggaa aaactttacg aagaagacat tggcgcaggt     1320
atgtacgctt tgtatccata tggaggcatt atggacgaga tctcagagct ggcgatcccc     1380
ttcccgcaca gagctgggat actctacgag ctatggtaca tctgctcttg ggagaaacaa     1440
gaagacaacg agaaacatct caattggatt cggaacatat acaactttat gaccccatac     1500
gtatcaaaaa acccgcgctt agcatacttg aattacagag acttagatat cggtatcaat     1560
gatcctaaga atcctaacaa ttacacccaa gcccgtattt ggggtgagaa atatttcggc     1620
aagaattttg acagattagt taaggtcaaa acactcgtgg accccaacaa cttttttccga    1680 aacgagcagt cgattccacc actacccagg catagacact ga                        1722
```

<210> SEQ ID NO 104
<211> LENGTH: 1632
<212> TYPE: DNA
<213> ORGANISM: Artificial Sequence
<220> FEATURE:
<223> OTHER INFORMATION: CBD1dNS2

<400> SEQUENCE: 104

```
atgcaattgt cattgtcagt tttgtcaaca gttgcaacag cattgttgtc attgacaaca      60
gcagttgatg caaagtcaca taacccaagg gaaaacttcc ttaagtgttt tctgcagtac     120
atccctaaca atgcaacaaa cctcaagttg gtgtacactc aaaacaatcc actctatatg     180
agcgtgctta atagcacaat ccacaacttg cgcttcacgt cagatactac gcctaagcca     240
ctagtgatcg ttacaccatc acacgtcagc catattcaag gaacgatcct atgtctgaaa     300
aaggtcgggt tgcaaatcag gactcgatca ggagggcacg atagtgaggg aatgagttac     360
atctcgcaag tacccttcgt gatagttgac ttgcgaaata tgcggtctat taaaattgac     420
gtacatagcc agaccgcctg ggttgaagca ggggcaacct tgggtgaagt ttattactgg     480
gtcaatgaaa aaaacgaaaa cctaagtctt gctgctggat attgccccac cgtttgcgcg     540
ggtggtcatt ttggaggcgg cggatatggt ccgttgatga gaaattatgg acttgcagca     600
gacaatatta tagatgccca cttggtgaac gttcatggaa aggtcttgga ccgtaagtcc     660
atgggtgaag atctttttctg ggccttgaga ggtggtggag cggaatcgtt tggcatcatc     720
gttgcctgga aaattaggtt ggttgcggtc ccgaagagta caatgttctc cgtgaagaag     780
attatggaaa tacatgagct tgtcaagtta gttaacaagt ggcaaaatat cgcttataag     840
tatgataaag acttgctttt gatgactcat tttattacgc gaaacataac cgataaccag     900
ggcaagaaca agactgctat tcacacgtac ttctcctctg tatttcttgg aggagtagac     960
tccttagttg acttgatgaa caagagtttc ccagaattgg ggattaagaa gacagattgc    1020
agacaattat cgtggataga tacaatcata ttctatagcg gtgtcgtcaa ttacgatact    1080
gataatttta ataaagaaat cctcctagat cgttcagctg gcaaaacgg  ggcattcaaa    1140 attaaattgg attatgtgaa gaaaccaatt ccagagctgg tgtttgttca gatattggaa    1200
```

```
aaactttacg aagaagacat tggcgcaggt atgtacgctt tgtatccata tggaggcatt    1260
atggacgaga tctcagagct ggcgatcccc ttcccgcaca gagctgggat actctacgag    1320
ctatggtaca tctgctcttg ggagaaacaa gaagacaacg agaaacatct caattggatt    1380
cggaacatat acaactttat gaccccatac gtatcaaaaa acccgcgctt agcatacttg    1440
aattacagag acttagatat cggtatcaat gatcctaaga atcctaacaa ttacacccaa    1500
gcccgtattt ggggtgagaa atatttcggc aagaattttg acagattagt taaggtcaaa    1560
acactcgtgg accccaacaa cttttttccga aacgagcagt cgattccacc actacccagg    1620
catagacact ga                                                        1632

<210> SEQ ID NO 105
<211> LENGTH: 1827
<212> TYPE: DNA
<213> ORGANISM: Artificial Sequence
<220> FEATURE:
<223> OTHER INFORMATION: CBD1dNV1

<400> SEQUENCE: 105
atgcaattgt ccttgtcggt tttatcaacc gttgccacgg ccttgttgtc cctaaccacc      60
gccgtcgatg ctaagtccca caacatcaag ttgtccaagt tgtccaacga agaaacattg     120
gacgcctcca cattccaaga atacacgagc tccttggcca acaagtacat gaacttgttc     180
aacgccgctc acggtaaccc aaccagcttt ggcttgcaac acgtcttgtc caaccaagaa     240
gctgaagtcc cattcgttac cccacaaaag ggtggcaacc aagggaaaa cttccttaag     300 tgttttctgc agtacatccc taacaatgca acaaacctca gttggtgta cactcaaaac     360 aatccactct atatgagcgt gcttaatagc acaatccaca acttgcgctt cacgtcagat     420
actacgccta agccactagt gatcgttaca ccatcacacg tcagccatat tcaaggaacg     480
atcctatgtc tgaaaaaggt cgggttgcaa atcaggactc gatcaggagg gcacgatagt     540
gagggaatga gttacatctc gcaagtaccc ttcgtgatag ttgacttgcg aaatatgcgg     600
tctattaaaa ttgacgtaca tagccagacc gcctgggttg aagcaggggc aaccttgggt     660
gaagtttatt actgggtcaa tgaaaaaaac gaaaacctaa gtcttgctgc tggatattgc     720
cccaccgttt gcgcgggtgg tcattttgga ggcggcggat atggtccgtt gatgagaaat     780 tatgacttg cagcagacaa tattatagat gcccacttgg tgaacgttca tggaaaggtc     840
ttggaccgta agtccatggg tgaagatctt ttctgggcct tgagaggtgg tggagcggaa     900
tcgtttggca tcatcgttgc ctggaaaatt aggttggttg cggtcccgaa gagtacaatg     960
ttctccgtga agaagattat ggaaatacat gagcttgtca agttagttaa caagtggcaa    1020
aatatcgctt ataagtatga taaagacttg cttttgatga ctcattttat tacgcgaaac    1080
ataaccgata accagggcaa gaacaagact gctattcaca cgtacttctc ctctgtattt    1140
cttggaggag tagactcctt agttgacttg atgaacaaga gtttcccaga attgggggatt    1200 aagaagacag attgcagaca attatcgtgg atagatacaa tcatattcta tagcggtgtc    1260
gtcaattacg atactgataa ttttaataaa gaaatcctcc tagatcgttc agctgggcaa    1320
aacggggcat tcaaaattaa attggattat gtgaagaaac caattccaga gctggtgttt    1380
gttcagatat tggaaaaact ttacgaagaa gacattggcg caggtatgta cgctttgtat    1440
ccatatggag gcattatgga cgagatctca gagctggcga tccccttccc gcacagagct    1500
gggatactct acgagctatg gtacatctgc tcttgggaga acaagaaga caacgagaaa    1560 catctcaatt ggattcggaa catatacaac tttatgaccc catacgtatc aaaaaacccg    1620
```
cgcttagcat acttgaatta cagagactta gatatcggta tcaatgatcc taagaatcct    1680
aacaattaca cccaagcccg tatttggggt gagaaatatt tcggcaagaa ttttgacaga    1740
ttagttaagg tcaaaacact cgtggacccc acaacttttt tccgaaacga gcagtcgatt    1800
ccaccactac ccaggcatag acactga                                        1827

<210> SEQ ID NO 106
<211> LENGTH: 1572
<212> TYPE: DNA
<213> ORGANISM: Artificial Sequence
<220> FEATURE:
<223> OTHER INFORMATION: CvCBD1dNP1

<400> SEQUENCE: 106
atgaacccaa gggaaaactt ccttaagtgt tttctgcagt acatccctaa caatgcaaca      60
aacctcaagt tggtgtacac tcaaaacaat ccactctata tgagcgtgct aatagcaca     120 atccacaact tgcgcttcac gtcagatact acgcctaagc cactagtgat cgttacacca    180
tcacacgtca gccatattca aggaacgatc ctatgtctga aaaggtcgg gttgcaaatc     240 aggactcgat caggagggca cgatagtgag ggaatgagtt acatctcgca gtacccttc     300 gtgatagttg acttgcgaaa tatgcggtct attaaaattg acgtacatag ccagaccgcc    360
tgggttgaag caggggcaac cttgggtgaa gtttattact gggtcaatga aaaaacgaa     420 aacctaagtc ttgctgctgg atattgcccc accgtttgcg cgggtggtca ttttggaggc    480
ggcggatatg gtccgttgat gagaaattat ggacttgcag cagacaatat tatagatgcc    540
cacttggtga acgttcatgg aaaggtcttg gaccgtaagt ccatgggtga agatcttttc    600
tgggccttga gaggtggtgg agcggaatcg tttggcatca tcgttgcctg gaaaattagg    660
ttggttgcgg tcccgaagag tacaatgttc tccgtgaaga agattatgga aatacatgag    720
cttgtcaagt tagttaacaa gtggcaaaat atcgcttata agtatgataa agacttgctt    780
ttgatgactc attttattac gcgaaacata accgataacc agggcaagaa caagactgct    840
attcacacgt acttctcctc tgtatttctt ggaggagtag actccttagt tgacttgatg    900
aacaagagtt cccagaatt ggggattaag aagacagatt gcagacaatt atcgtggata     960
gatacaatca tattctatag cggtgtcgtc aattacgata ctgataattt taataaagaa    1020
atcctcctag atcgttcagc tgggcaaaac ggggcattca aaattaaatt ggattatgtg    1080
aagaaaccaa ttccagagct ggtgtttgtt cagatattgg aaaaacttta cgaagaagac    1140
attggcgcag gtatgtacgc tttgtatcca tatggaggca ttatggacga gatctcagag    1200
ctggcgatcc ccttcccgca cagagctggg atactctacg agctatggta catctgctct    1260
tgggagaaac aagaagacaa cgagaaacat ctcaattgga ttcggaacat atacaacttt    1320
atgaccccat acgtatcaaa aaacccgcgc ttagcatact tgaattacag agacttagat    1380
atcggtatca atgatcctaa gaatcctaac aattacaccc aagcccgtat tggggtgag     1440 aaatatttcg gcaagaattt tgacagatta gttaaggtca aaacactcgt ggaccccaac    1500
aactttttcc gaaacgagca gtcgattcca ccactaccca ggcatagaca cggaagaagg    1560
gcaaagttgt aa                                                        1572

<210> SEQ ID NO 107
<211> LENGTH: 1638
<212> TYPE: DNA
<213> ORGANISM: Artificial Sequence
<220> FEATURE:

<223> OTHER INFORMATION: CvTHC1 Gene

<400> SEQUENCE: 107

| | |
|---|---|
| atgaattgtt cagcatttag tttttggttt gtttgtaaga ttattttctt cttttgtca | 60 |
| tttaacattc aaatttcaat tgcaaaccca caagaaaact ttttgaagtg tttttcagaa | 120 |
| tacattccaa acaatccagc taacccaaag tttatttaca cacaacatga tcaattgtac | 180 |
| atgtcagttt tgaactcaac aattcaaaac ttgagattta catcagatac cacaccaaag | 240 |
| ccattggtta ttgttacacc atcaaacgtt tcccatattc aagcatcaat cttgtgttca | 300 |
| aagaaggttg gattgcaaat tagaaccaga tcaggaggac acgatgcaga aggaatgtca | 360 |
| tacatttcac aagttccatt cgttgttgtt gatttgagaa acatgcactc aattaagatt | 420 |
| gatgttcatt cacaaacagc atgggttgaa gcaggagcaa cattgggtga agtttactac | 480 |
| tggattaacg aaaagaacga aaacttcagt tttccaggag gttactgtcc aacagttgga | 540 |
| gttggaggac attttcagg tggaggatac ggagcattga tgagaaacta cggattggca | 600 |
| gcagataaca ttattgatgc acacttggtt aacgttgatg aaaaggtttt ggatagaaag | 660 |
| tcaatgggag aagatttgtt tgggcaatt agaggaggtg gtggagagaa ctttggaatt | 720 |
| attgcagcat ggaagatcaa gttggttgca gttccatcaa agtcaacaat cttttcagtt | 780 |
| aagaagaaca tggaaattca tggttttggtt aagttgttta caagtggca aaacattgca | 840 |
| tacaagtacg ataaggattt ggttttgatg acacattta ttacaaagaa cattacagat | 900 |
| aaccatggaa agaacaagac aacagttcac ggatactttt catcaattt tcacggagga | 960 |
| gttgattcat ggttgactt gatgaacaag tcatttccag aattgggaat caagaagaca | 1020 |
| gattgtaagg aattttcatg gattgataca acaatttctt actcaggagt tgttaacttt | 1080 |
| aacacagcaa acttaagaa ggaaattttg ttggacagat cagcaggaaa gaagaccgca | 1140 |
| ttttccatta gttggatta cgttaagaaa ccaattccag aaacagcaat ggttaagatt | 1200 |
| ttggaaaagt tgtacgaaga gatgttggt gttggaatgt acgttttgta cccatacgga | 1260 |
| ggaattatgg aagaaatctc agaatcagca attccatttc cacatagagc aggtattatg | 1320 |
| tacgaattgt ggtacacagc atcatgggaa aagcaagaag ataatgaaaa gcatattaac | 1380 |
| tgggttagat cagtttacaa cttacaaca ccatacgtt cacaaaaccc aagattggca | 1440 |
| tacttgaact acagagattt ggatttggga aagacaaacc cagaatcacc aaacaactat | 1500 |
| acacaagcta gaatttgggg agaaaagtac tttggtaaga acttcaacag attggttaaa | 1560 |
| gttaagacaa aggcagatcc aaataacttc tttagaaacg aacaatcaat tccaccattg | 1620 |
| ccaccacatc atcattaa | 1638 |

<210> SEQ ID NO 108
<211> LENGTH: 1728
<212> TYPE: DNA
<213> ORGANISM: Artificial Sequence
<220> FEATURE:
<223> OTHER INFORMATION: THC1dNS1 Gene

<400> SEQUENCE: 108

| | |
|---|---|
| atgttcttga aacacatttt tgttgctctc gcttttgcct tgttagctga cgctaccccca | 60 |
| gcccagaaga gatctcccgg cttcgttgct ttagactttg acatcgtcaa ggttcaaaag | 120 |
| aacgtgactg ccaacgacga cgccgctgcc attgttgcca agagacagac caacccacaa | 180 |
| gaaaactttt tgaagtgttt ttcagaatac attccaaaca atccagctaa cccaaagttt | 240 |
| atttacacac aacatgatca attgtacatg tcagttttga actcaacaat tcaaaacttg | 300 |

```
agatttacat cagataccac accaaagcca ttggttattg ttacaccatc aaacgtttcc    360
catattcaag catcaatctt gtgttcaaag aaggttggat tgcaaattag aaccagatca    420
ggaggacacg atgcagaagg aatgtcatac atttcacaag ttccattcgt tgttgttgat    480
ttgagaaaca tgcactcaat taagattgat gttcattcac aaacagcatg ggttgaagca    540
ggagcaacat ggggtgaagt ttactactgg attaacgaaa agaacgaaaa cttcagttttt   600 ccaggaggtt actgtccaac agttggagtt ggaggacatt tttcaggtgg aggatacgga    660
gcattgatga gaaactacgg attggcagca gataacatta ttgatgcaca cttggttaac    720
gttgatggaa aggttttgga tagaaagtca atgggagaag atttgttttg ggcaattaga    780
ggaggtggtg agagaacctt tggaattatt gcagcatgga agatcaagtt ggttgcagtt    840
ccatcaaagt caacaatctt ttcagttaag aagaacatgg aaattcatgg tttggttaag    900
ttgtttaaca gtggcaaaaa cattgcatac aagtacgata aggatttggt tttgatgaca    960 catttttatta caaagaacat tacagataac catggaaaga acaagacaac agttcacgga   1020
tacttttcat caattttttca cggaggagtt gattcattgg ttgacttgat gaacaagtca   1080
tttccagaat tgggaatcaa gaagacagat tgtaaggaat tttcatggat tgatacaaca   1140 atttttctact caggagttgt taactttaac acagcaaact ttaagaagga aattttgttg   1200
gacagatcag caggaaagaa gaccgcattt tccattaagt tggattacgt taagaaacca   1260
attccagaaa cagcaatggt taagatttttg gaaaagttgt acgaagaaga tgttggtgtt   1320
ggaatgtacg ttttgtaccc atacggagga attatgggaag aaatctcaga atcagcaatt   1380
ccatttccac atagagcagg tattatgtac gaattgtggt acacagcatc atgggaaaag   1440
caagaagata tgaaaagca tattaactgg gttagatcag tttacaactt tacaacacca   1500
tacgtttcac aaaacccaag attggcatac ttgaactaca gagatttgga tttgggaaag   1560
acaaacccag aatcaccaaa caactataca caagctagaa tttgggggaga aaagtacttt   1620 ggtaagaact tcaacagatt ggttaaagtt aagacaaagg cagatccaaa taacttcttt   1680
agaaacgaac aatcaattcc accattgcca ccacatcatc attaataa                1728
```

<210> SEQ ID NO 109
<211> LENGTH: 1638
<212> TYPE: DNA
<213> ORGANISM: Artificial Sequence
<220> FEATURE:
<223> OTHER INFORMATION: THC1dNS2

<400> SEQUENCE: 109

```
atgcaattgt cattgtcagt tttgtcaaca gttgcaacag cattgttgtc attgacaaca     60
gcagttgatg caaagtcaca taacccacaa gaaaacttttt tgaagtgttt ttcagaatac    120
attccaaaca atccagctaa cccaaagttt atttacacac aacatgatca attgtacatg    180
tcagttttga actcaacaat tcaaaacttg agatttacat cagataccac accaaagcca    240
ttggttattg ttacaccatc aaacgtttcc catattcaag catcaatctt gtgttcaaag    300
aaggttggat tgcaaattag aaccagatca ggaggacacg atgcagaagg aatgtcatac    360
atttcacaag ttccattcgt tgttgttgat ttgagaaaca tgcactcaat taagattgat    420
gttcattcac aaacagcatg ggttgaagca ggagcaacat ggggtgaagt ttactactgg    480
attaacgaaa agaacgaaaa cttcagttttt ccaggaggtt actgtccaac agttggagtt    540
ggaggacatt tttcaggtgg aggatacgga gcattgatga gaaactacgg attggcagca    600
```

```
gataacatta ttgatgcaca cttggttaac gttgatggaa aggttttgga tagaaagtca    660
atgggagaag atttgttttg ggcaattaga ggaggtggtg gagagaactt tggaattatt    720
gcagcatgga agatcaagtt ggttgcagtt ccatcaaagt caacaatctt ttcagttaag    780
aagaacatgg aaattcatgg tttggttaag ttgtttaaca agtggcaaaa cattgcatac    840
aagtacgata aggatttggt tttgatgaca cattttatta caaagaacat tacagataac    900
catggaaaga caagacaac  agttcacgga tactttcat  caattttca  cggaggagtt    960 gattcattgg ttgacttgat gaacaagtca tttccagaat tgggaatcaa gaagacagat   1020
tgtaaggaat tttcatggat tgatacaaca atttctact  caggagttgt taactttaac   1080
acagcaaact ttaagaagga aattttgttg gacagatcag caggaaagaa gaccgcattt   1140
tccattaagt tggattacgt taagaaacca attccagaaa cagcaatggt taagattttg   1200
gaaaagttgt acgaagaaga tgttggtgtt ggaatgtacg ttttgtaccc atacggagga   1260
attatgaaag aaatctcaga atcagcaatt ccatttccac atagagcagg tattatgtac   1320
gaattgtggt acacagcatc atgggaaaag caagaagata tgaaaagca  tattaactgg   1380 gttagatcag tttacaactt tacaacacac tacgtttcac aaaacccaag attggcatac   1440
ttgaactaca gagatttgga tttgggaaag acaaacccag aatcaccaaa caactataca   1500
caagctagaa tttggggaga aaagtacttt ggtaagaact tcaacagatt ggttaaagtt   1560
aagacaaagg cagatccaaa taacttcttt agaaacgaac aatcaattcc accattgcca   1620
ccacatcatc attaataa                                                 1638

<210> SEQ ID NO 110
<211> LENGTH: 1833
<212> TYPE: DNA
<213> ORGANISM: Artificial Sequence
<220> FEATURE:
<223> OTHER INFORMATION: THC1dNV1

<400> SEQUENCE: 110
atgcaattgt ccttgtcggt tttatcaacc gttgccacgg ccttgttgtc cctaaccacc     60
gccgtcgatg ctaagtccca caacatcaag ttgtccaagt tgtccaacga agaaacattg    120
gacgcctcca cattccaaga atacacgagc tccttggcca caagtacat  gaacttgttc    180 aacgccgctc acggtaaccc aaccagcttt ggcttgcaac acgtcttgtc caaccaagaa    240
gctgaagtcc cattcgttac cccacaaaag ggtggcaacc cacaagaaaa cttttttgaag   300 tgttttttcag aatacattcc aaacaatcca gctaacccaa agtttattta cacacaacat    360
gatcaattgt acatgtcagt tttgaactca acaattcaaa acttgagatt tacatcagat    420
accacaccaa agccattggt tattgttaca ccatcaaacg tttcccatat tcaagcatca    480
atcttgtgtt caagaaggt  tggattgcaa attagaacca gatcaggagg acacgatgca    540
gaaggaatgt catacatttc acaagttcca ttcgttgttg ttgatttgag aaacatgcac    600
tcaattaaga ttgatgttca ttcacaaaca gcatggggtt aagcaggagc aacattgggt    660
gaagtttact actggattaa cgaaagaac  gaaaacttca gttttccagg aggttactgt    720
ccaacagttg gagttggagg acattttttca ggtggaggat acggagcatt gatgagaaac    780
tacggattgg cagcagataa cattattgat gcacacttgg ttaacgttga tggaaaggtt    840
ttggatagaa agtcaatggg agaagatttg ttttggcaa  ttagaggagg tggtggagag    900
aactttggaa ttattgcagc atggaagatc aagttggttg cagttccatc aaagtcaaca    960
atcttttcag ttaagaagaa catggaaatt catggtttgg ttaagttgtt taacaagtgg   1020
```

| | | | |
|---|---|---|---|
| caaaacattg | catacaagta | cgataaggat ttggttttga tgacacattt tattacaaag | 1080 |
| aacattacag | ataaccatgg | aaagaacaag acaacagttc acggatactt ttcatcaatt | 1140 |
| tttcacggag | gagttgattc | attggttgac ttgatgaaca agtcatttcc agaattggga | 1200 |
| atcaagaaga | cagattgtaa | ggaattttca tggattgata caacaatttt ctactcagga | 1260 |
| gttgttaact | ttaacacagc | aaactttaag aaggaaattt tgttggacag atcagcagga | 1320 |
| aagaagaccg | cattttccat | taagttggat tacgttaaga aaccaattcc agaaacagca | 1380 |
| atggttaaga | ttttggaaaa | gttgtacgaa gaagatgttg tgttggaat gtacgttttg | 1440 |
| tacccatacg | gaggaattat | ggaagaaatc tcagaatcag caattccatt tccacataga | 1500 |
| gcaggtatta | tgtacgaatt | gtggtacaca gcatcatggg aaaagcaaga agataatgaa | 1560 |
| aagcatatta | ctgggttag | atcagtttac aactttacaa caccatacgt ttcacaaaac | 1620 |
| ccaagattgg | catacttgaa | ctacagagat ttggatttgg gaaagacaaa cccagaatca | 1680 |
| ccaaacaact | atacacaagc | tagaatttgg ggagaaaagt actttggtaa gaacttcaac | 1740 |
| agattggtta | aagttaagac | aaaggcagat ccaaataact tctttagaaa cgaacaatca | 1800 |
| attccaccat | tgccaccaca | tcatcattaa taa | 1833 |

<210> SEQ ID NO 111
<211> LENGTH: 1638
<212> TYPE: DNA
<213> ORGANISM: Artificial Sequence
<220> FEATURE:
<223> OTHER INFORMATION: CvCBC1 Gene

<400> SEQUENCE: 111

| | | | |
|---|---|---|---|
| atgaattgta | gcactttctc | attctggttt gtttgtaaga ttatttctt tttcttgtca | 60 |
| tttaacattc | aaatttcaat | tgcaaaccca caagagaact ttttgaagtg tttctcagaa | 120 |
| tacattccaa | caacccagc | taacccaaag tttatttaca cccaacacga tcaattgtac | 180 |
| atgtcagttt | tgaactcaac | aattcaaaac ttgagattta catcagatac aacaccaaag | 240 |
| ccattggtta | ttgttacacc | atcaaacgtt agtcatattc aagcatcaat cttgtgttca | 300 |
| aagaaggttg | gattgcaaat | tagaactaga tcaggaggac atgatgcaga aggattgtca | 360 |
| tacatttcac | aagttccatt | tgcaattgtt gatttgagaa acatgcacac agttaaggtt | 420 |
| gatattcatt | cacaaacagc | atgggttgaa gcaggagcaa cattgggtga agtttactac | 480 |
| tggattaacg | aaatgaacga | aaacttctca tttccaggag gatactgtcc aacagttggt | 540 |
| gttggaggac | acttttcagg | tggtggatac ggagcattga tgagaaacta cggattggca | 600 |
| gcagataaca | ttattgatgc | acatttggtt aacgttgatg gaaaggtttt ggatagaaag | 660 |
| tcaatgggag | aagattgtt | tgggcaatt agaggaggtg gaggagaaaa ctttggaatc | 720 |
| attgcagcat | gtaagatcaa | gttggttgtt gttccatcaa aggcaacaat cttttcagtt | 780 |
| aagaagaaca | tggaaatcca | tggattggtt aagttgttta caagtggca aaacattgca | 840 |
| tacaagtacg | ataaggattt | gatgttgaca acacatttta gaacaagaaa cattacagat | 900 |
| aaccacggaa | agaataagac | aacagttcat ggatactttt catcaatttt cttgggagga | 960 |
| gttgattcat | tggttgactt | gatgaacaag agttttccag aattgggaat caagaagaca | 1020 |
| gattgtaagg | aattgtcatg | gatcgataca accatttttct actcaggagt tgttaactac | 1080 |
| aacacagcta | actttaagaa | ggaaattttg ttggacagat cagcaggtaa aaagacagca | 1140 |
| ttttcaatta | agttggatta | cgttaagaaa ttgattccag aaacagcaat ggttaagatt | 1200 |

```
ttggaaaagt tgtacgaaga agaagttgga gttggaatgt acgttttgta cccatacgga    1260
ggaattatgg atgaaatttc agaatcagca attccatttc cacatagagc aggtattatg    1320
tacgaattgt ggtacacagc aacatgggaa aagcaagaag ataacgaaaa gcatattaac    1380
tgggttagat cagtttacaa ctttacaacc ccatacgttt cacaaaaccc aagattggca    1440
tacttgaact acagagattt ggatttggga aagacaaacc cagaatcacc aaataactac    1500
acacaagcta gaatttgggg agaaaagtac tttggtaaga actttaacag attggtgaag    1560
gttaagacaa aggcagaccc aaacaatttc tttagaaacg aacaatcaat tccaccattg    1620
ccaccaagac atcattaa                                                  1638

<210> SEQ ID NO 112
<211> LENGTH: 2130
<212> TYPE: DNA
<213> ORGANISM: Artificial Sequence
<220> FEATURE:
<223> OTHER INFORMATION: YlACO1P Gene

<400> SEQUENCE: 112
atgaccgaag tagttgacag agcctcatcc cccgcatccc ctggctcaac tacggccgcc      60
gcagacggtg ctaaggtggc cgtcgagccc cgagtagatg tggctgcgct gggagagcag    120
ctgctgggcc gatgggctga tatccgtctc cacgcccggg accttgcggg acgagaggta    180
gttcagaagg tggagggtct gactcataca gagcaccgct ctcgcgtctt ggccagctc     240 aagtacttgg tcgataacaa cgcagttcac cgagcctttc cttctcgact gggtggtagt    300
gacgaccacg gcgaaacat cgctggtttt gaggagcttg tcacggcgga cccctccctc    360
cagatcaagg ccggcgtcca gtggggactg ttcggctccg ctgttatgca cttgggaact    420
agggagcacc acgacaagtg gctcccaggc atcatgtctc tggaaatccc tggttgcttt    480
gccatgactg agactggcca tggctccgat gtcgcttcca ttgctacaac ggccacctat    540
gatgaggaaa cccaggagtt cgttattgac accccgttcc gagccgcctg gaaggactac    600
attggaaacg ccgctaacga cggtttggcc gctgtcgtgt ttgcccaact gattactcga    660
aaggttaacc atggagtgca cgccttctac gtcgatctga gagatcccgc caccggagac    720
tttctccctg gtattggtgg agaggacgac ggtattaagg ggggactaaa cggaattgat    780 aacgacgtc tccatttcac caatgttcgc attccccgaa ccaacctgct taaccgttac    840
ggcgatgttg ccgtcgatgg cacctacagc tcaaccatcg aatctccggg gcgaagattc    900
tttacaatgc taggtacgct ggtccagggc cgagtcagcc tggacggtgc tgcagtggct    960
gcatcgaagg ttgctctgca atccgccatc cactacgccg ctgagcgaag acagttcaac   1020
gccacttcgc ccacagagga ggaggtgctc ctggattacc agcgacacca gcggcgcctc   1080
tttacccgac tcgccaccac ctacgccgca tcgttcgccc atgagcaact gctgcagaaa   1140
ttcgacgacg tgttctcggg tgctcatgat actgacgccg accgtcagga ccttgagaca   1200
ctggctgctg ctctgaagcc ccttttctac tggcatgctc tcgataccct acaagagtgc   1260
cgagaagcgt gtggggtgc aggttttctg attgagaacc gattcgcttc tctccgggcc   1320
gatctcgacg tctacgtgac cttcgaagga gacaacaccg tgcttcttca gttggtggcc   1380
aagaggctgc tcgctgacta tgctaaggag ttccgaggtg ccaacttcgg cgtgctcgcg   1440
cggtacgtcg tggaccaggc tgccggagtc gcgctacacc gaaccggact gcgacaggtc   1500
gctcagttcg tggccgacag tggatctgtc cagaaatctg ctcttgccct ccgagacgaa   1560
gaaggtcagc gaactctgct gaccgacaga gtccagtcca tggttgcaga ggttggcgct   1620
```

```
gctctcaaag gcgcgggcaa gctcccccag caccaggcgg cagcactgtt caatcagcat    1680
caaaacgaac tgatcgaggc tgcccaggcc acgctgagc ttttacagtg ggaggccttt    1740
actgaggctt tggccaaggt ggacgacgct ggcactaagg aagtgttgac ccgattgcgt    1800 gaccttttg gtctgtccct tatcgagaag cacctcagct ggtatctgat gaacggtagg    1860
ctctcgatgc agagaggccg aacggtcggc acttacatta atcgtcttct cgttaagatc    1920
cgaccacacg cacttgatct ggttgatgcc ttcggctacg gagccgagca ccttcgggcc    1980
gctatcgcca ccggcgctga ggccaccccga caggacgagg cccgaaccta cttcagacag    2040
caacgagcct ccggtagcgc ccctgctgac gagaagacac tcctcgctat caaggccggc    2100
aagtctcggg gacgacgagc caaactgtaa                                     2130
```

<210> SEQ ID NO 113
<211> LENGTH: 2163
<212> TYPE: DNA
<213> ORGANISM: Artificial Sequence
<220> FEATURE:
<223> OTHER INFORMATION: YlHXS1 Gene

<400> SEQUENCE: 113

```
atgggaaaga attacaaaag tctagattct gtcgttgcca gtgacttcat cgcgttaggc     60
attacatccg aggtcgctga gactctgcac ggacggcttg ccgagattgt gtgcaactac    120
ggagccgcta cccctcagac ttggattaac atcgccaacc acattctgtc gccggacctc    180
cccttctctt tgcaccagat gttattctac ggatgctaca aggattttgg ccctgcacct    240
cctgcctgga ttccggaccc cgaaaaagtc aagtccacca acctaggtgc cctgctggaa    300
aagcgaggaa aggagttcct tggtgtcaag tacaaggacc ccatttcttc tttttctcat    360
ttccaggaat tttcggtgcg taatcctgag gtgtattggc gaactgtgct catggacgag    420
atgaaaatct ccttcagcaa ggacccagag tgtatcctgc gacgagacga cattaacaac    480
ccaggaggct cggagtggct tcccggcgga tacctaaact cagctaagaa ttgtctcaac    540
gtgaactcta acaagaagtt gaacgacacc atgatcgtgt ggcgtgacga aggcaacgac    600
gacctgcccc tgaacaagtt gactctggac cagctgcgaa gagggtctg gttggttggc    660 tacgccctcg aagagatggg cttagagaag ggttgcgcta ttgctattga tatgcccatg    720
cacgtcgatg ctgtagtgat ctaccttgcc attgtgttag ccggttacgt ggtcgtatcg    780
attgccgatt cgttctccgc tccggagatt tccacccgac tcagacttag caaggccaag    840
gcaatcttta ctcaagatca catcatccga ggtaagaaga gaatccctct ctattctcgc    900
gtggttgagg ccaagtcccc aatggctatc gtcataccctt gcagcggatc aaacatcggg    960
gctgagctac gggacggtga tatctcctgg gattacttcc tggagcgagc caaagagttc   1020
aagaactgcg agtttacagc gcgtgagcag cccgtcgatg cctacacgaa cattctattc   1080
tcatcgggca acgggagag cccaaggcc atccctgga cccaagctac cccttgaaa     1140 gctgccgctg atggttggtc ccatctcgac atcagaaaag gcgatgtgat cgtttggccc   1200
actaacctgg gctggatgat gggtccttgg ctggtatatg ccagcctact gaacggcgct   1260
tcaatcgcac tgtacaacgg atctccactc gtcagcggct tgccaagtt tgttcaagac   1320 gccaaagtca ccatgctggg tgttgttcct tcaatcgtgc gaagttggaa gagtaccaac   1380
tgtgtctctg gatacgactg gagcaccatt cgatgcttca gttcctccgg cgaggcttcc   1440
aacgttgatg agtacctctg gcttatgggt cgtgcgaatt acaagcctgt gatcgagatg   1500
```

| | | | | |
|---|---|---|---|---|
| tgtggtggaa | cagaaattgg | tggtgctttt | tcggccgggt | cctttcttca ggctcagtct | 1560 |
| ctctcctctt | tctcttccca | gtgtatggga | tgcaccctgt | atattctcga caagaacggt | 1620 |
| taccccatgc | cgaagaataa | acccggtatt | ggggagcttg | ctcttggccc cgtcatgttt | 1680 |
| ggtgcatcga | agaccctcct | gaacggaaac | catcacgacg | tctacttcaa gggcatgccc | 1740 |
| acacttaacg | gcgaagttct | tcggcgacat | ggagacattt | tcgaacttac atcgaacgga | 1800 |
| tactaccacg | cccacgggcg | agcagatgat | acgatgaaca | tcgggggcat caagatatct | 1860 |
| tctatcgaga | ttgaaagagt | gtgtaacgag | gtagacgacc | gcgtcttcga gactactgcg | 1920 |
| atcggcgtcc | cccccctggg | cggtggcccg | gagcagctag | tcattttttt tgtgctcaag | 1980 |
| gactctaacg | acacgaccat | cgacctcaat | cagctgcgac | tctccttcaa ccttggattg | 2040 |
| cagaagaagc | tgaaccctct | cttcaaggtc | actcgggttg | ttcccttgtc ctctcttcct | 2100 |
| cgaaccgcca | ccaacaagat | tatgcgacga | gtgctccgac | agcagttctc ccacttcgag | 2160 |
| taa | | | | | 2163 |

<210> SEQ ID NO 114
<211> LENGTH: 1158
<212> TYPE: DNA
<213> ORGANISM: Artificial Sequence
<220> FEATURE:
<223> OTHER INFORMATION: YlTKS1 Gene

<400> SEQUENCE: 114

| | | | | |
|---|---|---|---|---|
| atgaatcatc | taagagccga | aggaccagca | agtgtactcg | ctattggtac tgctaacccc | 60 |
| gagaacattc | ttattcagga | tgagttcccg | gactactatt | tcagggttac caagagcgag | 120 |
| catatgaccc | agcttaaaga | gaagttccgc | aagatatgcg | acaagtccat gatccgaaag | 180 |
| cggaactgct | ttctcaatga | ggagcacttg | aagcaaaacc | cccgactggt tgagcacgag | 240 |
| atgcagacct | tggacgcgcg | acaagacatg | ctcgtcgtcg | aggtgcccaa actcggtaag | 300 |
| gatgcttgcg | ctaaggccat | taaggagtgg | ggtcagccca | gtcgaagat tacccaccta | 360 |
| atcttcacct | ccgcaagcac | tacagacatg | cccggtgcag | actaccactg tgccaagctg | 420 |
| ctcggactgt | caccgtcggt | caagcgagtg | atgatgtacc | agctcggctg ttacgggggt | 480 |
| ggaaccgttc | tccgtatcgc | caaggatatc | gctgagaaca | caaaggagc tcgtgtcctg | 540 |
| gctgtgtgtt | gcgacatcat | ggcctgcttg | ttcagaggcc | ctagtgattc cgatctggaa | 600 |
| ttacttgtcg | gtcaggccat | cttttggagat | ggcgccgccg | ctgtcatcgt gggtgccgaa | 660 |
| cccgacgagt | ctgttggaga | aagaccccatc | tttgagcttg | tctccacggg ccagaccatc | 720 |
| ctccctaaca | gcgagggcac | aattggaggc | catattcgag | aggccggtct gattttgac | 780 |
| ctgcataagg | acgtgcctat | gctgatttcg | aacaacatcg | agaagtgtct catcgaggcc | 840 |
| ttcactccca | tcggcatttc | ggactggaac | tcaatcttct | ggatcaccca cccaggaggc | 900 |
| aaggcgattc | tggataaagt | tgaggaaaag | ctcgacctta | agaaggagaa gtttgtggat | 960 |
| tctcgacacg | tcctgtctga | acacggtaac | atgtcttcct | ctactgtcct gttcgtaatg | 1020 |
| gacgagcttc | gaaagcgatc | tctggaggaa | ggaaagtcca | cgaccggcga cggttttgag | 1080 |
| tggggcgtgc | tgttcgggtt | cggtcctggc | ctcactgtgg | agcgagttgt tgtccggtcc | 1140 |
| gtgcctatta | agtactaa | | | | 1158 |

<210> SEQ ID NO 115
<211> LENGTH: 1176
<212> TYPE: DNA
<213> ORGANISM: Artificial Sequence
<220> FEATURE:
<223> OTHER INFORMATION: Y1TKS1P Gene

<400> SEQUENCE: 115

```
atgaatcatc taagagccga aggaccagca agtgtactcg ctattggtac tgctaacccc      60
gagaacattc ttattcagga tgagttcccg gactactatt tcagggttac caagagcgag     120
catatgaccc agcttaaaga gaagttccgc aagatatgcg acaagtccat gatccgaaag     180
cggaactgct ttctcaatga ggagcacttg aagcaaaacc cccgactggt tgagcacgag     240
atgcagacct tggacgcgcg acaagacatg ctcgtcgtcg aggtgcccaa actcggtaag     300
gatgcttgcg ctaaggccat taaggagtgg ggtcagccca gtcgaagat tacccaccta      360
atcttcacct ccgcaagcac tacagacatg cccggtgcag actaccactg tgccaagctg     420
ctcggactgt caccgtcggt caagcgagtg atgatgtacc agctcggctg ttacgggggt     480
ggaaccgttc tccgtatcgc caaggatatc gctgagaaca caaaggagc tcgtgtcctg      540
gctgtgtgtt gcgacatcat ggcctgcttg ttcagaggcc ctagtgattc cgatctggaa     600
ttacttgtcg gtcaggccat cttttggagat ggcgccgccg ctgtcatcgt gggtgccgaa    660
cccgacgagt ctgttggaga aagacccatc tttgagcttg tctccacggg ccagaccatc    720
ctccctaaca gcgagggcac aattggaggc catattcgag aggccggtct gattttgac      780
ctgcataagg acgtgcctat gctgatttcg aacaacatcg agaagtgtct catcgaggcc    840
ttcactccca tcggcatttc ggactggaac tcaatcttct ggatcaccca cccaggaggc    900
aaggcgattc tggataaagt tgaggaaaag ctcgacctta agaaggagaa gtttgtggat    960
tctcgacacg tcctgtctga acacggtaac atgtcttcct ctactgtcct gttcgtaatg   1020
gacgagcttc gaaagcgatc tctggaggaa ggaaagtcca cgaccggcga cggttttgag   1080
tggggcgtgc tgttcgggtt cggtcctggc ctcactgtgg agcgagttgt tgtccggtcc   1140
gtgcctatta agtacggaag aagggcaaag ttgtaa                              1176
```

<210> SEQ ID NO 116
<211> LENGTH: 318
<212> TYPE: DNA
<213> ORGANISM: Artificial Sequence
<220> FEATURE:
<223> OTHER INFORMATION: Y1OAC1 Gene

<400> SEQUENCE: 116

```
atggccgtca acacccttat tgtcctcaag ttcaaagatg agatcactga agcccagaag      60
gaggagtttt tcaagaccta cgtcaatttg gtcaacatca ttccagcaat gaaggatgtg     120
tactggggca aggacgtgac ccagaagaac aaggaagagg ttataccca tatcgttgag      180
gttacgttcg agtctgtgga gacaatccaa gactacatca ttcacccgc tcacgtgggc      240
tttggagacg tttacagatc cttctgggag aagctcctga ttttgacta cactcctcga      300
aagctgaagc ccaagtaa                                                   318
```

<210> SEQ ID NO 117
<211> LENGTH: 336
<212> TYPE: DNA
<213> ORGANISM: Artificial Sequence
<220> FEATURE:
<223> OTHER INFORMATION: Y1OAC1P Gene

<400> SEQUENCE: 117

```
atggccgtca acacccttat tgtcctcaag ttcaaagatg agatcactga agcccagaag      60
```

```
gaggagtttt tcaagaccta cgtcaatttg gtcaacatca ttccagcaat gaaggatgtg    120
tactggggca aggacgtgac ccagaagaac aaggaagagg gttatacccca tatcgttgag   180 gttacgttcg agtctgtgga gacaatccaa gactacatca ttcacccccgc tcacgtgggc   240 tttggagacg tttacagatc cttctgggag aagctcctga ttttttgacta cactcctcga   300 aagctgaagc ccaagggaag aagggcaaag ttgtaa                              336
```

<210> SEQ ID NO 118
<211> LENGTH: 1197
<212> TYPE: DNA
<213> ORGANISM: Artificial Sequence
<220> FEATURE:
<223> OTHER INFORMATION: YlPTS2 Gene

<400> SEQUENCE: 118

```
atgggcctct ctctagtatg taccttctct ttccagacca actatcacac tctactgaac    60
ccccataaca agaaccctaa aaattctctt ctcagttacc agcacccccaa gacgcctatc   120 attaagtcct cctacgacaa cttttccctct aagtactgcc tgaccaaaaa cttccatctc   180
ctgggactga actctcataa cagaattagt agccagtccc gatctatccg agctggctct   240
gaccagattg agggctcccc tcaccatgaa tccgacaaca gcatcgctac caagattttg   300
aattttggtc acacatgctg gaagctccag cgaccgtacg tcgtgaaggg tatgatctcg   360
attgcctgtg gactgttcgg acgtgagctt tttaataatc gacacttgtt ttcatggggc   420
ctcatgtgga aggctttttt cgccctcgtg cccattctgt ctttcaactt ctttgccgct   480
attatgaacc aaatctacga cgttgatatt gataggatca caagcctgac ctgccgctc    540 gtctcgggg agatgtctat cgagacagcg tggattcttt cgattatcgt cgcgctgact    600
ggccttatcg ttaccataaa gttgaagtct gcaccctct tcgtgttttat ctacatttttc   660 ggtattttg ctggattcgc gtactccgtt ccccctatca gatggaagca gtacccctt    720 actaactttc tgattactat cagcagccac gtcggtttag cctttacctc atattcggcc   780
accaccagtg cactgggcct ccccttcgtc tggcgacctg cattttcatt catcatcgcc   840
ttcatgactg tgatgggtat gaccatcgct ttcgctaagg acatctccga catcgagggt   900
gatgctaaat atggagtgtc caccgtggcc actaagctgg gagcccggaa catgacgttc   960
gtcgtctctg tgttctgct ccttaactac ttggtttcga tctccattgg cattatctgg   1020
ccacaagtct tcaagtccaa cattatgatt ctgtcccacg ccattcttgc cttttgcctg   1080
atcttccaga cacgcgaact cgctctcgct aactacgcct ccgccccatc gcgacagttc   1140
ttcgagttca tctggctgct ttactacgcc gagtacttcg tttacgtgtt catctaa     1197
```

<210> SEQ ID NO 119
<211> LENGTH: 1635
<212> TYPE: DNA
<213> ORGANISM: Artificial Sequence
<220> FEATURE:
<223> OTHER INFORMATION: YlCBD1 Gene

<400> SEQUENCE: 119

```
atgaagtgtt cgacgttttc ttttttggttt gtttgtaaaa tcatttttctt tttcttttct    60 ttcaacatcc aaacgtcgat cgcaaaccct agagagaact ttcttaagtg cttctcgcag   120
tacatcccta ataacgctac caaccttaag ctggtgtaca cccagaacaa ccctcttttac   180 atgtctgttc taaacagcac catccacaat cttagattca catcagacac cactcccaag   240
ccgctcgtca tcgtgacccc gagtcatgtg tcccatatcc aaggcactat cctgtgctct   300
```

```
aaaaaggtcg gtctgcagat tcggactcgc tccggtggac atgattcgga gggcatgtcc    360
tacattagcc aggtccccct tgtgatcgtg gacctgagga catgcggtc  tattaagatt    420
gatgtgcact cacagaccgc ttgggtcgag gctggtgcga cattgggtga ggtgtactac    480
tgggtgaacg agaagaacga gaacctgagc ctcgccgctg gctactgtcc caccgtttgt    540
gccggtggac acttcggcgg aggcggatac ggtccactta tgcgaaacta cgggctcgca    600
gctgataata tcatcgacgc acaccttgtt aacgttcacg gcaaggtgct ggaccgaaaa    660
agcatgggtg aggacctatt tgggccttgc gaggcggtg  gtgccgaatc cttcggaatt    720
atcgtggcct ggaagatccg actggtcgct gtgccaaagt ccactatgtt ctccgtcaag    780
aaaattatgg agatccacga actcgtaaag ctcgtcaata gtggcagaa  catcgcctac    840
aagtatgaca aggatctgct gctcatgact cacttcatca cgcgaaacat tacagacaac    900
cagggaaaga acaagaccgc tatccatacc tacttctcct ctgtcttcct tgggggtgtc    960
gattccctcg ttgatctcat gaacaaatct tttccagagc tcggaatcaa gaagaccgac   1020
tgccgacagc tctcttggat cgacaccatt attttctact caggagtcgt aaactacgat   1080
actgacaact ttaacaagga gattctgtta gatcgatcgg ccggccagaa cggtgccttc   1140
aagatcaagc tcgactatgt caaaaagccc attcctgaat ccgtcttcgt tcaaattctt   1200
gaaaagttgt acgaggagga tatcggcgcc ggaatgtacg cgctgtaccc ctacggtggc   1260
attatggacg agatttctga agtgctatt  cccttccccc accgtgctgg cattctgtat   1320
gagctgtggt acatttgctc ctgggaaaag caggaggaca acgagaagca cttgaactgg   1380
atacgaaaca tttacaattt catgaccccc tatgtttcga agaaccctcg actggcctac   1440
ctgaattacc gcgacctcga catcggaatt aacgacccta agaacccaa  taactatact   1500
caggccagaa tctggggcga gaagtacttc ggcaagaact tgaccgtct  ggttaaggtc   1560
aagaccctcg tggaccctaa caacttcttc cgaaacgagc agtctatccc ccctctgccc   1620
cgacaccggc attaa                                                    1635
```

<210> SEQ ID NO 120
<211> LENGTH: 1638
<212> TYPE: DNA
<213> ORGANISM: Artificial Sequence
<220> FEATURE:
<223> OTHER INFORMATION: YlTHC1 Gene

<400> SEQUENCE: 120

```
atgaattgtt cagctttctc ttttggtttt gtctgtaaga tcatttcttt ctttctatcc     60
tttcacatcc aaatttccat agccaaccct cgtgagaact tccttaagtg cttttccaag    120
cacattccaa ataacgtcgc caatcccaag ctggtgtaca cgcagcatga ccagctctac    180
atgtcgatcc tcaattccac cattcaaaac cttagattca ttagtgacac cactcccaag    240
cccctagtca ttgtcacccc ttcgaacaac tcgcatattc aggcaactat tctctgctcc    300
aagaaggttg gtttacagat ccgaacccgg tcaggtggtc acgacgctga gggcatgtct    360
tacatttccc aggtccccct tgtggtggtc gatctgcgca acatgcactc cattaaaatc    420
gacgtccact cgcagactgc ctgggtcgag gctggagcca cccttggcga ggtctactac    480
tggattaacg agaagaacga aaacctgtcg ttccctggcg gctactgtcc gactgttgga    540
gtcggcggac actttctgg  tgcgggatat ggtgctctca tgcgaaacta cggactggcg    600
gcagacaaca tcatcgatgc ccaccttgtg aacgttgacg gtaaggtact ggaccgaaag    660
```

```
tctatgggcg aggacttgtt ttgggccatc cgaggtggag gtggtgagaa cttcgggatc    720
atcgccgcct ggaagatcaa gctggtggat gtgcccagta agtctaccat ttttagcgtg    780
aagaagaaca tggagatcca cgggctggtg aagctgttca acaagtggca gaatattgcg    840
tacaaatacg acaaggacct ggtgcttatg acccatttca tcaccaagaa catcacggat    900
aaccacggta aaacaagac tactgttcac ggttacttct cttcaattt ccatggtggt    960 gtggattccc tcgttgattt gatgaacaag tccttcccag agctgggcat taagaagaca   1020
gactgcaagg aatttagctg gattgatacc accatcttct actctggagt tgtcaacttc   1080
aacaccgcaa acttcaagaa ggaaatcctc ttggaccgat ctgccggcaa gaagacagct   1140
ttttcgatta aactggatta cgtgaagaag cccatccctg agacagctat ggtcaagatc   1200
cttgaaaaac tttatgagga ggacgtcgga gccggaatgt acgttctcta tccttacggc   1260
ggcatcatgg aggaaatttc tgagtctgct atccccttcc cccatcgagc cggaatcatg   1320
tacgagctgt ggtacaccgc tagttgggag aagcaggagg ataacgagaa acatatcaat   1380
tgggtccgta gcgtatacaa tttcacgaca ccctacgtgt cccagaaccc tcgactcgct   1440
tacctgaact atagggacct ggacctcggc aagactaacc acgctagccc gaacaactac   1500
acccaggcca gaatttgggg cgaaaagtac ttcggaaaga acttcaaccg actcgttaag   1560
gttaagacca agttgacccc caacaacttt ttccggaacg agcagtccat ccctccactc   1620
cctccccacc atcactga                                                 1638
```

<210> SEQ ID NO 121
<211> LENGTH: 26
<212> TYPE: DNA
<213> ORGANISM: Artificial Sequence
<220> FEATURE:
<223> OTHER INFORMATION: CvACT1

<400> SEQUENCE: 121

```
cccaattcct gtggtgggtt gattcg                                          26
```

<210> SEQ ID NO 122
<211> LENGTH: 29
<212> TYPE: DNA
<213> ORGANISM: Artificial Sequence
<220> FEATURE:
<223> OTHER INFORMATION: CvACT1

<400> SEQUENCE: 122

```
ctctcaattc gttgtagaag gtgtggtgc                                       29
```

<210> SEQ ID NO 123
<211> LENGTH: 29
<212> TYPE: DNA
<213> ORGANISM: Artificial Sequence
<220> FEATURE:
<223> OTHER INFORMATION: CvHXS1

<400> SEQUENCE: 123

```
ctttggactc agttgtggct agtgacttc                                       29
```

<210> SEQ ID NO 124
<211> LENGTH: 34
<212> TYPE: DNA
<213> ORGANISM: Artificial Sequence
<220> FEATURE:
<223> OTHER INFORMATION: CvHXS1

<400> SEQUENCE: 124
gatcaagagt caatttattc aatgggagat cgtc                                   34

<210> SEQ ID NO 125
<211> LENGTH: 23
<212> TYPE: DNA
<213> ORGANISM: Artificial Sequence
<220> FEATURE:
<223> OTHER INFORMATION: CvTKS1

<400> SEQUENCE: 125
gagcagaagg acccgcatca gtg                                               23

<210> SEQ ID NO 126
<211> LENGTH: 28
<212> TYPE: DNA
<213> ORGANISM: Artificial Sequence
<220> FEATURE:
<223> OTHER INFORMATION: CvTKS1

<400> SEQUENCE: 126
gtcaccaaaa attgcctgtc cgacaagc                                          28

<210> SEQ ID NO 127
<211> LENGTH: 31
<212> TYPE: DNA
<213> ORGANISM: Artificial Sequence
<220> FEATURE:
<223> OTHER INFORMATION: CvOAC1

<400> SEQUENCE: 127
cacgacataa tggcagtcaa acacctaata g                                      31

<210> SEQ ID NO 128
<211> LENGTH: 31
<212> TYPE: DNA
<213> ORGANISM: Artificial Sequence
<220> FEATURE:
<223> OTHER INFORMATION: CvOAC1

<400> SEQUENCE: 128
ctagttttgt gttcggagta tgcatacaac g                                      31

<210> SEQ ID NO 129
<211> LENGTH: 25
<212> TYPE: DNA
<213> ORGANISM: Artificial Sequence
<220> FEATURE:
<223> OTHER INFORMATION: CvPTS1

<400> SEQUENCE: 129
ctaccacacc ctcctaaacc ctcac                                             25

<210> SEQ ID NO 130
<211> LENGTH: 31
<212> TYPE: DNA
<213> ORGANISM: Artificial Sequence
<220> FEATURE:
<223> OTHER INFORMATION: CvPTS1

<400> SEQUENCE: 130
cgaagcagta cccgaatata taatggac c                                        31

<210> SEQ ID NO 131
<211> LENGTH: 29
<212> TYPE: DNA

```
<213> ORGANISM: Artificial Sequence
<220> FEATURE:
<223> OTHER INFORMATION: CvCBD1

<400> SEQUENCE: 131
ccttcaacat tcagacatca atcgccaac                                        29

<210> SEQ ID NO 132
<211> LENGTH: 22
<212> TYPE: DNA
<213> ORGANISM: Artificial Sequence
<220> FEATURE:
<223> OTHER INFORMATION: CvCBD1

<400> SEQUENCE: 132
cacccaaggt tgcccctgct tc                                               22

<210> SEQ ID NO 133
<211> LENGTH: 24
<212> TYPE: DNA
<213> ORGANISM: Artificial Sequence
<220> FEATURE:
<223> OTHER INFORMATION: CvACO1

<400> SEQUENCE: 133
gagcaagttc cccagcaagt ccag                                             24

<210> SEQ ID NO 134
<211> LENGTH: 26
<212> TYPE: DNA
<213> ORGANISM: Artificial Sequence
<220> FEATURE:
<223> OTHER INFORMATION: CvACO1

<400> SEQUENCE: 134
catgatgttc acgggttccc aagtgc                                           26

<210> SEQ ID NO 135
<211> LENGTH: 25
<212> TYPE: DNA
<213> ORGANISM: Artificial Sequence
<220> FEATURE:
<223> OTHER INFORMATION: CvPTS2

<400> SEQUENCE: 135
catacatgct ggaagctaca gcgac                                            25

<210> SEQ ID NO 136
<211> LENGTH: 27
<212> TYPE: DNA
<213> ORGANISM: Artificial Sequence
<220> FEATURE:
<223> OTHER INFORMATION: CvPTS2

<400> SEQUENCE: 136
cagtactcac cccatatttt gcatcgc                                          27

<210> SEQ ID NO 137
<211> LENGTH: 36
<212> TYPE: DNA
<213> ORGANISM: Artificial Sequence
<220> FEATURE:
<223> OTHER INFORMATION: CvTHC1

<400> SEQUENCE: 137
gttaagttgt ttaacaagtg gcaaaacatt gcatac                                36
```

<210> SEQ ID NO 138
<211> LENGTH: 34
<212> TYPE: DNA
<213> ORGANISM: Artificial Sequence
<220> FEATURE:
<223> OTHER INFORMATION: CvTHC1

<400> SEQUENCE: 138
ccaaaatctt aaccattgct gtttctggaa ttgg    34

<210> SEQ ID NO 139
<211> LENGTH: 29
<212> TYPE: DNA
<213> ORGANISM: Artificial Sequence
<220> FEATURE:
<223> OTHER INFORMATION: Candida viswanathii

<400> SEQUENCE: 139
gatttgtttt gggcaattag aggaggtgg    29

<210> SEQ ID NO 140
<211> LENGTH: 32
<212> TYPE: DNA
<213> ORGANISM: Artificial Sequence
<220> FEATURE:
<223> OTHER INFORMATION: Candida viswanathii

<400> SEQUENCE: 140
caactcctga gtagaaaatg gttgtatcga tc    32

<210> SEQ ID NO 141
<211> LENGTH: 29
<212> TYPE: DNA
<213> ORGANISM: Artificial Sequence
<220> FEATURE:
<223> OTHER INFORMATION: Yarrowia lipolytica

<400> SEQUENCE: 141
ttgttaccaa ctgggatgac atggagaag    29

<210> SEQ ID NO 142
<211> LENGTH: 28
<212> TYPE: DNA
<213> ORGANISM: Artificial Sequence
<220> FEATURE:
<223> OTHER INFORMATION: Yarrowia lipolytica

<400> SEQUENCE: 142
ctgatggacg tgttttcga catgaacc    28

<210> SEQ ID NO 143
<211> LENGTH: 34
<212> TYPE: DNA
<213> ORGANISM: Artificial Sequence
<220> FEATURE:
<223> OTHER INFORMATION: Yarrowia lipolytica

<400> SEQUENCE: 143
gaaaggaaca tagtcatttc caaacttgaa agtc    34

<210> SEQ ID NO 144
<211> LENGTH: 24
<212> TYPE: DNA
<213> ORGANISM: Artificial Sequence
<220> FEATURE:

<223> OTHER INFORMATION: Yarrowia lipolytica

<400> SEQUENCE: 144
cagacggagt actttcgctc gagg 24

<210> SEQ ID NO 145
<211> LENGTH: 29
<212> TYPE: DNA
<213> ORGANISM: Artificial Sequence
<220> FEATURE:
<223> OTHER INFORMATION: Yarrowia lipolytica

<400> SEQUENCE: 145
cccaaattta gctgcatcat tcatcaacc 29

<210> SEQ ID NO 146
<211> LENGTH: 27
<212> TYPE: DNA
<213> ORGANISM: Artificial Sequence
<220> FEATURE:
<223> OTHER INFORMATION: Yarrowia lipolytica

<400> SEQUENCE: 146
ccgtgcttaa gagcaagttc cttgagg 27

<210> SEQ ID NO 147
<211> LENGTH: 23
<212> TYPE: DNA
<213> ORGANISM: Artificial Sequence
<220> FEATURE:
<223> OTHER INFORMATION: Yarrowia lipolytica

<400> SEQUENCE: 147
ctacgacatg cccaaggagc agc 23

<210> SEQ ID NO 148
<211> LENGTH: 26
<212> TYPE: DNA
<213> ORGANISM: Artificial Sequence
<220> FEATURE:
<223> OTHER INFORMATION: Yarrowia lipolytica

<400> SEQUENCE: 148
ggattcgcac attggtgaac tggatc 26

<210> SEQ ID NO 149
<211> LENGTH: 24
<212> TYPE: DNA
<213> ORGANISM: Artificial Sequence
<220> FEATURE:
<223> OTHER INFORMATION: Yarrowia lipolytica

<400> SEQUENCE: 149
ccaagcgacg acaagctgtt gagc 24

<210> SEQ ID NO 150
<211> LENGTH: 21
<212> TYPE: DNA
<213> ORGANISM: Artificial Sequence
<220> FEATURE:
<223> OTHER INFORMATION: Yarrowia lipolytica

<400> SEQUENCE: 150
cgtgtgggta gcagagtggg c 21

```
<210> SEQ ID NO 151
<211> LENGTH: 26
<212> TYPE: DNA
<213> ORGANISM: Artificial Sequence
<220> FEATURE:
<223> OTHER INFORMATION: Yarrowia lipolytica

<400> SEQUENCE: 151
ctttgccatg actgagactg gccatg                                         26

<210> SEQ ID NO 152
<211> LENGTH: 18
<212> TYPE: DNA
<213> ORGANISM: Artificial Sequence
<220> FEATURE:
<223> OTHER INFORMATION: Yarrowia lipolytica

<400> SEQUENCE: 152
gaggcgccgc tggtgtcg                                                  18

<210> SEQ ID NO 153
<211> LENGTH: 27
<212> TYPE: DNA
<213> ORGANISM: Artificial Sequence
<220> FEATURE:
<223> OTHER INFORMATION: Yarrowia lipolytica

<400> SEQUENCE: 153
tccgaaagcg gaactgcttt ctcaatg                                        27

<210> SEQ ID NO 154
<211> LENGTH: 23
<212> TYPE: DNA
<213> ORGANISM: Artificial Sequence
<220> FEATURE:
<223> OTHER INFORMATION: Yarrowia lipolytica

<400> SEQUENCE: 154
cagaccggcc tctcgaatat ggc                                            23

<210> SEQ ID NO 155
<211> LENGTH: 26
<212> TYPE: DNA
<213> ORGANISM: Artificial Sequence
<220> FEATURE:
<223> OTHER INFORMATION: Yarrowia lipolytica

<400> SEQUENCE: 155
ctagactaca cgggcaacct taaccc                                         26

<210> SEQ ID NO 156
<211> LENGTH: 25
<212> TYPE: DNA
<213> ORGANISM: Artificial Sequence
<220> FEATURE:
<223> OTHER INFORMATION: Yarrowia lipolytica

<400> SEQUENCE: 156
cttgggcttc agctttcgag gagtg                                          25

<210> SEQ ID NO 157
<211> LENGTH: 4435
<212> TYPE: DNA
<213> ORGANISM: Artificial Sequence
<220> FEATURE:
<223> OTHER INFORMATION: pLD1
```

<400> SEQUENCE: 157

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtgggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg gatggtggtt agtgcgttcc tgacaaaccc     900
agagtacgcc gcctcaaacc acgtcacatt cgcccttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga attttttgcac   1320
acacaccgat taacatttcc cttttttgtc caccgataca cgcttgcctc ttcttatttt    1380
ctctgtgctt cccctcctg tgactttttc caccattgat ataaaatcaa ctccatttcc     1440
ctaaaatctc cccagattct aaaaacaact tcttctcttc tgcttttcct tattttttgtt   1500
atatttattt accatccctt attttgaata gttattcccc actaacattg ttcaaatctt    1560
cacgacataa gaagagcccg ggtctagatg tgtgctcttc cgagtgactc ttttgataag    1620
agtcgcaaat ttgatttcat aagtatatat tcattatgta aagtagtaaa tggaaaattc    1680
attaaaaaaa aagcaaattt ccgttgtatg catactccga acacaaaact agccccggaa    1740
aaacccttag ttgatagttg cgaatttagg tcgaccatat gcgacgggta caacgagaat    1800
tgtattgaat tgatcaagaa catgatcttg gtgttacaga acatcaagtt cttggaccag    1860
actgagaatg cacagatata caaggcgtca tgtgataaaa tggatgagat ttatccacaa    1920
ttgaagaaag agtttatgga agtggtcaa ccagaagcta aacaggaaga agcaaacgaa      1980
gaggtgaaac aagaagaaga aggtaaataa gtattttgta ttatataaca aacaaagtaa    2040
ggaatacaga tttatacaat aaaattgccat actagtcacg tgagatatct catccattcc   2100
ccaactccca agaaaataaa aaagtgaaaa ataaaatcaa acccaaagat caacctcccc    2160
atcatcatcg tcatcaaacc cccagctcaa ttcgcaatgg ttagcacaaa acatacaca    2220
gaaagggcat cagcacaccc ctccaaggtt gcccaacgtt tattaattaa aggctaggtg    2280
gaggctcagt gatgataagt ctgcgatggt ggatgcatgt gtcatggtca tagctgtttc    2340
```

```
ctgtgtgaaa ttgttatccg ctcagagggc acaatcctat tccgcgctat ccgacaatct   2400
ccaagacatt aggtggagtt cagttcggcg tatggcatat gtcgctggaa agaacatgtg   2460
agcaaaaggc cagcaaaagg ccaggaaccg taaaaaggcc gcgttgctgg cgttttttcca  2520
taggctccgc ccccctgacg agcatcacaa aaatcgacgc tcaagtcaga ggtggcgaaa   2580
cccgacagga ctataaagat accaggcgtt tccccctgga agctccctcg tgcgctctcc   2640
tgttccgacc ctgccgctta ccggatacct gtccgccttt ctcccttcgg aagcgtggc    2700
gctttctcat agctcacgct gtaggtatct cagttcggtg taggtcgttc gctccaagct   2760
gggctgtgtg cacgaacccc ccgttcagcc cgaccgctgc gccttatccg gtaactatcg   2820
tcttgagtcc aacccggtaa gacacgactt atcgccactg gcagcagcca ctggtaacag   2880
gattagcaga gcgaggtatg taggcggtgc tacagagttc ttgaagtggt ggcctaacta   2940
cggctacact agaagaacag tatttggtat ctgcgctctg ctgaagccag ttaccttcgg   3000
aaaaagagtt ggtagctctt gatccggcaa acaaaccacc gctggtagcg gtggtttttt   3060
tgtttgcaag cagcagatta cgcgcagaaa aaaaggatct caagaagatc ctttgatctt   3120
ttctacgggg tctgacgctc tattcaacaa agccgccgtc cgtcaagtc agcgtaaatg    3180
ggtagggggc ttcaaatcgt ccgctctgcc agtgttacaa ccaattaaca aattctgatt   3240
agaaaaactc atcgagcatc aaatgaaact gcaatttatt catatcagga ttatcaatac   3300
catatttttg aaaaagccgt ttctgtaatg aaggagaaaa ctcaccgagg cagttccata   3360
ggatggcaag atcctggtat cggtctgcga ttccgactcg tccaacatca atacaaccta   3420
ttaatttccc ctcgtcaaaa ataaggttat caagtgagaa atcaccatga gtgacgactg   3480
aatccggtga gaatggcaaa agcttatgca tttctttcca gacttgttca acaggccagc   3540
cattacgctc gtcatcaaaa tcactcgcat caaccaaacc gttattcatt cgtgattgcg   3600
cctgagcgag acgaaatacg cgatcgctgt taaaaggaca attacaaaca ggaatcgaat   3660
gcaaccggcg caggaacact gccagcgcat caacaatatt ttcacctgaa tcaggatatt   3720
cttctaatac ctggaatgct gttttcccgg ggatcgcagt ggtgagtaac catgcatcat   3780
caggagtacg gataaaatgc ttgatggtcg gaagaggcat aaattccgtc agccagttta   3840
gtctgaccat ctcatctgta acatcattgg caacgctacc tttgccatgt ttcagaaaca   3900
actctggcgc atcgggcttc ccatacaatc gatagattgt cgcacctgat tgcccgacat   3960
tatcgcgagc ccatttatac ccatataaat cagcatccat gttggaattt aatcgcggcc   4020
tcgagcaaga cgtttcccgt tgaatatggc tcataacacc ccttgtatta ctgtttatgt   4080
aagcagacag ttttattgtt catgatgata tatttttatc ttgtgcaatg taacatcaga   4140
gattttgaga cacaacgtgg ctttcccccg ccgctctaga actagtggat ccaaataaaa   4200
cgaaaggctc agtcgaaaga ctgggccttt cgttttatct gttgtttgtc gcattatacg   4260
agacgtccag gttgggatac ctgaaacaaa acccatcgta cggccaagga agtctccaat   4320
aactgtgatc caccacaagc gccagggttt tcccagtcac gacgttgtaa aacgacggcc   4380
agtcatgcat aatccgcacg catctggaat aaggaagtgc cattccgcct gacct         4435
```

<210> SEQ ID NO 158
<211> LENGTH: 5564
<212> TYPE: DNA
<213> ORGANISM: Artificial Sequence
<220> FEATURE:
<223> OTHER INFORMATION: pLD10

```
<400> SEQUENCE: 158
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg gatggtggtt agtgcgttcc tgacaaaccc     900
agagtacgcc gcctcaaacc acgtcacatt cgcccttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga attttttgcac   1320
acacaccgat taacatttcc ctttttttgtc caccgataca cgcttgcctc ttcttatttt    1380
ctctgtgctt ccccctcctg tgactttttc caccattgat ataaaatcaa ctccatttcc    1440
ctaaaatctc cccagattct aaaaacaact tcttctcttc tgcttttcct tattttttgtt    1500
atatttattt accatccctt attttgaata gttattcccc actaacattg ttcaaatctt    1560
cacgacataa tgaatcattt aagagcagaa ggacccgcat cagtgttagc gataggtaca    1620
gctaacccag agaatatctt aatccaagat gaatttcctg actactattt ccgtgttact    1680
aaatcggaac atatgactca acttaaagag aagttccgga aaatctgcga taaatccatg    1740
atccgaaaga gaaactgttt ccttaacgaa gaacatctca agcaaaaccc gaggttggta    1800
gagcacgaaa tgcagaccct tggatgctagg caggacatgt tggtggtcga agtgccaaaa    1860
ctcggcaagg acgcgtgcgc taaggcaatc aaggagtggg gtcaaccgaa gtctaaaatc    1920
acgcatctaa tatttacatc tgcactgaca accgacatgc cgggtgccga ttatcactgc    1980
gccaagctac ttggattgag tccactggtt aagagagtta tgatgtatca attggggtgt    2040
tacggagggg gcacagtcct cagaattgct aaggatattg cggaaaataa caagggcgcg    2100
agggtccttg ctgtatgttg tgatattatg gcctgtttgt ttcgcgggcc ctcggattca    2160
gatttggaat tgcttgtcgg acaggcaatt tttggtgacg gggccgcagc agtcatagtg    2220
ggagccgaac cagacgaaag cgtgggtgaa agaccaatct ttgagttggt tctgaccgga    2280
caaacgatct tacctaactc ggaaggtacg attggaggac atattagaga agccggccta    2340
```

-continued

```
attttcgatc ttcacaaaga cgttccaatg ttaatctcca ataacataga aaagtgcttg    2400
atagaagcat ttactcccat tggtattagt gactggaaca gcattttctg gatcacccac    2460
cctggaggaa aagctatact cgataaggtt gaagagaaac tcgacttgaa aaggagaaa     2520 ttcgttgact cacgacatgt gttatcagag cacgggaata tgagttcatc cacagtcttg    2580
ttcgtaatgg atgaattgcg aaaacgctct cttgaggagg gaaagagcac aaccggtgac    2640
gggtttgagt ggggcgtgct attcggtttt ggcccaggtt tgactgtcga gcgggttgtt    2700
gttcgtagtg taccaattaa gtactgataa gagtgactct tttgataaga gtcgcaaatt    2760
tgatttcata agtatatatt cattatgtaa agtagtaaat ggaaaattca ttaaaaaaaa    2820
agcaaatttc cgttgtatgc atactccgaa cacaaaacta gccccggaaa aacccttagt    2880
tgatagttgc gaattaggt cgaccatatg cgacgggtac aacgagaatt gtattgaatt     2940
gatcaagaac atgatcttgg tgttacagaa catcaagttc ttggaccaga ctgagaatgc    3000
acagatatac aaggcgtcat gtgataaaat ggatgagatt tatccacaat tgaagaaaga    3060
gtttatggaa agtggtcaac cagaagctaa acaggaagaa gcaaacgaag aggtgaaaca    3120
agaagaagaa ggtaaataag tattttgtat tatataacaa acaaagtaag gaatacagat    3180
ttatacaata aattgccata ctagtcacgt gagatatctc atccattccc caactcccaa    3240
gaaaataaaa aagtgaaaaa taaaatcaaa cccaaagatc aacctcccca tcatcatcgt    3300
catcaaaccc ccagctcaat cgcaatggt tagcacaaaa acatacacag aaagggcatc     3360
agcacacccc tccaaggttg cccaacgttt attaattaaa ggctaggtgg aggctcagtg    3420
atgataagtc tgcgatggtg gatgcatgtg tcatggtcat agctgttcc tgtgtgaaat     3480 tgttatccgc tcagggggca caatcctatt ccgcgctatc cgacaatctc caagacatta    3540
ggtggagttc agttcggcgt atggcatatg tcgctggaaa gaacatgtga gcaaaaggcc    3600
agcaaaaggc caggaaccgt aaaaaggccg cgttgctggc gtttttccat aggctccgcc    3660
cccctgacga gcatcacaaa aatcgacgct caagtcagag gtggcgaaac ccgacaggac    3720
tataaagata ccaggcgttt ccccctggaa gctccctcgt gcgctctcct gttccgaccc    3780
tgccgcttac cggatacctg tccgcctttc tcccttcggg aagcgtggcg ctttctcata    3840
gctcacgctg taggtatctc agttcggtgt aggtcgttcg ctccaagctg ggctgtgtgc    3900
acgaaccccc cgttcagccc gaccgctgcg ccttatccgg taactatcgt cttgagtcca    3960
acccggtaag acacgactta tcgccactgg cagcagccac tggtaacagg attagcagag    4020
cgaggtatgt aggcggtgct acagagttct tgaagtggtg gcctaactac ggctacacta    4080
gaagaacagt atttggtatc tgcgctctgc tgaagccagt taccttcgga aaaagagttg    4140
gtagctcttg atccggcaaa caaaccaccg ctggtagcgg tggttttttt gtttgcaagc    4200
agcagattac gcgcagaaaa aaaggatctc aagaagatcc tttgatcttt tctacggggt    4260
ctgacgctct attcaacaaa gccgccgtcc cgtcaagtca gcgtaaatgg taggggct     4320 tcaaatcgtc cgctctgcca gtgttacaac caattaacaa attctgatta gaaaaactca    4380
tcgagcatca aatgaaactg caatttattc atatcaggat tatcaatacc atattttga    4440 aaaagccgtt tctgtaatga aggagaaaac tcaccgagg agttccatag gatggcaaga    4500
tcctggtatc ggtctgcgat tccgactcgt ccaacatcaa tacaacctat aatttcccc     4560 tcgtcaaaaa taaggttatc aagtgagaaa tcaccatgag tgacgactga atccggtgag    4620
aatggcaaaa gcttatgcat ttctttccag acttgttcaa caggccagcc attacgctcg    4680
```

```
tcatcaaaat cactcgcatc aaccaaaccg ttattcattc gtgattgcgc ctgagcgaga    4740
cgaaatacgc gatcgctgtt aaaaggacaa ttacaaacag gaatcgaatg caaccggcgc    4800
aggaacactg ccagcgcatc aacaatattt tcacctgaat caggatattc ttctaatacc    4860
tggaatgctg ttttcccggg gatcgcagtg gtgagtaacc atgcatcatc aggagtacgg    4920
ataaaatgct tgatggtcgg aagaggcata aattccgtca gccagtttag tctgaccatc    4980
tcatctgtaa catcattggc aacgctacct ttgccatgtt tcagaaacaa ctctggcgca    5040
tcgggcttcc catacaatcg atagattgtc gcacctgatt gcccgacatt atcgcgagcc    5100
catttatacc catataaatc agcatccatg ttggaattta atcgcggcct cgagcaagac    5160
gtttcccgtt gaatatggct cataacaccc cttgtattac tgtttatgta agcagacagt    5220
tttattgttc atgatgatat attttttatct tgtgcaatgt aacatcagag attttgagac    5280
acaacgtggc tttcccccgc cgctctagaa ctagtggatc caaataaaac gaaaggctca    5340
gtcgaaagac tgggcctttc gttttatctg ttgtttgtcg cattatacga gacgtccagg    5400
ttgggatacc tgaaacaaaa cccatcgtac ggccaaggaa gtctccaata actgtgatcc    5460
accacaagcg ccagggtttt cccagtcacg acgttgtaaa acgacggcca gtcatgcata    5520
atccgcacgc atctggaata aggaagtgcc attccgcctg acct    5564
```

<210> SEQ ID NO 159
<211> LENGTH: 4724
<212> TYPE: DNA
<213> ORGANISM: Artificial Sequence
<220> FEATURE:
<223> OTHER INFORMATION: pLD12

<400> SEQUENCE: 159

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaagggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtgggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg atggtggtt agtgcgttcc tgacaaaccc     900
agagtacgcc gcctcaaacc acgtcacatt cgcccttttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
```

```
gttatgcata cacacggtta ttcggttgaa ttgtggagta aaaattgtct gagttgtgtc    1260
ttagctactg gctggccccc cgcgaaagat aatcaaaatt acacttgtga attttttgcac   1320 acacaccgat taacattttcc ctttttttgtc caccgataca cgcttgcctc ttcttatttt   1380
ctctgtgctt ccccctcctg tgactttttc caccattgat ataaaatcaa ctccatttcc    1440
ctaaaatctc cccagattct aaaaacaact tcttctcttc tgcttttcct tatttttgtt    1500
atatttattt accatccctt attttgaata gttattcccc actaacattg ttcaaatctt    1560
cacgacataa tggcagtcaa acacctaata gttctcaaat ttaaagacga gattactgaa    1620
gctcagaagg aagagttctt taagacatat gttaacttag tcaacatcat ccccgcgatg    1680
aaggacgtct actggggcaa ggatgtgacg caaaaaaata aggaagaagg atacacacat    1740
atcgttgagg tgacctttga gagtgtggaa actattcaag attatattat tcacccagcc    1800
catgtagggt tcggtgacgt ttatcgatca ttctgggaaa agttgcttat atttgattac    1860
accccaagaa aattgaagcc taagtgataa gagtgactct tttgataaga gtcgcaaatt    1920
tgatttcata agtatatatt cattatgtaa agtagtaaat ggaaaattca ttaaaaaaaa    1980
agcaaatttc cgttgtatgc atactccgaa cacaaaacta gccccggaaa aacccttagt    2040
tgatagttgc gaatttaggt cgaccatatg cgacgggtac aacgagaatt gtattgaatt    2100
gatcaagaac atgatcttgg tgttacagaa catcaagttc ttggaccaga ctgagaatgc    2160
acagatatac aaggcgtcat gtgataaaat ggatgagatt tatccacaat gaagaaaga    2220 gtttatggaa agtggtcaac cagaagctaa acaggaagaa gcaaacgaag aggtgaaaca    2280
agaagaagaa ggtaaataag tattttgtat tatataacaa acaaagtaag gaatacagat    2340
ttatacaata aattgccata ctagtcacgt gagatatctc atccattccc caactcccaa    2400
gaaaataaaa aagtgaaaaa taaatcaaa cccaaagatc aacctcccca tcatcatcgt     2460
catcaaaccc ccagctcaat tcgcaatggt tagcacaaaa acatacacag aaagggcatc    2520
agcacacccc tccaaggttg cccaacgttt attaattaaa ggctaggtgg aggctcagtg    2580
atgataagtc tgcgatggtg gatgcatgtg tcatggtcat agctgtttcc tgtgtgaaat    2640
tgttatccgc tcagagggca caatcctatt ccgcgctatc cgacaatctc caagacatta    2700
ggtggagttc agttcggcgt atggcatatg tcgctggaaa gaacatgtga gcaaaaggcc    2760
agcaaaaggc caggaaccgt aaaaaggccg cgttgctggc gttttttccat aggctccgcc    2820 cccctgacga gcatcacaaa aatcgacgct caagtcagag gtggcgaaac ccgacaggac    2880
tataaagata ccaggcgttt ccccctggaa gctccctcgt gcgctctcct gttccgaccc    2940
tgccgcttac cggatacctg tccgcctttc tcccttcggg aagcgtggcg ctttctcata    3000
gctcacgctg taggtatctc agttcggtgt aggtcgttcg ctccaagctg gctgtgtgc    3060 acgaacccc cgttcagccc gaccgctgcg ccttatccgg taactatcgt cttgagtcca    3120
acccggtaag acacgactta tcgccactgg cagcagccac tggtaacagg attagcagag    3180
cgaggtatgt aggcggtgct acagagttct tgaagtggtg gcctaactac ggctacacta    3240
gaagaacagt atttggtatc tgcgctctgc tgaagccagt taccttcgga aaaagagttg    3300
gtagctcttg atccggcaaa caaaccaccg ctggtagcgg tggttttttt gtttgcaagc    3360
agcagattac gcgcagaaaa aaaggatctc aagaagatcc tttgatcttt tctacggggt    3420
ctgacgctct attcaacaaa gccgccgtcc cgtcaagtca gcgtaaatgg taggggggct    3480
tcaaatcgtc cgctctgcca gtgttacaac caattaacaa attctgatta gaaaaactca    3540
```

```
tcgagcatca aatgaaactg caatttattc atatcaggat tatcaatacc atatttttga   3600
aaaagccgtt tctgtaatga aggagaaaac tcaccgaggc agttccatag gatggcaaga   3660
tcctggtatc ggtctgcgat tccgactcgt ccaacatcaa tacaacctat taatttcccc   3720
tcgtcaaaaa taaggttatc aagtgagaaa tcaccatgag tgacgactga atccggtgag   3780
aatggcaaaa gcttatgcat ttctttccag acttgttcaa caggccagcc attacgctcg   3840
tcatcaaaat cactcgcatc aaccaaaccg ttattcattc gtgattgcgc ctgagcgaga   3900
cgaaatacgc gatcgctgtt aaaaggacaa ttacaaacag gaatcgaatg caaccggcgc   3960
aggaacactg ccagcgcatc aacaatattt tcacctgaat caggatattc ttctaatacc   4020
tggaatgctg ttttcccggg gatcgcagtg gtgagtaacc atgcatcatc aggagtacgg   4080
ataaaatgct tgatggtcgg aagaggcata aattccgtca gccagtttag tctgaccatc   4140
tcatctgtaa catcattggc aacgctacct ttgccatgtt tcagaaacaa ctctggcgca   4200
tcgggcttcc catacaatcg atagattgtc gcacctgatt gcccgacatt atcgcgagcc   4260
catttatacc catataaatc agcatccatg ttggaattta atcgcggcct cgagcaagac   4320
gtttcccgtt gaatatggct cataacaccc cttgtattac tgtttatgta agcagacagt   4380
tttattgttc atgatgatat ttttttatct tgtgcaatgt aacatcagag attttgagac   4440
acaacgtggc tttccccgc cgctctagaa ctagtggatc caaataaaac gaaaggctca   4500
gtcgaaagac tgggcctttc gttttatctg ttgtttgtcg cattatacga gacgtccagg   4560
ttgggatacc tgaaacaaaa cccatcgtac ggccaaggaa gtctccaata actgtgatcc   4620
accacaagcg ccagggtttt cccagtcacg acgttgtaaa acgacggcca gtcatgcata   4680
atccgcacgc atctggaata aggaagtgcc attccgcctg acct                    4724
```

<210> SEQ ID NO 160
<211> LENGTH: 4742
<212> TYPE: DNA
<213> ORGANISM: Artificial Sequence
<220> FEATURE:
<223> OTHER INFORMATION: pLD14

<400> SEQUENCE: 160

```
ttaattaatt ccgcttaatg gagtccaaaa agaccaacct ctgcgcctcg atcgacgtga     60
ccacaaccgc cgagttcctt tcgctcatcg acaagctcgg tccccacatc tgtctcgtga    120
agacgcacat cgatatcatc tcagacttca gctacgaggg cacgattgag ccgttgcttg    180
tgcttgcaga gcgccacggg ttcttgatat tcgaggacag gaagtttgct gatatcggaa    240
acaccgtgat gttgcagtac acctcggggg tataccggat cgcggcgtgg agtgacatca    300
cgaacgcgca cggagtgact gggaagggcg tcgttgaagg gttgaaacgc ggtgcggagg    360
gggtagaaaa ggaaggggc gtgttgatgt tggcggagtt gtcgagtaaa ggctcgttgg     420
cgcatggtga atatcccgt gagacgatcg agattgcgaa gagtgatcgg gagttcgtga    480
ttgggttcat cgcgcagcgg gacatggggg gtagagaaga agggtttgat tggatcatca    540
tgacgcctgg tgtggggttg gatgataaag gcgatgcgtt gggccagcag tataggactg    600
ttgatgaggt ggttctgact ggtaccgatg tgattattgt cggagagggg ttgtttggaa    660
aaggaagaga ccctgaggtg gagggaaaga gatacaggga tgctggatgg aaggcatact    720
tgaagagaac tggtcagtta gaataaatat tgtaataaat aggtctatat acatacacta    780
agcttctagg acgtcattgt agtcttcgaa gttgtctgct agtttagttc tcatgatttc    840 gaaaccaat aacgcaatgg atgtagcagg atggtggtt agtgcgttcc tgacaaaccc    900
```

```
agagtacgcc gcctcaaacc acgtcacatt cgcccttttgc ttcatccgca tcacttgctt    960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcgttgaa ttgtggagta aaaattgtct gagttgtgtc    1260
ttagctactg gctggccccc cgcgaaagat aatcaaaatt acacttgtga attttttgcac   1320
acacaccgat taacatttcc cttttttgtc caccgataca cgcttgcctc ttcttatttt   1380
ctctgtgctt cccctcctg tgactttttc caccattgat ataaaatcaa ctccatttcc    1440
ctaaaatctc cccagattct aaaaacaact tcttctcttc tgcttttcct tattttgtt    1500
atatttattt accatccctt attttgaata gttattcccc actaacattg ttcaaatctt   1560
cacgacataa tggcagtcaa acacctaata gttctcaaat ttaaagacga gattactgaa   1620
gctcagaagg aagagttctt taagacatat gttaacttag tcaacatcat ccccgcgatg   1680
aaggacgtct actggggcaa ggatgtgacg caaaaaaata aggaagaagg atacacacat   1740
atcgttgagg tgacctttga gagtgtggaa actattcaag attatattat tcacccagcc   1800
catgtagggt tcggtgacgt ttatcgatca ttctgggaaa agttgcttat atttgattac   1860
accccaagaa aattgaagcc taagggaaga cgagctaagt tgtgataaga gtgactcttt   1920
tgataagagt cgcaaatttg atttcataag tatatattca ttatgtaaag tagtaaatgg   1980
aaaattcatt aaaaaaaaag caaatttccg ttgtatgcat actccgaaca caaaactagc   2040
cccggaaaaa cccttagttg atagttgcga atttaggtcg accatatgcg acgggtacaa   2100
cgagaattgt attgaattga tcaagaacat gatcttggtg ttacagaaca tcaagttctt   2160
ggaccagact gagaatgcac agatatacaa ggcgtcatgt gataaaatgg atgagattta   2220
tccacaattg aagaaagagt ttatggaaag tggtcaacca gaagctaaac aggaagaagc   2280
aaacgaagag gtgaaacaag aagaagaagg taaataagta ttttgtatta tataacaaac   2340
aaagtaagga atacagattt atacaataaa ttgccatact agtcacgtga gatatctcat   2400
ccattcccca actcccaaga aaataaaaaa gtgaaaaata aaatcaaacc caaagatcaa   2460
cctcccccatc atcatcgtca tcaaaccccc agctcaattc gcaatggtta gcacaaaaac   2520
atacacagaa agggcatcag cacacccctc caaggttgcc caacgtttat taattaaagg   2580
ctaggtggag gctcagtgat gataagtctg cgatggtgga tgcatgtgtc atggtcatag   2640
ctgtttcctg tgtgaaattg ttatccgctc agagggcaca atcctattcc gcgctatccg   2700
acaatctcca agacattagg tggagttcag ttcggcgtat ggcatatgtc gctgaaaga    2760
acatgtgagc aaaaggccag caaaaggcca ggaaccgtaa aaaggccgcg ttgctggcgt   2820
ttttccatag gctccgcccc cctgacgagc atcacaaaaa tcgacgctca agtcagaggt   2880
ggcgaaaccc gacaggacta taaagatacc aggcgtttcc ccctggaagc tccctcgtgc   2940
gctctcctgt tccgaccctg ccgcttaccg gatacctgtc cgcctttctc ccttcgggaa   3000
gcgtggcgct ttctcatagc tcacgctgta ggtatctcag ttcggtgtag tcgttcgct    3060
ccaagctggg ctgtgtgcac gaaccccccg ttcagcccga ccgctgcgcc ttatccggta   3120
actatcgtct tgagtccaac ccggtaagac acgacttatc gccactggca gcagccactg   3180
gtaacaggat tagcagagcg aggtatgtag gcggtgctac agagttcttg aagtggtggc   3240
```

| | |
|---|---|
| ctaactacgg ctacactaga agaacagtat ttggtatctg cgctctgctg aagccagtta | 3300 |
| ccttcggaaa aagagttggt agctcttgat ccggcaaaca aaccaccgct ggtagcggtg | 3360 |
| gtttttttgt ttgcaagcag cagattacgc gcagaaaaaa aggatctcaa gaagatcctt | 3420 |
| tgatcttttc tacggggtct gacgctctat tcaacaaagc cgccgtcccg tcaagtcagc | 3480 |
| gtaaatgggt agggggcttc aaatcgtccg ctctgccagt gttacaacca attaacaaat | 3540 |
| tctgattaga aaaactcatc gagcatcaaa tgaaactgca atttattcat atcaggatta | 3600 |
| tcaataccat attttttgaaa aagccgtttc tgtaatgaag gagaaaactc accgaggcag | 3660 |
| ttccatagga tggcaagatc ctggtatcgg tctgcgattc cgactcgtcc aacatcaata | 3720 |
| caacctatta atttcccctc gtcaaaaata aggttatcaa gtgagaaatc accatgagtg | 3780 |
| acgactgaat ccggtgagaa tggcaaaagc ttatgcattt ctttccagac ttgttcaaca | 3840 |
| ggccagccat tacgctcgtc atcaaaatca ctcgcatcaa ccaaaccgtt attcattcgt | 3900 |
| gattgcgcct gagcgagacg aaatacgcga tcgctgttaa aaggacaatt acaaacagga | 3960 |
| atcgaatgca accggcgcag gaacactgcc agcgcatcaa caatatttc acctgaatca | 4020 |
| ggatattctt ctaatacctg gaatgctgtt ttcccgggga tcgcagtggt gagtaaccat | 4080 |
| gcatcatcag gagtacggat aaaatgcttg atggtcggaa gaggcataaa ttccgtcagc | 4140 |
| cagtttagtc tgaccatctc atctgtaaca tcattggcaa cgctacctt gccatgtttc | 4200 |
| agaaacaact ctggcgcatc gggcttccca tacaatcgat agattgtcgc acctgattgc | 4260 |
| ccgacattat cgcgagccca tttatacccca tataaatcag catccatgtt ggaatttaat | 4320 |
| cgcggcctcg agcaagacgt ttcccgttga atatggctca taacacccct tgtattactg | 4380 |
| tttatgtaag cagacagttt tattgttcat gatgatatat ttttatcttg tgcaatgtaa | 4440 |
| catcagagat tttgagacac aacgtggctt tccccccgccg ctctagaact agtggatcca | 4500 |
| aataaaacga aaggctcagt cgaaagactg ggcctttcgt tttatctgtt gtttgtcgca | 4560 |
| ttatacgaga cgtccaggtt gggatacctg aaacaaaacc catcgtacgg ccaaggaagt | 4620 |
| ctccaataac tgtgatccac cacaagcgcc agggttttcc cagtcacgac gttgtaaaac | 4680 |
| gacggccagt catgcataat ccgcacgcat ctggaataag gaagtgccat tccgcctgac | 4740 |
| ct | 4742 |

<210> SEQ ID NO 161
<211> LENGTH: 6569
<212> TYPE: DNA
<213> ORGANISM: Artificial Sequence
<220> FEATURE:
<223> OTHER INFORMATION: pLD16

<400> SEQUENCE: 161

| | |
|---|---|
| ttaattaatt ccgcttaatg gagtccaaaa agaccaacct ctgcgcctcg atcgacgtga | 60 |
| ccacaaccgc cgagttcctt tcgctcatcg acaagctcgg tccccacatc tgtctcgtga | 120 |
| agacgcacat cgatatcatc tcagacttca gctacgaggg cacgattgag ccgttgcttg | 180 |
| tgcttgcaga gcgccacggg ttcttgatat tcgaggacag gaagtttgct gatatcggaa | 240 |
| acaccgtgat gttgcagtac acctcggggg tataccggat cgcggcgtgg agtgacatca | 300 |
| cgaacgcgca cggagtgact gggaagggcg tcgttgaagg gttgaaacgc ggtgcggagg | 360 |
| gggtagaaaa ggaaggggc gtgttgatgt tggcggagtt gtcgagtaaa ggctcgttgg | 420 |
| cgcatggtga atatacccgt gagacgatcg agattgcgaa gagtgatcgg gagttcgtga | 480 |
| ttgggttcat cgcgcagcgg gacatggggg gtagagaaga agggtttgat tggatcatca | 540 |

-continued

```
tgacgcctgg tgtggggttg gatgataaag gcgatgcgtt gggccagcag tataggactg    600
ttgatgaggt ggttctgact ggtaccgatg tgattattgt cgggagaggg ttgtttggaa    660
aaggaagaga ccctgaggtg gagggaaaga gatacaggga tgctggatgg aaggcatact    720
tgaagagaac tggtcagtta gaataaatat tgtaataaat aggtctatat acatacacta    780
agcttctagg acgtcattgt agtcttcgaa gttgtctgct agtttagttc tcatgatttc    840
gaaaaccaat aacgcaatgg atgtagcagg atggtggtg agtgcgttcc tgacaaaccc    900
agagtacgcc gcctcaaacc acgtcacatt cgcccttgtc ttcatccgca tcacttgctt    960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcggttgaa ttgtggagta aaaattgtct gagttgtgtc   1260
ttagctactg gctggccccc cgcgaaagat aatcaaaatt acacttgtga attttgcac    1320 acacaccgat taacatttcc cttttttgtc caccgataca cgcttgcctc ttcttatttt   1380
ctctgtgctt cccctcctg tgacttttc caccattgat ataaaatcaa ctccatttcc    1440
ctaaaatctc cccagattct aaaaacaact tcttctcttc tgcttttcct tattttgtt    1500 atatttattt accatccctt attttgaata gttattcccc actaacattg ttcaaatctt   1560
cacgacataa tgggaaaaaa ttataaatct ttggactcag ttgtggctag tgacttcatt   1620
gcacttggga tcacatcaga agttgctgag acattgcacg gacgcttggc agagatagtt   1680
tgcaactacg gcgccgcaac acctcagacc tggattaaca tcgcaaacca tattctaagt   1740
ccagatcttc catttagtct ccatcagatg ttgttctacg gttgttataa ggactttggt   1800
ccagcacccc cagcttggat accagacccc gaaaaagtaa agtccacgaa cttaggtgcc   1860
ttgttagaaa agcggggaaa ggagtttcta ggcgttaagt ataaggaccc aataagtctg   1920 tttctctcact tccaggagtt tagcgttcga aatccggaag tctactggcg gacggtactt   1980
atggatgaaa tgaagatact gttcagcaaa gatcccgaat gtatcctcag acgcgacgac   2040
attaacaacc caggggctc tgagtggcta ccaggtggat atctcaacct ggccaagaac   2100
tgtttgaatg taaatagtaa caaaaaactt aacgacacta tgatagtgtg gagagatgaa   2160
ggaaatgacg atctcccatt gaataaattg actcttgatc aattacgaaa acgagtctgg   2220
ttggttggat acgccctaga agagatgggc cttgagaagg gatgtgcgat tgcaattgac   2280
atgcccatgc acgtagatgc ggttgtgatc tatttagcta tcgtcttggc aggctacgtc   2340
gttgtctcca ttgcagattc attctcagca ccggaaattt ccacaagatt gcgtctatca   2400
aaggctaagg ctattttac acaagatcat atcatccgag ggaaaaagcg tataccttg    2460 tacctgcgtg tcgtcgaggc caagtctccg atggcaatag ttatcccgtg ttcgggttca   2520
aatattggtg cggaattgcg ggatggtgat attctgtggg attacttctt agaacgcgca   2580
aaggaattta gaactgcga atttacagcc cgtgaacagc cagtggacgc gtacacaaat   2640 atttgttct catcgggaac caccggagag ccaaaggcga taccatggac tcaagctacg   2700
cctctcaagg cggctgctga tggttggtca cacttggaca ttagaaaggg tgacgtaatt   2760
gtatggccta ccaatttggg gtggatgatg gggccttggt tggtctatgc ttcactcctt   2820
aacggggcaa gcatcgcatt gtataacgga tctccactag tgtccggctt tgccaaattc   2880
```

```
gttcaagatg cgaaagttac tatgctagga gttgtcccct ccatcgtacg aagctggaaa    2940
agcactaatt gcgttagtgg gtacgattgg tctacaatca gatgcttctc ctcatcgggt    3000
gaggcatcga atgtcgatga atacttatgg ctaatgggaa gggctaacta caaaccggtc    3060
atcgaaatgt gcggtggcac agagatcggg ggtgccttca gcgccggttc gttttttacaa   3120 gcccaatctt tgagtagctt ctcatcccaa tgtatgggat gcaccttgta cattctcgac    3180
aagaatggct acccgatgcc aaagaacaag ccgggtatag gtgaattggc cttgggaccc    3240
gtgatgttcg gtgcttccaa gactttactt aacggaaacc atcatgacgt ttatttcaaa    3300
ggcatgccca ccttgaacgg agaagtcttg aggagacacg gagatatctt cgaactcact    3360
tcgaacggct attatcacgc tcatggtaga gcagatgaca cgatgaatat cggggggatt    3420
aaaatttcct caatcgagat tgaaagggtg tgtaatgaag ttgacgatag agtgtttgag    3480
actacggcca ttggagtgcc tccattgggc ggaggtccag agcagctcgt tatctttttt    3540
gttcttaagg acagcaatga tacgaccatc gacctaaacc aattgcgact tagttttaat    3600
cttgggttac aaaagaaatt gaacccactt tttaaggtga cgagggttgt gccactttcg    3660
ctgttgccta ggacagccac caacaaaata atgagaagag tgcttagaca gcaatttagt    3720
catttcgagt gataagagtg actcttttga taagagtcgc aaatttgatt tcataagtat    3780
atattcatta tgtaaagtag taaatggaaa attcattaaa aaaaagcaa atttccgttg     3840 tatgcatact ccgaacacaa aactagcccc ggaaaaaccc ttagttgata gttgcgaatt    3900
taggtcgacc atatgcgacg ggtacaacga gaattgtatt gaattgatca agaacatgat    3960
cttggtgtta cagaacatca agttcttgga ccagactgag aatgcacaga tatacaaggc    4020
gtcatgtgat aaaatggatg agatttatcc acaattgaag aaagagttta tggaaagtgg    4080
tcaaccagaa gctaaacagg aagaagcaaa cgaagaggtg aaacaagaag aagaaggtaa    4140
ataagtattt tgtattatat aacaaacaaa gtaaggaata cagatttata caataaattg    4200
ccatactagt cacgtgagat atctcatcca ttccccaact cccaagaaaa taaaaaagtg    4260
aaaaataaaa tcaaacccaa agatcaacct ccccatcatc atcgtcatca aacccccagc    4320
tcaattcgca atggttagca caaaaacata cacagaaagg gcatcagcac accctccaa     4380 ggttgcccaa cgtttattaa ttaaaggcta ggtggaggct cagtgatgat aagtctgcga    4440
tggtggatgc atgtgtcatg gtcatagctg tttcctgtgt gaaattgtta ccgctcaga    4500 gggcacaatc ctattccgcg ctatccgaca atctccaaga cattaggtgg agttcagttc    4560
ggcgtatggc atatgtcgct ggaaagaaca tgtgagcaaa aggccagcaa aaggccagga    4620
accgtaaaaa ggccgcgttg ctggcgtttt tccataggct ccgcccccct gacgagcatc    4680
acaaaaatcg acgctcaagt cagaggtggc gaaacccgac aggactataa agataccagg    4740
cgtttccccc tggaagctcc ctcgtgcgct ctcctgttcc gaccctgccg cttaccggat    4800
acctgtccgc ctttctccct tcgggaagcg tggcgctttc tcatagctca cgctgtaggt    4860
atctcagttc ggtgtaggtc gttcgctcca agctgggctg tgtgcacgaa ccccccgttc    4920
agcccgaccg ctgcgcctta tccggtaact atcgtcttga gtccaacccg gtaagacacg    4980
acttatcgcc actggcagca gccactggta acaggattag cagagcgagg tatgtaggcg    5040
gtgctacaga gttcttgaag tggtggccta actacggcta cactagaaga acagtatttg    5100
gtatctgcgc tctgctgaag ccagttacct tcggaaaaag agttggtagc tcttgatccg    5160
gcaaacaaac caccgctggt agcggtggtt ttttgtttg caagcagcag attacgcgca    5220
gaaaaaaagg atctcaagaa gatcctttga tcttttctac ggggtctgac gctctattca    5280
```

```
acaaagccgc cgtcccgtca agtcagcgta aatgggtagg gggcttcaaa tcgtccgctc    5340
tgccagtgtt acaaccaatt aacaaattct gattagaaaa actcatcgag catcaaatga    5400
aactgcaatt tattcatatc aggattatca ataccatatt tttgaaaaag ccgtttctgt    5460
aatgaaggag aaaactcacc gaggcagttc cataggatgg caagatcctg gtatcggtct    5520
gcgattccga ctcgtccaac atcaatacaa cctattaatt tcccctcgtc aaaaataagg    5580
ttatcaagtg agaaatcacc atgagtgacg actgaatccg gtgagaatgg caaaagctta    5640
tgcatttctt tccagacttg ttcaacaggc cagccattac gctcgtcatc aaaatcactc    5700
gcatcaacca aaccgttatt cattcgtgat tgcgcctgag cgagacgaaa tacgcgatcg    5760
ctgttaaaag gacaattaca aacaggaatc gaatgcaacc ggcgcaggaa cactgccagc    5820
gcatcaacaa tattttcacc tgaatcagga tattcttcta atacctggaa tgctgttttc    5880
ccggggatcg cagtggtgag taaccatgca tcatcaggag tacggataaa atgcttgatg    5940
gtcggaagag gcataaattc cgtcagccag tttagtctga ccatctcatc tgtaacatca    6000
ttggcaacgc tacctttgcc atgtttcaga acaactctg gcgcatcggg cttcccatac    6060
aatcgataga ttgtcgcacc tgattgcccg acattatcgc gagcccattt atacccatat    6120
aaatcagcat ccatgttgga atttaatcgc ggcctcgagc aagacgtttc ccgttgaata    6180
tggctcataa cacccttgt attactgttt atgtaagcag acagttttat tgttcatgat    6240
gatatatttt tatcttgtgc aatgtaacat cagagatttt gagacacaac gtggctttcc    6300
cccgccgctc tagaactagt ggatccaaat aaaacgaaag gctcagtcga agactgggc    6360 cttcgttttt atctgttgtt tgtcgcatta tacgagacgt ccaggttggg atacctgaaa    6420
caaaacccat cgtacggcca aggaagtctc caataactgt gatccaccac aagcgccagg    6480
gttttcccag tcacgacgtt gtaaaacgac ggccagtcat gcataatccg cacgcatctg    6540
gaataaggaa gtgccattcc gcctgacct                                       6569
```

<210> SEQ ID NO 162
<211> LENGTH: 6041
<212> TYPE: DNA
<213> ORGANISM: Artificial Sequence
<220> FEATURE:
<223> OTHER INFORMATION: pLD20

<400> SEQUENCE: 162

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480 tgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cggagagggg ttgtttggaa     660
aaggaagaga ccctgaggtg gagggaaaga gatacaggga tgctggatgg aaggcatact     720
```

```
tgaagagaac tggtcagtta gaataaatat tgtaataaat aggtctatat acatacacta    780
agcttctagg acgtcattgt agtcttcgaa gttgtctgct agtttagttc tcatgatttc    840
gaaaaccaat aacgcaatgg atgtagcagg gatggtggtt agtgcgttcc tgacaaaccc    900
agagtacgcc gcctcaaacc acgtcacatt cgcccttgc ttcatccgca tcacttgctt    960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcggttgaa ttgtggagta aaaattgtct gagttgtgtc   1260
ttagctactg gctggccccc cgcgaaagat aatcaaaatt acacttgtga attttttgcac  1320
acacaccgat taacatttcc cttttttgtc caccgataca cgcttgcctc ttcttatttt   1380
ctctgtgctt cccctcctg tgactttttc caccattgat ataaaatcaa ctccatttcc    1440
ctaaaatctc cccagattct aaaaacaact tcttctcttc tgcttttcct tattttttgtt   1500
atatttattt accatccctt attttgaata gttattcccc actaacattg ttcaaatctt   1560
cacgacataa tgaagtgttc tacgtttagt ttttggtttg tttgtaaaat tatattcttc   1620
ttttttttcct tcaacattca gacatcaatc gccaacccaa gggaaaactt ccttaagtgt   1680
tttctgcagt acatccctaa caatgcaaca aacctcaagt tggtgtacac tcaaaacaat   1740
ccactctata tgagcgtgct taatagcaca atccacaact tgcgcttcac gtcagatact   1800
acgcctaagc cactagtgat cgttacacca tcacacgtca gccatattca aggaacgatc   1860
ctatgtctga aaaggtcgg gttgcaaatc aggactcgat caggagggca cgatagtgag   1920
ggaatgagtt acatctcgca agtacccttc gtgatagttg acttgcgaaa tatgcggtct   1980
attaaaattg acgtacatag ccagaccgcc tgggttgaag caggggcaac cttgggtgaa   2040
gtttattact gggtcaatga aaaaaacgaa aacctaagtc ttgctgctgg atattgcccc   2100
accgtttgcg cgggtggtca ttttggaggc ggcggatatg gtccgttgat gagaaattat   2160
ggacttgcag cagacaatat tatagatgcc cacttggtga acgttcatgg aaaggtcttg   2220
gaccgtaagt ccatgggtga agatcttttc tgggccttga gaggtggtgg agcggaatcg   2280
tttggcatca tcgttgcctg gaaaattagg ttggttgcgg tcccgaagag tacaatgttc   2340
tccgtgaaga agattatgga aatacatgag cttgtcaagt tagttaacaa gtggcaaaat   2400
atcgcttata agtatgataa agacttgctt ttgatgactc attttattac gcgaaacata   2460
accgataacc agggcaagaa caagactgct attcacacgt acttctcctc tgtatttctt   2520
ggaggagtag actccttagt tgacttgatg aacaagagtt tcccagaatt ggggattaag   2580
aagacagatt gcagacaatt atcgtggata gatacaatca tattctatag cggtgtcgtc   2640
aattacgata ctgataattt taataaagaa atcctcctag atcgttcagc tgggcaaaac   2700
ggggcattca aaattaaatt ggattatgtg aagaaaccaa ttccagagct ggtgtttgtt   2760
cagatattgg aaaaacttta cgaagaagac attggcgcag gtatgtacgc tttgtatcca   2820
tatgaggca ttatgacga gatctcagag ctggcgatcc ccttcccgca cagagctggg    2880
atactctacg agctatggta catctgctct tgggagaaac aagaagacaa cgagaaacat   2940
ctcaattgga ttcggaacat atacaacttt atgaccccat acgtatcaaa aaacccgcgc   3000
ttagcatact tgaattacag agacttagat atcggtatca atgatcctaa gaatcctaac   3060
aattacaccc aagcccgtat ttgggggtgag aaatatttcg gcaagaattt tgacagatta   3120
```

-continued

```
gttaaggtca aaacactcgt ggaccccaac aacttttcc gaaacgagca gtcgattcca   3180
ccactaccca ggcatagaca ctgataagag tgactctttt gataagagtc gcaaatttga   3240
tttcataagt atatattcat tatgtaaagt agtaaatgga aaattcatta aaaaaaagc    3300 aaatttccgt tgtatgcata ctccgaacac aaaactagcc ccggaaaaac ccttagttga   3360
tagttgcgaa tttaggtcga ccatatgcga cgggtacaac gagaattgta ttgaattgat   3420
caagaacatg atcttggtgt tacagaacat caagttcttg gaccagactg agaatgcaca   3480
gatatacaag gcgtcatgtg ataaaatgga tgagatttat ccacaattga gaaagagtt    3540 tatggaaagt ggtcaaccag aagctaaaca ggaagaagca aacgaagagg tgaaacaaga   3600
agaagaaggt aaataagtat tttgtattat ataacaaaca aagtaaggaa tacagattta   3660
tacaataaat tgccatacta gtcacgtgag atatctcatc cattcccaa ctcccaagaa    3720 aataaaaaag tgaaaaataa aatcaaaccc aaagatcaac ctccccatca tcatcgtcat   3780
caaaccccca gctcaattcg caatggttag cacaaaaaca tacacagaaa gggcatcagc   3840
acacccctcc aaggttgccc aacgtttatt aattaaaggc taggtggagg ctcagtgatg   3900
ataagtctgc gatggtggat gcatgtgtca tggtcatagc tgtttcctgt gtgaaattgt   3960
tatccgctca gagggcacaa tcctattccg cgctatccga caatctccaa gacattaggt   4020
ggagttcagt tcggcgtatg gcatatgtcg ctggaaagaa catgtgagca aaaggccagc   4080
aaaaggccag gaaccgtaaa aaggccgcgt tgctggcgtt tttccatagg ctccgccccc   4140
ctgacgagca tcacaaaaat cgacgctcaa gtcagaggtg gcgaaacccg acaggactat   4200
aaagatacca ggcgtttccc cctggaagct ccctcgtgcg ctctcctgtt ccgaccctgc   4260
cgcttaccgg atacctgtcc gcctttctcc cttcgggaag cgtggcgctt tctcatagct   4320
cacgctgtag gtatctcagt tcggtgtagg tcgttcgctc caagctgggc tgtgtgcacg   4380
aaccccccgt tcagcccgac cgctgcgcct tatccggtaa ctatcgtctt gagtccaacc   4440
cggtaagaca cgacttatcg ccactggcag cagccactgg taacaggatt agcagagcga   4500
ggtatgtagg cggtgctaca gagttcttga agtggtggcc taactacggc tacactagaa   4560
gaacagtatt tggtatctgc gctctgctga agccagttac cttcggaaaa agagttggta   4620
gctcttgatc cggcaaacaa accaccgctg gtagcggtgg tttttttgtt tgcaagcagc   4680
agattacgcg cagaaaaaaa ggatctcaag aagatccttt gatcttttct acggggtctg   4740
acgctctatt caacaaagcc gccgtcccgt caagtcagcg taaatgggta gggggcttca   4800
aatcgtccgc tctgccagtg ttacaaccaa ttaacaaatt ctgattagaa aaactcatcg   4860
agcatcaaat gaaactgcaa tttattcata tcaggattat caataccata tttttgaaaa   4920
agccgtttct gtaatgaagg agaaaactca ccgaggcagt tccataggat ggcaagatcc   4980
tggtatcggt ctgcgattcc gactcgtcca acatcaatac aacctattaa tttcccctcg   5040
tcaaaaataa ggttatcaag tgagaaatca ccatgagtga cgactgaatc cggtgagaat   5100
ggcaaaagct tatgcatttc tttccagact tgttcaacag gccagccatt acgctcgtca   5160
tcaaaatcac tcgcatcaac caaaccgtta ttcattcgtg attgcgcctg agcgagacga   5220
aatacgcgat cgctgttaaa aggacaatta caaacaggaa tcgaatgcaa ccggcgcagg   5280
aacactgcca gcgcatcaac aatatttca  cctgaatcag gatattcttc taatacctgg   5340
aatgctgttt tccgggggat cgcagtggtg agtaaccatg catcatcagg agtacggata   5400
aaatgcttga tggtcggaag aggcataaat tccgtcagcc agtttagtct gaccatctca   5460
```

```
tctgtaacat cattggcaac gctacctttg ccatgtttca gaaacaactc tggcgcatcg    5520
ggcttcccat acaatcgata gattgtcgca cctgattgcc cgacattatc gcgagcccat    5580
ttatacccat ataaatcagc atccatgttg gaatttaatc gcggcctcga gcaagacgtt    5640
tcccgttgaa tatggctcat aacaccccct gtattactgt ttatgtaagc agacagtttt    5700
attgttcatg atgatatatt tttatcttgt gcaatgtaac atcagagatt ttgagacaca    5760
acgtggcttt cccccgccgc tctagaacta gtggatccaa ataaaacgaa aggctcagtc    5820
gaaagactgg gcctttcgtt ttatctgttg tttgtcgcat tatacgagac gtccaggttg    5880
ggatacctga aacaaaaccc atcgtacggc caaggaagtc tccaataact gtgatccacc    5940
acaagcgcca gggttttccc agtcacgacg ttgtaaaacg acggcagtc  atgcataatc    6000 cgcacgcatc tggaataagg aagtgccatt ccgcctgacc t                        6041
```

<210> SEQ ID NO 163
<211> LENGTH: 6536
<212> TYPE: DNA
<213> ORGANISM: Artificial Sequence
<220> FEATURE:
<223> OTHER INFORMATION: pLD22

<400> SEQUENCE: 163

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag ataggactgg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg gatggtggtt agtgcgttcc tgacaaaccc     900
agagtacgcc gcctcaaacc acgtcacatt cgcccttttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga attttgcac     1320 acacaccgat taacatttcc cttttttgtc caccgataca cgcttgcctc ttcttatttt    1380
ctctgtgctt ccccctcctg tgactttttc caccattgat ataaaatcaa ctccatttcc    1440
ctaaaatctc cccagattct aaaaacaact tcttctcttc tgcttttcct tatttttgtt    1500
```

```
atatttattt accatccctt attttgaata gttattcccc actaacattg ttcaaatctt    1560
cacgacataa tgacagaagt agtagataga gcaagttccc cagcaagtcc aggatctacg    1620
accgccgccg cagacggtgc taaggtggcg gtggagccac gcgtagatgt agcggccctt    1680
ggcgagcagt tgctagggcg atgggctgac atcagattgc acgcacgaga cttagcaggc    1740
cgcgaagtgg tccaaaaggt tgaaggactt acgcacactg agcatcggag tagagtcttt    1800
ggacagttga agtacttggt agacaacaat gctgttcaca gagcttttcc ctccaggcta    1860
ggtggatcag atgaccatgg cggtaatata gctggattcg aggaattagt tactgctgat    1920
ccatcattgc aaataaaggc cggcgttcag tggggtttgt ttggttctgc agtgatgcac    1980
ttgggaaccc gtgaacatca tgacaagtgg ttgccaggta ttatgtcgtt agaaataccg    2040
gggtgtttcg cgatgacaga aaccgggcac ggtagcgacg tggcctctat tgctacaaca    2100
gcaacttatg atgaggaaac ccaagagttt gttattgata ccccgttcag agccgcttgg    2160
aaagattata tcggtaatgc agcgaacgat ggtttggcgg cagttgtttt cgcacaatta    2220
atcacgagga aagtgaacca tggtgtacac gccttttacg tggatctcag agatcctgcg    2280
actggagact tcctacccgg aataggagga gaggacgatg gaatcaaggg gggattgaat    2340
ggcattgaca acggtagact acattttacg aacgtacgca ttcctagaac taatcttctt    2400
aacagatatg gcgatgtggc ggtcgacggc acatacctgt cgaccatcga atcaccaggg    2460
cgccggttct ttacgatgct tggtactcta gtccagggta gagttagtct cgatggagca    2520
gctgtcgctg cactgaaggt cgcattgcaa agtgcaattc actacgctgc ggagaggaga    2580
caatttaatg cgacttcacc tactgaagaa gaggtccttc ttgattatca gaggcatcaa    2640
aggagactct ttacacgact tgcaacgacg tacgccgcat ctttcgccca cgagcagcta    2700
ttgcaaaagt tcgatgatgt cttttcaggg gcacatgata ccgacgccga ccggcaggac    2760
ttggaaaccc tagccgccgc tttgaagcca ttgagcacat ggcatgcact tgacacgtta    2820
caagaatgca gagaggcctg tggggggggcc ggattttttga tagaaaaccg tttcgcgagc    2880
ttgcgtgctg acttggacgt ttacgtcaca ttcgagggtg ataacacagt tttattgcaa    2940
ttggttgcta acggctcttt ggcagactac gcaaaagagt tcagaggggc caacttcggc    3000
gttcttgcca ggtatgtggt tgaccaagcc gcgggagtgg cgctccaccg aacaggacta    3060
aggcaagtcg ctcaatttgt tgcagacagc gggtccgttc agaagtcggc tcttgcgctt    3120
cgcgatgaag agggtcaacg aacattgtta acggacagag tacagagcat ggttgccgaa    3180
gtgggggctg ccttgaaagg cgcaggcaaa ttaccccaac atcaagcagc tgcattgttc    3240
aaccaacacc agaacgaact tattgaggct gcccaggccc atgcagaact cctccaatgg    3300
gaggcattta cagaagctct cgctaaagtc gacgatgctg gtacaaagga agtgcttact    3360
cgattgcgag atctctttgg tttgtccttg attgaaaaac acttgctgtg gtatcttatg    3420 aatgacgtt tgtccatgca aagaggcagg acagttggaa cttacattaa tcgtttactt    3480
gtcaagatcc gtccacacgc actagacttg gttgatgcct tcggttacgg cgcggagcat    3540
ttgcgtgctg ctatcgccac cggagcggaa gcaacccgac aggatgaagc ccgaacgtat    3600
tttagacaac aacgggcatc gggactggcc ccggccgatg aaaagacctt actcgctatc    3660
aaagctggta atcaagagg gcgaagggca aagctatgat aagagtgact cttttgataa    3720
gagtcgcaaa tttgatttca taagtatata ttcattatgt aaagtagtaa atggaaaatt    3780
cattaaaaaa aaagcaaatt tccgttgtat gcatactccg aacacaaaac tagccccgga    3840
```

```
aaaacccctta gttgatagtt gcgaatttag gtcgaccata tgcgacgggt acaacgagaa    3900
ttgtattgaa ttgatcaaga acatgatctt ggtgttacag aacatcaagt tcttggacca    3960
gactgagaat gcacagatat acaaggcgtc atgtgataaa atggatgaga tttatccaca    4020
attgaagaaa gagtttatgg aaagtggtca accagaagct aaacaggaag aagcaaacga    4080
agaggtgaaa caagaagaag aaggtaaata agtattttgt attatataac aaacaaagta    4140
aggaatacag atttatacaa taaattgcca tactagtcac gtgagatatc tcatccattc    4200
cccaactccc aagaaaataa aaagtgaaa aataaaatca acccaaaga tcaacctccc     4260 catcatcatc gtcatcaaac ccccagctca attcgcaatg gttagcacaa aaacatacac    4320
agaaagggca tcagcacacc cctccaaggt tgcccaacgt ttattaatta aaggctaggt    4380
ggaggctcag tgatgataag tctgcgatgg tggatgcatg tgtcatggtc atagctgttt    4440
cctgtgtgaa attgttatcc gctcagaggg cacaatccta ttccgcgcta tccgacaatc    4500
tccaagacat taggtggagt tcagttcggc gtatggcata tgtcgctgga agaacatgt     4560 gagcaaaagg ccagcaaaag gccaggaacc gtaaaaaggc cgcgttgctg gcgttttccc    4620
ataggctccg ccccccctgac gagcatcaca aaaatcgacg ctcaagtcag aggtggcgaa    4680
acccgacagg actataaaga taccaggcgt ttccccctgg aagctccctc gtgcgctctc    4740
ctgttccgac cctgccgctt accggatacc tgtccgcctt ctcccttcg ggaagcgtgg     4800 cgctttctca tagctcacgc tgtaggtatc tcagttcggt gtaggtcgtt cgctccaagc    4860
tgggctgtgt gcacgaaccc cccgttcagc ccgaccgctg cgccttatcc ggtaactatc    4920
gtcttgagtc aacccggta agacacgact tatcgccact ggcagcagcc actggtaaca     4980
ggattagcag agcgaggtat gtaggcggtg ctacagagtt cttgaagtgg tggcctaact    5040
acggctacac tagaagaaca gtatttggta tctgcgctct gctgaagcca gttaccttcg    5100
gaaaaagagt tggtagctct tgatccggca aacaaccac cgctggtagc ggtggttttt      5160
ttgtttgcaa gcagcagatt acgcgcagaa aaaaaggatc tcaagaagat cctttgatct    5220
tttctacggg gtctgacgct ctattcaaca aagccgccgt cccgtcaagt cagcgtaaat    5280
gggtaggggg cttcaaatcg tccgctctgc cagtgttaca accaattaac aaattctgat    5340
tagaaaaact catcgagcat caaatgaaac tgcaatttat tcatatcagg attatcaata    5400
ccatattttt gaaaaagccg tttctgtaat gaaggagaaa actcaccgag gcagttccat    5460
aggatggcaa gatcctggta tcggtctgcg attccgactc gtccaacatc aatacaacct    5520
attaatttcc cctcgtcaaa aataaggtta tcaagtgaga atcaccatg agtgacgact     5580 gaatccggtg agaatggcaa aagcttatgc atttctttcc agacttgttc aacaggccag    5640
ccattacgct cgtcatcaaa atcactcgca tcaaccaaac cgttattcat tcgtgattgc    5700
gcctgagcga gacgaaatac gcgatcgctg ttaaaaggac aattacaaac aggaatcgaa    5760
tgcaaccggc gcaggaacac tgccagcgca tcaacaatat tttcacctga atcaggatat    5820
tcttctaata cctggaatgc tgttttcccg gggatcgcag tggtgagtaa ccatgcatca    5880
tcaggagtac ggataaaatg cttgatggtc ggaagaggca taaattccgt cagccagttt    5940
agtctgacca tctcatctgt aacatcattg gcaacgctac ctttgccatg tttcagaaac    6000
aactctggcg catcgggctt cccatacaat cgatagattg tcgcacctga ttgcccgaca    6060
ttatcgcgag cccatttata cccatataaa tcagcatcca tgttggaatt taatcgcggc    6120
ctcgagcaag acgtttcccg ttgaatatgg ctcataacac cccttgtatt actgtttatg    6180
taagcagaca gttttattgt tcatgatgat atatttttat cttgtgcaat gtaacatcag    6240
```

-continued

```
agattttgag acacaacgtg gctttccccc gccgctctag aactagtgga tccaaataaa    6300
acgaaaggct cagtcgaaag actgggcctt tcgttttatc tgttgtttgt cgcattatac    6360
gagacgtcca ggttgggata cctgaaacaa aacccatcgt acggccaagg aagtctccaa    6420
taactgtgat ccaccacaag cgccagggtt ttcccagtca cgacgttgta aaacgacggc    6480
cagtcatgca taatccgcac gcatctggaa taaggaagtg ccattccgcc tgacct        6536
```

<210> SEQ ID NO 164
<211> LENGTH: 5582
<212> TYPE: DNA
<213> ORGANISM: Artificial Sequence
<220> FEATURE:
<223> OTHER INFORMATION: pLD24

<400> SEQUENCE: 164

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaagggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg atggtggtt agtgcgttcc tgacaaaccc     900
agagtacgcc gcctcaaacc acgtcacatt cgccctttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga atttttgcac    1320
acacaccgat taacatttcc cttttttgtc caccgataca cgcttgcctc ttcttatttt    1380
ctctgtgctt cccctcctg tgactttttc caccattgat ataaaatcaa ctccatttcc    1440
ctaaaatctc cccagattct aaaaacaact tcttctcttc tgcttttcct tattttgtt    1500 atatttattt accatccctt attttgaata gttattcccc actaacattg ttcaaatctt    1560
cacgacataa tgaatcattt aagagcagaa ggacccgcat cagtgttagc gataggtaca    1620
gctaacccag agaatatctt aatccaagat gaatttcctg actactattt ccgtgttact    1680
aaatcggaac atatgactca acttaaagag aagttccgga aaatctgcga taaatccatg    1740
```

| | | | | | |
|---|---|---|---|---|---|
| atccgaaaga | gaaactgttt | ccttaacgaa | gaacatctca | agcaaaaccc | gaggttggta | 1800 |
| gagcacgaaa | tgcagacctt | ggatgctagg | caggacatgt | tggtggtcga | agtgccaaaa | 1860 |
| ctcggcaagg | acgcgtgcgc | taaggcaatc | aaggagtggg | gtcaaccgaa | gtctaaaatc | 1920 |
| acgcatctaa | tatttacatc | tgcactgaca | accgacatgc | cgggtgccga | ttatcactgc | 1980 |
| gccaagctac | ttggattgag | tccactggtt | aagagagtta | tgatgtatca | attggggtgt | 2040 |
| tacggagggg | gcacagtcct | cagaattgct | aaggatattg | cggaaaataa | caagggcgcg | 2100 |
| agggtccttg | ctgtatgttg | tgatattatg | gcctgtttgt | ttcgcgggcc | ctcggattca | 2160 |
| gatttggaat | tgcttgtcgg | acaggcaatt | tttggtgacg | gggccgcagc | agtcatagtg | 2220 |
| ggagccgaac | cagacgaaag | cgtgggtgaa | agaccaatct | ttgagttggt | tctgaccgga | 2280 |
| caaacgatct | tacctaactc | ggaaggtacg | attggaggac | atattagaga | agccggccta | 2340 |
| attttcgatc | ttcacaaaga | cgttccaatg | ttaatctcca | ataacataga | aaagtgcttg | 2400 |
| atagaagcat | ttactcccat | tggtattagt | gactggaaca | gcattttctg | gatcacccac | 2460 |
| cctggaggaa | aagctatact | cgataaggtt | gaagagaaac | tcgacttgaa | aaaggagaaa | 2520 |
| ttcgttgact | cacgacatgt | gttatcagag | cacgggaata | tgagttcatc | cacagtcttg | 2580 |
| ttcgtaatgg | atgaattgcg | aaaacgctct | cttgaggagg | gaaagagcac | aaccggtgac | 2640 |
| gggtttgagt | ggggcgtgct | attcggtttt | ggcccaggtt | tgactgtcga | gcgggttgtt | 2700 |
| gttcgtagtg | taccaattaa | gtacggaaga | agggcaaagt | tgtgataaga | gtgactcttt | 2760 |
| tgataagagt | cgcaaatttg | atttcataag | tatatattca | ttatgtaaag | tagtaaatgg | 2820 |
| aaaattcatt | aaaaaaaaag | caaatttccg | ttgtatgcat | actccgaaca | caaaactagc | 2880 |
| cccggaaaaa | cccttagttg | atagttgcga | atttaggtcg | accatatgcg | acgggtacaa | 2940 |
| cgagaattgt | attgaattga | tcaagaacat | gatcttggtg | ttacagaaca | tcaagttctt | 3000 |
| ggaccagact | gagaatgcac | agatatacaa | ggcgtcatgt | gataaaatgg | atgagattta | 3060 |
| tccacaattg | aagaaagagt | ttatggaaag | tggtcaacca | gaagctaaac | aggaagaagc | 3120 |
| aaacgaagag | gtgaaacaag | aagaagaagg | taaataagta | ttttgtatta | tataacaaac | 3180 |
| aaagtaagga | atacagatttt | atacaataaa | ttgccatact | agtcacgtga | gatatctcat | 3240 |
| ccattcccca | actcccaaga | aaataaaaaa | gtgaaaaata | aaatcaaacc | caaagatcaa | 3300 |
| cctcccatc | atcatcgtca | tcaaaccccc | agctcaattc | gcaatggtta | gcacaaaaac | 3360 |
| atacacagaa | agggcatcag | cacacccctc | caaggttgcc | caacgtttat | taattaaagg | 3420 |
| ctaggtggag | gctcagtgat | gataagtctg | cgatggtgga | tgcatgtgtc | atggtcatag | 3480 |
| ctgtttcctg | tgtgaaattg | ttatccgctc | agagggcaca | atcctattcc | gcgctatccg | 3540 |
| acaatctcca | agacattagg | tggagttcag | ttcggcgtat | ggcatatgtc | gctgaaaga | 3600 |
| acatgtgagc | aaaaggccag | caaaaggcca | ggaaccgtaa | aaaggccgcg | ttgctggcgt | 3660 |
| ttttccatag | gctccgcccc | cctgacgagc | atcacaaaaa | tcgacgctca | agtcagaggt | 3720 |
| ggcgaaaccc | gacaggacta | taaagatacc | aggcgtttcc | ccctggaagc | tccctcgtgc | 3780 |
| gctctcctgt | tccgaccctg | ccgcttaccg | gatacctgtc | gcctttctc | ccttcgggaa | 3840 |
| gcgtggcgct | ttctcatagc | tcacgctgta | ggtatctcag | ttcggtgtag | gtcgttcgct | 3900 |
| ccaagctggg | ctgtgtgcac | gaaccccccg | ttcagcccga | ccgctgcgcc | ttatccggta | 3960 |
| actatcgtct | tgagtccaac | ccggtaagac | acgacttatc | gccactggca | gcagccactg | 4020 |
| gtaacaggat | tagcagagcg | aggtatgtag | gcggtgctac | agagttcttg | aagtggtggc | 4080 |
| ctaactacgg | ctacactaga | agaacagtat | ttggtatctg | cgctctgctg | aagccagtta | 4140 |

```
ccttcggaaa aagagttggt agctcttgat ccggcaaaca aaccaccgct ggtagcggtg    4200 gttttttgt  ttgcaagcag cagattacgc gcagaaaaaa aggatctcaa gaagatcctt    4260 tgatctttc  tacggggtct gacgctctat tcaacaaagc cgccgtcccg tcaagtcagc    4320
gtaaatgggt aggggcttc  aaatcgtccg ctctgccagt gttacaacca attaacaaat    4380
tctgattaga aaaactcatc gagcatcaaa tgaaactgca atttattcat atcaggatta    4440
tcaataccat attttgaaa  aagccgtttc tgtaatgaag gagaaaactc accgaggcag    4500
ttccatagga tggcaagatc ctggtatcgg tctgcgattc cgactcgtcc aacatcaata    4560
caacctatta atttcccctc gtcaaaaata aggttatcaa gtgagaaatc accatgagtg    4620
acgactgaat ccggtgagaa tggcaaaagc ttatgcattt cttccagac  ttgttcaaca    4680 ggccagccat tacgctcgtc atcaaaatca ctcgcatcaa ccaaaccgtt attcattcgt    4740
gattgcgcct gagcgagacg aaatacgcga tcgctgttaa aaggacaatt acaaacagga    4800
atcgaatgca accggcgcag gaacactgcc agcgcatcaa caatatttc  acctgaatca    4860 ggatattctt ctaatacctg gaatgctgtt ttcccgggga tcgcagtggt gagtaaccat    4920
gcatcatcag gagtacggat aaaatgcttg atggtcggaa gaggcataaa ttccgtcagc    4980
cagtttagtc tgaccatctc atctgtaaca tcattggcaa cgctacctt  gccatgtttc    5040 agaaacaact ctggcgcatc gggcttccca tacaatcgat agattgtcgc acctgattgc    5100
ccgacattat cgcgagccca tttatacccca tataaatcag catccatgtt ggaatttaat    5160
cgcggcctcg agcaagacgt ttcccgttga atatggctca taacacccct tgtattactg    5220
tttatgtaag cagacagttt tattgttcat gatgatatat ttttatcttg tgcaatgtaa    5280
catcagagat tttgagacac aacgtggctt tccccgccg  ctctagaact agtggatcca    5340
aataaaacga aaggctcagt cgaaagactg gcctttcgt  tttatctgtt gtttgtcgca    5400
ttatacgaga cgtccaggtt gggatacctg aaacaaaacc catcgtacgg ccaaggaagt    5460
ctccaataac tgtgatccac cacaagcgcc agggttttcc cagtcacgac gttgtaaaac    5520
gacggccagt catgcataat ccgcacgcat ctggaataag gaagtgccat tccgcctgac    5580
ct                                                                   5582
```

<210> SEQ ID NO 165
<211> LENGTH: 5606
<212> TYPE: DNA
<213> ORGANISM: Artificial Sequence
<220> FEATURE:
<223> OTHER INFORMATION: pLD56

<400> SEQUENCE: 165

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcgggggg tataccggat cgcggcgtgg agtgacatca     300
cgaacgcgca cggagtgact gggaagggcg tcgttaagg  gttgaaacgc ggtgcggagg     360
gggtagaaaa ggaaagggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
```

```
tgacgcctgg tgtggggttg gatgataaag gcgatgcgtt gggccagcag tataggactg    600
ttgatgaggt ggttctgact ggtaccgatg tgattattgt cgggagaggg ttgtttggaa    660
aaggaagaga ccctgaggtg gagggaaaga gatacaggga tgctggatgg aaggcatact    720
tgaagagaac tggtcagtta gaataaatat tgtaataaat aggtctatat acatacacta    780
agcttctagg acgtcattgt agtcttcgaa gttgtctgct agtttagttc tcatgatttc    840
gaaaaccaat aacgcaatgg atgtagcagg atggtggtt agtgcgttcc tgacaaaccc      900
agagtacgcc gcctcaaacc acgtcacatt cgcccttgc ttcatccgca tcacttgctt      960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcggttgaa ttgtggagta aaaattgtct gagttgtgtc   1260
ttagctactg gctggccccc cgcgaaagat aatcaaaatt acacttgtga attttttgcac  1320 acacaccgat taacatttcc cttttttgtc caccgataca cgcttgcctc ttcttatttt   1380
ctctgtgctt cccctcctg tgacttttc caccattgat ataaaatcaa ctccatttcc     1440
ctaaaatctc cccagattct aaaaacaact tcttctcttc tgcttttcct tattttgtt    1500 atatttattt accatccctt attttgaata gttattcccc actaacattg ttcaaatctt   1560
cacgacataa tggggttgtc cttagttgt acgttcagtt tccaaactaa ctaccacaca    1620
ctactaaatc cgcacaacaa aaacccgaaa aattcattgc tctcctatca gcacccaaaa   1680
acacccatta tcaagtctag ttacgacaac tttccatcaa aatactgtct aacgaaaaac   1740
tttcatttgt tgggcttaaa ttctcataat cgtatttcca gtcagtcccg atcgatcagg   1800
gccgggagtg accaaattga aggttctcca catcatgaaa gtgacaattc aattgctacg   1860
aagattttaa actttgggca tacatgctgg aagctacagc gaccgtatgt agttaagggg   1920
atgatcagca ttgcctgcgg cctattcgga agggaactct tcaataatag acatcttttt   1980
tcttggggtt taatgtggaa agcttttttc gctttggttc ctatccttag ttttaacttc   2040
ttcgccgcta ttatgaatca aatttacgat gttgacatcg accgtattaa caaacccgat   2100 ctccccttg tttcaggcga gatgtccatt gaaacggcat ggattttgtc catcattgtt    2160
gcgcttactg gcttgattgt taccattaag cttaaaagcg ctcccttgtt cgttttata     2220 tacattttcg gcattttgc cggattcgca tacagtgtcc cgcctatacg ttggaaacaa     2280
tatccattca cgaacttctt gatcacgatc tcatcacatg ttggattggc ctttacgtcc   2340
tacagtgcta ccacatctgc ccttggattg ccttttcgttt ggaggcctgc cttctcgttt   2400
atcattgcat ttatgacagt gatgggaatg actatcgcat ttgctaaaga tatcagcgac   2460
atagagggcg atgcaaaata tggggtgagt actgttgcga cgaagttggg cgcccgaaat   2520
atgaccttcg ttgtttccgg cgttctttta cttaactatt tagtatcgat tagcatcggg   2580
atcatctggc cacaggtgtt taaatcaaat attatgatct tgtcgcatgc catcctagct   2640
ttctgtctta tatttcaaac aagagaatta gccctagcga actacgcctc agcaccaagt   2700
cgtcagttct tcgaatttat atggctactc tactacgccg aatacttcgt ctatgtcttc   2760
atttagtaat aagagtgact cttttgataa gagtcgcaaa tttgatttca taagtatata   2820
ttcattatgt aaagtagtaa atggaaaatt cattaaaaaa aaagcaaatt tccgttgtat   2880
gcatactccg aacacaaaac tagccccgga aaaacccttta gttgatagtt gcgaatttag   2940
```

-continued

```
gtcgaccata tgcgacgggt acaacgagaa ttgtattgaa ttgatcaaga acatgatctt    3000
ggtgttacag aacatcaagt tcttggacca gactgagaat gcacagatat acaaggcgtc    3060
atgtgataaa atggatgaga tttatccaca attgaagaaa gagtttatgg aaagtggtca    3120
accagaagct aaacaggaag aagcaaacga agaggtgaaa caagaagaag aaggtaaata    3180
agtattttgt attatataac aaacaaagta aggaatacag atttatacaa taaattgcca    3240
tactagtcac gtgagatatc tcatccattc cccaactccc aagaaaataa aaagtgaaa     3300 aataaaatca aacccaaaga tcaacctccc catcatcatc gtcatcaaac ccccagctca    3360
attcgcaatg gttagcacaa aaacatacac agaaagggca tcagcacacc cctccaaggt    3420
tgcccaacgt ttattaatta aaggctaggt ggaggctcag tgatgataag tctgcgatgg    3480
tggatgcatg tgtcatggtc atagctgttt cctgtgtgaa attgttatcc gctcagaggg    3540
cacaatccta ttccgcgcta tccgacaatc tccaagacat taggtggagt tcagttcggc    3600
gtatggcata tgtcgctgga aagaacatgt gagcaaaagg ccagcaaaag gccaggaacc    3660
gtaaaaaggc cgcgttgctg cgttttttcc ataggctccg ccccctgac gagcatcaca     3720 aaaatcgacg ctcaagtcag aggtggcgaa acccgacagg actataaaga taccaggcgt    3780
ttccccctgg aagctccctc gtgcgctctc ctgttccgac cctgccgctt accggatacc    3840
tgtccgcctt tctcccttcg ggaagcgtgg cgctttctca tagctcacgc tgtaggtatc    3900
tcagttcggt gtaggtcgtt cgctccaagc tgggctgtgt gcacgaaccc cccgttcagc    3960
ccgaccgctg cgccttatcc ggtaactatc gtcttgagtc caacccggta agacacgact    4020
tatcgccact ggcagcagcc actggtaaca ggattagcag agcgaggtat gtaggcggtg    4080
ctacagagtt cttgaagtgg tggcctaact acggctacac tagaagaaca gtatttggta    4140
tctgcgctct gctgaagcca gttaccttcg gaaaaagagt tggtagctct tgatccggca    4200
aacaaaccac cgctggtagc ggtggttttt tgtttgcaa gcagcagatt acgcgcagaa     4260
aaaaaggatc tcaagaagat cctttgatct tttctacggg gtctgacgct ctattcaaca    4320
aagccgccgt cccgtcaagt cagcgtaaat gggtagggggg cttcaaatcg tccgctctgc    4380
cagtgttaca accaattaac aaattctgat tagaaaaact catcgagcat caaatgaaac    4440
tgcaatttat tcatatcagg attatcaata ccatattttt gaaaaagccg tttctgtaat    4500
gaaggagaaa actcaccgag gcagttccat aggatggcaa gatcctggta tcggtctgcg    4560
attccgactc gtccaacatc aatacaacct attaatttcc cctcgtcaaa aataaggtta    4620
tcaagtgaga aatcaccatg agtgacgact gaatccggtg agaatggcaa aagcttatgc    4680
atttctttcc agacttgttc aacaggccag ccattacgct cgtcatcaaa atcactcgca    4740
tcaaccaaac cgttattcat tcgtgattgc gcctgagcga gacgaaatac gcgatcgctg    4800
ttaaaaggac aattacaaac aggaatcgaa tgcaaccggc gcaggaacac tgccagcgca    4860
tcaacaatat tttcacctga atcaggatat tcttctaata cctggaatgc tgttttcccg    4920
gggatcgcag tggtgagtaa ccatgcatca tcaggagtac ggataaaatg cttgatggtc    4980
ggaagaggca taaattccgt cagccagttt agtctgacca tctcatctgt aacatcattg    5040
gcaacgctac ctttgccatg tttcagaaac aactctggcg catcgggctt cccatacaat    5100
cgatagattg tcgcacctga ttgcccgaca ttatcgcgag cccatttata cccatataaa    5160
tcagcatcca tgttggaatt taatcgcggc ctcgagcaag acgtttcccg ttgaatatgg    5220
ctcataacac cccttgtatt actgtttatg taagcagaca gttttattgt tcatgatgat    5280
```

```
atattttat cttgtgcaat gtaacatcag agattttgag acacaacgtg gctttccccc    5340
gccgctctag aactagtgga tccaaataaa acgaaaggct cagtcgaaag actgggcctt    5400
tcgttttatc tgttgtttgt cgcattatac gagacgtcca ggttgggata cctgaaacaa    5460
aacccatcgt acggccaagg aagtctccaa taactgtgat ccaccacaag cgccagggtt    5520
ttcccagtca cgacgttgta aaacgacggc cagtcatgca taatccgcac gcatctggaa    5580
taaggaagtg ccattccgcc tgacct                                         5606
```

<210> SEQ ID NO 166
<211> LENGTH: 5071
<212> TYPE: DNA
<213> ORGANISM: Artificial Sequence
<220> FEATURE:
<223> OTHER INFORMATION: pLD87

<400> SEQUENCE: 166

```
aggctaggtg gaggctcagt gatgataagt ctgcgatggt ggatgcatgt gtcatggtca      60
tagctgtttc ctgtgtgaaa ttgttatccg ctcagagggc acaatcctat tccgcgctat     120
ccgacaatct ccaagacatt aggtggagtt cagttcggcg tatggcatat gtcgctggaa     180
agaacatgtg agcaaaaggc cagcaaaagg ccaggaaccg taaaaaggcc gcgttgctgg     240
cgttttccca taggctccgc ccccctgacg agcatcacaa aaatcgacgc tcaagtcaga     300
ggtggcgaaa cccgacagga ctataaagat accaggcgtt tccccctgga agctccctcg     360
tgcgctctcc tgttccgacc ctgccgctta ccggatacct gtccgccttt ctcccttcgg     420
gaagcgtggc gctttctcat agctcacgct gtaggtatct cagttcggtg taggtcgttc     480
gctccaagct gggctgtgtg cacgaacccc ccgttcagcc cgaccgctgc gccttatccg     540
gtaactatcg tcttgagtcc aacccggtaa gacacgactt atcgccactg gcagcagcca     600
ctggtaacag gattagcaga gcgaggtatg taggcggtgc tacagagttc ttgaagtggt     660
ggcctaacta cggctacact agaagaacag tatttggtat ctgcgctctg ctgaagccag     720
ttaccttcgg aaaaagagtt ggtagctctt gatccggcaa acaaaccacc gctggtagcg     780
gtggtttttt tgtttgcaag cagcagatta cgcgcagaaa aaaaggatct caagaagatc     840
ctttgatctt ttctacgggg tctgacgctc tattcaacaa agccgccgtc cgtcaagtc      900 agcgtaaatg ggtaggggc ttcaaatcgt ccgctctgcc agtgttacaa ccaattaaca      960
aattctgatt agaaaaactc atcgagcatc aaatgaaact gcaatttatt catatcagga    1020
ttatcaatac catattttg aaaaagccgt ttctgtaatg aaggagaaaa ctcaccgagg    1080
cagttccata ggatggcaag atcctggtat cggtctgcga ttccgactcg tccaacatca    1140
atacaaccta ttaatttccc ctcgtcaaaa ataaggttat caagtgagaa atcaccatga    1200
gtgacgactg aatccggtga gaatggcaaa agcttatgca tttctttcca gacttgttca    1260
acaggccagc cattacgctc gtcatcaaaa tcactcgcat caaccaaacc gttattcatt    1320
cgtgattgcg cctgagcgag acgaaatacg cgatcgctgt taaaaggaca attacaaaca    1380
ggaatcgaat gcaaccggcg caggaacact gccagcgcat caacaatatt ttcacctgaa    1440
tcaggatatt cttctaatac ctggaatgct gttttcccgg ggatcgcagt ggtgagtaac    1500
catgcatcat caggagtacg gataaaatgc ttgatggtcg aagaggcat aaattccgtc    1560 agccagttta gtctgaccat ctcatctgta acatcattgg caacgctacc tttgccatgt    1620
ttcagaaaca actctggcgc atcgggcttc ccatacaatc gatagattgt cgcacctgat    1680
tgcccgacat tatcgcgagc ccatttatac ccatataaat cagcatccat gttggaattt    1740
```

```
aatcgcggcc tcgagcaaga cgtttcccgt tgaatatggc tcataacacc ccttgtatta    1800
ctgtttatgt aagcagacag tttttattgtt catgatgata tatttttatc ttgtgcaatg    1860
taacatcaga gattttgaga cacaacgtgg cttcccccg ccgctctaga actagtggat    1920
ccaaataaaa cgaaaggctc agtcgaaaga ctgggccttt cgttttatct gttgtttgtc    1980
gcattatacg agacgtccag gttgggatac ctgaaacaaa acccatcgta cggccaagga    2040
agtctccaat aactgtgatc caccacaagc gccagggttt tcccagtcac gacgttgtaa    2100
aacgacggcc agtcatgcat aatccgcacg catctggaat aaggaagtgc cattccgcct    2160
gacctttaat taagtcgact tgatgtttag agtgtccaga tccgcaagat cggctcgcac    2220
ttgtgttgtg ttgtttcaaa tcagcctgtc gttttgtgtc gtttgagatc attctgtctc    2280
actcttaggc tcgcttagaa ccgacaacgg agaatccggg ctcggttttt cggtcggcct    2340
tgatctgggc cttggacttg tactggtcgg ccatctccac gttgaccagc tccttgacct    2400
tgtagagctg accggcgata ccaggagaca ccttgtagta cttctgggag ccgaccttgc    2460
ccagaccgag ggtcttgagc acgtcacgtg ttctccacgg cattcgcagg atagatcgga    2520
cctgtgtgac tttgtagaac atggcgtttc aggtggttgc gtgagtgtgt aaaatcgtgt    2580 cttcagaag ttacaaattt caccgcattt agagtttatg cagatgggcg gtgtgtggtt    2640
gggagttcga tttccgtgcg tgcatttgat cttgatgaat tggatttgta catggggaat    2700
agcacgtcaa gaaccgccta ctgcaaactc gtgaatattg agattattga ggaaattcaa    2760
ggaaaattca gatcagattt gagagcaaag tccaacaata ctacacaatc cctttcctgt    2820
attcttccac catcgtcatc gtcgtctgtc ttctcttcag cttttttaat tcactcccca    2880
caaacccaaa tttagctgca tcattcatca acctccaatt ataactatac atcgcgacac    2940
gaacacgaaa cacgaaccac gaaccgccgc tttgtcgacg gagtgagacg ggagagagac    3000
catggtctct cgctcgtctc acgcttagcg gccgcgtcga cataacttcg tatagcatac    3060
attatacgaa gttatttttct aatttggacc gatagccgta tagtccagtc tatctataag    3120
ttcaactaac tcgtaactat taccataaca tatacttcac tgccccagat aaggttccga    3180
taaaaagttg tgcagactaa atttatttca gtctcctctt caccaccaaa atgccctcct    3240
acgaagcgcg agctaacgtc cacaagtccg cctttgccgc ccgagtgctc aagctcgtgg    3300
cagccaagaa aaccaacctg tgtgcttctc tggatgttac caccaccaag gagctcattg    3360
agcttgccga taaggtcgga ccttatgtgt gcatgatcaa gacccatatc gacatcattg    3420
acgacttcac ctacgccgga actgtgctcc ccctcaagga acttgctctt aagcacggtt    3480
tcttcctgtt cgaggacaga aagttcgcag atattggcaa cactgtcaag caccagtaca    3540
agaacggtgt ctaccgaatc gccgagtggt ccgatatcac caacgccac ggtgtacccg    3600 gaaccggaat cattgctggc ctgcgagctg gtgccgagga aactgtctct gaacagaaga    3660
aggaggatgt ctctgactac gagaactccc agtacaagga gttcctggtc ccctctccca    3720
acgagaagct ggccagaggt ctgctcatgc tggccgagct gtcttgcaag ggctctctgg    3780
ccactggcga gtactccaag cagaccattg agcttgcccg atccgacccc gagtttgtgg    3840
ttggcttcat tgcccagaac cgacctaagg gcgactctga ggactggctt attctgaccc    3900
ccggggtggg tcttgacgac aagggagatg ctctcggaca gcagtaccga actgttgagg    3960
atgtcatgtc taccggaacg gatatcataa ttgtcggccg aggtctgtac ggccagaacc    4020
gagatcctat tgaggaggcc aagcgatacc agaaggctgg ctgggaggct taccagaaga    4080
```

```
ttaactgtta gaggttagac tatggatatg tcatttaact gtgtatatag agagcgtgca    4140
agtatggagc gcttgttcag cttgtatgat ggtcagacga cctgtctgat cgagtatgta    4200
tgatactgca caacctgata acttcgtata gcatacatta tacgaagtta tctcgaggga    4260
tccctaggga ggcacatcta aacgaataac gaatattaat gataccatca tatctcagaa    4320
catgtatgac tgctgcttcc aaacgatatg aggatgagtc ctctttcaga ttaagataga    4380
gtacaaatat attatctata tactggtgtc tgtgcgatgt cgtatgagcg gtgaatcatg    4440
tgactgtcac gtggtttggc ccaagttaca ccgtagctac gcctttcttg accgactcca    4500
tggtcttctg ggcgggttga cagtttccac tggatgagcg tccgcctcct gttcctgtcg    4560
ttgtccctgc agctcagcct caatcttctg accgagctcg gagtccaggg aaatgccaac    4620
aggttgtcca gcaacatca tggtttggtg ggcagccgtg atctcatcgt cgttggatac    4680
cattcggtac ttggcctcaa tctgcacaaa gtagcggtac cactggtttc gagcaaaccg    4740
ctccaattga gcctctccgt cgagagagag agtaggtgat tgctccaact tgcggccaaa    4800
atgaagttct cgactcacct tttgaagcg gttcttcttg cccatcttgg tggcgaaagt    4860
agtggctagt ggtggatgac tttgtataat gtaccgatga agagggttgt atttgctcag    4920
taagaagtag cgagtgaaat cagatcactt aacgagagca aagggcaatg gaatacctgc    4980
tgcctgatta acaacagctt ctgtgtcgtt tctctcttgt gaatgagtgt gttgctagag    5040
gtaggttggc actccaatgt tacttaatta a                                   5071
```

<210> SEQ ID NO 167
<211> LENGTH: 5096
<212> TYPE: DNA
<213> ORGANISM: Artificial Sequence
<220> FEATURE:
<223> OTHER INFORMATION: pLD101

<400> SEQUENCE: 167

```
aggctaggtg gaggctcagt gatgataagt ctgcgatggt ggatgcatgt gtcatggtca      60
tagctgtttc ctgtgtgaaa ttgttatccg ctcagagggc acaatcctat tccgcgctat     120
ccgacaatct ccaagacatt aggtggagtt cagttcggcg tatggcatat gtcgctggaa     180
agaacatgtg agcaaaaggc cagcaaaagg ccaggaaccg taaaaaggcc gcgttgctgg     240
cgttttccca taggctccgc cccctgacg agcatcacaa aaatcgacgc tcaagtcaga     300
ggtggcgaaa cccgacagga ctataaagat accaggcgtt tcccctgga agctccctcg     360
tgcgctctcc tgttccgacc ctgccgctta ccggatacct gtccgccttt ctcccttcgg     420
gaagcgtggc gctttctcat agctcacgct gtaggtatct cagttcggtg taggtcgttc     480
gctccaagct gggctgtgtg cacgaacccc ccgttcagcc cgaccgctgc gccttatccg     540
gtaactatcg tcttgagtcc aacccggtaa gacacgactt atcgccactg gcagcagcca     600
ctggtaacag gattagcaga gcgaggtatg taggcggtgc tacagagttc ttgaagtggt     660
ggcctaacta cggctacact agaagaacag tatttggtat ctgcgctctg ctgaagccag     720
ttaccttcgg aaaaagagtt ggtagctctt gatccggcaa acaaaccacc gctggtagcg     780
gtggtttttt tgtttgcaag cagcagatta cgcgcagaaa aaaaggatct caagaagatc     840
ctttgatctt ttctacgggg tctgacgctc tattcaacaa agccgccgtc cgtcaagtc      900
agcgtaaatg ggtagggggc ttcaaatcgt cctcgtgata ccaattcgga gcctgctttt     960
ttgtacaaac ttgttgataa tggcaattca aggatcttca cctagatcct tttaaattaa    1020
aaatgaagtt ttaaatcaat ctaaagtata tatgagtaaa cttggtctga cagttaccaa    1080
```

```
tgcttaatca gtgaggcacc tatctcagcg atctgtctat ttcgttcatc catagttgcc  1140
tgactccccg tcgtgtagat aactacgata cgggagggct taccatctgg ccccagtgct  1200
gcaatgatac cgcgagagcc acgctcaccg gctccagatt tatcagcaat aaaccagcca  1260
gccggaaggg ccgagcgcag aagtggtcct gcaactttat ccgcctccat ccagtctatt  1320
aattgttgcc gggaagctag agtaagtagt tcgccagtta atagtttgcg caacgttgtt  1380
gccattgcta caggcatcgt ggtgtcacgc tcgtcgtttg gtatggcttc attcagctcc  1440
ggttcccaac gatcaaggcg agttacatga tcccccatgt tgtgcaaaaa agcggttagc  1500
tccttcggtc ctccgatcgt tgtcagaagt aagttggccg cagtgttatc actcatggtt  1560
atggcagcac tgcataattc tcttactgtc atgccatccg taagatgctt ttctgtgact  1620
ggtgagtact caaccaagtc attctgagaa tagtgtatgc ggcgaccgag ttgctcttgc  1680
ccggcgtcaa tacgggataa taccgcgcca catagcagaa ctttaaaagt gctcatcatt  1740
ggaaaacgtt cttcggggcg aaaactctca aggatcttac cgctgttgag atccagttcg  1800
atgtaaccca ctcgtgcacc caactgatct tcagcatctt ttactttcac cagcgtttct  1860
gggtgagcaa aaacaggaag gcaaaatgcc gcaaaaaagg gaataagggc gacacggaaa  1920
tgttgaatac tcatactctt cctttttcaa tattattgaa gcatttatca gggttattgt  1980
ctcatgagcg gatacatatt tgaatgtatt tagaaaaata aacaaatagg ggttccgcgc  2040
acatttcccc gaaaagtgcc agatacctga acaaaaccc atcgtacggc caaggaagtc  2100
tccaataact gtgatccacc acaagcgcca gggttttccc agtcacgacg ttgtaaaacg  2160
acggccagtc atgcataatc cgcacgcatc tggaataagg aagtgccatt ccgcctgacc  2220
tttaattaac gatccgcgta aattcagagc aatgccaaga tccttatttc cgataacagc  2280
gagatacaca tcagaagagg tggagactct ggccccgcac gaccaccacg tcgtcactca  2340
aagcaaagtc acgatgtaga aatcacaatc gtccccataa gcacgtggat tcccctggtt  2400
ttgtttcggc ctcggcagtg gcaattctgg ggtatataaa ccagcaaggt tatgacctga  2460
ttgacctgct tgtggcctga taaaccgcct gacttttgtg ataaggttgg gagcatgcgg  2520
ctcgggccat tgtgagcatt ttcgtcaagg actggccaag tccaactgga agagacatgg  2580
gcaaaatgtc gactttacag atgtacccga aattgcttca attgctctca gctgccggaa  2640
ccggatctat cggtgcaagt atcgtacagt agacatgtgc tattggtaac cctcggtatt  2700
ggctaggttt cgtatcaggg atacagttca acgctgatcg catatggcat gattccggct  2760
cgacacagcg accaagaacc aagcgtgtat gtcgtagact tgcaaatcat gtgggcttta  2820
tccccggatt tccccaagtc acgttttcac aaaggctgtc tcccgaatgc atgagccgag  2880
gcaggctaaa ctggtttgtt catgtaccc cacaacgta aagatgcacc ccatgtgcag  2940
tgaaatacca caagtatata tataccgacc tacccgagat agcaaattga ttctacactt  3000
acactaccaa ttcttacatc aaaccaaacc gcttgagacc atccggtctc tgatcatcct  3060
cgagataact tcgtataatg tatgctatac gaagttatca ggttgtgcag tatcatacat  3120
actcgatcag acaggtcgtc tgaccatcat acaagctgaa caagcgctcc atacttgcac  3180
gctctctata tacacagtta aatgacatat ccatagtcta acctctaaca gttaatcttc  3240
tggtaagcct cccagccagc cttctggtat cgcttggcct cctcaatagg atctcggttc  3300
tggccgtaca gacctcggcc gacaattatg atatccgttc cggtagacat gacatcctca  3360
acagttcggt actgctgtcc gagagcatct cccttgtcgt caagacccac cccggggggtc  3420
```

```
agaataagcc agtcctcaga gtcgcccttaggtcggttct gggcaatgaa gccaaccaca  3480
aactcgggt cggatcgggc aagctcaatg gtctgcttgg agtactcgcc agtggccaga   3540
gagcccttgc aagacagctc ggccagcatg agcagacctc tggccagctt ctcgttggga  3600
gaggggacca ggaactcctt gtactgggag ttctcgtagt cagagacatc ctccttcttc  3660
tgttcagaga cagtttcctc ggcaccagct cgcaggccag caatgattcc ggttccgggt  3720
acaccgtggg cgttggtgat atcgaccac tcggcgattc ggtagacacc gttcttgtac   3780
tggtgcttga cagtgttgcc aatatctgcg aactttctgt cctcgaacag gaagaaaccg  3840
tgcttaagag caagttcctt gaggggagc acagttccgg cgtaggtgaa gtcgtcaatg   3900
atgtcgatat gggtcttgat catgcacaca taaggtccga ccttatcggc aagctcaatg  3960
agctccttgg tggtggtaac atccagaaa gcacacaggt tggttttctt ggctgccacg   4020
agcttgagca ctcggcggc aaaggcggac ttgtggacgt tagctcgcgc ttcgtaggag    4080
ggcattttgg tggtgaagag gagactgaaa taaatttagt ctgcacaact tttttatcgga 4140
accttatctg gggcagtgaa gtatatgtta tggtaatagt tacgagttag ttgaacttat   4200
agatagactg gactatacgg ctatcggtcc aaattagaaa ataacttcgt ataatgtatg   4260
ctatacgaag ttatgtcgac gcggccgcac aagcactaca tggacgaggt caaggctgcc   4320
aacaaccctc gtaacaccca tgctccttac tacgagacaa agctgcgacc cttcctgttc   4380
cgacccgatg aggacgagga gatttgcgac ctggacgagt aggttgttgt aatactatga   4440
tttattgtgt ttatatgtta ttgatactat tgaaagagtt attgtgtaat tttagatgct   4500
gtatgttaac tagaagctca gattctacaa agagatcctc agatctgagg aatgatctac   4560
gttctgcaat agaagggaca actgcagctc tgaatgacca caaaagaat acaccacaag    4620
cagttgtaac tgagctatta gccttgcttt cgcaccattc gcttttctgg atggtagccc   4680
tttactacaa gtagctaata tggaatgtac attaccgtct cattacaata tgtatatgca   4740
agttcatggc acttcatgca caccagcccc ttcgttaagt accttccaaa aagtgatcaa   4800
tgataagtga tatatctaat ttagagatct ggacacacga acaagtcggg aacacaaatc   4860
ccgagatgat tgcctgctca gaggagtcca attagtcttt acaccattcg tgctaatgaa   4920
gggcacagaa tattccactt tgaaagttta agattaagct cggctcgcaa ttatgcatga   4980
aaaatatgta gggagagaac gatcccacga gttctgtttg gttgcgagag tgttcgggtt   5040
ttctcctaaa aagaataggg gagggaaaaa ttatcgccta agtcaccatt aattaa       5096
```

<210> SEQ ID NO 168
<211> LENGTH: 5096
<212> TYPE: DNA
<213> ORGANISM: Artificial Sequence
<220> FEATURE:
<223> OTHER INFORMATION: pLD102

<400> SEQUENCE: 168

```
aggctaggtg gaggctcagt gatgataagt ctgcgatggt ggatgcatgt gtcatggtca    60
tagctgtttc ctgtgtgaaa ttgttatccg ctcagagggc acaatcctat tccgcgctat   120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgttttttcca taggctccgc cccccctgacg agcatcacaa aaatcgacgc tcaagtcaga 300
ggtggcgaaa cccgacagga ctataaagat accaggcgtt tcccccctgga agctccctcg  360
tgcgctctcc tgttccgacc ctgccgctta ccggatacct gtccgccttt ctcccttcgg   420
```

```
gaagcgtggc gctttctcat agctcacgct gtaggtatct cagttcggtg taggtcgttc    480
gctccaagct gggctgtgtg cacgaacccc ccgttcagcc cgaccgctgc gccttatccg    540
gtaactatcg tcttgagtcc aacccggtaa gacacgactt atcgccactg gcagcagcca    600
ctggtaacag gattagcaga gcgaggtatg taggcggtgc tacagagttc ttgaagtggt    660
ggcctaacta cggctacact agaagaacag tatttggtat ctgcgctctg ctgaagccag    720
ttaccttcgg aaaaagagtt ggtagctctt gatccggcaa acaaaccacc gctggtagcg    780
gtggtttttt tgtttgcaag cagcagatta cgcgcagaaa aaaggatctc aagaagatc     840
ctttgatctt ttctacgggg tctgacgctc tattcaacaa agccgccgtc cgtcaagtc     900
agcgtaaatg ggtaggggc ttcaaatcgt cctcgtgata ccaattcgga gcctgctttt     960
ttgtacaaac ttgttgataa tggcaattca aggatcttca cctagatcct tttaaattaa   1020
aaatgaagtt ttaaatcaat ctaaagtata tatgagtaaa cttggtctga cagttaccaa   1080
tgcttaatca gtgaggcacc tatctcagcg atctgtctat ttcgttcatc catagttgcc   1140
tgactccccg tcgtgtagat aactacgata cgggagggct taccatctgg ccccagtgct   1200
gcaatgatac cgcgagagcc acgctcaccg gctccagatt tatcagcaat aaaccagcca   1260
gccggaaggg ccgagcgcag aagtggtcct gcaactttat ccgcctccat ccagtctatt   1320
aattgttgcc gggaagctag agtaagtagt tcgccagtta atagtttgcg caacgttgtt   1380
gccattgcta caggcatcgt ggtgtcacgc tcgtcgtttg gtatggcttc attcagctcc   1440
ggttcccaac gatcaaggcg agttacatga tcccccatgt tgtgcaaaaa agcggttagc   1500
tccttcggtc ctccgatcgt tgtcagaagt aagttggccg cagtgttatc actcatggtt   1560
atggcagcac tgcataattc tcttactgtc atgccatccg taagatgctt ttctgtgact   1620
ggtgagtact caaccaagtc attctgagaa tagtgtatgc ggcgaccgag ttgctcttgc   1680
ccggcgtcaa tacgggataa taccgcgcca catagcagaa ctttaaaagt gctcatcatt   1740
ggaaaacgtt cttcggggcg aaaactctca aggatcttac cgctgttgag atccagttcg   1800
atgtaaccca ctcgtgcacc caactgatct tcagcatctt ttactttcac cagcgtttct   1860
gggtgagcaa aaacaggaag gcaaaatgcc gcaaaaaagg aataagggc gacacggaaa    1920
tgttgaatac tcatactctt cctttttcaa tattattgaa gcatttatca gggttattgt   1980
ctcatgagcg gatacatatt tgaatgtatt tagaaaaata acaaataggg gttccgcgc    2040
acatttcccc gaaaagtgcc agatacctga aacaaaaccc atcgtacggc caaggaagtc   2100
tccataact gtgatccacc acaagcgcca gggttttccc agtcacgacg ttgtaaaacg   2160
acggccagtc atgcataatc cgcacgcatc tggaataagg aagtgccatt ccgcctgacc   2220
tttaattaat tggcaaattt tactgtggcc ttcagaacgg taaaaataga ccaatcagaa   2280
ttctgaaaag cacatcttga tctcctcatt gcggggagtc caacggtggt cttattcccc   2340
cgaatttccc gctcaatctc gttccagacc gacccggaca cagtgcttaa cgccgttccg   2400
aaactctacc gcagatatgc tccaacggac tgggctgcat agatgtgatc ctcggcttgg   2460
agaaatggat aaaagccggc caaaaaaaaa gcggaaaaaa gcggaaaaaa agagaaaaaa   2520
aatcgcaaaa tttgaaaaat aggggggaaa gacgcaaaaa cgcaaggagg gggagtata   2580
tgacactgat aagcaagctc acaacggttc ctcttatttt tttcctcatc ttctgcctag   2640
gttcccaaaa tccagatgc ttctctccag tgccaaaagt aagtacccca caggttttcg   2700
gccgaaaatt ccacgtgcag caacgtcgtg tggggtgtta aatgtgggg gcggggaacc   2760
```

| | |
|---|---|
| aggacaagag gctcttgtgg gagccgaatg agagcacaaa gcgggcgggt gtgataaggg | 2820 |
| catttttgcc catttccct tctcctgtct ctccgacggt gatggcgttg tgcgtcctct | 2880 |
| atctatttct ttttatttct ttttgtttta tttctctgac taccgatttg gcttgatttc | 2940 |
| ctcaacccca cacaaataag ctcgggccga ggaatatata tatacacgga cacagtcgcc | 3000 |
| ctgtggacaa cacgtcacta cctctacgac gcttgagacc atccggtctc tgatcatcct | 3060 |
| cgagataact tcgtataatg tatgctatac gaagttatca ggttgtgcag tatcatacat | 3120 |
| actcgatcag acaggtcgtc tgaccatcat acaagctgaa caagcgctcc atacttgcac | 3180 |
| gctctctata tacacagtta aatgacatat ccatagtcta acctctaaca gttaatcttc | 3240 |
| tggtaagcct cccagccagc cttctggtat cgcttggcct cctcaatagg atctcggttc | 3300 |
| tggccgtaca gacctcggcc gacaattatg atatccgttc cggtagacat gacatcctca | 3360 |
| acagttcggt actgctgtcc gagagcatct cccttgtcgt caagacccac cccggggtc | 3420 |
| agaataagcc agtcctcaga gtcgccctta ggtcggttct gggcaatgaa gccaaccaca | 3480 |
| aactcggggt cggatcgggc aagctcaatg gtctgcttgg agtactcgcc agtggccaga | 3540 |
| gagcccttgc aagacagctc ggccagcatg agcagacctc tggccagctt ctcgttggga | 3600 |
| gaggggacca ggaactcctt gtactgggag ttctcgtagt cagagacatc ctccttcttc | 3660 |
| tgttcagaga cagtttcctc ggcaccagct cgcaggccag caatgattcc ggttccgggt | 3720 |
| acaccgtggg cgttggtgat atcggaccac tcggcgattc ggtagacacc gttcttgtac | 3780 |
| tggtgcttga cagtgttgcc aatatctgcg aactttctgt cctcgaacag gaagaaaccg | 3840 |
| tgcttaagag caagttcctt gaggggagc acagttccgg cgtaggtgaa gtcgtcaatg | 3900 |
| atgtcgatat gggtcttgat catgcacaca taaggtccga ccttatcggc aagctcaatg | 3960 |
| agctccttgg tggtggtaac atccagagaa gcacacaggt tggttttctt ggctgccacg | 4020 |
| agcttgagca ctcgggcggc aaaggcggac ttgtggacgt tagctcgcgc ttcgtaggag | 4080 |
| ggcatttttgg tggtgaagag gagactgaaa taaatttagt ctgcacaact ttttatcgga | 4140 |
| accttatctg gggcagtgaa gtatatgtta tggtaatagt tacgagttag ttgaacttat | 4200 |
| agatagactg gactatacgg ctatcggtcc aaattagaaa ataacttcgt ataatgtatg | 4260 |
| ctatacgaag ttatgtcgac gcggccgcat ggagcgtgtg ttctgagtcg atgttttcta | 4320 |
| tggagttgtg agtgttagta gacatgatgg gtttatatat gatgaatgaa tagatgtgat | 4380 |
| tttgatttgc acgatggaat tgagaacttt gtaaacgtac atgggaatgt atgaatgtgg | 4440 |
| gggttttgtg actggataac tgacggtcag tggacgccgt tgttcaaata tccaagagat | 4500 |
| gcgagaaact ttgggtcaag tgaacatgtc ctctctgttc aagtaaacca tcaactatgg | 4560 |
| gtagtatatt tagtaaggac aagagttgag attccttgga gtcctagaaa cgtattttcg | 4620 |
| cgttccaaga tcaaattagt agagtaatac gggcacggga atccattcat agtctcaatt | 4680 |
| ttcccatagg tgtgctacaa ggtgttgaga tgtggtacag taccaccatg attcgaggta | 4740 |
| aagagcccag aagtcattga tgaggtcaag aaatacacag atctacagct caatacaatg | 4800 |
| aatatcttct ttcatattct tcaggtgaca ccaagggtgt ctattttccc cagaaatgcg | 4860 |
| tgaaaaggcg cgtgtgtagc gtggagtatg ggttcggttg gcgtatcctt catatatcga | 4920 |
| cgaaatagta gggcaagaga tgacaaaaag tatctatatg tagacagcgt agaatatgga | 4980 |
| tttgattggt ataaattcat ttattgcgtg tctcacaaat actctcgata agttggggtt | 5040 |
| aaactggaga tggaacaatg tcgatatctc gacatatttt gatatttgtt aattaa | 5096 |

<210> SEQ ID NO 169
<211> LENGTH: 6044
<212> TYPE: DNA
<213> ORGANISM: Artificial Sequence
<220> FEATURE:
<223> OTHER INFORMATION: pLD111

<400> SEQUENCE: 169

| | | | | | |
|---|---|---|---|---|---|
| ttaattaatt | ccgcttaatg | gagtccaaaa | agaccaacct | ctgcgcctcg | atcgacgtga | 60 |
| ccacaaccgc | cgagttcctt | tcgctcatcg | acaagctcgg | tccccacatc | tgtctcgtga | 120 |
| agacgcacat | cgatatcatc | tcagacttca | gctacgaggg | cacgattgag | ccgttgcttg | 180 |
| tgcttgcaga | gcgccacggg | ttcttgatat | tcgaggacga | gaagtttgct | gatatcggaa | 240 |
| acaccgtgat | gttgcagtac | acctcggggg | tataccggat | cgcggcgtgg | agtgacatca | 300 |
| cgaacgcgca | cggagtgact | gggaagggcg | tcgttgaagg | gttgaaacgc | ggtgcggagg | 360 |
| gggtagaaaa | ggaaaggggc | gtgttgatgt | tggcggagtt | gtcgagtaaa | ggctcgttgg | 420 |
| cgcatggtga | atatacccgt | gagacgatcg | agattgcgaa | gagtgatcgg | gagttcgtga | 480 |
| ttgggttcat | cgcgcagcgg | gacatggggg | gtagagaaga | agggtttgat | tggatcatca | 540 |
| tgacgcctgg | tgtggggttg | gatgataaag | gcgatgcgtt | gggccagcag | tataggactg | 600 |
| ttgatgaggt | ggttctgact | ggtaccgatg | tgattattgt | cgggagaggg | ttgtttggaa | 660 |
| aaggaagaga | ccctgaggtg | gagggaaaga | gatacaggga | tgctggatgg | aaggcatact | 720 |
| tgaagagaac | tggtcagtta | gaataaatat | tgtaataaat | aggtctatat | acatacacta | 780 |
| agcttctagg | acgtcattgt | agtcttcgaa | gtttgtctgct | agtttagttc | tcatgatttc | 840 |
| gaaaaccaat | aacgcaatgg | atgtagcagg | gatggtggtt | agtgcgttcc | tgacaaaccc | 900 |
| agagtacgcc | gcctcaaacc | acgtcacatt | cgccctttgc | ttcatccgca | tcacttgctt | 960 |
| gaaggtatcc | acgtacgagt | tgtaatacac | cttgaagaac | ggcttcgtct | agttcggcat | 1020 |
| ggcagatcat | catgcctgca | ggagctccaa | ttgtaatatt | tcgggagaaa | tatcgttggg | 1080 |
| gtaaaacaac | agagagagag | agggagagat | ggttctggta | gaattataat | ctggttgttg | 1140 |
| caaatgctac | tgatcgactc | tggcaatgtc | tgtagctcgc | tagttgtatg | caacttaggt | 1200 |
| gttatgcata | cacacggtta | ttcggttgaa | ttgtggagta | aaaattgtct | gagttgtgtc | 1260 |
| ttagctactg | gctggccccc | cgcgaaagat | aatcaaaatt | acacttgtga | attttttgcac | 1320 |
| acacaccgat | taacatttcc | cttttttgtc | caccgataca | cgcttgcctc | ttcttatttt | 1380 |
| ctctgtgctt | cccccctcctg | tgacttttttc | caccattgat | ataaaatcaa | ctccatttcc | 1440 |
| ctaaaatctc | cccagattct | aaaaacaact | tcttctcttc | tgcttttcct | tatttttgtt | 1500 |
| atatttattt | accatcccctt | attttgaata | gttattcccc | actaacattg | ttcaaatctt | 1560 |
| cacgacataa | tgaattgttc | agcatttagt | ttttggtttg | tttgtaagat | tatttcttc | 1620 |
| tttttgtcat | ttaacattca | aatttcaatt | gcaaacccac | aagaaaactt | tttgaagtgt | 1680 |
| ttttcagaat | acattccaaa | caatccagct | aacccaaagt | ttatttacac | acaacatgat | 1740 |
| caattgtaca | tgtcagtttt | gaactcaaca | attcaaaact | tgagatttac | atcagatacc | 1800 |
| acaccaaagc | cattggttat | tgttacacca | tcaaacgttt | cccatattca | agcatcaatc | 1860 |
| ttgtgttcaa | agaaggttgg | attgcaaatt | agaaccagat | caggaggaca | cgatgcagaa | 1920 |
| ggaatgtcat | acatttcaca | agttccattc | gttgttgttg | atttgagaaa | catgcactca | 1980 |
| attaagattg | atgttcattc | acaaacagca | tgggttgaag | caggagcaac | attgggtgaa | 2040 |
| gtttactact | ggattaacga | aaagaacgaa | aacttcagtt | ttccaggagg | ttactgtcca | 2100 |

```
acagttggag ttggaggaca tttttcaggt ggaggatacg gagcattgat gagaaactac    2160
ggattggcag cagataacat tattgatgca cacttggtta acgttgatgg aaaggttttg    2220
gatagaaagt caatgggaga agatttgttt tgggcaatta gaggaggtgg tggagagaac    2280
tttggaatta ttgcagcatg gaagatcaag ttggttgcag ttccatcaaa gtcaacaatc    2340
ttttcagtta agaagaacat ggaaattcat ggtttggtta agttgtttaa caagtggcaa    2400
aacattgcat acaagtacga taaggatttg gttttgatga cacattttat tacaaagaac    2460
attacagata accatggaaa gaacaagaca acagttcacg gatactttc atcaattttt    2520 cacggaggag ttgattcatt ggttgacttg atgaacaagt catttccaga attgggaatc    2580
aagaagacag attgtaagga attttcatgg attgatacaa caattttcta ctcaggagtt    2640
gttaacttta acacagcaaa ctttaagaag gaaattttgt tggacagatc agcaggaaag    2700
aagaccgcat tttccattaa gttggattac gttaagaaac caattccaga aacagcaatg    2760
gttaagattt tggaaaagtt gtacgaagaa gatgttggtg ttggaatgta cgttttgtac    2820
ccatacggag gaattatgga agaaatctca gaatcagcaa ttccatttcc acatagagca    2880
ggtattatgt acgaattgtg gtacacagca tcatgggaaa agcaagaaga taatgaaaag    2940
catattaact gggttagatc agtttacaac tttacaacac catacgtttc acaaaaccca    3000
agattggcat acttgaacta cagagatttg gatttgggaa agacaaaccc agaatcacca    3060
aacaactata cacaagctag aatttgggga gaaaagtact tggtaagaa cttcaacaga    3120 ttggttaaag ttaagacaaa ggcagatcca ataacttct ttagaaacga caatcaatt     3180 ccaccattgc caccacatca tcattaataa gagtgactct tttgataaga gtcgcaaatt    3240
tgatttcata agtatatatt cattatgtaa agtagtaaat ggaaaattca ttaaaaaaaa    3300
agcaaatttc cgttgtatgc atactccgaa cacaaaacta gccccggaaa acccttagt     3360 tgatagttgc gaatttaggt cgaccatatg cgacgggtac aacgagaatt gtattgaatt    3420
gatcaagaac atgatcttgg tgttacagaa catcaagttc ttggaccaga ctgagaatgc    3480
acagatatac aaggcgtcat gtgataaaat ggatgagatt tatccacaat gaagaaaga    3540 gtttatggaa agtggtcaac cagaagctaa acaggaagaa gcaaacgaag aggtgaaaca    3600
agaagaagaa ggtaaataag tattttgtat tatataacaa acaaagtaag gaatacagat    3660
ttatacaata aattgccata ctagtcacgt gagatatctc atccattccc caactcccaa    3720
gaaaataaaa aagtgaaaaa taaaatcaaa cccaaagatc aacctcccca tcatcatcgt    3780
catcaaaccc ccagctcaat tcgcaatggt tagcacaaaa acatacacag aaagggcatc    3840
agcacacccc tccaaggttg cccaacgttt attaattaaa ggctaggtgg aggctcagtg    3900
atgataagtc tgcgatggtg gatgcatgtg tcatggtcat agctgtttcc tgtgtgaaat    3960
tgttatccgc tcagagggca caatcctatt ccgcgctatc cgacaatctc caagacatta    4020
ggtggagttc agttcggcgt atggcatatg tcgctgaaaa gaacatgtga gcaaaaggcc    4080
agcaaaaggc caggaaccgt aaaaaggccg cgttgctggc gttttccat aggctccgcc     4140 cccctgacga gcatcacaaa aatcgacgct caagtcagag gtggcgaaac ccgacaggac    4200
tataaagata ccaggcgttt cccccctggaa gctccctcgt gcgctctcct gttccgaccc    4260
tgccgcttac cggatacctg tccgcctttc tcccttcggg aagcgtggcg ctttctcata    4320
gctcacgctg taggtatctc agttcggtgt aggtcgttcg ctccaagctg ggctgtgtgc    4380 acgaacccc cgttcagccc gaccgctgcg ccttatccgg taactatcgt cttgagtcca    4440
acccggtaag acacgactta tcgccactgg cagcagccac tggtaacagg attagcagag    4500
```

| | | | | |
|---|---|---|---|---|
| cgaggtatgt | aggcggtgct | acagagttct | tgaagtggtg | gcctaactac | ggctacacta | 4560 |
| gaagaacagt | atttggtatc | tgcgctctgc | tgaagccagt | taccttcgga | aaaagagttg | 4620 |
| gtagctcttg | atccggcaaa | caaaccaccg | ctggtagcgg | tggttttttt | gtttgcaagc | 4680 |
| agcagattac | gcgcagaaaa | aaaggatctc | aagaagatcc | tttgatcttt | tctacggggt | 4740 |
| ctgacgctct | attcaacaaa | gccgccgtcc | cgtcaagtca | gcgtaaatgg | gtaggggct | 4800 |
| tcaaatcgtc | cgctctgcca | gtgttacaac | caattaacaa | attctgatta | gaaaaactca | 4860 |
| tcgagcatca | aatgaaactg | caatttattc | atatcaggat | tatcaatacc | atattttga | 4920 |
| aaaagccgtt | tctgtaatga | aggagaaaac | tcaccgaggc | agttccatag | gatggcaaga | 4980 |
| tcctggtatc | ggtctgcgat | tccgactcgt | ccaacatcaa | tacaacctat | taatttcccc | 5040 |
| tcgtcaaaaa | taaggttatc | aagtgagaaa | tcaccatgag | tgacgactga | atccggtgag | 5100 |
| aatggcaaaa | gcttatgcat | ttctttccag | acttgttcaa | caggccagcc | attacgctcg | 5160 |
| tcatcaaaat | cactcgcatc | aaccaaaccg | ttattcattc | gtgattgcgc | ctgagcgaga | 5220 |
| cgaaatacgc | gatcgctgtt | aaaaggacaa | ttacaaacag | gaatcgaatg | caaccggcgc | 5280 |
| aggaacactg | ccagcgcatc | aacaatattt | tcacctgaat | caggatattc | ttctaatacc | 5340 |
| tggaatgctg | ttttcccggg | gatcgcagtg | gtgagtaacc | atgcatcatc | aggagtacgg | 5400 |
| ataaaatgct | tgatggtcgg | aagaggcata | aattccgtca | gccagtttag | tctgaccatc | 5460 |
| tcatctgtaa | catcattggc | aacgctacct | ttgccatgtt | tcagaaacaa | ctctggcgca | 5520 |
| tcgggcttcc | catacaatcg | atagattgtc | gcacctgatt | gcccgacatt | atcgcgagcc | 5580 |
| catttatacc | catataaatc | agcatccatg | ttggaattta | atcgcggcct | cgagcaagac | 5640 |
| gtttcccgtt | gaatatggct | cataacaccc | cttgtattac | tgtttatgta | agcagacagt | 5700 |
| tttattgttc | atgatgatat | atttttatct | tgtgcaatgt | aacatcagag | attttgagac | 5760 |
| acaacgtggc | tttcccccgc | cgctctagaa | ctagtggatc | caaataaaac | gaaaggctca | 5820 |
| gtcgaaagac | tgggcctttc | gttttatctg | ttgtttgtcg | cattatacga | gacgtccagg | 5880 |
| ttgggatacc | tgaaacaaaa | cccatcgtac | ggccaaggaa | gtctccaata | actgtgatcc | 5940 |
| accacaagcg | ccagggtttt | cccagtcacg | acgttgtaaa | acgacggcca | gtcatgcata | 6000 |
| atccgcacgc | atctggaata | aggaagtgcc | attccgcctg | acct | | 6044 |

<210> SEQ ID NO 170
<211> LENGTH: 6044
<212> TYPE: DNA
<213> ORGANISM: Artificial Sequence
<220> FEATURE:
<223> OTHER INFORMATION: pLD112

<400> SEQUENCE: 170

| | | | | |
|---|---|---|---|---|
| ttaattaatt | ccgcttaatg | gagtccaaaa | agaccaacct | ctgcgcctcg | atcgacgtga | 60 |
| ccacaaccgc | cgagttcctt | tcgctcatcg | acaagctcgg | tccccacatc | tgtctcgtga | 120 |
| agacgcacat | cgatatcatc | tcagacttca | gctacgaggg | cacgattgag | ccgttgcttg | 180 |
| tgcttgcaga | gcgccacggg | ttcttgatat | tcgaggacag | gaagtttgct | gatatcggaa | 240 |
| acaccgtgat | gttgcagtac | acctcggggg | tataccggat | cgcggcgtgg | agtgacatca | 300 |
| cgaacgcgca | cggagtgact | gggaagggcg | tcgttgaagg | gttgaaacgc | ggtgcggagg | 360 |
| gggtagaaaa | ggaagggggc | gtgttgatgt | tggcggagtt | gtcgagtaaa | ggctcgttgg | 420 |
| cgcatggtga | atatacccgt | gagacgatcg | agattgcgaa | gagtgatcgg | gagttcgtga | 480 |

```
ttgggttcat cgcgcagcgg gacatggggg gtagagaaga agggtttgat tggatcatca    540
tgacgcctgg tgtggggttg gatgataaag gcgatgcgtt gggccagcag tataggactg    600
ttgatgaggt ggttctgact ggtaccgatg tgattattgt cgggagaggg ttgtttggaa    660
aaggaagaga ccctgaggtg gagggaaaga gatacaggga tgctggatgg aaggcatact    720
tgaagagaac tggtcagtta gaataaatat tgtaataaat aggtctatat acatacacta    780
agcttctagg acgtcattgt agtcttcgaa gttgtctgct agtttagttc tcatgatttc    840
gaaaaccaat aacgcaatgg atgtagcagg gatggtggtt agtgcgttcc tgacaaaccc    900
agagtacgcc gcctcaaacc acgtcacatt cgccctttgc ttcatccgca tcacttgctt    960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcggttgaa ttgtggagta aaaattgtct gagttgtgtc   1260
ttagctactg gctggccccc cgcgaaagat aatcaaaatt acacttgtga attttttgcac  1320
acacaccgat taacatttcc cttttttgtc caccgataca cgcttgcctc ttcttatttt   1380
ctctgtgctt cccctcctg tgacttttc caccattgat ataaaatcaa ctccatttcc    1440
ctaaaatctc cccagattct aaaaacaact tcttctcttc tgcttttcct tattttttgtt  1500
atatttattt accatccctt attttgaata gttattcccc actaacattg ttcaaatctt   1560
cacgacataa tgaattgtag cactttctca ttctggtttg tttgtaagat tattttcttt   1620
ttcttgtcat ttaacattca aatttcaatt gcaaacccac aagagaactt tttgaagtgt   1680
ttctcagaat acattccaaa caacccagct aacccaaagt ttatttacac ccaacacgat   1740
caattgtaca tgtcagtttt gaactcaaca attcaaaact tgagatttac atcagataca   1800
acaccaaagc cattggttat tgttacacca tcaaacgtta gtcatattca agcatcaatc   1860
ttgtgttcaa agaaggttgg attgcaaatt agaactagat caggaggaca tgatgcagaa   1920
ggattgtcat acatttcaca agttccattt gcaattgttg atttgagaaa catgcacaca   1980
gttaaggttg atattcattc acaaacagca tgggttgaag caggagcaac attgggtgaa   2040
gtttactact ggattaacga aatgaacgaa aacttctcat ttccaggagg atactgtcca   2100
acagttggtg ttggaggaca cttttcaggt ggtggatacg gagcattgat gagaaactac   2160
ggattggcag cagataacat tattgatgca catttggtta acgttgatgg aaaggttttg   2220
gatagaaagt caatgggaga agatttgttt tgggcaatta gaggaggtgg aggagaaaac   2280
tttggaatca ttgcagcatg taagatcaag ttggttgttg ttccatcaaa ggcaacaatc   2340
ttttcagtta agaagaacat ggaaatccat ggattggtta agttgtttaa caagtggcaa   2400
aacattgcat acaagtacga taaggatttg atgttgacaa cacattttag aacaagaaac   2460
attacagata accacggaaa gaataagaca acagttcatg gatactttc atcaattttc    2520
ttgggaggag ttgattcatt ggttgacttg atgaacaaga gttttccaga attgggaatc   2580
aagaagacag attgtaagga attgtcatgg atcgatacaa ccatttttcta ctcaggagtt   2640
gttaactaca acacagctaa cttaagaag gaaatttttgt tggacagatc agcaggtaaa    2700
aagacagcat tttcaattaa gttggattac gttaagaaat tgattccaga acagcaatg    2760
gttaagattt tggaaaagtt gtacgaagaa gaagttggag ttggaatgta cgttttgtac   2820
ccatacggag gaattatgga tgaaatttca gaatcagcaa ttccatttcc acatagagca   2880
```

-continued

| | |
|---|---|
| ggtattatgt acgaattgtg gtacacagca acatgggaaa agcaagaaga taacgaaaag | 2940 |
| catattaact gggttagatc agtttacaac tttacaaccc catacgtttc acaaaaccca | 3000 |
| agattggcat acttgaacta cagagatttg gatttgggaa agacaaaccc agaatcacca | 3060 |
| aataactaca cacaagctag aatttgggga gaaaagtact tggtaagaa ctttaacaga | 3120 |
| ttggtgaagg ttaagacaaa ggcagaccca aacaatttct ttagaaacga acaatcaatt | 3180 |
| ccaccattgc caccaagaca tcattaataa gagtgactct tttgataaga gtcgcaaatt | 3240 |
| tgatttcata agtatatatt cattatgtaa agtagtaaat ggaaaattca ttaaaaaaaa | 3300 |
| agcaaatttc cgttgtatgc atactccgaa cacaaaacta gccccggaaa aacccttagt | 3360 |
| tgatagttgc gaatttaggt cgaccatatg cgacgggtac aacgagaatt gtattgaatt | 3420 |
| gatcaagaac atgatcttgg tgttacagaa catcaagttc ttggaccaga ctgagaatgc | 3480 |
| acagatatac aaggcgtcat gtgataaaat ggatgagatt tatccacaat gaagaaaga | 3540 |
| gtttatggaa agtggtcaac cagaagctaa acaggaagaa gcaaacgaag aggtgaaaca | 3600 |
| agaagaagaa ggtaaataag tattttgtat tatataacaa acaaagtaag gaatacagat | 3660 |
| ttatacaata aattgccata ctagtcacgt gagatatctc atccattccc caactcccaa | 3720 |
| gaaaataaaa aagtgaaaaa taaaatcaaa cccaaagatc aacctcccca tcatcatcgt | 3780 |
| catcaaaccc ccagctcaat tcgcaatggt tagcacaaaa acatacacag aaagggcatc | 3840 |
| agcacacccc tccaaggttg cccaacgttt attaattaaa ggctaggtgg aggctcagtg | 3900 |
| atgataagtc tgccgatggtg gatgcatgtg tcatggtcat agctgtttcc tgtgtgaaat | 3960 |
| tgttatccgc tcagagggca caatcctatt ccgcgctatc cgacaatctc caagacatta | 4020 |
| ggtggagttc agttcggcgt atggcatatg tcgctggaaa gaacatgtga gcaaaaggcc | 4080 |
| agcaaaaggc caggaaccgt aaaaaggccg cgttgctggc gttttttccat aggctccgcc | 4140 |
| cccctgacga gcatcacaaa aatcgacgct caagtcagag gtggcgaaac ccgacaggac | 4200 |
| tataaagata ccaggcgttt ccccctggaa gctccctcgt gcgctctcct gttccgaccc | 4260 |
| tgccgcttac cggatacctg tccgcctttc tcccttcggg aagcgtggcg ctttctcata | 4320 |
| gctcacgctg taggtatctc agttcggtgt aggtcgttcg ctccaagctg ggctgtgtgc | 4380 |
| acgaaccccc cgttcagccc gaccgctgcg ccttatccgg taactatcgt cttgagtcca | 4440 |
| acccggtaag acacgactta tcgccactgg cagcagccac tggtaacagg attagcagag | 4500 |
| cgaggtatgt aggcggtgct acagagttct tgaagtggtg gcctaactac ggctacacta | 4560 |
| gaagaacagt atttggtatc tgcgctctgc tgaagccagt taccttcgga aaaagagttg | 4620 |
| gtagctcttg atccggcaaa caaaccaccg ctggtagcgg tggttttttt gtttgcaagc | 4680 |
| agcagattac gcgcagaaaa aaaggatctc aagaagatcc tttgatcttt tctacggggt | 4740 |
| ctgacgctct attcaacaaa gccgccgtcc cgtcaagtca gcgtaaatgg tagggggct | 4800 |
| tcaaatcgtc cgctctgcca gtgttacaac caattaacaa attctgatta gaaaaactca | 4860 |
| tcgagcatca aatgaaactg caatttattc atatcaggat tatcaatacc atattttga | 4920 |
| aaaagccgtt tctgtaatga aggagaaaac tcaccgaggc agttccatag gatggcaaga | 4980 |
| tcctggtatc ggtctgcgat tccgactcgt ccaacatcaa tacaacctat taatttcccc | 5040 |
| tcgtcaaaaa taaggttatc aagtgagaaa tcaccatgag tgacgactga atccggtgag | 5100 |
| aatggcaaaa gcttatgcat ttcttccag acttgttcaa caggccagcc attacgctcg | 5160 |
| tcatcaaaat cactcgcatc aaccaaaccg ttattcattc gtgattgcgc ctgagcgaga | 5220 |

| | |
|---|---:|
| cgaaatacgc gatcgctgtt aaaaggacaa ttacaaacag gaatcgaatg caaccggcgc | 5280 |
| aggaacactg ccagcgcatc aacaatattt tcacctgaat caggatattc ttctaatacc | 5340 |
| tggaatgctg ttttcccggg gatcgcagtg gtgagtaacc atgcatcatc aggagtacgg | 5400 |
| ataaaatgct tgatggtcgg aagaggcata aattccgtca gccagtttag tctgaccatc | 5460 |
| tcatctgtaa catcattggc aacgctacct tgccatgtt tcagaaacaa ctctggcgca | 5520 |
| tcgggcttcc catacaatcg atagattgtc gcacctgatt gcccgacatt atcgcgagcc | 5580 |
| catttatacc catataaatc agcatccatg ttggaattta atcgcggcct cgagcaagac | 5640 |
| gtttcccgtt gaatatggct cataacaccc cttgtattac tgtttatgta agcagacagt | 5700 |
| tttattgttc atgatgatat attttatct tgtgcaatgt aacatcagag attttgagac | 5760 |
| acaacgtggc tttccccgc cgctctagaa ctagtggatc caaataaaac gaaaggctca | 5820 |
| gtcgaaagac tgggcctttc gttttatctg ttgtttgtcg cattatacga gacgtccagg | 5880 |
| ttgggatacc tgaaacaaaa cccatcgtac ggccaaggaa gtctccaata actgtgatcc | 5940 |
| accacaagcg ccagggtttt cccagtcacg acgttgtaaa acgacggcca gtcatgcata | 6000 |
| atccgcacgc atctggaata aggaagtgcc attccgcctg acct | 6044 |

<210> SEQ ID NO 171
<211> LENGTH: 7167
<212> TYPE: DNA
<213> ORGANISM: Artificial Sequence
<220> FEATURE:
<223> OTHER INFORMATION: pLD113

<400> SEQUENCE: 171

| | |
|---|---:|
| aggctaggtg gaggctcagt gatgataagt ctgcgatggt ggatgcatgt gtcatggtca | 60 |
| tagctgtttc ctgtgtgaaa ttgttatccg ctcagagggc acaatcctat tccgcgctat | 120 |
| ccgacaatct ccaagacatt aggtggagtt cagttcggcg tatggcatat gtcgctggaa | 180 |
| agaacatgtg agcaaaaggc cagcaaaagg ccaggaaccg taaaaaggcc gcgttgctgg | 240 |
| cgtttttcca taggctccgc ccccctgacg agcatcacaa aaatcgacgc tcaagtcaga | 300 |
| ggtggcgaaa cccgacagga ctataaagat accaggcgtt tccccctgga agctccctcg | 360 |
| tgcgctctcc tgttccgacc ctgccgctta ccggatacct gtccgccttt ctcccttcgg | 420 |
| gaagcgtggc gctttctcat agctcacgct gtaggtatct cagttcggtg taggtcgttc | 480 |
| gctccaagct gggctgtgtg cacgaacccc ccgttcagcc cgaccgctgc gccttatccg | 540 |
| gtaactatcg tcttgagtcc aacccggtaa gacacgactt atcgccactg gcagcagcca | 600 |
| ctggtaacag gattagcaga gcgaggtatg taggcggtgc tacagagttc ttgaagtggt | 660 |
| ggcctaacta cggctacact agaagaacag tatttggtat ctgcgctctg ctgaagccag | 720 |
| ttaccttcgg aaaaagagtt ggtagctctt gatccggcaa acaaaccacc gctggtagcg | 780 |
| gtggtttttt tgtttgcaag cagcagatta cgcgcagaaa aaaaggatct caagaagatc | 840 |
| ctttgatctt ttctacgggg tctgacgctc tattcaacaa agccgccgtc ccgtcaagtc | 900 |
| agcgtaaatg ggtaggggc ttcaaatcgt ccgctctgcc agtgttacaa ccaattaaca | 960 |
| aattctgatt agaaaaactc atcgagcatc aaatgaaact gcaatttatt catatcagga | 1020 |
| ttatcaatac catattttg aaaaagccgt ttctgtaatg aaggagaaaa ctcaccgagg | 1080 |
| cagttccata ggatggcaag atcctggtat cggtctgcga ttccgactcg tccaacatca | 1140 |
| atacaaccta ttaatttccc ctcgtcaaaa ataaggttat caagtgagaa atcaccatga | 1200 |
| gtgacgactg aatccggtga gaatggcaaa agcttatgca tttctttcca gacttgttca | 1260 |

-continued

```
acaggccagc cattacgctc gtcatcaaaa tcactcgcat caaccaaacc gttattcatt    1320
cgtgattgcg cctgagcgag acgaaatacg cgatcgctgt taaaaggaca attacaaaca    1380
ggaatcgaat gcaaccggcg caggaacact gccagcgcat caacaatatt ttcacctgaa    1440
tcaggatatt cttctaatac ctggaatgct gttttcccgg ggatcgcagt ggtgagtaac    1500
catgcatcat caggagtacg gataaaatgc ttgatggtcg gaagaggcat aaattccgtc    1560
agccagttta gtctgaccat ctcatctgta acatcattgg caacgctacc tttgccatgt    1620
ttcagaaaca actctggcgc atcgggcttc ccatacaatc gatagattgt cgcacctgat    1680
tgcccgacat tatcgcgagc ccatttatac ccatataaat cagcatccat gttggaattt    1740
aatcgcggcc tcgagcaaga cgtttcccgt tgaatatggc tcataacacc ccttgtatta    1800
ctgtttatgt aagcagacag ttttattgtt catgatgata tatttttatc ttgtgcaatg    1860
taacatcaga gattttgaga cacaacgtgg cttccccccg ccgctctaga actagtggat    1920
ccaaataaaa cgaaaggctc agtcgaaaga ctgggccttt cgttttatct gttgtttgtc    1980
gcattatacg agacgtccag gttgggatac ctgaaacaaa acccatcgta cggccaagga    2040
agtctccaat aactgtgatc caccacaagc gccagggttt tcccagtcac gacgttgtaa    2100
aacgacggcc agtcatgcat aatccgcacg catctggaat aaggaagtgc cattccgcct    2160
gacctgatcc caatattaca cccaagtagc atgcataagc taaaagtaac tcgcagcgca    2220
caccgtgcag attcataagt ctatgattaa ttgaacgcca ataacccggc ttactacaag    2280
tacaagtagg tatacatagc ggtaatgaat cattagaaaa ataaaaaaca aaaaaaaaca    2340
aaacaaactg ttgtggatgc atcaacagta gtacatagtt gtacgatgta cttgtacttg    2400
taaaagcaaa aatgtacaat atctcaggga gcgcaacttt tacgttcgaa gaacaatgta    2460
ccgcataccg cattctagat tctgcggaac gtctaacctg gaaatacgat ttttatttc    2520 tttcattttt tttgcttctt caaaagtatg gtaatttcct accattacag ttgacactga    2580 acgaggggg attgaattta agcaaaaaat taaatcaaaa tacctttatg tatccagccc    2640
atgtaataaa caaaaggatt atataacaag aaataaatat ataccttta tggatcatta    2700 gaataaaaat aaatacgaga agcacaccag agaagctttt tgattgccac tataccgcta    2760
ctttggtata tcttattata attgttgaat ttgcaagata gaatgtcatt cattggagag    2820
aaatccaagg aatatgtggg atgaaatgac tagaagtatg aacaatgaga atagtacata    2880
cttgtacctg tatttctaga agagagaaag acagttgagt gtgtgattct cgtccaataa    2940
taatctcaat agtaacgtgt gaatagctgt tctttgatag ttgatatttc tcgatgacta    3000
tttatgttgt acaagggatt ttttcgttg ctgttgattt cgaattaggc aatgcagata    3060
tcatttatgc tatccatatt taagatttcc catacgcatt tataacattt attctacata    3120
aattgttaaa tgaacgaact gccattataa attgtttcct aaataggaag tgttttcat    3180 aaagcaagta agttgtctaa taatactaag taataaaaat aagttcatac aatatatttt    3240
gagaacatca tttggaggcg gtagatggag tctgtttatt attaaacaat gcgagatgac    3300
cccttaaata ttgagaacat cagttggagg cggcagatgg agtctgtcta tttagcaatg    3360
ggacatgact gtcagtatca tcatatgtat atatataata catataatat tatataacac    3420 gatttttta aattattggc ccgaaaatta atcagtgtag actggatcct cgagaaccat    3480
ttaattaaca agtcgagaac gtaccactgt cctccactac aaacacaccc aatctgcttc    3540
ttctagtcaa ggttgctaca ccggtaaatt ataaatcatc atttcattag cagggctggg    3600
```

```
cccttttttat agagtcttat acactagcgg accctgccgg tagaccaacc cgcaggcgcg    3660
tcagtttgct ccttccatca atgcgtcgta gaaacgactt actccttctt gagcagctcc    3720
ttgaccttgt tggcaacaaa gtctccgacc tcggaggtgg aggaggagcc tccgatatcg    3780
gcggtagtga taccagcctc gacggactcc ttgacggcag cctcaacagc gtcaccggcg    3840
ggcttcatgt taagagagaa cttgagcatc atggcggcag acagaatggt ggcaatgggg    3900
ttgaccttct gcttgccgag atcgggggca gatccgtgac agggctcgta cagaccgaac    3960
gcctcgttgg tgtcgggcag agaagccaga gaggcggagg gcagcagacc cagagaaccg    4020
gggatgacgg aggcctcgtc ggagatgata tcgccaaaca tgttggtggt gatgatgata    4080
ccattcatct tggagggctg cttgatgagg atcatggcgg ccgagtcgat cagctggtgg    4140
ttgagctcca gctgggggaa ttcgtccttg aggactcggg tgacggtctt tcgccaaagt    4200
cgagaggagg ccagcacgtt ggccttgtca agggaccaca cggaagagg ggggttgtgc    4260
tgaagggcca ggaaggcggc cattcgggca attcgctcaa cctcaggaac ggagtaagtc    4320
tcagtgtcgg aagcgacgcc agatccgtca tcctcctttc gctctccaaa gtagatacct    4380
ccgacgagct ctcggacaat gatgaagtcg gtgccctcaa cgtttcggat gggggagaga    4440
tcggcgagct tgggcgacag cagctggcag ggtcgcaggt tggcgtacag gttcaggtcc    4500
tttcgcagct tgagaagacc ctgctcgggt cgcacgtcgg ttcgtccgtc gggagtggtc    4560
catacggtgt tggcagcgcc tccgacagca ccgagcataa tagagtcagc cttttcggcag    4620
atgtcgagag tagcgtcggt gatgggctcg ccctccttct caatggcagc tcctccaatg    4680
agtcggtcct caaacacaaa ctcggtgccg gaggcctcag caacagactt gagcaccttg    4740
acggcctcgg caatcacctc ggggccacag aagtcgccgc cgagaagaac aatcttcttg    4800
gagtcagtct tggtcttctt agtttcgggt tccattgtgg atgtgtgtgg ttgtatgtgt    4860
gatgtggtgt gtggagtgaa aatctgtggc tggcaaacgc tcttgtatat atacgcactt    4920
ttgcccgtgc tatgtggaag actaaacctc gaagattgt gactcaggta gtgcggtatc    4980
ggctagggac ccaaaccttg tcgatgccga tagcgctatc gaacgtaccc cagccggccg    5040
ggagtatgtc ggaggggaca tacgagatcg tcaagggttt gtggccaact ggtaaataaa    5100
tgatgactca ggcgacgacg gaattcgaca gcaactactc ctttcaccaa ccatgtgcat    5160
tttagctcga ataacattca caggcttggt gatctacatc catggtgtct ggccgattac    5220
cgtggtgttt tggcagtaac gagaatattg agtgaactct tcccatcacc aataaagact    5280
catactacaa tcacgagcgc ttcagctgcc actatagtgt tggtgacaca ataccoctcg    5340
atgctgggca ttactgtagc aagagatatt atttcatggc gcattttcca gtctacctga    5400
ctttttagtg tgatttcttc tccacatttt atgctcagtg tgaaaagttg gagtgcacac    5460
ttaattatcg ccggttttcg gaaagtacta tgtgctcaag gttgcacccc acgttacgta    5520
tgcagcacat tgagcagcct ttggaccgtg gagataacgg tgtggagata gcaacgggta    5580
gtcttcgtat taattcaatg cattgttagt tttatatgat atggtgtcga gcggccgcga    5640
ccgggttggc ggcgcatttg tgtcccaaaa acagcccca attgccccaa ttgaccccaa    5700
attgacccag tagcgggccc aacccgcgcg agagccccct tctccccaca tatcaaacct    5760
cccccggttc ccacacttgc cgttaagggc gtagggtact gcagtctgga atctacgctt    5820
gttcagactt tgtactagtt tctttgtctg gccatccggg taaccatgc cggacgcaaa    5880
atagactact gaaaattttt ttgctttgtg gttgggactt tagccaaggg tataaaagac    5940
caccgtcccc gaattacctt tcctcttctt ttctctctct ccttgtcaac tcacacccga    6000
```

```
aatcgttaag catttccttc tgagtataag aatcattcaa aatgtccaac ctcctcaccg    6060
tccaccagaa ccttcccgcc cttcccgtgg acgccacctc cgacgaggtc cgaaagaacc    6120
tcatggacat gttccgagat cgacaggcct tctccgagca cacttggaag atgctcctct    6180
ccgtctgccg atcctgggcc gcctggtgca agctcaacaa ccgaaagtgg ttccccgccg    6240
agcccgagga cgtccgagac tacctccttt acctccaggc ccgaggcctc gccgtcaaga    6300
ccatccagca gcacctcggc cagctcaaca tgctccaccg acgatccggc ctcccccgac    6360
cctccgactc caacgccgtg tccctcgtca tgcgacgaat ccgaaaggag aacgtggacg    6420
ccggcgagcg agccaagcag gcccttgcct tcgagcgaac cgacttcgac caggtccgat    6480
ccctcatgga gaactccgac cgatgccagg acatccgaaa cctcgccttc cttggcatcg    6540
cctacaacac cctccttcga atcgccgaga tcgcccgaat ccgagtcaag gacatctccc    6600
gaaccgacgg cggccgaatg ctcatccaca tcggccgaac caagaccctc gtgtccaccg    6660
ccggcgtcga gaaggccctc tccctcggcg tcaccaagct cgtcgagcga tggatctccg    6720
tgtccggcgt cgctgacgac cccaacaact acctcttctg ccgagtccga agaacggcg     6780 tcgctgctcc ctccgccacc tcccagctct ccacccgagc ccttgagggc atcttcgagg    6840
ccacccaccg actcatctac ggcgccaagg acgactccgg ccagcgatac ctcgcctggt    6900
ccggccactc tgctcgagtc ggtgccgccc gagacatggc ccgagccggt gtctccatcc    6960
ccgagatcat gcaggccggc ggctggacca acgtcaacat cgtcatgaac tacatccgaa    7020
acctcgactc cgagactggc gccatggtcc gacttcttga ggacggcgac tgatgatcat    7080
atgattacat taatagctaa ttacgtgtat ccgatatata tactaattac aatagtacat    7140
attagaacat acaatagttt taattaa                                        7167
```

<210> SEQ ID NO 172
<211> LENGTH: 6125
<212> TYPE: DNA
<213> ORGANISM: Artificial Sequence
<220> FEATURE:
<223> OTHER INFORMATION: pLD125

<400> SEQUENCE: 172

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacga gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cggagagggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
```

```
gaaaaccaat aacgcaatgg atgtagcagg gatggtggtt agtgcgttcc tgacaaaccc    900
agagtacgcc gcctcaaacc acgtcacatt cgccctttgc ttcatccgca tcacttgctt    960
gaaggtatcc acgtacgagt tgtaatacac cttgaagaac ggcttcgtct agttcggcat   1020
ggcagatcat catgcctgca ggagctccaa ttgtaatatt tcgggagaaa tatcgttggg   1080
gtaaaacaac agagagagag agggagagat ggttctggta gaattataat ctggttgttg   1140
caaatgctac tgatcgactc tggcaatgtc tgtagctcgc tagttgtatg caacttaggt   1200
gttatgcata cacacggtta ttcggttgaa ttgtggagta aaaattgtct gagttgtgtc   1260
ttagctactg gctggccccc cgcgaaagat aatcaaaatt acacttgtga attttttgcac   1320
acacaccgat taacatttcc cttttttgtc caccgataca cgcttgcctc ttcttatttt   1380
ctctgtgctt cccctcctg tgactttttc caccattgat ataaaatcaa ctccatttcc   1440
ctaaaatctc cccagattct aaaaacaact tcttctcttc tgcttttcct tattttttgtt   1500
atatttattt accatccctt attttgaata gttattcccc actaacattg ttcaaatctt   1560
cacgacataa tgttcttgaa acacattttt gttgctctcg cttttgcctt gttagctgac   1620
gctaccccag cccagaagag atctcccggc ttcgttgctt tagactttga catcgtcaag   1680
gttcaaaaga acgtgactgc caacgacgac gccgctgcca ttgttgccaa gagacagacc   1740
aacccaaggg aaaacttcct taagtgtttt ctgcagtaca tccctaacaa tgcaacaaac   1800
ctcaagttgg tgtacactca aaacaatcca ctctatatga gcgtgcttaa tagcacaatc   1860
cacaacttgc gcttcacgtc agatactacg cctaagccac tagtgatcgt tacaccatca   1920
cacgtcagcc atattcaagg aacgatccta tgtctgaaaa aggtcgggtt gcaaatcagg   1980
actcgatcag gagggcacga tagtgaggga atgagttaca tctcgcaagt acccttcgtg   2040
atagttgact tgcgaaatat gcggtctatt aaaattgacg tacatagcca gaccgcctgg   2100
gttgaagcag gggcaaccct gggtgaagtt tattactggg tcaatgaaaa aaacgaaaac   2160
ctaagtcttg ctgctggata ttgccccacc gtttgcgcgg gtggtcattt tggaggcggc   2220
ggatatggtc cgttgatgag aaattatgga cttgcagcag acaatattat agatgcccac   2280
ttggtgaacg ttcatggaaa ggtcttggac cgtaagtcca tgggtgaaga tcttttctgg   2340
gccttgagag gtggtggagc ggaatcgttt ggcatcatcg ttgcctggaa aattaggttg   2400
gttgcggtcc cgaagagtac aatgttctcc gtgaagaaga ttatggaaat acatgagctt   2460
gtcaagttag ttaacaagtg gcaaaatatc gcttataagt atgataaaga cttgcttttg   2520
atgactcatt ttattacgcg aaacataacc gataaccagg gcaagaacaa gactgctatt   2580
cacacgtact tctcctctgt atttcttgga ggagtagact ccttagttga cttgatgaac   2640
aagagtttcc cagaattggg gattaagaag acagattgca gacaattatc gtggatagat   2700
acaatcatat tctatagcgg tgtcgtcaat tacgatactg ataattttaa taagaaaatc   2760
ctcctagatc gttcagctgg gcaaaacggg gcattcaaaa ttaaattgga ttatgtgaag   2820
aaaccaattc cagagctggt gtttgttcag atattggaaa aactttacga agaagacatt   2880
ggcgcaggta tgtacgcttt gtatccatat ggaggcatta tggacgagat ctcagagctg   2940
gcgatcccct tcccgcacag agctgggata ctctacgagc tatggtacat ctgctcttgg   3000
gagaaacaag aagacaacga gaaacatctc aattggattc ggaacatata caactttatg   3060
accccatacg tatcaaaaaa cccgcgctta gcatacttga attacagaga cttagatatc   3120
ggtatcaatg atcctaagaa tcctaacaat tacacccaag cccgtatttg gggtgagaaa   3180
tatttcggca agaattttga cagattagtt aaggtcaaaa cactcgtgga ccccaacaac   3240
```

```
tttttccgaa acgagcagtc gattccacca ctacccaggc atagacactg agagtgactc    3300
ttttgataag agtcgcaaat ttgatttcat aagtatatat tcattatgta aagtagtaaa    3360
tggaaaattc attaaaaaaa aagcaaattt ccgttgtatg catactccga acacaaaact    3420
agccccggaa aaacccttag ttgatagttg cgaatttagg tcgaccatat gcgacgggta    3480
caacgagaat tgtattgaat tgatcaagaa catgatcttg gtgttacaga acatcaagtt    3540
cttggaccag actgagaatg cacagatata caaggcgtca tgtgataaaa tggatgagat    3600
ttatccacaa ttgaagaaag agtttatgga aagtggtcaa ccagaagcta acaggaaga     3660
agcaaacgaa gaggtgaaac aagaagaaga aggtaaataa gtattttgta ttatataaca    3720
aacaaagtaa ggaatacaga tttatacaat aaattgccat actagtcacg tgagatatct    3780
catccattcc ccaactccca agaaaataaa aaagtgaaaa ataaaatcaa acccaaagat    3840
caacctcccc atcatcatcg tcatcaaacc cccagctcaa ttcgcaatgg ttagcacaaa    3900
aacatacaca gaaagggcat cagcacaccc ctccaaggtt gcccaacgtt tattaattaa    3960
aggctaggtg gaggctcagt gatgataagt ctgcgatggt ggatgcatgt gtcatggtca    4020
tagctgtttc ctgtgtgaaa ttgttatccg ctcagagggc acaatcctat tccgcgctat    4080
ccgacaatct ccaagacatt aggtggagtt cagttcggcg tatggcatat gtcgctggaa    4140
agaacatgtg agcaaaaggc cagcaaaagg ccaggaaccg taaaaaggcc gcgttgctgg    4200
cgttttttcca taggctccgc cccctgacg agcatcacaa aaatcgacgc tcaagtcaga   4260
ggtggcgaaa cccgacagga ctataaagat accaggcgtt tccccctgga agctccctcg    4320
tgcgctctcc tgttccgacc ctgccgctta ccggatacct gtccgccttt ctcccttcgg    4380
gaagcgtggc gctttctcat agctcacgct gtaggtatct cagttcggtg taggtcgttc    4440
gctccaagct gggctgtgtg cacgaacccc ccgttcagcc cgaccgctgc gccttatccg    4500
gtaactatcg tcttgagtcc aacccggtaa gacacgactt atcgccactg gcagcagcca    4560
ctggtaacag gattagcaga gcgaggtatg taggcggtgc tacagagttc ttgaagtggt    4620
ggcctaacta cggctacact agaagaacag tatttggtat ctgcgctctg ctgaagccag    4680
ttaccttcgg aaaaagagtt ggtagctctt gatccggcaa acaaaccacc gctggtagcg    4740
gtggtttttt tgtttgcaag cagcagatta cgcgcagaaa aaaaggatct caagaagatc    4800
ctttgatctt ttctacgggg tctgacgctc tattcaacaa agccgccgtc ccgtcaagtc    4860
agcgtaaatg ggtaggggggc ttcaaatcgt ccgctctgcc agtgttacaa ccaattaaca    4920
aattctgatt agaaaaactc atcgagcatc aaatgaaact gcaatttatt catatcagga    4980
ttatcaatac catattttg aaaaagccgt ttctgtaatg aaggagaaaa ctcaccgagg     5040
cagttccata ggatggcaag atcctggtat cggtctgcga ttccgactcg tccaacatca    5100
atacaaccta ttaatttccc ctcgtcaaaa ataaggttat caagtgagaa atcaccatga    5160
gtgacgactg aatccggtga gaatggcaaa agcttatgca tttcttttcca gacttgttca    5220
acaggccagc cattacgctc gtcatcaaaa tcactcgcat caaccaaacc gttattcatt    5280
cgtgattgcg cctgagcgag acgaaatacg cgatcgctgt taaaaggaca attacaaaca    5340
ggaatcgaat gcaaccggcg caggaacact gccagcgcat caacaatatt ttcacctgaa    5400
tcaggatatt cttctaatac ctggaatgct gttttcccgg ggatcgcagt ggtgagtaac    5460
catgcatcat caggagtacg gataaaatgc ttgatggtcg gaagaggcat aaattccgtc    5520
agccagttta gtctgaccat ctcatctgta acatcattgg caacgctacc tttgccatgt    5580
```

```
ttcagaaaca actctggcgc atcgggcttc ccatacaatc gatagattgt cgcacctgat    5640
tgcccgacat tatcgcgagc ccatttatac ccatataaat cagcatccat gttggaattt    5700
aatcgcggcc tcgagcaaga cgtttcccgt tgaatatggc tcataacacc ccttgtatta    5760
ctgtttatgt aagcagacag ttttattgtt catgatgata tatttttatc ttgtgcaatg    5820
taacatcaga gattttgaga cacaacgtgg ctttcccccg ccgctctaga actagtggat    5880
ccaaataaaa cgaaaggctc agtcgaaaga ctgggccttt cgttttatct gttgtttgtc    5940
gcattatacg agacgtccag gttgggatac ctgaaacaaa acccatcgta cggccaagga    6000
agtctccaat aactgtgatc caccacaagc gccagggttt tcccagtcac gacgttgtaa    6060
aacgacggcc agtcatgcat aatccgcacg catctggaat aaggaagtgc cattccgcct    6120
gacct                                                                6125
```

<210> SEQ ID NO 173
<211> LENGTH: 6230
<212> TYPE: DNA
<213> ORGANISM: Artificial Sequence
<220> FEATURE:
<223> OTHER INFORMATION: pLD127

<400> SEQUENCE: 173

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaagggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg atggtggtt agtgcgttcc tgacaaaccc     900
agagtacgcc gcctcaaacc acgtcacatt cgcccttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga attttgcac    1320
acacaccgat taacatttcc cttttttgtc caccgataca cgcttgcctc ttcttatttt    1380
ctctgtgctt cccctcctg tgactttttc caccattgat ataaaatcaa ctccatttcc    1440
ctaaaatctc cccagattct aaaaacaact tcttctcttc tgcttttcct tatttttgtt    1500
```

```
atatttattt accatccctt attttgaata gttattcccc actaacattg ttcaaatctt    1560
cacgacataa tgcaattgtc cttgtcggtt ttatcaaccg ttgccacggc cttgttgtcc    1620
ctaaccaccg ccgtcgatgc taagtcccac aacatcaagt tgtccaagtt gtccaacgaa    1680
gaaacattgg acgcctccac attccaagaa tacacgagct ccttggccaa caagtacatg    1740
aacttgttca cgccgctca cggtaaccca accagctttg gcttgcaaca cgtcttgtcc    1800
aaccaagaag ctgaagtccc attcgttacc ccacaaaagg gtggcaaccc aagggaaaac    1860
ttccttaagt gttttctgca gtacatccct aacaatgcaa caaacctcaa gttggtgtac    1920
actcaaaaca atccactcta tatgagcgtg cttaatagca caatccacaa cttgcgcttc    1980
acgtcagata ctacgcctaa gccactagtg atcgttacac catcacacgt cagccatatt    2040
caaggaacga tcctatgtct gaaaaaggtc gggttgcaaa tcaggactcg atcaggaggg    2100
cacgatagtg agggaatgag ttacatctcg caagtaccct tcgtgatagt tgacttgcga    2160
aatatgcggt ctattaaaat tgacgtacat agccagaccg cctgggttga agcaggggca    2220
accttgggtg aagtttatta ctgggtcaat gaaaaaaacg aaaacctaag tcttgctgct    2280
ggatattgcc ccaccgtttg cgcggtggt cattttggag gcggcggata tggtccgttg    2340
atgagaaatt atggacttgc agcagacaat attatagatg cccacttggt gaacgttcat    2400
ggaaaggtct tggaccgtaa gtccatgggt gaagatcttt tctgggcctt gagaggtggt    2460
ggagcggaat cgtttggcat catcgttgcc tggaaaatta ggttggttgc ggtcccgaag    2520
agtacaatgt tctccgtgaa gaagattatg gaaatacatg agcttgtcaa gttagttaac    2580
aagtggcaaa atatcgctta taagtatgat aaagacttgc ttttgatgac tcattttatt    2640
acgcgaaaca taaccgataa ccagggcaag aacaagactg ctattcacac gtacttctcc    2700
tctgtatttc ttggaggagt agactcctta gttgacttga tgaacaagag tttcccagaa    2760
ttggggatta agaagacaga ttgcagacaa ttatcgtgga tagatacaat catattctat    2820
agcggtgtcg tcaattacga tactgataat tttaataaag aaatcctcct agatcgttca    2880
gctgggcaaa acgggcatt caaaattaaa ttggattatg tgaagaaacc aattccagag    2940
ctggtgtttg ttcagatatt ggaaaaactt tacgaagaag acattggcgc aggtatgtac    3000
gctttgtatc catatggagg cattatggac gagatctcag agctggcgat ccccttcccg    3060
cacagagctg ggatactcta cgagctatgg tacatctgct cttgggagaa caagaagac    3120
aacgagaaac atctcaattg gattcggaac atatacaact ttatgacccc atacgtatca    3180
aaaaacccgc gcttagcata cttgaattac agagacttag atatcggtat caatgatcct    3240
aagaatccta acaattacac ccaagcccgt atttggggtg agaaatattt cggcaagaat    3300
tttgacagat tagttaaggt caaaacactc gtggacccca acaactttt ccgaaacgag    3360
cagtcgattc caccactacc caggcataga cactgagagt gactcttttg ataagagtcg    3420
caaatttgat ttcataagta tatattcatt atgtaaagta gtaaatggaa aattcattaa    3480
aaaaaaagca aatttccgtt gtatgcatac tccgaacaca aaactagccc cggaaaaacc    3540
cttagttgat agttgcgaat ttaggtcgac catatgcgac gggtacaacg agaattgtat    3600
tgaattgatc aagaacatga tcttggtgtt acagaacatc aagttcttgg accagactga    3660
gaatgcacag atatacaagg cgtcatgtga taaaatggat gagatttatc cacaattgaa    3720
gaaagagttt atgaaagtg gtcaaccaga agctaaacag gaagaagcaa acgaagaggt    3780
gaaacaagaa gaagaaggta ataagtatt ttgtattata taacaaacaa agtaaggaat    3840
```

```
acagatttat acaataaatt gccatactag tcacgtgaga tatctcatcc attccccaac    3900
tcccaagaaa ataaaaaagt gaaaaataaa atcaaaccca aagatcaacc tccccatcat    3960
catcgtcatc aaaccccag ctcaattcgc aatggttagc acaaaaacat acacagaaag     4020
ggcatcagca cacccctcca aggttgccca acgtttatta attaaaggct aggtggaggc    4080
tcagtgatga taagtctgcg atggtggatg catgtgtcat ggtcatagct gtttcctgtg    4140
tgaaattgtt atccgctcag agggcacaat cctattccgc gctatccgac aatctccaag    4200
acattaggtg gagttcagtt cggcgtatgg catatgtcgc tggaaagaac atgtgagcaa    4260
aaggccagca aaaggccagg aaccgtaaaa aggccgcgtt gctggcgttt ttccataggc    4320
tccgcccccc tgacgagcat cacaaaaatc gacgctcaag tcagaggtgg cgaaacccga    4380
caggactata aagataccag gcgtttcccc ctggaagctc cctcgtgcgc tctcctgttc    4440
cgaccctgcc gcttaccgga tacctgtccg cctttctccc ttcgggaagc gtggcgcttt    4500
ctcatagctc acgctgtagg tatctcagtt cggtgtaggt cgttcgctcc aagctgggct    4560
gtgtgcacga accccccgtt cagcccgacc gctgcgcctt atccggtaac tatcgtcttg    4620
agtccaaccc ggtaagacac gacttatcgc cactggcagc agccactggt aacaggatta    4680
gcagagcgag gtatgtaggc ggtgctacag agttcttgaa gtggtggcct aactacggct    4740
acactagaag aacagtattt ggtatctgcg ctctgctgaa gccagttacc ttcggaaaaa    4800
gagttggtag ctcttgatcc ggcaaacaaa ccaccgctgg tagcggtggt ttttttgttt    4860
gcaagcagca gattacgcgc agaaaaaaag gatctcaaga agatcctttg atcttttcta    4920
cggggtctga cgctctattc aacaaagccg ccgtcccgtc aagtcagcgt aaatgggtag    4980
ggggcttcaa atcgtccgct ctgccagtgt tacaaccaat taacaaattc tgattagaaa    5040
aactcatcga gcatcaaatg aaactgcaat ttattcatat caggattatc aataccatat    5100
ttttgaaaaa gccgtttctg taatgaagga gaaaactcac cgaggcagtt ccataggatg    5160
gcaagatcct ggtatcggtc tgcgattccg actcgtccaa catcaataca acctattaat    5220
ttcccctcgt caaaaataag gttatcaagt gagaaatcac catgagtgac gactgaatcc    5280
ggtgagaatg gcaaaagctt atgcatttct ttccagactt gttcaacagg ccagccatta    5340
cgctcgtcat caaaatcact cgcatcaacc aaaccgttat tcattcgtga ttgcgcctga    5400
gcgagacgaa atacgcgatc gctgttaaaa ggacaattac aaacaggaat cgaatgcaac    5460
cggcgcagga acactgccag cgcatcaaca atattttcac ctgaatcagg atattcttct    5520
aatacctgga atgctgtttt cccggggatc gcagtggtga gtaaccatgc atcatcagga    5580
gtacggataa aatgcttgat ggtcggaaga ggcataaatt ccgtcagcca gtttagtctg    5640
accatctcat ctgtaacatc attggcaacg ctacctttgc catgtttcag aaacaactct    5700
ggcgcatcgg gcttcccata caatcgatag attgtcgcac ctgattgccc gacattatcg    5760
cgagcccatt tatacccata taaatcagca tccatgttgg aatttaatcg cggcctcgag    5820
caagacgttt cccgttgaat atggctcata acacccctg tattactgtt tatgtaagca     5880
gacagtttta ttgttcatga tgatatattt ttatcttgtg caatgtaaca tcagagattt    5940
tgagacacaa cgtggctttc ccccgccgct ctagaactag tggatccaaa taaaacgaaa    6000
ggctcagtcg aaagactggg cctttcgttt tatctgttgt ttgtcgcatt atacgagacg    6060
tccaggttgg gatacctgaa acaaaaccca tcgtacggcc aaggaagtct ccaataactg    6120
tgatccacca caagcgccag ggttttccca gtcacgacgt tgtaaaacga cggccagtca    6180
tgcataatcc gcacgcatct ggaataagga agtgccattc cgcctgacct    6230
```

-continued

<210> SEQ ID NO 174
<211> LENGTH: 8110
<212> TYPE: DNA
<213> ORGANISM: Artificial Sequence
<220> FEATURE:
<223> OTHER INFORMATION: pLD131

<400> SEQUENCE: 174

```
aggctaggtg gaggctcagt gatgataagt ctgcgatggt ggatgcatgt gtcatggtca      60
tagctgtttc ctgtgtgaaa ttgttatccg ctcagagggc acaatcctat tccgcgctat     120
ccgacaatct ccaagacatt aggtggagtt cagttcggcg tatggcatat gtcgctggaa     180
agaacatgtg agcaaaaggc cagcaaaagg ccaggaaccg taaaaaggcc gcgttgctgg     240
cgttttccca taggctccgc cccctgacg  agcatcacaa aaatcgacgc tcaagtcaga     300
ggtggcgaaa cccgacagga ctataaagat accaggcgtt tcccctggaa gctccctcg     360
tgcgctctcc tgttccgacc tgccgctta  ccggatacct gtccgccttt ctcccttcgg     420
gaagcgtggc gctttctcat agctcacgct gtaggtatct cagttcggtg taggtcgttc     480
gctccaagct gggctgtgtg cacgaacccc ccgttcagcc cgaccgctgc gccttatccg     540
gtaactatcg tcttgagtcc aacccggtaa gacacgactt atcgccactg gcagcagcca     600
ctggtaacag gattagcaga gcgaggtatg taggcggtgc tacagagttc ttgaagtggt     660
ggcctaacta cggctacact agaagaacag tatttggtat ctgcgctctg ctgaagccag     720
ttaccttcgg aaaagagtt  ggtagctctt gatccggcaa acaaaccacc gctggtagcg     780
gtggttttt  tgtttgcaag cagcagatta cgcgcagaaa aaaaggatct caagaagatc     840
ctttgatctt ttctacgggg tctgacgctc tattcaacaa agccgccgtc cgtcaagtc      900
agcgtaaatg ggtaggggc  ttcaaatcgt ccgctctgcc agtgttacaa ccaattaaca     960
aattctgatt agaaaactc  atcgagcatc aaatgaaact gcaatttatt catatcagga    1020
ttatcaatac catattttg  aaaaagccgt ttctgtaatg aaggagaaaa ctcaccgagg    1080
cagttccata ggatggcaag atcctggtat cggtctgcga ttccgactcg tccaacatca    1140
atacaaccta ttaatttccc ctcgtcaaaa ataaggttat caagtgagaa atcaccatga    1200
gtgacgactg aatccggtga gaatggcaaa agcttatgca tttctttcca gacttgttca    1260
acaggccagc cattacgctc gtcatcaaaa tcactcgcat caaccaaacc gttattcatt    1320
cgtgattgcg cctgagcgag acgaaatacg cgatcgctgt taaaaggaca attacaaaca    1380
ggaatcgaat gcaaccggcg caggaacact gccagcgcat caacaatatt ttcacctgaa    1440
tcaggatatt cttctaatac ctggaatgct gttttcccgg ggatcgcagt ggtgagtaac    1500
catgcatcat caggagtacg gataaaatgc ttgatggtcg aagaggcat  aaattccgtc    1560
agccagttta gtctgaccat ctcatctgta acatcattgg caacgctacc tttgccatgt    1620
ttcagaaaca actctggcgc atcgggcttc ccatacaatc gatagattgt cgcacctgat    1680
tgcccgacat tatcgcgagc ccatttatac ccatataaat cagcatccat gttggaattt    1740
aatcgcggcc tcgagcaaga cgtttcccgt tgaatatggc tcataacacc ccttgtatta    1800
ctgtttatgt aagcagacag ttttattgtt catgatgata tatttttatc ttgtgcaatg    1860
taacatcaga gattttgaga cacaacgtgg ctttcccccg ccgctctaga actagtggat    1920
ccaaataaaa cgaaaggctc agtcgaaaga ctgggccttt cgttttatct gttgtttgtc    1980
gcattatacg agacgtccag gttgggatac ctgaaacaaa acccatcgta cggccaagga    2040
```

```
agtctccaat aactgtgatc caccacaagc gccagggttt tcccagtcac gacgttgtaa    2100
aacgacggcc agtcatgcat aatccgcacg catctggaat aaggaagtgc cattccgcct    2160
gacctgatcc caatattaca cccaagtagc atgcataagc taaaagtaac tcgcagcgca    2220
caccgtgcag attcataagt ctatgattaa ttgaacgcca ataacccggc ttactacaag    2280
tacaagtagg tatacatagc ggtaatgaat cattagaaaa ataaaaaaca aaaaaaaaca    2340
aaacaaactg ttgtggatgc atcaacagta gtacatagtt gtacgatgta cttgtacttg    2400
taaaagcaaa aatgtacaat atctcaggga gcgcaacttt tacgttcgaa gaacaatgta    2460
ccgcataccg cattctagat tctgcggaac gtctaacctg gaaatacgat tttttatttc    2520
tttcattttt tttgcttctt caaaagtatg gtaatttcct accattacag ttgacactga    2580
acgaggggg attgaattta agcaaaaaat taaatcaaaa tacctttatg tatccagccc    2640
atgtaataaa caaaaggatt atataacaag aaataaatat ataccttaa tggatcatta     2700
gaataaaaat aaatacgaga agcacaccag agaagctttt tgattgccac tataccgcta    2760
ctttggtata tcttattata attgttgaat ttgcaagata gaatgtcatt cattggagag    2820
aaatccaagg aatatgtggg atgaaatgac tagaagtatg aacaatgaga atagtacata    2880
cttgtacctg tatttctaga agagagaaag acagttgagt gtgtgattct cgtccaataa    2940
taatctcaat agtaacgtgt gaatagctgt tctttgatag ttgatatttc tcgatgacta    3000
tttatgttgt acaagggatt tttttcgttg ctgttgattt cgaattaggc aatgcagata    3060
tcatttatgc tatccatatt taagatttcc catacgcatt tataacattt attctacata    3120
aattgttaaa tgaacgaact gccattataa attgtttcct aaataggaag tgtttttcat    3180
aaagcaagta agttgtctaa taatactaag taataaaaat aagttcatac aatatatttt    3240
gagaacatca tttggaggcg gtagatggag tctgtttatt attaaacaat gcagatgac    3300
cccttaaata ttgagaacat cagttggagg cggcagatgg agtctgtcta tttagcaatg    3360
ggacatgact gtcagtatca tcatatgtat atatataata catataatat tatataacac    3420
gatttttta aattattggc ccgaaaatta atcagtgtag actggatcct cgagaaccat     3480
ttaattaaga tcgtcgacga ttccgccaag tgagactggc gatcgggaga agggttggtg    3540
gtcatggggg atagaatttg tacaagtgga aaaaccacta cgagtagcgg atttgatacc    3600
acaagtagca gagatataca gcaatggtgg gagtgcaagt atcggaatgt actgtacctc    3660
ctgtactcgt actcgtacgg cactcgtaga aacggggcaa tacgggggag aagcgatcgc    3720
ccgtctgttc aatcgccaca agtccgagta atgcttgagt atcgaagtct tgtacctccc    3780
tgtcaatcat ggcaccactg gtcttgactt gtctattcat actggacaag cgccagagtt    3840
aagcttgtag cgaatttcgc cctcggacat caccccatac gacggacaca catgcccgac    3900
aaacagcctc tcttattgta gctgaaagta tattgaatgt gaacgtgtac aatatcaggt    3960
accagcggga ggttacggcc aaggtgatac cggataacc ctggcttgga gatggtcggt     4020
ccattgtact gaagtgtccg tgtcgtttcc gtcactgccc caattggaca tgtttgtttt    4080
tccgatcttt cgggcgccct ctccttgtct ccttgtctgt ctcctggact gttgctaccc    4140
catttctttg gcctccattg gttcctcccc gtctttcacg tcgtctatgg ttgcatggtt    4200
tcccttatac ttttccccac agtcacatgt tatggagggg tctagatgga ggcctaattt    4260
tgacgtgcaa ggggcgaatt ggggcgagaa acacgtcgtg gacatggtgc aaggcccgca    4320
gggttgattc gacgcttttc cgcgaaaaaa acaagtccaa atacccccgt ttattctccc    4380
tcggctctcg gtatttcaca tgaaaactat aacctagact acacgggcaa ccttaacccc    4440
```

```
agagtatact tatataccaa agggatgggt cctcaaaaat cacacaagca acgacgccat   4500
gggcctctct ctagtatgta ccttctcttt ccagaccaac tatcacactc tactgaaccc   4560
ccataacaag aaccctaaaa attctcttct cagttaccag caccccaaga cgcctatcat   4620
taagtcctcc tacgacaact ttccctctaa gtactgcctg accaaaaact tccatctcct   4680
gggactgaac tctcataaca gaattagtag ccagtcccga tctatccgag ctggctctga   4740
ccagattgag ggctcccctc accatgaatc cgacaacagc atcgctacca agattttgaa   4800
ttttggtcac acatgctgga agctccagcg accgtacgtc gtgaagggta tgatctcgat   4860
tgcctgtgga ctgttcggac gtgagctttt taataatcga cacttgtttt catggggcct   4920
catgtggaag gcttttttcg ccctcgtgcc cattctgtct ttcaacttct ttgccgctat   4980
tatgaaccaa atctacgacg ttgatattga taggatcaac aagcctgacc tgccgctcgt   5040
ctcgggggag atgtctatcg agacagcgtg gattctttcg attatcgtcg cgctgactgg   5100
ccttatcgtt accataaagt tgaagtctgc acccctcttc gtgtttatct acattttcgg   5160
tatttttgct ggattcgcgt actccgttcc ccctatcaga tggaagcagt acccctttac   5220
taactttctg attactatca gcagccacgt cggtttagcc tttacctcat attcggccac   5280
caccagtgca ctgggcctcc ccttcgtctg gcgacctgca ttttcattca tcatcgcctt   5340
catgactgtg atgggtatga ccatcgcttt cgctaaggac atctccgaca tcgagggtga   5400
tgctaaatat ggagtgtcca ccgtggccac taagctggga gcccggaaca tgacgttcgt   5460
cgtctctggt gttctgctcc ttaactactt ggtttcgatc tccattggca ttatctggcc   5520
acaagtcttc aagtccaaca ttatgattct gtcccacgcc attcttgcct tttgcctgat   5580
cttccagaca cgcgaactcg ctctcgctaa ctacgcctcc gccccatcgc gacagttctt   5640
cgagttcatc tggctgcttt actacgccga gtacttcgtt tacgtgttca tctaataaga   5700
gtaggcaatt aacagatagt ttgccggtga taattctctt aacctcccac actcctttga   5760
cataacgatt tatgtaacga aactgaaatt tgaccagata ttgttgtaaa tagaaaatct   5820
ggcttgtagg tggcaaaatg cggcgtcttt gttcatcaat tccctctgtg actactcgtc   5880 atcccttttat gttcgactgt cgtatttctt attttccata catatgcaag tgagatgccc   5940
gtgtccgaat tcgctatgga tccatagcgt cgacaccata tcatataaaa ctaacaatgc   6000
attgaattaa tacgaagact acccgttgct atctccacac cgttatctcc acggtccaaa   6060
ggctgctcaa tgtgctgcat acgtaacgtg gggtgcaacc ttgagcacat agtactttcc   6120
gaaaaccggc gataattaag tgtgcactcc aactttcac actgagcata aaatgtggag   6180
aagaaatcac actaaaaagt caggtagact ggaaaatgcg ccatgaaata atatctcttg   6240
ctacagtaat gcccagcatc gagggggtatt gtgtcaccaa cactatagtg gcagctgaag   6300
cgctcgtgat tgtagtatga gtctttattg gtgatgggaa gagttcactc aatattctcg   6360
ttactgccaa acaccacgg taatcggcca gacaccatgg atgtagatca ccaagcctgt   6420
gaatgttatt cgagctaaaa tgcacatggt tggtgaaagg agtagttgct gtcgaattcc   6480
gtcgtcgcct gagtcatcat ttatttacca gttggccaca aacccttgac gatctcgtat   6540
gtcccctccg acatactccc ggccggctgg ggtacgttcg atagcgctat cggcatcgac   6600
aaggtttggg tccctagccg ataccgcact acctgagtca caatcttcgg aggtttagtc   6660
ttccacatag cacgggcaaa agtgcgtata tatacaagag cgtttgccag ccacagattt   6720
tcactccaca caccacatca cacatacaac cacacacatc cacaatggaa cccgaaacta   6780
```

```
agaagaccaa gactgactcc aagaagattg ttcttctcgg cggcgacttc tgtggccccg    6840
aggtgattgc cgaggccgtc aaggtgctca agtctgttgc tgaggcctcc ggcaccgagt    6900
tgtgtttga ggaccgactc attggaggag ctgccattga aaggagggc gagcccatca     6960
ccgacgctac tctcgacatc tgccgaaagg ctgactctat tatgctcggt gctgtcggag    7020
gcgctgccaa caccgtatgg accactcccg acggacgaac cgacgtgcga cccgagcagg    7080
gtcttctcaa gctgcgaaag gacctgaacc tgtacgccaa cctgcgaccc tgccagctgc    7140
tgtcgcccaa gctcgccgat ctctccccca tccgaaacgt tgagggcacc gacttcatca    7200
ttgtccgaga gctcgtcgga ggtatctact ttggagagcg aaaggaggat gacggatctg    7260
gcgtcgcttc cgacactgag acttactccg ttcctgaggt tgagcgaatt gcccgaatgg    7320
ccgccttcct ggcccttcag cacaaccccc ctcttcccgt gtggtccctt gacaaggcca    7380
acgtgctggc ctcctctcga ctttggcgaa agaccgtcac ccgagtcctc aaggacgaat    7440
tcccccagct ggagctcaac caccagctga tcgactcggc cgccatgatc ctcatcaagc    7500
agccctccaa gatgaatggt atcatcatca ccaccaacat gtttggcgat atcatctccg    7560
acgaggcctc cgtcatcccc ggttctctgg gtctgctgcc ctccgcctct ctggcttctc    7620
tgcccgacac caacgaggcg ttcggtctgt acgagccctg tcacggatct gcccccgatc    7680
tcggcaagca aaggtcaac cccattgcca ccattctgtc tgccgccatg atgctcaagt    7740
tctctcttaa catgaagccc gccggtgacg ctgttgaggc tgccgtcaag gagtccgtcg    7800
aggctggtat cactaccgcc gatatcggag ctcctcctc cacctccgag gtcggagact    7860
tgttgccaa caaggtcaag gagctgctca agaaggagta agtcgtttct acgacgcatt    7920
gatggaagga gcaaactgac gcgcctgcgg gttggtctac cggcagggtc cgctagtgta    7980
taagactcta taaaagggc ccagccctgc taatgaaatg atgatttata atttaccggt     8040
gtagcaacct tgactagaag aagcagattg ggtgtgtttg tagtggagga cagtggtacg    8100
ttttaattaa                                                           8110
```

<210> SEQ ID NO 175
<211> LENGTH: 7557
<212> TYPE: DNA
<213> ORGANISM: Artificial Sequence
<220> FEATURE:
<223> OTHER INFORMATION: pLD132

<400> SEQUENCE: 175

```
ttaattaaga tcgtcgacga ttccgccaag tgagactggc gatcgggaga agggttggtg      60
gtcatggggg atagaatttg tacaagtgga aaaaccacta cgagtagcgg atttgatacc     120
acaagtagca gagatataca gcaatggtgg gagtgcaagt atcggaatgt actgtacctc     180
ctgtactcgt actcgtacgg cactcgtaga acggggcaa tacgggggag aagcgatcgc      240
ccgtctgttc aatcgccaca agtccgagta atgcttgagt atcgaagtct tgtacctccc     300
tgtcaatcat ggcaccactg gtcttgactt gtctattcat actggacaag cgccagagtt     360
aagcttgtag cgaatttcgc cctcggacat caccccatac gacggacaca catgcccgac     420
aaacagcctc tcttattgta gctgaaagta tattgaatgt gaacgtgtac aatatcaggt     480
accagcggga ggttacggcc aaggtgatac cggaataacc ctggcttgga gatggtcggt    540
ccattgtact gaagtgtccg tgtcgttccc gtcactgccc caattggaca tgtttgtttt    600
tccgatcttt cgggcgccct ctccttgtct ccttgtctgt cctctggact gttgctaccc    660
catttctttg gcctccattg gttcctcccc gtctttcacg tcgtctatgg ttgcatggtt    720
```

```
tcccttatac ttttcccccac agtcacatgt tatggagggg tctagatgga ggcctaatt       780
tgacgtgcaa ggggcgaatt ggggcgagaa acacgtcgtg acatggtgc aaggcccgca        840
gggttgattc gacgcttttc cgcgaaaaaa acaagtccaa ataccccgt ttattctccc        900
tcggctctcg gtatttcaca tgaaaactat aacctagact acacgggcaa ccttaacccc      960
agagtatact tatataccaa agggatgggt cctcaaaaat cacacaagca acgacgccat      1020
gaagtgttcg acgttttctt tttggtttgt ttgtaaaatc attttctttt tcttttcttt      1080
caacatccaa acgtcgatcg caaaccctag agagaacttt cttaagtgct tctcgcagta     1140
catccctaat aacgctacca accttaagct ggtgtacacc cagaacaacc ctctttacat     1200
gtctgttcta aacagcacca tccacaatct tagattcaca tcagacacca ctcccaagcc     1260
gctcgtcatc gtgaccccga gtcatgtgtc ccatatccaa ggcactatcc tgtgctctaa     1320
aaaggtcggt ctgcagattc ggactcgctc cggtggacat gattcggagg gcatgtccta    1380
cattagccag gtccccttg tgatcgtgga cctgaggaac atgcggtcta ttaagattga     1440
tgtgcactca cagaccgctt gggtcgaggc tggtgcgaca ttgggtgagg tgtactactg    1500
ggtgaacgag aagaacgaga acctgagcct cgccgctggc tactgtccca ccgtttgtgc    1560
cggtggacac ttcggcggag gcggatacgg tccacttatg cgaaactacg ggctcgcagc    1620
tgataatatc atcgacgcac accttgttaa cgttcacggc aaggtgctgg accgaaaaag    1680
catgggtgag gacctatttt gggccttgcg aggcggtggt gccgaatcct tcggaattat    1740
cgtggcctgg aagatccgac tggtcgctgt gccaaagtcc actatgttct ccgtcaagaa    1800
aattatggag atccacgaac tcgtaaagct cgtcaataag tggcagaaca tcgcctacaa    1860
gtatgacaag gatctgctgc tcatgactca cttcatcacg cgaaacatta cagacaacca   1920
gggaaagaac aagaccgcta tccataccta cttctcctct gtcttccttg ggggtgtcga    1980
ttccctcgtt gatctcatga acaaatcttt tccagagctc ggaatcaaga agaccgactg    2040
ccgacagctc tcttggatcg acaccattat tttctactca ggagtcgtaa actacgatac    2100
tgacaacttt aacaaggaga ttctgttaga tcgatcggcc ggccagaacg gtgccttcaa    2160
gatcaagctc gactatgtca aaaagcccat tcctgaatcc gtcttcgttc aaattcttga    2220
aaagttgtac gaggaggata tcggcgccgg aatgtacgcg ctgtaccccct acggtggcat   2280
tatgacgag atttctgaaa gtgctattcc cttccccccac cgtgctggca ttctgtatga    2340
gctgtggtac atttgctcct gggaaaagca ggaggacaac gagaagcact tgaactggat    2400
acgaaacatt tacaatttca tgaccccccta tgtttcgaag aaccctcgac tggcctacct    2460
gaattaccgc gacctcgaca tcggaattaa cgaccctaag aaccccaata actatactca    2520
ggccagaat tggggcgaga agtacttcgg caagaacttt gaccgtctgg ttaaggtcaa    2580
gaccctcgtg gaccctaaca acttcttccg aaacgagcag tctatccccc ctctgccccg    2640
acaccggcat taataagagt aggcaattaa cagatagttt gccggtgata attctcttaa    2700
cctcccacac tccttttgaca taacgattta tgtaacgaaa ctgaaatttg accagatatt    2760
gttgtaaata gaaaatctgg cttgtaggtg gcaaatgcg gcgtctttgt tcatcaattc     2820
cctctgtgac tactcgtcat cccttatgt tcgactgtcg tatttcttat tttccataca    2880
tatgcaagtg agatgcccgt gtccgaattc gctatggatc catagcgcag gttgtgcagt    2940
atcatacata ctcgatcaga caggtcgtct gaccatcata caagctgaac aagcgctcca   3000
tacttgcacg ctctctatat acacagttaa atgacatatc catagtctaa cctctaacag   3060
```

```
ttaatcttct ggtaagcctc ccagccagcc ttctggtatc gcttggcctc ctcaatagga    3120
tctcggttct ggccgtacag acctcggccg acaattatga tatccgttcc ggtagacatg    3180
acatcctcaa cagttcggta ctgctgtccg agagcatctc ccttgtcgtc aagacccacc    3240 ccggggtca gaataagcca gtcctcagag tcgcccttag gtcggttctg ggcaatgaag     3300
ccaaccacaa actcggggtc ggatcgggca agctcaatgg tctgcttgga gtactcgcca    3360
gtggccagag agcccttgca agacagctcg gccagcatga gcagacctct ggccagcttc    3420
tcgttgggag aggggaccag gaactccttg tactgggagt tctcgtagtc agagacatcc    3480
tccttcttct gttcagagac agtttcctcg gcaccagctc gcaggccagc aatgattccg    3540
gttccgggta caccgtgggc gttggtgata tcggaccact cggcgattcg gtagacaccg    3600
ttcttgtact ggtgcttgac agtgttgcca atatctgcga actttctgtc ctcgaacagg    3660
aagaaaccgt gcttaagagc aagttccttg aggggagca cagttccggc gtaggtgaag     3720
tcgtcaatga tgtcgatatg ggtcttgatc atgcacacat aaggtccgac cttatcggca    3780
agctcaatga gctccttggt ggtggtaaca tccagagaag cacacaggtt ggttttcttg    3840
gctgccacga gcttgagcac tcgggcggca aggcggact tgtggacgtt agctcgcgct     3900
tcgtaggagg gcattttggt ggtgaagagg agactgaaat aaatttagtc tgcacaactt    3960
tttatcggaa ccttatctgg ggcagtgaag tatatgttat ggtaatagtt acgagttagt    4020
tgaacttata gatagactgg actatacggc tatcggtcca aattagaaat taattaaatg    4080
gttctcgagg atccagtcta cactgattaa ttttcgggcc aataatttaa aaaaatcgtg    4140
ttatataata ttatatgtat tatatatata catatgatga tactgacagt catgtcccat    4200
tgctaaatag acagactcca tctgccgcct ccaactgatg ttctcaatat ttaaggggtc    4260
atctcgcatt gtttaataat aaacagactc catctaccgc ctccaaatga tgttctcaaa    4320
atatattgta tgaacttatt tttattactt agtattatta gacaacttac ttgctttatg    4380
aaaaacactt cctatttagg aaacaattta taatggcagt tcgttcattt aacaatttat    4440
gtagaataaa tgttataaat gcgtatggga atcttaaat atggatagca taaatgatat     4500
ctgcattgcc taattcgaaa tcaacagcaa cgaaaaaaat cccttgtaca acataaaatag    4560 tcatcgagaa atatcaacta tcaaagaaca gctattcaca cgttactatt gagattatta    4620
ttggacgaga atcacacact caactgtctt tctctcttct agaaatacag gtacaagtat    4680
gtactattct cattgttcat acttctagtc atttcatccc acatattcct tggatttctc    4740
tccaatgaat gacattctat cttgcaaatt caacaattat aataagatat accaaagtag    4800
cggtatagtg gcaatcaaaa agcttctctg gtgtgcttct cgtatttatt tttattctaa    4860
tgatccatta aaggtatata tttatttctt gttatataat cctttgttt attacatggg     4920 ctggatacat aaaggtattt tgatttaatt ttttgcttaa attcaatccc cctcgttca     4980 gtgtcaactg taatggtagg aaattaccat acttttgaag aagcaaaaaa atgaaagaa     5040 ataaaaaatc gtatttccag gttagacgtt ccgcagaatc tagaatgcgg tatgcggtac    5100
attgttcttc gaacgtaaaa gttgcgctcc ctgagatatt gtacatttttt gcttttacaa    5160 gtacaagtac atcgtacaac tatgtactac tgttgatgca tccacaacag tttgttttgt    5220
ttttttttgt tttttatttt tctaatgatt cattaccgct atgtatacct acttgtactt    5280
gtagtaagcc gggttattgg cgttcaatta atcatagact tatgaatctg cacggtgtgc    5340
gctgcgagtt acttttagct tatgcatgct acttgggtgt aatattggga tcaggtcagg    5400
cggaatggca cttccttatt ccagatgcgt gcggattatg catgactggc cgtcgtttta    5460
```

-continued

```
caacgtcgtg actgggaaaa ccctggcgct tgtggtggat cacagttatt ggagacttcc    5520
ttggccgtac gatgggtttt gtttcaggta tcccaacctg gacgtctcgt ataatgcgac    5580
aaacaacaga taaaacgaaa ggcccagtct ttcgactgag cctttcgttt tatttggatc    5640
cactagttct agagcggcgg gggaaagcca cgttgtgtct caaaatctct gatgttacat    5700
tgcacaagat aaaatatat catcatgaac aataaaactg tctgcttaca taaacagtaa    5760
tacaaggggt gttatgagcc atattcaacg ggaaacgtct tgctcgaggc cgcgattaaa    5820
ttccaacatg gatgctgatt tatatgggta taaatgggct cgcgataatg tcggcaatc     5880 aggtgcgaca atctatcgat tgtatgggaa gcccgatgcg ccagagttgt ttctgaaaca    5940
tggcaaaggt agcgttgcca atgatgttac agatgagatg gtcagactaa actggctgac    6000
ggaatttatg cctcttccga ccatcaagca ttttatccgt actcctgatg atgcatggtt    6060
actcaccact gcgatccccg ggaaaacagc attccaggta ttagaagaat atcctgattc    6120
aggtgaaaat attgttgatg cgctggcagt gttcctgcgc cggttgcatt cgattcctgt    6180
ttgtaattgt ccttttaaca gcgatcgcgt atttcgtctc gctcaggcgc aatcacgaat    6240
gaataacggt ttggttgatg cgagtgattt tgatgacgag cgtaatggct ggcctgttga    6300
acaagtctgg aaagaaatgc ataagctttt gccattctca ccggattcag tcgtcactca    6360
tggtgatttc tcacttgata accttatttt tgacgagggg aaattaatag gttgtattga    6420
tgttggacga gtcggaatcg cagaccgata ccaggatctt gccatcctat ggaactgcct    6480
cggtgagttt tctccttcat tacagaaacg gcttttttcaa aaatatggta ttgataatcc    6540
tgatatgaat aaattgcagt ttcatttgat gctcgatgag ttttttctaat cagaatttgt    6600 taattggttg taacactggc agagcggacg atttgaagcc ccctacccat ttacgctgac    6660
ttgacgggac ggcggctttg ttgaatagag cgtcagaccc cgtagaaaag atcaaaggat    6720
cttcttgaga tccttttttt ctgcgcgtaa tctgctgctt gcaaacaaaa aaaccaccgc    6780
taccagcggt ggtttgtttg ccggatcaag agctaccaac tctttttccg aaggtaactg    6840
gcttcagcag agcgcagata ccaaatactg ttcttctagt gtagccgtag ttaggccacc    6900
acttcaagaa ctctgtagca ccgcctacat acctcgctct gctaatcctg ttaccagtgg    6960
ctgctgccag tggcgataag tcgtgtctta ccgggttgga ctcaagacga tagttaccgg    7020
ataaggcgca gcggtcgggc tgaacggggg gttcgtgcac acagcccagc ttggagcgaa    7080
cgacctacac cgaactgaga tacctacagc gtgagctatg agaaagcgcc acgcttcccg    7140
aagggagaaa ggcggacagg tatccggtaa gcggcagggt cggaacagga gagcgcacga    7200
gggagcttcc agggggaaac gcctggtatc tttatagtcc tgtcgggttt cgccacctct    7260
gacttgagcg tcgatttttg tgatgctcgt caggggggcg gagcctatgg aaaaacgcca    7320
gcaacgcggc ctttttacgg ttcctggcct tttgctggcc ttttgctcac atgttctttc    7380
cagcgacata tgccatacgc cgaactgaac tccacctaat gtcttggaga ttgtcggata    7440
gcgcggaata ggattgtgcc ctctgagcgg ataacaattt cacacaggaa acagctatga    7500
ccatgacaca tgcatccacc atcgcagact tatcatcact gagcctccac ctagcct      7557
```

<210> SEQ ID NO 176
<211> LENGTH: 8500
<212> TYPE: DNA
<213> ORGANISM: Artificial Sequence
<220> FEATURE:
<223> OTHER INFORMATION: pLD135

<400> SEQUENCE: 176

```
aggctaggtg gaggctcagt gatgataagt ctgcgatggt ggatgcatgt gtcatggtca      60
tagctgtttc ctgtgtgaaa ttgttatccg ctcagagggc acaatcctat tccgcgctat     120
ccgacaatct ccaagacatt aggtggagtt cagttcggcg tatggcatat gtcgctggaa     180
agaacatgtg agcaaaaggc cagcaaaagg ccaggaaccg taaaaaggcc gcgttgctgg     240
cgttttccca taggctccgc cccctgacg agcatcacaa aaatcgacgc tcaagtcaga     300
ggtggcgaaa cccgacagga ctataaagat accaggcgtt tcccctgga agctccctcg     360
tgcgctctcc tgttccgacc ctgccgctta ccggatacct gtccgccttt ctcccttcgg     420
gaagcgtggc gctttctcat agctcacgct gtaggtatct cagttcggtg taggtcgttc     480
gctccaagct gggctgtgtg cacgaacccc cgttcagcc cgaccgctgc gccttatccg     540
gtaactatcg tcttgagtcc aacccggtaa gacacgactt atcgccactg gcagcagcca     600
ctggtaacag gattagcaga gcgaggtatg taggcggtgc tacagagttc ttgaagtggt     660
ggcctaacta cggctacact agaagaacag tatttggtat ctgcgctctg ctgaagccag     720
ttaccttcgg aaaaagagtt ggtagctctt gatccggcaa acaaaccacc gctggtagcg     780
gtggtttttt tgtttgcaag cagcagatta cgcgcagaaa aaaaggatct caagaagatc     840
ctttgatctt ttctacgggg tctgacgctc tattcaacaa agccgccgtc ccgtcaagtc     900
agcgtaaatg ggtaggggc ttcaaatcgt cctcgtgata ccaattcgga gcctgctttt     960
ttgtacaaac ttgttgataa tggcaattca aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140
tgactccccg tcgtgtagat aactacgata cgggagggct taccatctgg ccccagtgct    1200
gcaatgatac cgcgagagcc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc agataccctga aacaaacccc atcgtacggc caaggaagtc    2100
tccaataact gtgatccacc acaagcgcca gggttttccc agtcacgacg ttgtaaaacg    2160
acggccagtc atgcataatc cgcacgcatc tggaataagg aagtgccatt ccgcctgacc    2220
tttaattaat tggcaaattt tactgtgcc ttcagaacgg taaaaataga ccaatcagaa    2280
ttctgaaaag cacatcttga tctcctcatt gcggggagtc caacggtggt cttattcccc    2340
```

```
cgaatttccc gctcaatctc gttccagacc gacccggaca cagtgcttaa cgccgttccg    2400
aaactctacc gcagatatgc tccaacggac tgggctgcat agatgtgatc ctcggcttgg    2460
agaaatggat aaaagccggc caaaaaaaaa gcggaaaaaa gcggaaaaaa agagaaaaaa    2520
aatcgcaaaa tttgaaaaat aggggggaaaa gacgcaaaaa cgcaaggagg ggggagtata    2580
tgacactgat aagcaagctc acaacggttc ctcttatttt tttcctcatc ttctgcctag    2640
gttcccaaaa tcccagatgc ttctctccag tgccaaaagt aagtacccca caggttttcg    2700
gccgaaaatt ccacgtgcag caacgtcgtg tggggtgtta aaatgtgggg gcggggaacc    2760
aggacaagag gctcttgtgg gagccgaatg agagcacaaa gcgggcgggt gtgataaggg    2820
catttttgcc catttttccct tctcctgtct ctccgacggt gatggcgttg tgcgtcctct    2880
atctatttct ttttatttct ttttgtttta tttctctgac taccgatttg gcttgatttc    2940 ctcaaccccca cacaaataag ctcgggccga ggaatatata tatacacgga cacagtcgcc    3000
ctgtggacaa cacgtcacta cctctacgac gctatggatc catagcgaat tcggacacgg    3060
gcatctcact tgcatatgta tggaaaataa gaaatacgac agtcgaacat aaagggatga    3120
cgagtagtca cagagggaat tgatgaacaa agacgccgca ttttgccacc tacaagccag    3180
attttctatt tacaacaata tctggtcaaa tttcagtttc gttacataaa tcgttatgtc    3240
aaaggagtgt gggaggttaa gagaattatc accggcaaac tatctgttaa ttgcctactc    3300
ttattacagt ttggctcgtc gtccccgaga cttgccggcc ttgatagcga ggagtgtctt    3360
ctcgtcagca ggggcgctac cggaggctcg ttgctgtctg aagtaggttc gggcctcgtc    3420
ctgtcgggtg gcctcagcgc cggtggcgat agcggcccga aggtgctcgg ctccgtagcc    3480
gaaggcatca accagatcaa gtgcgtgtgg tcggatctta acgagaagac gattaatgta    3540
agtgccgacc gttcggcctc tctgcatcga gagcctaccg ttcatcagat accagctgag    3600
gtgcttctcg ataagggaca gaccaaaaag gtcacgcaat cgggtcaaca cttccttagt    3660
gccagcgtcg tccaccttgg ccaaagcctc agtaaaggcc tcccactgta aaagctcagc    3720
gtgggcctgg gcagcctcga tcagttcgtt ttgatgctga ttgaacagtg ctgccgcctg    3780 gtgctgggggg agcttgcccg cgcctttgag agcagcgcca acctctgcaa ccatggactg    3840
gactctgtcg gtcagcagag ttcgctgacc ttcttcgtct cggagggcaa gagcagattt    3900
ctggacagat ccactgtcgg ccacgaactg agcgacctgt cgcagtccgg ttcggtgtag    3960
cgcgactccg gcagcctggt ccacgacgta ccgcgcgagc acgccgaagt tggcacctcg    4020
gaactcctta gcatagtcag cgagcagcct cttggccacc aactgaagaa gcacggtgtt    4080
gtctccttcg aaggtcacgt agacgtcgag atcggcccgg agagaagcga atcggttctc    4140
aatcagaaaa cctgcaccccc cacacgcttc tcggcactct tgtagggtat cgagagcatg    4200
ccaggtagaa aggggcttca gagcagcagc cagtgtctca aggtcctgac ggtcggcgtc    4260
agtatcatga gcacccgaga acacgtcgtc gaatttctgc agcagttgct catgggcgaa    4320
cgatgcggcg taggtggtgg cgagtcgggt aaagaggcgc cgctggtgtc gctggtaatc    4380
caggagcacc tcctcctctg tgggcgaagt ggcgttgaac tgtcttcgct cagcggcgta    4440
gtggatggcg gattgcagag caaccttcga tgcagccact gcagccacgt ccaggctgac    4500
tcggccctgg accagcgtac ctagcattgt aaagaatctt cgccccggag attcgatggt    4560
tgagctgtag gtgccatcga cggcaacatc gccgtaacgg ttaagcaggt tggttcgggg    4620
aatgcgaaca ttggtgaaat ggagacgtcc gttatcaatt ccgtttagtc ccccccttaat    4680
```

```
accgtcgtcc tctccaccaa taccaggag aaagtctccg gtggcgggat ctctcagatc   4740
gacgtagaag gcgtgcactc catggttaac ctttcgagta atcagttggg caaacacgac   4800
agcggccaaa ccgtcgttag cggcgtttcc aatgtagtcc ttccaggcgg ctcggaacgg   4860
ggtgtcaata acgaactcct gggtttcctc atcataggtg gccgttgtag caatggaagc   4920
gacatcggag ccatggccag tctcagtcat ggcaaagcaa ccagggattt ccagagacat   4980
gatgcctggg agccacttgt cgtggtgctc cctagttccc aagtgcataa cagcggagcc   5040
gaacagtccc cactggacgc cggccttgat ctggagggag gggtccgccg tgacaagctc   5100
ctcaaaacca gcgatgtttc cgccgtggtc gtcactacca cccagtcgag aaggaaaggc   5160
tcggtgaact gcgttgttat cgaccaagta cttgagctgg ccaaagacgc gagagcggtg   5220
ctctgtatga gtcagaccct ccaccttctg aactacctct cgtcccgcaa ggtcccgggc   5280
gtggagacgg atatcagccc atcggcccag cagctgctct cccagcgcag ccacatctac   5340
tcggggctcg acggccacct tagcaccgtc tgcggcggcc gtagttgagc caggggatgc   5400
gggggatgag gctctgtcaa ctacttcggt catggcgtcg ttgcttgtgt gattttgag   5460 gacccatccc tttggtatat aagtatactc tggggttaag gttgcccgtg tagtctaggt   5520
tatagttttc atgtgaaata ccgagagccg agggagaata acgggggta tttggacttg   5580 tttttttcgc ggaaaagcgt cgaatcaacc ctgcgggcct tgcaccatgt ccacgacgtg   5640
tttctcgccc caattcgccc cttgcacgtc aaaattaggc ctccatctag acccctccat   5700
aacatgtgac tgtggggaaa agtataaggg aaaccatgca accatagacg acgtgaaaga   5760
cggggaggaa ccaatggagg ccaaagaaat ggggtagcaa cagtccagga gacagacaag   5820
gagacaagga gagggcgccc gaaagatcgg aaaaacaaac atgtccaatt ggggcagtga   5880
cggaaacgac acgacacttt cagtacaatg gaccgaccat ctccaagcca gggttattcc   5940
ggtatcacct tggccgtaac ctcccgctgg tacctgatat tgtacacgtt cacattcaat   6000
atactttcag ctacaataag agaggctgtt tgtcgggcat gtgtgtccgt cgtatggggt   6060
gatgtccgag ggcgaaaatt gctacaagct taactctggc gcttgtccag tatgaataga   6120
caagtcaaga ccagtggtgc catgattgac agggaggtac aagacttcga tactcaagca   6180
ttactcggac ttgtggcgat tgaacagacg ggcgatcgct tctccccgt attgccccgt   6240 ttctacgagt gccgtacgag tacgagtaca ggaggtacag tacattccga tacttgcact   6300
cccaccattg ctgtatatct ctgctacttg tggtatcaaa tccgctactc gtagtggttt   6360
ttccacttgt acaaattcta tcccccatga ccaccaaccc ttctcccgat cgccagtctc   6420
acttggcgga atcgtcgacg atcatcctcg agatgcggcc gcgtcgacat aacttcgtat   6480
agcatacatt atacgaagtt attttctaat ttggaccgat agccgtatag tccagtctat   6540
ctataagttc aactaactcg taactattac cataacatat acttcactgc cccagataag   6600
gttccgataa aaagttgtgc agactaaatt tatttcagtc tcctcttcac caccaaaatg   6660
ccctcctacg aagcgcgagc taacgtccac aagtccgcct tgccgcccg agtgctcaag   6720 ctcgtggcag ccaagaaaac caacctgtgt gcttctctgg atgttaccac caccaaggag   6780
ctcattgagc ttgccgataa ggtcggacct tatgtgtgca tgatcaagac ccatatcgac   6840
atcattgacg acttcaccta cgccggaact gtgctccccc tcaaggaact tgctcttaag   6900
cacggttttc tcctgttcga ggacagaaag ttcgcagata ttggcaacac tgtcaagcac   6960
cagtacaaga acgtgtcta ccgaatcgcc gagtggtccg atatcaccaa cgcccacggt   7020
gtacccggaa ccggaatcat tgctggcctg cgagctggtg ccgaggaaac tgtctctgaa   7080
```

```
cagaagaagg aggatgtctc tgactacgag aactcccagt acaaggagtt cctggtcccc    7140
tctcccaacg agaagctggc cagaggtctg ctcatgctgg ccgagctgtc ttgcaagggc    7200
tctctggcca ctggcgagta ctccaagcag accattgagc ttgcccgatc cgaccccgag    7260
tttgtggttg gcttcattgc ccagaaccga cctaagggcg actctgagga ctggcttatt    7320 ctgaccccg gggtgggtct tgacgacaag ggagatgctc tcggacagca gtaccgaact     7380
gttgaggatg tcatgtctac cggaacggat atcataattg tcggccgagg tctgtacggc    7440
cagaaccgag atcctattga ggaggccaag cgataccaga aggctggctg ggaggcttac    7500
cagaagatta actgttagag gttagactat ggatatgtca tttaactgtg tatatagaga    7560
gcgtgcaagt atggagcgct tgttcagctt gtatgatggt cagacgacct gtctgatcga    7620
gtatgtatga tactgcacaa cctgataact tcgtatagca tacattatac gaagttatct    7680
cgaggcggcc gcatggagcg tgtgttctga gtcgatgttt tctatggagt tgtgagtgtt    7740
agtagacatg atgggtttat atatgatgaa tgaatagatg tgattttgat ttgcacgatg    7800
gaattgagaa ctttgtaaac gtacatggga atgtatgaat gtggggtttt tgtgactgga    7860
taactgacgg tcagtggacg ccgttgttca aatatccaag agatgcgaga acttttgggt    7920
caagtgaaca tgtcctctct gttcaagtaa accatcaact atgggtagta tatttagtaa    7980
ggacaagagt tgagattctt tggagtccta gaaacgtatt ttcgcgttcc aagatcaaat    8040
tagtagagta atacgggcac gggaatccat tcatagtctc aattttccca taggtgtgct    8100
acaaggtgtt gagatgtggt acagtaccac catgattcga ggtaaagagc ccagaagtca    8160
ttgatgaggt caagaaatac acagatctac agctcaatac aatgaatatc ttctttcata    8220
ttcttcaggt gacaccaagg gtgtctattt tccccagaaa tgcgtgaaaa ggcgcgtgtg    8280
tagcgtggag tatgggttcg gttggcgtat ccttcatata tcgacgaaat agtagggcaa    8340
gagatgacaa aaagtatcta tatgtagaca gcgtagaata tggatttgat tggtataaat    8400
tcatttattg cgtgtctcac aaatactctc gataagttgg ggttaaactg gagatggaac    8460
aatgtcgata tctcgacata ttttgatatt tgttaattaa                          8500
```

<210> SEQ ID NO 177
<211> LENGTH: 5655
<212> TYPE: DNA
<213> ORGANISM: Artificial Sequence
<220> FEATURE:
<223> OTHER INFORMATION: pLD137

<400> SEQUENCE: 177

```
aggctaggtg gaggctcagt gatgataagt ctgcgatggt ggatgcatgt gtcatggtca     60
tagctgtttc ctgtgtgaaa ttgttatccg ctcagagggc acaatcctat tccgcgctat    120
ccgacaatct ccaagacatt aggtggagtt cagttcggcg tatggcatat gtcgctggaa    180
agaacatgtg agcaaaaggc cagcaaaagg ccaggaaccg taaaaaggcc gcgttgctgg    240 cgttttttcca taggctccgc ccccctgacg agcatcacaa aaatcgacgc tcaagtcaga    300
ggtggcgaaa cccgacagga ctataaagat accaggcgtt tcccctggaa gctccctcg     360 tgcgctctcc tgttccgacc ctgccgctta ccggatacct gtccgccttt ctcccttcgg    420
gaagcgtggc gctttctcat agctcacgct gtaggtatct cagttcggtg taggtcgttc    480
gctccaagct gggctgtgtg cacgaacccc ccgttcagcc cgaccgctgc gccttatccg    540
gtaactatcg tcttgagtcc aacccggtaa gacacgactt atcgccactg gcagcagcca    600
```

```
ctggtaacag gattagcaga gcgaggtatg taggcggtgc tacagagttc ttgaagtggt      660
ggcctaacta cggctacact agaagaacag tatttggtat ctgcgctctg ctgaagccag      720
ttaccttcgg aaaagagtt ggtagctctt gatccggcaa acaaaccacc gctggtagcg       780
gtggtttttt tgtttgcaag cagcagatta cgcgcagaaa aaaggatct caagaagatc       840 ctttgatctt ttctacgggg tctgacgctc tattcaacaa agccgccgtc ccgtcaagtc      900
agcgtaaatg ggtaggggc ttcaaatcgt ccgctctgcc agtgttacaa ccaattaaca       960
aattctgatt agaaaactc atcgagcatc aaatgaaact gcaatttatt catatcagga       1020
ttatcaatac catatttttg aaaagccgt ttctgtaatg aaggagaaaa ctcaccgagg       1080
cagttccata ggatggcaag atcctggtat cggtctgcga ttccgactcg tccaacatca     1140
atacaaccta ttaatttccc ctcgtcaaaa ataaggttat caagtgagaa ataccatga     1200 gtgacgactg aatccggtga atggcaaa agcttatgca tttctttcca gacttgttca      1260
acaggccagc cattacgctc gtcatcaaa tcactcgcat caaccaaacc gttattcatt     1320
cgtgattgcg cctgagcgag acgaaatacg cgatcgctgt aaaaggaca attacaaaca     1380 ggaatcgaat gcaaccggcg caggaacact gccagcgcat caacaatatt ttcacctgaa   1440
tcaggatatt cttctaatac ctggaatgct gttttcccgg ggatcgcagt ggtgagtaac     1500
catgcatcat caggagtacg gataaaatgc ttgatggtcg aagaggcat aaattccgtc    1560 agccagttta gtctgaccat ctcatctgta acatcattgg caacgctacc tttgccatgt    1620
ttcagaaaca actctggcgc atcgggcttc ccatacaatc gatagattgt cgcacctgat   1680
tgcccgacat tatcgcgagc ccatttatac ccatataaat cagcatccat gttggaattt    1740
aatcgcggcc tcgagcaaga cgtttcccgt tgaatatggc tcataacacc ccttgtatta    1800
ctgtttatgt aagcagacag ttttattgtt catgatgata tatttttatc ttgtgcaatg     1860
taacatcaga gattttgaga cacaacgtgg ctttcccccg ccgctctaga actagtggat   1920
ccaaataaaa cgaaggctc agtcgaaaga ctgggccttt cgttttatct gttgtttgtc    1980
gcattatacg agacgtccag gttgggatac ctgaaacaaa acccatcgta cggccaagga   2040
agtctccaat aactgtgatc caccacaagc gccagggttt tcccagtcac gacgttgtaa    2100
aacgacggcc agtcatgcat aatccgcacg catctggaat aaggaagtgc cattccgcct    2160
gacctgatcc caatattaca cccaagtagc atgcataagc taaagtaac tcgcagcgca   2220 caccgtgcag attcataagt ctatgattaa ttgaacgcca ataacccggc ttactacaag    2280
tacaagtagg tatacatagc ggtaatgaat cattagaaaa ataaaaaaca aaaaaaaca    2340 aaacaaactg ttgtggatgc atcaacagta gtacatagtt gtacgatgta cttgtacttg    2400
taaaagcaaa aatgtacaat atctcaggga gcgcaacttt tacgttcgaa gaacaatgta   2460
ccgcataccg cattctagat tctgcggaac gtctaacctg gaaatacgat ttttttatttc  2520 tttcatttt tttgcttctt caaaagtatg gtaatttcct accattacag ttgacactga     2580
acgagggggg attgaattta gcaaaaaat taaatcaaaa tacctttatg tatccagccc     2640
atgtaataaa caaaaggatt atataacaag aaataaatat atacctttaa tggatcatta   2700 gaataaaat aaatacgaga agcacaccag agaagcttt tgattgccac tataccgcta    2760
ctttggtata tcttattata attgttgaat ttgcaagata gaatgtcatt cattggagag     2820
aaatccaagg aatatgtggg atgaaatgac tagaagtatg aacatgaga atagtacata     2880 cttgtacctg tatttctaga agagagaaag acagttgagt gtgtgattct cgtccaataa    2940
taatctcaat agtaacgtgt gaatagctgt tctttgatag ttgatatttc tcgatgacta    3000
```

```
tttatgttgt acaagggatt tttttcgttg ctgttgattt cgaattaggc aatgcagata   3060
tcatttatgc tatccatatt taagatttcc catacgcatt tataacattt attctacata   3120
aattgttaaa tgaacgaact gccattataa attgtttcct aaataggaag tgtttttcat   3180
aaagcaagta agttgtctaa taatactaag taataaaaat aagttcatac aatatatttt   3240
gagaacatca tttggaggcg gtagatggag tctgtttatt attaaacaat gcgagatgac   3300
cccttaaata ttgagaacat cagttggagg cggcagatgg agtctgtcta tttagcaatg   3360
ggacatgact gtcagtatca tcatatgtat atatataata catataatat tatataacac   3420 gatttttta aattattggc ccgaaaatta atcagtgtag actggatcct cgagaaccat   3480
ttaattaaga tcagagaccg gatggtctca agcgtcgaca ccatatcata taaaactaac   3540
aatgcattga attaatacga agactacccg ttgctatctc cacaccgtta tctccacggt   3600
ccaaaggctg ctcaatgtgc tgcatacgta acgtggggtg caaccttgag cacatagtac   3660
tttccgaaaa ccggcgataa ttaagtgtgc actccaactt ttcacactga cataaaatg    3720 tggagaagaa atcacactaa aaagtcaggt agactggaaa atgcgccatg aaataatatc   3780
tcttgctaca gtaatgccca gcatcgaggg gtattgtgtc accaacacta tagtggcagc   3840
tgaagcgctc gtgattgtag tatgagtctt tattggtgat gggaagagtt cactcaatat   3900
tctcgttact gccaaaacac cacggtaatc ggccagacac catggatgta gatcaccaag   3960
cctgtgaatg ttattcgagc taaaatgcac atggttggtg aaaggagtag ttgctgtcga   4020
attccgtcgt cgcctgagtc atcatttatt taccagttgg ccacaaaccc ttgacgatct   4080
cgtatgtccc ctccgacata ctcccggccg gctgggtac gttcgatagc gctatcggca    4140
tcgacaaggt ttgggtccct agccgatacc gcactacctg agtcacaatc ttcggaggtt   4200
tagtcttcca catagcacgg gcaaaagtgc gtatatatac aagagcgttt gccagccaca   4260
gattttcact ccacacacca catcacacat acaaccacac acatccacaa tggaacccga   4320
aactaagaag accaagactg actccaagaa gattgttctt ctcggcggcg acttctgtgg   4380
ccccgaggtg attgccgagg ccgtcaaggt gctcaagtct gttgctgagg cctccggcac   4440
cgagtttgtg tttgaggacc gactcattgg aggagctgcc attgagaagg agggcgagcc   4500
catcaccgac gctactctcg acatctgccg aaaggctgac tctattatgc tcggtgctgt   4560
cggaggcgct gccaacaccg tatggaccac tcccgacgga cgaaccgacg tgcgacccga   4620
gcagggtctt ctcaagctgc gaaaggacct gaacctgtac gccaacctgc gaccctgcca   4680
gctgctgtcg cccaagctcg ccgatctctc ccccatccga aacgttgagg gcaccgactt   4740
catcattgtc cgagagctcg tcggaggtat ctactttgga gagcgaaagg aggatgacgg   4800
atctggcgtc gcttccgaca ctgagactta ctccgttcct gaggttgagc gaattgcccg   4860
aatggccgcc ttcctggccc ttcagcacaa ccccctctt cccgtgtggt cccttgacaa    4920
ggccaacgtg ctggcctcct ctcgactttg gcgaaagacc gtcacccgag tcctcaagga   4980
cgaattcccc cagctggagc tcaaccacca gctgatcgac tcggccgcca tgatcctcat   5040
caagcagccc tccaagatga atggtatcat catcaccacc aacatgtttg gcgatatcat   5100
ctccgacgag gcctccgtca tccccggttc tctgggtctg ctgccctccg cctctctggc   5160
ttctctgccc gacaccaacg aggcgttcgg tctgtacgag ccctgtcacg atctgccccc   5220
cgatctcggc aagcagaagg tcaacccat gccaccatt ctgtctgccg ccatgatgct    5280
caagttctct cttaacatga agcccgccgg tgacgctgtt gaggctgccg tcaaggagtc   5340
```

-continued

| | |
|---|---|
| cgtcgaggct ggtatcacta ccgccgatat cggaggctcc tcctccacct ccgaggtcgg | 5400 |
| agactttgtt gccaacaagg tcaaggagct gctcaagaag gagtaagtcg tttctacgac | 5460 |
| gcattgatgg aaggagcaaa ctgacgcgcc tgcgggttgg tctaccggca gggtccgcta | 5520 |
| gtgtataaga ctctataaaa agggcccagc cctgctaatg aaatgatgat ttataattta | 5580 |
| ccggtgtagc aaccttgact agaagaagca gattgggtgt gtttgtagtg gaggacagtg | 5640 |
| gtacgtttta attaa | 5655 |

<210> SEQ ID NO 178
<211> LENGTH: 4664
<212> TYPE: DNA
<213> ORGANISM: Artificial Sequence
<220> FEATURE:
<223> OTHER INFORMATION: pLD138

<400> SEQUENCE: 178

| | |
|---|---|
| aggctaggtg gaggctcagt gatgataagt ctgcgatggt ggatgcatgt gtcatggtca | 60 |
| tagctgtttc ctgtgtgaaa ttgttatccg ctcagagggc acaatcctat tccgcgctat | 120 |
| ccgacaatct ccaagacatt aggtggagtt cagttcggcg tatggcatat gtcgctggaa | 180 |
| agaacatgtg agcaaaaggc cagcaaaagg ccaggaaccg taaaaaggcc gcgttgctgg | 240 |
| cgttttccca taggctccgc cccccctgacg agcatcacaa aaatcgacgc tcaagtcaga | 300 |
| ggtggcgaaa cccgacagga ctataaagat accaggcgtt tccccctgga agctccctcg | 360 |
| tgcgctctcc tgttccgacc ctgccgctta ccggatacct gtccgccttt ctcccttcgg | 420 |
| gaagcgtggc gctttctcat agctcacgct gtaggtatct cagttcggtg taggtcgttc | 480 |
| gctccaagct gggctgtgtg cacgaacccc ccgttcagcc cgaccgctgc gccttatccg | 540 |
| gtaactatcg tcttgagtcc aacccggtaa gacacgactt atcgccactg gcagcagcca | 600 |
| ctggtaacag gattagcaga gcgaggtatg taggcggtgc tacagagttc ttgaagtggt | 660 |
| ggcctaacta cggctacact agaagaacag tatttggtat ctgcgctctg ctgaagccag | 720 |
| ttaccttcgg aaaaagagtt ggtagctctt gatccggcaa acaaaccacc gctggtagcg | 780 |
| gtggtttttt tgtttgcaag cagcagatta cgcgcagaaa aaaaggatct caagaagatc | 840 |
| ctttgatctt ttctacgggg tctgacgctc tattcaacaa agccgccgtc ccgtcaagtc | 900 |
| agcgtaaatg ggtaggggc ttcaaatcgt ccgctctgcc agtgttacaa ccaattaaca | 960 |
| aattctgatt agaaaaactc atcgagcatc aaatgaaact gcaatttatt catatcagga | 1020 |
| ttatcaatac catattttg aaaaagccgt ttctgtaatg aaggagaaaa ctcaccgagg | 1080 |
| cagttccata ggatggcaag atcctggtat cggtctgcga ttccgactcg tccaacatca | 1140 |
| atacaaccta ttaatttccc ctcgtcaaaa ataaggttat caagtgagaa atcaccatga | 1200 |
| gtgacgactg aatccggtga gaatggcaaa agcttatgca tttctttcca gacttgttca | 1260 |
| acaggccagc cattacgctc gtcatcaaaa tcactcgcat caaccaaacc gttattcatt | 1320 |
| cgtgattgcg cctgagcgag acgaaatacg cgatcgctgt taaaaggaca attacaaaca | 1380 |
| ggaatcgaat gcaaccggcg caggaacact gccagcgcat caacaatatt tcacctgaa | 1440 |
| tcaggatatt cttctaatac ctggaatgct gttttcccgg ggatcgcagt ggtgagtaac | 1500 |
| catgcatcat caggagtacg gataaaatgc ttgatggtcg gaagaggcat aaattccgtc | 1560 |
| agccagttta gtctgaccat ctcatctgta acatcattgg caacgctacc tttgccatgt | 1620 |
| ttcagaaaca actctggcgc atcgggcttc ccatacaatc gatagattgt cgcacctgat | 1680 |
| tgcccgacat tatcgcgagc ccatttatac ccatataaat cagcatccat gttggaattt | 1740 |

```
aatcgcggcc tcgagcaaga cgtttcccgt tgaatatggc tcataacacc ccttgtatta   1800
ctgtttatgt aagcagacag tttttattgtt catgatgata tattttttatc ttgtgcaatg  1860 taacatcaga gattttgaga cacaacgtgg cttttccccg ccgctctaga actagtggat   1920
ccaaataaaa cgaaaggctc agtcgaaaga ctgggccttt cgttttatct gttgtttgtc   1980
gcattatacg agacgtccag gttgggatac ctgaaacaaa acccatcgta cggccaagga   2040
agtctccaat aactgtgatc caccacaagc gccagggttt tcccagtcac gacgttgtaa   2100
aacgacggcc agtcatgcat aatccgcacg catctggaat aaggaagtgc cattccgcct   2160
gacctgatcc caatattaca cccaagtagc atgcataagc taaaagtaac tcgcagcgca   2220
caccgtgcag attcataagt ctatgattaa ttgaacgcca ataacccggc ttactacaag   2280
tacaagtagg tatacatagc ggtaatgaat cattagaaaa ataaaaaaca aaaaaaaaca   2340
aaacaaactg ttgtggatgc atcaacagta gtacatagtt gtacgatgta cttgtacttg   2400
taaaagcaaa aatgtacaat atctcaggga gcgcaacttt tacgttcgaa gaacaatgta   2460
ccgcataccg cattctagat tctgcggaac gtctaacctg gaaatacgat ttttttatttc  2520 tttcattttt tttgcttctt caaaagtatg gtaatttcct accattacag ttgacactga   2580
acgagggggg attgaattta agcaaaaaat taaatcaaaa tacctttatg tatccagccc   2640
atgtaataaa caaaggatt atataacaag aaataaatat ataccttaa tggatcatta   2700 gaataaaaat aaatacgaga agcacaccag agaagctttt tgattgccac tataccgcta   2760 cttttggtata tcttattata attgttgaat ttgcaagata gaatgtcatt cattggagag   2820
aaatccaagg aatatgtggg atgaaatgac tagaagtatg aacaatgaga atagtacata   2880
cttgtacctg tatttctaga agagagaaag acagttgagt gtgtgattct cgtccaataa   2940
taatctcaat agtaacgtgt gaatagctgt tctttgatag ttgatatttc tcgatgacta   3000
tttatgttgt acaagggatt tttttcgttg ctgttgattt cgaattaggc aatgcagata   3060
tcatttatgc tatccatatt taagatttcc catacgcatt tataacattt attctacata   3120
aattgttaaa tgaacgaact gccattataa attgttttcct aaataggaag tgttttttcat 3180 aaagcaagta agttgtctaa taatactaag taataaaaat aagttcatac aatatatttt   3240
gagaacatca tttggaggcg gtagatggag tctgtttatt attaaacaat gcgagatgac   3300
cccttaaata ttgagaacat cagttggagg cggcagatgg agtctgtcta tttagcaatg   3360
ggacatgact gtcagtatca tcatatgtat atatataata catataatat tatataacac   3420 gatttttttta aattattggc ccgaaaatta atcagtgtag actggatcct cgagaaccat  3480
ttaattaatt tctaatttgg accgatagcc gtatagtcca gtctatctat aagttcaact   3540
aactcgtaac tattaccata acatatactt cactgcccca gataaggttc cgataaaaag   3600
ttgtgcagac taaatttatt tcagtctcct cttcaccacc aaaatgccct cctacgaagc   3660
gcgagctaac gtccacaagt ccgcctttgc cgcccgagtg ctcaagctcg tggcagccaa   3720
gaaaaccaac ctgtgtgctt ctctggatgt taccaccacc aaggagctca ttgagcttgc   3780
cgataaggtc ggaccttatg tgtgcatgat caagacccat atcgacatca ttgacgactt   3840
cacctacgcc ggaactgtgc tcccctcaa ggaacttgct cttaagcacg gtttcttcct   3900
gttcgaggac agaaagttcg cagatattgg caacactgtc aagcaccagt acaagaacgg   3960
tgtctaccga atcgccgagt ggtccgatat caccaacgcc cacggtgtac ccggaaccgg   4020
aatcattgct ggcctgcgag ctggtgccga ggaaactgtc tctgaacaga agaaggagga   4080
```

```
tgtctctgac tacgagaact cccagtacaa ggagttcctg gtcccctctc ccaacgagaa    4140
gctggccaga ggtctgctca tgctggccga gctgtcttgc aagggctctc tggccactgg    4200
cgagtactcc aagcagacca ttgagcttgc ccgatccgac cccgagtttg tggttggctt    4260
cattgcccag aaccgaccta agggcgactc tgaggactgg cttattctga cccccggggt    4320
gggtcttgac gacaagggag atgctctcgg acagcagtac cgaactgttg aggatgtcat    4380
gtctaccgga acggatatca taattgtcgg ccgaggtctg tacggccaga accgagatcc    4440
tattgaggag gccaagcgat accagaaggc tggctgggag gcttaccaga agattaactg    4500
ttagaggtta gactatggat atgtcattta actgtgtata tagagagcgt gcaagtatgg    4560
agcgcttgtt cagcttgtat gatggtcaga cgacctgtct gatcgagtat gtatgatact    4620
gcacaacctg cgcttgagac catccggtct ctgatcttaa ttaa                    4664
```

<210> SEQ ID NO 179
<211> LENGTH: 5975
<212> TYPE: DNA
<213> ORGANISM: Artificial Sequence
<220> FEATURE:
<223> OTHER INFORMATION: pLD139

<400> SEQUENCE: 179

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtgggggttg gatgataaag gcgatgcgtt gggccagcag tataggactg     600
ttgatgaggt ggttctgact ggtaccgatg tgattattgt cgggagaggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg gatggtggtt agtgcgttcc tgacaaaccc     900
agagtacgcc gcctcaaacc acgtcacatt cgccctttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga attttttgcac    1320 acacaccgat taacatttcc cttttttgtc caccgataca cgcttgcctc ttcttattt     1380 ctctgtgctt ccccctcctg tgacttttc caccattgat ataaaatcaa ctccatttcc    1440
ctaaaatctc cccagattct aaaaacaact tcttctcttc tgctttttcct tatttttgtt    1500
```

```
atatttattt accatccctt attttgaata gttattcccc actaacattg ttcaaatctt    1560
cacgacataa tgaacccaag ggaaaacttc cttaagtgtt ttctgcagta catccctaac    1620
aatgcaacaa acctcaagtt ggtgtacact caaaacaatc cactctatat gagcgtgctt    1680
aatagcacaa tccacaactt cgcgcttcacg tcagatacta cgcctaagcc actagtgatc   1740
gttacaccat cacacgtcag ccatattcaa ggaacgatcc tatgtctgaa aaggtcggg    1800 ttgcaaatca ggactcgatc aggagggcac gatagtgagg gaatgagtta catctcgcaa    1860
gtacccttcg tgatagttga cttgcgaaat atgcggtcta ttaaaattga cgtacatagc    1920
cagaccgcct gggttgaagc aggggcaacc ttgggtgaag tttattactg ggtcaatgaa    1980
aaaaacgaaa acctaagtct tgctgctgga tattgcccca ccgtttgcgc gggtggtcat    2040
tttggaggcg gcggatatgg tccgttgatg agaaattatg gacttgcagc agacaatatt    2100
atagatgccc acttggtgaa cgttcatgga aaggtcttgg accgtaagtc catgggtgaa    2160
gatcttttct gggccttgag aggtggtgga gcggaatcgt ttggcatcat cgttgcctgg    2220
aaaattaggt tggttgcggt cccgaagagt acaatgttct ccgtgaagaa gattatggaa    2280
atacatgagc ttgtcaagtt agttaacaag tggcaaaata tcgcttataa gtatgataaa    2340
gacttgcttt tgatgactca ttttattacg cgaaacataa ccgataacca gggcaagaac    2400
aagactgcta ttcacacgta cttctcctct gtatttcttg gaggagtaga ctccttagtt    2460
gacttgatga acaagagttt cccagaattg gggattaaga agacagattg cagacaatta    2520
tcgtggatag atacaatcat attctatagc ggtgtcgtca attacgatac tgataaatttt   2580 aataaagaaa tcctcctaga tcgttcagct gggcaaaacg gggcattcaa aattaaattg    2640
gattatgtga agaaaccaat tccagagctg gtgtttgttc agatattgga aaaactttac    2700
gaagaagaca ttggcgcagg tatgtacgct ttgtatccat atggaggcat tatggacgag    2760
atctcagagc tggcgatccc cttcccgcac agagctggga tactctacga gctatggtac    2820
atctgctctt gggagaaaca agaagacaac gagaaacatc tcaattggat tcggaacata    2880
tacaacttta tgacccccata cgtatcaaaa acccgcgct tagcatactt gaattacaga    2940
gacttagata tcggtatcaa tgatcctaag aatcctaaca attacaccca agcccgtatt    3000
tggggtgaga atatttcgg caagaatttt gacagattag ttaaggtcaa aacactcgtg    3060
gaccccaaca acttttttccg aaacgagcag tcgattccac cactacccag gcatagacac    3120
ggaagaaggg caaagttgta agagtgactc ttttgataag agtcgcaaat ttgatttcat    3180
aagtatatat tcattatgta aagtagtaaa tggaaaattc attaaaaaaa agcaaatttt    3240
ccgttgtatg catactccga acacaaaact agccccggaa aaacccttag ttgatagttg    3300
cgaatttagg tcgaccatat gcgacgggta caacgagaat tgtattgaat tgatcaagaa    3360
catgatcttg gtgttacaga acatcaagtt cttggaccag actgagaatg cacagatata    3420
caaggcgtca tgtgataaaa tggatgagat ttatccacaa ttgaagaaag agtttatgga    3480
aagtggtcaa ccagaagcta acaggaaga agcaaacgaa gaggtgaaac aagaagaaga    3540
aggtaaataa gtattttgta ttatataaca aacaaagtaa ggaatacaga tttatacaat    3600
aaattgccat actagtcacg tgagatatct catccattcc ccaactccca agaaaataaa    3660
aaagtgaaaa ataaaatcaa acccaaagat caacctcccc atcatcatcg tcatcaaacc    3720
cccagctcaa ttcgcaatgg ttagcacaaa aacatacaca gaaagggcat cagcacaccc    3780
ctccaaggtt gcccaacgtt tattaattaa aggctaggtg gaggctcagt gatgataagt    3840
```

```
ctgcgatggt ggatgcatgt gtcatggtca tagctgtttc ctgtgtgaaa ttgttatccg    3900
ctcagagggc acaatcctat tccgcgctat ccgacaatct ccaagacatt aggtggagtt    3960
cagttcggcg tatggcatat gtcgctggaa agaacatgtg agcaaaaggc cagcaaaagg    4020
ccaggaaccg taaaaaggcc gcgttgctgg cgttttttcca taggctccgc cccctgacg    4080
agcatcacaa aaatcgacgc tcaagtcaga ggtggcgaaa cccgacagga ctataaagat    4140
accaggcgtt tccccctgga agctccctcg tgcgctctcc tgttccgacc ctgccgctta    4200
ccggatacct gtccgccttt ctcccttcgg gaagcgtggc gctttctcat agctcacgct    4260
gtaggtatct cagttcggtg taggtcgttc gctccaagct gggctgtgtg cacgaacccc    4320
ccgttcagcc cgaccgctgc gccttatccg gtaactatcg tcttgagtcc aacccggtaa    4380
gacacgactt atcgccactg gcagcagcca ctggtaacag gattagcaga gcgaggtatg    4440
taggcggtgc tacagagttc ttgaagtggt ggcctaacta cggctacact agaagaacag    4500
tatttggtat ctgcgctctg ctgaagccag ttaccttcgg aaaaagagtt ggtagctctt    4560
gatccggcaa acaaaccacc gctggtagcg gtggtttttt tgtttgcaag cagcagatta    4620
cgcgcagaaa aaaaggatct caagaagatc ctttgatctt ttctacgggg tctgacgctc    4680
tattcaacaa agccgccgtc ccgtcaagtc agcgtaaatg ggtaggggc ttcaaatcgt    4740
ccgctctgcc agtgttacaa ccaattaaca aattctgatt agaaaaactc atcgagcatc    4800
aaatgaaact gcaatttatt catatcagga ttatcaatac catattttg aaaaagccgt    4860
ttctgtaatg aaggagaaaa ctcaccgagg cagttccata ggatggcaag atcctggtat    4920
cggtctgcga ttccgactcg tccaacatca atacaaccta ttaatttccc ctcgtcaaaa    4980
ataaggttat caagtgagaa atcaccatga gtgacgactg aatccggtga gaatggcaaa    5040
agcttatgca tttctttcca gacttgttca acaggccagc cattacgctc gtcatcaaaa    5100
tcactcgcat caaccaaacc gttattcatt cgtgattgcg cctgagcgag acgaaatacg    5160
cgatcgctgt taaaaggaca attacaaaca ggaatcgaat gcaaccggcg caggaacact    5220
gccagcgcat caacaatatt ttcacctgaa tcaggatatt cttctaatac ctggaatgct    5280
gttttcccgg ggatcgcagt ggtgagtaac catgcatcat caggagtacg gataaaatgc    5340
ttgatggtcg aagaggcat aaattccgtc agccagttta gtctgaccat ctcatctgta    5400
acatcattgg caacgctacc tttgccatgt ttcagaaaca actctggcgc atcgggcttc    5460
ccatacaatc gatagattgt cgcacctgat tgcccgacat tatcgcgagc ccatttatac    5520
ccatataaat cagcatccat gttggaattt aatcgcggcc tcgagcaaga cgtttcccgt    5580
tgaatatggc tcataacacc ccttgtatta ctgtttatgt aagcagacag ttttattgtt    5640
catgatgata tatttttatc ttgtgcaatg taacatcaga gattttgaga cacaacgtgg    5700
ctttcccccg ccgctctaga actagtggat ccaaataaaa cgaaaggctc agtcgaaaga    5760
ctgggccttt cgttttatct gttgtttgtc gcattatacg agacgtccag gttgggatac    5820
ctgaaacaaa acccatcgta cggccaagga agtctccaat aactgtgatc cacccacaagc    5880
gccagggttt tcccagtcac gacgttgtaa aacgacggcc agtcatgcat aatccgcacg    5940
catctggaat aaggaagtgc cattccgcct gacct                                5975
```

<210> SEQ ID NO 180
<211> LENGTH: 5594
<212> TYPE: DNA
<213> ORGANISM: Artificial Sequence
<220> FEATURE:
<223> OTHER INFORMATION: pLD19

<400> SEQUENCE: 180

```
ttaattaatt ccgcttaatg gagtccaaaa agaccaacct ctgcgcctcg atcgacgtga      60
ccacaaccgc cgagttcctt tcgctcatcg acaagctcgg tccccacatc tgtctcgtga     120
agacgcacat cgatatcatc tcagacttca gctacgaggg cacgattgag ccgttgcttg     180
tgcttgcaga gcgccacggg ttcttgatat tcgaggacag gaagtttgct gatatcggaa     240
acaccgtgat gttgcagtac acctcggggg tataccggat cgcggcgtgg agtgacatca     300
cgaacgcgca cggagtgact gggaagggcg tcgttgaagg gttgaaacgc ggtgcggagg     360
gggtagaaaa ggaaggggc gtgttgatgt tggcggagtt gtcgagtaaa ggctcgttgg     420
cgcatggtga atatacccgt gagacgatcg agattgcgaa gagtgatcgg gagttcgtga     480
ttgggttcat cgcgcagcgg gacatggggg gtagagaaga agggtttgat tggatcatca     540
tgacgcctgg tgtggggttg gatgataaag gcgatgcgtt gggccagcag tataggactg     600
ttgatgaggt ggttctgact ggtaccgatg tgattattgt cggagagggg ttgtttggaa     660
aaggaagaga ccctgaggtg gagggaaaga gatacaggga tgctggatgg aaggcatact     720
tgaagagaac tggtcagtta gaataaatat tgtaataaat aggtctatat acatacacta     780
agcttctagg acgtcattgt agtcttcgaa gttgtctgct agtttagttc tcatgatttc     840
gaaaaccaat aacgcaatgg atgtagcagg atggtggtt agtgcgttcc tgacaaaccc     900
agagtacgcc gcctcaaacc acgtcacatt cgcccttgc ttcatccgca tcacttgctt     960
gaaggtatcc acgtacgagt tgtaatacac cttgaagaac ggcttcgtct agttcggcat    1020
ggcagatcat catgcctgca ggagctccaa ttgtaatatt tcgggagaaa tatcgttggg    1080
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaattgtct gagttgtgtc    1260
ttagctactg gctggccccc cgcgaaagat aatcaaaatt acacttgtga atttttgcac    1320
acacaccgat taacatttcc cttttttgtc caccgataca cgcttgcctc ttcttatttt    1380
ctctgtgctt cccctcctg tgacttttc caccattgat ataaaatcaa ctccatttcc    1440
ctaaaatctc cccagattct aaaaacaact tcttctcttc tgcttttcct tattttttgtt    1500
atatttattt accatccctt attttgaata gttattcccc actaacattg ttcaaatctt    1560
cacgacataa tgggtttatc gtcagtgtgc acttttttctt ttcaaacaaa ctaccacacc    1620
ctcctaaacc ctcacaataa taacccaaaa acctccttgc tatgttacag acatccaaag    1680
acaccgatca agtattcata caacaatttt cccagtaaac attgctcaac gaagtccttc    1740
cacttgcaaa acaaatgcag cgaatcattg tcgatagcta aaaactcgat acgtgcggca    1800
accactaacc aaactgagcc accagagagc gataatcatt cagtcgccac caagattttg    1860
aactttggaa aagcctgttg gaaacttcaa aggccttaca ccattatcgc atttaccagt    1920
tgcgcatgtg gtttgttcgg gaaggaatta ttacacaaca caaatttgat cagctggagc    1980
ctaatgttta aggcattttt cttcttagtt gcaattttgt gtatagcttc gtttacaacg    2040
accattaatc agatttacga ccttcacatc gatcggatca ataaaccaga cttgcccctt    2100
gcctctgggg aaatctctgt aaatactgca tggatcatgc tgataatcgt ggctttgttt    2160
ggattgatta ttacaattaa gatgaagggg ggtccattat atatattcgg gtactgcttc    2220
ggcattttcg gtggtatcgt ttactccgtc ccacccttta gatggaaaca gaaccccagt    2280
```

```
acggcctttc tactcaattt cttggctcat atcatcacaa acttcacatt ctattatgca    2340
agccgagcgg cgcttggttt gccgttcgaa ctcagaccga gttttacatt tctccttgcc    2400
ttcatgaaac tgatgggact ggcccttgca ttgatcaagg atgcgtcaga tgtcgaaggc    2460
gacactaagt tcggcattct gacgcttgct tccaagtatg gaagtagaaa tctaacgctt    2520
ttttgttcag gaatagtgct acttagttat gttgctgcta tactcgctgg cattatttgg    2580
cctcaggcct tcaactctaa cgtaatgttg ttatcccatg ctattttggc gttctggttg    2640
atcttgcaaa cgcgagattt tgcactcact aactacgacc cagaggcagg aaggcgcttt    2700
tacgagttta tgtggaagtt gtattatgcc gaatacttgg tttatgtttt catttgataa    2760
gagtgactct tttgataaga gtcgcaaatt tgatttcata agtatatatt cattatgtaa    2820
agtagtaaat ggaaaattca ttaaaaaaaa agcaaatttc cgttgtatgc atactccgaa    2880
cacaaaacta gccccggaaa aacccttagt tgatagttgc gaatttaggt cgaccatatg    2940
cgacgggtac aacgagaatt gtattgaatt gatcaagaac atgatcttgg tgttacagaa    3000
catcaagttc ttggaccaga ctgagaatgc acagatatac aaggcgtcat gtgataaaat    3060
ggatgagatt tatccacaat tgaagaaaga gtttatggaa agtggtcaac cagaagctaa    3120
acaggaagaa gcaaacgaag aggtgaaaca agaagaagaa ggtaaataag tattttgtat    3180
tatataacaa acaaagtaag gaatacagat ttatacaata aattgccata ctagtcacgt    3240
gagatatctc atccattccc caactcccaa gaaaataaaa aagtgaaaaa taaaatcaaa    3300
cccaaagatc aacctcccca tcatcatcgt catcaaaccc ccagctcaat tcgcaatggt    3360
tagcacaaaa acatacacag aaagggcatc agcacacccc tccaaggttg cccaacgttt    3420
attaattaaa ggctaggtgg aggctcagtg atgataagtc tgcgatggtg gatgcatgtg    3480
tcatggtcat agctgtttcc tgtgtgaaat tgttatccgc tcagagggca caatcctatt    3540
ccgcgctatc cgacaatctc caagacatta ggtggagttc agttcggcgt atggcatatg    3600
tcgctggaaa gaacatgtga gcaaaaggcc agcaaaaggc caggaaccgt aaaaaggccg    3660
cgttgctggc gttttttcat aggctccgcc cccctgacga gcatcacaaa aatcgacgct    3720
caagtcagag gtggcgaaac ccgacaggac tataaagata ccaggcgttt ccccctggaa    3780
gctccctcgt gcgctctcct gttccgaccc tgccgcttac cggatacctg tccgcctttc    3840
tcccttcggg aagcgtggcg ctttctcata gctcacgctg taggtatctc agttcggtgt    3900
aggtcgttcg ctccaagctg ggctgtgtgc acgaaccccc cgttcagccc gaccgctgcg    3960
ccttatccgg taactatcgt cttgagtcca acccggtaag acacgactta tcgccactgg    4020
cagcagccac tggtaacagg attagcagag cgaggtatgt aggcggtgct acagagttct    4080
tgaagtggtg gcctaactac ggctacacta gaagaacagt attggtatc tgcgctctgc    4140 tgaagccagt taccttcgga aaaagagttg gtagctcttg atccggcaaa caaaccaccg    4200
ctggtagcgg tggttttttt gtttgcaagc agcagattac gcgcagaaaa aaaggatctc    4260
aagaagatcc tttgatcttt tctacggggt ctgacgctct attcaacaaa gccgccgtcc    4320
cgtcaagtca gcgtaaatgg gtagggggct tcaaatcgtc cgctctgcca gtgttacaac    4380
caattaacaa attctgatta gaaaaactca tcgagcatca aatgaaactg caatttattc    4440
atatcaggat tatcaatacc atattttga aaaagccgtt tctgtaatga aggagaaaac    4500
tcaccgaggc agttccatag gatggcaaga tcctggtatc ggtctgcgat tccgactcgt    4560
ccaacatcaa tacaacctat taatttcccc tcgtcaaaaa taaggttatc aagtgagaaa    4620
tcaccatgag tgacgactga atccggtgag aatggcaaaa gcttatgcat ttctttccag    4680
```

```
acttgttcaa caggccagcc attacgctcg tcatcaaaat cactcgcatc aaccaaaccg      4740
ttattcattc gtgattgcgc ctgagcgaga cgaaatacgc gatcgctgtt aaaaggacaa      4800
ttacaaacag gaatcgaatg caaccggcgc aggaacactg ccagcgcatc aacaatattt      4860
tcacctgaat caggatattc ttctaatacc tggaatgctg ttttcccggg gatcgcagtg      4920
gtgagtaacc atgcatcatc aggagtacgg ataaaatgct tgatggtcgg aagaggcata      4980
aattccgtca gccagtttag tctgaccatc tcatctgtaa catcattggc aacgctacct      5040
ttgccatgtt tcagaaacaa ctctggcgca tcgggcttcc catacaatcg atagattgtc      5100
gcacctgatt gcccgacatt atcgcgagcc catttatacc catataaatc agcatccatg      5160
ttggaattta atcgcggcct cgagcaagac gtttcccgtt gaatatggct cataacaccc      5220
cttgtattac tgtttatgta agcagacagt tttattgttc atgatgatat attttttatct      5280 tgtgcaatgt aacatcagag attttgagac acaacgtggc tttcccccgc cgctctagaa      5340
ctagtggatc caaataaaac gaaaggctca gtcgaaagac tgggcctttc gttttatctg      5400
ttgtttgtcg cattatacga gacgtccagg ttgggatacc tgaaacaaaa cccatcgtac      5460
ggccaaggaa gtctccaata actgtgatcc accacaagcg ccagggtttt cccagtcacg      5520
acgttgtaaa acgacggcca gtcatgcata tccgcacgc atctggaata aggaagtgcc      5580
attccgcctg acct                                                        5594

<210> SEQ ID NO 181
<211> LENGTH: 5372
<212> TYPE: DNA
<213> ORGANISM: Artificial Sequence
<220> FEATURE:
<223> OTHER INFORMATION: pLD26

<400> SEQUENCE: 181
ttaattaatt ccgcttaatg gagtccaaaa agaccaacct ctgcgcctcg atcgacgtga        60
ccacaaccgc cgagttcctt tcgctcatcg acaagctcgg tccccacatc tgtctcgtga       120
agacgcacat cgatatcatc tcagacttca gctacgaggg cacgattgag ccgttgcttg       180
tgcttgcaga gcgccacggg ttcttgatat tcgaggacag gaagtttgct gatatcggaa       240
acaccgtgat gttgcagtac acctcggggg tataccggat cgcggcgtgg agtgacatca       300
cgaacgcgca cggagtgact gggaagggcg tcgttgaagg gttgaaacgc ggtgcggagg       360
gggtagaaaa ggaaagggc gtgttgatgt tggcggagtt gtcgagtaaa ggctcgttgg       420
cgcatggtga atatacccgt gagacgatcg agattgcgaa gagtgatcgg gagttcgtga       480
ttgggttcat cgcgcagcgg gacatggggg gtagagaaga agggtttgat tggatcatca       540
tgacgcctgg tgtggggttg gatgataaag gcgatgcgtt gggccagcag tataggactg       600
ttgatgaggt ggttctgact ggtaccgatg tgattattgt cgggagaggg ttgtttggaa       660
aaggaagaga ccctgaggtg gagggaaaga gatacaggga tgctggatgg aaggcatact       720
tgaagagaac tggtcagtta gaataaatat tgtaataaat aggtctatat acatacacta       780
agcttctagg acgtcattgt agtcttcgaa gttgtctgct agtttagttc tcatgatttc       840
gaaaaccaat aacgcaatgg atgtagcagg atggtggtt agtgcgttcc tgacaaaccc       900
agagtacgcc gcctcaaacc acgtcacatt cgcccttgc ttcatccgca tcacttgctt       960
gaaggtatcc acgtacgagt tgtaatacac cttgaagaac ggcttcgtct agttcggcat      1020
ggcagatcat catgcctgca ggagctccaa ttgtaatatt tcgggagaaa tatcgttggg      1080
```

```
gtaaaacaac agagagagag agggagagat ggttctggta gaattataat ctggttgttg    1140
caaatgctac tgatcgactc tggcaatgtc tgtagctcgc tagttgtatg caacttaggt    1200
gttatgcata cacacggtta ttcggttgaa ttgtggagta aaaattgtct gagttgtgtc    1260
ttagctactg gctggccccc cgcgaaagat aatcaaaatt acacttgtga atttttgcac    1320
acacaccgat taacatttcc cttttttgtc caccgataca cgcttgcctc ttcttatttt    1380
ctctgtgctt cccctcctg tgacttttc caccattgat ataaaatcaa ctccatttcc    1440
ctaaaatctc cccagattct aaaaacaact tcttctcttc tgcttttcct tattttgtt    1500
atatttattt accatccctt attttgaata gttattcccc actaacattg ttcaaatctt    1560
cacgacataa tggcggcaac cactaaccaa actgagccac cagagagcga taatcattca    1620
gtcgccacca agattttgaa ctttggaaaa gcctgttgga aacttcaaag gccttacacc    1680
attatcgcat ttaccagttg cgcatgtggt ttgttcggga aggaattatt acacaacaca    1740
aatttgatca gctggagcct aatgtttaag gcatttttct tcttagttgc aattttgtgt    1800
atagcttcgt ttacaacgac cattaatcag atttacgacc ttcacatcga tcggatcaat    1860
aaaccagact tgccccttgc ctctggggaa atctctgtaa atactgcatg gatcatgctg    1920
ataatcgtgg ctttgtttgg attgattatt acaattaaga tgaaggggg tccattatat    1980
atattcgggt actgcttcgg cattttcggt ggtatcgttt actccgtccc cccctttaga    2040
tggaaacaga accccagtac ggcctttcta ctcaatttct tggctcatat catcacaaac    2100
ttcacattct attatgcaag ccgagcggcg cttggtttgc cgttcgaact cagaccgagt    2160
tttacatttc tccttgcctt catgaaactg atgggactgg cccttgcatt gatcaaggat    2220
gcgtcagatg tcgaaggcga cactaagttc ggcattctga cgcttgcttc caagtatgga    2280
agtagaaatc taacgctttt ttgttcagga atagtgctac ttagttatgt tgctgctata    2340
ctcgctggca ttatttggcc tcaggccttc aactctaacg taatgttgtt atcccatgct    2400
attttggcgt tctggttgat cttgcaaacg cgagattttg cactcactaa ctacgaccca    2460
gaggcaggaa ggcgctttta cgagtttatg tggaagttgt attatgccga atacttggtt    2520
tatgttttca tttgataaga gtgactcttt tgataagagt cgcaaatttg atttcataag    2580
tatatattca ttatgtaaag tagtaaatgg aaaattcatt aaaaaaaag caaatttccg    2640
ttgtatgcat actccgaaca caaaactagc cccggaaaaa cccttagttg atagttgcga    2700
atttaggtcg accatatgcg acgggtacaa cgagaattgt attgaattga tcaagaacat    2760
gatcttggtg ttacagaaca tcaagttctt ggaccagact gagaatgcac agatatacaa    2820
ggcgtcatgt gataaaatgg atgagattta tccacaattg aagaaagagt ttatggaaag    2880
tggtcaacca gaagctaaac aggaagaagc aaacgaagag gtgaaacaag aagaagaagg    2940
taaataagta ttttgtatta tataacaaac aaagtaagga atacagattt atacaataaa    3000
ttgccatact agtcacgtga gatatctcat ccattcccca actcccaaga aaataaaaaa    3060
gtgaaaaata aaatcaaacc caaagatcaa cctccccatc atcatcgtca tcaaacccccc    3120
agctcaattc gcaatggtta gcacaaaaac atacacagaa agggcatcag cacacccctc    3180
caaggttgcc caacgtttat taattaaagg ctaggtggag gctcagtgat gataagtctg    3240
cgatggtgga tgcatgtgtc atggtcatag ctgtttcctg tgtgaaattg ttatccgctc    3300
agagggcaca atcctattcc gcgctatccg acaatctcca agacattagg tggagttcag    3360
ttcggcgtat ggcatatgtc gctggaaaga acatgtgagc aaaaggccag caaaaggcca    3420
ggaaccgtaa aaaggccgcg ttgctggcgt ttttccatag gctccgcccc cctgacgagc    3480
```

```
atcacaaaaa tcgacgctca agtcagaggt ggcgaaaccc gacaggacta taaagatacc    3540
aggcgtttcc ccctggaagc tccctcgtgc gctctcctgt tccgaccctg ccgcttaccg    3600
gatacctgtc cgccttctc ccttcgggaa gcgtggcgct ttctcatagc tcacgctgta    3660
ggtatctcag ttcggtgtag gtcgttcgct ccaagctggg ctgtgtgcac gaaccccccg    3720
ttcagcccga ccgctgcgcc ttatccggta actatcgtct tgagtccaac ccggtaagac    3780
acgacttatc gccactggca gcagccactg gtaacaggat tagcagagcg aggtatgtag    3840
gcggtgctac agagttcttg aagtggtggc ctaactacgg ctacactaga agaacagtat    3900
ttggtatctg cgctctgctg aagccagtta ccttcggaaa agagttggt agctcttgat    3960 ccggcaaaca accaccgct ggtagcggtg ttttttttgt ttgcaagcag cagattacgc    4020
gcagaaaaaa aggatctcaa gaagatcctt tgatctttc tacggggtct gacgctctat    4080
tcaacaaagc cgccgtcccg tcaagtcagc gtaaatgggt aggggggcttc aaatcgtccg    4140 ctctgccagt gttacaacca attaacaaat tctgattaga aaaactcatc gagcatcaaa    4200
tgaaactgca atttattcat atcaggatta tcaataccat attttgaaa aagccgtttc    4260 tgtaatgaag gagaaaactc accgaggcag ttccatagga tggcaagatc ctggtatcgg    4320
tctgcgattc cgactcgtcc aacatcaata aacctatta atttcccctc gtcaaaata    4380 aggttatcaa gtgagaaatc accatgagtg acgactgaat ccggtgagaa tggcaaaagc    4440
ttatgcattt ctttccagac ttgttcaaca ggccagccat tacgctcgtc atcaaaatca    4500
ctcgcatcaa ccaaaccgtt attcattcgt gattgcgcct gagcgagacg aaatacgcga    4560
tcgctgttaa aaggacaatt acaaacagga atcgaatgca accggcgcag gaacactgcc    4620
agcgcatcaa caatattttc acctgaatca ggatattctt ctaatacctg gaatgctgtt    4680
ttcccgggga tcgcagtggt gagtaaccat gcatcatcag gagtacggat aaaatgcttg    4740
atggtcggaa gaggcataaa ttccgtcagc cagtttagtc tgaccatctc atctgtaaca    4800
tcattggcaa cgctacctt gccatgtttc agaaacaact ctggcgcatc gggcttccca    4860
tacaatcgat agattgtcgc acctgattgc ccgacattat cgcgagccca tttatacca    4920 tataaatcag catccatgtt ggaatttaat cgcggcctcg agcaagacgt ttcccgttga    4980
atatggctca taacacccct tgtattactg tttatgtaag cagacagttt tattgttcat    5040
gatgatatat ttttatcttg tgcaatgtaa catcagagat tttgagacac aacgtggctt    5100
tcccccgccg ctctagaact agtggatcca aataaaacga aggctcagt cgaaagactg    5160 ggcctttcgt tttatctgtt gtttgtcgca ttatacgaga cgtccaggtt gggatacctg    5220
aaacaaaacc catcgtacgg ccaaggaagt ctccaataac tgtgatccac cacaagcgcc    5280
agggttttcc cagtcacgac gttgtaaaac gacggccagt catgcataat ccgcacgcat    5340
ctggaataag gaagtgccat tccgcctgac ct    5372
```

<210> SEQ ID NO 182
<211> LENGTH: 11
<212> TYPE: PRT
<213> ORGANISM: Artificial Sequence
<220> FEATURE:
<223> OTHER INFORMATION: VSV-G

<400> SEQUENCE: 182

Tyr Thr Asp Ile Glu Met Asn Arg Leu Gly Lys
1               5                   10

GENETICALLY MODIFIED ORGANISMS FOR PRODUCTION OF POLYKETIDES

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. patent application Ser. No. 16/783,122, filed Feb. 5, 2020, which is a continuation of PCT International Application No. PCT/US2019/051357, filed Sep. 16, 2019, designating the United States and published in English, which claims the benefit of U.S. Provisional Application No. 62/731,978, filed Sep. 17, 2018. and U.S. Provisional Application No. 62/731,980, filed, filed Sep. 17, 2018. Each of the aforementioned applications is incorporated by reference herein in its entirety, and each is hereby expressly made a part of this specification.

FIELD

Strains of yeasts are provided containing the genes for the production of cannabinoids from fatty acids. The enzymes that mediate cannabinoid production are localized to the cytosol, peroxisome or different compartments within the secretory pathway (e.g., endoplasmic reticulum, Golgi, vacuole) to ensure efficient production. The engineered microorganisms produce cannabinoids in a controlled fermentation process.

REFERENCE TO SEQUENCE LISTING

This application is filed with an electronic sequence listing entitled LBIO0003C1SEQLIST.txt, created on Oct. 1, 2021, which is 492 KB in size. The information in the electronic sequence listing is hereby incorporated by reference in its entirety.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules by the organism.

SUMMARY

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Advances in recombinant molecular biology methodology also allow endogenous genes, carried in the genomic DNA of a microorganism, to be increased in copy number, thus altering the cellular synthesis of enzymes or other proteins. Such genetic engineering can change the biological pathways within the host organism, causing it to produce a desired product.

Microorganic industrial production instead of plant production can increase the availability of natural products while reducing the manufacturing and environmental cost.

DETAILED DESCRIPTION

Figure 1:
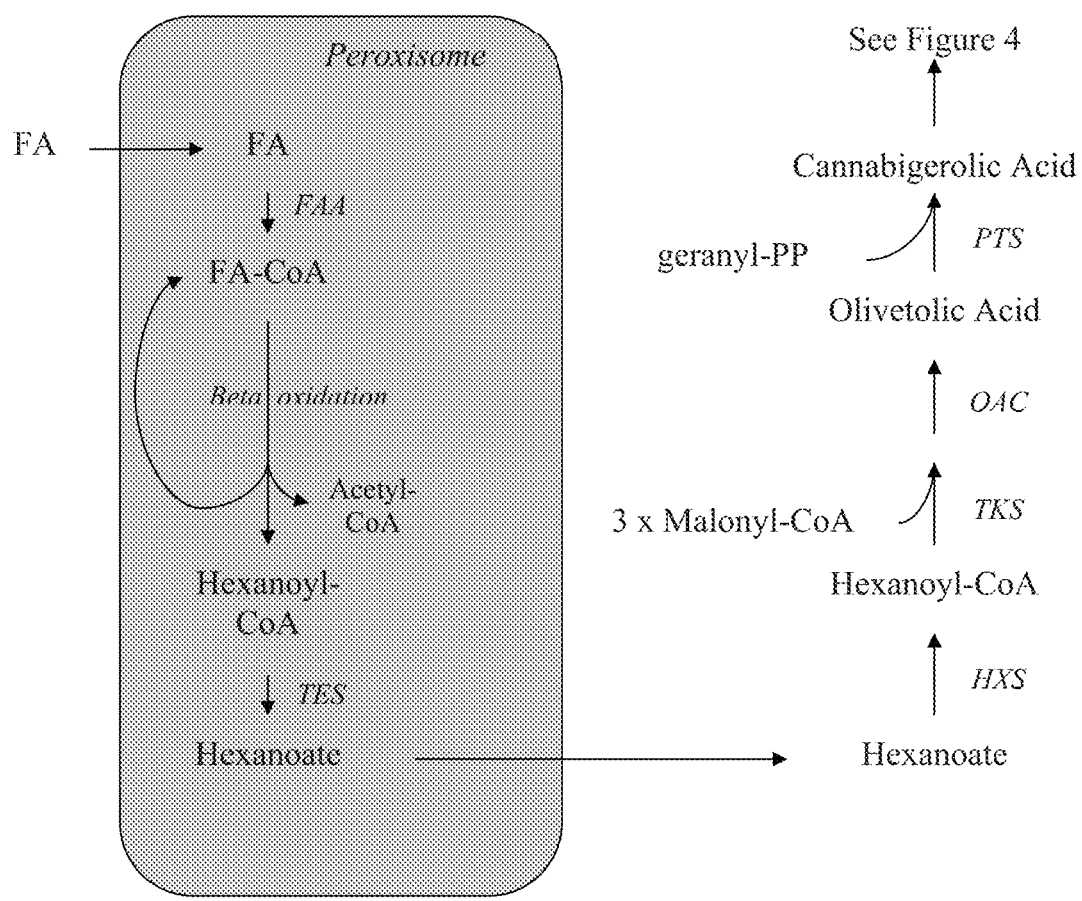
FIG. 1 depicts production of cannabinoids by producing hexanoic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced. An acyl-CoA thioesterase (TES) acts on the hexanoyl-CoA to produce hexanoic acid (hexanoate). The hexanoic acid leaves the peroxisome and is activated by a hexanoyl-CoA synthetase (HXS) to become hexanoyl-CoA, which is then acted upon by a polyketide synthase (TKS) and olivetolic acid cyclase (OAC) to produce olivetolic acid. A prenyltransferase (PTS) adds a geranyl moiety to olivetolic acid to produce cannabigerolic acid, which is converted to one of several cannabinoids as described in FIG. 4.

*Cannabis* is the dried preparation of the *Cannabis sativa* plant and has been widely used to treat disease or alleviate disease symptoms. The flowers of the plant are used to produce *cannabis*, but other parts of the plant can be used as well. According to some accounts, *cannabis* is composed of at least 483 known chemical compounds, which include cannabinoids, terpenoids, flavonoids, nitrogenous compounds, amino acids, proteins, glycoproteins, enzymes, sugars and related compounds, hydrocarbons, alcohols, aldehydes, ketones, acids, fatty acids, esters, lactones, steroids, terpenes, non-cannabinoid phenols, vitamins, and pigments.

The cannabinoids are believed to mediate the medical and recreational properties of the plant. Cannabinoids act by binding to cannabinoid receptors found in the brain to mediate many of the effects of *cannabis*. The efficacy of cannabinoids for treating specific ailments is the subject of ongoing research with either a purified cannabinoid, a synthetic cannabinoid or *cannabis*.

For medical applications, the use of a purified cannabinoid is preferred to a mixture of molecules extracted from *cannabis*. One option for the production of cannabinoids is synthetic biology: the construction of specific strains of bacteria, yeast or filamentous fungi that will produce cannabinoids in a fermentation process. Producing cannabinoids with a genetically modified organism in fermentation has multiple advantages.

A fermentation-based process is more controlled and economical than the current process of isolating cannabinoids from *Cannabis sativa* plants, which requires expensive indoor facilities and cloning of plant strains under sterile conditions to ensure consistent distribution of cannabinoids in the final plant material.

Usually, cannabinoids are extracted from the *cannabis* plant as part of a crude mixture, combined with other chemical compounds found in the *cannabis* plant. Most extractions of *cannabis* plant matter aim to extract cannabinoids, particularly tetrahydrocannabinol (THC). THC is useful for relieving pain, treating glaucoma, and relieving nausea. THC is also gaining immense popularity as a recreational drug substance. Other cannabinoids of interest include, Cannabigerol (CBG), Cannabigerolic Acid (CBGA), Cannabidiol (CBD), Cannabinol (CBN), Cannabichromene (CBC), Tetrahydrocannabivarin (THCV), Cannabigerovarin (CBGV), and Cannabigerovarinic Acid (CBGVA).

A variety of growing and cultivating techniques have been developed for increasing the production of secondary compounds within plants of genus *cannabis*. These techniques include outdoor cultivation, indoor cultivation, hydroponics, fertilization, atmospheric manipulation, cloning, crossbreeding, Screen of Grow (SCROG), Sea of Green (SOG), pinching, training, topping, etc.

While breeding and farming techniques yield plants with high concentrations of cannabinoids, these techniques fail to provide the level of control and production needed. In addition, the production time is measured in multiple weeks if not months.

Production of a single cannabinoid by fermentation with a microorganism, will provide the cannabinoid of interest in less complex chemical matrix facilitating the isolation of purified cannabinoid. This will result in less equipment needed and lower cost of purification. In addition, a fermentation-based process timeline will be measured in days and not weeks, allowing production to quickly adapt to changing market needs. Finally, a fermentation-based process footprint will allow production of cannabinoids in a smaller facility that those required for plant-based process where big greenhouses are required.

Microorganisms

A microorganism selected often is suitable for genetic manipulation and often can be cultured at cell densities useful for industrial production of a target fatty dicarboxylic acid product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is a yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi*, *C. viswanathii*, *C. pukherrima*, *C. tropicalis*, *C. utilis*), *Rhodotorula* yeast (e.g., *R. glutinus*, *R. graminis*), *Rhodosporidium* yeast (e.g., *R. toruloides*), *Saccharomyces* yeast (e.g., *S. cerevisiae*, *S. bayanus*, *S. pastorianus*, *S. carlsbergensis*), *Cryptococcus* yeast, *Trichosporon* yeast (e.g., *T. pullans*, *T cutaneum*), *Pichia* yeast (e.g., *P. pastoris*) and *Lipomyces* yeast (e.g., *L. starkeyii*, *L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon*, or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. *diffluens, Cryptococcus laurentii, Cryptococcus neofomans, Debaryomyces hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii, Lipomyces hpoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica*, or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3−/ura3−), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases, strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et. al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental stains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus*, *A. nidulans*), Thraustochytrium fungi, Schizochytrium fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), Acinetobacter bacteria, Norcardia baceteria, *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188)), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria, *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*)), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexicanheather), *Cuphea hyssopoides, Cuphea ignea, Cuphea ingrata, Cuphea jorullensis, Cuphea lanceolata, Cuphea linarioides, Cuphea Ilavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea splendida* var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii, Cuphea lanceolata*)).

Microorganisms or cells used as host organisms or source for a heterologous polynucleotide are commercially available. Microorganisms and cells described herein, and other suitable microorganisms and cells are available, for example, from Invitrogen Corporation (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Important Pathways for Cannabinoid Production—Beta Oxidation

Cellular fatty acid degradation occurs via the β-oxidation pathway in all organisms. See, e.g., European Published Application No. EP2502932A1. So far it has been established that there are two different β-oxidation systems in eukaryotes: the β-oxidation located in mitochondria for mammals and some filamentous fungi and the β-oxidation system located in peroxisomes for plants, fungi and animals.

Fatty acid beta-oxidation begins with the addition of coenzyme A to a fatty acid, and occurs by successive cycles of reactions during each of which the fatty acid is shortened by a two-carbon fragment removed as acetyl coenzyme A, generating trans-2,3 hydroxyl, and 3-keto intermediates, until only two or three carbons remain (as acetyl-CoA or propionyl-CoA respectively). The proteins involved in the mitochondrial β-oxidation and in the peroxisomal β-oxidation are however different. Multifunctional proteins (MFPs) or multifunctional enzymes (MFEs) are involved in the peroxisomal β-oxidation pathway, whereas β-oxidation consists of monofunctional enzymes.

The peroxisomal β-oxidation process begins with oxidation of the acyl-CoA substrate into trans-2-enoyl-CoA by Acyl-CoA oxidase, namely Fox1p/Pox1p. It has been demonstrated that Pox1Δ yeasts are unable to grow on fatty acids as sole carbon atoms. Then the peroxisomal β-oxidation proceeds from trans-2-enoyl-CoA to 3-ketoacyl-CoA via the (3R)-hydroxyacyl-CoA ester intermediates. In the yeast oxidation system, the second and third reactions of the β-oxidation cycle are catalyzed by the same enzymes called Mfe2p, Fox2p or again Pox2p, which contains both the 3-hydroxyacyl-CoA and 2-enoyl-CoA hydratase activities. The 2-enoyl-CoA hydratase converts the trans-2-enoyl CoA esters into (3R)-hydroxyacyl-CoA esters, whereas the hydratase 2 produces the 3-ketoacyl-CoA. This enzyme was first isolated from *Candida tropicalis* and comprise a duplicated domain organization in its N-terminal region, which contains two deshydrogenase active domains A and B. Domain A was demonstrated to have highest activity with long and medium chain substrates, whereas domain B has the highest activity with short-chain substrates. The C-terminal region of the Fox2p enzyme contains the 2-enoyl-CoA hydratase 2 activity. Hiltunen et al. (JBC, Vol. 267, No. 10, Apr. 5, 1992, pp 6646-6653) showed that fatty acid catabolism in yeast was mainly based on the activity of Fox2p and that disruption of FOX2 resulted in the inability of yeast cells to grow on fatty acids as their sole carbon source. At the next reaction of the β-oxidation cycle the ketoacyl-CoA intermediate undergoes thiolytic cleavage by a 3-ketoacyl-CoA thiolase, namely Pot1p/Fox3p. The Pot1p/Fox3p is a dimeric protein with a subunit size of 45 kDa. A single subunit comprises three domains: two core domains, and a loop domain of 120 residues. The active site of yeast thiolase is shaped by residues from the two core domains and surrounded by the loop domain. The products of this last step are acetyl-CoA and a C2-shortened acyl-CoA, which acts as substrate for Pox1p/Fox1p for an additional cycle. The acetyl-CoA which is produced by peroxisomal beta oxidation is then used in the glyoxilic cycle, thereby allowing the transformation of acetyl-CoA into oxaloacetate. These reactions are catalyzed by two enzymes: isocitrate lyase (Icl1p) and malate synthase (Mls1p) which permits the use of two carbon atoms such as acetate, in the neoglucogenese.

Cannabinoid Production

Acyl-CoA oxidase (EC 1.3.3.6) is the first reported enzyme of the fatty acid β-oxidation pathway. See, e.g., U.S. Pat. No. 6,518,488. This enzyme catalyzes the desaturation of acyl-CoAs longer than eight carbons to 2-trans-enoyl-CoAs, by donating electrons directly to molecular oxygen and releasing $H_2O_2$ (Lazarow et al., 1976). There are multiple isozymes of acyl-CoA oxidase and these isozymes show specificity towards short, medium and long chain fatty acyl-CoAs (Hooks et al., *Biochem J.*, 320:607-614 (1996); Hooks et al., *Plant J.*, 20:1-13 (1999)). For example, *Arabidopsis thaliana* acyl-CoA oxidase isoform 1 (ACX1) has optimal activity on an acyl-CoA substrate that is fourteen carbons long and minimal activity on substrates shorter than six carbons. However, ACX2 has optimal activity on an acyl-CoA substrate that is eighteen carbons long and minimal activity on substrates shorter than ten carbons. In *Y. lipolytica*, there are five acyl-CoA oxidase isoforms that have different activities on acyl-CoA substrates of different lengths. For example, the protein encoded by PDX3 has maximal activity on C6 and C8 acyl-CoA substrates.

Cannabinoids have their biosynthetic origins in both polyketide and terpenoid metabolism and are termed terpenophenolics or prenylated polyketides (See, e.g., US Patent Publication No. US20190169661; Page J., Nagel J. (2006) Biosynthesis of terpenophenolics in hop and *cannabis*. In J T Romeo, ed, Integrative Plant Biochemistry, Vol. 40. Elsevier, Oxford, pp 179-210.).

Polyketides represent a large family of diverse compounds ultimately synthesized from 2-carbon units through a series of Claisen-type condensations and subsequent modifications. See, e.g., US Patent Publication No. US20050032176. Members of this group include antibiotics such as tetracyclines, anticancer agents such as daunomycin, and immunosuppressants such as FK506 and rapamycin. Polyketides occur in many types of organisms including fungi and mycelial bacteria, in particular, the actinomycetes.

The structural diversity of polyketides is achieved through the series of reactions catalyzed by polyketide synthases (PKS), with features that contribute to diversity including the selection of various starter and extender units, final chain length, cyclization, degree of reduction, and the like. See, e.g., US20120122180. Downstream reactions such as glycosylation, hydroxylation, halogenation, prenylation, acylation, and alkylation can add additional diversity to the resulting products. This group of enzymatically active proteins is considered in a different category from the fatty acid synthases which also catalyze condensation of 2-carbon units to result in, for example, fatty acids and prostaglandins. Two major types of PKS are known which are vastly different in their construction and mode of synthesis. These are commonly referred to as Type I or "modular" and Type II, "aromatic."

There is a third class of PKS enzymes, the Type III PKS synthases, which consist of a small homodimer containing one active site where both chain extension and cyclization take place (See. e.g., US20190078098; Austin, M. B. and J. P. Noel. Natural Product Reports, 2002. 20(1): p. 79-110; Lim, Y., et al. Molecules, 2016. 21(6): p. 806; Yu, D., et al. IUBMB Life, 2012. 64(4): p. 285-295). Type III PKSs are able to produce a wide diversity of polyketide products by using a variety of larger, CoA-containing precursors as a starting unit. These starters range from small aliphatic molecules, such as acetyl-CoA, to larger ring-containing compounds derived from the phenylpropanoid pathway, such as 4-coumaroyl-CoA. Often, these CoA molecules are formed through the function of acid CoA ligases that convert carboxylic acids into corresponding CoA molecules.

Cannabinoid biosynthesis occurs primarily in glandular trichomes that cover female flowers at a high density. See, e.g., US20190169661. Cannabinoids are formed by a three-step biosynthetic process: polyketide formation, aromatic prenylation and cyclization (see FIG. 1).

The first enzymatic step in cannabinoid biosynthesis is the formation of olivetolic acid by a putative polyketide synthase enzyme that catalyzes the condensation of hexanoyl coenzyme A (CoA) and malonyl CoA. A Type III polyketide synthase, termed "olivetol synthase" and referred to herein as polyketide synthase/olivetol synthase (CsPKS/olivetol synthase), from *Cannabis sativa* has recently been shown to form olivetol and several pyrone products but not olivetolic acid (Taura F, Tanaka S, Taguchi C, Fukamizu T, Tanaka H, Shoyama Y, Morimoto, S. (2009) Characterization of olivetol synthase, Type III a polyketide synthase putatively involved in cannabinoid biosynthetic pathway. FEBS Lett. 583: 2061-2066.). The nucleotide sequence of the gene encoding CsPKS/olivetol synthase is found in GenBank under accession number AB164375 with the polypeptide as accession BAG14339. The aforementioned products include the pyrones hexanoyltriacetic lactone (HTAL) and pentyldiacetic lactone (PDAL). The reason for the inability of this enzyme to form olivetolic acid, which is clearly a pathway intermediate based on the carboxylate structure of the cannabinoids, is not known. The lack of olivetolic acid formation by this polyketide synthase from *cannabis* was confirmed by the inventors, as further described herein and also by Marks et al. (Marks M D, Tian L, Wenger J P, Omburo S N, Soto-Fuentes W, He J, Gang D R, Weiblen G D, Dixon R A. (2009) Identification of candidate genes affecting Delta9-tetrahydrocannabinol biosynthesis in *Cannabis sativa*. J Exp Bot. 60, 3715-3726.).

The second enzymatic step is the prenylation of olivetolic acid to form cannabigerolic acid (CBGA) by the enzyme geranylpyrophosphate:olivetolate geranyltransferase. This enzyme is an aromatic prenyltransferase and is the subject of commonly owned U.S. Provisional patent applications U.S. Ser. No. 61/272,057 filed Aug. 12, 2009 and U.S. Ser. No. 61/272,117 filed Aug. 18, 2009. CBGA is a central branch-point intermediate for the biosynthesis of the different classes of cannabinoids. Cyclization of CBGA yields Δ9-tetrahydrocannabinolic acid (THCA) or its isomers cannabidiolic acid (CBDA) or cannabichromenic acid (CBCA) (see FIG. 1). The Shoyama group has previously published the identification and purification of the three enzymes responsible for these cyclizations (Morimoto S, Komatsu K, Taura F, Shoyama, Y. (1998) Purification and characterization of cannabichromenic acid synthase from *Cannabis sativa*. Phytochemistry. 49: 1525-1529; Taura F, Morimoto S, Shoyama Y. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. 271: 17411-17416; and Taura F, Morimoto S, Shoyama Y, Mechoulam R. (1995) First direct evidence for the mechanism of 1-tetrahydrocannabinolic acid biosynthesis. J Am Chem Soc. 117: 9766-9767). Cloning of THCA and CBDA synthases has also been previously published (Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted into the storage cavity of the glandular trichomes. Plant Cell Physiol. 46: 1578-1582.; Taura F, Sirikantaramas S, Shoyama Y, Yoshikai K, Shoyama Y, Morimoto S. (2007) Cannabidiolic-acid synthase, the chemotype-determining enzyme in the fiber-type *Cannabis sativa*. FEBS Lett. 581: 2929-2934. The genes for THCA synthase and CBDA synthase have been reported in Japan (Japanese Patent Publication 2000-078979; Japanese Patent Publication 2001-029082).

Beta-Oxidation Activities

The term "beta oxidation pathway" as used herein, refers to a series of enzymatic activities utilized to metabolize fatty alcohols, fatty acids, or dicarboxylic acids. The activities utilized to metabolize fatty alcohols, fatty acids, or dicarboxylic acids include, but are not limited to, acyl-CoA ligase activity, acyl-CoA oxidase activity, acyl-CoA hydrolase activity, acyl-CoA thioesterase activity, enoyl-CoA hydratase activity, 3-hydroxyacyl-CoA dehydrogenase activity and acetyl-CoA C-acyltransferase activity. The term "beta oxidation activity" refers to any of the activities in the beta oxidation pathway utilized to metabolize fatty alcohols, fatty acids or dicarboxylic acids.

Beta-Oxidation—Acyl-CoA Ligase

An acyl-CoA ligase enzyme sometimes is encoded by the host organism and can be added to generate an engineered organism. In some embodiments, host acyl-CoA ligase activity can be increased by increasing the number of copies of an acyl-CoA ligase gene, by increasing the activity of a promoter that regulates transcription of an acyl-CoA ligase gene, or by increasing the number copies of the gene and by increasing the activity of a promoter that regulates transcription of the gene, thereby increasing production of target due to increased carbon flux through the pathway. In certain embodiments, the acyl-CoA ligase gene can be isolated from any suitable organism. Non-limiting examples of organisms that include, or can be used as donors for, acyl-CoA ligase enzymes include *Arxula, Candida, Saccharomyces,* or *Yarrowia.*

Beta-Oxidation—Enoyl-CoA Hydratase

An enoyl-CoA hydratase enzyme catalyzes the addition of a hydroxyl group and a proton to the unsaturated β-carbon on a fatty-acyl CoA and sometimes is encoded by the host organism and sometimes can be added to generate an engineered organism. In certain embodiments, the enoyl-CoA hydratase activity is unchanged in a host or engineered organism. In some embodiments, the host enoyl-CoA hydratase activity can be increased by increasing the number of copies of an enoyl-CoA hydratase gene, by increasing the activity of a promoter that regulates transcription of an enoyl-CoA hydratase gene, or by increasing the number copies of the gene and by increasing the activity of a promoter that regulates transcription of the gene, thereby increasing the production of target product (due to increased carbon flux through the pathway. In certain embodiments, the enoyl-CoA hydratase gene can be isolated from any suitable organism. Non-limiting examples of organisms that include, or can be used as donors for, enoyl-CoA hydratase enzymes include *Arxula, Candida, Saccharomyces,* or *Yarrowia.*

Beta-Oxidation—3-Hydroxyacyl-CoA Dehydrogenase 3-hydroxyacyl-CoA dehydrogenase enzyme catalyzes the formation of a 3-ketoacyl-CoA by removal of a hydrogen from the newly formed hydroxyl group created by the activity of enoyl-CoA hydratase. In some embodiments, the activity is encoded by the host organism and sometimes can be added or increased to generate an engineered organism. In certain embodiments, the 3-hydroxyacyl-CoA activity is unchanged in a host or engineered organism. In some embodiments, the host 3-hydroxyacyl-CoA dehydrogenase activity can be increased by increasing the number of copies of a 3-hydroxyacyl-CoA dehydrogenase gene, by increasing the activity of a promoter that regulates transcription of a 3-hydroxyacyl-CoA dehydrogenase gene, or by increasing the number copies of the gene and by increasing the activity of a promoter that regulates transcription of the gene, thereby increasing production of target product (e.g., sebacic or dodecanedioic acid) due to increased carbon flux through the pathway. In certain embodiments, the 3-hydroxyacyl-CoA dehydrogenase gene can be isolated from any suitable organism. Non-limiting examples of organisms that include, or can be used as donors for, 3-hydroxyacyl-CoA dehydrogenase enzymes include *Arxula, Candida, Saccharomyces,* or *Yarrowia.*

Beta-Oxidation—Acetyl-CoA C-Acyltransferase

An Acetyl-CoA C-acyltransferase (e.g., beta-ketothiolase) enzyme catalyzes the formation of a fatty acyl-CoA shortened by 2 carbons by cleavage of the 3-ketoacyl-CoA by the thiol group of another molecule of CoA. The thiol is inserted between C-2 and C-3, which yields an acetyl CoA molecule and an acyl CoA molecule that is two carbons shorter. An Acetyl-CoA C-acyltransferase sometimes is encoded by the host organism and sometimes can be added to generate an engineered organism. In certain embodiments, the acetyl-CoA C-acyltransferase activity is unchanged in a host or engineered organism. In some embodiments, the host acetyl-CoA C-acyltransferase activity can be increased by increasing the number of copies of an acetyl-CoA C-acyltransferase gene, or by increasing the activity of a promoter that regulates transcription of an acetyl-CoA C-acyltransferase gene, thereby increasing the production of target product due to increased carbon flux through the pathway. In certain embodiments, the acetyl-CoA C-acyltransferase gene can be isolated from any suitable organism. Non-limiting examples of organisms that include, or can be used as donors for, acetyl-CoA C-acyltransferase enzymes include *Arxula, Candida, Saccharomyces,* or *Yarrowia.*

Altered Activities and Engineering Pathways

In one embodiment, which is represented by FIG. 1, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus to the protein. A PTS sequence can be GRRAKL or a smaller subset of those amino acids based on the consensus sequence [S/A/H/C/E/P/Q/V]-[K/R/H/Q]-[L/F]. Alternatively, a microorganism that naturally consumes fatty acids can be used. The microorganism will be constructed to express a hexanoate-acyl activating enzyme (HXS), an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 2:
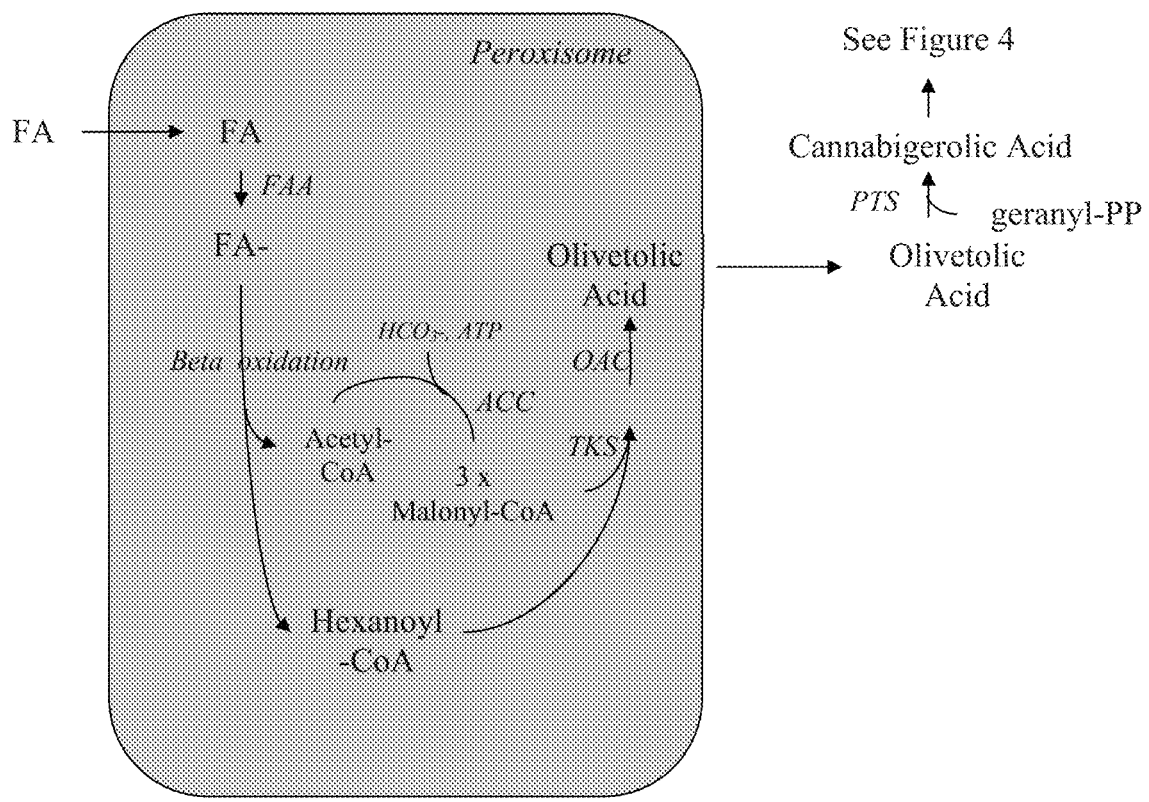
FIG. 2 depicts production of cannabinoids by producing olivetolic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced, which is then acted upon by a polyketide synthase (TKS) and olivetolic acid cyclase (OAC) to produce olivetolic acid. If necessary, an acetyl-CoA carboxylase (ACC) will be localized to the peroxisome to produce additional malonyl-CoA. The olivetolic acid leaves the peroxisome and enters the cytosol. A prenyltransferase (PTS) adds a geranyl moiety to olivetolic acid to produce cannabigerolic acid, which is converted to one of several cannabinoids as described in FIG. 4.

In one embodiment, which is represented by FIG. 2, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus of the protein. A PTS sequence can be GRRAKL or a smaller subset of those amino acids based on the consensus sequence [S/A/H/C/E/P/Q/V]-[K/R/H/Q]-[L/F]. Alternatively, a microorganism that naturally consumes fatty acids can be used. The microorganism will be constructed to express an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The TKS and OAC enzymes will be targeted to the peroxisome by the addition of a PTS sequence, such as GRRAKL or a smaller subset of those amino acids based on the consensus sequence of [S/A/H/C/E/P/Q/V]-[K/R/H/Q]-[L/F], which will be added to the carboxyl terminus of the proteins. An alternative mechanism of targeting to the peroxisome is the use of a PTS2 sequence near the N-terminus of the protein, which is defined by the consensus sequence -(R/K)(L/V/I/Q)XX(L/V/I/H/Q)(L/S/G/A/K)X(H/Q)(L/A/F)-. An example could be RRMLSSKQL as found in Pcd1p from *S. cerevisiae*. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 3:
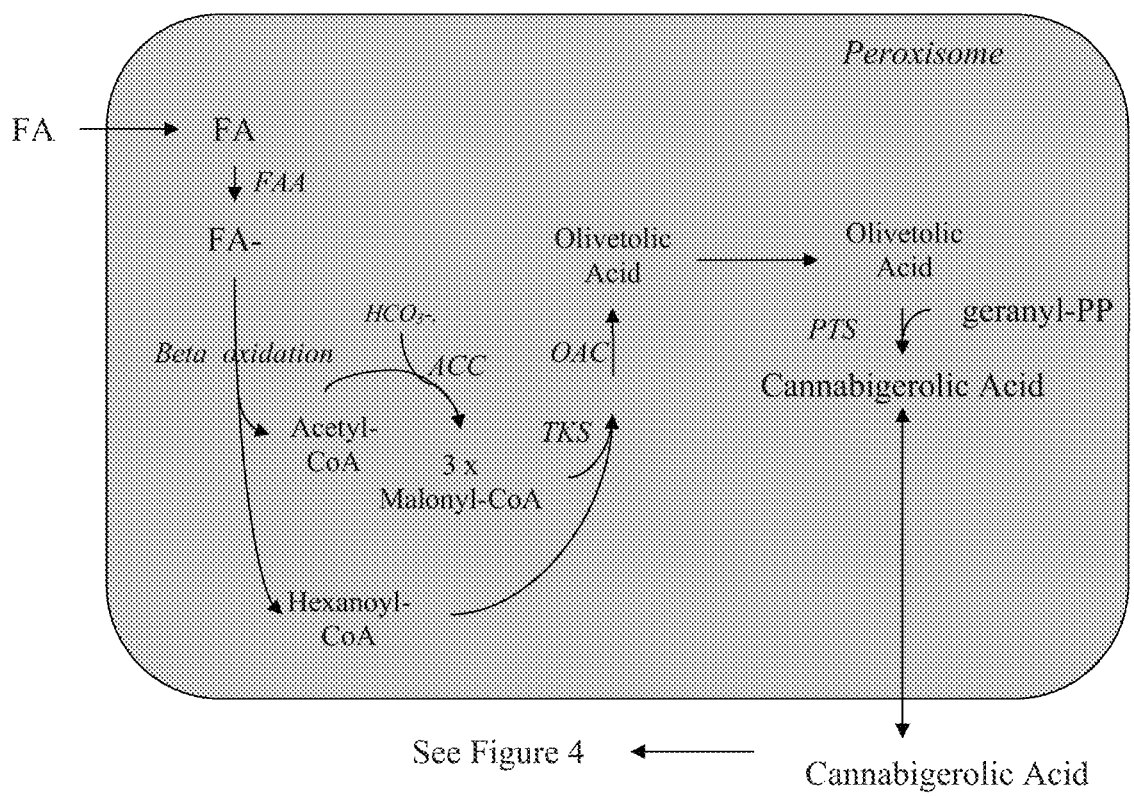
FIG. 3 depicts production of cannabinoids by producing cannabigerolic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced, which is then acted upon by a polyketide synthase (TKS) and olivetolic acid cyclase (OAC) to produce olivetolic acid. If necessary, an acetyl-CoA carboxylase (ACC) will be localized to the peroxisome to produce additional malonyl-CoA. A prenyltransferase (PTS) adds a geranyl moiety to olivetolic acid to produce cannabigerolic acid, which is converted to one of several cannabinoids as described in FIG. 4.

In one embodiment, which is represented by FIG. 3, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus of the protein. A PTS sequence can be GRRAKL or a smaller subset of those amino acids based on the consensus sequence of [S/A/H/C/E/P/Q/V]-[K/R/H/Q]-[L/F]. Alternatively, a microorganism that naturally consumes fatty acids can be used. The microorganism will be constructed to express an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The TKS, OAC and PTS enzymes will be targeted to the peroxisome by the addition of a PTS sequence, such as GRRAKL or a smaller subset of those amino acids based on the consensus sequence of [S/A/H/C/E/P/Q/V]-[K/R/H/Q]-[L/F], which will be added to the carboxyl terminus of the proteins. An alternative mechanism of targeting to the peroxisome is the use of a PTS2 sequence near the N-terminus of the protein, which is defined by the consensus sequence (R/K)(L/V/I/Q)XX(L/V/I/H/Q)(L/S/G/A/K)X(H/Q)(L/A/F)-. An example could be RRMLSSKQL as found in Pcd1p from *S. cerevisiae*. If necessary, an acetyl-CoA carboxylase will be expressed and targeted to the peroxisome through a PTS1 or PTS2. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 4:
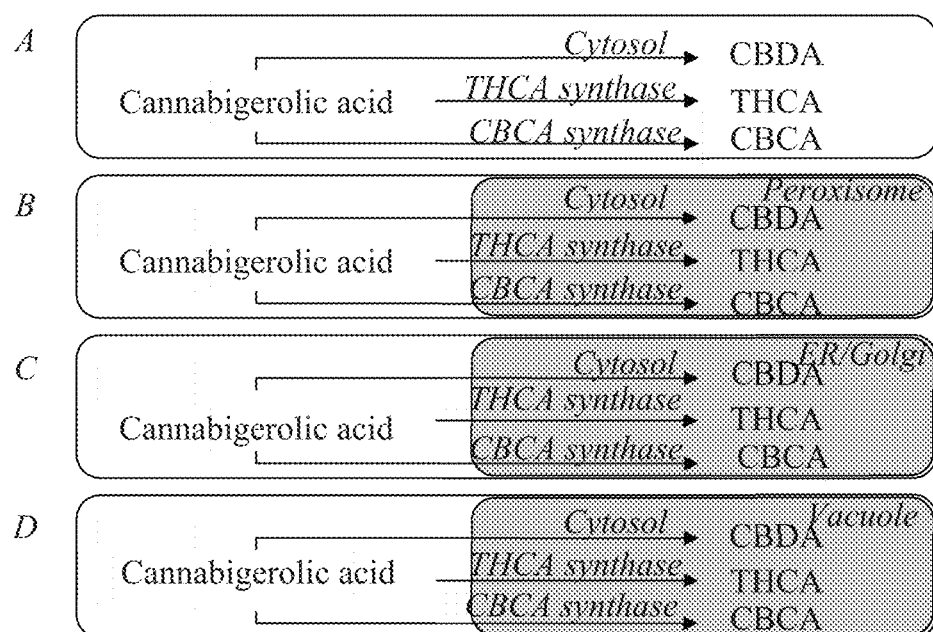
FIG. 4 depicts compartmentalization of enzymes for cannabinoid production. Cannabidiolic acid (CBDA) synthase, tetrahydrocannabidiolic acid (THCA) synthase or cannabichromenic acid (CBCA) synthase will be localized to: A) the cytoplasm, B) the peroxisome, C) compartments of the secretory pathway, such as the endoplasmic reticulum (ER) or Golgi or D) the vacuole. The enzymes will be localized to different compartments through the use of signal sequences.
Figure 5:
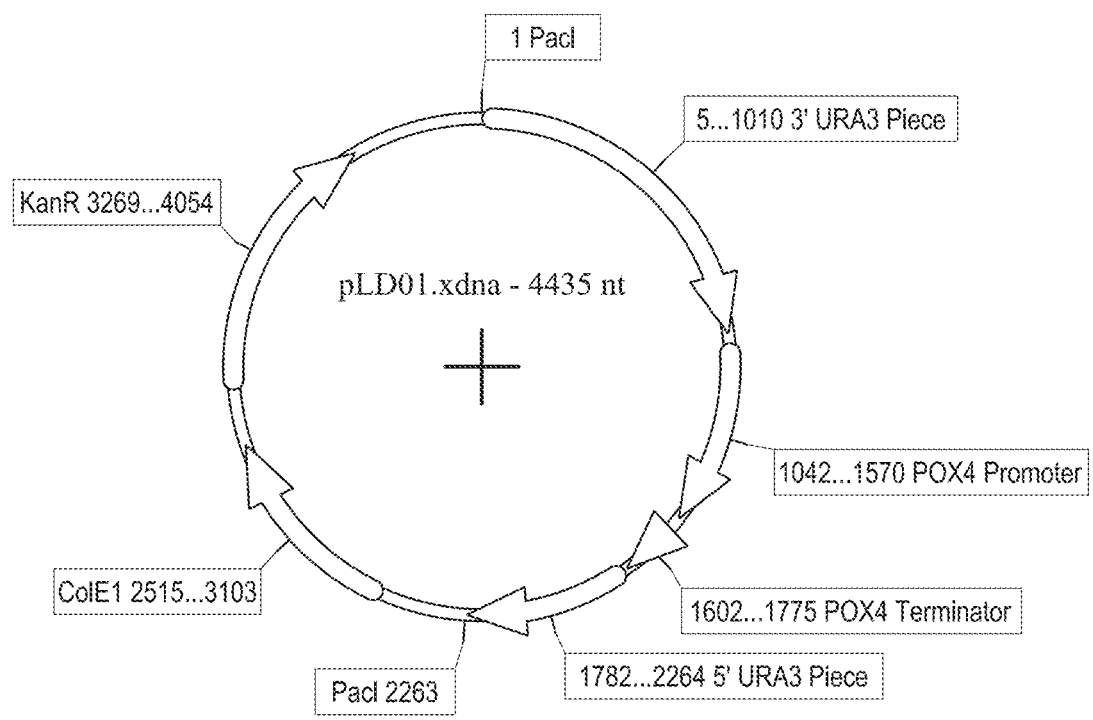
FIG. 5 provides a map of plasmid pLD1.
Figure 6:
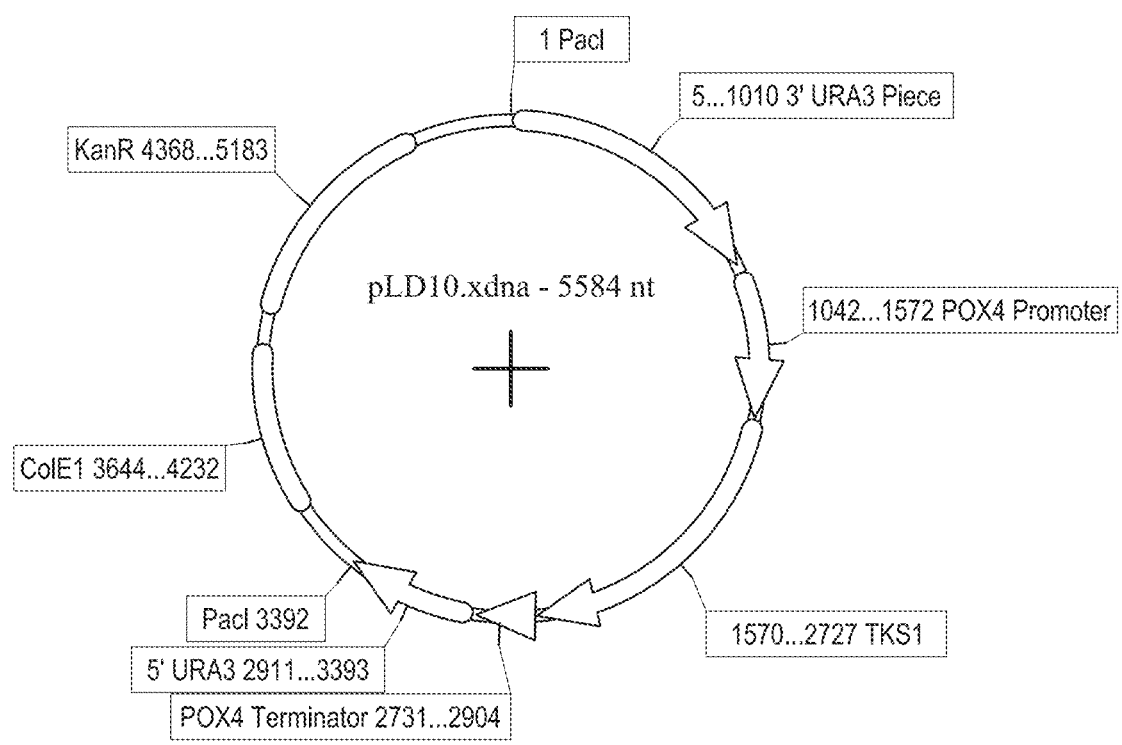
FIG. 6 provides a map of plasmid pLD10.
Figure 7:
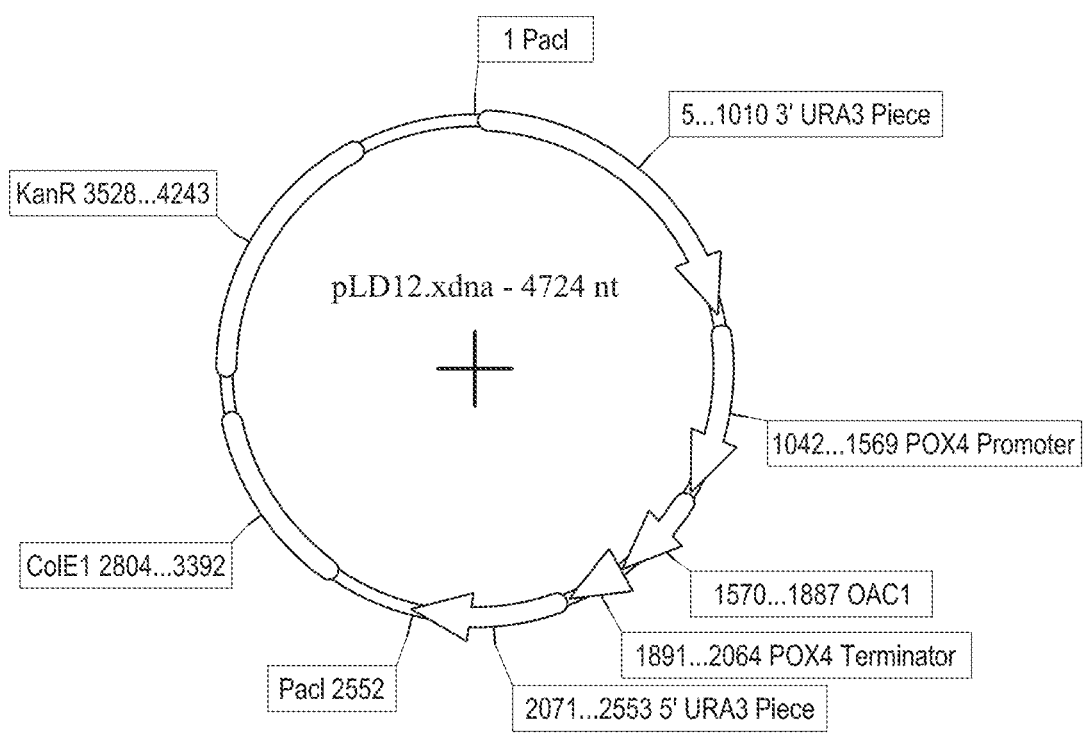
FIG. 7 provides a map of plasmid pLD12.
Figure 8:
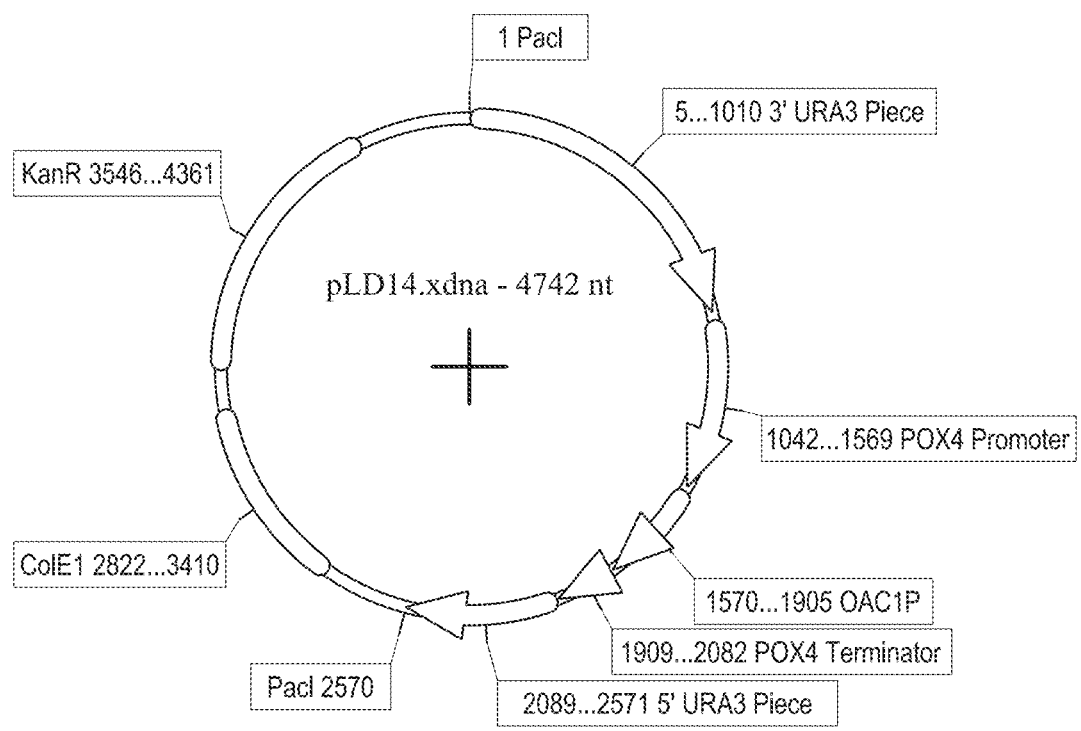
FIG. 8 provides a map of plasmid pLD14.
Figure 9:
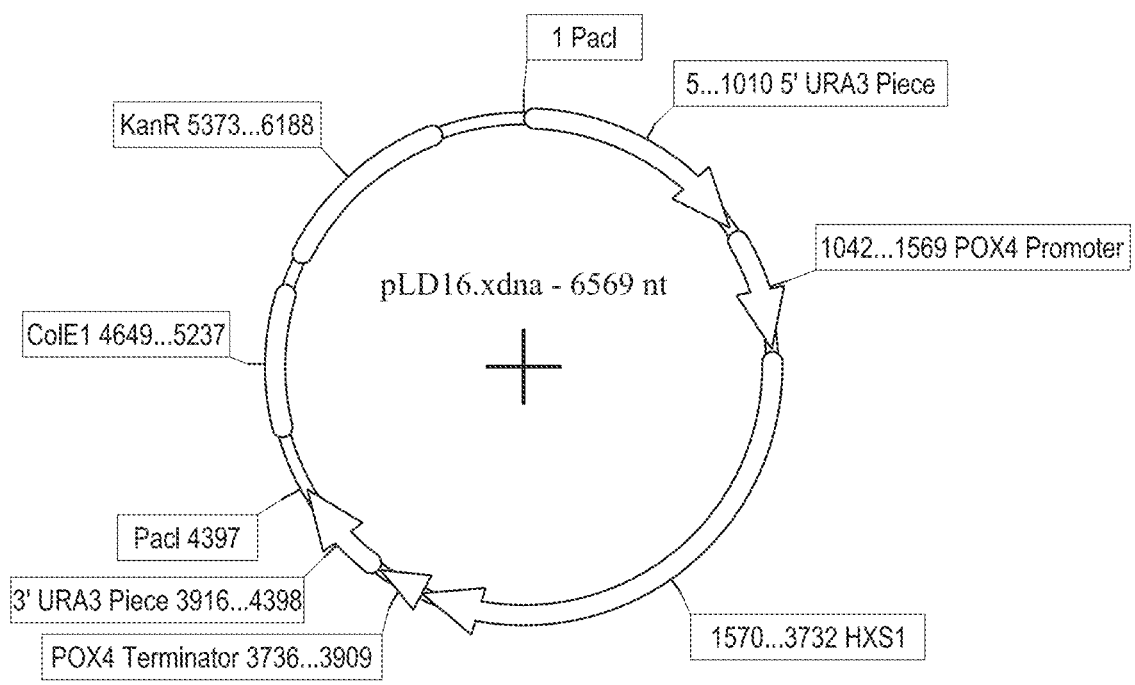
FIG. 9 provides a map of plasmid pLD16.
Figure 10:
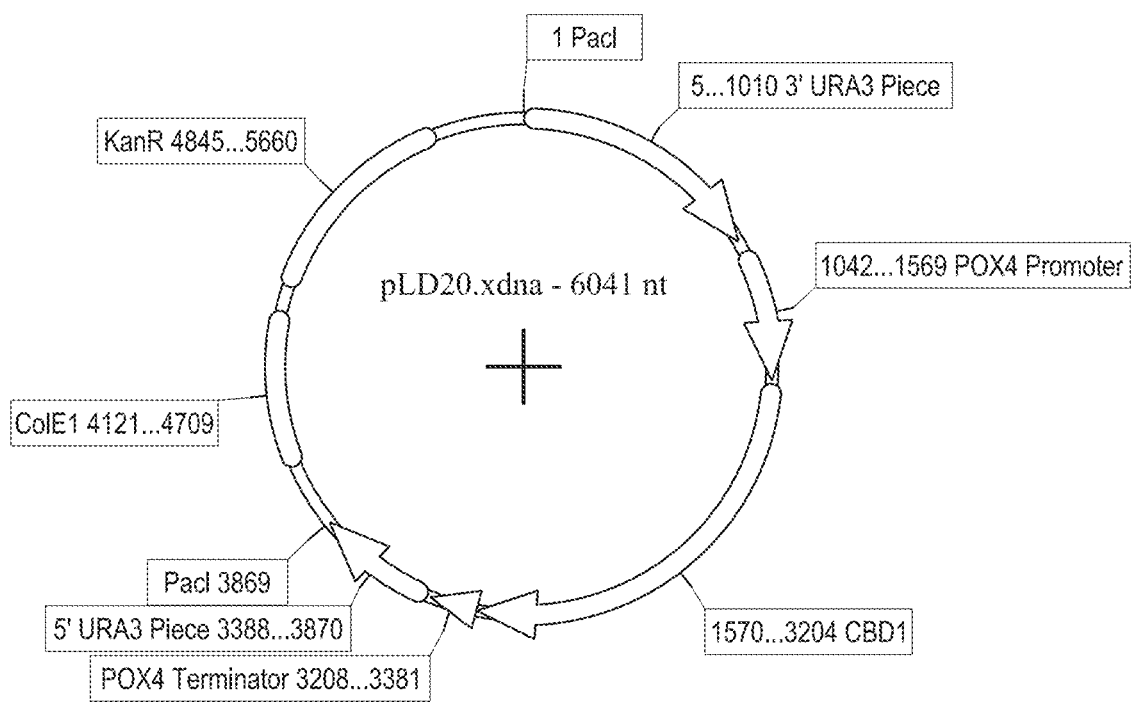
FIG. 10 provides a map of plasmid pLD20.
Figure 11:
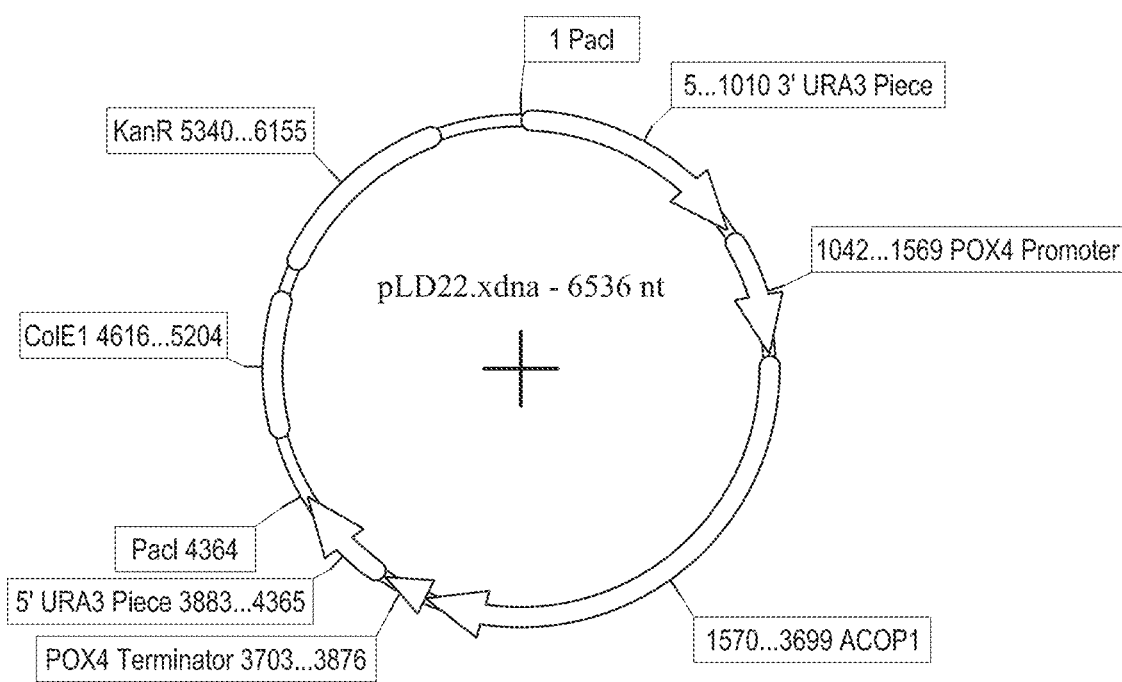
FIG. 11 provides a map of plasmid pLD22.
Figure 12:
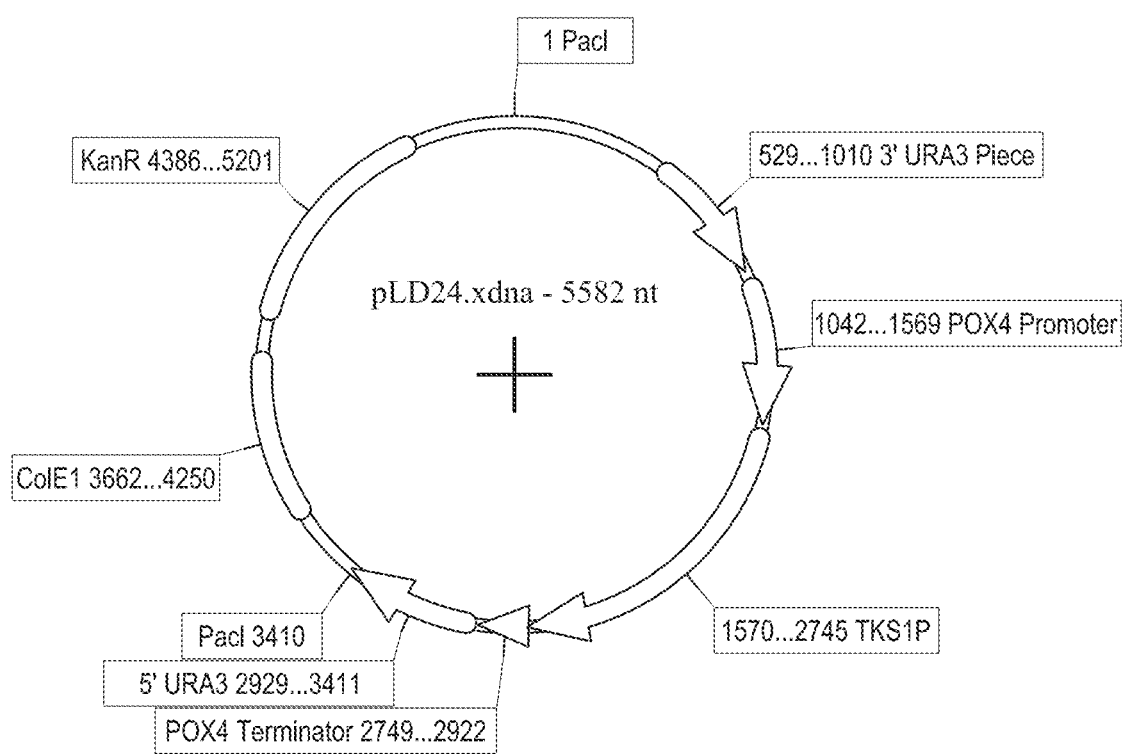
FIG. 12 provides a map of plasmid pLD24.
Figure 13:
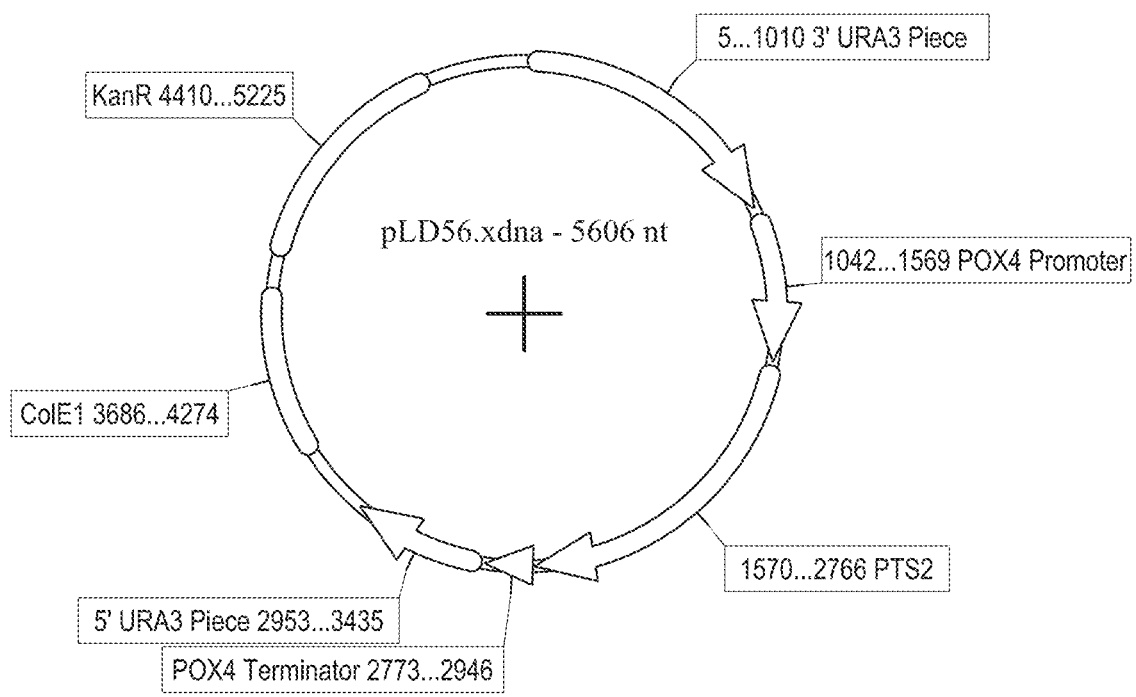
FIG. 13 provides a map of plasmid pLD56.
Figure 14:
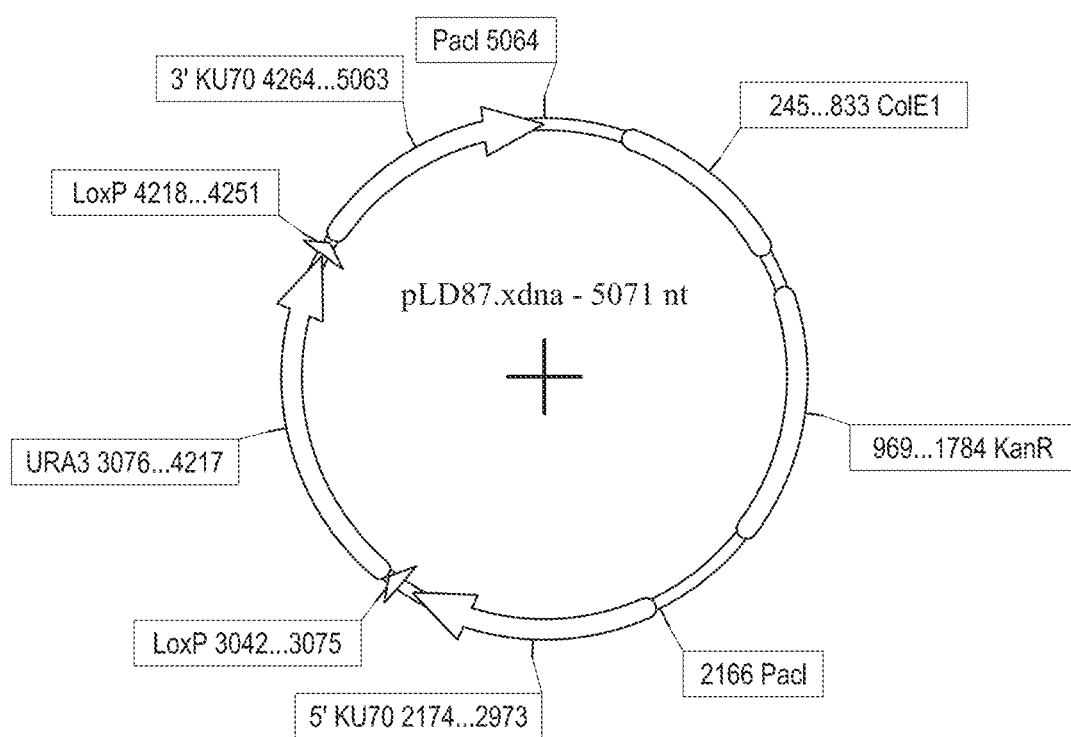
FIG. 14 provides a map of plasmid pLD87.
Figure 15:
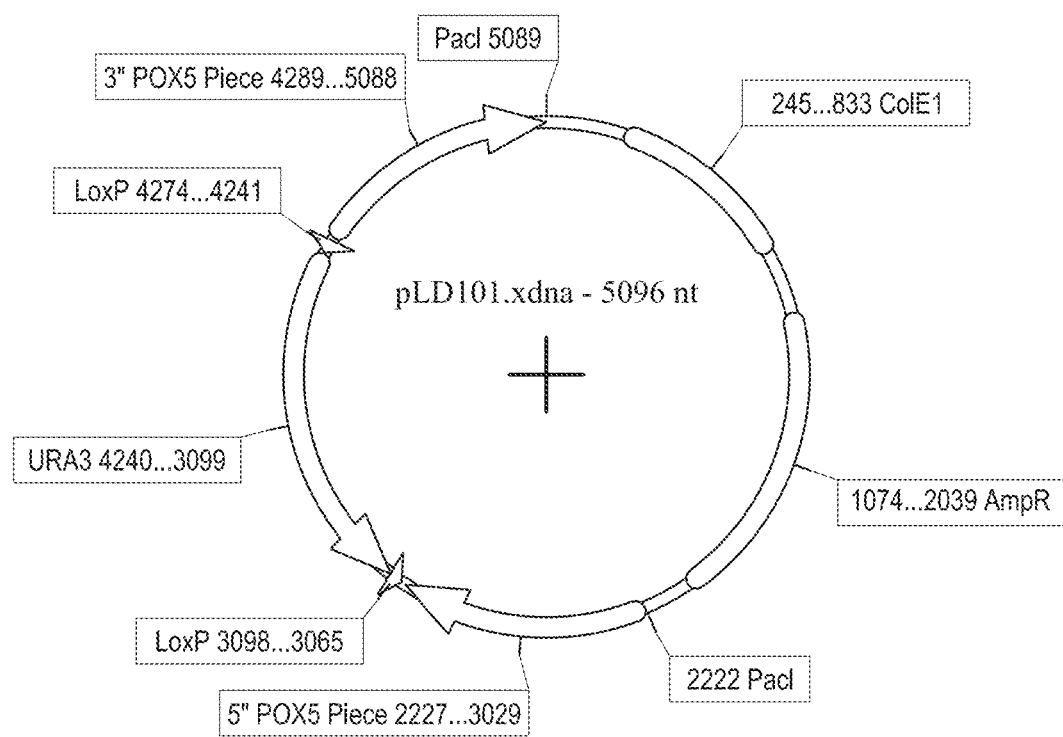
FIG. 15 provides a map of plasmid pLD101.
Figure 16:
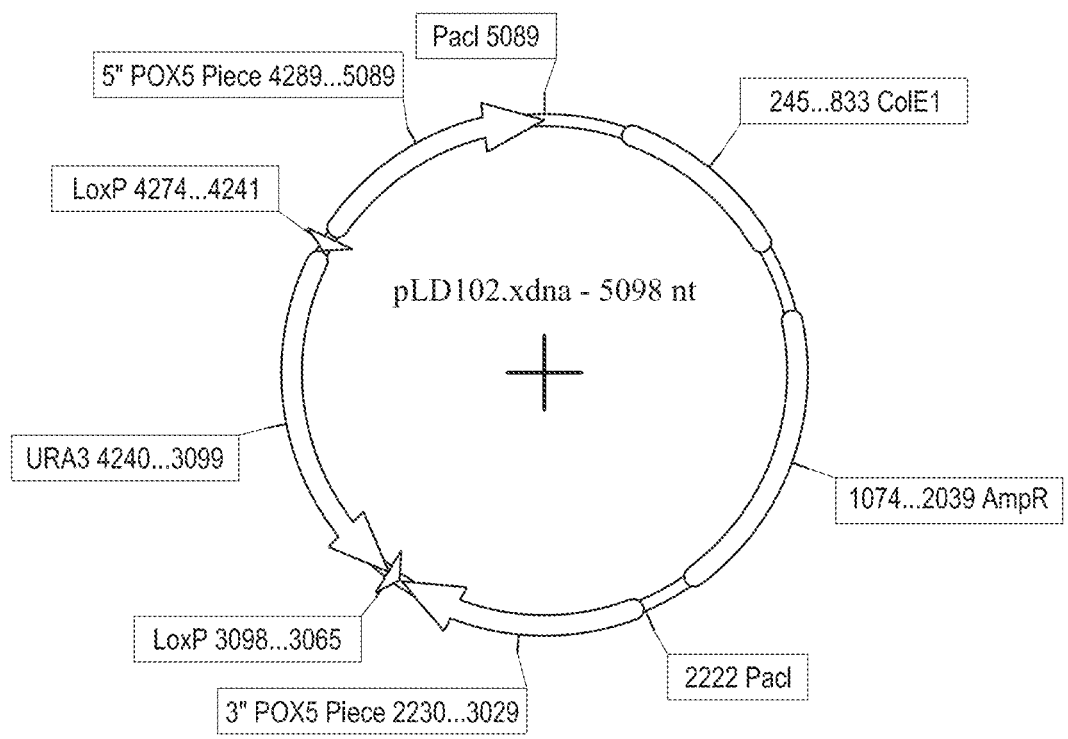
FIG. 16 provides a map of plasmid pLD102.
Figure 17:
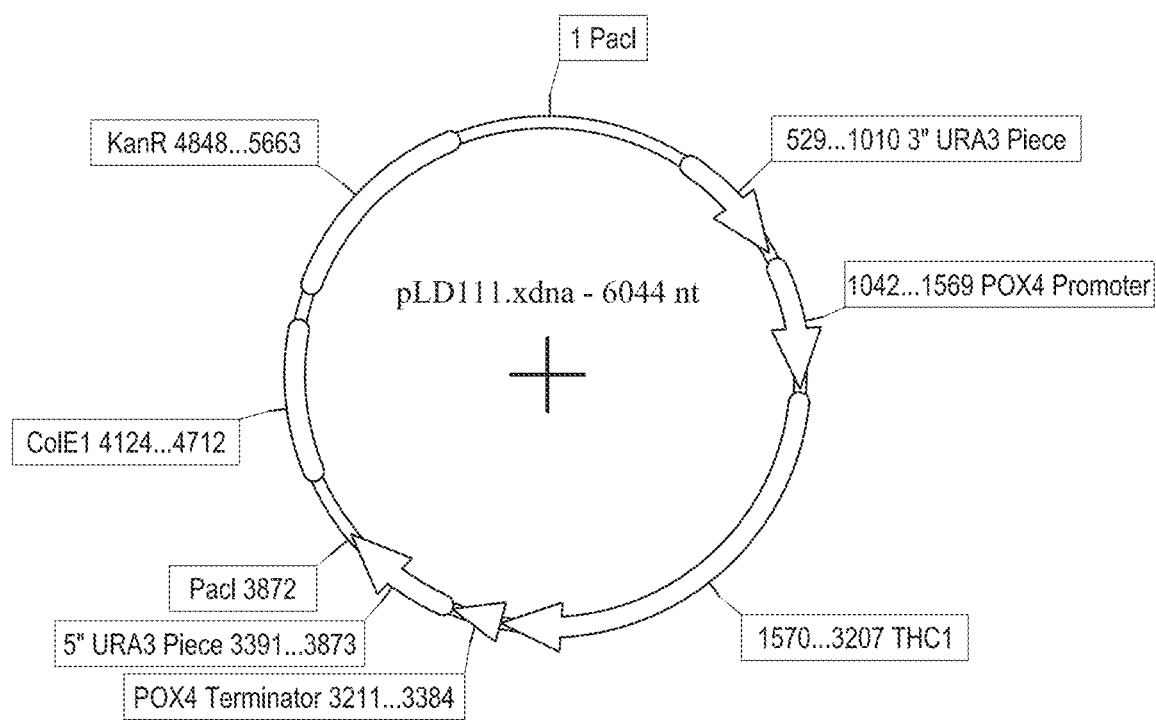
FIG. 17 provides a map of plasmid pLD111.
Figure 18:
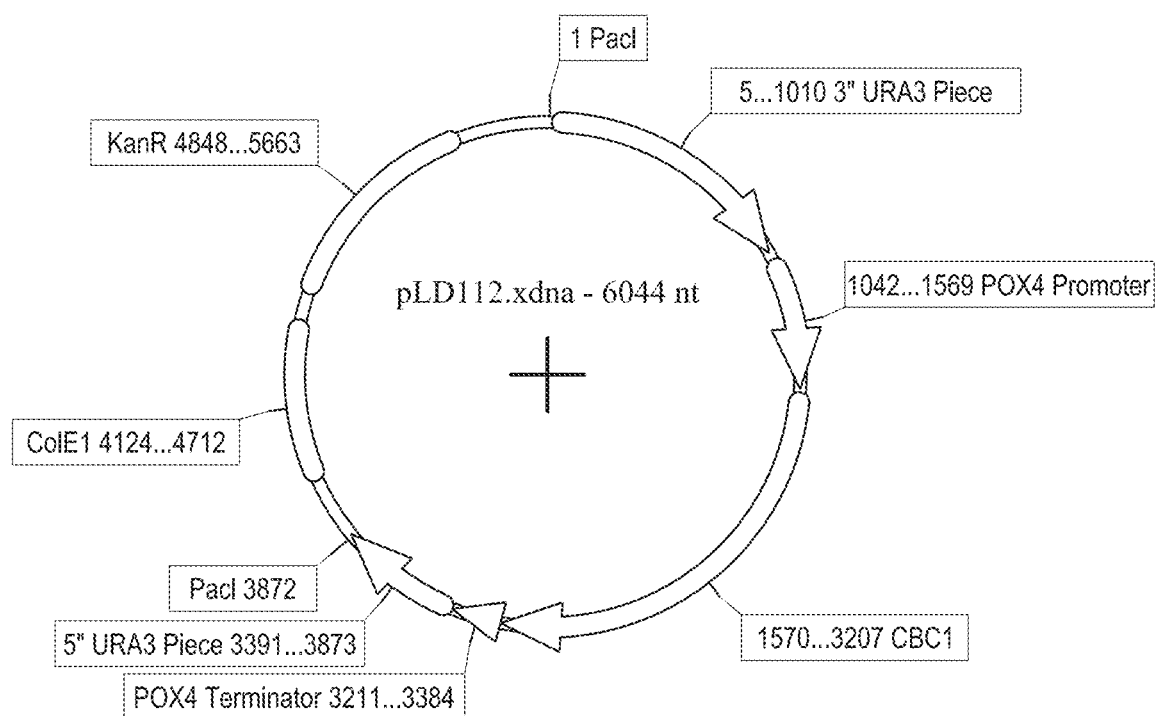
FIG. 18 provides a map of plasmid pLD112.
Figure 19:
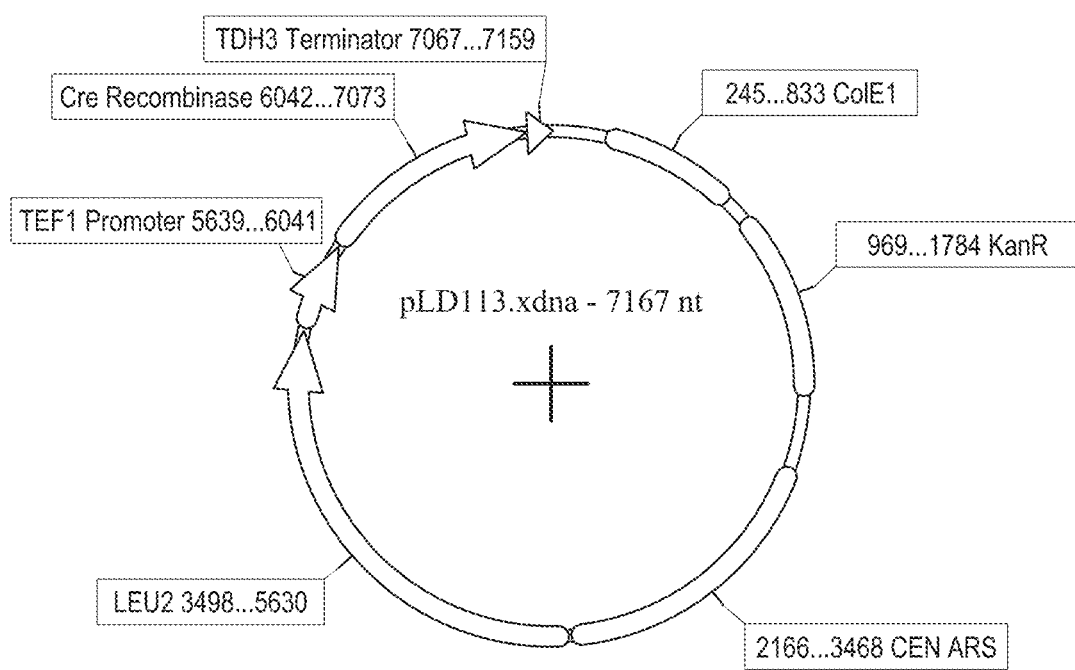
FIG. 19 provides a map of plasmid pLD113.
Figure 20:
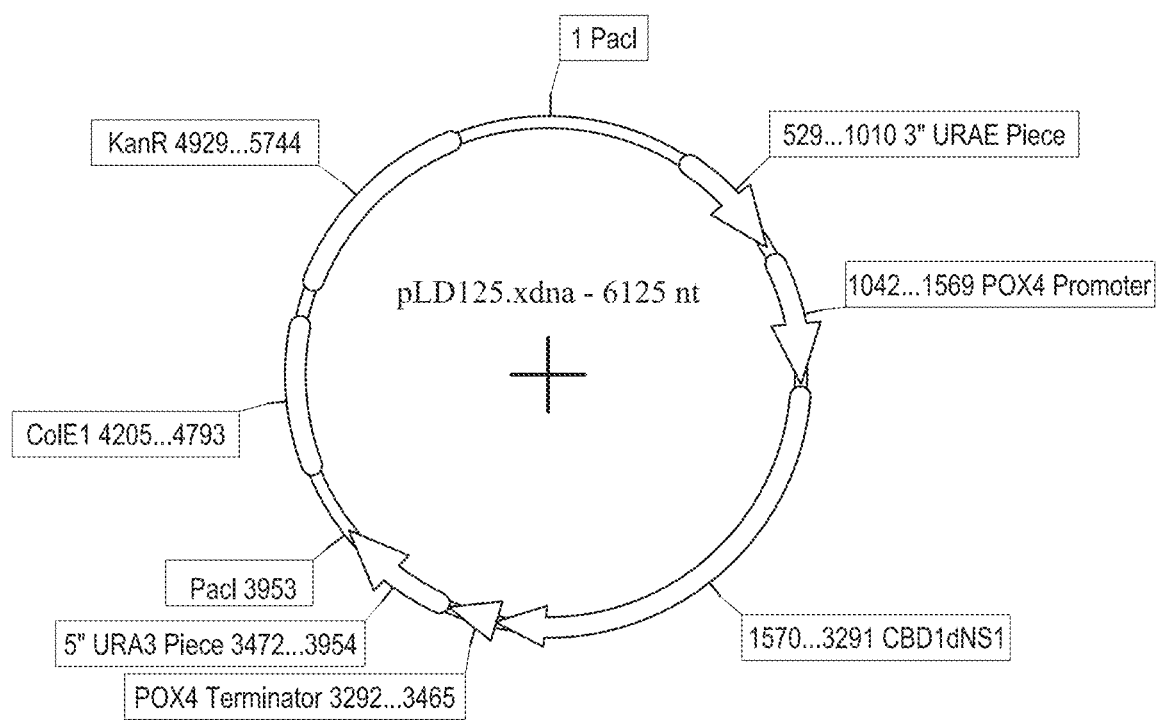
FIG. 20 provides a map of plasmid pLD125.
Figure 21:
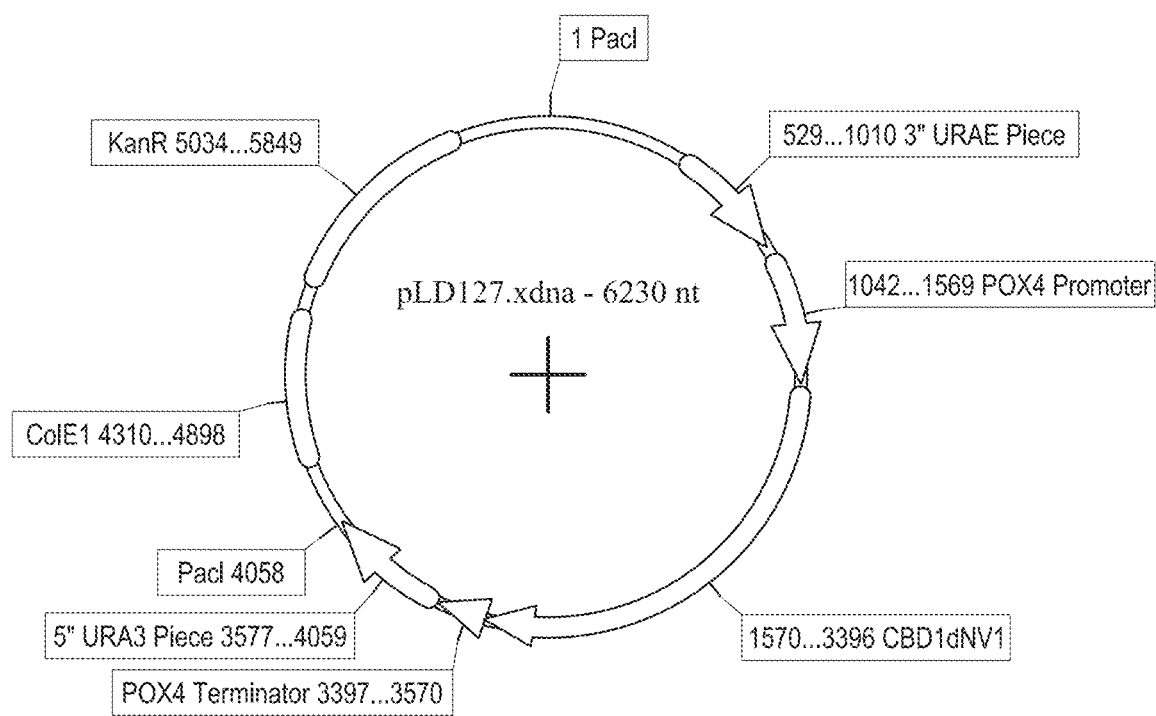
FIG. 21 provides a map of plasmid pLD127.
Figure 22:
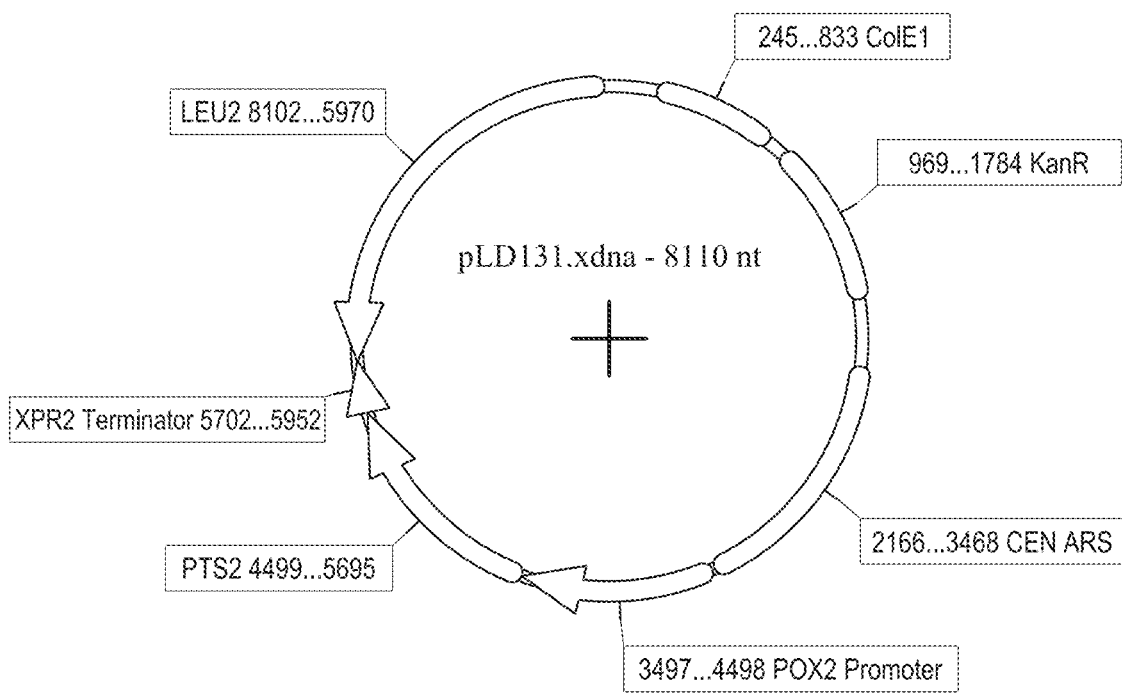
FIG. 22 provides a map of plasmid pLD131.
Figure 23:
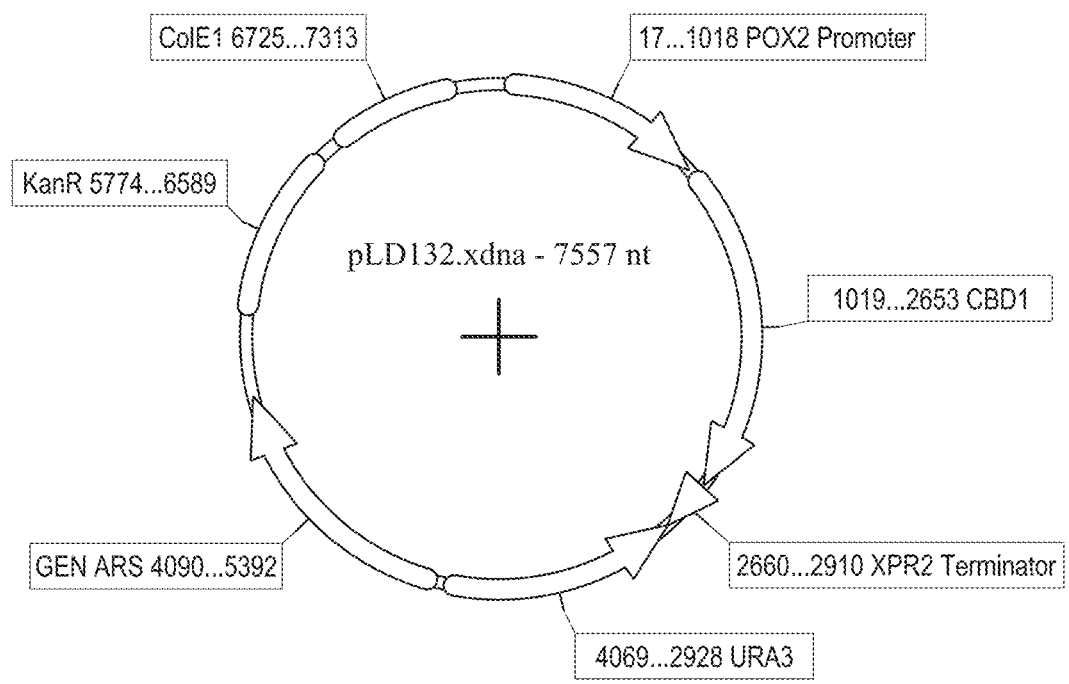
FIG. 23 provides a map of plasmid pLD132.
Figure 24:
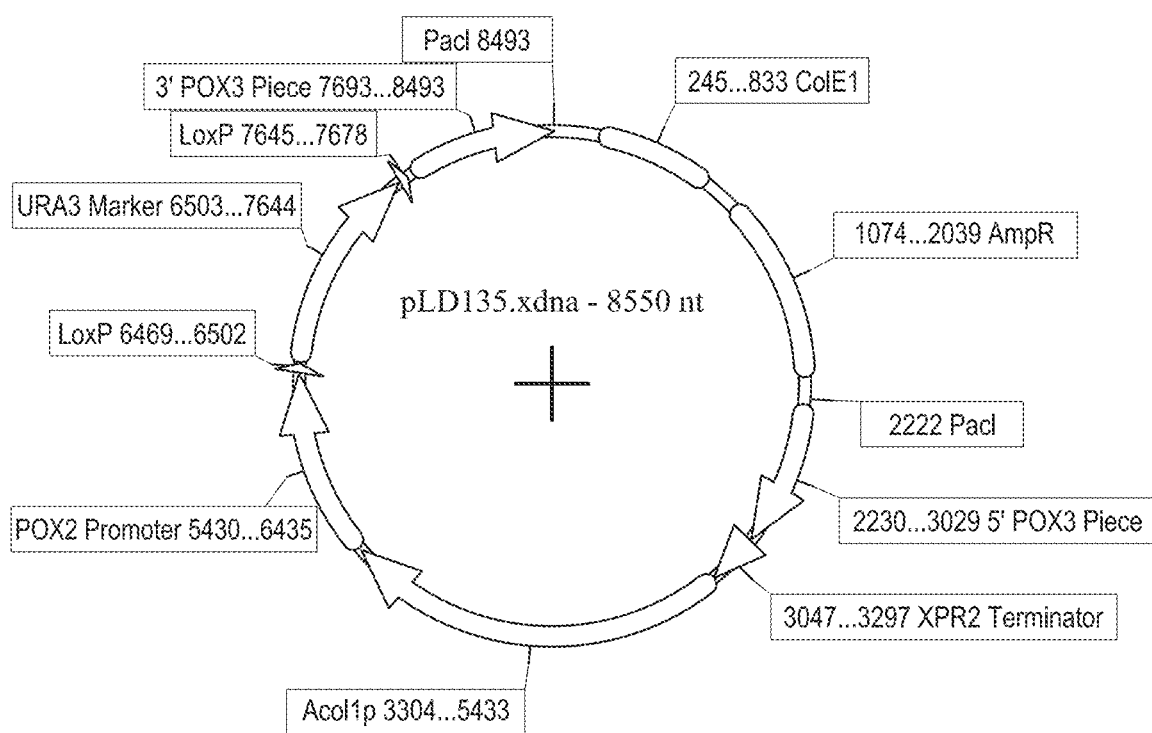
FIG. 24 provides a map of plasmid pLD135.
Figure 25:
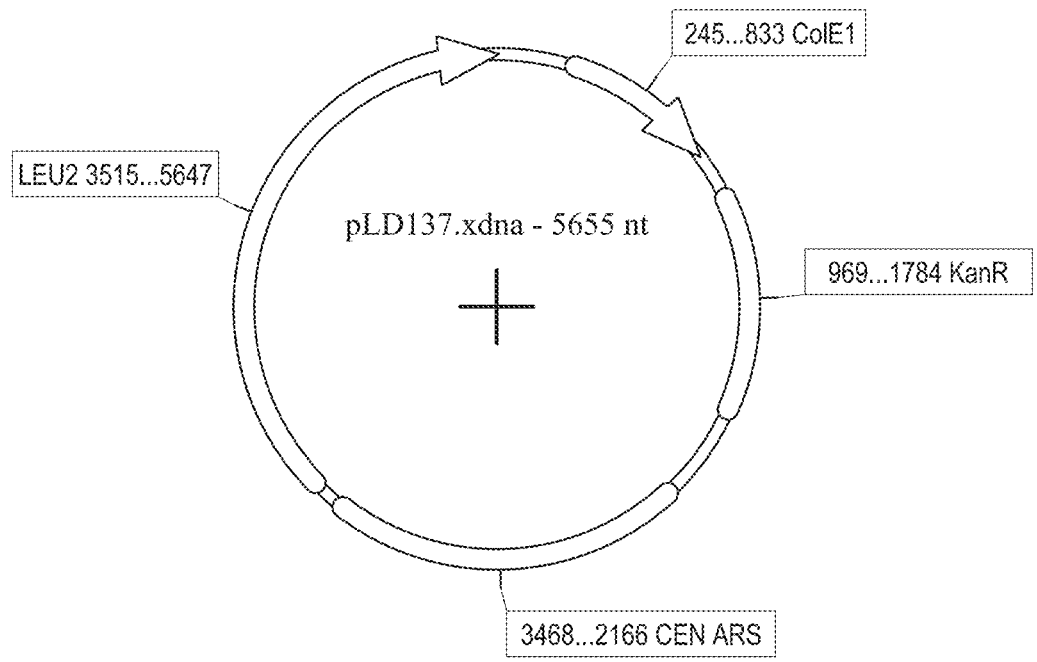
FIG. 25 provides a map of plasmid pLD137.
Figure 26:
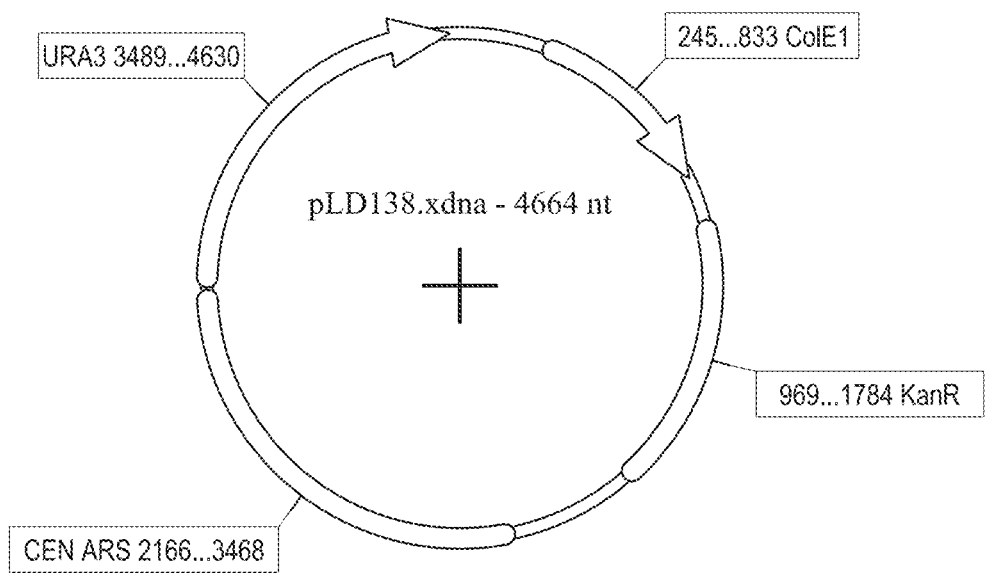
FIG. 26 provides a map of plasmid pLD138.
Figure 27:
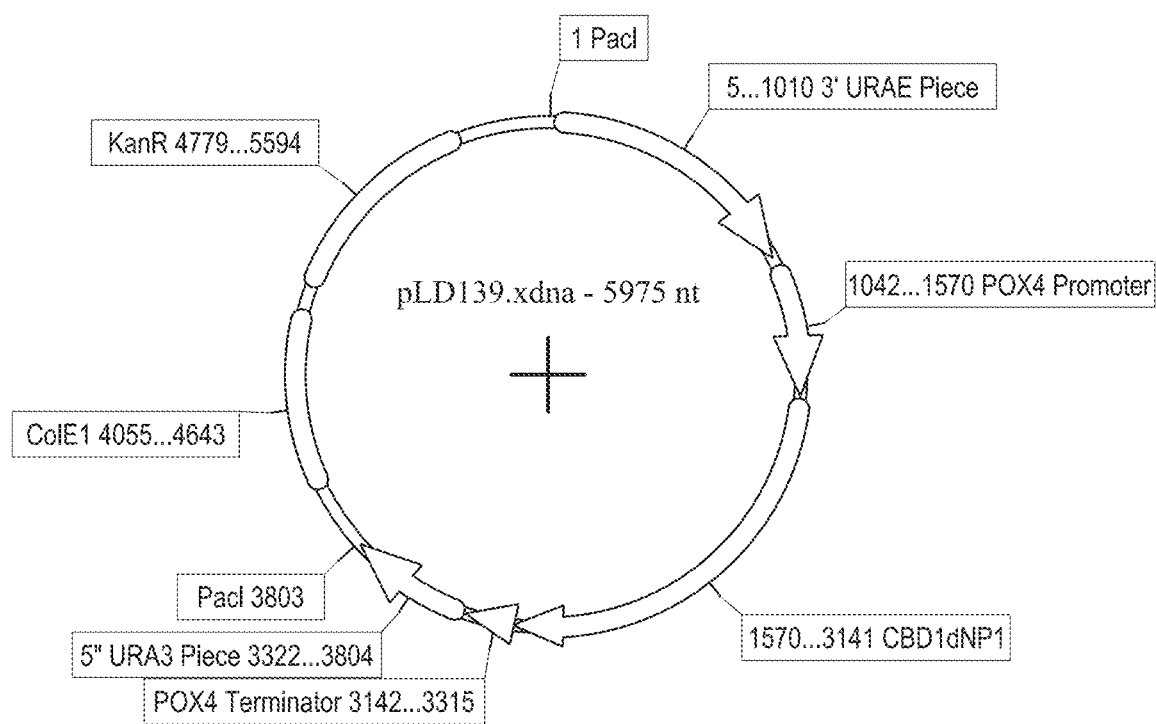
FIG. 27 provides a map of plasmid pLD139.
Figure 28:
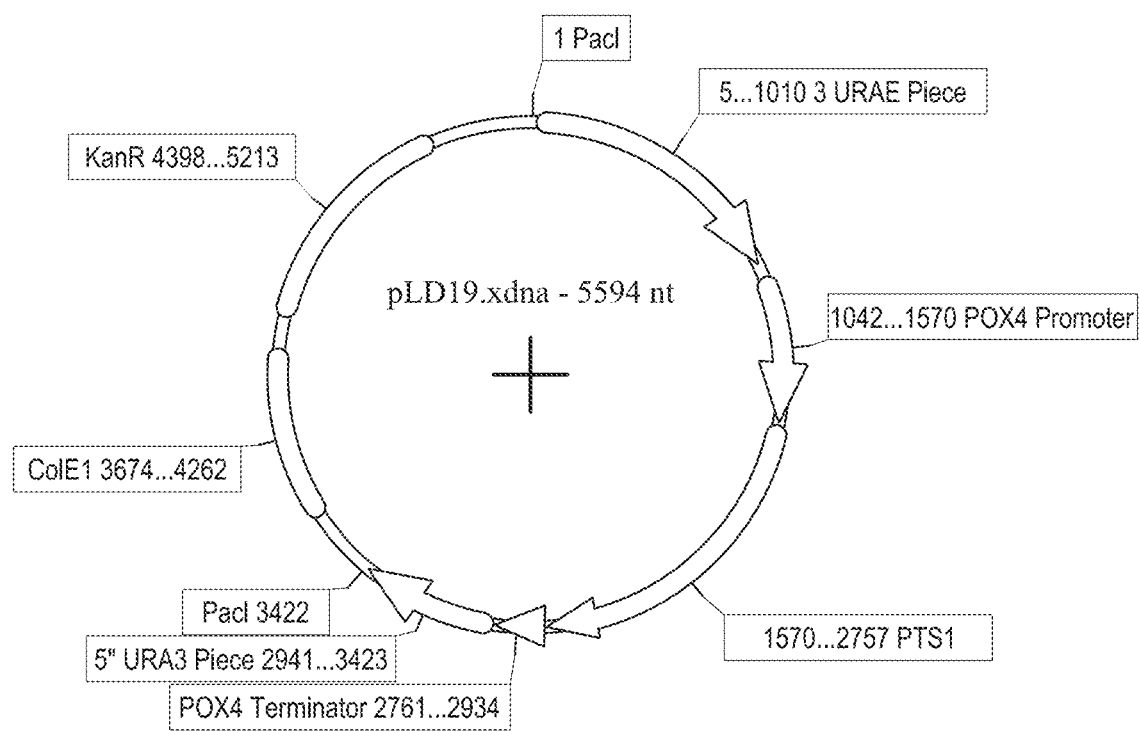
FIG. 28 provides a map of plasmid pLD19.
Figure 29:
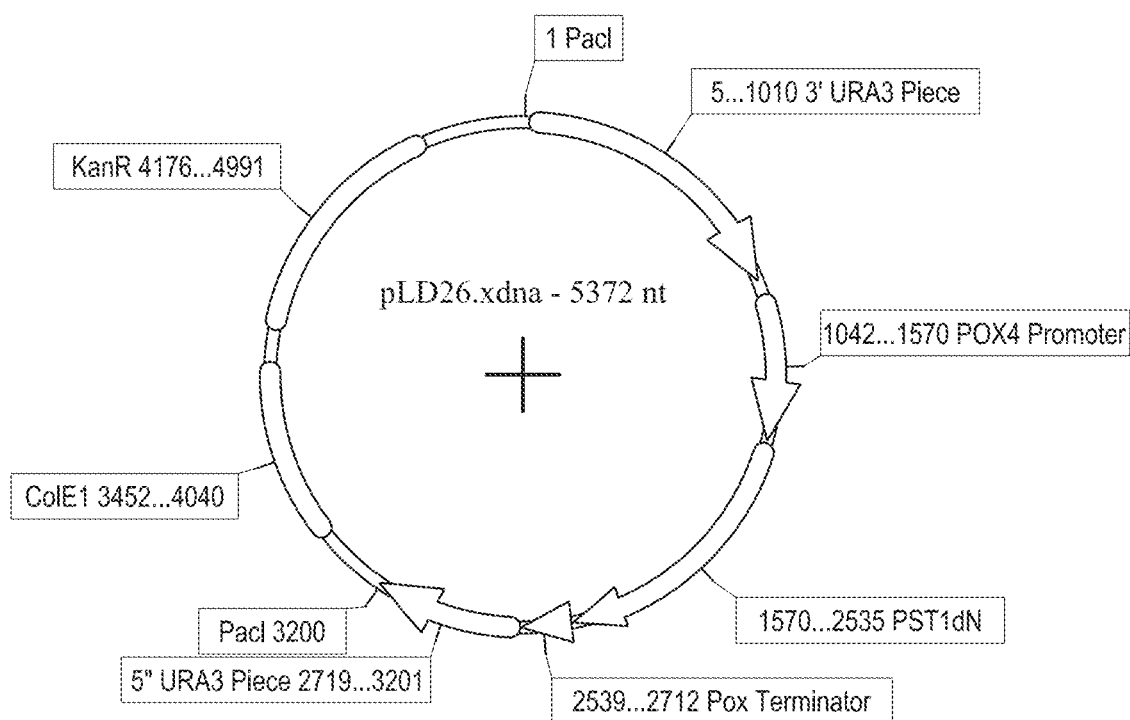
FIG. 29 provides a map of plasmid pLD26.

In one embodiment, which is represented by "A" of FIG. 4, the THCA synthase, CBDA synthase or CBCA synthase enzyme is expressed in the cytoplasm or cytosol as the native form of the enzyme.

In one embodiment, which is represented by "B" of FIG. 4, the THCA synthase, CBDA synthase or CBCA synthase enzyme is targeted to the vacuole by the addition of a KFERQ motif to the enzyme or the addition of an N-terminal QRPL motif found on carboxypeptidase Y from *Saccharomyces cerevisiae*. An alternative vacuolar targeting sequence is the hydrophobic 22 amino acid signal sequence, or pre sequence (MFSLKALLPLALLLVSANQVAA) (SEQ ID NO: 1), and 54 amino acid propeptide (KVHKAK-IYKHELSDEMKEVTFEQHLAHLGQKYLTQFE-KANPEVVFSREHPFFTE) (SEQ ID NO: 2) of pre-pro Proteinase A from *Saccharomyces cerevisiae* or of the particular yeast that will be engineered for cannabinoid production. Deletions in proteinases, such as PEP4, may be performed to ensure the targeted enzyme is not degraded in the vacuole.

In one embodiment, which is represented by "C" of FIG. 4, the THCA synthase, CBDA synthase or CBCA synthase enzyme is targeted to the endoplasmic reticulum (ER), Golgi or generally to the secretory pathway by the addition of some or all of the pre-pro region of alpha-factor from *Saccharomyces cerevisiae* or the Ost1p signal sequence from *Saccharomyces cerevisiae*. The alpha-factor or Ost1p secretion signal from the non-conventional yeast that will be engineered will be identified and considered as well. Other possible secretion signals include the 22 amino acid pre sequence of Proteinase A from *Saccharomyces cerevisiae*, MVRMVPVLLSLLLLLGPA (SEQ ID NO: 3) from human zinc-binding alpha-2-glycoprotein, MLFSNTLLIAAASAL-LAEA (SEQ ID NO: 4) from *Kluyveromyces marxianus* polygalacturonase, and MKFGVLFSVFAAIVSALPA (SEQ ID NO: 5) from *Saccharomycopsis fibuligera* glucoamylase. An HDEL motif can be added to the C-terminus of a protein to ensure retention in the ER.

In one embodiment, which is represented by "D" FIG. 4, the THCA synthase, CBDA synthase or CBCA synthase enzyme is targeted to the peroxisome by the addition of some or all of the PTS sequence GRRAKL (SEQ ID NO: 6) or a smaller subset of those amino acids based on the consensus sequence of [S/A/H/C/E/P/Q/V]-[K/R/H/Q]-[L/F] (SEQ ID NO: 7) to the C-terminus of each protein. An alternative mechanism of targeting to the peroxisome is the use of a PTS2 sequence near the N-terminus of the protein, which is defined by the consensus sequence -(R/K)(LN/I/Q)XX(L/V/I/H/Q)(L/S/G/A/K)X(H/Q)(L/A/F)- (SEQ ID NO: 8). An example could be RRMLSSKQL (SEQ ID NO: 9) as found in Pcd1p from *S. cerevisiae.*

One of the intermediates for the production of some polyketides a fatty is acid. For example, an intermediate for cannabinoids is hexanoic acid. This six-carbon liner carboxylic acid is toxic to yeast at low concentration. This lipophilic weak acid crosses the plasma membrane by passive diffusion and dissociate in the neutral cytosol leading to a decrease in the intracellular pH and accumulating. This cause inhibition of growth and death. For example, at pH 5, the specific growth of *Saccharomyces cerevisiae* in minimum media drops from 0.4 hr-1 to 0.22 hr-1 at a hexanoic concentration of 2 mm (0.3 g/L). The inhibition and toxicity of hexanoic acid and some other short fatty acids makes it a challenge to run a fermentation with it. The fermentation will need to be run in a fed batch form adding hexanoic acid at a very low rate to avoid accumulating and causing toxicity. The fermentation will be needed to run at a higher pH where the toxicity of fatty acids are less. This will make the fermentation more prone to contamination. Some short fatty acids such as hexanoic acid can be corrosive to metals so special metallurgy needs to be used for the piping of the feedstock.

Herein, also disclosed is the use of fatty acid esters for the production of polyketides by fermentation. Some suitable fatty acid esters include methyl, ethyl, butyl, allyl, isobutyl, hexyl, propyl, and geranyl fatty acid esters. Of special interest are ethyl esters, as the ethyl group can be used to produce acetyl coA as a carbon source, and geraryl caproate as it will provide two intermediates for the cannabinoid pathway. In addition, this process may require the expression of an esterase to slowly cleave the fatty acid ester if there is not an endogenous esterase being produced.

Figure 30:
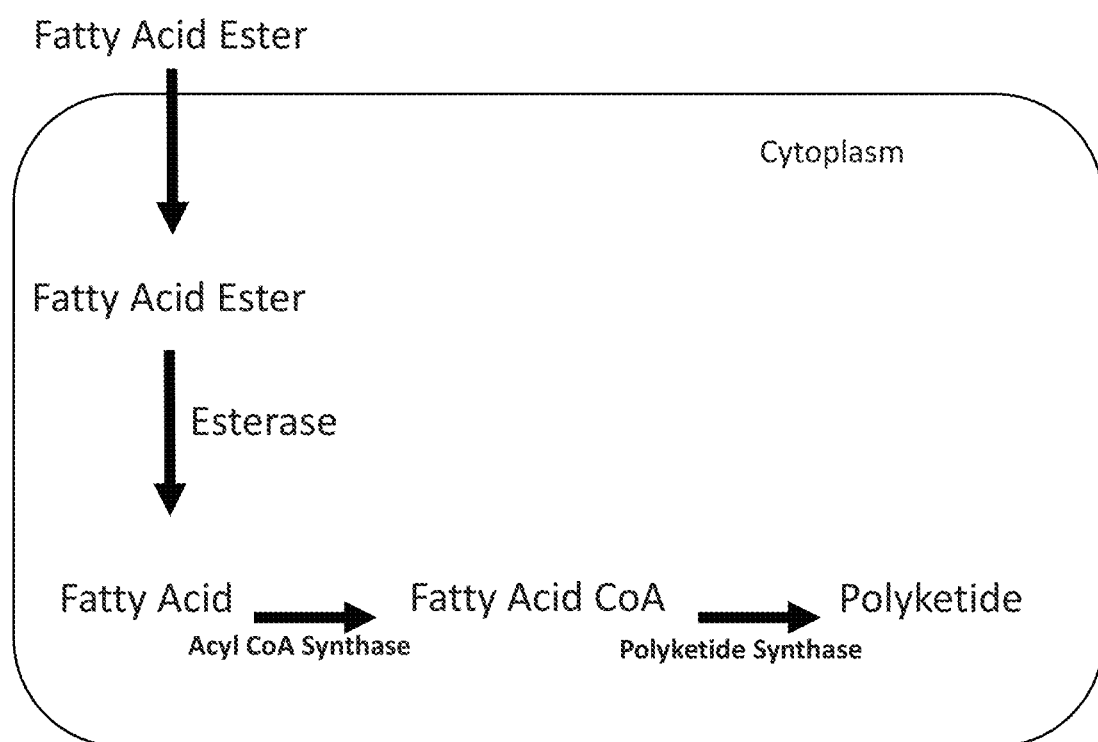
FIG. 30 depicts the use of a fatty acid ester where the fatty acid ester is transported to the cytoplasm. In the cytoplasm a native or introduce fatty acid esterase cleaves the fatty acid ester to release the fatty acid. This fatty acid is then the substrate for a acyl-CoA synthase forming the corresponding fatty acid CoA. This fatty acid CoA is then the substrate of a polyketide synthase to crease a polyketide.

In one embodiment as illustrated in FIG. 30 for the production of the polyketides, a strain from yeast that had been modified to produce polyketides from a fatty and dextrose, is modified to express an esterase or it has an endogenous cytoplasmic fatty acid esterase.

Figure 31:
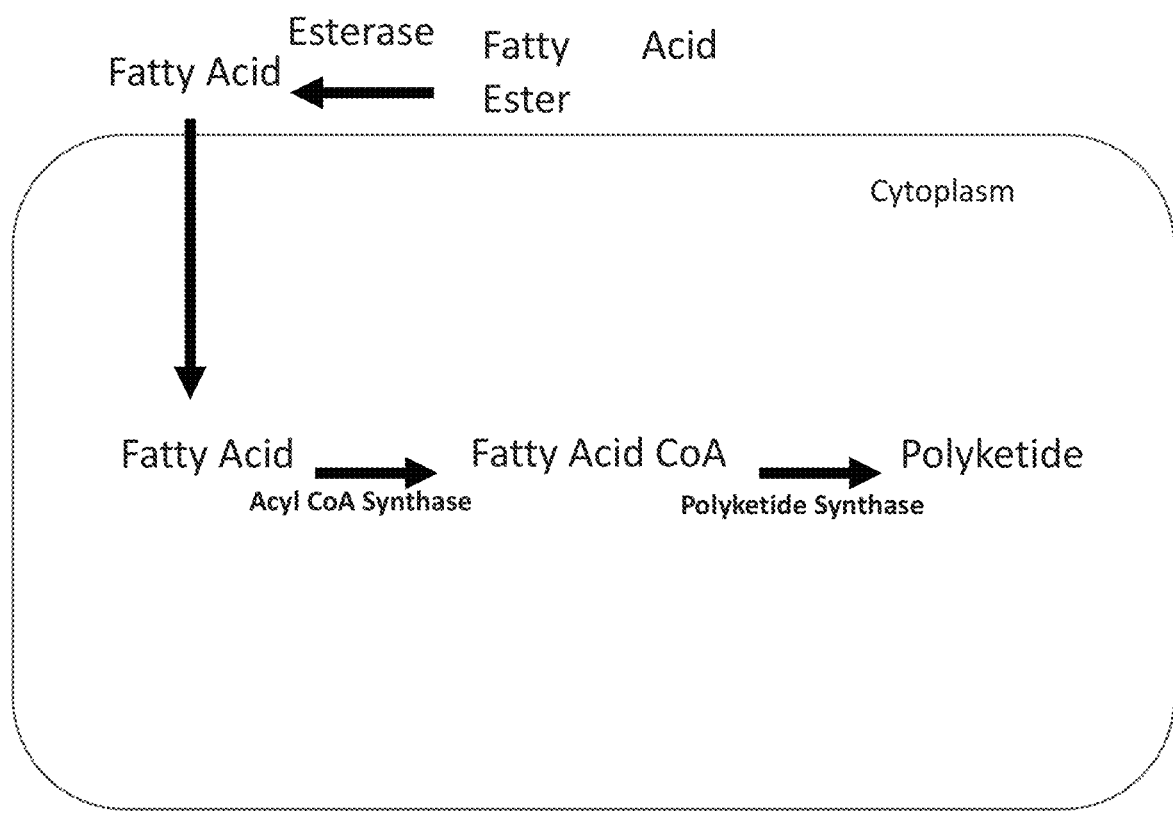
FIG. 31 depicts the use of a fatty acid ester where the fatty acid ester is cleaved outside of the cell by a native or introduced fatty acid esterase to release the fatty acid. This fatty acid is then transported into the cytoplasm where it is the substrate for a acyl-CoA synthase forming the corresponding fatty acid CoA. This fatty acid CoA is then the substrate of a polyketide synthase to crease a polyketide.

In another embodiment as illustrated in FIG. 31, a strain from a yeast that had been modified to produce cannabinoids from hexanoic acid and dextrose is modified to express a hexanoate esterase or it has an endogenous secreted hexanoate esterase. The hexanoate esterase has been targeted for secretion by a terminal fusion with a secretion motif such as the leader sequence of the yeast mating pheromone alpha-factor or invertase. In addition to the motifs mention here, other motifs could be used.

Some potential sources for the hexanoate ester are as follows: *Lactobacillus casei* EstB, *Lactobacillus plantarum* Lp_0796, *Acinetobacter* sp. ADP1 AreA, and *Lactococcus lactis* EstA.

The methods used to construct these strains are commonly known, have been used extensively to engineer *S. cerevisiae* and non-conventional yeasts and are described in numerous scientific publications and patents. Promoters will be used that are active during the preferred fermentation conditions. Some examples of promoters that could be used are those of the genes encoding glyceraldehyde 3-phosphate dehydrogenase and the translational elongation factor EF-1 alpha. Genes will be inserted in intergenic regions or non-essential genes.

Sources for Enzymes

Expressing one of these proteins in a acyl-CoA oxidase null mutant may result in the production of hexanoate CoA.

```
ACO1P Protein (Source Anthrobacter)
                              (SEQ ID NO: 10)
MTEVVDRASSPASPGSTTAAADGAKVAVEPRVDVA

ALGEQLLGRWADIRLHARDLAGREVVQKVEGLTHT

EHRSRVFGQLKYLVDNNAVHRAFPSRLGGSDDHGG

NIAGFEELVTADPSLQIKAGVQWGLFGSAVMHLGT

REHHDKWLPGIMSLEIPGCFAMTETGHGSDVASIA

TTATYDEETQEFVIDTPFRAAWKDYIGNAANDGLA

AVVFAQLITRKVNHGVHAFYVDLRDPATGDFLPGI

GGEDDGIKGGLNGIDNGRLHFTNVRIPRTNLLNRY

GDVAVDGTYSSTIESPGRRFFTMLGTLVQGRVSLD

GAAVAASKVALQSAIHYAAERRQFNATSPTEEEVL

LDYQRHQRRLFTRLATTYAASFAHEQLLQKFDDVF

SGARDTDADRQDLETLAAALKPLSTWHALDTLQEC

REACGGAGFLIENRFASLRADLDVYVTFEGDNTVL

LQLVAKRLLADYAKEFRGANFGVLARYVVDQAAGV

ALHRTGLRQVAQFVADSGSVQKSALALRDEEGQRT

LLTDRVQSMVAEVGAALKGAGKLPQHQAAALFNQH

QNELIEAAQAHAELLQWEAFTEALAKVDDAGTKEV

LTRLRDLFGLSLIEKHLSWYLMNGRLSMQRGRTVG

TYINRLLVKIRPHALDLVDAFGYGAEHLRAAIATG

AEATRQDEARTYFRQQRASGSAPADEKTLLAIKAG

KSRGRRAKL

ACO2 Protein
(Source Yarrowia lipolytica)
                              (SEQ ID NO: 11)
MNPNNTGTIEINGKEYNTFTEPPVAMAQERAKTSF

PVREMTYFLDGGEKNTLKNEQIMEEIERDPLFNND

NYYDLNKEQIRELTMERVAKLSLFVRDQPEDDIKK

RFALIGIADMGTYTRLGVHYGLFFGAVRGTGTAEQ

FGHWISKGAGDLRKFYGCFSMTELGHGSNLAGLET

TAIYDEETDEFIINTPHIAATKWWIGGAAHTATHT

VVFARLIVKGKDYGVKTFVVQLRNINDHSLKVGIS

IGDIGKKMGRDGIDNGWIQFTNVRIPRQNLLMKYT

KVDREGNVTQPPLAQLTYGSLITGRVSMASDSHQV

GKRFITIALRYACIRRQFSTTPGQPETKIIDYPYH

QRRLLPLLAYVYALKMTADEVGALFSRTMLKMDDL

KPDDKAGLNEVVSDVKELFSVSAGLKAFSTWACAD

VIDKTRQACGGHGYSGYNGFGQAYADWVVQCTWEG

DNNILTLSAGRALIQSAVALRKGEPVGNAVSYLKR

YKDLANAKLNGRSLTDPKVLVEAWEVAAGNIINRA

TDQYEKLIGEGLNADQAFEVLSQQRFQAAKVHTRR

HLIAAFFSRIDTEAGEAIKQPLLNLALLFALWSIE

EDSGLFLREGFLEPKDIDTVTELVNKYCTTVREEV

IGYTDAFNLSDYFINAPIGCYDGDAYRHYFQKVNE

QNPARDPRPPYYASTLKPFLFREEEDDDICELDEE

ACO3 Protein
(Source Rattus norvegicus)
                              (SEQ ID NO: 12)
MNPDLRKERASATFNPELITHILDGSPENTRRRE

IENLILNDPDFQHEDYNFLTRSQRYEVAVKKSATM

VKKMREYGISDPEEIMWFKKLYLANFVEPVGLNYS

MFIPTLLNQGTTAQQEKWMRPSQELQIIGTYAQTE

MGHGTHLRGLETTATYDPKTQEFILNSPTVTSIKW

WPGGLGKTSNHAIVLAQLITQGECYGLHAFVVPIR

EIGTHKPLPGITVGDIGPKFGYEEMDNGYLKMDNY

RIPRENMLMKYAQVKPDGTYVKPLSNKLTYGTMVF

VRSFLVGNAAQSLSKACTIAIRYSAVRRQSEIKQS

EPEPQILDFQTQQYKLFPLLATAYAFHFVGRYMKE

TYLRINESIGQGDLSELPELHALTAGLKAFTTWTA

NAGIEECRMACGGHGYSHSSGIPNIYVTFTPACTF

EGENTVMMLQTARFLMKIYDQVRSGKLVGGMVSYL

NDLPSQRIQPQQVAVWPTMVDINSLEGLTEAYKLR

AARLVEIAAKNLQTHVSHRKSKEVAWNLTSVDLVR

ASEAHCHYVVVKVFSDKLPKIQDKAVQAVLRNLCL

LYSLYGISQKGGDFLEGSIITGAQLSQVNARILEL

LTLIRPNAVALVDAFDFKDMTLGSVLGRYDGNVYE

NLFEWAKKSPLNKTEVHESYHKHLKPLQSKL
```

ACO4 Protein
(Source *Rattus norvegicus*)
(SEQ ID NO: 13)
MNPDLRKERASATFNPELITHILDGSPENTRRRRE
IENLILNDPDFQHEDYNFLTRSQRYEVAVKKSATM
VKKMREYGISDPEEIMWFKNSVHRGHPEPLDLHLG
MFLPTLLHQATAEQQERFFMPAWNLEITGTYAQTE
MGHGTHLRGLETTATYDPKTQEFILNSPTVTSIKW
WPGGLGKTSNHAIVLAQLITQGECYGLHAFVVPIR
EIGTHKPLPGITVGDIGPKFGYEEMDNGYLKMDNY
RIPRENMLMKYAQVKPDGTYVKPLSNKLTYGTMVF
VRSFLVGNAAQSLSKACTIAIRYSAVRRQSEIKQS
EPEPQILDFQTQQYKLFPLLATAYAFHFVGRYMKE
TYLRINESIGQGDLSELPELHALTAGLKAFTTWTA
NAGIEECRMACGGHGYSHSSGIPNIYVTFTPACTF
EGENTVMMLQTARFLMKIYDQVRSGKLVGGMVSYL
NDLPSQRIQPQQVAVWPTMVDINSLEGLTEAYKLR
AARLVEIAAKNLQTHVSHRKSKEVAWNLTSVDLVR
ASEAHCHYVVVKVFSDKLPKIQDKAVQAVLRNLCL
LYSLYGISQKGGDFLEGSIITGAQLSQVNARILEL
LTLIRPNAVALVDAFDFKDMTLGSVLGRYDGNVYE
NLFEWAKKSPLNKTEVHESYHKHLKPLQSKL ACO5 Protein
(Glycine max)
(SEQ ID NO: 14)
MEDGVDHLAFERNKAQFDVEDMKIIWAGSRQDFEL
SDRIRSRLVASDPAFRKDDRTRLIGRLFKNTLRKAA
YAWKRINELRLNEQEAYKLRSFVDQPAFTDLHWGM
FVPAIQGQGTDEQQQKWLPLAYGMQIIGCYAQTEL
GHGSNVQGLETTATFDPKTDEFVIHSPTLTSSKWW
PGGLGKISTHAVAYARLIIGGEDHGVHGFIVQLRS
LDDHLPLPGITIGDIGMKFGNAAYNTMDNGVLRFD
HVRIPRNQMLMRVSQVTREGRYVSSNVPRQLVYGT
MVNVRQKIVADASVALSRAVCIATRYSAVRRQFGS
HNGGLETQVIDYKTQQARLFPLLASAYAFRFVGGW
LKWLYMDVTERLQANDFSTLPEAHACTAGLKSLTT
TATADGIEECRKLCGGHGYLCSSGLPELFAVYVPA
CTYEGDNVVLLLQVARHLMKTVSQLGSGNKPVGTT
AYMARVEQLMQYHSDVEKAEDWLKPNVVLEAFEAR
ASRMSVACAQNLSKFANPEEGFQELAADLVDAAVA
HCQLIVVSKFIEKLQQDIPGKGVKKQLEVLCSIYA
LFLLHKHLGDFLSTGCINPKQGSLASEQLRNLYSQ
VRPNAIALVDAFNYTDHYLGSILGRYDGNVYPKMN
EEAWKDPLNDSVVPDGFKEYIQPMLKQQLRNARL ACO6 Protein
(Glycine Max)
(SEQ ID NO: 15)
MEGMVDHLAFERNNSQFDVDEMKIVWAGSRHAFEV
SDKMARLVASDPAFRKDDRVVLDRKALFKNTLRKA
AYAWKRBELRLSEEEAAMLRSFVDQPAFTDLHWGM
FVPAIKGQGTEEQQKKWLPLAHKMQIIGCYAQTEL
GHGSNVQGLETTATFDPRTDEFVIHSPTLTSSKWW
PGGLGKVSTHAVVYARLITDGQDHGVHGFIVQLRS
LDDHLPLPGITVGDIGMKFGNGAYNSMDNGMLRFD
HVRIPRNQMLMRVSQVTREGKYVQSSVPRQLVYGT
MVYVRQTIVSDASVALSRAVCIATRYSAVRRQFGS
KEGGLETQVIDYKTQQARLFPLLASAYAFRFVGEW
LKWLYMDVMKRLQASDFSTLPEAHACTAGLKSLTT
SATADGIEECRKLCGGHGYLCSSGLPELFAVYIPT
CTYEGDNTVLLLQVARHLIKTISQLGSRNKPVGTT
SYIGRVEQLMQYRSDVQKVEDWLKPNAVLGAFEAR
AAKKVVACAQNLSKFTNPEEGFQELSVDLVEAAVA
HCQLIVVSKFIEKLQQDIPGKGVKQQLELLCSIYA
LFLLHKHLGDFLATGCITPKQGSLANELLRSLYSQ
VRPNAIALVDAFNYTDHYLGSVLGRYDGDVYPKLY
EEAWKDPLNDSVVPDGFQEYIRPMLKQQLRNARL ACO7 Protein
(Source *Beuvaria bassiana*)
(SEQ ID NO: 16)
MSFPDNLKPKEPSGSSLLEKERRQSPVDVDALGKH
IFAGTSFLERQARVLRAIEQEPLFDKSRQQQLSRV
ERVKLGLARGKLMRRLQDRHGWDMDDYHMAAYLVG
EQSPYRLHVGMFRTTVEEQSSDAQRAYWMPRVNGW
EVSGAYSQTELGHGSNVRGVELEARWDPAAREFVV
HSPTLTAAKWWNGSLGRTANHAILMAQLMVPDPKR
EGQYISHGPQAFIAQIRDLKTNLPLEGVVIGDIGV
KIGFTSMDNGYMLFNQFRIPHSALLSRYVQLDPET
GVFSKSPNPALAYGTMTSIRTMLVEEAGTHLARAV
TIAIRYTAIRQQFRDKDSQDPSSAELQVLDYPTVQ
VRLFPLLAAAFALQYTGKVMRQDYAKTRGEVEKGN
LEGLAVMHSNSSGLKSLSTEITNAGIETCRRAMGG
HGYGSGSGLVEMQKDYQAKPILEGDNWMITQQTSS
FLIKRMTAAAKTRNEPPKDQIDAQLKTFLHQKDKG
RTFDILNSDSDIEESFKWRAASMTYDAYEARVIKK
KRHNDLLIQFHKLSHAHSQSIMVSSFLTTLTSSND -continued
LAHETKEIVFDLYRLFAYTTIQAESYEFLRCGAAS

SKDLDALPERIQALLTRIRPHAVKLVDAWKIPDYL

LDSALGRYDGNVYEDLFNRAHRLNPLNDIVFNPDY

KDDEIVKGSGERKPLSPKL

ACO8 Protein
(Source *Aspergillus nidulans*)
(SEQ ID NO: 17)
MPNPPPAWVQALKPASPQGTELLTQERAQSNIDVD

TLGDLLHTKEALKKQDEILSVLKSEKVFDKSRNHV

LGRTEKIQLALARGKRLQQLKKAHNWSDEDVHVAN

DLVSEPTPYGLHASMFLVTLREQGTPEQHKLFYER

ARNYEIIGCYAQTELGHGSNVRGLETTATWDPSDQ

TFIIHSPTLTASKWWIGSLGRTANHAVVMAQLYIG

GKNYGPHPFVVQIRDMETHQPLENVYVGDIGPKFG

YNTMDNGFLLFNKLKIPHVNMLARFAQVDKATNKY

IRPASPSLMYGTMTWVRSNIVLQAGGVLARGVTIA

VRYCAVRRQFQDRDAKANAEENQVLNYKMVQIRLL

PLLAAMYALHFTGRGMMRLYEENQERMKAAAQADQ

EKRGAGPEQLRAGSDLLADLHATSCGLKALASTTA

GEGLEVCRRACGGHGYSNYSGIGPWYADYLPTLTW

EGDNYMLTQQVARYLLKSARAVLAGKGTANDTSRI

LQAYLARRDKGASFDILGNDADIVAAFAWRTAHLT

FETLKYRDVEKRSWNSLLINFWRLSTALSQYLVVK

NFYEAVNSPEIRSSLDKDTASTLRSLFRLHALHTL

DREASEFFSSAAVTVRQIGLTQTSEVPKLLDEIRP

HAVRLVDSWKIPDWQLDSALGRSDGDVYPDLFKRA

SMQNPVNDLVFDPYPWNENVLKNAGEIKSKL

ACO9 Protein
(Source *Arabidopsis thaliana*)
(SEQ ID NO: 18)
MESRREKNPMTEEESDGLIAARRIQRLSLHLSPSL

TPSPSLPLVQTETCSARSKKLDVNGEALSLYWIRG

KHIDIQEKIFDFFNSRPDLQTPIEISKDDHRELCM

NQLIGLVREAGVRPFRYVADDPEKYFAIMEAVGSV

DMSLGIKMGVQYSLWGGSVINLGTKKHRDKYFDGI

DNLDYTGCFAMTELHEGSNVQGLQTTATFDPLKDE

FVIDTPNDGAIKWWIGNAAVHGKFATVFARLILPT

HDSKGVSDMGVHAFIVPIRDMKTHQTLPGVEIQDC

GHKVGLNGVDNGALRFRSVRIPRDNLLNRFGDVSR

DGTYTSSLPTINKRFGATLGELVGGRVGLAYASVG

VLKISATIAIRYSLLRQQFGPPKQPEVSILDYQSQ

QHKLMPMLASTYAYHFATVYLVEKYSEMKKTHDEQ

LVADVHALSAGLKSYVTSYTAKALSVCREACGGHG

YAAVNRFGSLRNDHDIFQTFEGDNTVLLQQVAADL

LKRYKEKFQGGTLTVTWSYLRESMNTYLSQPNPVT

ARWEGEDHLRDPKFQLDAFRYRTSRLLQNVAARLQ

KHSKTLGGFGAWNRCLNHLLTLAESHIETVILAKF

IEAVKNCPDPSAKAALKLACDLYALDRIWKDIGTY

RNVDYVAPNKAKVCFLV

ACO10 Protein
(Source *Arabidopsis thaliana*)
(SEQ ID NO: 19)
MESRREKNPMTEEESDGLIAARRIQRLSLHLSPSL

TPSPSLPLVQTETCSARSKKLDVNGEALSLYWIRG

KHIDIQEKIFDFFNSRPDLQTPIEISKDDHRELCM

NQLIGLVREAGVRPFRYVADDPEKYFAIMEAVGSV

DMSLGIKMGVQYSLWGGSVINLGTKKHRDKYFDGI

DNLDYTGCFAMTELHHGSNVQGLQTTATFDPLKDE

FVIDTPNDGAIKWWIGNAAVHGKFATVFARLILPT

HDSKGVSDMGVHAFIVPIRDMKTHQTLPGVEIQDC

GHKVGLNGVDNGALRFRSVRIPRDNLLNRFGDVSR

DGTYTSSLPTINKRFGATLGELVGGRVGLAYASVG

VLKISATIAIRYSLLRQQFGPPKQPEVSILDYQSQ

QHKLMPMLASTYAYHFATVYLVEKYSEMKKTHDEQ

LVADVHALSAGLKSYVTSYTAKALSVCREACGGHG

YAAVNRFGSLRNDHDIFQTFEGDNTVLLQQVAADL

LKRYKEKFQGGTLTVTWSYLRESMNTYLSQPNPVT

ARWEGEDHLRDPKFQLDAFRYRTSRLLQNVAARLQ

KHSKTLGGFGAWNRCLNHLLTLAESHIETVILAKF

IEAVKNCPDPSAKAALKLACDLYALDRIWKDIGTY

RNVDYVAPNKAKAIHKLTEYLSFQVRNVAKELVDA

FELPDHVTRAPIAMQSDAYSQYTQVVGF

Proteins involved in beta-oxidation that their encoding gene may be modified, disrupted or replaced to produce a short-chain fatty acid intermediate.

POX4 Acyl-CoA Oxidase (Source *Candida viswanathii*)
(SEQ ID NO: 20)
MTFTKKNVSVSQGPDPRTSIQTERANSKFDPVTMNYFLEGSKERSELMKSLAQQIERDPI

LFTDGSYYDLTKDQQRELTVLKINRLSRYREGDSVDTFNKRLSIMGVVDPQVATRIGVNL

GLFLSCISGNGTAEQFKYWAIDKGTHNIQGLYGCFGMTELGHGSNVAGVETTATFDKETD

-continued

EFVINTPHIGATKWWIGGAAHSATHCSVYARLVVDGKDYGVKTFVVPLRDSNHDLMPGVT

VGDIGAKMGRDGIDNGWIQFSNVRIPRFFMLQKFCKVSAEGEVVLPPLEQLSYSALLGGR

VMMVLDSYRMLARVSTIALRYAIGRRQFKGDNVDQNDPNALETQLIDYPLHQKRLFPYLA

AAYVVSTGALKVEHTIQSTLATLDAAVENNDTTAIFKSIDDMKSLFIDSGSLKATTTWLA

AEAIDQCRQACGGHGYSSYNGFAKAFNDWVVQCTWEGDNNVLSLSVGKPIIKQIIGIEDN

GKTVRGSTAFLNQVKDFTGSNASKVVLNNTSDLNDINKVIKSIEVAIIRLAHEAAISVRK

ESLDFAGAELVQISKLKAHHYLLTEFVKRVGEFEHKELVPFLNTIGRLYSATVVLDKFAG

VFLTFNVASPQAITDLASTQIPKLCAEVRPNVVAYTDSFQQSDMVINSAIGKYDGDVYEN

YFDLVKQLNPPKNTKAPYTAALEGMLNRPSLEARERYEKSDETAAILSKPOX5

POX5 Acyl-CoA Oxidase (Source Candida viswanathii)
(SEQ ID NO: 21)
MPTELQKERELTKFNPKELNYFLEGSQERSEIISNMVEQMQKDPILKVDASYYNLTKDQQ

REVTAKKIARLSRYFEHEYPDQQAQRLSILGVFDPQVFTRIGVNLGLFVSCVRGNGTNSQ

FFYWTINKGIDKLRGIYGCFGMTELAHGSNVQGIETTATFDEDTDEFVINTPHIGATKWW

IGGAAHSATHCSVYARLVKGKDYGVKTFVVPLRDSNHDLEPGVTVGDIGAKMGRDGIDN

GWIQFSNVRIPRFFMLQKYCKVSRSGEVTMPPSEQLSYSALIGGRVTMMMDSYRMTSRFI

TIALRYAIHRRQFKKKDTDTIETKLIDYPLHQKRLFPPLAAAYLFSQGALYLEQTMNATN

DKLDEAVSAGEKEAIDAAIVESKKLFVASGCLKSTCTWLTAEAIDEARQACGGHGYSSYN

GFGKAYSDWVVQCTWEGDNNILAMNVAKPMVRDLLKEPEQKGLVLSSVADLDDPAKLVKA

FDHALSGLARDIGAVAEDKGFDITGPSLVLVSKLNAHRFLIDGFFKRITPEWSEVLRPLG

FLYADWILTNFGATFLQYGIITPDVSRKISSEHFPALCAKVRPNVVGLTDGFNLTDMMTN

AAIGRYDGNVYEHYFETVKALNPPENTKAPYSKALEDMLNRPDLEVRERGEKSEEAAEIL

SS

POX1 Acyl-CoA Oxidase (Source Yarrowia lipolytica)
(SEQ ID NO: 22)
MTTNTFTDPPVEMAKERGKTQFTVRDVTNFLNGGEEETQIVEKIMSSIERDPVLSVTADY

DCNLQQARKQTMERVAALSPYLVTDTEKLSLWRAQLHGMVDMSTRTRLSIHNNLFIGSIR

GSGTPEQFKYWVKKGAVAVKQFYGCFAMTELGHGSNLKGLETTATYDQDSDQFIINTPHI

GATKWWIGGAAHTSTHCVCFAKLIVHGKDYGTRNFVVPLRNVHDHSLKVGVSIGDIGKKM

GRDGVDNGWIQFTNVRIPRQNMLMRYAKVSDTGVVTKPALDQLTYGALIRGRVSMIADSF

HVSKRFLTIALRYACVRRQFGTSGDTKETKIIDYPYHQRRLLPLLAYCYAMKMGADEAQK

TWIETTDRILALNPNDPAQKNDLEKAVTDTKELFAASAGMKAFTTWGCAKIIDECRQACG

GHGYSGYNGFGQGYADWVVQCTWEGDNNVLCLSMGRGLVQSALQILAGKHVGASIQYVGD

KSKISQNGQGTPREQLLSPEFLVEAFRTASRNNILRTTDKYQELVKTLNPDQAFEELSQQ

RFQCARIHTRQHLISSFYARIATAKDDIKPHLLKLANLFALWSIEEDTGIFLRENILTPG

DIDLINSLVDELCVAVRDQVIGLTDAFGLSDFFINAPIGSYDGNVYEKYFAKVNQQNPAT

NPRPPYYESTLKPFLFREEEDDEICDLDE

POX2 Acyl-CoA Oxidase (Source Yarrowia lipolytica)
(SEQ ID NO: 23)
MNPNNTGTIEINGKEYNTFTEPPVAMAQERAKTSFPVREMTYFLDGGEKNTLKNEQIMEE

IERDPLFNNDNYYDLNKEQIRELTMERVAKLSLFVRDQPEDDIKKRFALIGIADMGTYTR

LGVHYGLFFGAVRGTGTAEQFGHWISKGAGDLRKFYGCFSMTELGHGSNLAGLETTAIYD

EETDEFIINTPHIAATKWWIGGAAHTATHTVVFARLIVKGKDYGVKTFVVQLRNINDHSL

KVGISIGDIGKKMGRDGIDNGWIQFTNVRIPRQNLLMKYTKVDREGNVTQPPLAQLTYGS

-continued

LITGRVSMASDSHQVGKRFITIALRYACIRRQFSTTPGQPETKIIDYPYHQRRLLPLLAY

VYALKMTADEVGALFSRTMLKMDDLKPDDKAGLNEVVSDVKELFSVSAGLKAFSTWACAD

VIDKTRQACGGHGYSGYNGFGQAYADWVVQCTWEGDNNILTLSAGRALIQSAVALRKGEP

VGNAVSYLKRYKDLANAKLNGRSLTDPKVLVEAWEVAAGNIINRATDQYEKLIGEGLNAD

QAFEVLSQQRFQAAKVHTRRHLIAAFFSRIDTEAGEAIKQPLLNLALLFALWSIEEDSGL

FLREGFLEPKDIDTVTELVNKYCTTVREEVIGYTDAFNLSDYFINAPIGCYDGDAYRHYF

QKVNEQNPARDPRPPYYASTLKPFLFREEEDDDICELDEE

POX3 Acyl-CoA Oxidase (Source Yarrowia lipolytica)
(SEQ ID NO: 24)
MISPNLTANVEIDGKQYNTFTEPPKALAGERAKVKFPIKDMTEFLHGGEENVTMIERLMT

ELERDPVLNVSGDYDMPKEQLRETAVARIAALSGHWKKDTEKEALLRSQLHGIVDMGTRI

RLGVHTGLFMGAIRGSGTKEQYDYWVRKGAADVKGFYGCFAMTELGHGSNVAGLETTATY

IQDTDEFIINTPNTGATKWWIGGAAHSATHTACFARLLVDGKDYGVKIFVVQLRDVSSHS

LMPGIALGDIGKKMGRDAIDNGWIQFTNVRIPRQNMLMKYAKVSSTGKVSQPPLAQLTYG

ALIGGRVTMIADSFFVSQRFITIALRYACVRRQFGTTPGQPETKIIDYPYHQRRLLPLLA

FTYAMKMAADQSQIQYDQTTDLLQTIDPKDKGALGKAIVDLKELFASSAGLKAFTTWTCA

NIIDQCRQACGGHGYSGYNGFGQAYADWVVQCTWEGDNNVLCLSMGRGLIQSCLGHRKGK

PLGSSVGYLANKGLEQATLSGRDLKDPKVLIEAWEKVANGAIQRATDKFVELTKGGLSPD

QAFEELSQQRFQCAKIHTRKHLVTAFYERINASAKADVKPYLINLANLFTLWSIEEDSGL

FLREGFLQPKDIDQVTELVNHYCKEVRDQVAGYTDAFGLSDWFINAPIGNYDGDVYKHYF

AKVNQQNPAQNPRPPYYESTLRPFLFREDEDDDICELDEE*

POX4 Acyl-CoA Oxidase (Source Yarrowia lipolytica)
(SEQ ID NO: 25)
MITPNPANDIVHDGKLYDTFTEPPKLMAQERAQLDFDPRDITYFLDGSKEETELLESLML

MYERDPLFNNQNEYDESFETLRERSVKRIFQLSKSIAMDPEPMSFRKIGFLGILDMGTYA

RLGVHYALFCNSIRGQGTPDQLMYWLDQGAMVIKGFYGCFAMTEMGHGSNLSRLETIATF

DKETDEFIINTPHVGATKWWIGGAAHTATHTLAFARLQVDGKDYGVKSFVVPLRNLDDHS

LRPGIATGDIGKKMGRDAVDNGWIQFTNVRVPRNYMLMKHTKVLRDGTVKQPPLAQLTYG

SLITGRVQMTTDSHNVSKKFLTIALRYATIRRQFSSTPGEPETRLIDYLYHQRRLLPLMA

YSYAMKLAGDHVRELFFASQEKAESLKEDDKAGVESYVQDIKELFSVSAGLKAATTWACA

DIIDKARQACGGHGYSAYNGFGQAFQDWVVQCTWEGDNTVLTLSAGRALIQSALVYRKEG

KLGNATKYLSRSKELANAKRNGRSLEDPKLLVEAWEAVSAGAINAATDAYEELSKQGVSV

DECFEQVSQERFQAARIHTRRALIEAFYSRIATADEKVKPHLIPLANLFALWSTEEDSAL

FLAEGYFEPEDIIEVTSLVNKYCGIVRKNVIGYTDAFNLSDYFINAAIGRYDGDVYKNYF

EKVKQQYPPEGGKPHYYEDVMKPFLHRERIPDVPMEPEDIQ

POX5 Acyl-CoA Oxidase (Source Yarrowia lipolytica)
(SEQ ID NO: 26)
MNNNPTNVILGGKEYDTFTEPPAQMELERAKTQFKVRDVTNFLTGSEQETLLTERIMREI

ERDPVLNVAGDYDADLPTKRRQAVERIGALARYLPKDSEKEAILRGQLHGIVDMGTRTRI

AVHYGLFMGAIRGSGTKEQYDYWVAKGAATLHKFYGCFAMTELGHGSNVAGLETTATLDK

DTDEFIINTPNSGATKWWIGGAAHSATHTACLARLIVDGKDYGVKIFIVQLRDLNSHSLL

NGIAIGDIGKKMGRDAIDNGWIQFTDVRIPRQNMLMRYDRVSRDGEVTTSELAQLTYGAL

LSGRVTMIAESHLLSARFLTIALRYACIRRQFGAVPDKPETKLIDYPYHQRRLLPLLAYT

-continued

YAMKMGADEAQQQYNSSFGALLKLNPVKDAEKFAVATADLKALFASSAGMKAFTTWAAAK

IIDECRQACGGHGYSGYNGFGQAYADWVVQCTWEGDNNVLCLSMGRSLIQSCIAMRKKKG

HVGKSVEYLQRRDELQNARVDNKPLTDPAVLITAWEKVACEAINRATDSFIKLTQEGLSP

DQAFEELSQQRFECARIHTRKHLITSFYARISKAKARVKPHLTVLANLFAVWSIEEDSGL

FLREGCFEPAEMDEITALVDELCCEAREQVIGFTDAFNLSDFFINAPIGRFDGDAYKHYM

DEVKAANNPRNTHAPYYETKLRPFLFRPDEDEEICDLDE

POX6 Acyl-CoA Oxidase (Source Yarrowia lipolytica)
(SEQ ID NO: 27)
MLSQQSLNTFTEPPVEMARERNQTSFNPRLLTYFLDGGEKNTLLMDRLMQEYERDPVFRN

EGDYDITDVAQSRELAFKRIAKLIEYVHTDDEETYLYRCMLLGQIDMGAFARYAIHHGVW

GGAIRGAGTPEQYEFWVKKGSLSVKKFYGSFSMTELGHGSNLVGLETTATLDKNADEFVI

NTPNVAATKWWIGGAADTATHTAVFARLIVDGEDHGVKTFVVQLRDVETHNLMPGIAIGD

CGKKMGRQGTDNGWIQFTHVRIPRQNMLRYCHVDSDGNVTEPMMAQMAYGALLAGRVGM

AMDSYFTSRKFLTIALRYATIRRAFAAGGGQETKLIDYPYHQRRLLPLMAQTYAIKCTAD

KVRDQFVKVTDMLLNLDVSDQEAVPKAIAEAKELFSVSAGVKATTTWACAHTIDQCRQAC

GGHGYSAYNGFGRAYSDWVIQCTWEGDNNILCLSAGRALVQSNRAVRAGKPIGGPTAYLA

APAGSPKLAGRNLYDPKVMIGAWETVSRALINRTTDEFEVLAKKGLSTAQAYEELSQQRF

LCTRIHTRLYMVKNFYERIAEEGTEFTKEPLTRLANLYAFWSVEEEAGIFLREGYITPQE

LKYISAEIRKQLLEVRKDVIGYTDAFNVPDFFLNSAIGRADGDVYKNYFKVVNTQNPPQD

PRPPYYESVIRPFLFRKDEDEEICSLEDE

FOX2 Peroxisomal hydratase-dehydrogenase-epimerase
(Source Candida viswanathii)
(SEQ ID NO: 28)
MSPVDFKDKVVIITGAGGGLGKYYSLEFAKLGAKVVVNDLGGALNGQGGNSKAADVVVDE

IVKNGGVAVADYNNVLDGDKIVETAVKNFGTVHVIINNAGILRDASMKKMTEKDYKLVID

VHLNGAFAVTKAAWPYFQKQKYGRIVNTSSPAGLYGNFGQANYASAKSALLGFAETLAKE

GAKYNIKANAIAPLARSRMTESILPPPMLEKLGPEKVAPLVLYLSSAENELTGQFFEVAA

GFYAQIRWERSGGVLFKPDQSFTAEVVAKRFSEILDYDDSRKPEYLKNQYPFMLNDYATL

TNEARKLPANDASGAPTVSLKDKVVLITGAGAGLGKEYAKWFAKYGAKVVVNDFKDATKT

VDEIKAAGGEAWPDQHDVAKDSEAIIKNVIDKYGTIDILVNNAGILRDRSFAKMSKQEWD

SVQQVHLIGTFNLSRLAWPYFVEKQFGRIINITSTSGIYGNFGQANYSSSKAGILGLSKT

MAIEGAKNNIKVNIVAPHAETAMTLTIFREQDKNLYHADQVAPLLVYLGTDDVPVTGETF

EIGGGWIGNTRWQRAKGAVSHDEHTTVEFIKEHLNEITDFTTDTENPKSTTESSMAILSA

VGGDDDDDEDEEEDEGDEEEDEEDEEEDDPVWRFDDRDVILYNIALGATTKQLKYVYEN

DSDFQVIPTFGHLITFNSGKSQNSFAKLLRNFNPMLLLHGEHYLKVHSWPPPTEGEIKTT

FEPIATTPKGTNVVIVHGSKSVDNKSGELIYSNEATYFIRNCQADNKVYADRPAFATNQF

LAPKRAPDYQVDVPVSEDLAALYRLSGDRNPLHIDPNFAKGAKFPKPILHGMCTYGLSAK

ALIDKEGMENEIKARFTGIVFPGETLRVLAWKESDDTIVFQTHVVDRGTIAINNAAIKLV

GDKAKI

Proteins with motifs or regions important for cellular localization are as follows.

```
OST1 (Source Candida viswanathii)
                                          (SEQ ID NO: 29)
MMWKFLIAIGLIFSYCCNAQLLDSLSFDNNWVNTHYIRTIDLSKGFVKETDLIQIKNIND

KPQDEYYFVVNDGFDSIDELSIFSAFVGDQALEVEVDEVVPDKVFKLKLPVPIAPNSDLE

LRINFVYIDSLVSVPSKIAMDATQQLLYKTNKFPFSPYVTQEYTLALSGMSKGQEMDLHI

DVEDTPGLPDLKPRVESQVLKYGPIAEDIPAFALKPMGLMYDHNRPLTKAVSLNRSIWLP

ASDINKVSIEEYYELTNTGAELDKGFSRVDWMKGRFESTRNHWALSHLEIPLLERGFDDY

YYTDKVGVVSTHKIFKNHLLLQPRYPVFGGWKYNFTLGWSEELSKFLHKLHDNQDEYIIK

FPILNSLRDVTYQDVYLEFYLPENAEFQNISSPIAFESISIENELSYLDVSKGHTKITVH

YTNLFDDLHKLDVFVKYQYTQVAFIYKIAKISGFVFLGLVSYYLLGLLDLSI

GlU1 Glucoamylase (Source Saccharomyces fibuligera)
                                          (SEQ ID NO: 30)
MKFGVLFSVFAAIVSALPLQEGPLNKRAYPSFEAYSNYKVDRTDLETFLDKQKEVSLYYL

LQNIAYPEGQFNNGVPGTVIASPSTSNPDYYYQWTRDSAITFLTVLSELEDNNFNTTLAK

AVEYYINTSYNLQRTSNPSGSFDDENHKGLGEPKFNTDGSAYTGAWGRPQNDGPALRAYA

ISRYLNDVNSLNEGKLVLTDSGDINFSSTEDIYKNIIKPDLEYVIGYWDSTGFDLWEENQ

GRHFFTSLVQQKALAYAVDIAKSFDDGDFANTLSSTASTLESYLSGSDGGFVNTDVNHIV

ENPDLLQQNSRQGLDSATYIGPLLTHDIGESSSTPFDVDNEYVLQSYYLLLEDNKDRYSV

NSAYSAGAAIGRYPEDVYNGDGSSEGNPWFLATAYAAQVPYKLAYDAKSASNDITINKIN

YDFFNKYIVDLSTINSAYQSSDSVTIKSGSDEFNTVADNLVTFGDSFLQVILDHINDDGS

LNEQLNRYTGYSTGAYSLTWSSGALLEAIRLRNKVKALA

SIAT1_RAT alpha-2,6-sialyltransferase (Source
Rat norvegicus)
                                          (SEQ ID NO: 31)
MIHTNLKKKFSLFILVFLLFAVICVWKKGSDYEALTLQAKEFQMPKSQEKVAMGSASQVV

FSNSKQDPKEDIPILSYHRVTAKVKPQPSFQVWDKDSTYSKLNPRLLKIWRNYLNMNKYK

VSYKGPGPGVKFSVEALRCHLRDHVNVSMIEATDFPFNTTEWEGYLPKENFRTKVGPWQR

CAVVSSAGSLKNSQLGREIDNHDAVLRFNGAPTDNFQQDVGSKTTIRLMNSQLVTTEKRF

LKDSLYTEGILIVWDPSVYHADIPKWYQKPDYNFFETYKSYRRLNPSQPFYILKPQMPWE

LWDIIQEISADLIQPNPPSSGMLGIIIMMTLCDQVDIYEFLPSKRKTDVCYYHQKFFDSA

CTMGAYDPLLFEKNMVKHLNEGTDEDIYLFGKATLSGFRNIRC

B4galt1 Beta-1,4-galactosyltransferase 1 (Source
Homo sapiens)
                                          (SEQ ID NO: 32)
MRLREPLLSGSAAMPGASLQRACRLLVAVCALHLGVTLVYYLAGRDLSRLPQLVGVSTPL

QGGSNSAAAIGQSSGELRTGGARPPPPLGASSQPRPGGDSSPVVDSGPGPASNLTSVPVP

HTTALSLPACPEESPLLVGPMLIEFNMPVDLELVAKQNPNVKMGGRYAPRDCVSPHKVAI

IIPFRNRQEHLKYWLYYLHPVLQRQQLDYGIYVINQISF

DOA4 Ubiquitin carboxyl-terminalhydrolase4
(Source Candida viswanathii)
                                          (SEQ ID NO: 33)
MTLLLKPTSELDATSRKIIERIQSNSPTFQHLFDLLLNLLPFFDKTVSLLGSIGYCDYEV

AYVTYQTCIQVVGLMKPKTNSLNQDIFKGVQLQTRKRASTFKAILSYFAEPETQEEDPLL

NRFKSLSGGGSKTKSSQDEVFHEWITSSELQRELSSKKVLLIDFRPRKDYLNNHIKYKDL

VHIEPTQLETLLDSASDQDLETLVKKSAPYDQYHIFLERHKYDLIVVYNYNYGSESTDRL

LGIIDVVSKPNPFTKLITILMNNKYISSRLKVKPLFLSGGVLNWYKTFGIEYLERTLVQN
```

-continued

```
GVAHTSDNQYLKSFNDYVSTSKETPKTQVKTQNGDYIRPSQRKVNQFDPVPVKSGPTVFA

SAKVDLPPTPGSPAVSTPSPPRAPAPPTKTTSLTHVPEKEAKSPSPVTKEVTVSSKKSQF

LELYTTGLVNLGNSCYMNCVVQCLAAAPQLTSFFFPTITESFSDHSYRQHINSNNKLGTK

GELTTSFVELILNMLNNNGKAFSPTKFKRTMGSLSPSQQFLTYDQQDCIEFLNFLLDALH

EDLNNVTITDPSERKLITDLSPEQEKSRETLPVRLASTIEWERYLKLNFSVIVDYFQGQH

LSQLKCLECGFTSTTYNAFSILSLPIPQKLNNLGKVLLKDCLEEFVTTELLDDNNKWYCP

QCKRFTRLTKKIAITRLPQVLIVNFNRFKMTNTGGFNKLETFVTYPVNEELDMTPYWPDV

GSRINENSTMSIEMEQDLLQSFPIRNQTPPFKYKLFGVANHFGNLTTGHYTSYVYKHSDS

KKTRNWCYFDDSKITYNVSPSQVVNKNAYCLFFQRV

APR1 Vacuolar aspartic protease (Source
Candida viswanathii)
                                                  (SEQ ID NO: 34)
MQLSLSVLSTVATALLSLTTAVDAKSHNIKLSKLSNEETLDASTFQEYTSSLANKYMNLF

NAAHGNPTSFGLQHVLSNQEAEVPFVTPQKGGKYDAPLTNYLNAQYFTEIEIGTPGQPFK

VILDTGSSNLWVPSQDCTSLACFLHSKYDHDASSTYKANGSEFSIQYGSGSMEGYISQDI

LTIGDLVIPKQDFAEATSEPGLAFAFGKFDGILGLAYDSISVNHIVPPVYNAINQGLLDK

PQVSFYLGNTEKDENDGGLATFGGYDASLFQGKITWLPVRRKAYWEVSFEGIGLGDEYAE

LQKTGAAIDTGTSLITLPSSLAEIINAKIGATKSWSGQYQIDCAKRDELPDLTLTFAGHN

FTLTAHDYILEVSGSCISVFTPMDFPKPIGDLAIIGDAFLRKYYSIYDLDKNAVGLAPSK

A

PHO8 (Source Candida viswanathii)
                                                  (SEQ ID NO: 35)
MGITNETQALLGGDSLSCLNKKKSNTKRNLSYLLNIITVSIIAYLCFFATHNHHNDSGIP

KVDPHKKKNIIMMVTDGMGPASLSAARSFRQFRDKLAINDILTLDQYLIGSSRTRSSSSL

VTDSAAGATAFSCALKSYNGAIGVSPDKSPCGTILEALKLQGYYTGLVVTTRITDATPAA

FSAHVDYRFQEDLIAEHQLGEYPFGRAVDLILGGGRCHFLPTAQGGCRADDRNLIKESSD

TWQYVGDRQQFDQLKGGKNVSLPLLGLLANTDIPYAIDRDEKEYPSLAEQVKVALTALSD

ATKDSDQGFFLLIEGSRIDHAGHEINDPTAVREVLAYDEAFGEVIKFIDSTDVETVATS

TSDHETGGLVVSRQVTPEYPDYIWYPEVLLNSTHSGDYLAHKIADYKNKDDTAKLTKFIK

HEILETDLGVTDYTDKDVQAILDKVNDPANLLYVLNDIVSFRAQIGWTTHGHSAVDVNIY

AHTNSPAIRAKLASAKAYHGLSGNHENIEIGAFMEEITGSNLSRVTELIKKTAHSPSLSK

KEFSVDEFHGNV

SNA4 (Source Saccharomyces cerevisiae)
                                                  (SEQ ID NO: 36)
MCCYCVCCTVSDFILYIVAFFFPPAAVLLRSGPCSSDFLLNVLLTLLGFLPGMLHAFYYI

TITSPLRNAEYVYYYQQGWVDSERNVPSNRPQNSQTPQNRPQQGSSARNVYPSVETPLLQ

GAAPHDNKQSLVESPPPYVP

OCH1 (Source Candida viswanathii)
                                                  (SEQ ID NO: 37)
MRLKDIKLILIGILTISVTYFLISSFSGPRAYTTSDPNSSKMQFLRALESHPNWKETGLN

FQPTKKLEVDDSSTPVRQQLAARFPYDPTQPFPKNIWQTWKVGIEDETFPKRYLKFQLSW

DTKNPEYKHHVIPDDQCDELVAQLFEDVPDVARAYKVMPKSILKADFFRYLILFARGGVY

TDIDTVGLKPIDTWMSNMELLWGEPNRAGLVVGIEADPDRPDWADWYARRIQFCQWTIQL
```

-continued

KKGHPMLRELITKITDITLTREKRNELKKVLGKDEGGDIMNWTGPGIFTDTVFSYMNAIL

QAPEVITGKYKWDNIVDWKVFTGMQMPIAIDDVLVLPITSFSPDVSQMGSKSSTDPMAYA

KHMFLGSWKDDGMPEME

Proteins for use in the cannabinoid pathway are as follows.

HXS1 Protein (Source *Cannabis sativa*)
(SEQ ID NO: 38)
MGKNYKSLDSVVASDFIALGITSEVAETLHGRLAEIVCNYGAATPQTWINIANHILSPDL

PFSLHQMLFYGCYKDFGPAPPAWIPDPEKVKSTNLGALLEKRGKEFLGVKYKDPISSFSH

FQEFSVRNPEVYWRTVLMDEMKISFSKDPECILRRDDINNPGGSEWLPGGYLNSAKNCLN

VNSNKKLNDTMIVWRDEGNDDLPLNKLTLDQLRKRVWLVGYALEEMGLEKGCAIAIDMPM

HVDAVVIYLAIVLAGYVVVSIADSFSAPEISTRLRLSKAKAIFTQDHIIRGKKRIPLYSR

VVEAKSPMAIVIPCSGSNIGAELRDGDISWDYFLERAKEFKNCEFTAREQPVDAYTNILF

SSGTTGEPKAIPWTQATPLKAAADGWSHLDIRKGDVIVWPTNLGWMMGPWLVYASLLNGA

SIALYNGSPLVSGFAKFVQDAKVTMLGVVPSIVRSWKSTNCVSGYDWSTIRCFSSSGEAS

NVDEYLWLMGRANYKPVIEMCGGTEIGGAFSAGSFLQAQSLSSFSSQCMGCTLYILDKNG

YPMPKNKPGIGELALGPVMFGASKTLLNGNHHDVYFKGMPTLNGEVLRRHGDIFELTSNG

YYHAHGRADDTMNIGGIKISSIEIERVCNEVDDRVFETTAIGVPPLGGGPEQLVIFFVLK

DSNDTTIDLNQLRLSFNLGLQKKLNPLFKVTRVVPLSSLPRTATNKIMRRVLRQQFSHFE

TKS1 Protein (Source *Cannabis sativa*)
(SEQ ID NO: 39)
MNHLRAEGPASVLAIGTANPENILIQDEFPDYYFRVTKSEHMTQLKEKFRKICDKSMIRK

RNCFLNEEHLKQNPRLVEHEMQTLDARQDMLVVEVPKLGKDACAKAIKEWGQPKSKITHL

IFTSASTTDMPGADYHCAKLLGLSPSVKRVMMYQLGCYGGGTVLRIAKDIAENNKGARVL

AVCCDIMACLFRGPSDSDLELLVGQAIFGDGAAAVIVGAEPDESVGERPIFELVSTGQTI

LPNSEGTIGGHIREAGLIFDLHKDVPMLISNNIEKCLIEAFTPIGISDWNSIFWITHPGG

KAILDKVEEKLDLKKEKFVDSRHVLSEHGNIVISSSTVLFVMDELRKRSLEEGKSTTGDG

FEWGVLFGFGPGLTVERVVVRSVPIKY

TKS1P Protein (Source *Cannabis sativa*)
(SEQ ID NO: 40)
MNHLRAEGPASVLAIGTANPENILIQDEFPDYYFRVTKSEHMTQLKEKFRKICDKSMIRK

RNCFLNEEHLKQNPRLVEHEMQTLDARQDMLVVEVPKLGKDACAKAIKEWGQPKSKITHL

IFTSASTTDMPGADYHCAKLLGLSPSVKRVMMYQLGCYGGGTVLRIAKDIAENNKGARVL

AVCCDIMACLFRGPSDSDLELLVGQAIFGDGAAAVIVGAEPDESVGERPIFELVSTGQTI

LPNSEGTIGGHIREAGLIFDLHKDVPMLISNNIEKCLIEAFTPIGISDWNSIFWITHPGG

KAILDKVEEKLDLKKEKFVDSRHVLSEHGNMSSSTVLFVMDELRKRSLEEGKSTTGDGFE

WGVLFGFGPGLTVERVVVRSVPIKYGRRAKL

OAC1 Protein (Source *Cannabis sativa*)
(SEQ ID NO: 41)
MAVKHLIVLKFKDEITEAQKEEFFKTYVNLVNIIPAMKDVYWGKDVTQKNKEEGYTHIVE

VTFESVETIQDYIIHPAHVGFGDVYRSFWEKLLIFDYTPRKLKPK

```
OAC1P Protein (Source Cannabis sativa)
                                            (SEQ ID NO: 42)
MAVKHLIVLKFKDEITEAQKEEFFKTYVNLVNIIPAMKDVYWGKDVTQKNKEEGYTHIVE

VTFESVETIQDYIIHPAHVGFGDVYRSFWEKLLIFDYTPRKLKPKGRRAKL

PTS1 Protein (Source Cannabis sativa)
                                            (SEQ ID NO: 43)
MGLSSVCTFSFQTNYHTLLNPHNNNPKTSLLCYRHPKTPIKYSYNNFPSKHTKS1FHLQN

KCSESLSIAKNSIRAATTNQTEPPESDNHSVATKILNFGKACWKLQRPYTHAFTSCACGL

FGKELLHNTNLISWSLMFKAFFFLVAILCIASFTTTINQIYDLHIDRINKPDLPLASGEI

SVNTAWIMSIIVALFGLITTIKMKGGPLYIFGYCFGIFGGIVYSVPPFRWKQNPSTAFLL

NFLAHIITNFTFYYASRAALGLPFELRPSFTFLLAFMKSMGSALALIKDASDVEGDTKFG

ISTLASKYGSRNLTLFCSGIVLLSYVAAILAGIIWPQAFNSNVMLLSHAILAFWLILQTR

DFALTNYDPEAGRRFYEFMWKLYYAEYLVYVFI

PTS1dN (Source Cannabis sativa)
                                            (SEQ ID NO: 44)
MAATTNQTEPPESDNHSVATKILNFGKACWKLQRPYTIIAFTSCACGLFGKELLHNTNLI

SWSLMFKAFFFLVAILCIASFTTTINQIYDLHIDRINKPDLPLASGEISVNTAWIMSIIV

ALFGLIITIKMKGGPLYIFGYCFGIFGGIVYSVPPFRWKQNPSTAFLLNFLAHIITNFTF

YYASRAALGLPFELRPSFTFLLAFMKSMGSALALIKDASDVEGDTKFGISTLASKYGSRN

LTLFCSGIVLLSYVAAILAGIIWPQAFNSNVMLLSHAILAFWLILQTRDFALTNYDPEAG

RRFYEFMWKLYYAEYLVYVFI

PTS2 Protein (Source Cannabis sativa)
                                            (SEQ ID NO: 45)
MGLSLVCTFSFQTNYHTLLNPHNKNPKNSLLSYQHPKTPIIKSSYDNFPSKYCLTKNFHL

LGLNSHNRISSQSRSIRAGSDQIEGSPHHESDNSIATKILNFGHTCWKLQRPYVVKGMIS

IACGLFGRELFNNRHLFSWGLMWKAFFALVPILSFNFFAAIMNQIYDVDIDRINKPDLPL

VSGEMSIETAWILSIIVALTGLIVTIKLKSAPLFVFIYIFGIFAGFAYSVPPIRWKQYPF

TNFLITISSHVGLAFTSYSATTSALGLPFVWRPAFSFITAFMTVMGMTIAFAKDISDIEG

DAKYGVSTVATKLGARNMTFVVSGVLLLNYLVSISIGIIWPQVFKSNIMILSHAILAFCL

IFQTRELALANYASAPSRQFFEFIWLLYYAEYFVYVFI

PTS3 Protein (Source Cannabis sativa)
                                            (SEQ ID NO: 46)
MGLSSVCTFSFQTNYHTLLNPHNNNPKTSLLYRHPKTPIKYSYNNFPSKHCSTKSFHLQN

KCSESLSIAKNSIRAATTNQTEPPESDNHSVATKILNFGKACWKLQRPYTIIAFTSCACG

LFGKELLHNTNLISWSLMFKAFFFLVAVLCIASFTTTINQIYDLHIDRINKPDLPLASGE

ISVNTAWIMSIIVALFGLIITIKMKGGPLYIFGYCFGIFGGTVYSVPPFRWKQNPSTAFL

LNFLAHIITNFTFYHASRAALGLPFELRPSFTFLLAFMKSMGSALALIKDASDVEGDTKF

GISTLASKYGSRNLTLFCSGIVLLSYVAAILAGIIWPQAFNSNVMLLSHAILAFWLILQT

RDFALTNYDPEAGRRFYEFMWKLYYAEYLVYVFI

PTS4 Protein (Source Cannabis sativa)
                                            (SEQ ID NO: 47)
MELSSICNFSFQTNYHTLLNPHNKNPKSSLLSHQHPKTPIITSSYNNFPSNYCSNKNFHL

QNRCSKSLLIAKNSIRTDTANQTEPPESNTKYSVVTKILSFGHTCWKLQRPYTFIGVISC

ACGLFGRELFHNTNLLSWSLMLKAFSSLMVILSVNLCTNIINQITDLDIDRINKPDLPLA

SGEMSIETAWIMSIIVALTGLILTIKLNCGPLFISLYCVSILVGALYSVPPFRWKQNPNT

AFSSYFMGLVIVNFTCYYASRAAFGLPFEMSPPFTFILAFVKSMGSALFLCKDVSDIEGD
```

```
SKHGISTLATRYGAKNITFLCSGIVLLTYVSAILAAIIWPQAFKSNVMLLSHATLAFWLI

FQTREFALTNYNPEAGRKFYEFMWKLHYAEYLVYVFI
```

PTS5 Protein (Source *Cannabis sativa*)
(SEQ ID NO: 48)
```
MVFSSVCSFPSSLGTNFKLVPRSNFKASSSHYHEINNFINNKPIKFSYFSSRLYCSAKPI

VHRENKFTKSFSLSHLQRKSSIKAHGEIEADGSNGTSEFNVMKSGNAIWRFVRPYAAKGV

LFNSAAMFAKELVGNLNLFSWPLMFKILSFTLVILCIFVSTSGINQIYDLDIDRLNKPNL

PVASGEISVELAWLLTIVCTISGLTLTIITNSGPFFPPFLYSASIFFGFLYSAPPFRWKKN

PFTACFCNVMLYVGTSVGVYYACKASLGLPANWSPAFCLLFWFISLLSIPISIAKDLSDI

EGDRKFGIITFSTKFGAKPIAYICHGLMLLNYVSVMAAAIIWPQFFNSSVILLSHAFMAI

WVLYQAWILEKSNYATETCQKYYIFLWIIFSLEHAFYLFM
```

PTS6 Protein (Source *Cannabis sativa*)
(SEQ ID NO: 49)
```
MELSLSLGGPTIFPRYRASYTSTKLTTHFSNFPSKFSTKNFHQTLSFYGPTRGSKSLLNT

HQWRNSIRACAEAGAAGSNPVLNKVSDFRDACWRFLRPHTIRGTTLGSIALVARALIENP

NLIKWSLLLKAFSGLLALICGNGYIVGINQIYDIGIDKVNKPYLPIAAGDLSVQSAWYLV

ILFAVAGLLTVGFNFGPFITSLYCLGLVLGTIYSVPPFRMKRFPVAAFLIIATVRGFLLN

FGVYYATRAALGLTFEWSSAVAFITTFVTLFALVIAITKDLPDVEGDRKFQISTFATKLG

VRNIAYLGSGLLLLNYIGAIAAAIYMPQAFKRNLMLPIHTILALSLVFQAWVLEQANYTK

EAIAGFYRFIWNLFYVEYIIFPFI
```

PTS7 Protein (Source *Cannabis sativa*)
(SEQ ID NO: 50)
```
MAIALWLPRISRSTTRRFLKPSSSLTLFSVSHSHNYIVTSNRSPIPRLFTVPNQSHGREW

VSVSEVRLGYVSHISTAGKSDENRSRDAQVADVSWIDLYLPRQIHPYVRLARLDKPIGTW

LLAWPCMWSISLAANPGHLPDIKMMTLFGCGALLLRGAGCTINDLLDRDIDTMVERTKLR

PVASGIITPFQGICFLGFQLLLGLGILLQLNNYSRILGASSLLLVFSYPLMKRLTFWPQA

YLGLTFNWGALLGWAAVKGNIDPAIVLPLYASGVFWTLVYDTIYAHQDKEDDVRVGIKST

ALRFGDLTKQWNMGFGAACISSLALSGYNAEIGWPFYASLVAASGQLAWQISTVDLSSRD

DCNKKFVSNKWFGAIIFSGIVLARISS
```

PTS8 Protein (Source *Cannabis sativa*)
(SEQ ID NO: 51)
```
MSEAADVERVYAAMEEAAGLLGVACARDKIYPLLSTFQDTLVEGGSVVVFSMASGRHSTE

LDFSISVPTSHGDPYATVVEKGLFPATGHPVDDLLADTQKHLPVSMFAIDGEVTGGFKKT

YAFFPTDNMPGVAELSAIPSMPPAVAENAELFARYGLDKVQMTSMDYKKRQVNLYFSELS

AQTLEAESVLALVRELGLHVPNELGLKFCKRSFSVYPTLNWETGKIDRLCFAVISNDPTL

VPSSDEGDIEKFHNYATKAPYAYVGEKRTLVYGLTLSPKEEYYKLGAYYHITDVQRGLLK

AFDSLEDG
```

PTS9 Protein (ScNphB) (Source *Streptomyces*)
(SEQ ID NO: 52)
```
MSEAADVERVYAAMEEAAGLLGVACARDKIYPLLSTFQDTLVEGGSVVVFSMASGRHSTE

LDFSISVPTSHGDPYATVVEKGLFPATGHPVDDLLADTQKHLPVSMFAIDGEVTGGFKKT

YAFFPTDNMPGVAELSAIPSMPPAVAENAELFARYGLDKVQMTSMDYKKRQVNLYFSELS

AQTLEAESVLALVRELGLHVPNELGLKFCKRSFSVYPTLNWETGKIDRLCFAVISNDPTL

VPSSDEGDIEKFHNYATKAPYAYVGEKRTLVYGLTLSPKEEYYKLGAYYHITDVQRGLLK

AFDSLEDGMKCSTFSFWFVCKIIFFFFSFNIQTSIANPRENFLKCFSQYIPNNATNLKLV

YTQNNPLYMSVLNSTIHNLRFTSDTTPKPLVIVTPSHVSHIQGTILCSKKVGLQIRTRSG
```

-continued

GHDSEGMSYISQVPFVIVDLRNMRSIKIDVHSQTAWVEAGATLGEVYYWVNEKNENLSLA

AGYCPTVCAGGHFGGGGYGPLMRNYGLAADNIIDAHLVNVHGKVLDRKSMGEDLFWALRG

GGAESFGIIVAWKIRLVAVPKSTMFSVKKIMEIHELVKLVNKWQNIAYKYDKDLLLMTHF

ITRNITDNQGKNKTAIHTYFSSVFLGGVDSLVDLMNKSFPELGIKKTDCRQLSWIDTIIF

YSGVVNYDTDNFNKEILLDRSAGQNGAFKIKLDYVKKPIPESVFVQILEKLYEEDIGAGM

YALYPYGGIMDEISESAIPFPHRAGILYELWYICSWEKQEDNEKHLNWIRNIYNFMTPYV

SKNPRLAYLNYRDLDIGINDPKNPNNYTQARIWGEKYFGKNFDRLVKVKTLVDPNNFFRN

EQSIPPLPRHRH

CBD1dNS1 Protein (Source Cannabis sativa)
(SEQ ID NO: 53)
MFLKHIFVALAFALLADATPAQKRSPGFVALDFDIVKVQKNVTANDDAAAIVAKRQTNPR

ENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEA

GATLGEVYYWVNEKNENLSLAAGYCPTVCAGGHFGGGGYGPLMRNYGLAADNIIDAHLVN

VHGKVLDRKSMGEDLFWALRGGGAESFGIIVAWKIRLVAVPKSTMFSVKKIMEIHELVKL

VNKWQNIAYKYDKDLLLMTHFITRNITDNQGKNKTAIHTYFSSVFLGGVDSLVDLMNKSF

PELGIKKTDCRQLSWIDTIIFYSGVVNYDTDNFNKEILLDRSAGQNGAFKIKLDYVKKPI

PESVFVQILEKLYEEDIGAGMYALYPYGGIMDEISESAIPFPHRAGILYELWYICSWEKQ

EDNEKHLNWIRNIYNFMTPYVSKNPRLAYLNYRDLDIGINDPKNPNNYTQARIWGEKYFG

KNFDRLVKVKTLVDPNNFFRNEQSIPPLPRHRH

CBD1dNS2 Protein (Source Cannabis sativa)
(SEQ ID NO: 54)
MQLSLSVLSTVATALLSLTTAVDAKSHNPRENFLKCFSQYIPNNATNLKLVYTQNNPLYM

SVLNSTIHNLRFTSDTTPKPLVIVTPSHVSHIQGTILCSKKVGLQIRTRSGGHDSEGMSY

ISQVPFVIVDLRNMRSIKIDVHSQTAWVEAGATLGEVYYWVNEKNENLSLAAGYCPTVCA

GGHFGGGGYGPLMRNYGLAADNIIDAHLVNVHGKVLDRKSMGEDLFWALRGGGAESFGII

VAWKIRLVAVPKSTMFSVKKIMEIHELVKLVNKWQNIAYKYDKDLLLMTHFITRNITDNQ

GKNKTAIHTYFSSVFLGGVDSLVDLMNKSFPELGIKKTDCRQLSWIDTIIFYSGVVNYDT

DNFNKEILLDRSAGQNGAFKIKLDYVKKPIPESVFVQILEKLYEEDIGAGMYALYPYGGI

MDEISESAIPFPHRAGILYELWYICSWEKQEDNEKHLNWIRNIYNFMTPYVSKNPRLAYL

NYRDLDIGINDPKNPNNYTQARIWGEKYFGKNFDRLVKVKTLVDPNNFFRNEQSIPPLPR

HRH

CBD1dNV1 Protein (Source Cannabis sativa)
(SEQ ID NO: 55)
MQLSLSVLSTVATALLSLTTAVDAKSHNIKLSKLSNEETLDASTFQEYTSSLANKYMNLF

NAAHGNPTSFGLQHVLSNQEAEVPFVTPQKGGNPRENFLKCFSQYIPNNATNLKLVYTQN

NPLYMSVLNSTIHNLRFTSDTTPKPLVIVTPSHVSHIQGTILCSKKVGLQIRTRSGGHDS

EGMSYISQVPFVIVDLRNMRSIKIDVHSQTAWVEAGATLGEVYYWVNEKNENLSLAAGYC

PTVCAGGHFGGGGYGPLMRNYGLAADNIIDAHLVNVHGKVLDRKSMGEDLFWALRGGGAE

SFGIIVAWKIRLVAVPKSTMFSVKKIMEIHELVKLVNKWQNIAYKYDKDLLLMTHFITRN

ITDNQGKNKTAIHTYFSSVFLGGVDSLVDLMNKSFPELGIKKTDCRQLSWIDTIIFYSGV

VNYDTDNFNKEILLDRSAGQNGAFKIKLDYVKKPIPESVFVQILEKLYEEDIGAGMYALY

PYGGIMDEISESAIPFPHRAGILYELWYICSWEKQEDNEKHLNWIRNIYNFMTPYVSKNP

-continued

RLAYLNYRDLDIGINDPKNPNNYTQARIWGEKYFGKNFDRLVKVKTLVDPNNFFRNEQSI

PPLPRHRH

CBD1dNP1 Protein (Source Cannabis sativa)
(SEQ ID NO: 56)
MNPRENFLKCFSQYIPNNATNLKLVYTQNNPLYMSVLNSTIHNLRFTSDTTPKPLVIVTP

SHVSHIQGTILCSKKVGLQIRTRSGGHDSEGMSYISQVPFVIVDLRNMRSIKIDVHSQTA

WVEAGATLGEVYYWVNEKNENLSLAAGYCPTVCAGGHFGGGGYGPLMRNYGLAADNBDAH

LVNVHGKVLDRKSMGEDLFWALRGGGAESFGIIVAWKIRLVAVPKSTMFSVKKIMEIHEL

VKLVNKWQNIAYKYDKDLLLMTHFITRNITDNQGKNKTAIHTYFSSVFLGGVDSLVDLMN

KSFPELGIKKTDCRQLSWIDTIIFYSGVVNYDTDNFNKEILLDRSAGQNGAFKIKLDYVK

KPIPESVFVQILEKLYEEDIGAGMYALYPYGGIMDEISESAIPFPHRAGILYELWYICSW

EKQEDNEKHLNWIRNIYNFMTPYVSKNPRLAYLNYRDLDIGINDPKNPNNYTQARIWGEK

YFGKNFDRLVKVKTLVDPNNFFRNEQSIPPLPRHRHGRRAKL

THC1 Protein (Source Cannabis sativa)
(SEQ ID NO: 57)
MNCSAFSFWFVCKIIFFFLSFNIQISIANPQENFLKCFSEYIPNNPANPKFIYTQHDQLY

MSVLNSTIQNLRFTSDTTPKPLVIVTPSNVSHIQASILCSKKVGLQIRTRSGGHDAEGMS

YISQVPFVVVDLRNMEISIKIDVHSQTAWVEAGATLGEVYYWINEKNENFSFPGGYCPTV

GVGGHFSGGGYGALMRNYGLAADNIIDAHLVNVDGKVLDRKSMGEDLFWAIRGGGGENFG

IIAAWKIKLVAVPSKSTIFSVKKNMEIHGLVKLFNKWQNIAYKYDKDLVLMTHFITKNIT

DNHGKNKTTVHGYFSSIFHGGVDSLVDLMNKSFPELGIKKTDCKEFSWIDTTIFYSGVVN

FNTANFKKEILLDRSAGKKTAFSIKLDYVKKPIPETAMVKILEKLYEEDVGVGMYVLYPY

GGIMEEISESAIPFPHRAGIMYELWYTASWEKQEDNEKHINWVRSVYNFTTPYVSQNPRL

AYLNYRDLDLGKTNPESPNNYTQARIWGEKYFGKNFNRLVKVKTKADPNNFFRNEQSIPP

LPPHHH

THC1dNS1 Protein (Source Cannabis sativa)
(SEQ ID NO: 58)
MFLKHIFVALAFALLADATPAQKRSPGFVALDFDIVKVQKNVTANDDAAAIVAKRQTNPQ

ENFLKCFSEYIPNNPANPKFIYTQHDQLYMSVLNSTIQNLRFTSDTTPKPLVIVTPSNVS

HIQASILCSKKVGLQIRTRSGGHDAEGMSYISQVPFVVVDLRNIVIHSIKIDVHSQTAWV

EAGATLGEVYYWINEKNENFSFPGGYCPTVGVGGHFSGGGYGALMRNYGLAADNIIDAHL

VNVDGKVLDRKSMGEDLFWAIRGGGGENFGIIAAWKIKLVAVPSKSTIFSVKKNMEIHGL

VKLFNKWQNIAYKYDKDLVLMTHFITKNITDNHGKNKTTVHGYFSSIFHGGVDSLVDLMN

KSFPELGIKKTDCKEFSWIDTTIFYSGVVNFNTANFKKEILLDRSAGKKTAFSIKLDYVK

KPIPETAMVKILEKLYEEDVGVGMYVLYPYGGIMEEISESAIPFPHRAGIMYELWYTASW

EKQEDNEKHINWVRSVYNFTTPYVSQNPRLAYLNYRDLDLGKTNPESPNNYTQARIWGEK

YFGKNFNRLVKVKTKADPNNFFRNEQSIPPLPPHHH

THC1dNS2 Protein (Source Cannabis sativa)
(SEQ ID NO: 59)
MQLSLSVLSTVATALLSLTTAVDAKSHNPQENFLKCFSEYIPNNPANPKFIYTQHDQLYM

SVLNSTIQNLRFTSDTTPKPLVIVTPSNVSHIQASILCSKKVGLQIRTRSGGHDAEGMSY

ISQVPFVVVDLRNMHSIKIDVHSQTAWVEAGATLGEVYYWINEKNENFSFPGGYCPTVGV

GGHFSGGGYGALMRNYGLAADNIIDAHLVNVDGKVLDRKSMGEDLFWAIRGGGGENFGII

AAWKIKLVAVPSKSTIFSVKKNMEIHGLVKLFNKWQNIAYKYDKDLVLMTHFITKNITDN

HGKNKTTVHGYFSSIFHGGVDSLVDLMNKSFPELGIKKTDCKEFSWIDTTIFYSGVVNFN

```
TANFKKEILLDRSAGKKTAFSIKLDYVKKPIPETAMVKILEKLYEEDVGVGMYVLYPYGG

IMEEISESAIPFPHRAGIMYELWYTASWEKQEDNEKHINWVRSVYNFTTPYVSQNPRLAY

LNYRDLDLGKTNPESPNNYTQARIWGEKYFGKNFNRLVKVKTKADPNNFFRNEQSIPPLP

PHHH

THC1dNV1 Protein (Source Cannabis sativa)
                                                  (SEQ ID NO: 60)
MQLSLSVLSTVATALLSLTTAVDAKSHNIKLSKLSNEETLDASTFQEYTSSLANKYMNLF

NAAHGNPTSFGLQHVLSNQEAEVPFVTPQKGGNPQENFLKCFSEYIPNNPANPKFIYTQH

DQLYMSVLNSTIQNLRFTSDTTPKPLVIVTPSNVSHIQASILCSKKVGLQIRTRSGGHDA

EGMSYISQVPFVVVDLRNMHSIKIDVHSQTAWVEAGATLGEVYYWINEKNENFSFPGGYC

PTVGVGGHFSGGGYGALMRNYGLAADNIIDAHLVNVDGKVLDRKSMGEDLFWAIRGGGGE

NFGIIAAWKIKLVAVPSKSTIFSVKKNMEIHGLVKLFNKWQNIAYKYDKDLVLMTHFITK

NITDNHGKNKTTVHGYFSSIFHGGVDSLVDLMNKSFPELGIKKTDCKEFSWIDTTIFYSG

VVNFNTANFKKEILLDRSAGKKTAFSIKLDYVKKPIPETAMVKILEKLYEEDVGVGMYVL

YPYGGIMEEISESAIPFPHRAGIMYELWYTASWEKQEDNEKHINWVRSVYNFTTPYVSQN

PRLAYLNYRDLDLGKTNPESPNNYTQARIWGEKYFGKNFNRLVKVKTKADPNNFFRNEQS

IPPLPPHHH

THC1dNP1 Protein (Source Cannabis sativa)
                                                  (SEQ ID NO: 61)
MSNPQENFLKCFSEYIPNNPANPKFIYTQHDQLYMSVLNSTIQNLRFTSDTTPKPLVIVT

PSNVSHIQASILCSKKVGLQIRTRSGGHDAEGMSYISQVPFVVVDLRNMHSIKIDVHSQT

AWVEAGATLGEVYYWINEKNENFSFPGGYCPTVGVGGHFSGGGYGALMRNYGLAADNIID

AHLVNVDGKVLDRKSMGEDLFWAIRGGGGENFGIIAAWKIKLVAVPSKSTIFSVKKNMEI

HGLVKLFNKWQNIAYKYDKDLVLMTHFITKNITDNHGKNKTTVHGYFSSIFHGGVDSLVD

LMNKSFPELGIKKTDCKEFSWIDTTIFYSGVVNFNTANFKKEILLDRSAGKKTAFSIKLD

YVKKPIPETAMVKILEKLYEEDVGVGMYVLYPYGGIMEEISESAIPFPHRAGIMYELWYT

ASWEKQEDNEKHINWVRSVYNFTTPYVSQNPRLAYLNYRDLDLGKTNPESPNNYTQARIW

GEKYFGKNFNRLVKVKTKADPNNFFRNEQSIPPLPPHHHGRRAKL

CBC1 Protein (Source Cannabis sativa)
                                                  (SEQ ID NO: 62)
MNCSTFSFWFVCKIIFFFLSFNIQISIANPQENFLKCFSEYIPNNPANPKFIYTQHDQLY

MSVLNSTIQNLRFTSDTTPKPLVIVTPSNVSHIQASILCSKKVGLQIRTRSGGHDAEGLS

YISQVPFAIVDLRNMHTVKVDIHSQTAWVEAGATLGEVYYWINEMNENFSFPGGYCPTVG

VGGHFSGGGYGALMRNYGLAADNIIDAHLVNVDGKVLDRKSMGEDLFWAIRGGGGENFGI

IAACKIKLVVVPSKATIFSVKKNMEIHGLVKLFNKWQNIAYKYDKDLMLTTHFRTRNITD

NHGKNKTTVHGYFSSIFLGGVDSLVDLMNKSFPELGIKKTDCKELSWIDTTIFYSGVVNY

NTANFKKEILLDRSAGKKTAFSIKLDYVKKLIPETAMVKILEKLYEEEVGVGMYVLYPYG

GIMDEISESAIPFPHRAGIIVIYELWYTATWEKQEDNEKHINWVRSVYNFTTPYVSQNPR

LAYLNYRDLDLGKTNPESPNNYTQARIWGEKYFGKNFNRLVKVKTKADPNNFFRNEQSIP

PLPPRHH
```

Promoters for Use in *Candida*

Multiple promoters can be used including synthetic ones. The following are some examples.

PEX11 Promoter Cv (SEQ ID NO: 63)
GAGGATGAAGAAGACGAAGACGAATTGGATGAAGATGAAGCGTATGAGTA

TTATGAGTACTGTCGGACGTTGGAAGGTGGCAGAGTTAAGCCCGAGAAAG

CAAGGAAGGAGTGGGAGATGATGAGTGATGCGGCCAAGAGGATGTGAAGG

CTGCGTATCTGTTTTTGATAGCTGGTGGTAGCCGAATAGAGGAAGGCAAG

CTTGTTCATATTGGATGATGATGGTAGATGGTGGCTGCCAAAGTGGTTGT

AAATAGAAAAAAGTGGGTTTGGGTCTGTTGATAGTTAGTGGTGGCGGCTG

TCTGTGATTACGTCAGCAAGTAGCACCTCGGCAGTTAAAACAGCAGCAAC

AGAAAAAAAATGTGTGAAAGTTTGATTCCCCCACAGTCTACCACACCCAG

AGTTCCATTTATCCATAATATCACAAGCAATAGAAAAATAAAAAATTATC

AACAAATCACAACGAAAAGATTCTGCAAAATTATTTTCACTTCTTCTTTT

GACTTCCTCTTCTTCTTGTTAGGTTCTTTCCATATTTTCCCCTTAAACCC

ATACACAACGCAGCCAT

PoX4 Promoter CV (SEQ ID NO: 64)
GAGCTCCAATTGTAATATTTCGGGAGAAATATCGTTGGGGTAAAACAACA

GAGAGAGAGAGGGAGAGATGGTTCTGGTAGAATTATAATCTGGTTGTTGC

AAATGCTACTGATCGACTCTGGCAATGTCTGTAGCTCGCTAGTTGTATGC

AACTTAGGTGTTATGCATACACACGGTTATTCGGTTGAATTGTGGAGTAA

AAATTGTCTGAGTTGTGTCTTAGCTACTGGCTGGCCCCCCGCGAAAGATA

ATCAAAATTACACTTGTGAATTTTTGCACACACACCGATTAACATTTCCC

TTTTTTGTCCACCGATACACGCTTGCCTCTTCTTATTTTCTCTGTGCTTC

CCCCTCCTGTGACTTTTTCCACCATTGATATAAAATCAACTCCATTTCCC

TAAAATCTCCCCAGATTCTAAAAACAACTTCTTCTCTTCTGCTTTTCCTT

ATTTTTGTTATATTTATTTACCATCCCTTATTTTGAATAGTTATTCCCCA

CTAACATTGTTCAAATCTTCACGACATAA

POX2 Promoter CV (SEQ ID NO: 65)
GTGCCGACGGAGTAACAAAAATGTTACAGTGCGCACTACTTATCCCGCTA

AGGTGATAAACTGCAAAAACACACCGTCAAGGAGAAGTCGACGTTTTGCC

GCCACTTGTGAAGGGAAGAAGAGTCGTTGAGTTGATGTAATTAAGCTGGC

ACGTAGATACCAGAAGGTTCTAGAGTAGAGCTTGGGTGGTGTTTGGCCCT

GTTTGGACCACGGATAGAGATGGAGAATCCCTTGGTTAGAGCGGAGAGGA

AAAAATTGAAACTTTGCATATCCCACTTCATTATCCTTGATGTAACCGTT

TTATGGGGTAATTAAAGTGTGGAAAAATAATCAGGGAGACATATTCCCGA

TCAATTGGGTGGTGGTCGCTCAATTTCTGTGAGTAGTAGGCTCAGTGGTG

TGTATTGGGATTGGTAGTAGTCTGTATAAGCAGTGTTATATAACCCATTG

CTTGTTGATTCCTATTTTGCTGGCAAAAGTGACAACTGTAGTTGTGAGAT

AATCCTCGGTTATTACGCCTGGGGGGGCAGACAGCCAAAGTTGTGCCCGT

GCGACAATGGCATCAGAAGAAACAGAAAAAAAAAACACAGGCATTTTTAT

CCACATGCACACTACCCCCACTATTCCTGTCTGCAGTGTGCTTGTGTGTG

GCCCCCCGCAGAATCAACAGGGCAAACTCTGGAGCCTGAATCTTTATATA

AACTTCAGGCATTGGCCCCCCTTTTCACAATTCTTCACATCCACCATTTT

TTTTCTTCTTTCCTACCATATTAGTTTTTTTTATTCTTTTCCTACCTAT

CTGATTATTATCAAACATCTGGTCATCCTCAAAAGAAAGAAAGAAACTAT

AACAATCAATC

FOX3 Promoter CV (SEQ ID NO: 66)
TGGATTATGTAATCACAGGCTGTTTCTCCATTCCTGCATGTAGGCTGGCC

CGCGGTATCAACCATCGTCCCGCTTCTTCTGGTTTTTTTTTTTTTCCGC

TATGATATTTTTGATCTCTTGGGGGATTTGGTGGGTCTGCCCCCCCCGCT

ACTACAAGCTCAAACACCCGAAACCTTACAACACACACACACACATCCCG

CTTAGTTGCGGGTTGAAGAACGTGTATTCCCGTAGGGTTAATGGTGTGTC

CCCCCCTAGTCACCCGCTTCTGCCATTCTGGGTTTGCCTTCAAAGCTGGC

ATAAATGACGAAAAAAAAGCACAGCATCCTGCACACAACCCTGCTCAGTG

TGACAGGTGGTGGTGTAATAGAAAACCTCGGCTTAAAACCTCTGGTCAGA

GCATCAACTGCAATCTTGTCTTTTTCTGCTGCCCTCACATTCTCCCCACA

CATTCCCACCCTCAAGATTTCACAGGCAAAAACTGCAAATATATATAAAT

CTACAACCAATTCTTTCCCCAGATGGAAAATCTAATTTTTGTTCACCCTT

TTTCTTTCTCCTGCTATCACTGCTACTGCACATATTCAACACCACAACC

TEF1 promoter CV (SEQ ID NO: 67)
GACTGGGAGAACAGACCAAGGATGCCCATACACCATTAATAACAAGCACA

CCTTGATAAATCTCTAGTGTTGACAAATTGGTGATTTGAACATGACTGTA

GAGAGAGAGACAAGTAACCACTGATGGATTGGTGGTGGCAAATAACCACT

TTAAATAAAGACCAACTCACACACAAAGACAGCAGGTCGTGTTCCTATTT

CCAATTTTCACAAGGAGAAGAATAAAAATTTTTCAATGAGATTAACTAAA

GAAACAGACAGGCAGCCCACAAGAAGAAGAAGAAGAGAGGAAGAGGAAG

AAGAAGAAGAAGAAGAAGAAGAGAAAAAAAATTTTTCCCTCTGCGTT

GCGTTGGGCTTGGGTTGCCAGCACCCACCATATATAACTCTCATCAAATA

CCCAGTAGAGAAAAATTTTTCCTCCCTCTTTTTCTTTCTTTCTTCTCCTT

CTTTTGCTACTCTTTCTGTTTTTCATCAAAAAGATATATATAATCAATCA

TG

TDH3 Promoter CV (SEQ ID NO: 68)
ACCAAACGTTACTTTTTTTTTGCAATCGGATGGTATGGGTCTGGGGTTCA

CCTGTTTTGTAAAGCTACAGAAGGTGGCATATTTCTCTGATCAGGTGTTT

TTTTTTTCGGCTGCTGCTGCTCGTGGTGGTGTAGTGGTAGTGGTGTGTGT

GTGTGTGTGCGTGCGTGTGGAAGGACGCTTTTTGCTCTCTGACTCCTC

CCAATCAGAAGTTGCTATAGTGGTGAAACAACAATGGATGATAATGCCCC

GGGCGGTGCGTGTCCGACACAAACCACTACATTTTTTAGCTGGGAGCCTA

CTGCCACTACGACCCACCCACCCATGGTCAACAAAAAAATTCTGACAAAT

TATAAAATAACCCTTGAATTCCCCCTTGGAAAATTTTTGGTATTTCTCT

CTCTCTTTTCCTTTCCCTCTTCTTTTTCTCTCCATCAATCAATTGACGTT

-continued

CAGTAACTCAATTAATTACATCACATCCCTCAATTAAAGAATTTAAACAA

TG

Promoters for Use in *Yarrowia*

Multiple promoters can be used including synthetic ones. The following are some examples.

POX2 Promoter Yl
(SEQ ID NO: 69)
ACGATTCCGCCAAGTGAGACTGGCGATCGGGAGAAGGGTTGGTGGTCATG

GGGGATAGAATTTGTACAAGTGGAAAAACCACTACGAGTAGCGGATTTGA

TACCACAAGTAGCAGAGATATACAGCAATGGTGGGAGTGCAAGTATCGGA

ATGTACTGTACCTCCTGTACTCGTACTCGTACGGCACTCGTAGAAACGGG

GCAATACGGGGAGAAGCGATCGCCCGTCTGTTCAATCGCCACAAGTCCG

AGTAATGCTTGAGTATCGAAGTCTTGTACCTCCCTGTCAATCATGGCACC

ACTGGTCTTGACTTGTCTATTCATACTGGACAAGCGCCAGAGTTAAGCTT

GTAGCGAATTTCGCCCTCGGACATCACCCCATACGACGGACACACATGCC

CGACAAACAGCCTCTCTTATTGTAGCTGAAAGTATATTGAATGTGAACGT

GTACAATATCAGGTACCAGCGGGAGGTTACGGCCAAGGTGATACCGGAAT

AACCCTGGCTTGGAGATGGTCGGTCCATTGTACTGAAGTGTCCGTGTCGT

TTCCGTCACTGCCCCAATTGGACATGTTTGTTTTTCCGATCTTTCGGGCG

CCCTCTCCTTGTCTCCTTGTCTGTCTCCTGGACTGTTGCTACCCCATTTC

TTTGGCCTCCATTGGTTCCTCCCCGTCTTTCACGTCGTCTATGGTTGCAT

GGTTTCCCTTATACTTTTCCCCACAGTCACATGTTATGGAGGGGTCTAGA

TGGAGGCCTAATTTTGACGTGCAAGGGGCGAATTGGGGCGAGAAACACGT

CGTGGACATGGTGCAAGGCCCGCAGGGTTGATTCGACGCTTTTCCGCGAA

AAAAACAAGTCCAAATACCCCCGTTTATTCTCCCTCGGCTCTCGGTATTT

CACATGAAAACTATAACCTAGACTACACGGGCAACCTTAACCCCAGAGTA

TACTTATATACCAAAGGGATGGGTCCTCAAAAATCACACAAGCAACGACG

CCATGA

LIP2 promoter Yl
(SEQ ID NO: 70)
AAACTTCTCCGAGTCTGTGCCTTCAGGTGGGCATAGTTGATGGGTGTTTT

GAAGTTAATAGTGGGGAAGAACTATGGCAAACAAGCAGATGCAGGCACCT

TGTAACTGCAGACCGGTTCTTGTCTACCGACTCCGCTGCACCTGTGCCGC

GGTACATGTCGTCACAGGCTGCGGGGTTCGGAGGCCCCCTTGCAACCTCC

TTTGATAGTTGCTATGGCCCCAAAGAGTTATACGAGATAGACCCACAGAT

CTACTTGACTGTTGTCACAGAACCTGCTAGGTTTGCTTATTGTACCCGCT

TTGTAGCTACTGTACAACGACAACGTCAAAAATTGAGACGCGAACAAACT

CCAGATGCAGAACCCAAACCTCTCTCTCAGAGTTTCGAGTGCTTCTACCT

CACAGTAAAGTGGAGGTGGACCTGCAAGGGAATTCAGTCACAAGGCCCCG

AATGTCTCCGAAACTCCAATCGGACCGTTTAAACAGACTAATATCACGTC

ATTGATTGATATTAGCATCCGGCAAGAGCCGCAAGGTTATCTCCTCACCA

ATGAGCCTGTTGTACGGCTCATTCCGCATCTGCGGCTGATTCAGTTTCGA

-continued

GTGGGGATGGTAGACTTCATTGCAGCATTCCTAACCTTCTACTTGGTCCG

TGGAGATGTCATGGACATCGATTTTGGGCTGAGAAGCCTTTTGACGATGT

TGATATCACTGACCGCTAATTTACTCTGGCAGTTTCTCCGGCTCTCGAGG

CATCGTCGATCACCAAACACTATCTGCTAGTCTAAATGTCCGACACGACA

GCTTTTGATCGCCGTGAACGGCGCAGACCTCATGCACCATGCACCAGGGC

CAAATCAATTACGGGTCGCTTAGCGTTGCAGTCGGGGCATTATGGTGGAA

GTTCCGATACGGCACAGACACATTCCATAGTGGGGGATTGGATTATAAA

AGGGCCATAGAAAGCCCTCAATTGATACCCAAGTACCAGCTCTCCTCACT

ATGA

ICL1 Promoter Yk
(SEQ ID NO: 71)
GACCCCCTCCTTTTGCCAGTATATCCACCGCAACACCCACCATGAGCGAC

ATCTGATACCGTGCCGCGACCACTACCCCAAATAAGCTCCAACTAATATG

CCGAGGCAGGTGGGAAACTATGCACTCCAGACGACGTGTAGAAGCACAT

GGAAGGTGCGGAGGCGGTGGCAACGAGGGGCATGAGCCATCAACGAGTAA

CCACAGACAAGGCAAGGGGGGAAACGCGACCGGAATCTCTCGCGGTCACG

TGACCCGCCCGGGTTCCACTCGTCCATGTTGTGTCTCTGGTGTCTTCGGC

CGACTCGCATTGGTTAAACTTCCACCACCGCAATCACGTCCCACTGGCCA

AACTTTTTCTGCTTTCTCTGACTTTTTCTGGCCAAAAGGCAACGTCGGAA

AGGGTCGGGAGGATTCGGAACCGACGAAAATCGGCCGGCTCCAGCGGGGG

TAGTTCGGCAGTCCTGGTGGGAGCTCTAGGGGAGCTGTGGTCTGTGTAGG

GCGCGGGTCCGGGTTTGTTGGGTGTCAAATCACGTGTTTTTGCCCCCCCG

CTGAGCCGGACTCCGACAACCGTGTCTCCAACGGCCTGACTAAGCTGCTC

CCAGCACTCTGCCGTAGCGTTGGTCTGTCCTGTCGCACTCTGTTCAAAGA

CAGAAGAAAGAAAAAGCTAACCTCCACGTCAGAGACAATGGTAGAAGGCT

TGTTCCTTGCAACCGAGGAGAGTGAGTGTTCTCGGCACGAGCATCATGGG

CGATCTGGAGGGTATTTTTGAGGGGAAAAAACGGGATCAGGACAAACAGA

GGCCACAGACCGGGAATCTGGGCCCCAAAACGGCCTTTTCCCGTCGCAAA

ACCGGTCTACATACACCCCTTCGGCCCGCCACAGGCCGGTGTGAAAAACC

CTAAAGCTTGCTTCAAACCAGACGGACGCACAGCAAGACACATCATGAAG

AGTCACCTGCAGTATATATAGATCTGGGGATTCCCAGTAGACTGACCAAG

CATACAAAAGTGAGTATCCAACAGCGACACGTGAGATGGCAGAGACACAG

AGACGTGTCTACATGGTTGGACAAGTCTCCACATTCGCCAGAGACGTATC

CACATACAAACACAATCTCACAGCTGATCTGCTCCTGTGACAGCACAGTA

CATGTTAGTGGATGAGGTGTTGTGTAGTGGGTTAAATGGGTGGACTGATT

CAGTGGCATCGGTGGCGACACCCTCTACTCTTCATGTCGTCACCTACCGT

TCGGAATCCCAATTATCTGATGAACTAAACGATTTCTGGCCAAAACACAA

TTTTGCCAAAGAAGTCGTTCTCACCAATGCAAGTGTCACATCAAACATCT

GTCCCGTACTAACCCAG

POT1 Promoter Yl
(SEQ ID NO: 72)
CCACAATACCCCACAGTGTGCATATCAAACCTACCGGTTGTTGCTCTCTC

CAGCCTTACTAAGAAGGAGGCGACGTGGCAGTGGCTCGCGGGAGGATCGG

-continued

CGGGAAACTCCGGGATATCCGTCGAGAGTTTACACGTGAATGGGCAGCGC

AATCCGTTGACGACGATACGACTGGCAAAGTAGCGACGATACCTGCCAGA

CAGGTGACATGTGCAGGCCGCACTAACAAGGAAACGGGCGCTGGGGGGGG

CGGGCTTCTAGACTTTGCCCTTGAACAGGAATCTAGTGGGGGCTTGTCTT

TCCGCCAATGGGGGAGCGCCTGTTGAGCGACCGTGCATGCTGGAACGCCA

AGTGTATGTACAGCTGGTGTTCTCGCAGCGGTATGTGACGGGACTTACAT

CTCTCGTTTTTTCATGACCACGTTTTCACAGGCTCGGAGGTACGTTAAAG

TTTTGAAGGCTGCATCTGAACCGAGGTATGGGGAGTTTGAGGAGCAACA

GTGTTGGGGCTGAGGGGGCCAAGATCGGGGCAAGCAGAGGTCTTAGATCA

ATTGTGGGAATCCCAAAGGGCTCGTTATCACCTTTTTCCACCCAATTCGG

GTCCCAATTGATCCACTACTGGCTTGCCCAAGTTACCCCAGAAATGCCGC

CCCGGATTTCTCCAAAAACCTAATAAGCTTCATGGAACTTGGTGGAAGTG

ACTTTCTACAGAGTGGAGAGAACCGTGGACACGTGGCAATGGCGCTGACC

GTGTCCCCGAGCCGAATCGACGTGAGGGGAGAACGGAGTATCTGCGGTCA

TGTGACCTTCCAGAGCGGCGTCGCCAGTGTGCACGCGGTGACCCCCAGTT

TGGTTCTCTGTCACACGCATACTACCTCGGCTCTCCACATGCTGAACTTT

ATCTTTCGTGGGGATCATACCGAAAGTTGCAACTACCAGGTGTATATAAA

GCCTGGTAGACTCCCCCCACTTTGGACCTCATCCAACCAAGACACACAAA

AATG

Terminators to Use in *Candida viswanathii*

Multiple terminators can be used. The following are some examples.

POX4 Terminator Cv
(SEQ ID NO: 73)
GAGTGACTCTTTTGATAAGAGTCGCAAATTTGATTTCATAAGTATATATT

CATTATGTAAAGTAGTAAATGGAAAATTCATTAAAAAAAAAGCAAATTTC

CGTTGTATGCATACTCCGAACACAAAACTAGCCCCGGAAAAACCCTTAGT

TGATAGTTGCGAATTTAGGTCGAC

PEX11 Terminator CV
(SEQ ID NO: 74)
AGCTCCAGGCTTGTTATGACTCTAGAGAGAAGTGTGTGTGTTTGCGTTTG

TTTTACTATACATTCAACATGTTCTTTTTCTTTTTTGATATTTATTCCAA

CTATAATTATACACAGATTCGTATATACTTTACTTTACCCTCTTTCGTAG

TTTTTTAATTTGATGATTTTTGAGTTTCATATCCAAGGTCAAAACCCGAC

Terminators to Use in *Yarrowia lipolytica*

Multiple terminators can be used. The following are some examples.

XPR2 Terminato Yl
(SEQ ID NO: 75)
TAGGCAATTAACAGATAGTTTGCCGGTGATAATTCTCTTAACCTCCCACA

CTCCTTTGACATAACGATTTATGTAACGAAACTGAAATTTGACCAGATAT

TGTTGTAAATAGAAAATCTGGCTTGTAGGTGGCAAAATGCGGCGTCTTTG

TTCATCAATTCCCTCTGTGACTACTCGTCATCCCTTTATGTTCGACTGTC

GTATTTCTTATTTTCCATACATATGCAAGTGAGATGCCCGTGTCCGAATT

C

TDH3 terminator YL
(SEQ ID NO: 76)
CTTCCGAGTAGCTATCCGAAGATCAAGAGCGAAGCAAGTTGTAAGTCCAG

GACATGTTTCCCGCCCACGCGAGTGATTTATAACACCTCTCTTTTTTGAC

ACCCGCTCGCCTTGAAATTCATGTCACATAAATTATAGTCAACGACGTTT

GAATAACTTGTCTTGTAGTTCGATGATGATCATATGATTACATTAATAGT

AATTACTGTATTTGATATATATACTAATTACAATAGTACATATTAGAACA

TACAATAGTTAGTGCCGTGAAGTGGCTTAAAATACCGCGAGTCGATTACG

TAATATTA

Markers for Use in *Yarrowia*

LEU2 Marker Yl
(SEQ ID NO: 77)
AACGTACCACTGTCCTCCACTACAAACACACCCAATCTGCTTCTTCTAGTCAAGGTT

GCTACACCGGTAAATTATAAATCATCATTTCATTAGCAGGGCTGGGCCCTTTTTATA

GAGTCTTATACACTAGCGGACCCTGCCGGTAGACCAACCCGCAGGCGCGTCAGTTTG

CTCCTTCCATCAATGCGTCGTAGAAACGACTTACTCCTTCTTGAGCAGCTCCTTGACC

TTGTTGGCAACAAAGTCTCCGACCTCGGAGGTGGAGGAGGAGCCTCCGATATCGGC

GGTAGTGATACCAGCCTCGACGGACTCCTTGACGGCAGCCTCAACAGCGTCACCGG

CGGGCTTCATGTTAAGAGAGAACTTGAGCATCATGGCGGCAGACAGAATGGTGGCA

ATGGGGTTGACCTTCTGCTTGCCGAGATCGGGGGCAGATCCGTGACAGGGCTCGTAC

AGACCGAACGCCTCGTTGGTGTCGGGCAGAGAAGCCAGAGAGGCGGAGGGCAGCA

GACCCAGAGAACCGGGGATGACGGAGGCCTCGTCGGAGATGATATCGCCAAACATG

TTGGTGGTGATGATGATACCATTCATCTTGGAGGGCTGCTTGATGAGGATCATGGCG

GCCGAGTCGATCAGCTGGTGGTTGAGCTCCAGCTGGGGGAATTCGTCCTTGAGGACT

-continued

```
CGGGTGACGGTCTTTCGCCAAAGTCGAGAGGAGGCCAGCACGTTGGCCTTGTCAAG

GGACCACACGGGAAGAGGGGGGTTGTGCTGAAGGGCCAGGAAGGCGGCCATTCGG

GCAATTCGCTCAACCTCAGGAACGGAGTAAGTCTCAGTGTCGGAAGCGACGCCAGA

TCCGTCATCCTCCTTTCGCTCTCCAAAGTAGATACCTCCGACGAGCTCTCGGACAAT

GATGAAGTCGGTGCCCTCAACGTTTCGGATGGGGGAGAGATCGGCGAGCTTGGGCG

ACAGCAGCTGGCAGGGTCGCAGGTTGGCGTACAGGTTCAGGTCCTTTCGCAGCTTGA

GAAGACCCTGCTCGGGTCGCACGTCGGTTCGTCCGTCGGGAGTGGTCCATACGGTGT

TGGCAGCGCCTCCGACAGCACCGAGCATAATAGAGTCAGCCTTTCGGCAGATGTCG

AGAGTAGCGTCGGTGATGGGCTCGCCCTCCTTCTCAATGGCAGCTCCTCCAATGAGT

CGGTCCTCAAACACAAACTCGGTGCCGGAGGCCTCAGCAACAGACTTGAGCACCTT

GACGGCCTCGGCAATCACCTCGGGGCCACAGAAGTCGCCGCCGAGAAGAACAATCT

TCTTGGAGTCAGTCTTGGTCTTCTTAGTTTCGGGTTCCATTGTGGATGTGTGTGGTTG

TATGTGTGATGTGGTGTGTGGAGTGAAAATCTGTGGCTGGCAAACGCTCTTGTATAT

ATACGCACTTTTGCCCGTGCTATGTGGAAGACTAAACCTCCGAAGATTGTGACTCAG

GTAGTGCGGTATCGGCTAGGGACCCAAACCTTGTCGATGCCGATAGCGCTATCGAAC

GTACCCCAGCCGGCCGGGAGTATGTCGGAGGGGACATACGAGATCGTCAAGGGTTT

GTGGCCAACTGGTAAATAAATGATGACTCAGGCGACGACGGAATTCGACAGCAACT

ACTCCTTTCACCAACCATGTGCATTTTAGCTCGAATAACATTCACAGGCTTGGTGATC

TACATCCATGGTGTCTGGCCGATTACCGTGGTGTTTTGGCAGTAACGAGAATATTGA

GTGAACTCTTCCCATCACCAATAAAGACTCATACTACAATCACGAGCGCTTCAGCTG

CCACTATAGTGTTGGTGACACAATACCCCTCGATGCTGGGCATTACTGTAGCAAGAG

ATATTATTTCATGGCGCATTTTCCAGTCTACCTGACTTTTTAGTGTGATTTCTTCTCCA

CATTTTATGCTCAGTGTGAAAAGTTGGAGTGCACACTTAATTATCGCCGGTTTTCGG

AAAGTACTATGTGCTCAAGGTTGCACCCCACGTTACGTATGCAGCACATTGAGCAGC

CTTTGGACCGTGGAGATAACGGTGTGGAGATAGCAACGGGTAGTCTTCGTATTAATT

CAATGCATTGTTAGTTTTATATGATATGGTGTCGA
```

URA3 Marker Yl (SEQ ID NO: 78)
```
TTTCTAATTTGGACCGATAGCCGTATAGTCCAGTCTATCTATAAGTTCAACTAACTCG

TAACTATTACCATAACATATACTTCACTGCCCCAGATAAGGTTCCGATAAAAAGTTG

TGCAGACTAAATTTATTTCAGTCTCCTCTTCACCACCAAAATGCCCTCCTACGAAGC

GCGAGCTAACGTCCACAAGTCCGCCTTTGCCGCCCGAGTGCTCAAGCTCGTGGCAGC

CAAGAAAACCAACCTGTGTGCTTCTCTGGATGTTACCACCACCAAGGAGCTCATTGA

GCTTGCCGATAAGGTCGGACCTTATGTGTGCATGATCAAGACCCATATCGACATCAT

TGACGACTTCACCTACGCCGGAACTGTGCTCCCCCTCAAGGAACTTGCTCTTAAGCA

CGGTTTCTTCCTGTTCGAGGACAGAAAGTTCGCAGATATTGGCAACACTGTCAAGCA

CCAGTACAAGAACGGTGTCTACCGAATCGCCGAGTGGTCCGATATCACCAACGCCC

ACGGTGTACCCGGAACCGGAATCATTGCTGGCCTGCGAGCTGGTGCCGAGGAAACT

GTCTCTGAACAGAAGAAGGAGGATGTCTCTGACTACGAGAACTCCCAGTACAAGGA

GTTCCTGGTCCCCTCTCCCAACGAGAAGCTGGCCAGAGGTCTGCTCATGCTGGCCGA

GCTGTCTTGCAAGGGCTCTCTGGCCACTGGCGAGTACTCCAAGCAGACCATTGAGCT

TGCCCGATCCGACCCCGAGTTTGTGGTTGGCTTCATTGCCCAGAACCGACCTAAGGG
```

-continued

```
CGACTCTGAGGACTGGCTTATTCTGACCCCCGGGGTGGGTCTTGACGACAAGGGAG

ATGCTCTCGGACAGCAGTACCGAACTGTTGAGGATGTCATGTCTACCGGAACGGATA

TCATAATTGTCGGCCGAGGTCTGTACGGCCAGAACCGAGATCCTATTGAGGAGGCC

AAGCGATACCAGAAGGCTGGCTGGGAGGCTTACCAGAAGATTAACTGTTAGAGGTT

AGACTATGGATATGTCATTTAACTGTGTATATAGAGAGCGTGCAAGTATGGAGCGCT

TGTTCAGCTTGTATGATGGTCAGACGACCTGTCTGATCGAGTATGTATGATACTGCA

CAACCTG
```

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsa I, Bsm I, BsmBI, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sap I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like). The terms "amplify", "amplification", "amplification reaction", or "amplifying" as used herein, refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein. The term "operably linked" as used herein with respect to promoters refers to a nucleic acid sequence (e.g., a coding sequence) present on the same nucleic acid molecule as a promoter element and whose expression is under the control of said promoter element.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise nonfunctional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a 6th order Markov background model and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose.

In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate on that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 70% or more identical to the foregoing (or to the complementary sequences). That is, a nucleotide sequence that is at least 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address at world wide web uniform resource locator gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address at world wide web uniform resource locator gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also comprise one or more 5' UTR's, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, -35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address at world wide web uniform resource locator interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide or protein of interest, and may be a ribonucleotide sequence or a deoxyribonucleotide sequence.

A target nucleic acid sometimes can comprise a chimeric nucleic acid (or chimeric nucleotide sequence), which can encode a chimeric protein (or chimeric amino acid sequence). The term "chimeric" as used herein refers to a nucleic acid or nucleotide sequence, or encoded product thereof, containing sequences from two or more different sources. Any suitable source can be selected, including, but not limited to, a sequence from a nucleic acid, nucleotide sequence, ribosomal nucleic acid, RNA, DNA, regulatory nucleotide sequence (e.g., promoter, URL, enhancer, repressor and the like), coding nucleic acid, gene, nucleic acid linker, nucleic acid tag, amino acid sequence, peptide, polypeptide, protein, chromosome, and organism. A chimeric molecule can include a sequence of contiguous nucleotides or amino acids from a source including, but not limited to, a virus, prokaryote, eukaryote, genus, species, homolog, ortholog, paralog and isozyme, nucleic acid linkers, nucleic acid tags, the like and combinations thereof). A chimeric molecule can be generated by placing in juxtaposition fragments of related or unrelated nucleic acids, nucleotide sequences or DNA segments, in some embodiments. In certain embodiments the nucleic acids, nucleotide sequences or DNA segments can be native or wild type sequences, mutant sequences or engineered sequences (completely engineered or engineered to a point, for example).

In some embodiments, a chimera includes about 1, 2, 3, 4 or 5 sequences (e.g., contiguous nucleotides, contiguous amino acids) from one organism and 1, 2, 3, 4 or 5 sequences (e.g., contiguous nucleotides, contiguous amino acids) from another organism. The organisms sometimes are a microbe, such as a bacterium (e.g., gram positive, gram negative), yeast or fungus (e.g., aerobic fungus, anaerobic fungus), for example. In some embodiments, the organisms are bacteria, the organisms are yeast or the organisms are fungi (e.g., different species), and sometimes one organism is a bacterium or yeast and another is a fungus. A chimeric molecule may contain up to about 99% of sequences from one organism (e.g., about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99%) and the balance percentage from one or more other organisms. In certain embodiments, a chimeric molecule includes altered codons (in the case of a chimeric nucleic acid) and one or more mutations (e.g., point mutations, nucleotide substitutions, amino acid substitutions).

A chimera sometimes is the result of recombination between two or more nucleic acids, nucleotide sequences or genes, and sometimes is the result of genetic manipulation (e.g., designed and/or generated by the hand of a human being). Any suitable nucleic acid or nucleotide sequence and method for combining nucleic acids or nucleotide sequences can be used to generate a chimeric nucleic acid or nucleotide sequence. Non-limiting examples of nucleic acid and nucleotide sequence sources and methods for generating chimeric nucleic acids and nucleotide sequences are presented herein.

In some embodiments, fragments used to generate a chimera can be juxtaposed as units (e.g., nucleic acid from the sources are combined end to end and not interspersed. In embodiments where a chimera includes one stretch of contiguous nucleotides for each organism, nucleotide sequence combinations can be noted as DNA source 1 DNA source 2 or DNA source 1/DNA source 2/DNA source 3, the like and combinations thereof, for example. In certain embodiments, fragments used to generate a chimera can be juxtaposed such that one or more fragments from one or more sources can be interspersed with other fragments used to generate the chimera (e.g., DNA source 1/DNA source 2/DNA source 1/DNA source 3/DNA source 2/DNA source 1). In some embodiments, the nucleotide sequence length of the fragments used to generate a chimera can be in the range from about 5 base pairs to about 5,000 base pairs (e.g., about 5 base pairs (bp), about 10 bp, about 15 bp, about 20 bp, about 25 bp, about 30 bp, about 35 bp, about 40 bp, about 45 bp, about 50 bp, about 55 bp, about 60 bp, about bp, about 65 bp, about 70 bp, about 75 bp, about 80 bp, about 85 bp, about 90 bp, about 95 bp, about 100 bp, about 125 bp, about 150 bp, about 175 bp, about 200 bp, about 250 bp, about 300 bp, about 350 bp, about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1500 bp, about 2000 bp, about 2500 bp, about 3000 bp, about 3500 bp, about 4000 bp, about 4500 bp, or about 5000 bp).

In certain embodiments, a chimeric nucleic acid or nucleotide sequence encodes the same activity as the activity encoded by the source nucleic acids or nucleotide sequences. In some embodiments, a chimeric nucleic acid or nucleotide sequence has a similar or the same activity, but the amount of the activity, or kinetics of the activity, are altered (e.g., increased, decreased). In certain embodiments, a chimeric nucleic acid or nucleotide sequence encodes a different activity, and in some embodiments a chimeric nucleic acid or nucleotide sequences encodes a chimeric activity (e.g., a combination of two or more activities).

A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a person of ordinary skill in the art. Representative proteins include enzymes (e.g., phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed hereafter. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG (SEQ ID NO: 79)), V5 (e.g., GKPIPNPLLGLDST (SEQ ID NO: 80)), c-MYC (e.g., EQKLISEEDL (SEQ ID NO: 81)), HSV (e.g., QPELAPEDPED (SEQ ID NO: 82)), influenza hemaglutinin, HA (e.g., YPYDVPDYA (SEQ ID NO: 83)), VSV-G (e.g., YTDIEMNRLGK (SEQ ID NO: 182)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 84)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 85), wherein X is any amino acid and n is 1 to 3, and the cysteine-rich sequence sometimes is CCPGCC (SEQ ID NO: 86). In certain embodiments, the tag comprises a cysteine-rich element and a polyhistidine element (e.g., CCPGCC (SEQ ID NO: 87) and His6 (SEQ ID NO: 88)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences").

Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS (SEQ ID NO: 89)), enterokinase (e.g., recognition site DDDDK (SEQ ID NO: 90)), TEV protease (e.g., recognition site ENLYFQG (SEQ ID NO: 91)) or PreScission™ protease (e.g., recognition site LEVLFQGP (SEQ ID NO: 92)), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon readthrough) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address at world wide web uniform resource locator invitrogen.com/content/sfs/manuals/tagondemand_supernatant_man.pdf; Tag-On-Demand™ Gateway® Vector Instruction Manual, Version B, 20 June, 2003 at http address at world wide web uniform resource locator invitrogen.com/content/sfs/manuals/tagondemand_vectors-_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described hereafter. In some embodiments, a cloning strategy can be combined with genetic manipulation such as recombination (e.g., recombination of a nucleic acid reagent with a nucleic acid sequence of interest into the genome of the organism to be modified, as described further below). In some embodiments, the cloned ORF(s) can produce (directly or indirectly) a desired product, by engineering a microorganism with one or more ORFs of interest, which microorganism comprises one or more altered activities selected from the group consisting of phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity, sugar transport activity, phosphoglucoisomerase activity, transaldolase activity, transketolase activity, glucose-6-phosphate dehydrogenase activity, 6-phosphogluconolactonase activity, 6-phosphogluconate dehydrogenase (decarboxylating) activity, and thymidylate synthase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and Ser. No. 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the ura3 gene (e.g., for *S. cerevisiae* and *C. albicans*, for example) or ura4 and ura5 genes (e.g., for *S. pombe*, for example) and toxicity of the nucleotide analogue 5-Fluoroorotic acid (5-FOA). The ura3 or ura4 and ura5 genes encode orotine-5'-monophosphate (OMP) dicarboxylase. Yeast with an active ura3 or ura4 and ura5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisiae*), flanked on either side by the same nucleotide sequence in the same orientation. The ura3 cassette comprises a promoter, the ura3 gene and a functional transcription terminator. Target sequences which direct the construct to a particular nucleic acid region of interest in the organism to be engineered are added such that the target sequences are adjacent to and abut the flanking sequences on either side of the ura3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the ura3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner. Further detail will be described below in the engineering section and in the example section.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T)CCTT-PO4-TOPO, a complex of the topoisomerase covalently bound to the 3' phosphate via a tyrosine in the topoisomerase (e.g., Shuman, J. Biol. Chem. 266: 11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., http address at world wide web uniform resource locator invitrogen.com/downloads/F-13512_Topo_Flyer.pdf; http address at world wide web uniform resource locator invitrogen.com/content/sfs/brochures/710-021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address world wide web uniform resource locator devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include, deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) Molecular Cloning: a Laboratory Manual; Cold Spring Harbor Laboratory, Cold Spring Harbor, N.Y.

The term "genetic modification" as used herein refers to any suitable nucleic acid addition, removal or alteration that facilitates production of a target product (e.g., phosphogluconate dehydratase activity, 2-keto-3-deoxygluconate-6-phosphate aldolase activity, xylose isomerase activity, or phosphoenolpyruvate carboxylase activity, for example). in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

The term "altered activity" as used herein refers to an activity in an engineered microorganism that is added or modified relative to the host microorganism (e.g., added, increased, reduced, inhibited or removed activity). An activity can be altered by introducing a genetic modification to a host microorganism that yields an engineered microorganism having added, increased, reduced, inhibited or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, 595936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences).

An AU-rich element (ARE, e.g., AUUUA repeats) and/or splicing junction that follows a non-sense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce or potentially reduce translation efficiency are present in the elements, and adding, removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. For example, the codon usage, and therefore the codon triplets encoded by a nucleic acid sequence from bacteria may be different from the preferred codon usage in eukaryotes like yeast or plants. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiment, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like) can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., *C. tropicalis* and *C. maltosa*) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either *Candida* yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter and the like). A modification sometimes is made that can add or enhance binding of a feedback regulator and sometimes a modification is made that can reduce, inhibit or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins or other desired products (e.g., adipic acid, for example). A modification sometimes can be made that can alter, add or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding or removing sequences involved in the expression of an anti-sense RNA, RNAi, siRNA, ribozyme and the like. The methods described above can be used to modify expression of anti-sense RNA, RNAi, siRNA, ribozyme and the like.

Engineered microorganisms can be prepared by altering, introducing or removing nucleotide sequences in the host genome or in stably maintained epigenetic nucleic acid reagents, as noted above. The nucleic acid reagents use to alter, introduce or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures available in Maniatis, T., E. F. Fritsch and J. Sambrook (1982) Molecular Cloning: a Laboratory Manual; Cold Spring Harbor Laboratory, Cold Spring Harbor, N.Y. or with commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3 SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification and the like, for example). Standard cloning procedures (e.g., enzymic digestion, ligation, and the like) are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some embodiments, nucleic acid sequences prepared by isolation or amplification can be used, without any further modification, to add an activity to a microorganism and thereby generate a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., E. coli, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophoretic procedures. A modification of this method uses linear amplification methods and a pair of mutagenic primers that amplify the entire plasmid. The procedure takes advantage of the E. coli Dam methylase system which causes DNA replicated in vivo to be sensitive to the restriction endonucleases DpnI. PCR synthesized DNA is not methylated and is therefore resistant to DpnI. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both server to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

In yeast the cassettes are typically of two different overall structures, as follows:

<5' homology region-promoter-coding sequence-terminator-3' homology region>

<5' homology region-promoter-coding sequence-terminator-marker-3' homology region>

The parts of the DNA transformation cassette possess the following properties:

5' and 3' homology regions—these DNA sequences dictate the specific location in the chromosome where the DNA transformation cassette will insert through homologous recombination. The 5' homology region indicates the upstream boundary for insertion while the 3' homology indicates the downstream boundary. The homology regions may constitute a gene that rescues auxotrophy in an engineered microorganism, i.e. the homology regions mediate insertion into a non-functional gene that results in an auxotrophic phenotype and insertion of the cassette restores function to the gene. For example, the 5' and 3' homology regions may represent the two halves of the URA3 gene and direct homologous recombination in a mutant or loss-of-function ura3 gene, which rescues the loss-of-function.

Promoter—this DNA sequence drives transcription of the coding sequence immediately downstream of the promoter. A promoter will often be turned on or off when the microorganism is exposed to specific compounds or grown under certain conditions.

Coding sequence—the sequence of codons that are translated into the desired protein. The codons can be optimized to reflect the endogenous codon frequency of the engineered microorganism.

Terminator—this DNA sequence marks the end of the sequence to be transcribed, as indicated by the promoter. It may or may not contain sequences that positively or negatively regulate the activity of the promoter.

Marker—this DNA sequence encodes information that will confer properties to a yeast cell that mediate growth under selective or auxotrophic conditions. For example, if the initial cell line is auxotrophic for uracil and is transformed with a cassette containing a URA3 marker, any transformant that contains the URA3 marker will now be able to grow in the absence of uracil.

The DNA transformation cassette is generated through conventional molecular biology methods such as PCR, restriction enzyme digestion and DNA ligation and/or Gibson assembly. The cassette is transformed into the yeast and clones of interest are identified as colonies that grow on the appropriate selective or auxotrophic media, e.g. synthetic complete yeast media lacking uracil.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to "pop out" the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes in to the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis, and allows counter selection for recombination out of the LYS2 gene using alpha-amino adipate (α-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 kan$^r$, Cm$^r$, Hyg$^r$, CUP1, and DHFR. Tn903 kan$^r$ encodes an activity involved in kanamycin antibiotic resistance (e.g., typically neomycin phosphotransferase II or NPTII, for example). Cm$^r$ encodes an activity involved in chloramphenicol antibiotic resistance (e.g., typically chloramphenicol acetyl transferase or CAT, for example). Hyg$^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamide compounds.

In contrast to site-directed or specific mutagenesis, random mutagenesis does not require any sequence information and can be accomplished by a number of widely different methods. Random mutagenesis often is used to generate mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1,2,7,8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9 (3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organism's DNA replication and repair mechanisms to incorporate and replicate the mutagenized base or bases.

Another type of chemical mutagenesis involves the use of base-analogs. The use of base-analogs cause incorrect base pairing which in the following round of replication is corrected to a mismatched nucleotide when compared to the starting sequence. Base analog mutagenesis introduces a small amount of non-randomness to random mutagenesis, because specific base analogs can be chosen which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultra violet (UV) induced mutagenesis is caused by the formation of thymidine dimers when UV light irradiates chemical bonds between two adjacent thymine residues. Excision repair mechanism of the host organism correct the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 kan$^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self-priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL strategene.com and World Wide Web URL clontech.com, respectively, for example). Rolling circle error-prone PCR is a variant of error-prone PCR in which wild-type sequence is first cloned into a plasmid, the whole plasmid is then amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods available to one of skill in the art can be found in Maniatis, T., E. F. Fritsch and J. Sambrook (1982) Molecular Cloning: a Laboratory Manual; Cold Spring Harbor Laboratory, Cold Spring Harbor, N.Y.

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances, the addition of carrier molecules (e.g., bis-benzimdazolyl compounds, for example, see U.S. Pat. No. 5,595, 899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

Usually a DNA piece is constructed (called cassette) for the integration of the gene of interest into the genome.

Culture, Production and Process Methods

Engineered microorganisms often are cultured under conditions that optimize yield of a target molecule. A non-limiting example of such a target molecule is ethanol. Culture conditions often can alter (e.g., add, optimize, reduce or eliminate, for example) activity of one or more of the following activities: phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activities. In general, conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

The term "fermentation conditions" as used herein refers to any culture conditions suitable for maintaining a microorganism (e.g., in a static or proliferative state). Fermentation conditions can include several parameters, including without limitation, temperature, oxygen content, nutrient content (e.g., glucose content), pH, agitation level (e.g., revolutions per minute), gas flow rate (e.g., air, oxygen, nitrogen gas), redox potential, cell density (e.g., optical density), cell viability and the like. A change in fermentation conditions (e.g., switching fermentation conditions) is an alteration, modification or shift of one or more fermentation parameters. For example, one can change fermentation conditions by increasing or decreasing temperature, increasing or decreasing pH (e.g., adding or removing an acid, a base or carbon dioxide), increasing or decreasing oxygen content (e.g., introducing air, oxygen, carbon dioxide, nitrogen) and/or adding or removing a nutrient (e.g., one or more sugars or sources of sugar, biomass, vitamin and the like), or combinations of the foregoing. Examples of fermentation conditions are described herein. Aerobic conditions often comprise greater than about 50% dissolved oxygen (e.g., about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Anaerobic conditions often comprise less than about 50% dissolved oxygen (e.g., about 1%, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48%, or less than any one of the foregoing).

Culture media generally contain a suitable carbon source. Carbon sources may include, but are not limited to, monosaccharides (e.g., glucose, fructose, xylose), disaccharides (e.g., lactose, sucrose), oligosaccharides, polysaccharides (e.g., starch, cellulose, hemicellulose, other lignocellulosic materials or mixtures thereof), sugar alcohols (e.g., glycerol), and renewable feedstocks (e.g., cheese whey permeate, corn steep liquor, sugar beet molasses, barley malt). Carbon sources also can be selected from one or more of the following non-limiting examples: linear or branched alkanes (e.g., hexane), linear or branched alcohols (e.g., hexanol), fatty acids (e.g., about 10 carbons to about 22 carbons), esters of fatty acids, monoglycerides, diglycerides, triglycerides, phospholipids and various commercial sources of fatty acids including vegetable oils (e.g., soybean oil) and animal fats. A carbon source may include one-carbon sources (e.g., carbon dioxide, methanol, formaldehyde, formate and carbon-containing amines) from which metabolic conversion into key biochemical intermediates can occur. It is expected that the source of carbon utilized may encompass a wide variety of carbon-containing sources and will only be limited by the choice of the engineered microorganism(s).

Nitrogen may be supplied from an inorganic (e.g., $(NH_4)_2SO_4$) or organic source (e.g., urea or glutamate). In addition to appropriate carbon and nitrogen sources, culture media also can contain suitable minerals, salts, cofactors, buffers, vitamins, metal ions (e.g., $Mn^{+2}$, $Co^{+2}$, $Zn^{+2}$, $Mg^{+2}$) and other components suitable for culture of microorganisms. Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known.

A variety of host organisms can be selected for the production of engineered microorganisms. Non-limiting examples include yeast and fungi. In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L $NaNO_3$, 10.4 g/L KCl, 10.4 g/L $MgSO_4.7H_2O$), 1 mL/L 1000× Trace Elements (22 g/L $ZnSO_4.7H_2O$, 11 g/L $H_3BO_3$, 5 g/L $MnCl_2.7H_2O$, 5 g/L $FeSO_4.7H_2O$, 1.7 g/L $CoCl_2.6H_2O$, 1.6 g/L $CuSO_4.5H_2O$, 1.5 g/L $Na_2MoO_4.2H_2O$, and 50 g/L $Na_4EDTA$), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Culturing may be conducted under aerobic or anaerobic conditions, where microaerobic conditions sometimes are maintained. A two-stage process may be utilized, where one stage promotes microorganism proliferation and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions).

A variety of fermentation processes may be applied for commercial biological production of a target product. In some embodiments, commercial production of a target product from a recombinant microbial host is conducted using a batch, fed-batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen and the partial pressure of waste gases (e.g., $CO_2$). Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In various embodiments ethanol may be purified from the culture media or extracted from the engineered microorganisms. Culture media may be tested for ethanol concentration and drawn off when the concentration reaches a predetermined level. Detection methods are known in the art, including but not limited to the use of a hydrometer and infrared measurement of vibrational frequency of dissolved ethanol using the CH band at 2900 $cm^{-1}$. Ethanol may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to methods known in the art.

In certain embodiments, target product is extracted from the cultured engineered microorganisms. The microorganism cells may be concentrated through centrifugation at speed sufficient to shear the cell membranes. In some embodiments, the cells may be physically disrupted (e.g., shear force, sonication) or chemically disrupted (e.g., contacted with detergent or other lysing agent).

The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, cannabidiolic acid may be derivatized or further processed to be an ingredient in food, drinks, vape pens, gum, skin lotions, pharmaceuticals, and supplements.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free. In some embodiments target product or modified target product purified from microbes is provided, and target product sometimes is provided in substantially pure form. In certain embodiments, ethanol can be provided in anhydrous or hydrous forms. Ethanol may be transported in a variety of containers including pints, quarts, liters, gallons, drums (e.g., 10 gallon or 55 gallon, for example) and the like.

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) *Molecular Cloning: a Laboratory Manual;* Cold Spring Harbor Laboratory, Cold Spring Harbor, N.Y. DNA mutagenesis can be accomplished using the Stratagene (San Diego, Calif.) "QuickChange" kit according to the manufacturer's instructions, or by one of the other types of mutagenesis described above. 5,000 bp DNA pieces can also be manufactured to order by companies such as Twist Biosciences.

Example 1—Construction of Plasmids for *Candida viswanathii*

Protein sequence was reverse translated into DNA sequence to reflect the use of yeast alternative genetic code and codon usage in *Candida viswanathii*, reduction of secondary structure, and absence of certain restriction enzyme recognition sites. Other DNA sequences that encode the same protein may also be used. The following sequences were used as open reading frames for genes used to genetically modify *Candida viswanathii*.

CvACO1P Gene (SEQ ID NO: 93)
ATGACAGAAGTAGTAGATAGAGCAAGTTCCCCAGCAAGTCCAGGATCTACGACCGC

CGCCGCAGACGGTGCTAAGGTGGCGGTGGAGCCACGCGTAGATGTAGCGGCCCTTG

```
GCGAGCAGTTGCTAGGGCGATGGGCTGACATCAGATTGCACGCACGAGACTTAGCA

GGCCGCGAAGTGGTCCAAAAGGTTGAAGGACTTACGCACACTGAGCATCGGAGTAG

AGTCTTTGGACAGTTGAAGTACTTGGTAGACAACAATGCTGTTCACAGAGCTTTTCC

CTCCAGGCTAGGTGGATCAGATGACCATGGCGGTAATATAGCTGGATTCGAGGAAT

TAGTTACTGCTGATCCATCATTGCAAATAAAGGCCGGCGTTCAGTGGGGTTTGTTTG

GTTCTGCAGTGATGCACTTGGGAACCCGTGAACATCATGACAAGTGGTTGCCAGGTA

TTATGTCGTTAGAAATACCGGGGTGTTTCGCGATGACAGAAACCGGGCACGGTAGC

GACGTGGCCTCTATTGCTACAACAGCAACTTATGATGAGGAAACCCAAGAGTTTGTT

ATTGATACCCCGTTCAGAGCCGCTTGGAAAGATTATATCGGTAATGCAGCGAACGAT

GGTTTGGCGGCAGTTGTTTTCGCACAATTAATCACGAGGAAAGTGAACCATGGTGTA

CACGCCTTTTACGTGGATCTCAGAGATCCTGCGACTGGAGACTTCCTACCCGGAATA

GGAGGAGAGGACGATGGAATCAAGGGGGGATTGAATGGCATTGACAACGGTAGAC

TACATTTTACGAACGTACGCATTCCTAGAACTAATCTTCTTAACAGATATGGCGATG

TGGCGGTCGACGGCACATACCTGTCGACCATCGAATCACCAGGGCGCCGGTTCTTTA

CGATGCTTGGTACTCTAGTCCAGGGTAGAGTTAGTCTCGATGGAGCAGCTGTCGCTG

CACTGAAGGTCGCATTGCAAAGTGCAATTCACTACGCTGCGGAGAGGAGACAATTT

AATGCGACTTCACCTACTGAAGAAGAGGTCCTTCTTGATTATCAGAGGCATCAAAGG

AGACTCTTTACACGACTTGCAACGACGTACGCCGCATCTTTCGCCCACGAGCAGCTA

TTGCAAAAGTTCGATGATGTCTTTTCAGGGGCACATGATACCGACGCCGACCGGCAG

GACTTGGAAACCCTAGCCGCCGCTTTGAAGCCATTGAGCACATGGCATGCACTTGAC

ACGTTACAAGAATGCAGAGAGGCCTGTGGGGGGCCGGATTTTTGATAGAAAACCG

TTTCGCGAGCTTGCGTGCTGACTTGGACGTTTACGTCACATTCGAGGGTGATAACAC

AGTTTTATTGCAATTGGTTGCTAAACGGCTCTTGGCAGACTACGCAAAAGAGTTCAG

AGGGGCCAACTTCGGCGTTCTTGCCAGGTATGTGGTTGACCAAGCCGCGGGAGTGG

CGCTCCACCGAACAGGACTAAGGCAAGTCGCTCAATTTGTTGCAGACAGCGGGTCC

GTTCAGAAGTCGGCTCTTGCGCTTCGCGATGAAGAGGGTCAACGAACATTGTTAACG

GACAGAGTACAGAGCATGGTTGCCGAAGTGGGGGCTGCCTTGAAAGGCGCAGGCAA

ATTACCCCAACATCAAGCAGCTGCATTGTTCAACCAACACCAGAACGAACTTATTGA

GGCTGCCCAGGCCCATGCAGAACTCCTCCAATGGGAGGCATTTACAGAAGCTCTCG

CTAAAGTCGACGATGCTGGTACAAAGGAAGTGCTTACTCGATTGCGAGATCTCTTTG

GTTTGTCCTTGATTGAAAAACACTTGCTGTGGTATCTTATGAATGGACGTTTGTCCAT

GCAAAGAGGCAGGACAGTTGGAACTTACATTAATCGTTTACTTGTCAAGATCCGTCC

ACACGCACTAGACTTGGTTGATGCCTTCGGTTACGGCGCGGAGCATTTGCGTGCTGC

TATCGCCACCGGAGCGGAAGCAACCCGACAGGATGAAGCCCGAACGTATTTTAGAC

AACAACGGGCATCGGGACTGGCCCCGGCCGATGAAAAGACCTTACTCGCTATCAAA

GCTGGTAAATCAAGAGGGCGAAGGGCAAAGCTATGA
```

CvHXS1 Gene
                                                    (SEQ ID NO: 94)
```
ATGGGAAAAAATTATAAATCTTTGGACTCAGTTGTGGCTAGTGACTTCATTGCACTT

GGGATCACATCAGAAGTTGCTGAGACATTGCACGGACGCTTGGCAGAGATAGTTTG

CAACTACGGCGCCGCAACACCTCAGACCTGGATTAACATCGCAAACCATATTCTAA
```

-continued

```
GTCCAGATCTTCCATTTAGTCTCCATCAGATGTTGTTCTACGGTTGTTATAAGGACTT

TGGTCCAGCACCCCCAGCTTGGATACCAGACCCCGAAAAAGTAAAGTCCACGAACT

TAGGTGCCTTGTTAGAAAAGCGGGGAAAGGAGTTTCTAGGCGTTAAGTATAAGGAC

CCAATAAGTCTGTTTTCTCACTTCCAGGAGTTTAGCGTTCGAAATCCGGAAGTCTACT

GGCGGACGGTACTTATGGATGAAATGAAGATACTGTTCAGCAAAGATCCCGAATGT

ATCCTCAGACGCGACGACATTAACAACCCAGGGGGCTCTGAGTGGCTACCAGGTGG

ATATCTCAACCTGGCCAAGAACTGTTTGAATGTAAATAGTAACAAAAAACTTAACG

ACACTATGATAGTGTGGAGAGATGAAGGAAATGACGATCTCCCATTGAATAAATTG

ACTCTTGATCAATTACGAAAACGAGTCTGGTTGGTTGGATACGCCCTAGAAGAGATG

GGCCTTGAGAAGGGATGTGCGATTGCAATTGACATGCCCATGCACGTAGATGCGGTT

GTGATCTATTTAGCTATCGTCTTGGCAGGCTACGTCGTTGTCTCCATTGCAGATTCAT

TCTCAGCACCGGAAATTTCCACAAGATTGCGTCTATCAAAGGCTAAGGCTATTTTTA

CACAAGATCATATCATCCGAGGGAAAAAGCGTATACCTTTGTACCTGCGTGTCGTCG

AGGCCAAGTCTCCGATGGCAATAGTTATCCCGTGTTCGGGTTCAAATATTGGTGCGG

AATTGCGGGATGGTGATATTCTGTGGGATTACTTCTTAGAACGCGCAAAGGAATTTA

AGAACTGCGAATTTACAGCCCGTGAACAGCCAGTGGACGCGTACACAAATATTTTGT

TCTCATCGGGAACCACCGGAGAGCCAAAGGCGATACCATGGACTCAAGCTACGCCT

CTCAAGGCGGCTGCTGATGGTTGGTCACACTTGGACATTAGAAAGGGTGACGTAATT

GTATGGCCTACCAATTTGGGGTGGATGATGGGCCTTGGTTGGTCTATGCTTCACTC

CTTAACGGGGCAAGCATCGCATTGTATAACGGATCTCCACTAGTGTCCGGCTTTGCC

AAATTCGTTCAAGATGCGAAAGTTACTATGCTAGGAGTTGTCCCCTCCATCGTACGA

AGCTGGAAAAGCACTAATTGCGTTAGTGGGTACGATTGGTCTACAATCAGATGCTTC

TCCTCATCGGGTGAGGCATCGAATGTCGATGAATACTTATGGCTAATGGGAAGGGCT

AACTACAAACCGGTCATCGAAATGTGCGGTGGCACAGAGATCGGGGGTGCCTTCAG

CGCCGGTTCGTTTTTACAAGCCCAATCTTTGAGTAGCTTCTCATCCCAATGTATGGGA

TGCACCTTGTACATTCTCGACAAGAATGGCTACCCGATGCCAAAGAACAAGCCGGG

TATAGGTGAATTGGCCTTGGGACCCGTGATGTTCGGTGCTTCCAAGACTTTACTTAA

CGGAAACCATCATGACGTTTATTTCAAAGGCATGCCCACCTTGAACGGAGAAGTCTT

GAGGAGACACGGAGATATCTTCGAACTCACTTCGAACGGCTATTATCACGCTCATGG

TAGAGCAGATGACACGATGAATATCGGGGGATTAAAATTTCCTCAATCGAGATTG

AAAGGGTGTGTAATGAAGTTGACGATAGAGTGTTTGAGACTACGGCCATTGGAGTG

CCTCCATTGGGCGGAGGTCCAGAGCAGCTCGTTATCTTTTTTGTTCTTAAGGACAGC

AATGATACGACCATCGACCTAAACCAATTGCGACTTAGTTTTAATCTTGGGTTACAA

AAGAAATTGAACCCACTTTTTAAGGTGACGAGGGTTGTGCCACTTTCGCTGTTGCCT

AGGACAGCCACCAACAAAATAATGAGAAGAGTGCTTAGACAGCAATTTAGTCATTT

CGAGTGA
```

CvTKS1 Gene (SEQ ID NO: 95)

```
ATGAATCATTTAAGAGCAGAAGGACCCGCATCAGTGTTAGCGATAGGTACAGCTAA

CCCAGAGAATATCTTAATCCAAGATGAATTTCCTGACTACTATTTCCGTGTTACTAA

ATCGGAACATATGACTCAACTTAAAGAGAAGTTCCGGAAAATCTGCGATAAATCCA

TGATCCGAAAGAGAAACTGTTTCCTTAACGAAGAACATCTCAAGCAAAACCCGAGG
```

-continued

TTGGTAGAGCACGAAATGCAGACCTTGGATGCTAGGCAGGACATGTTGGTGGTCGA

AGTGCCAAAACTCGGCAAGGACGCGTGCGCTAAGGCAATCAAGGAGTGGGGTCAAC

CGAAGTCTAAAATCACGCATCTAATATTTACATCTGCACTGACAACCGACATGCCGG

GTGCCGATTATCACTGCGCCAAGCTACTTGGATTGAGTCCACTGGTTAAGAGAGTTA

TGATGTATCAATTGGGGTGTTACGGAGGGGGCACAGTCCTCAGAATTGCTAAGGAT

ATTGCGGAAAATAACAAGGGCGCGAGGGTCCTTGCTGTATGTTGTGATATTATGGCC

TGTTTGTTTCGCGGGCCCTCGGATTCAGATTTGGAATTGCTTGTCGGACAGGCAATTT

TTGGTGACGGGGCCGCAGCAGTCATAGTGGGAGCCGAACCAGACGAAAGCGTGGGT

GAAAGACCAATCTTTGAGTTGGTTCTGACCGGACAAACGATCTTACCTAACTCGGAA

GGTACGATTGGAGGACATATTAGAGAAGCCGGCCTAATTTTCGATCTTCACAAAGAC

GTTCCAATGTTAATCTCCAATAACATAGAAAAGTGCTTGATAGAAGCATTTACTCCC

ATTGGTATTAGTGACTGGAACAGCATTTTCTGGATCACCCACCCTGGAGGAAAAGCT

ATACTCGATAAGGTTGAAGAGAAACTCGACTTGAAAAAGGAGAAATTCGTTGACTC

ACGACATGTGTTATCAGAGCACGGGAATATGAGTTCATCCACAGTCTTGTTCGTAAT

GGATGAATTGCGAAAACGCTCTCTTGAGGAGGGAAAGAGCACAACCGGTGACGGGT

TTGAGTGGGGCGTGCTATTCGGTTTTGGCCCAGGTTTGACTGTCGAGCGGGTTGTTG

TTCGTAGTGTACCAATTAAGTACTGA

CvTKS1P Gene (SEQ ID NO: 96)

ATGAATCATTTAAGAGCAGAAGGACCCGCATCAGTGTTAGCGATAGGTACAGCTAA

CCCAGAGAATATCTTAATCCAAGATGAATTTCCTGACTACTATTTCCGTGTTACTAA

ATCGGAACATATGACTCAACTTAAAGAGAAGTTCCGGAAAATCTGCGATAAATCCA

TGATCCGAAAGAGAAACTGTTTCCTTAACGAAGAACATCTCAAGCAAAACCCGAGG

TTGGTAGAGCACGAAATGCAGACCTTGGATGCTAGGCAGGACATGTTGGTGGTCGA

AGTGCCAAAACTCGGCAAGGACGCGTGCGCTAAGGCAATCAAGGAGTGGGGTCAAC

CGAAGTCTAAAATCACGCATCTAATATTTACATCTGCACTGACAACCGACATGCCGG

GTGCCGATTATCACTGCGCCAAGCTACTTGGATTGAGTCCACTGGTTAAGAGAGTTA

TGATGTATCAATTGGGGTGTTACGGAGGGGGCACAGTCCTCAGAATTGCTAAGGAT

ATTGCGGAAAATAACAAGGGCGCGAGGGTCCTTGCTGTATGTTGTGATATTATGGCC

TGTTTGTTTCGCGGGCCCTCGGATTCAGATTTGGAATTGCTTGTCGGACAGGCAATTT

TTGGTGACGGGGCCGCAGCAGTCATAGTGGGAGCCGAACCAGACGAAAGCGTGGGT

GAAAGACCAATCTTTGAGTTGGTTCTGACCGGACAAACGATCTTACCTAACTCGGAA

GGTACGATTGGAGGACATATTAGAGAAGCCGGCCTAATTTTCGATCTTCACAAAGAC

GTTCCAATGTTAATCTCCAATAACATAGAAAAGTGCTTGATAGAAGCATTTACTCCC

ATTGGTATTAGTGACTGGAACAGCATTTTCTGGATCACCCACCCTGGAGGAAAAGCT

ATACTCGATAAGGTTGAAGAGAAACTCGACTTGAAAAAGGAGAAATTCGTTGACTC

ACGACATGTGTTATCAGAGCACGGGAATATGAGTTCATCCACAGTCTTGTTCGTAAT

GGATGAATTGCGAAAACGCTCTCTTGAGGAGGGAAAGAGCACAACCGGTGACGGGT

TTGAGTGGGGCGTGCTATTCGGTTTTGGCCCAGGTTTGACTGTCGAGCGGGTTGTTG

TTCGTAGTGTACCAATTAAGTACGGAAGAAGGGCAAAGTTGTGA

-continued

CvOAC1 Gene (SEQ ID NO: 97)

ATGGCAGTCAAACACCTAATAGTTCTCAAATTTAAAGACGAGATTACTGAAGCTCAG

AAGGAAGAGTTCTTTAAGACATATGTTAACTTAGTCAACATCATCCCCGCGATGAAG

GACGTCTACTGGGGCAAGGATGTGACGCAAAAAAATAAGGAAGAAGGATACACAC

ATATCGTTGAGGTGACCTTTGAGAGTGTGGAAACTATTCAAGATTATATTATTCACC

CAGCCCATGTAGGGTTCGGTGACGTTTATCGATCATTCTGGGAAAAGTTGCTTATAT

TTGATTACACCCCAAGAAAATTGAAGCCTAAGTGA

CvOACP1 Gene (SEQ ID NO: 98)

ATGGCAGTCAAACACCTAATAGTTCTCAAATTTAAAGACGAGATTACTGAAGCTCAG

AAGGAAGAGTTCTTTAAGACATATGTTAACTTAGTCAACATCATCCCCGCGATGAAG

GACGTCTACTGGGGCAAGGATGTGACGCAAAAAAATAAGGAAGAAGGATACACAC

ATATCGTTGAGGTGACCTTTGAGAGTGTGGAAACTATTCAAGATTATATTATTCACC

CAGCCCATGTAGGGTTCGGTGACGTTTATCGATCATTCTGGGAAAAGTTGCTTATAT

TTGATTACACCCCAAGAAAATTGAAGCCTAAGGGAAGACGAGCTAAGTTGTGA

CvPTS1 Gene (SEQ ID NO: 99)

ATGGGTTTATCGTCAGTGTGCACTTTTTCTTTTCAAACAAACTACCACACCCTCCTAA

ACCCTCACAATAATAACCCAAAAACCTCCTTGCTATGTTACAGACATCCAAAGACAC

CGATCAAGTATTCATACAACAATTTTCCCAGTAAACATTGCTCAACGAAGTCCTTCC

ACTTGCAAAACAAATGCAGCGAATCATTGTCGATAGCTAAAAACTCGATACGTGCG

GCAACCACTAACCAAACTGAGCCACCAGAGAGCGATAATCATTCAGTCGCCACCAA

GATTTTGAACTTTGGAAAAGCCTGTTGGAAACTTCAAAGGCCTTACACCATTATCGC

ATTTACCAGTTGCGCATGTGGTTTGTTCGGGAAGGAATTATTACACAACACAAATTT

GATCAGCTGGAGCCTAATGTTTAAGGCATTTTTCTTCTTAGTTGCAATTTTGTGTATA

GCTTCGTTTACAACGACCATTAATCAGATTTACGACCTTCACATCGATCGGATCAAT

AAACCAGACTTGCCCCTTGCCTCTGGGGAAATCTCTGTAAATACTGCATGGATCATG

CTGATAATCGTGGCTTTGTTTGGATTGATTATTACAATTAAGATGAAGGGGGGTCCA

TTATATATATTCGGGTACTGCTTCGGCATTTTCGGTGGTATCGTTTACTCCGTCCCAC

CCTTTAGATGGAAACAGAACCCCAGTACGGCCTTTCTACTCAATTTCTTGGCTCATAT

CATCACAAACTTCACATTCTATTATGCAAGCCGAGCGGCGCTTGGTTTGCCGTTCGA

ACTCAGACCGAGTTTTACATTTCTCCTTGCCTTCATGAAACTGATGGGACTGGCCCTT

GCATTGATCAAGGATGCGTCAGATGTCGAAGGCGACACTAAGTTCGGCATTCTGAC

GCTTGCTTCCAAGTATGGAAGTAGAAATCTAACGCTTTTTTGTTCAGGAATAGTGCT

ACTTAGTTATGTTGCTGCTATACTCGCTGGCATTATTTGGCCTCAGGCCTTCAACTCT

AACGTAATGTTGTTATCCCATGCTATTTTGGCGTTCTGGTTGATCTTGCAAACGCGAG

ATTTTGCACTCACTAACTACGACCCAGAGGCAGGAAGGCGCTTTTACGAGTTTATGT

GGAAGTTGTATTATGCCGAATACTTGGTTTATGTTTTCATTTGA

CVPTS1dN Gene (SEQ ID NO: 100)

ATGGCGGCAACCACTAACCAAACTGAGCCACCAGAGAGCGATAATCATTCAGTCGC

CACCAAGATTTTGAACTTTGGAAAAGCCTGTTGGAAACTTCAAAGGCCTTACACCAT

TATCGCATTTACCAGTTGCGCATGTGGTTTGTTCGGGAAGGAATTATTACACAACAC

-continued

```
AAATTTGATCAGCTGGAGCCTAATGTTTAAGGCATTTTTCTTCTTAGTTGCAATTTTG

TGTATAGCTTCGTTTACAACGACCATTAATCAGATTTACGACCTTCACATCGATCGG

ATCAATAAACCAGACTTGCCCCTTGCCTCTGGGGAAATCTCTGTAAATACTGCATGG

ATCATGCTGATAATCGTGGCTTTGTTTGGATTGATTATTACAATTAAGATGAAGGGG

GGTCCATTATATATATTCGGGTACTGCTTCGGCATTTTCGGTGGTATCGTTTACTCCG

TCCCACCCTTTAGATGGAAACAGAACCCCAGTACGGCCTTTCTACTCAATTTCTTGG

CTCATATCATCACAAACTTCACATTCTATTATGCAAGCCGAGCGGCGCTTGGTTTGC

CGTTCGAACTCAGACCGAGTTTTACATTTCTCCTTGCCTTCATGAAACTGATGGGACT

GGCCCTTGCATTGATCAAGGATGCGTCAGATGTCGAAGGCGACACTAAGTTCGGCAT

TCTGACGCTTGCTTCCAAGTATGGAAGTAGAAATCTAACGCTTTTTTGTTCAGGAAT

AGTGCTACTTAGTTATGTTGCTGCTATACTCGCTGGCATTATTTGGCCTCAGGCCTTC

AACTCTAACGTAATGTTGTTATCCCATGCTATTTTGGCGTTCTGGTTGATCTTGCAAA

CGCGAGATTTTGCACTCACTAACTACGACCCAGAGGCAGGAAGGCGCTTTTACGAGT

TTATGTGGAAGTTGTATTATGCCGAATACTTGGTTTATGTTTTCATTTGA

CvPTS2 Gene
                                          (SEQ ID NO: 101)
ATGGGGTTGTCCTTAGTTTGTACGTTCAGTTTCCAAACTAACTACCACACACTACTAA

ATCCGCACAACAAAAACCCGAAAAATTCATTGCTCTCCTATCAGCACCCAAAAACA

CCCATTATCAAGTCTAGTTACGACAACTTTCCATCAAAATACTGTCTAACGAAAAAC

TTTCATTTGTTGGGCTTAAATTCTCATAATCGTATTTCCAGTCAGTCCCGATCGATCA

GGGCCGGGAGTGACCAAATTGAAGGTTCTCCACATCATGAAAGTGACAATTCAATT

GCTACGAAGATTTTAAACTTTGGGCATACATGCTGGAAGCTACAGCGACCGTATGTA

GTTAAGGGGATGATCAGCATTGCCTGCGGCCTATTCGGAAGGGAACTCTTCAATAAT

AGACATCTTTTTTCTTGGGGTTTAATGTGGAAAGCTTTTTTCGCTTTGGTTCCTATCCT

TAGTTTTAACTTCTTCGCCGCTATTATGAATCAAATTTACGATGTTGACATCGACCGT

ATTAACAAACCCGATCTCCCCCTTGTTTCAGGCGAGATGTCCATTGAAACGGCATGG

ATTTTGTCCATCATTGTTGCGCTTACTGGCTTGATTGTTACCATTAAGCTTAAAAGCG

CTCCCTTGTTCGTTTTTATATACATTTTCGGCATTTTTGCCGGATTCGCATACAGTGTC

CCGCCTATACGTTGGAAACAATATCCATTCACGAACTTCTTGATCACGATCTCATCA

CATGTTGGATTGGCCTTTACGTCCTACAGTGCTACCACATCTGCCCTTGGATTGCCTT

TCGTTTGGAGGCCTGCCTTCTCGTTTATCATTGCATTTATGACAGTGATGGGAATGAC

TATCGCATTTGCTAAAGATATCAGCGACATAGAGGGCGATGCAAAATATGGGGTGA

GTACTGTTGCGACGAAGTTGGGCGCCCGAAATATGACCTTCGTTGTTTCCGGCGTTC

TTTTACTTAACTATTTAGTATCGATTAGCATCGGGATCATCTGGCCACAGGTGTTTAA

ATCAAATATTATGATCTTGTCGCATGCCATCCTAGCTTTCTGTCTTATATTTCAAACA

AGAGAATTAGCCCTAGCGAACTACGCCTCAGCACCAAGTCGTCAGTTCTTCGAATTT

ATATGGCTACTCTACTACGCCGAATACTTCGTCTATGTCTTCATTTAG

CvCBD1 Gene
                                          (SEQ ID NO: 102)
ATGAAGTGTTCTACGTTTAGTTTTTGGTTTGTTTGTAAAATTATATTCTTCTTTTTTTC

CTTCAACATTCAGACATCAATCGCCAACCCAAGGGAAAACTTCCTTAAGTGTTTTCT

GCAGTACATCCCTAACAATGCAACAAACCTCAAGTTGGTGTACACTCAAAACAATC

CACTCTATATGAGCGTGCTTAATAGCACAATCCACAACTTGCGCTTCACGTCAGATA
```

-continued

```
CTACGCCTAAGCCACTAGTGATCGTTACACCATCACACGTCAGCCATATTCAAGGAA

CGATCCTATGTCTGAAAAAGGTCGGGTTGCAAATCAGGACTCGATCAGGAGGGCAC

GATAGTGAGGGAATGAGTTACATCTCGCAAGTACCCTTCGTGATAGTTGACTTGCGA

AATATGCGGTCTATTAAAATTGACGTACATAGCCAGACCGCCTGGGTTGAAGCAGG

GGCAACCTTGGGTGAAGTTTATTACTGGGTCAATGAAAAAAACGAAAACCTAAGTC

TTGCTGCTGGATATTGCCCCACCGTTTGCGCGGGTGGTCATTTTGGAGGCGGCGGAT

ATGGTCCGTTGATGAGAAATTATGGACTTGCAGCAGACAATATTATAGATGCCCACT

TGGTGAACGTTCATGGAAAGGTCTTGGACCGTAAGTCCATGGGTGAAGATCTTTTCT

GGGCCTTGAGAGGTGGTGGAGCGGAATCGTTTGGCATCATCGTTGCCTGGAAAATTA

GGTTGGTTGCGGTCCCGAAGAGTACAATGTTCTCCGTGAAGAAGATTATGGAAATAC

ATGAGCTTGTCAAGTTAGTTAACAAGTGGCAAAATATCGCTTATAAGTATGATAAAG

ACTTGCTTTTGATGACTCATTTTATTACGCGAAACATAACCGATAACCAGGGCAAGA

ACAAGACTGCTATTCACACGTACTTCTCCTCTGTATTTCTTGGAGGAGTAGACTCCTT

AGTTGACTTGATGAACAAGAGTTTCCCAGAATTGGGGATTAAGAAGACAGATTGCA

GACAATTATCGTGGATAGATACAATCATATTCTATAGCGGTGTCGTCAATTACGATA

CTGATAATTTTAATAAAGAAATCCTCCTAGATCGTTCAGCTGGGCAAAACGGGGCAT

TCAAAATTAAATTGGATTATGTGAAGAAACCAATTCCAGAGCTGGTGTTTGTTCAGA

TATTGGAAAAACTTTACGAAGAAGACATTGGCGCAGGTATGTACGCTTTGTATCCAT

ATGGAGGCATTATGGACGAGATCTCAGAGCTGGCGATCCCCTTCCCGCACAGAGCT

GGGATACTCTACGAGCTATGGTACATCTGCTCTTGGGAGAAACAAGAAGACAACGA

GAAACATCTCAATTGGATTCGGAACATATACAACTTTATGACCCCATACGTATCAAA

AAACCCGCGCTTAGCATACTTGAATTACAGAGACTTAGATATCGGTATCAATGATCC

TAAGAATCCTAACAATTACACCCAAGCCCGTATTTGGGGTGAGAAATATTTCGGCAA

GAATTTTGACAGATTAGTTAAGGTCAAAACACTCGTGGACCCCAACAACTTTTTCCG

AAACGAGCAGTCGATTCCACCACTACCCAGGCATAGACACTGA

CBD1dNS1
                                                     (SEQ ID NO: 103)
ATGTTCTTGAAACACATTTTTGTTGCTCTCGCTTTTGCCTTGTTAGCTGACGCTACCC

CAGCCCAGAAGAGATCTCCCGGCTTCGTTGCTTTAGACTTTGACATCGTCAAGGTTC

AAAAGAACGTGACTGCCAACGACGACGCCGCTGCCATTGTTGCCAAGAGACAGACC

AACCCAAGGGAAAACTTCCTTAAGTGTTTTCTGCAGTACATCCCTAACAATGCAACA

AACCTCAAGTTGGTGTACACTCAAAACAATCCACTCTATATGAGCGTGCTTAATAGC

ACAATCCACAACTTGCGCTTCACGTCAGATACTACGCCTAAGCCACTAGTGATCGTT

ACACCATCACACGTCAGCCATATTCAAGGAACGATCCTATGTCTGAAAAAGGTCGG

GTTGCAAATCAGGACTCGATCAGGAGGGCACGATAGTGAGGGAATGAGTTACATCT

CGCAAGTACCCTTCGTGATAGTTGACTTGCGAAATATGCGGTCTATTAAAATTGACG

TACATAGCCAGACCGCCTGGGTTGAAGCAGGGGCAACCTTGGGTGAAGTTTATTACT

GGGTCAATGAAAAAACGAAAACCTAAGTCTTGCTGCTGGATATTGCCCCACCGTTT

GCGCGGGTGGTCATTTTGGAGGCGGCGGATATGGTCCGTTGATGAGAAATTATGGA

CTTGCAGCAGACAATATTATAGATGCCCACTTGGTGAACGTTCATGGAAAGGTCTTG

GACCGTAAGTCCATGGGTGAAGATCTTTTCTGGGCCTTGAGAGGTGGTGGAGCGGA
```

-continued

ATCGTTTGGCATCATCGTTGCCTGGAAAATTAGGTTGGTTGCGGTCCCGAAGAGTAC

AATGTTCTCCGTGAAGAAGATTATGGAAATACATGAGCTTGTCAAGTTAGTTAACAA

GTGGCAAAATATCGCTTATAAGTATGATAAAGACTTGCTTTTGATGACTCATTTTATT

ACGCGAAACATAACCGATAACCAGGGCAAGAACAAGACTGCTATTCACACGTACTT

CTCCTCTGTATTTCTTGGAGGAGTAGACTCCTTAGTTGACTTGATGAACAAGAGTTTC

CCAGAATTGGGGATTAAGAAGACAGATTGCAGACAATTATCGTGGATAGATACAAT

CATATTCTATAGCGGTGTCGTCAATTACGATACTGATAATTTTAATAAAGAAATCCT

CCTAGATCGTTCAGCTGGGCAAAACGGGGCATTCAAAATTAAATTGGATTATGTGAA

GAAACCAATTCCAGAGCTGGTGTTTGTTCAGATATTGGAAAAACTTTACGAAGAAG

ACATTGGCGCAGGTATGTACGCTTTGTATCCATATGGAGGCATTATGGACGAGATCT

CAGAGCTGGCGATCCCCTTCCCGCACAGAGCTGGGATACTCTACGAGCTATGGTACA

TCTGCTCTTGGGAGAAACAAGAAGACAACGAGAAACATCTCAATTGGATTCGGAAC

ATATACAACTTTATGACCCCATACGTATCAAAAAACCCGCGCTTAGCATACTTGAAT

TACAGAGACTTAGATATCGGTATCAATGATCCTAAGAATCCTAACAATTACACCCAA

GCCCGTATTTGGGGTGAGAAATATTTCGGCAAGAATTTTGACAGATTAGTTAAGGTC

AAAACACTCGTGGACCCCAACAACTTTTTCCGAAACGAGCAGTCGATTCCACCACTA

CCCAGGCATAGACACTGA

CBD1dNS2

(SEQ ID NO: 104)

ATGCAATTGTCATTGTCAGTTTTGTCAACAGTTGCAACAGCATTGTTGTCATTGACAA

CAGCAGTTGATGCAAAGTCACATAACCCAAGGGAAAACTTCCTTAAGTGTTTTCTGC

AGTACATCCCTAACAATGCAACAAACCTCAAGTTGGTGTACACTCAAAACAATCCA

CTCTATATGAGCGTGCTTAATAGCACAATCCACAACTTGCGCTTCACGTCAGATACT

ACGCCTAAGCCACTAGTGATCGTTACACCATCACACGTCAGCCATATTCAAGGAACG

ATCCTATGTCTGAAAAAGGTCGGGTTGCAAATCAGGACTCGATCAGGAGGGCACGA

TAGTGAGGGAATGAGTTACATCTCGCAAGTACCCTTCGTGATAGTTGACTTGCGAAA

TATGCGGTCTATTAAAATTGACGTACATAGCCAGACCGCCTGGGTTGAAGCAGGGG

CAACCTTGGGTGAAGTTTATTACTGGGTCAATGAAAAAAACGAAAACCTAAGTCTTG

CTGCTGGATATTGCCCCACCGTTTGCGCGGGTGGTCATTTTGGAGGCGGCGGATATG

GTCCGTTGATGAGAAATTATGGACTTGCAGCAGACAATATTATAGATGCCCACTTGG

TGAACGTTCATGGAAAGGTCTTGGACCGTAAGTCCATGGGTGAAGATCTTTTCTGGG

CCTTGAGAGGTGGTGGAGCGGAATCGTTTGGCATCATCGTTGCCTGGAAAATTAGGT

TGGTTGCGGTCCCGAAGAGTACAATGTTCTCCGTGAAGAAGATTATGGAAATACATG

AGCTTGTCAAGTTAGTTAACAAGTGGCAAAATATCGCTTATAAGTATGATAAAGACT

TGCTTTTGATGACTCATTTTATTACGCGAAACATAACCGATAACCAGGGCAAGAACA

AGACTGCTATTCACACGTACTTCTCCTCTGTATTTCTTGGAGGAGTAGACTCCTTAGT

TGACTTGATGAACAAGAGTTTCCCAGAATTGGGGATTAAGAAGACAGATTGCAGAC

AATTATCGTGGATAGATACAATCATATTCTATAGCGGTGTCGTCAATTACGATACTG

ATAATTTTAATAAAGAAATCCTCCTAGATCGTTCAGCTGGGCAAAACGGGGCATTCA

AAATTAAATTGGATTATGTGAAGAAACCAATTCCAGAGCTGGTGTTTGTTCAGATAT

TGGAAAAACTTTACGAAGAAGACATTGGCGCAGGTATGTACGCTTTGTATCCATATG

GAGGCATTATGGACGAGATCTCAGAGCTGGCGATCCCCTTCCCGCACAGAGCTGGG

-continued

ATACTCTACGAGCTATGGTACATCTGCTCTTGGGAGAAACAAGAAGACAACGAGAA

ACATCTCAATTGGATTCGGAACATATACAACTTTATGACCCCATACGTATCAAAAAA

CCCGCGCTTAGCATACTTGAATTACAGAGACTTAGATATCGGTATCAATGATCCTAA

GAATCCTAACAATTACACCCAAGCCCGTATTTGGGGTGAGAAATATTTCGGCAAGA

ATTTTGACAGATTAGTTAAGGTCAAAACACTCGTGGACCCCAACAACTTTTTCCGAA

ACGAGCAGTCGATTCCACCACTACCCAGGCATAGACACTGA

CBD1dNV1

(SEQ ID NO: 105)
ATGCAATTGTCCTTGTCGGTTTTATCAACCGTTGCCACGGCCTTGTTGTCCCTAACCA

CCGCCGTCGATGCTAAGTCCCACAACATCAAGTTGTCCAAGTTGTCCAACGAAGAA

ACATTGGACGCCTCCACATTCCAAGAATACACGAGCTCCTTGGCCAACAAGTACATG

AACTTGTTCAACGCCGCTCACGGTAACCCAACCAGCTTTGGCTTGCAACACGTCTTG

TCCAACCAAGAAGCTGAAGTCCCATTCGTTACCCCACAAAAGGGTGGCAACCCAAG

GGAAAACTTCCTTAAGTGTTTTCTGCAGTACATCCCTAACAATGCAACAAACCTCAA

GTTGGTGTACACTCAAAACAATCCACTCTATATGAGCGTGCTTAATAGCACAATCCA

CAACTTGCGCTTCACGTCAGATACTACGCCTAAGCCACTAGTGATCGTTACACCATC

ACACGTCAGCCATATTCAAGGAACGATCCTATGTCTGAAAAAGGTCGGGTTGCAAA

TCAGGACTCGATCAGGAGGGCACGATAGTGAGGGAATGAGTTACATCTCGCAAGTA

CCCTTCGTGATAGTTGACTTGCGAAATATGCGGTCTATTAAAATTGACGTACATAGC

CAGACCGCCTGGGTTGAAGCAGGGGCAACCTTGGGTGAAGTTTATTACTGGGTCAAT

GAAAAAAACGAAAACCTAAGTCTTGCTGCTGGATATTGCCCCACCGTTTGCGCGGGT

GGTCATTTTGGAGGCGGCGGATATGGTCCGTTGATGAGAAATTATGGACTTGCAGCA

GACAATATTATAGATGCCCACTTGGTGAACGTTCATGGAAAGGTCTTGGACCGTAAG

TCCATGGGTGAAGATCTTTTCTGGGCCTTGAGAGGTGGTGGAGCGGAATCGTTTGGC

ATCATCGTTGCCTGGAAAATTAGGTTGTTGCGGTCCCGAAGAGTACAATGTTCTCC

GTGAAGAAGATTATGGAAATACATGAGCTTGTCAAGTTAGTTAACAAGTGGCAAAA

TATCGCTTATAAGTATGATAAAGACTTGCTTTTGATGACTCATTTTATTACGCGAAAC

ATAACCGATAACCAGGGCAAGAACAAGACTGCTATTCACACGTACTTCTCCTCTGTA

TTTCTTGGAGGAGTAGACTCCTTAGTTGACTTGATGAACAAGAGTTTCCCAGAATTG

GGGATTAAGAAGACAGATTGCAGACAATTATCGTGGATAGATACAATCATATTCTAT

AGCGGTGTCGTCAATTACGATACTGATAATTTTAATAAAGAAATCCTCCTAGATCGT

TCAGCTGGGCAAAACGGGGCATTCAAAATTAAATTGGATTATGTGAAGAAACCAAT

TCCAGAGCTGGTGTTTGTTCAGATATTGGAAAAACTTTACGAAGAAGACATTGGCGC

AGGTATGTACGCTTTGTATCCATATGGAGGCATTATGGACGAGATCTCAGAGCTGGC

GATCCCCTTCCCGCACAGAGCTGGGATACTCTACGAGCTATGGTACATCTGCTCTTG

GGAGAAACAAGAAGACAACGAGAAACATCTCAATTGGATTCGGAACATATACAACT

TTATGACCCCATACGTATCAAAAAACCCGCGCTTAGCATACTTGAATTACAGAGACT

TAGATATCGGTATCAATGATCCTAAGAATCCTAACAATTACACCCAAGCCCGTATTT

GGGGTGAGAAATATTTCGGCAAGAATTTTGACAGATTAGTTAAGGTCAAAACACTC

GTGGACCCCAACAACTTTTTCCGAAACGAGCAGTCGATTCCACCACTACCCAGGCAT

AGACACTGA

-continued

CvCBD1dNP1
(SEQ ID NO: 106)
ATGAACCCAAGGGAAAACTTCCTTAAGTGTTTTCTGCAGTACATCCCTAACAATGCA

ACAAACCTCAAGTTGGTGTACACTCAAACAATCCACTCTATATGAGCGTGCTTAAT

AGCACAATCCACAACTTGCGCTTCACGTCAGATACTACGCCTAAGCCACTAGTGATC

GTTACACCATCACACGTCAGCCATATTCAAGGAACGATCCTATGTCTGAAAAAGGTC

GGGTTGCAAATCAGGACTCGATCAGGAGGGCACGATAGTGAGGGAATGAGTTACAT

CTCGCAAGTACCCTTCGTGATAGTTGACTTGCGAAATATGCGGTCTATTAAAATTGA

CGTACATAGCCAGACCGCCTGGGTTGAAGCAGGGGCAACCTTGGGTGAAGTTTATT

ACTGGGTCAATGAAAAAAACGAAAACCTAAGTCTTGCTGCTGGATATTGCCCCACC

GTTTGCGCGGGTGGTCATTTTGGAGGCGGCGGATATGGTCCGTTGATGAGAAATTAT

GGACTTGCAGCAGACAATATTATAGATGCCCACTTGGTGAACGTTCATGGAAAGGTC

TTGGACCGTAAGTCCATGGGTGAAGATCTTTTCTGGGCCTTGAGAGGTGGTGGAGCG

GAATCGTTTGGCATCATCGTTGCCTGGAAAATTAGGTTGGTTGCGGTCCCGAAGAGT

ACAATGTTCTCCGTGAAGAAGATTATGGAAATACATGAGCTTGTCAAGTTAGTTAAC

AAGTGGCAAAATATCGCTTATAAGTATGATAAAGACTTGCTTTTGATGACTCATTTT

ATTACGCGAAACATAACCGATAACCAGGGCAAGAACAAGACTGCTATTCACACGTA

CTTCTCCTCTGTATTTCTTGGAGGAGTAGACTCCTTAGTTGACTTGATGAACAAGAGT

TTCCCAGAATTGGGGATTAAGAAGACAGATTGCAGACAATTATCGTGGATAGATAC

AATCATATTCTATAGCGGTGTCGTCAATTACGATACTGATAATTTTAATAAAGAAAT

CCTCCTAGATCGTTCAGCTGGGCAAAACGGGGCATTCAAAATTAAATTGGATTATGT

GAAGAAACCAATTCCAGAGCTGGTGTTTGTTCAGATATTGGAAAAACTTTACGAAG

AAGACATTGGCGCAGGTATGTACGCTTTGTATCCATATGGAGGCATTATGGACGAGA

TCTCAGAGCTGGCGATCCCCTTCCCGCACAGAGCTGGGATACTCTACGAGCTATGGT

ACATCTGCTCTTGGGAGAAACAAGAAGACAACGAGAAACATCTCAATTGGATTCGG

AACATATACAACTTTATGACCCCATACGTATCAAAAAACCCGCGCTTAGCATACTTG

AATTACAGAGACTTAGATATCGGTATCAATGATCCTAAGAATCCTAACAATTACACC

CAAGCCCGTATTTGGGGTGAGAAATATTTCGGCAAGAATTTTGACAGATTAGTTAAG

GTCAAAACACTCGTGGACCCCAACAACTTTTTCCGAAACGAGCAGTCGATTCCACCA

CTACCCAGGCATAGACACGGAAGAAGGGCAAAGTTGTAA

CvTHC1 Gene
(SEQ ID NO: 107)
ATGAATTGTTCAGCATTTAGTTTTTGGTTTGTTTGTAAGATTATTTCTTCTTTTTGTC

ATTTAACATTCAAATTTCAATTGCAAACCCACAAGAAAACTTTTTGAAGTGTTTTTCA

GAATACATTCCAAACAATCCAGCTAACCCAAAGTTTATTTACACACAACATGATCAA

TTGTACATGTCAGTTTTGAACTCAACAATTCAAAACTTGAGATTTACATCAGATACC

ACACCAAAGCCATTGGTTATTGTTACACCATCAAACGTTTCCCATATTCAAGCATCA

ATCTTGTGTTCAAAGAAGGTTGGATTGCAAATTAGAACCAGATCAGGAGGACACGA

TGCAGAAGGAATGTCATACATTTCACAAGTTCCATTCGTTGTTGTTGATTTGAGAAA

CATGCACTCAATTAAGATTGATGTTCATTCACAAACAGCATGGGTTGAAGCAGGAGC

AACATTGGGTGAAGTTTACTACTGGATTAACGAAAAGAACGAAAACTTCAGTTTTCC

AGGAGGTTACTGTCCAACAGTTGGAGTTGGAGGACATTTTTCAGGTGGAGGATACG

GAGCATTGATGAGAAACTACGGATTGGCAGCAGATAACATTATTGATGCACACTTG

```
GTTAACGTTGATGGAAAGGTTTTGGATAGAAAGTCAATGGGAGAAGATTTGTTTTGG

GCAATTAGAGGAGGTGGTGGAGAGAACTTTGGAATTATTGCAGCATGGAAGATCAA

GTTGGTTGCAGTTCCATCAAAGTCAACAATCTTTTCAGTTAAGAAGAACATGGAAAT

TCATGGTTTGGTTAAGTTGTTTAACAAGTGGCAAAACATTGCATACAAGTACGATAA

GGATTTGGTTTTGATGACACATTTTATTACAAAGAACATTACAGATAACCATGGAAA

GAACAAGACAACAGTTCACGGATACTTTTCATCAATTTTTCACGGAGGAGTTGATTC

ATTGGTTGACTTGATGAACAAGTCATTTCCAGAATTGGGAATCAAGAAGACAGATTG

TAAGGAATTTTCATGGATTGATACAACAATTTTCTACTCAGGAGTTGTTAACTTTAAC

ACAGCAAACTTTAAGAAGGAAATTTTGTTGGACAGATCAGCAGGAAAGAAGACCGC

ATTTTCCATTAAGTTGGATTACGTTAAGAAACCAATTCCAGAAACAGCAATGGTTAA

GATTTTGGAAAAGTTGTACGAAGAAGATGTTGGTGTTGGAATGTACGTTTTGTACCC

ATACGGAGGAATTATGGAAGAAATCTCAGAATCAGCAATTCCATTTCCACATAGAG

CAGGTATTATGTACGAATTGTGGTACACAGCATCATGGGAAAAGCAAGAAGATAAT

GAAAAGCATATTAACTGGGTTAGATCAGTTTACAACTTTACAACACCATACGTTTCA

CAAAACCCAAGATTGGCATACTTGAACTACAGAGATTTGGATTTGGGAAAGACAAA

CCCAGAATCACCAAACAACTATACACAAGCTAGAATTTGGGGAGAAAAGTACTTTG

GTAAGAACTTCAACAGATTGGTTAAAGTTAAGACAAAGGCAGATCCAAATAACTTC

TTTAGAAACGAACAATCAATTCCACCATTGCCACCACATCATCATTAA

THC1dNS1 Gene
                                                 (SEQ ID NO: 108)
ATGTTCTTGAAACACATTTTTGTTGCTCTCGCTTTTGCCTTGTTAGCTGACGCTACCC

CAGCCCAGAAGAGATCTCCCGGCTTCGTTGCTTTAGACTTTGACATCGTCAAGGTTC

AAAAGAACGTGACTGCCAACGACGACGCCGCTGCCATTGTTGCCAAGAGACAGACC

AACCCACAAGAAACTTTTTGAAGTGTTTTTCAGAATACATTCCAAACAATCCAGCT

AACCCAAAGTTTATTTACACACAACATGATCAATTGTACATGTCAGTTTTGAACTCA

ACAATTCAAAACTTGAGATTTACATCAGATACCACACCAAAGCCATTGGTTATTGTT

ACACCATCAAACGTTTCCCATATTCAAGCATCAATCTTGTGTTCAAAGAAGGTTGGA

TTGCAAATTAGAACCAGATCAGGAGGACACGATGCAGAAGGAATGTCATACATTTC

ACAAGTTCCATTCGTTGTTGTTGATTTGAGAAACATGCACTCAATTAAGATTGATGTT

CATTCACAAACAGCATGGGTTGAAGCAGGAGCAACATTGGGTGAAGTTTACTACTG

GATTAACGAAAAGAACGAAAACTTCAGTTTTCCAGGAGGTTACTGTCCAACAGTTG

GAGTTGGAGGACATTTTTCAGGTGGAGGATACGGAGCATTGATGAGAAACTACGGA

TTGGCAGCAGATAACATTATTGATGCACACTTGGTTAACGTTGATGGAAAGGTTTTG

GATAGAAAGTCAATGGGAGAAGATTGTTTTGGGCAATTAGAGGAGGTGGTGGAGA

GAACTTTGGAATTATTGCAGCATGGAAGATCAAGTTGGTTGCAGTTCCATCAAAGTC

AACAATCTTTTCAGTTAAGAAGAACATGGAAATTCATGGTTTGGTTAAGTTGTTTAA

CAAGTGGCAAAACATTGCATACAAGTACGATAAGGATTTGGTTTTGATGACACATTT

TATTACAAAGAACATTACAGATAACCATGGAAAGAACAAGACAACAGTTCACGGAT

ACTTTTCATCAATTTTTCACGGAGGAGTTGATTCATTGGTTGACTTGATGAACAAGTC

ATTTCCAGAATTGGGAATCAAGAAGACAGATTGTAAGGAATTTTCATGGATTGATAC

AACAATTTTCTACTCAGGAGTTGTTAACTTTAACACAGCAAACTTTAAGAAGGAAAT
```

-continued

TTTGTTGGACAGATCAGCAGGAAAGAAGACCGCATTTTCCATTAAGTTGGATTACGT

TAAGAAACCAATTCCAGAAACAGCAATGGTTAAGATTTTGGAAAAGTTGTACGAAG

AAGATGTTGGTGTTGGAATGTACGTTTTGTACCCATACGGAGGAATTATGGAAGAAA

TCTCAGAATCAGCAATTCCATTTCCACATAGAGCAGGTATTATGTACGAATTGTGGT

ACACAGCATCATGGGAAAAGCAAGAAGATAATGAAAAGCATATTAACTGGGTTAGA

TCAGTTTACAACTTTACAACACCATACGTTTCACAAAACCCAAGATTGGCATACTTG

AACTACAGAGATTTGGATTTGGGAAAGACAAACCCAGAATCACCAAACAACTATAC

ACAAGCTAGAATTTGGGGAGAAAAGTACTTTGGTAAGAACTTCAACAGATTGGTTA

AAGTTAAGACAAAGGCAGATCCAAATAACTTCTTTAGAAACGAACAATCAATTCCA

CCATTGCCACCACATCATCATTAATAA

THC1dNS2

(SEQ ID NO: 109)
ATGCAATTGTCATTGTCAGTTTTGTCAACAGTTGCAACAGCATTGTTGTCATTGACAA

CAGCAGTTGATGCAAAGTCACATAACCCACAAGAAAACTTTTTGAAGTGTTTTTCAG

AATACATTCCAAACAATCCAGCTAACCCAAAGTTTATTTACACACAACATGATCAAT

TGTACATGTCAGTTTTGAACTCAACAATTCAAAACTTGAGATTTACATCAGATACCA

CACCAAAGCCATTGGTTATTGTTACACCATCAAACGTTTCCCATATTCAAGCATCAA

TCTTGTGTTCAAAGAAGGTTGGATTGCAAATTAGAACCAGATCAGGAGGACACGAT

GCAGAAGGAATGTCATACATTTCACAAGTTCCATTCGTTGTTGTTGATTTGAGAAAC

ATGCACTCAATTAAGATTGATGTTCATTCACAAACAGCATGGGTTGAAGCAGGAGC

AACATTGGGTGAAGTTTACTACTGGATTAACGAAAAGAACGAAAACTTCAGTTTTCC

AGGAGGTTACTGTCCAACAGTTGGAGTTGGAGGACATTTTTCAGGTGGAGGATACG

GAGCATTGATGAGAAACTACGGATTGGCAGCAGATAACATTATTGATGCACACTTG

GTTAACGTTGATGGAAAGGTTTTGGATAGAAAGTCAATGGGAGAAGATTGTTTTGG

GCAATTAGAGGAGGTGGTGGAGAGAACTTTGGAATTATTGCAGCATGGAAGATCAA

GTTGGTTGCAGTTCCATCAAAGTCAACAATCTTTTCAGTTAAGAAGAACATGGAAAT

TCATGGTTTGGTTAAGTTGTTTAACAAGTGGCAAAACATTGCATACAAGTACGATAA

GGATTTGGTTTTGATGACACATTTTATTACAAAGAACATTACAGATAACCATGGAAA

GAACAAGACAACAGTTCACGGATACTTTTCATCAATTTTTCACGGAGGAGTTGATTC

ATTGGTTGACTTGATGAACAAGTCATTTCCAGAATTGGGAATCAAGAAGACAGATTG

TAAGGAATTTTCATGGATTGATACAACAATTTTCTACTCAGGAGTTGTTAACTTTAAC

ACAGCAAACTTTAAGAAGGAAATTTTGTTGGACAGATCAGCAGGAAAGAAGACCGC

ATTTTCCATTAAGTTGGATTACGTTAAGAAACCAATTCCAGAAACAGCAATGGTTAA

GATTTTGGAAAAGTTGTACGAAGAAGATGTTGGTGTTGGAATGTACGTTTTGTACCC

ATACGGAGGAATTATGGAAGAAATCTCAGAATCAGCAATTCCATTTCCACATAGAG

CAGGTATTATGTACGAATTGTGGTACACAGCATCATGGGAAAAGCAAGAAGATAAT

GAAAAGCATATTAACTGGGTTAGATCAGTTTACAACTTTACAACACCATACGTTTCA

CAAAACCCAAGATTGGCATACTTGAACTACAGAGATTTGGATTTGGGAAAGACAAA

CCCAGAATCACCAAACAACTATACACAAGCTAGAATTTGGGGAGAAAAGTACTTTG

THC1dNV1

(SEQ ID NO: 110)

ATGCAATTGTCCTTGTCGGTTTTATCAACCGTTGCCACGGCCTTGTTGTCCCTAACCA

CCGCCGTCGATGCTAAGTCCCACAACATCAAGTTGTCCAAGTTGTCCAACGAAGAA

ACATTGGACGCCTCCACATTCCAAGAATACACGAGCTCCTTGGCCAACAAGTACATG

AACTTGTTCAACGCCGCTCACGGTAACCCAACCAGCTTTGGCTTGCAACACGTCTTG

TCCAACCAAGAAGCTGAAGTCCCATTCGTTACCCCACAAAAGGGTGGCAACCCACA

AGAAAACTTTTTGAAGTGTTTTTCAGAATACATTCCAAACAATCCAGCTAACCCAAA

GTTTATTTACACACAACATGATCAATTGTACATGTCAGTTTTGAACTCAACAATTCA

AAACTTGAGATTTACATCAGATACCACACCAAAGCCATTGGTTATTGTTACACCATC

AAACGTTTCCCATATTCAAGCATCAATCTTGTGTTCAAAGAAGGTTGGATTGCAAAT

TAGAACCAGATCAGGAGGACACGATGCAGAAGGAATGTCATACATTTCACAAGTTC

CATTCGTTGTTGTTGATTTGAGAAACATGCACTCAATTAAGATTGATGTTCATTCACA

AACAGCATGGGTTGAAGCAGGAGCAACATTGGGTGAAGTTTACTACTGGATTAACG

AAAAGAACGAAAACTTCAGTTTTCCAGGAGGTTACTGTCCAACAGTTGGAGTTGGA

GGACATTTTTCAGGTGGAGGATACGGAGCATTGATGAGAAACTACGGATTGGCAGC

AGATAACATTATTGATGCACACTTGGTTAACGTTGATGGAAAGGTTTTGGATAGAAA

GTCAATGGGAGAAGATTTGTTTTGGGCAATTAGAGGAGGTGGTGGAGAGAACTTTG

GAATTATTGCAGCATGGAAGATCAAGTTGGTTGCAGTTCCATCAAAGTCAACAATCT

TTTCAGTTAAGAAGAACATGGAAATTCATGGTTTGGTTAAGTTGTTTAACAAGTGGC

AAAACATTGCATACAAGTACGATAAGGATTTGGTTTTGATGACACATTTTATTACAA

AGAACATTACAGATAACCATGGAAAGAACAAGACAACAGTTCACGGATACTTTTCA

TCAATTTTTCACGGAGGAGTTGATTCATTGGTTGACTTGATGAACAAGTCATTTCCA

GAATTGGGAATCAAGAAGACAGATTGTAAGGAATTTTCATGGATTGATACAACAAT

TTTCTACTCAGGAGTTGTTAACTTTAACACAGCAAACTTTAAGAAGGAAATTTTGTT

GGACAGATCAGCAGGAAAGAAGACCGCATTTTCCATTAAGTTGGATTACGTTAAGA

AACCAATTCCAGAAACAGCAATGGTTAAGATTTTGGAAAAGTTGTACGAAGAAGAT

GTTGGTGTTGGAATGTACGTTTTGTACCCATACGGAGGAATTATGGAAGAAATCTCA

GAATCAGCAATTCCATTTCCACATAGAGCAGGTATTATGTACGAATTGTGGTACACA

GCATCATGGGAAAAGCAAGAAGATAATGAAAAGCATATTAACTGGGTTAGATCAGT

TTACAACTTTACAACACCATACGTTTCACAAAACCCAAGATTGGCATACTTGAACTA

CAGAGATTTGGATTGGGAAAGACAAACCCAGAATCACCAAACAACTATACACAAG

CTAGAATTTGGGGAGAAAAGTACTTTGGTAAGAACTTCAACAGATTGGTTAAAGTTA

AGACAAAGGCAGATCCAAATAACTTCTTTAGAAACGAACAATCAATTCCACCATTG

CCACCACATCATCATTAATAA

CvCBC1 Gene (SEQ ID NO: 111)

ATGAATTGTAGCACTTTCTCATTCTGGTTTGTTTGTAAGATTATTTTCTTTTTCTTGTC

ATTTAACATTCAAATTTCAATTGCAAACCCACAAGAGAACTTTTTGAAGTGTTTCTC

AGAATACATTCCAAACAACCCAGCTAACCCAAAGTTTATTTACACCCAACACGATCA

```
-continued
ATTGTACATGTCAGTTTTGAACTCAACAATTCAAAACTTGAGATTTACATCAGATAC

AACACCAAAGCCATTGGTTATTGTTACACCATCAAACGTTAGTCATATTCAAGCATC

AATCTTGTGTTCAAAGAAGGTTGGATTGCAAATTAGAACTAGATCAGGAGGACATG

ATGCAGAAGGATTGTCATACATTTCACAAGTTCCATTTGCAATTGTTGATTTGAGAA

ACATGCACACAGTTAAGGTTGATATTCATTCACAAACAGCATGGGTTGAAGCAGGA

GCAACATTGGGTGAAGTTTACTACTGGATTAACGAAATGAACGAAAACTTCTCATTT

CCAGGAGGATACTGTCCAACAGTTGGTGTTGGAGGACACTTTTCAGGTGGTGGATAC

GGAGCATTGATGAGAAACTACGGATTGGCAGCAGATAACATTATTGATGCACATTT

GGTTAACGTTGATGGAAAGGTTTTGGATAGAAAGTCAATGGGAGAAGATTTGTTTTG

GGCAATTAGAGGAGGTGGAGGAGAAAACTTTGGAATCATTGCAGCATGTAAGATCA

AGTTGGTTGTTGTTCCATCAAAGGCAACAATCTTTTCAGTTAAGAAGAACATGGAAA

TCCATGGATTGGTTAAGTTGTTTAACAAGTGGCAAAACATTGCATACAAGTACGATA

AGGATTTGATGTTGACAACACATTTTAGAACAAGAAACATTACAGATAACCACGGA

AAGAATAAGACAACAGTTCATGGATACTTTTCATCAATTTTCTTGGGAGGAGTTGAT

TCATTGGTTGACTTGATGAACAAGAGTTTTCCAGAATTGGGAATCAAGAAGACAGAT

TGTAAGGAATTGTCATGGATCGATACAACCATTTTCTACTCAGGAGTTGTTAACTAC

AACACAGCTAACTTTAAGAAGGAAATTTTGTTGGACAGATCAGCAGGTAAAAAGAC

AGCATTTTCAATTAAGTTGGATTACGTTAAGAAATTGATTCCAGAAACAGCAATGGT

TAAGATTTTGGAAAAGTTGTACGAAGAAGAAGTTGGAGTTGGAATGTACGTTTTGTA

CCCATACGGAGGAATTATGGATGAAATTTCAGAATCAGCAATTCCATTTCCACATAG

AGCAGGTATTATGTACGAATTGTGGTACACAGCAACATGGGAAAAGCAAGAAGATA

ACGAAAAGCATATTAACTGGGTTAGATCAGTTTACAACTTTACAACCCCATACGTTT

CACAAAACCCAAGATTGGCATACTTGAACTACAGAGATTTGGATTTGGGAAAGACA

AACCCAGAATCACCAAATAACTACACACAAGCTAGAATTTGGGGAGAAAAGTACTT

TGGTAAGAACTTTAACAGATTGGTGAAGGTTAAGACAAAGGCAGACCCAAACAATT

TCTTTAGAAACGAACAATCAATTCCACCATTGCCACCAAGACATCATTAA
```

The following plasmids were constructed using modern molecular biology techniques described herein.

TABLE 1

| Plasmid | Seq ID | Important Features |
|---|---|---|
| pLD1 | 157 | Empty URA3 multi integration |
| pLD10 | 158 | PPOX4-CvTKS1 URA3 multi integration |
| pLD12 | 159 | PPOX4-CvOAC1 URA3 multi integration |
| pLD14 | 160 | PPOX4-CvOAC1P URA3 multi integration |
| pLD16 | 161 | PPOX4-CvHXS1 URA3 multi integration |
| pLD19 | 180 | PPOX4-PTS1 URA3 multi integration |
| pLD20 | 162 | PPOX4-CvCBD1 URA3 multi integration |
| pLD22 | 163 | PPOX4-CvACO1P URA3 multi integration |
| pLD24 | 164 | PPOX4-CvTKS1P URA3 multi integration |
| pLD26 | 181 | PPOX4-PTS1dN URA3 multi integration |
| pLD56 | 165 | PPOX4-CvPTS2 URA3 multi integration |
| pLD111 | 169 | PPOX4-CvTHC1 URA3 multi integration |
| pLD112 | 170 | PPOX4-CvCBC1 URA3 multi integration |
| pLD125 | 172 | PPOX4-CvCBD1dNS1 URA3 multi integration |

TABLE 1-continued

| Plasmid | Seq ID | Important Features |
|---|---|---|
| pLD127 | 173 | PPOX4-CvCBD1dNV1 URA3 multi integration |
| pLD139 | 179 | PPOX4-CvCBD1dNP1 URA3 multi integration |

Example 2—Construction of Plasmids for *Yarrowia lipolytica*

Protein sequence was reverse translated into DNA sequence to reflect the use of a universal genetic code and codon usage in *Yarrowia lipolytica*, reduction of secondary structure, and absence of certain restriction enzyme recognition sites. Other DNA sequences that encode the same protein may also be used. The following sequences were used as open reading frames for genes used to genetically modify *Yarrowia lipolytica*.

Y1ACO1P Gene
(SEQ ID NO: 112)
ATGACCGAAGTAGTTGACAGAGCCTCATCCCCCGC

ATCCCCTGGCTCAACTACGGCCGCCGCAGACGGTG

CTAAGGTGGCCGTCGAGCCCCGAGTAGATGTGGCT

GCGCTGGGAGAGCAGCTGCTGGGCCGATGGGCTGA

TATCCGTCTCCACGCCCGGGACCTTGCGGGACGAG

AGGTAGTTCAGAAGGTGGAGGGTCTGACTCATACA

GAGCACCGCTCTCGCGTCTTTGGCCAGCTCAAGTA

CTTGGTCGATAACAACGCAGTTCACCGAGCCTTTC

CTTCTCGACTGGGTGGTAGTGACGACCACGGCGGA

AACATCGCTGGTTTTGAGGAGCTTGTCACGGCGGA

CCCCTCCCTCCAGATCAAGGCCGGCGTCCAGTGGG

GACTGTTCGGCTCCGCTGTTATGCACTTGGGAACT

AGGGAGCACCACGACAAGTGGCTCCCAGGCATCAT

GTCTCTGGAAATCCCTGGTTGCTTTGCCATGACTG

AGACTGGCCATGGCTCCGATGTCGCTTCCATTGCT

ACAACGGCCACCTATGATGAGGAAACCCAGGAGTT

CGTTATTGACACCCCGTTCCGAGCCGCCTGGAAGG

ACTACATTGGAAACGCCGCTAACGACGGTTTGGCC

GCTGTCGTGTTTGCCCAACTGATTACTCGAAAGGT

TAACCATGGAGTGCACGCCTTCTACGTCGATCTGA

GAGATCCCGCCACCGGAGACTTTCTCCCTGGTATT

GGTGGAGAGGACGACGGTATTAAGGGGGGACTAAA

CGGAATTGATAACGGACGTCTCCATTTCACCAATG

TTCGCATTCCCCGAACCAACCTGCTTAACCGTTAC

GGCGATGTTGCCGTCGATGGCACCTACAGCTCAAC

CATCGAATCTCCGGGGCGAAGATTCTTTACAATGC

TAGGTACGCTGGTCCAGGGCCGAGTCAGCCTGGAC

GGTGCTGCAGTGGCTGCATCGAAGGTTGCTCTGCA

ATCCGCCATCCACTACGCCGCTGAGCGAAGACAGT

TCAACGCCACTTCGCCCACAGAGGAGGAGGTGCTC

CTGGATTACCAGCGACACCAGCGGCGCCTCTTTAC

CCGACTCGCCACCACCTACGCCGCATCGTTCGCCC

ATGAGCAACTGCTGCAGAAATTCGACGACGTGTTC

TCGGGTGCTCATGATACTGACGCCGACCGTCAGGA

CCTTGAGACACTGGCTGCTGCTCTGAAGCCCCTTT

CTACCTGGCATGCTCTCGATACCCTACAAGAGTGC

CGAGAAGCGTGTGGGGGTGCAGGTTTTCTGATTGA

GAACCGATTCGCTTCTCTCCGGGCCGATCTCGACG

TCTACGTGACCTTCGAAGGAGACAACACCGTGCTT

CTTCAGTTGGTGGCCAAGAGGCTGCTCGCTGACTA

TGCTAAGGAGTTCCGAGGTGCCAACTTCGGCGTGC

TCGCGCGGTACGTCGTGGACCAGGCTGCCGGAGTC

GCGCTACACCGAACCGGACTGCGACAGGTCGCTCA

GTTCGTGGCCGACAGTGGATCTGTCCAGAAATCTG

CTCTTGCCCTCCGAGACGAAGAAGGTCAGCGAACT

CTGCTGACCGACAGAGTCCAGTCCATGGTTGCAGA

GGTTGGCGCTGCTCTCAAAGGCGCGGGCAAGCTCC

CCCAGCACCAGGCGGCAGCACTGTTCAATCAGCAT

CAAAACGAACTGATCGAGGCTGCCCAGGCCCACGC

TGAGCTTTTACAGTGGGAGGCCTTTACTGAGGCTT

TGGCCAAGGTGGACGACGCTGGCACTAAGGAAGTG

TTGACCCGATTGCGTGACCTTTTTGGTCTGTCCCT

TATCGAGAAGCACCTCAGCTGGTATCTGATGAACG

GTAGGCTCTCGATGCAGAGAGGCCGAACGGTCGGC

ACTTACATTAATCGTCTTCTCGTTAAGATCCGACC

ACACGCACTTGATCTGGTTGATGCCTTCGGCTACG

GAGCCGAGCACCTTCGGGCCGCTATCGCCACCGGC

GCTGAGGCCACCCGACAGGACGAGGCCCGAACCTA

CTTCAGACAGCAACGAGCCTCCGGTAGCGCCCCTG

CTGACGAGAAGACACTCCTCGCTATCAAGGCCGGC

AAGTCTCGGGACGACGAGCCAAACTGTAA

Y1HXS1 Gene
(SEQ ID NO: 113)
ATGGGAAAGAATTACAAAAGTCTAGATTCTGTCGT

TGCCAGTGACTTCATCGCGTTAGGCATTACATCCG

AGGTCGCTGAGACTCTGCACGGACGGCTTGCCGAG

ATTGTGTGCAACTACGGAGCCGCTACCCCTCAGAC

TTGGATTAACATCGCCAACCACATTCTGTCGCCGG

ACCTCCCCTTCTCTTTGCACCAGATGTTATTCTAC

GGATGCTACAAGGATTTTGGCCCTGCACCTCCTGC

CTGGATTCCGGACCCCGAAAAAGTCAAGTCCACCA

ACCTAGGTGCCCTGCTGGAAAAGCGAGGAAAGGAG

TTCCTTGGTGTCAAGTACAAGGACCCCATTTCTTC

TTTTTCTCATTTCCAGGAATTTTCGGTGCGTAATC

CTGAGGTGTATTGGCGAACTGTGCTCATGGACGAG

ATGAAAATCTCCTTCAGCAAGGACCCAGAGTGTAT

CCTGCGACGAGACGACATTAACAACCCAGGAGGCT

CGGAGTGGCTTCCCGGCCGGATACCTAAACTCAGCT

AAGAATTGTCTCAACGTGAACTCTAACAAGAAGTT

GAACGACACCATGATCGTGTGGCGTGACGAAGGCA

ACGACGACCTGCCCCTGAACAAGTTGACTCTGGAC

```
CAGCTGCGAAAGAGGGTCTGGTTGGTTGGCTACGC
CCTCGAAGAGATGGGCTTAGAGAAGGGTTGCGCTA
TTGCTATTGATATGCCCATGCACGTCGATGCTGTA
GTGATCTACCTTGCCATTGTGTTAGCCGGTTACGT
GGTCGTATCGATTGCCGATTCGTTCTCCGCTCCGG
AGATTTCCACCCGACTCAGACTTAGCAAGGCCAAG
GCAATCTTTACTCAAGATCACATCATCCGAGGTAA
GAAGAGAATCCCTCTCTATTCTCGCGTGGTTGAGG
CCAAGTCCCCAATGGCTATCGTCATACCTTGCAGC
GGATCAAACATCGGGGCTGAGCTACGGGACGGTGA
TATCTCCTGGGATTACTTCCTGGAGCGAGCCAAAG
AGTTCAAGAACTGCGAGTTTACAGCGCGTGAGCAG
CCCGTCGATGCCTACACGAACATTCTATTCTCATC
GGGCACAACGGGAGAGCCCAAGGCCATCCCCTGGA
CCCAAGCTACCCCCTTGAAAGCTGCCGCTGATGGT
TGGTCCCATCTCGACATCAGAAAAGGCGATGTGAT
CGTTTGGCCCACTAACCTGGGCTGGATGATGGGTC
CTTGGCTGGTATATGCCAGCCTACTGAACGGCGCT
TCAATCGCACTGTACAACGGATCTCCACTCGTCAG
CGGCTTTGCCAAGTTTGTTCAAGACGCCAAAGTCA
CCATGCTGGGTGTTGTTCCTTCAATCGTGCGAAGT
TGGAAGAGTACCAACTGTGTCTCTGGATACGACTG
GAGCACCATTCGATGCTTCAGTTCCTCCGGCGAGG
CTTCCAACGTTGATGAGTACCTCTGGCTTATGGGT
CGTGCGAATTACAAGCCTGTGATCGAGATGTGTGG
TGGAACAGAAATTGGTGGTGCTTTTTCGGCCGGGT
CCTTTCTTCAGGCTCAGTCTCTCCTCTTTCTCT
TCCCAGTGTATGGGATGCACCCTGTATATTCTCGA
CAAGAACGGTTACCCCATGCCGAAGAATAAACCCG
GTATTGGGGAGCTTGCTCTTGGCCCCGTCATGTTT
GGTGCATCGAAGACCCTCCTGAACGGAAACCATCA
CGACGTCTACTTCAAGGGCATGCCCACACTTAACG
GCGAAGTTCTTCGGCGACATGGAGACATTTTCGAA
CTTACATCGAACGGATACTACCACGCCCACGGGCG
AGCAGATGATACGATGAACATCGGGGGCATCAAGA
TATCTTCTATCGAGATTGAAAGAGTGTGTAACGAG
GTAGACGACCGCGTCTTCGAGACTACTGCGATCGG
CGTCCCCCCCCTGGGCGGTGGCCCGGAGCAGCTAG
TCATTTTTTTTGTGCTCAAGGACTCTAACGACACG
ACCATCGACCTCAATCAGCTGCGACTCTCCTTCAA
CCTTGGATTGCAGAAGAAGCTGAACCCTCTCTTCA
AGGTCACTCGGGTTGTTCCCTTGTCCTCTCTTCCT
CGAACCGCCACCAACAAGATTATGCGACGAGTGCT
CCGACAGCAGTTCTCCCACTTCGAGTAA
```

Y1TKS1 Gene
(SEQ ID NO: 114)
```
ATGAATCATCTAAGAGCCGAAGGACCAGCAAGTGT
ACTCGCTATTGGTACTGCTAACCCCGAGAACATTC
TTATTCAGGATGAGTTCCCGGACTACTATTTCAGG
GTTACCAAGAGCGAGCATATGACCCAGCTTAAAGA
GAAGTTCCGCAAGATATGCGACAAGTCCATGATCC
GAAAGCGGAACTGCTTTCTCAATGAGGAGCACTTG
AAGCAAAACCCCCGACTGGTTGAGCACGAGATGCA
GACCTTGGACGCGCGACAAGACATGCTCGTCGTCG
AGGTGCCCAAACTCGGTAAGGATGCTTGCGCTAAG
GCCATTAAGGAGTGGGGTCAGCCCAAGTCGAAGAT
TACCCACCTAATCTTCACCTCCGCAAGCACTACAG
ACATGCCCGGTGCAGACTACCACTGTGCCAAGCTG
CTCGGACTGTCACCGTCGGTCAAGCGAGTGATGAT
GTACCAGCTCGGCTGTTACGGGGGTGGAACCGTTC
TCCGTATCGCCAAGGATATCGCTGAGAACAACAAA
GGAGCTCGTGTCCTGGCTGTGTGTTGCGACATCAT
GGCCTGCTTGTTCAGAGGCCCTAGTGATTCCGATC
TGGAATTACTTGTCGGTCAGGCCATCTTTGGAGAT
GGCGCCGCCGCTGTCATCGTGGGTGCCGAACCCGA
CGAGTCTGTTGGAGAAAGACCCATCTTTGAGCTTG
TCTCCACGGGCCAGACCATCCTCCCTAACAGCGAG
GGCACAATTGGAGGCCATATTCGAGAGGCCGGTCT
GATTTTTGACCTGCATAAGGACGTGCCTATGCTGA
TTTCGAACAACATCGAGAAGTGTCTCATCGAGGCC
TTCACTCCCATCGGCATTTCGGACTGGAACTCAAT
CTTCTGGATCACCCACCCAGGAGGCAAGGCGATTC
TGGATAAAGTTGAGGAAAAGCTCGACCTTAAGAAG
GAGAAGTTTGTGGATTCTCGACACGTCCTGTCTGA
ACACGGTAACATGTCTTCCTCTACTGTCCTGTTCG
TAATGGACGAGCTTCGAAAGCGATCTCTGGAGGAA
GGAAAGTCCACGACCGGCGACGGTTTTGAGTGGGG
CGTGCTGTTCGGGTTCGGTCCTGGCCTCACTGTGG
AGCGAGTTGTTGTCCGGTCCGTGCCTATTAAGTAC
TAA
```

Y1TKS1P Gene (SEQ ID NO: 115)

ATGAATCATCTAAGAGCCGAAGGACCAGCAAGTGT

ACTCGCTATTGGTACTGCTAACCCCGAGAACATTC

TTATTCAGGATGAGTTCCCGGACTACTATTTCAGG

GTTACCAAGAGCGAGCATATGACCCAGCTTAAAGA

GAAGTTCCGCAAGATATGCGACAAGTCCATGATCC

GAAAGCGGAACTGCTTTCTCAATGAGGAGCACTTG

AAGCAAAACCCCCGACTGGTTGAGCACGAGATGCA

GACCTTGGACGCGCGACAAGACATGCTCGTCGTCG

AGGTGCCCAAACTCGGTAAGGATGCTTGCGCTAAG

GCCATTAAGGAGTGGGGTCAGCCCAAGTCGAAGAT

TACCCACCTAATCTTCACCTCCGCAAGCACTACAG

ACATGCCCGGTGCAGACTACCACTGTGCCAAGCTG

CTCGGACTGTCACCGTCGGTCAAGCGAGTGATGAT

GTACCAGCTCGGCTGTTACGGGGGTGGAACCGTTC

TCCGTATCGCCAAGGATATCGCTGAGAACAACAAA

GGAGCTCGTGTCCTGGCTGTGTGTTGCGACATCAT

GGCCTGCTTGTTCAGAGGCCCTAGTGATTCCGATC

TGGAATTACTTGTCGGTCAGGCCATCTTTGGAGAT

GGCGCCGCCGCTGTCATCGTGGGTGCCGAACCCGA

CGAGTCTGTTGGAGAAAGACCCATCTTTGAGCTTG

TCTCCACGGGCCAGACCATCCTCCCTAACAGCGAG

GGCACAATTGGAGGCCATATTCGAGAGGCCGGTCT

GATTTTTGACCTGCATAAGGACGTGCCTATGCTGA

TTTCGAACAACATCGAGAAGTGTCTCATCGAGGCC

TTCACTCCCATCGGCATTTCGGACTGGAACTCAAT

CTTCTGGATCACCCACCCAGGAGGCAAGGCGATTC

TGGATAAAGTTGAGGAAAAGCTCGACCTTAAGAAG

GAGAAGTTTGTGGATTCTCGACACGTCCTGTCTGA

ACACGGTAACATGTCTTCCTCTACTGTCCTGTTCG

TAATGGACGAGCTTCGAAAGCGATCTCTGGAGGAA

GGAAAGTCCACGACCGGCGACGGTTTTGAGTGGGG

CGTGCTGTTCGGGTTCGGTCCTGGCCTCACTGTGG

AGCGAGTTGTTGTCCGGTCCGTGCCTATTAAGTAC

GGAAGAAGGGCAAAGTTGTAA

Y1OAC1 Gene (SEQ ID NO: 116)

ATGGCCGTCAAACACCTTATTGTCCTCAAGTTCAA

AGATGAGATCACTGAAGCCCAGAAGGAGGAGTTTT

TCAAGACCTACGTCAATTTGGTCAACATCATTCCA

GCAATGAAGGATGTGTACTGGGGCAAGGACGTGAC

CCAGAAGAACAAGGAAGAGGGTTATACCCATATCG

TTGAGGTTACGTTCGAGTCTGTGGAGACAATCCAA

GACTACATCATTCACCCCGCTCACGTGGGCTTTGG

AGACGTTTACAGATCCTTCTGGGAGAAGCTCCTGA

TTTTTGACTACACTCCTCGAAAGCTGAAGCCCAAG

TAA

Y1OAC1P Gene (SEQ ID NO: 117)

ATGGCCGTCAAACACCTTATTGTCCTCAAGTTCAA

AGATGAGATCACTGAAGCCCAGAAGGAGGAGTTTT

TCAAGACCTACGTCAATTTGGTCAACATCATTCCA

GCAATGAAGGATGTGTACTGGGGCAAGGACGTGAC

CCAGAAGAACAAGGAAGAGGGTTATACCCATATCG

TTGAGGTTACGTTCGAGTCTGTGGAGACAATCCAA

GACTACATCATTCACCCCGCTCACGTGGGCTTTGG

AGACGTTTACAGATCCTTCTGGGAGAAGCTCCTGA

TTTTTGACTACACTCCTCGAAAGCTGAAGCCCAAG

GGAAGAAGGGCAAAGTTGTAA

Y1PTS2 Gene (SEQ ID NO: 118)

ATGGGCCTCTCTCTAGTATGTACCTTCTCTTTCCA

GACCAACTATCACACTCTACTGAACCCCCATAACA

AGAACCCTAAAAATTCTCTTCTCAGTTACCAGCAC

CCCAAGACGCCTATCATTAAGTCCTCCTACGACAA

CTTTCCCTCTAAGTACTGCCTGACCAAAAACTTCC

ATCTCCTGGGACTGAACTCTCATAACAGAATTAGT

AGCCAGTCCCGATCTATCCGAGCTGGCTCTGACCA

GATTGAGGGCTCCCCTCACCATGAATCCGACAACA

GCATCGCTACCAAGATTTTGAATTTTGGTCACACA

TGCTGGAAGCTCCAGCGACCGTACGTCGTGAAGGG

TATGATCTCGATTGCCTGTGGACTGTTCGGACGTG

AGCTTTTTAATAATCGACACTTGTTTTCATGGGGC

CTCATGTGGAAGGCTTTTTTCGCCCTCGTGCCCAT

TCTGTCTTTCAACTTCTTTGCCGCTATTATGAACC

AAATCTACGACGTTGATATTGATAGGATCAACAAG

CCTGACCTGCCGCTCGTCTCGGGGGAGATGTCTAT

CGAGACAGCGTGGATTCTTTCGATTATCGTCGCGC

TGACTGGCCTTATCGTTACCATAAAGTTGAAGTCT

GCACCCCTCTTCGTGTTTATCTACATTTTCGGTAT

TTTTGCTGGATTCGCGTACTCCGTTCCCCCTATCA

GATGGAAGCAGTACCCCTTTACTAACTTTCTGATT

ACTATCAGCAGCCACGTCGGTTTAGCCTTTACCTC

ATATTCGGCCACCACCAGTGCACTGGGCCTCCCCT

TCGTCTGGCGACCTGCATTTTCATTCATCATCGCC

TTCATGACTGTGATGGGTATGACCATCGCTTTCGC

TAAGGACATCTCCGACATCGAGGGTGATGCTAAAT

ATGGAGTGTCCACCGTGGCCACTAAGCTGGGAGCC

CGGAACATGACGTTCGTCGTCTCTGGTGTTCTGCT

CCTTAACTACTTGGTTTCGATCTCCATTGGCATTA

TCTGGCCACAAGTCTTCAAGTCCAACATTATGATT

CTGTCCCACGCCATTCTTGCCTTTTGCCTGATCTT

CCAGACACGCGAACTCGCTCTCGCTAACTACGCCT

CCGCCCCATCGCGACAGTTCTTCGAGTTCATCTGG

CTGCTTTACTACGCCGAGTACTTCGTTTACGTGTT

CATCTAA

Y1CBD1 Gene (SEQ ID NO: 119)
ATGAAGTGTTCGACGTTTTCTTTTTGGTTTGTTTG

TAAAATCATTTTCTTTTTCTTTTCTTTCAACATCC

AAACGTCGATCGCAAACCCTAGAGAGAACTTTCTT

AAGTGCTTCTCGCAGTACATCCCTAATAACGCTAC

CAACCTTAAGCTGGTGTACACCCAGAACAACCCTC

TTTACATGTCTGTTCTAAACAGCACCATCCACAAT

CTTAGATTCACATCAGACACCACTCCCAAGCCGCT

CGTCATCGTGACCCCGAGTCATGTGTCCCATATCC

AAGGCACTATCCTGTGCTCTAAAAAGGTCGGTCTG

CAGATTCGGACTCGCTCCGGTGGACATGATTCGGA

GGGCATGTCCTACATTAGCCAGGTCCCCTTTGTGA

TCGTGGACCTGAGGAACATGCGGTCTATTAAGATT

GATGTGCACTCACAGACCGCTTGGGTCGAGGCTGG

TGCGACATTGGGTGAGGTGTACTACTGGGTGAACG

AGAAGAACGAGAACCTGAGCCTCGCCGCTGGCTAC

TGTCCCACCGTTTGTGCCGGTGGACACTTCGGCGG

AGGCGGATACGGTCCACTTATGCGAAACTACGGGC

TCGCAGCTGATAATATCATCGACGCACACCTTGTT

AACGTTCACGGCAAGGTGCTGGACCGAAAAAGCAT

GGGTGAGGACCTATTTTGGGCCTTGCGAGGCGGTG

GTGCCGAATCCTTCGGAATTATCGTGGCCTGGAAG

ATCCGACTGGTCGCTGTGCCAAAGTCCACTATGTT

CTCCGTCAAGAAAATTATGGAGATCCACGAACTCG

TAAAGCTCGTCAATAAGTGGCAGAACATCGCCTAC

AAGTATGACAAGGATCTGCTGCTCATGACTCACTT

CATCACGCGAAACATTACAGACAACCAGGGAAAGA

ACAAGACCGCTATCCATACCTACTTCTCCTCTGTC

TTCCTTGGGGGTGTCGATTCCCTCGTTGATCTCAT

GAACAAATCTTTTCCAGAGCTCGGAATCAAGAAGA

CCGACTGCCGACAGCTCTCTTGGATCGACACCATT

ATTTTCTACTCAGGAGTCGTAAACTACGATACTGA

CAACTTTAACAAGGAGATTCTGTTAGATCGATCGG

CCGGCCAGAACGGTGCCTTCAAGATCAAGCTCGAC

TATGTCAAAAAGCCCATTCCTGAATCCGTCTTCGT

TCAAATTCTTGAAAAGTTGTACGAGGAGGATATCG

GCGCCGGAATGTACGCGCTGTACCCCTACGGTGGC

ATTATGGACGAGATTCTGAAAGTGCTATTCCCTT

CCCCCACCGTGCTGGCATTCTGTATGAGCTGTGGT

ACATTTGCTCCTGGGAAAAGCAGGAGGACAACGAG

AAGCACTTGAACTGGATACGAAACATTTACAATTT

CATGACCCCTATGTTTCGAAGAACCCTCGACTGG

CCTACCTGAATTACCGCGACCTCGACATCGGAATT

AACGACCCTAAGAACCCCAATAACTATACTCAGGC

CAGAATCTGGGGCGAGAAGTACTTCGGCAAGAACT

TTGACCGTCTGGTTAAGGTCAAGACCCTCGTGGAC

CCTAACAACTTCTTCCGAAACGAGCAGTCTATCCC

CCCTCTGCCCCGACACCGGCATTAA

Y1THC1 Gene (SEQ ID NO: 120)
ATGAATTGTTCAGCTTTCTCTTTTTGGTTTGTCTG

TAAGATCATTTTCTTCTTTCTATCCTTTCACATCC

AAATTTCCATAGCCAACCCTCGTGAGAACTTCCTT

AAGTGCTTTTCCAAGCACATTCCAAATAACGTCGC

CAATCCCAAGCTGGTGTACACGCAGCATGACCAGC

TCTACATGTCGATCCTCAATTCCACCATTCAAAAC

CTTAGATTCATTAGTGACACCACTCCCAAGCCCCT

AGTCATTGTCACCCCTTCGAACAACTCGCATATTC

AGGCAACTATTCTCTGCTCCAAGAAGGTTGGTTTA

CAGATCCGAACCCGGTCAGGTGGTCACGACGCTGA

GGGCATGTCTTACATTTCCAGGTCCCCTTTGTGG

TGGTCGATCTGCGCAACATGCACTCCATTAAAATC

GACGTCCACTCGCAGACTGCCTGGGTCGAGGCTGG

AGCCACCCTTGGCGAGGTCTACTACTGGATTAACG

AGAAGAACGAAAACCTGTCGTTCCCTGGCGGCTAC

TGTCCGACTGTTGGAGTCGGCGGACACTTTCTGG

TGGCGGATATGGTGCTCTCATGCGAAACTACGGAC

TGGCGGCAGACAACATCATCGATGCCCACCTTGTG

AACGTTGACGGTAAGGTACTGGACCGAAAGTCTAT

GGGCGAGGACTTGTTTTGGGCCATCCGAGGTGGAG

-continued

```
GTGGTGAGAACTTCGGGATCATCGCCGCCTGGAAG

ATCAAGCTGGTGGATGTGCCCAGTAAGTCTACCAT

TTTTAGCGTGAAGAAGAACATGGAGATCCACGGGC

TGGTGAAGCTGTTCAACAAGTGGCAGAATATTGCG

TACAAATACGACAAGGACCTGGTGCTTATGACCCA

TTTCATCACCAAGAACATCACGGATAACCACGGTA

AAAACAAGACTACTGTTCACGGTTACTTCTCTTCA

ATTTTCCATGGTGGTGTGGATTCCCTCGTTGATTT

GATGAACAAGTCCTTCCCAGAGCTGGGCATTAAGA

AGACAGACTGCAAGGAATTTAGCTGGATTGATACC

ACCATCTTCTACTCTGGAGTTGTCAACTTCAACAC

CGCAAACTTCAAGAAGGAAATCCTCTTGGACCGAT

CTGCCGGCAAGAAGACAGCTTTTTCGATTAAACTG

GATTACGTGAAGAAGCCCATCCCTGAGACAGCTAT

GGTCAAGATCCTTGAAAAACTTTATGAGGAGGACG

TCGGAGCCGGAATGTACGTTCTCTATCCTTACGGC

GGCATCATGGAGGAAATTTCTGAGTCTGCTATCCC

CTTCCCCCATCGAGCCGGAATCATGTACGAGCTGT

GGTACACCGCTAGTTGGGAGAAGCAGGAGGATAAC

GAGAAACATATCAATTGGGTCCGTAGCGTATACAA

TTTCACGACACCCTACGTGTCCCAGAACCCTCGAC

TCGCTTACCTGAACTATAGGGACCTGGACCTCGGC

AAGACTAACCACGCTAGCCCGAACAACTACACCCA

GGCCAGAATTTGGGGCGAAAAGTACTTCGGAAAGA

ACTTCAACCGACTCGTTAAGGTTAAGACCAAAGTT

GACCCCAACAACTTTTTCCGGAACGAGCAGTCCAT

CCCTCCACTCCCTCCCCACCATCACTGA
```

The following plasmids were constructed using modern molecular biology techniques described herein.

TABLE 2

| Plasmid | Seq ID | Important Features |
|---|---|---|
| pLD87 | 166 | KU70 Disruption cassette with LoxP-URA3-LoxP |
| pLD101 | 167 | POX5 Disruption cassette with LoxP-URA3-LoxP |
| pLD102 | 168 | POX3 Disruption cassette with LoxP-URA3-LoxP |
| pLD131 | 174 | CEN-ARS LEU2 PPOX2-PTS2 |
| pLD132 | 175 | CEN-ARS URA3 PPOX-CBD1 |
| pLD135 | 176 | POX3 Disruption cassette URA3 ACO1P |
| pLD137 | 177 | CEN-ARS LEU |
| pLD138 | 178 | CEN-ARS URA |

Example 3—Transformation of *Candida viswanathii*

A starting *Candida viswanathii* strain, such as the uracil auxotroph produced in Example 2, is propagated in a 5 mL YPD culture that is incubated overnight at 30° C., 250 rpm. The next day, a 50 mL culture is initiated with part of the 5 mL YPD overnight culture and grown for a few hours to an OD (600 nm) absorbance of 1.0-2.0. The resulting cells are pelleted by centrifugation at 1000×g for 10 minutes. The cells are washed by resuspension in sterile water, centrifuged (10000×g, 1 min) and resuspended in 1 mL sterile TE/LiOAC solution, pH 7.5. The cells were centrifuged (10000×g, 1 min) again and resuspended in 500 ul of TE/LiOAC solution and incubated with shaking at 30° C. for 30 minutes.

For each transformation reaction, 50 uL aliquots of cell suspension are to be used. To 50 ul of cells, add 5 uL of carrier DNA (boiled and cooled salmon sperm DNA, 10 mg/mL) and incubate for 1-2 minutes at room temperature. The DNA that is to be used to transform the yeast is optimally inserted into the yeast genome as linearized DNA. Therefore, 2-5 ug of linearized DNA for integration is added to the mixture of cells and salmon sperm DNA. To this mixture, 300 uL of sterile PEG solution (40% PEG 3500, 1×TE, 1×LiOAC) is added and the final mixture is incubated at 30° C. for 30-60 minutes while being gently agitated. The cells are then pelleted by centrifugation at 1000×g 30 seconds, resuspended in 500 uL of YPD media and incubated at 30° C., 250 rpm for 1-2 hours.

After recovery in YPD the cells are then pelleted by centrifugation and washed twice with 1 mL of 1×TE before plating cells on the appropriate auxotrophic or selective media to identify transformants.

Example 4—Transformation of *Yarrowia lipolytica*

A starting *Yarrowia lipolytica* strain is propagated in 2 mL YPD culture that is incubated overnight (~20 hrs) at 30° C., 250 rpm. the resulting cells are pelleted by centrifugation at 6000×g. The cells are washed by resuspension in 250 ul of 0.3 M Li Acetate 10 mM Tris-HCl pH 8.0. The cells are then pelleted and resuspended in 100 ul of 0.3 M Li Acetate 10 mM Tris-HCl pH 8.0. To the cells 5 ul of salmon sperm DNA solution (8 mg/ml ssDNA 10 mM Tris-HCL pH 8.0 1 mM EDTA) is added, 1 to 10 ul of DNA (up to 1 ug) and 15 ul of triacetic solution (95 ul of triacetin+5 ul beta-mercaptoethanol). Cells are mix by pipetting and incubated 30 min at room temperature.

150 ul of PEG solution is added (40% PEG 3500, 1×TE, 1×LiOAC) and mix via pipetting. Incubate at 30 min at 30 min at room temperature. Heat shock at 37 C for 15 to 25 minutes in water batch. Add 1 ml water, mix well and then pellet at 6000×g. Decant, resuspend in 100 ul of TE (10 mM Tris-HCl pH 8.0+1 mM EDTA and plate in desired media.

Example 5—Production of an Uracil Auxotroph of ATCC 20962

ATCC 20962 is a prototrophic yeast strain that is able to grow in the absence of supplemented uracil. In order to utilize this strain for experiments, it must first be made auxotrophic for uracil. In the case of ATCC 20962, the URA3 gene must be inactivated to make the strain auxotrophic. This will allow for uracil auxotrophy to be rescued by the introduction of a functional URA3 gene via transformation, as described in Example 3.

To convert ATCC 20962 to a uracil auxotroph, an individual colony of the strain was grown in 5 mL of YPD overnight at 30 C, shaken at 250 rpm. From the overnight culture, 20 and 100 ul of culture were plated on plates containing 5-FOA (recipe). The chemical 5-FOA is converted into a toxic compound, fluorodeoxyuridine, by the enzyme encoded by the URA3 gene. Therefore, growth on 5-FOA selects for uracil auxotrophs that have spontaneously produced loss-of-function ura3 mutants. The plate was placed at 30 C for 3-6 days to produce colonies. The resulting colonies were tested for growth on media lacking uracil, e.g. synthetic complete yeast media lacking uracil and 5-FOA plates. One of these colonies did not grew on media lacking uracil but grew on 5-FOA plates, it was confirmed as uracil auxotrophs and named LCV32.

Example 6—Genomic DNA Extraction for PCR Analysis

An overnight culture in YPD or selective media was grown at 30 C 225 rpm. Cells were pelleted in an screw-cap 1.5 ml microcentrifuge tube. Supernatant was decanted and cells resuspended in 250 ul of extraction buffer (100 mM NaCl, 2% Triton X-100, 1% SDS, 10 mM Tris-Cl, 1 mM EDTA pH 8.0). 200 ul of acid washed glass-beads (425-600), and 300 ul of phenol:chorofom:isoamyl alcohol solution (25:24:1 ratio) that has been equilibrated with 100 mM Tris Cl pH 8.0 is added and vortexed for 5 min. The microcentrifuge is then centrifuge and the supernatant is removed. The supernatant then is extracted with 300 ul of chloroform. The aqueous solution is then transferred to a new microcentrifuge tube. 1.2 ml of ice-cold ethanol is added to the microcentrifuge tube. The tube is then mixed and placed at −20 C or colder for 1 hr. The DNA is then pelleted by centrifugation at 10,000×G. The pellets are then air-dried and resuspended in 500 ul of TE (10 mM Tris-HCl 1 mM EDTA pH 8.0).

Example 7—Verification of Integrations in *Candida viswanathii*

To verify the integration of exogenous genes into the genome of *Candida viswanathii* a PCR based method was developed where one or two of different exogenous genes were amplified in the same reaction as a section of the actin gene that serves as a control.

TABLE 3

| Gene | Forward Primer | Reverse Primer | Length |
|---|---|---|---|
| CvACT1 | 4 | 5 | 859 |
| CvHXS1 | 6 | 7 | 612 |
| CvTKS1 | 8 | 9 | 617 |
| CvOAC1 | 10 | 11 | 461 |
| CvPTS1 | 12 | 13 | 611 |
| CvCBD1 | 14 | 15 | 411 |
| CvACO1 | 16 | 17 | 414 |
| CvPTS2 | 41 | 42 | 616 |
| CvTHC1 | 168 | 169 | 397 |

For a 25 ul reaction, 12.5 ul of the 2× Master Mix, 0.5 ul of primers (10 μM of each), 1 ul of DNA template, and 11 ul of water. Standard running reactions are 95 C for 2 min, 30 cycles of 95 C for 30 sec, 55 C for 30 sec, and 72 C for 1 min, and a final step of 72 C for 2 min. 10 ul to 20 ul is loaded in a 1.4 to 2.0% agarose TAE gel.

TABLE 4

| Primer number | Sequence |
|---|---|
| 4 | CCCAATTCCTGTGGTGGGTTGATTCG (SEQ ID NO: 121) |
| 5 | CTCTCAATTCGTTGTAGAAGGTGTGGTGC (SEQ ID NO: 122) |
| 6 | CTTTGGACTCAGTTGTGGCTAGTGACTTC (SEQ ID NO: 123) |
| 7 | GATCAAGAGTCAATTTATTCAATGGGAGATCGTC (SEQ ID NO: 124) |
| 8 | GAGCAGAAGGACCCGCATCAGTG (SEQ ID NO: 125) |
| 9 | GTCACCAAAAATTGCCTGTCCGACAAGC (SEQ ID NO: 126) |
| 10 | CACGACATAATGGCAGTCAAACACCTAATAG (SEQ ID NO: 127) |
| 11 | CTAGTTTTGTGTTCGGAGTATGCATACAACG (SEQ ID NO: 128) |
| 12 | CTACCACACCCTCCTAAACCCTCAC (SEQ ID NO: 129) |
| 13 | CGAAGCAGTACCCGAATATATATAATGGACC (SEQ ID NO: 130) |
| 14 | CCTTCAACATTCAGACATCAATCGCCAAC (SEQ ID NO: 131) |
| 15 | CACCCAAGGTTGCCCCTGCTTC (SEQ ID NO: 132) |
| 16 | GAGCAAGTTCCCCAGCAAGTCCAG (SEQ ID NO: 133) |
| 17 | CATGATGTTCACGGGTTCCCAAGTGC (SEQ ID NO: 134) |
| 41 | CATACATGCTGGAAGCTACAGCGAC (SEQ ID NO: 135) |
| 42 | CAGTACTCACCCCATATTTTGCATCGC (SEQ ID NO: 136) |
| 168 | GTTAAGTTGTTTAACAAGTGGCAAAACATTGCATAC (SEQ ID NO: 137) |
| 169 | CCAAAATCTTAACCATTGCTGTTTCTGGAATTGG (SEQ ID NO: 138) |
| 170 | GATTTGTTTTGGGCAATTAGAGGAGGTGG (SEQ ID NO: 139) |
| 171 | CAACTCCTGAGTAGAAAATGGTTGTATCGATC (SEQ ID NO: 140) |

Example 8—Construction of Yeast Strains in *Candida viswanathii*

The following strains were constructed by transformation as described in the previous example with a PacI digested plasmid as shown in Table 5. Ura+ strains were tested for successful integration of the gene or genes of interest by using the PCR-based method described above. A correct strain was named according to the Table 5.

TABLE 5

| Strain | Parental Strain | Plasmid Transformed |
|---|---|---|
| LCV13 | ATCC20913 | pLD1 |
| LCV14 | ATCC20913 | pLD1 |
| LCV22 | ATCC20913 | pLD10, pLD12, pLD16 |
| LCV34 and LCV35 | LCV32 | pLD22 |
| LCV36 | LCV32 | pLD14, pLD22, pLD24 |
| LCV38 | LCV32 | pLD10, pLD12, pLD116, pLD22 |
| LCV40 | LCV32 | pLD1 |
| LCV49 | LCV32 | pLD14, pLD22, pLD24, pLD26 |
| LCV50 | ATCC20913 | pLD56, pLD111 |
| LCV51 | ATCC20913 | pLD19 |
| LCV55 | ATCC20913 | pLD56 |
| LCV59 | ATCC20913 | pLD20, pLD56 |
| LCV61 | ATCC20913 | pLD56, pLD111 |
| LCV63 | ATCC20913 | pLD56, pLD126 |
| LCV67 | ATCC20913 | pLD56, pLD140 |
| LCV70 | ATCC20913 | pLD56, pLD139 |

Example 9—Construction of Yeast Strains in *Yarrowia lipolytica*

MYA-2613 (ATCC) was transformed with PacI digested pLD87 and Ura+ transformants selected by growth in ScD-ura plates. Genomic DNA from the ura+ strains was purified as described above. To identify the disruption of the KU70 gene a four oligo PCR method was designed. Two primers (61+87) amplifies a 796 bp piece of the actin gene, and primers 63 and 64 amplifies a 558 bp piece that is replaced by the URA3 gene if the KU70 gene is disrupted.

Using genomic DNA as the template for the method described allowed to identify if the strain still had the KU70 gene (presence of both PCR fragments) or if the strain had a disrupted KU70 (presence of only the actin PCR fragment). One strain was identified with the correct PCR profile and named YYL2.

YYL2 was transformed with pLD113 and Leu+ transformants selected by growth in ScD-leu plates. Leu+ transformant was then streaked in ScD+ FOA plates. FOA resistant strains were isolated and its genomic DNA purified. To identify loss of the URA3 a four oligo PCR method was designed. Two primers (61+87) amplifies a 796 bp piece of the actin gene, and primers 115 and 116 amplifies a 594 bp piece ku70-URA3 piece that is lost if the URA3 piece is removed from the KU70 loci.

Using genomic DNA as the template for the method described allowed to identify if the strain still had the URA3 at the KU70 loci (presence of both PCR fragments) or if the strain had lost the URA3 at the KU70 loci (presence of only the actin PCR fragment). One strain was identified with the correct PCR profile and named YYL4.

TABLE 6

| Strain | Parental Strain | Plasmid Transform |
|---|---|---|
| YYL2 | MYA-2613 | PacI (pLD87) |
| YYL2L | YYL2 | pLD113 |
| YYL4 | YYL2L | |
| YYL6 | YYL4 | pLD101 |
| YYL27 | YYL25 | pLD102 |
| YYL29 | YYL25 | pLD135 |

TABLE 7

| Strain | Background | Plasmid |
|---|---|---|
| YYL7 | MYA-2613 | pLD131 |
| YYL9 | MYA-2613 | pLD132 |
| YYL11 | MYA-2613 | pLD137 |
| YYL13 | MYA-2613 | pLD138 |
| YYL17 | MYA-2613 | pLD131, pLD132 |
| YYL19 | MYA-2613 | pLD131, pLD138 |
| YYL21 | MYA-2613 | pLD137, pLD138 |

TABLE 8

| Primer number | Sequence |
|---|---|
| 61 | TTGTTACCAACTGGGATGACATGGAGAAG (SEQ ID NO: 141) |
| 63 | CTGATGGACGTGTTTTTCGACATGAACC (SEQ ID NO: 142) |
| 64 | GAAAGGAACATAGTCATTTCCAAACTTGAAAGTC (SEQ ID NO: 143) |
| 87 | CAGACGGAGTACTTTCGCTCGAGG (SEQ ID NO: 144) |
| 115 | CCCAAATTTAGCTGCATCATTCATCAACC (SEQ ID NO: 145) |
| 116 | CCGTGCTTAAGAGCAAGTTCCTTGAGG (SEQ ID NO: 146) |
| 177 | CTACGACATGCCCAAGGAGCAGC (SEQ ID NO: 147) |
| 178 | GGATTCGCACATTGGTGAACTGGATC (SEQ ID NO: 148) |
| 179 | CCAAGCGACGACAAGCTGTTGAGC (SEQ ID NO: 149) |
| 180 | CGTGTGGGTAGCAGAGTGGGC (SEQ ID NO: 150) |
| 181 | CTTTGCCATGACTGAGACTGGCCATG (SEQ ID NO: 151) |
| 182 | GAGGCGCCGCTGGTGTCG (SEQ ID NO: 152) |
| 183 | TCCGAAAGCGGAACTGCTTTCTCAATG (SEQ ID NO: 153) |
| 184 | CAGACCGGCCTCTCGAATATGGC (SEQ ID NO: 154) |
| 185 | CTAGACTACACGGGCAACCTTAACCC (SEQ ID NO: 155) |
| 186 | CTTGGGCTTCAGCTTTCGAGGAGTG (SEQ ID NO: 156) |

YYL4 was transformed with PacI digested pLD101 and Ura+ transformants selected by growth in ScD-ura plates. Genomic DNA from the ura+ strains was purified as described above. To identify the disruption of the PDX5 gene a four oligo PCR method was designed. Two primers (61+87) amplifies a 796 bp piece of the actin gene, and primers 179 and 180 amplifies a 395 bp PDX5 segment that is replaced by the URA3 gene.

Using genomic DNA as the template for the method described allowed to identify if the strain still had the PO5 gene (presence of both PCR fragments) or if the strain had been disrupted for PDX5 (presence of only the actin PCR fragment). One strain was identified with the correct PCR profile and named YYL6.

YYL6 is transformed with pLD113 and Leu+ transformants are selected by growth in ScD-leu plates. Leu+ transformant was then streaked in ScD+ FOA plates. FOA resistant strains will be isolated and its genomic DNA purified. To identify loss of the URA3 a four oligo PCR method was designed. Two primers (61+87) amplifies a 796 bp piece of the actin gene, and primers 116 and 237 amplifies a 598 bp piece PDX5-URA3 piece that is lost if the URA3 piece is removed from the URA loci. A strain with the correct PCR products was named YYL0025.

YYL25 is transformed with Pac1 digested pLD102 or pLD135, and Ura+ transformants selected by growth in ScD-ura plates. Genomic DNA from the ura+ strains is purified as described above. To identify the disruption of the PDX4 gene a four oligo PCR method was designed. Two primers (61+87) amplifies a 796 bp piece of the actin gene, and primers 177 and 178 amplifies a 596 bp PDX3 segment that is replaced by the URA3 gene. One strain transformed with either pLD102 or pLD135 is identified with the correct PCR profile and named YYL27 and YYL29, respectively.

Strain with plasmids were either transformed once (if containing one plasmid) or sequentially (if containing more than one plasmid).

Example 10—Quantification of Olivetolic Acid and Cannabinoids

To a 100 to 500 mg wet yeast pellet 50 ul of HCl was added and vortexed for 30 seconds. 400 ul of dichloromethane:ethyl ether (1:2) was added and vortexed for 1 min and centrifuged for 2 min at 10 k rpm. The top layer was removed, and the pellet was reextracted. The top layers were combined and dried under vacuum. The powder was reconstituted in 200 ul of acetonitrile and sonicated for 1 min. The solution was centrifuge for 2 min at 10 k rpm. Solution was then used for LC MS MS analysis.

For 0.5 ml of supernatant, 0.5 ml 1 M HCl was added and vortexed for 30 s. 500 ul of dichloromethane was added, vortexed for 30 sec and centrifuged for 2 min at 10 k rpm. The bottom layer was removed and the aqueous layer re-extracted. Both organic layer samples were combined and dry under vacuum. The powder was reconstituted in 200 ul of acetonitrile and sonicated for 1 min. The solution was centrifuge for 2 min at 10 k rpm. Solution was then used for LC MS MS analysis.

Example 11—Quantification of Hexanoic Acid and Fatty Acids

To 1 ml of supernatant, 0.8 ml of 6N HCl was added. 400 ul of dichloromethane:ethyl ether (1:2) was added, vortexed for 2 min and centrifuge for 2 min. The top layer was removed the extraction was repeated. The top layers were combined and dried under vacuum. The powder was reconstituted in 167 ul acetonitrile and 33 ul of acetonitrile with 20 mg/ml isopropyl alcohol and sonicated for 1 min. The solution was centrifuged for 2 m in at 10 k rpm. Solution was then used for GC FID analysis.

Example 12—Yeast Media

ScD-ura
1 L of liquid media was made by making a 100 ml solution of 20% dextrose and a 900 ml solution with 1.7 g of Yeast Nitrogen Base without ammonium sulfate and amino acids, 5 g of ammonium sulfate, and 2 g of dropout amino acid mix without uracil (Sunrise Science Products). Both solutions were combined, and filter sterilized or were autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without uracil, and a 450 ml solution with 20 g of agar. The solutions were autoclaved separately and combined.

ScD-leu
1 L of liquid media was made by making a 100 ml solution of 20% dextrose and a 900 ml solution with 1.7 g of Yeast Nitrogen Base without ammonium sulfate and amino acids, 5 g of ammonium sulfate, and 2 g of dropout amino acid mix without leucine (Sunrise Science Products). Both solutions were combined, and filter sterilized or were autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without leucine and a 450 ml solution with 20 g of agar. Both solutions were combined, and filter sterilized or autoclaved separately and combined.

ScD-ura-leu
1 L of liquid media was made by making a 100 ml solution of 20% dextrose and a 900 ml solution with 1.7 1.7 g of Yeast Nitrogen Base without ammonium sulfate and amino acids, 5 g of ammonium sulfate, and 2 g of dropout amino acid mix without leucine and uracil (Sunrise Science Products). Both solutions were combined, and filter sterilized or autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without leucine and uracil, and a 450 ml solution with 20 g of agar were made. The solutions were autoclaved separately and combined.

ScG-ura, ScG-leu, ScG-ura-leu was made the same as ScD-ura, ScD-leu or ScD-ura-leu respectively except the dextrose was replaced with glycerol at a 40 g/L concentration. ScGP-ura, ScGP-leu, ScGP-ura-leu was the same is the same as ScG-ura, ScG-leu or ScG-ura-leu, except, monopotassium and dipotassium phosphate was added to a final concentration of 1 g/L.

YPD
1 L of liquid media was made by making a 100 ml solution of 20% dextrose and a 900 ml solution with 10 g yeast extract and 20 g of peptone. Both solutions were combined, and filter sterilized or autoclaved separately and combined.

1 L worth of plates (~40 plates) was made by making a 100 ml solution of 20% dextrose, a 450 ml solution with 10 g yeast extract and 20 g of peptone, and a 450 ml solution with 20 g of agar. The solutions were autoclaved separately and combine afterwards.

SD+ FOA
1 L worth of plates (~40 plates) was made by making a 100 ml solution of 20% dextrose, a 450 ml solution with 1.7 g of yeast nitrogen base without ammonium sulfate and amino acids, 5 g of ammonium sulfate, and 2 g of amino acid mix without uracil, 0.5 g 5-FOA, 250 mg uracil, and a 450 ml solution with 20 g of agar. The solutions were autoclaved separately and combined.

SmP

1 L of liquid media was made by dissolving 1.7 g of yeast nitrogen base without ammonium sulfate and amino acids, 5 g of ammonium sulfate, 1 g potassium phosphate, monobasic and 1 g potassium phosphate, bibasic. The solution was then filter sterilized.

YNEP Media

1 L of YNEP was made by dissolving 3 g yeast extract, 1.7 g of yeast nitrogen base without ammonium sulfate and amino acids, 5 g of ammonium sulfate, 1 g potassium phosphate, monobasic and 1 g/l of dextrose or glycerol per liter. The solution was then filter sterilized.

MLM Media

1 L of MLM media was made by dissolving 3 g yeast extract, 1.7 g of yeast nitrogen base without ammonium sulfate and amino acids, 1 g potassium phosphate, monobasic and 1 g/l of dextrose or glycerol. Filter sterilized ScP-ura, ScP-leu, ScP-ura-leu was the same as Sc-ura, Sc-leu, Sc-ura-leu, respectively except monopotassium and dipotassium phosphate was added to a final concentration of 1 g/L.

For *Yarrowia* media a supplement of thiamine, biotin and Myo-inositol can be added to the media to a final concentration of 300 µg/L, 8 µg/L and 4 µg/L.

Example 13—Shake Flask Fermentation *Candida*

A shake flask fermentation is a small-scale culture to test for production of a cannabinoid or cannabinoid precursor. A yeast strain to be tested is grown on ScD-ura, or YPD for 2-3 days. Individual colonies from those plates are propagated overnight in 5 mL of YPD or ScD-ura (30 C, shaking at 250 rpm). The resulting culture is propagated overnight in 50 mL of YPD or 25 ml of YNEP media (30 C, shaking at 250 rpm). The biomass from the 50 mL culture is spun down and washed with water, then resuspended in 15 mL of 1×SMP or MLM media with 300 ul of oleic acid (technical grade, 90%). Yeast cells, media and oleic acid are placed into a 250 mL culture flask (it may be a baffled flask for increased aeration of the culture) and incubated at 30 C while shaking (250 rpm) for a 48-72 hours. The contents of the shake flask are spun down to produce a cell pellet and a supernatant, which is the culture media. The cell pellet and/or supernatant are analyzed for their contents by the appropriate method(s) as needed for the analyte(s) of interest.

Example 14—Shake Flask Fermentation *Yarrowia*

A shake flask fermentation is a small-scale culture to test for production of a cannabinoid or cannabinoid precursor. A yeast strain to be tested is grown on ScD-ura, ScD-leu, ScD-ura-leu or YPD for 2-3 days. Individual colonies from those plates are propagated overnight in 5 mL of YPD, ScD-ura, ScD-leu, or ScD-ura-leu (30 C, shaking at 250 rpm). The resulting culture is propagated overnight in 25 mL ScGP, ScGP-ura, ScGP-leu, or ScGP-ura-leu (30 C, shaking at 250 rpm). The biomass from the 25 mL culture is spun down and washed with water, then resuspended in 20 mL of ScP, ScP-ura, ScP-leu or ScP-ura-leu media with 800 ul of oleic acid (technical grade, 90%). Yeast cells, media and oleic acid are placed into a 250 mL culture flask (it may be a baffled flask for increased aeration of the culture) and incubated at 30 C while shaking (250 rpm) for a 24-72 hours. The contents of the shake flask are spun down to produce a cell pellet and a supernatant, which is the culture media. The cell pellet and/or supernatant are analyzed for their contents by the appropriate method(s) as needed for the analyte(s) of interest.

Example 15—Production of Olivetolic Acid from Hexanoic Acid or Hexanoate-Esters in *Candida*

Strain LCV22 (HXS1 TKS1 OAC) was grown overnight in 25 ml of YPD in a 250 ml flask at 225 rpm and 30 C. 3 ml of the overnight culture was used to inoculate 50 ml of YPD and grown overnight in a 250 ml flask at 225 rpm and 30 C. A total of seven flasks were started. The biomass from the 50 mL culture was spun down and washed with water, then resuspended in 15 mL of 1×SMP media with 300 ul of oleic acid (technical grade, 90%). Yeast cells, media and oleic acid are placed into a baffled 250 mL culture flask. Different amounts of hexanoic acid, ethyl hexanoate, and geranyl hexanoate were added to different flask as described in Table 9. and incubated at room temperature while shaking (250 rpm) for 72 hours. The contents of the shake flask were spun down to produce a cell pellet and a supernatant, which is the culture media. The cell pellets were analyzed for olivetolic acid using an LC-MS MS method.

As shown in Table 9, there was an increase in olivetolic production using hexanoate ester as opposed to hexanoic acid. This is consistent with hexanoic acid being more toxic per mole than geranyl hexanoate and ethyl hexanoate.

TABLE 9

| Flask | Addition | Amount (ul) | Olivetolic acid (Area per mg) |
|---|---|---|---|
| 1 | — | — | 5 |
| 2 | Hexanoic acid | 15 | 13 |
| 3 | Ethyl hexanoate | 20 | 56 |
| 4 | Geranyl hexanoate | 34 | 179 |
| 5 | Hexanoic acid | 30 | 101 |
| 6 | Ethyl hexanoate | 40 | 62 |
| 7 | Geranyl hexanoate | 68 | 344 |

Example 16—Production of Hexanoic Acid from Oleic Acid in *Candida*

Strain LCV14 (wildtype) and LCV35 (Δpox+ACO1P) were grown in 3 ml of YPD. These overnight cultures were used to inoculate 50 ml of YPD and grown overnight in a 250 ml flask at 225 rpm and 30 C. The biomass from the 50 mL culture was spun down and washed with water, then resuspended in 15 mL of 1×SMP media with 300 ul of oleic acid (technical grade, 90%). Yeast cells, media and oleic acid were placed into a 250 mL culture flask and incubated at 30 C while shaking (250 rpm) for 48 hours. The contents of the shake flask were spun down to produce a cell pellet and a supernatant, which is the culture media. The cell pellets were analyzed for hexanoic using an LC-MS MS method. As shown in Table 10, LCV35 produced more hexanoic acid than LCV35, which is consistent with the presence of an active pathway making hexanoic acid from oleic acid.

TABLE 10

| Strain | Hexanoic Acid (mg/L) |
|---|---|
| LCV14 | 9.7 |
| LCV35 | 61.2 |

Example 17—Production of Hexanoic Acid from Soybean Oil in *Candida*

Strain LCV14 (wildtype) and LCV34 (Δpox+ACO1P) were grown in 3 ml of YPD. These overnight cultures were used to inoculate 50 ml of YPD and grown overnight in a 250 ml flask at 225 rpm and 30 C. The biomass from the 50 mL culture was spun down and washed with water, then resuspended in 15 mL of 1×SMP media with 300 ul of soybean oil. Yeast cells, media and soybean oil were placed into a 250 mL culture flask and incubated at 30 C while shaking (250 rpm) for 48 hours. The contents of the shake flask were spun down to produce a cell pellet and a supernatant, which is the culture media. The cell pellets were analyzed for hexanoic acid using an LC-MS MS method. As shown in Table 11, LCV34 produced more hexanoic acid than LCV14 when using soybean and palm oil, consistent with the presence of an active pathway making hexanoic acid from soybean oil and palm oil.

Example 18—Production of Hexanoic Acid from Alkane in *Candida*

Strain LCV14 (wildtype) and LCV34 (Δpox+ACO1P) were grown in 3 ml of YPD. These overnight cultures were used to inoculate 50 ml of YPD and grown overnight in a 250 ml flask at 225 rpm and 30 C. The biomass from the 50 mL culture was spun down and washed with water, then resuspended in 15 mL of 1×SMP media with 300 ul of hexadecane or octadecane. Yeast cells, media and alkane were placed into a 250 mL culture flask and incubated at 30 C while shaking (250 rpm) for 48 hours. The contents of the shake flask were spun down to produce a cell pellet and a supernatant, which is the culture media. The cell pellets were analyzed for hexanoic acid using an LC-MS MS method. As shown in Table 11, LCV34 produced more hexanoic acid than LCV14 from hexadecane, which is consistent with the presence of an active pathway making hexanoic acid from hexadecane. Octadecane may not be utilized effectively by the yeast strains.

TABLE 11

| Strain | Substrate | Hexanoic Acid (mg/L) |
|---|---|---|
| LCV14 | Soybean Oil | 70 |
| LCV34 | Soybean Oil | 190 |
| LCV14 | Palm Oil | 47 |
| LCV34 | Palm Oil | 222 |
| LCV14 | Octadecane | 10 |
| LCV34 | Octadecane | 3 |
| LCV14 | Hexadecane | 2 |
| LCV34 | Hexadecane | 174 |

Example 19—Production of Olivetolic Acid from Oleic Acid in *Candida*

Strain LCV14 (wildtype), LCV36 (Δpox+ACO1P+TKS1P+OAC1P), and LCV38 (Δpox+ACO1P+HKS1+TKS1+OAC1) were grown in 3 ml of YPD. These overnight cultures were used to inoculate 50 ml of YPD and grown overnight in a 250 ml flask at 225 rpm and 30 C. The biomass from the 50 mL culture was spun down and washed with water, then resuspended in 15 mL of 1×SMP media with 300 ul of oleic acid (technical grade, 90%). Yeast cells, media and oleic acid were placed into a 250 mL culture flask and incubated at 30 C while shaking (250 rpm) for 48 hours. The contents of the shake flask were spun down to produce a cell pellet and a supernatant, which is the culture media. The supernatants were analyzed for olivetolic acid using an LC-MS MS method. As shown in Table 12, LCV36 and LCV38 produced more olivetolic acid than LCV14, which is consistent with the presence of an active pathway making olivetolic acid from oleic acid with either a peroxisomal TKS1P and OAC1P or a non-peroxisomal HKS1, TKS1 and OAC1.

TABLE 12

| Strain | Olivetolic Acid (Area/g) |
|---|---|
| LCV14 | 611 |
| LCV36 | 1094 |
| LCV38 | 1026 |

Example 20—Production of Olivetolic Acid from Soybean Oil and Palm Oil in *Candida*

Strain LCV14 (wildtype) and LCV36 (Δpox+ACO1P+TKS1P+OAC1P) are grown in 3 ml of YPD. These overnights are used to inoculate 50 ml of YPD and grown overnight in a 250 ml flask at 225 rpm and 30 C. The biomass from the 50 mL culture is spun down and washed with water. It is resuspended in 15 mL of 1×SMP media with 300 ul of soybean oil or 300 ul of palm oil. Yeast cells, media and soybean oil are placed into a 250 mL culture flask. and incubated at 30 C while shaking (250 rpm) for 48 hours. The contents of the shake flask str spun down to produce a cell pellet and a supernatant, which is the culture media. The cell pellets and supernatants are analyzed for olivetolic acid using an LC-MS MS method.

Example 21—Production of Olivetolic Acid from Alkanes in *Candida*

Strain LCV14 (wildtype) and LCV36 (Δpox+ACO1P+TKS1P+OAC1P) are grown in 3 ml of YPD. These overnights are used to inoculate 50 ml of YPD and grown overnight in a 250 ml flask at 225 rpm and 30 C. The biomass from the 50 mL culture is spun down and washed with water. It is resuspended in 15 mL of 1×SMP media with 300 ul of hexadecane or octadecane. Yeast cells, media and alkane is placed into a 250 mL culture flask. and incubated at 30 C while shaking (250 rpm) for 48 hours. The contents of the shake flask are spun down to produce a cell pellet and a supernatant, which is the culture media. The cell pellets and supernatant are analyzed for olivetolic acid using an LC-MS MS method.

Example 22—Production of CBGA from Olivetolic Acid in *Candida*

Strain LCV51 (PTS1), LCV55 (PTS2) and LCV13 (wildtype) were grown in 3 ml of YPD. These overnight cultures were used to inoculate 2× (for LCV55) or 1× (for LCV13 and LCV5150 ml cultures of YPD and grown overnight in a 250 ml flask at 225 rpm and 30 C. The biomass from the 50 mL cultures were spun down and washed with water, then resuspended in 15 mL of 1×SMP media with 300 ul of oleic acid. Yeast cells, media and oleic acid were placed into a 250 mL culture flask. To one of the LCV55 flasks and the LCV13 flask, olivetolic acid was added to a final concentration of 1 mM. The flasks were then incubated at 30 C while shaking (250 rpm) for 48 hours. The contents of the shake flask were spun down to produce a cell pellet and a supernatant, which is the culture media. The cell supernatants were analyzed for CBGA using an LC-MS MS method. As shown in Table 13, LCV51 and LCV55 produced more CBGA than LCV13 and LCV55 without olivetolic acid, which is consistent with the presence of an active pathway making CBGA acid from oleic acid when either PTS1 or PTS2 is expressed.

TABLE 13

| StrainStrain | | CBGA Area/ul |
|---|---|---|
| LCV13 | Yes | 18,200 |
| LCV51 | Yes | 21,920 |
| LCV55 | No | 0 |
| LCV55 | Yes | 36,000 |

Example 23—Production of CBDA from Olivetolic Acid in *Candida*

Strain LCV55 (PTS2) and LCV59 (PTS2 CBD1) is grown in 3 ml of YPD. These overnights are used to inoculate 2× (for LCV59) or 1× (for LCV55) 50 ml of YPD and grown overnight in a 250 ml flask at 225 rpm and 30 C. The biomass from the 50 mL culture is spun down and washed with water, then resuspended in 15 mL of 1×SMP media with 300 ul of oleic acid. Yeast cells, media and oleic acid are placed into a 250 mL culture flask. To one of the LCV59 flasks and the LCV55 flask, olivetolic acid is added to a final concentration of 1 mM. The flasks are then incubated at 30 C while shaking (250 rpm) for 48 hours. The contents of the shake flask are spun down to produce a cell pellet and a supernatant, which is the culture media. The cell pellets and supernatants are analyzed for CBDA using an LC-MS MS method.

Example 24—Production of THCA from Olivetolic Acid in *Candida*

Strain LCV55 (PTS2) and LC61 (PTS2 THC1) are grown in 3 ml of YPD. These overnight cultures are used to inoculate 2× (for LCV61) or 1× (for LCV155) 50 ml of YPD and grown overnight in a 250 ml flask at 225 rpm and 30 C. The biomass from the 50 mL culture is spun down and washed with water, then resuspended in 15 mL of 1×SMP media with 300 ul of oleic acid. Yeast cells, media and oleic acid are placed into a 250 mL culture flask. To one of the LCV61 flasks and the LCV55 flask, olivetolic acid is added to a final concentration of 1 mM. The flasks are then incubated at 30 C while shaking (250 rpm) for 48 hours. The contents of the shake flask are spun down to produce a cell pellet and a supernatant, which is the culture media. The cell pellets and supernatants are analyzed for THCA using an LC-MS MS method.

Example 25—Production of CBGA from Fatty Acids in *Candida*

Strain LCV36 (Δpox+ACO1P+TKS1P+OAC1P) and LCV49 (Δpox+ACO1P+TKS1P+OAC1P+PTS1dN), were grown in 3 ml of YPD. These overnight cultures were used to inoculate 50 ml of YPD and grown overnight in a 250 ml flask at 225 rpm and 30 C. The biomass from the 50 mL culture was spun down and washed with water, then resuspended in 15 mL of 1×SMP media with 300 ul of oleic acid (technical grade, 90%). Yeast cells, media and oleic acid were placed into a 250 mL culture flask and incubated at 30 C while shaking (250 rpm) for 48 hours. The contents of the shake flask were spun down to produce a cell pellet and a supernatant, which is the culture media. The supernatants were analyzed for CBGA using an LC-MS MS method. As shown in Table, LCV49 produced more CBGA than LCV36, which is consistent with the presence of an active pathway making CBGA from oleic acid.

TABLE 14

| Strain | CBGA Area/ul |
|---|---|
| LCV36 | 1,058 |
| LCV49 | 2,000 |

Example 26—Production of CBDA from Fatty Acids in *Candida*

A strain is created that expresses ACO1P, TKS1P, AOC1P, PTS2 and CBD1 in a pox deleted background. This strain is grown overnight in 3 mol of YPD. This overnight culture is used to inoculate 50 ml of YPD and grown overnight in a 250 ml flask at 225 rpm and 30 C. The biomass from the 50 mL culture is spun down and washed with water. It is resuspended in 15 mL of 1×SMP media supplemented with 300 ul of oleic acid. Yeast cells, media and oleic are placed into a 250 mL culture flask. The flasks are then incubated at 30 C while shaking (250 rpm) for 48 hours. The contents of the shake flask are spun down to produce a cell pellet and a supernatant. The cell pellet and supernatants are analyzed for CBDA acid using an LC-MS MS method.

Example 27—Production of THCA from Fatty Acids in *Candida*

A strain is created that expresses ACO1P, TKS1P, AOC1P, PTS2 and THC1 or ACO1, HXS1, TKS1, AOC1, PTS2, and THC1 in a pox deleted background. This strain is grown overnight in 3 mol of YPD. This overnight is used to inoculate 50 ml of YPD and grown overnight in a 250 ml flask at 225 rpm and 30 C. The biomass from the 50 mL culture is spun down and washed with water. It is resuspended in 15 mL of 1×SMP media with 300 ul of oleic acid. Yeast cells, media and oleic acid are placed into a 250 mL culture flask. The flask is then incubated at 30 C while shaking (250 rpm) for 48 hours. The contents of the shake flask are spun down to produce a cell pellet and a supernatant, which is the culture media. The cell pellet and supernatant is analyzed for THCA acid using an LC-MS MS method.

Example 28—Enhanced Secretion of CBDA in *Candida*

Strain LCV59 (PTS2 CBD1), LCV63 (PTS2 CBD1dNS1), LCV67 (PTS2 CBDdNV1), and LCV70 (PTS2 CBD1dNP1) are grown in 3 ml of ScD-ura. These overnight cultures are used to inoculate 50 ml of YPD and grown overnight in 1 250 ml flask at 225 rpm and 30 C. The biomass from the 50 mL culture is spun down and washed with water, then resuspended in 15 mL of 1×SMP media with 300 ul of oleic acid. Yeast cells, media and oleic acid is placed into a 250 mL culture flask. Olivetolic acid is added to a final concentration of 1 mM. The flasks are then incubated at 30 C while shaking (250 rpm) for 48 hours. The contents of the shake flask are spun down to produce a cell

Example 29—Enhanced Secretion of THCA in *Candida*

Strains expressing either (PTS2 THC1), (PTS2 THC1dNS1), (PTS2 THCdNV1), or (PTS2 THC1dNP1) were grown in 3 ml of ScD-ura. These overnight cultures are used to inoculate 50 ml of YPD and grown overnight in a 250 ml flask at 225 rpm and 30 C. The biomass from the 50 mL culture is spun down and washed with water, then resuspended in 15 mL of 1×SMP media with 300 ul of oleic acid. Yeast cells, media and oleic acid is placed into a 250 mL culture flask. Olivetolic acid is added to a final concentration of 1 mM. The flasks are then incubated at 30 C while shaking (250 rpm) for 48 hours. The contents of the shake flask are spun down to produce a cell pellet and a supernatant, which is the culture media. The cell pellets and supernatants are analyzed for THCA using an LC-MS MS method.

Example 30—Production of CBCA in *Candida* from Fatty Acids

A strain is created that expresses ACO1P, TKS1P, OAC1P, PTS2 and CBC1 or ACO1P, HXS1, TKS1, OAC1, PTS2, and CBC1 in a pox deleted background. This strain is grown overnight in 3 mol of YPD. This overnight culture is used to inoculate 50 ml of YPD and grown overnight in a 250 ml flask at 225 rpm and 30 C. The biomass from the 50 mL culture is spun down and washed with water, then resuspended in 15 mL of 1×SMP media with 300 ul of oleic acid. Yeast cells, media and oleic acid are placed into a 250 mL culture flask. The flask is then incubated at 30 C while shaking (250 rpm) for 48 hours. The contents of the shake flask are spun down to produce a cell pellet and a supernatant, which is the culture media. The cell pellet and supernatant are analyzed for CBCA acid using an LC-MS MS method.

Example 31—Production of Hexanoic Acid from Fatty Acids in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30 C. The biomass from the 25 mL culture was spun down and washed with water, then resuspended in 20 mL of ScP media with 800 ul of oleic acid (technical grade, 90%). Yeast cells, media and oleic acid were placed into a 250 mL culture flask and incubated at 30 C while shaking (250 rpm) for 48 hours. The fermentation is analyzed for hexanoic acid using an GC-FID method.

Example 32—Production of Hexanoic Acid from Soybean Oil and Palm Oil in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30 C. The biomass from the 25 mL culture was spun down and washed with water, then resuspended in 20 mL of ScP media with 800 ul of oleic acid (technical grade, 90%). Yeast cells, media and vegetable oil were placed into a 250 mL culture flask and incubated at 30 C while shaking (250 rpm) for 48 hours. The fermentation is analyzed for hexanoic acid using an GC-FID method.

Example 33—Production of Hexanoic Acid from Alkanes in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30 C. The biomass from the 25 mL culture is spun down and washed with water, then resuspended in 20 mL of ScP media with 800 ul of either hexadecane and octadecane. Yeast cells, media and oleic acid are placed into a 250 mL culture flask and incubated at 30 C while shaking (250 rpm) for 48 hours. The fermentation is analyzed for hexanoic acid using an GC-FID method.

Example 34—Production of Olivetolic Acid from Hexanoic Acid or Hexanoate-Esters in *Yarrowia*

A strain is created that expresses HXS1, TKS1 and OAC1 is grown overnight in 3 ml of YPD. This overnight culture is used to inoculate 25 ml of ScGP and grown overnight in a 250 ml flask at 225 rpm and 30 C. The biomass from the 25 mL culture is spun down and washed with water, then resuspended in 20 mL of ScP media with 800 ul oleic acid. Yeast cells, media and oleic acid is placed into a 250 mL culture flask. Hexanoic acid, ethyl-hexanoate, geranyl hexanoate or other hexanoate ester is added to the flask. The culture flask is incubated at 30 C while shaking (250 rpm) for 48 hours. The contents of the shake flask are spun down to produce a cell pellet and a supernatant. The cell pellets and supernatants are analyzed for olivetolic acid using an LC-MS MS method.

Example 35—Production of Olivetolic Acid from Fatty Acids in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water. It is resuspended in 20 mL of ScP media with 800 ul oleic acid. Yeast cells, media and oleic acid is placed into a 250 mL culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for olivetolic acid using an LC-MS MS method.

Example 36—Production of Olivetolic Acid 1 from Soybean Oil or Palm Oil in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water, then resuspended in 20 mL of ScP media with 800 ul soybean or palm oil. Yeast cells, media and vegetable oil is placed into a 250 mL culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for olivetolic acid using an LC MS MS method.

Example 37—Production of Olivetolic Acid from Alkanes in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water. It is resuspended in 20 mL of ScP media with 800 ul of hexadecane or octadecane. Yeast cells, media and alkane are placed into a 250 mL culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for olivetolic acid using an LC MS MS method.

Example 38—Production of CBGA from Olivetolic Acid in *Yarrowia*

YYL7 is grown overnight in 3 ml of ScD-leu. This overnight culture is used to inoculate 25 ml of ScGP-leu and grown overnight in a 250 ml flask at 225 rpm and 30 C. The biomass from the 25 mL culture is spun down and is washed with water, then resuspended in 20 mL of Sc-leu media with 800 ul oleic acid. Yeast cells, media and oleic are placed into a 250 mL culture flask. Olivetolic acid is added to a final concentration of 1 mM to the culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for CBGA using an LC-MS MS method.

Example 39—Production of CBDA from Olivetolic Acid in *Yarrowia*

YYL17 is grown overnight in 3 ml of ScD-leu-ura. This overnight culture is used to inoculate 25 ml of ScGP-leu-ura and grown overnight in a 250 ml flask at 225 rpm and 30 C. The biomass from the 25 mL culture is spun down and is washed with water, then resuspended in 20 mL of ScP-ura-leu media with 800 ul oleic acid. Yeast cells, media and oleic are placed into a 250 mL culture flask. Olivetolic acid is added to a final concentration of 1 mM to the culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for CBDA using an LC-MS MS method.

Example 40—Production of THCA from Olivetolic Acid in *Yarrowia*

A strain expressing PTS2 and THC1 is grown overnight in 3 ml of ScD-leu-ura (if genes are in a plasmid) or YPD (if genes are integrated). This overnight is used to inoculate 25 ml of ScGP-leu-ura if genes are in a plasmid) or ScGP (if genes are integrated) and grown overnight in a 250 ml flask at 225 rpm and 30 C. The biomass from the 25 mL culture is spun down and is washed with water, then resuspended in 20 mL of ScP-ura-leu media with 800 ul oleic acid (if genes are in a plasmid) or ScP (if genes are integrated) media with 800 ul oleic acid. Yeast cells, media and oleic are placed into a 250 mL culture flask. Olivetolic acid is added to a final concentration of 1 mM to the culture flask. The culture flask is incubated at 30 C while shaking (250 rpm) for 48 hours. The contents of the shake flask are spun down to produce a cell pellet and a supernatant. The cell pellets and supernatants are analyzed for THCA using an LC-MS MS method.

Example 41—Production of CBGA from Fatty Acids in *Yarrowia*

A strain that produces hexanoic acid that expresses TKS1P OAC1P PTS2 or HXS1 TKS1 OAC1 PTS2 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water, then resuspended in 20 mL of ScP media with 800 ul oleic acid. Yeast cells, media and oleic acid are placed into a 250 mL culture flask. The culture flask is incubated at 30 C while shaking (250 rpm) for 48 hours. The contents of the shake flask are spun down to produce a cell pellet and a supernatant. The cell pellets and supernatants are analyzed for CBGA using an LC-MS MS method.

Example 42—Production of CBDA from Fatty Acids in *Yarrowia*

A strain that produces hexanoic acid that expresses TKS1P OAC1P PTS2 CBD1 or HXS1 TKS1 OAC1 PTS2 CBD1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water, then resuspended in 20 mL of ScP media with 800 ul oleic acid. Yeast cells, media and oleic acid are placed into a 250 mL culture flask. The culture flask is incubated at 30 C while shaking (250 rpm) for 48 hours. The contents of the shake flask are spun down to produce a cell pellet and a supernatant. The cell pellets and supernatants are analyzed for CBDA using an LC-MS MS method

Example 43—Production of THCA from Fatty Acids in *Yarrowia*

A strain that produces hexanoic acid that expresses TKS1P OAC1P PTS2 THC1 or HXS1 TKS1 OAC1 PTS2 THC1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water, then resuspended in 20 mL of ScP media with 800 ul oleic acid. Yeast cells, media and oleic acid are placed into a 250 mL culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for THCA using an LC MS MS method

Example 44—Production of CBCA from Fatty Acids in *Yarrowia*

A strain that produces hexanoic acid that expresses TKS1P OAC1P PTS2 CBC1 or HXS1 TKS1 OAC1 PTS2

CBC1 is grown overnight in 3 ml of YPD. This overnight culture is used to inoculate 25 ml of ScGP and grown overnight in a 250 ml flask at 225 rpm and 30 C. The biomass from the 25 mL culture is spun down and is washed with water, then resuspended in 20 mL of ScP media with 800 ul oleic acid. Yeast cells, media and oleic acid are placed into a 250 mL culture flask. The culture flask is incubated at 30 C while shaking (250 rpm) for 48 hours. The contents of the shake flask are spun down to produce a cell pellet and a supernatant, which is the culture media. The cell pellets and supernatants are analyzed for CBC1 using an LC MS MS method Sequences (*Yarrowia*)

pLD1

(SEQ ID NO: 157)

```
TTAATTAATTCCGCTTAATGGAGTCCAAAAAGACCAACCTCTGCGCCTCGATCGACG
TGACCACAACCGCCGAGTTCCTTTCGCTCATCGACAAGCTCGGTCCCCACATCTGTC
TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
GATAAAGGCGATGCGTTGGGCCAGCAGTATAGGACTGTTGATGAGGTGGTTCTGAC
TGGTACCGATGTGATTATTGTCGGGAGAGGGTTGTTTGGAAAAGGAAGAGACCCTG
AGGTGGAGGGAAAGAGATACAGGGATGCTGGATGGAAGGCATACTTGAAGAGAAC
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCGCGAAAGATAATCAAAATTA
CACTTGTGAATTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACATAAGAAGAGCCCGGGTCTAGATGTGT
GCTCTTCCGAGTGACTCTTTTGATAAGAGTCGCAAATTTGATTTCATAAGTATATATT
CATTATGTAAAGTAGTAAATGGAAAATTCATTAAAAAAAAAGCAAATTTCCGTTGTA
TGCATACTCCGAACACAAAACTAGCCCCGGAAAAACCCTTAGTTGATAGTTGCGAAT
TTAGGTCGACCATATGCGACGGGTACAACGAGAATTGTATTGAATTGATCAAGAAC
ATGATCTTGGTGTTACAGAACATCAAGTTCTTGGACCAGACTGAGAATGCACAGATA
TACAAGGCGTCATGTGATAAAATGGATGAGATTTATCCACAATTGAAGAAAGAGTT
TATGGAAAGTGGTCAACCAGAAGCTAAACAGGAAGAAGCAAACGAAGAGGTGAAA
```

-continued

```
CAAGAAGAAGAAGGTAAATAAGTATTTTGTATTATATAACAAACAAAGTAAGGAAT

ACAGATTTATACAATAAATTGCCATACTAGTCACGTGAGATATCTCATCCATTCCCC

AACTCCCAAGAAAATAAAAAAGTGAAAAATAAAATCAAACCCAAAGATCAACCTCC

CCATCATCATCGTCATCAAACCCCCAGCTCAATTCGCAATGGTTAGCACAAAAACAT

ACACAGAAAGGGCATCAGCACACCCCTCCAAGGTTGCCCAACGTTTATTAATTAAA

GGCTAGGTGGAGGCTCAGTGATGATAAGTCTGCGATGGTGGATGCATGTGTCATGGT

CATAGCTGTTTCCTGTGTGAAATTGTTATCCGCTCAGAGGGCACAATCCTATTCCGC

GCTATCCGACAATCTCCAAGACATTAGGTGGAGTTCAGTTCGGCGTATGGCATATGT

CGCTGGAAAGAACATGTGAGCAAAAGGCCAGCAAAAGGCCAGGAACCGTAAAAAG

GCCGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCGTT

TCCCCCTGGAAGCTCCCTCGTGCGCTCTCCTGTTCCGACCCTGCCGCTTACCGGATAC

CTGTCCGCCTTTCTCCCTTCGGGAAGCGTGGCGCTTTCTCATAGCTCACGCTGTAGGT

ATCTCAGTTCGGTGTAGGTCGTTCGCTCCAAGCTGGGCTGTGTGCACGAACCCCCCG

TTCAGCCCGACCGCTGCGCCTTATCCGGTAACTATCGTCTTGAGTCCAACCCGGTAA

GACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGA

AGAACAGTATTTGGTATCTGCGCTCTGCTGAAGCCAGTTACCTTCGGAAAAAGAGTT

GGTAGCTCTTGATCCGGCAAACAAACCACCGCTGGTAGCGGTGGTTTTTTTGTTTGC

AAGCAGCAGATTACGCGCAGAAAAAAAGGATCTCAAGAAGATCCTTTGATCTTTTCT

ACGGGGTCTGACGCTCTATTCAACAAAGCCGCCGTCCCGTCAAGTCAGCGTAAATG

GGTAGGGGGCTTCAAATCGTCCGCTCTGCCAGTGTTACAACCAATTAACAAATTCTG

ATTAGAAAAACTCATCGAGCATCAAATGAAACTGCAATTTATTCATATCAGGATTAT

CAATACCATATTTTTGAAAAAGCCGTTTCTGTAATGAAGGAGAAAACTCACCGAGGC

AGTTCCATAGGATGGCAAGATCCTGGTATCGGTCTGCGATTCCGACTCGTCCAACAT

CAATACAACCTATTAATTTCCCCTCGTCAAAAATAAGGTTATCAAGTGAGAAATCAC

CATGAGTGACGACTGAATCCGGTGAGAATGGCAAAAGCTTATGCATTTCTTTCCAGA

CTTGTTCAACAGGCCAGCCATTACGCTCGTCATCAAAATCACTCGCATCAACCAAAC

CGTTATTCATTCGTGATTGCGCCTGAGCGAGACGAAATACGCGATCGCTGTTAAAAG

GACAATTACAAACAGGAATCGAATGCAACCGGCGCAGGAACACTGCCAGCGCATCA

ACAATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGATG

GTCGGAAGAGGCATAAATTCCGTCAGCCAGTTTAGTCTGACCATCTCATCTGTAACA

TCATTGGCAACGCTACCTTTGCCATGTTTCAGAAACAACTCTGGCGCATCGGGCTTC

CCATACAATCGATAGATTGTCGCACCTGATTGCCCGACATTATCGCGAGCCCATTTA

TACCCATATAAATCAGCATCCATGTTGGAATTTAATCGCGGCCTCGAGCAAGACGTT

TCCCGTTGAATATGGCTCATAACACCCCTTGTATTACTGTTTATGTAAGCAGACAGTT

TTATTGTTCATGATGATATATTTTTATCTTGTGCAATGTAACATCAGAGATTTTGAGA

CACAACGTGGCTTTCCCCCGCCGCTCTAGAACTAGTGGATCCAAATAAAACGAAAG

GCTCAGTCGAAAGACTGGGCCTTTCGTTTTATCTGTTGTTTGTCGCATTATACGAGAC

GTCCAGGTTGGGATACCTGAAACAAAACCCATCGTACGGCCAAGGAAGTCTCCAAT
```

-continued

```
AACTGTGATCCACCACAAGCGCCAGGGTTTTCCCAGTCACGACGTTGTAAAACGAC
GGCCAGTCATGCATAATCCGCACGCATCTGGAATAAGGAAGTGCCATTCCGCCTGA
CCT
``` pLD10

(SEQ ID NO: 158)
```
TTAATTAATTCCGCTTAATGGAGTCCAAAAAGACCAACCTCTGCGCCTCGATCGACG
TGACCACAACCGCCGAGTTCCTTTCGCTCATCGACAAGCTCGGTCCCCACATCTGTC
TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
GATAAAGGCGATGCGTTGGGCCAGCAGTATAGGACTGTTGATGAGGTGGTTCTGAC
TGGTACCGATGTGATTATTGTCGGGAGAGGGTTGTTTGGAAAAGGAAGAGACCCTG
AGGTGGAGGGAAAGAGATACAGGGATGCTGGATGGAAGGCATACTTGAAGAGAAC
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCCGCGAAAGATAATCAAAATTA
CACTTGTGAATTTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACataATGAATCATTTAAGAGCAGAAGGAC
CCGCATCAGTGTTAGCGATAGGTACAGCTAACCCAGAGAATATCTTAATCCAAGATG
AATTTCCTGACTACTATTTCCGTGTTACTAAATCGGAACATATGACTCAACTTAAAG
AGAAGTTCCGGAAAATCTGCGATAAATCCATGATCCGAAAGAGAAACTGTTTCCTTA
ACGAAGAACATCTCAAGCAAAACCCGAGGTTGGTAGAGCACGAAATGCAGACCTTG
GATGCTAGGCAGGACATGTTGGTGGTCGAAGTGCCAAAACTCGGCAAGGACGCGTG
CGCTAAGGCAATCAAGGAGTGGGGTCAACCGAAGTCTAAAATCACGCATCTAATAT
TTACATCTGCACTGACAACCGACATGCCGGGTGCCGATTATCACTGCGCCAAGCTAC
TTGGATTGAGTCCACTGGTTAAGAGAGTTATGATGTATCAATTGGGGTGTTACGGAG
```

-continued

```
GGGGCACAGTCCTCAGAATTGCTAAGGATATTGCGGAAAATAACAAGGGCGCGAGG

GTCCTTGCTGTATGTTGTGATATTATGGCCTGTTTGTTTCGCGGGCCCTCGGATTCAG

ATTTGGAATTGCTTGTCGGACAGGCAATTTTTGGTGACGGGGCCGCAGCAGTCATAG

TGGGAGCCGAACCAGACGAAAGCGTGGGTGAAAGACCAATCTTTGAGTTGGTTCTG

ACCGGACAAACGATCTTACCTAACTCGGAAGGTACGATTGGAGGACATATTAGAGA

AGCCGGCCTAATTTTCGATCTTCACAAAGACGTTCCAATGTTAATCTCCAATAACAT

AGAAAAGTGCTTGATAGAAGCATTTACTCCCATTGGTATTAGTGACTGGAACAGCAT

TTTCTGGATCACCCACCCTGGAGGAAAAGCTATACTCGATAAGGTTGAAGAGAAAC

TCGACTTGAAAAGGAGAAATTCGTTGACTCACGACATGTGTTATCAGAGCACGGG

AATATGAGTTCATCCACAGTCTTGTTCGTAATGGATGAATTGCGAAAACGCTCTCTT

GAGGAGGGAAAGAGCACAACCGGTGACGGGTTTGAGTGGGGCGTGCTATTCGGTTT

TGGCCCAGGTTTGACTGTCGAGCGGGTTGTTGTTCGTAGTGTACCAATTAAGTACTG

ATAAGAGTGACTCTTTTGATAAGAGTCGCAAATTTGATTTCATAAGTATATATTCATT

ATGTAAAGTAGTAAATGGAAAATTCATTAAAAAAAAAGCAAATTTCCGTTGTATGC

ATACTCCGAACACAAAACTAGCCCCGGAAAAACCCTTAGTTGATAGTTGCGAATTTA

GGTCGACCATATGCGACGGGTACAACGAGAATTGTATTGAATTGATCAAGAACATG

ATCTTGGTGTTACAGAACATCAAGTTCTTGGACCAGACTGAGAATGCACAGATATAC

AAGGCGTCATGTGATAAAATGGATGAGATTTATCCACAATTGAAGAAAGAGTTTAT

GGAAAGTGGTCAACCAGAAGCTAAACAGGAAGAAGCAAACGAAGAGGTGAAACAA

GAAGAAGAAGGTAAATAAGTATTTTGTATTATATAACAAACAAAGTAAGGAATACA

GATTTATACAATAAATTGCCATACTAGTCACGTGAGATATCTCATCCATTCCCCAAC

TCCCAAGAAAATAAAAAAGTGAAAAATAAAATCAAACCCAAAGATCAACCTCCCCA

TCATCATCGTCATCAAACCCCCAGCTCAATTCGCAATGGTTAGCACAAAAACATACA

CAGAAAGGGCATCAGCACACCCCTCCAAGGTTGCCCAACGTTTATTAATTAAAGGCT

AGGTGGAGGCTCAGTGATGATAAGTCTGCGATGGTGGATGCATGTGTCATGGTCATA

GCTGTTTCCTGTGTGAAATTGTTATCCGCTCAGAGGGCACAATCCTATTCCGCGCTAT

CCGACAATCTCCAAGACATTAGGTGGAGTTCAGTTCGGCGTATGGCATATGTCGCTG

GAAAGAACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAAATCGACG

CTCAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTAGGTATCTC

AGTTCGGTGTAGGTCGTTCGCTCCAAGCTGGGCTGTGTGCACGAACCCCCCGTTCAG

CCCGACCGCTGCGCCTTATCCGGTAACTATCGTCTTGAGTCCAACCCGGTAAGACAC

GACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAA

CAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGG

GGTCTGACGCTCTATTCAACAAAGCCGCCGTCCCGTCAAGTCAGCGTAAATGGGTAG

GGGGCTTCAAATCGTCCGCTCTGCCAGTGTTACAACCAATTAACAAATTCTGATTAG
```

-continued

AAAAACTCATCGAGCATCAAATGAAACTGCAATTTATTCATATCAGGATTATCAATA
CCATATTTTTGAAAAAGCCGTTTCTGTAATGAAGGAGAAAACTCACCGAGGCAGTTC
CATAGGATGGCAAGATCCTGGTATCGGTCTGCGATTCCGACTCGTCCAACATCAATA
CAACCTATTAATTTCCCCTCGTCAAAAATAAGGTTATCAAGTGAGAAATCACCATGA
GTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGACA
ATTACAAACAGGAATCGAATGCAACCGGCGCAGGAACACTGCCAGCGCATCAACAA
TATTTTCACCTGAATCAGGATATTCTTCTAATACCTGGAATGCTGTTTTCCCGGGGAT
CGCAGTGGTGAGTAACCATGCATCATCAGGAGTACGGATAAAATGCTTGATGGTCG
GAAGAGGCATAAATTCCGTCAGCCAGTTTAGTCTGACCATCTCATCTGTAACATCAT
TGGCAACGCTACCTTTGCCATGTTTCAGAAACAACTCTGGCGCATCGGGCTTCCCAT
ACAATCGATAGATTGTCGCACCTGATTGCCCGACATTATCGCGAGCCCATTTATACC
CATATAAATCAGCATCCATGTTGGAATTTAATCGCGGCCTCGAGCAAGACGTTTCCC
GTTGAATATGGCTCATAACACCCCTTGTATTACTGTTTATGTAAGCAGACAGTTTTAT
TGTTCATGATGATATATTTTTATCTTGTGCAATGTAACATCAGAGATTTTGAGACACA
ACGTGGCTTTCCCCCGCCGCTCTAGAACTAGTGGATCCAAATAAAACGAAAGGCTC
AGTCGAAAGACTGGGCCTTTCGTTTTATCTGTTGTTTGTCGCATTATACGAGACGTCC
AGGTTGGGATACCTGAAACAAAACCCATCGTACGGCCAAGGAAGTCTCCAATAACT
GTGATCCACCACAAGCGCCAGGGTTTTCCCAGTCACGACGTTGTAAAACGACGGCC
AGTCATGCATAATCCGCACGCATCTGGAATAAGGAAGTGCCATTCCGCCTGACCT pLD12

(SEQ ID NO: 159)
TTAATTAATTCCGCTTAATGGAGTCCAAAAAGACCAACCTCTGCGCCTCGATCGACG
TGACCACAACCGCCGAGTTCCTTTCGCTCATCGACAAGCTCGGTCCCCACATCTGTC
TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
GATAAAGGCGATGCGTTGGGCCAGCAGTATAGGACTGTTGATGAGGTGGTTCTGAC
TGGTACCGATGTGATTATTGTCGGGAGAGGGTTGTTTGGAAAAGGAAGAGACCCTG
AGGTGGAGGGAAAGAGATACAGGGATGCTGGATGGAAGGCATACTTGAAGAGAAC
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG

-continued

```
GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGCAGTCAAACACCTAATAGTTCT

CAAATTTAAAGACGAGATTACTGAAGCTCAGAAGGAAGAGTTCTTTAAGACATATG

TTAACTTAGTCAACATCATCCCCGCGATGAAGGACGTCTACTGGGGCAAGGATGTGA

CGCAAAAAAATAAGGAAGAAGGATACACACATATCGTTGAGGTGACCTTTGAGAGT

GTGGAAACTATTCAAGATTATATTATTCACCCAGCCCATGTAGGGTTCGGTGACGTT

TATCGATCATTCTGGGAAAAGTTGCTTATATTTGATTACACCCCAAGAAAATTGAAG

CCTAAGTGATAAGAGTGACTCTTTTGATAAGAGTCGCAAATTTGATTTCATAAGTAT

ATATTCATTATGTAAAGTAGTAAATGGAAAATTCATTAAAAAAAAAGCAAATTTCCG

TTGTATGCATACTCCGAACACAAAACTAGCCCCGGAAAAACCCTTAGTTGATAGTTG

CGAATTTAGGTCGACCATATGCGACGGGTACAACGAGAATTGTATTGAATTGATCAA

GAACATGATCTTGGTGTTACAGAACATCAAGTTCTTGGACCAGACTGAGAATGCACA

GATATACAAGGCGTCATGTGATAAAATGGATGAGATTTATCCACAATTGAAGAAAG

AGTTTATGGAAAGTGGTCAACCAGAAGCTAAACAGGAAGAAGCAAACGAAGAGGT

GAAACAAGAAGAAGAAGGTAAATAAGTATTTTGTATTATATAACAAACAAAGTAAG

GAATACAGATTTATACAATAAATTGCCATACTAGTCACGTGAGATATCTCATCCATT

CCCCAACTCCCAAGAAAATAAAAAAGTGAAAAATAAAATCAAACCCAAAGATCAA

CCTCCCCATCATCATCGTCATCAAACCCCCAGCTCAATTCGCAATGGTTAGCACAAA

AACATACACAGAAAGGGCATCAGCACACCCCTCCAAGGTTGCCCAACGTTTATTAA

TTAAAGGCTAGGTGGAGGCTCAGTGATGATAAGTCTGCGATGGTGGATGCATGTGTC

ATGGTCATAGCTGTTTCCTGTGTGAAATTGTTATCCGCTCAGAGGGCACAATCCTATT

CCGCGCTATCCGACAATCTCCAAGACATTAGGTGGAGTTCAGTTCGGCGTATGGCAT

ATGTCGCTGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACAC

TAGAAGAACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGT
```

-continued

```
TTGCAAGCAGCAGATTACGCGCAGAAAAAAAGGATCTCAAGAAGATCCTTTGATCT

TTTCTACGGGGTCTGACGCTCTATTCAACAAAGCCGCCGTCCCGTCAAGTCAGCGTA

AATGGGTAGGGGGCTTCAAATCGTCCGCTCTGCCAGTGTTACAACCAATTAACAAAT

TCTGATTAGAAAAACTCATCGAGCATCAAATGAAACTGCAATTTATTCATATCAGGA

TTATCAATACCATATTTTTGAAAAAGCCGTTTCTGTAATGAAGGAGAAAACTCACCG

AGGCAGTTCCATAGGATGGCAAGATCCTGGTATCGGTCTGCGATTCCGACTCGTCCA

ACATCAATACAACCTATTAATTTCCCCTCGTCAAAAATAAGGTTATCAAGTGAGAAA

TCACCATGAGTGACGACTGAATCCGGTGAGAATGGCAAAAGCTTATGCATTTCTTTC

CAGACTTGTTCAACAGGCCAGCCATTACGCTCGTCATCAAAATCACTCGCATCAACC

AAACCGTTATTCATTCGTGATTGCGCCTGAGCGAGACGAAATACGCGATCGCTGTTA

AAAGGACAATTACAAACAGGAATCGAATGCAACCGGCGCAGGAACACTGCCAGCG

CATCAACAATATTTTCACCTGAATCAGGATATTCTTCTAATACCTGGAATGCTGTTTT

CCCGGGGATCGCAGTGGTGAGTAACCATGCATCATCAGGAGTACGGATAAAATGCT

TGATGGTCGGAAGAGGCATAAATTCCGTCAGCCAGTTTAGTCTGACCATCTCATCTG

TAACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGCCC

ATTTATACCCATATAAATCAGCATCCATGTTGGAATTTAATCGCGGCCTCGAGCAAG

ACGTTTCCCGTTGAATATGGCTCATAACACCCCTTGTATTACTGTTTATGTAAGCAGA

CAGTTTTATTGTTCATGATGATATATTTTTATCTTGTGCAATGTAACATCAGAGATTT

TGAGACACAACGTGGCTTTCCCCCGCCGCTCTAGAACTAGTGGATCCAAATAAAAC

GAAAGGCTCAGTCGAAAGACTGGGCCTTTCGTTTTATCTGTTGTTTGTCGCATTATAC

GAGACGTCCAGGTTGGGATACCTGAAACAAAACCCATCGTACGGCCAAGGAAGTCT

CCAATAACTGTGATCCACCACAAGCGCCAGGGTTTTCCCAGTCACGACGTTGTAAAA

CGACGGCCAGTCATGCATAATCCGCACGCATCTGGAATAAGGAAGTGCCATTCCGC

CTGACCT
``` pLD14

(SEQ ID NO: 160)
```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGAAGGCATACTTGAAGAGAAC

TGGTCAGTTAGAATAAATATTGTAATAAATAGGTCTATATACATACACTAAGCTTCT
```

-continued

```
AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGCAGTCAAACACCTAATAGTTCT

CAAATTTAAAGACGAGATTACTGAAGCTCAGAAGGAAGAGTTCTTTAAGACATATG

TTAACTTAGTCAACATCATCCCCGCGATGAAGGACGTCTACTGGGGCAAGGATGTGA

CGCAAAAAAATAAGGAAGAAGGATACACACATATCGTTGAGGTGACCTTTGAGAGT

GTGGAAACTATTCAAGATTATATTATTCACCCAGCCCATGTAGGGTTCGGTGACGTT

TATCGATCATTCTGGGAAAAGTTGCTTATATTTGATTACACCCCAAGAAAATTGAAG

CCTAAGGGAAGACGAGCTAAGTTGTGATAAGAGTGACTCTTTTGATAAGAGTCGCA

AATTTGATTTCATAAGTATATATTCATTATGTAAAGTAGTAAATGGAAAATTCATTA

AAAAAAAAGCAAATTTCCGTTGTATGCATACTCCGAACACAAAACTAGCCCCGGAA

AAACCCTTAGTTGATAGTTGCGAATTTAGGTCGACCATATGCGACGGGTACAACGAG

AATTGTATTGAATTGATCAAGAACATGATCTTGGTGTTACAGAACATCAAGTTCTTG

GACCAGACTGAGAATGCACAGATATACAAGGCGTCATGTGATAAAATGGATGAGAT

TTATCCACAATTGAAGAAAGAGTTTATGGAAAGTGGTCAACCAGAAGCTAAACAGG

AAGAAGCAAACGAAGAGGTGAAACAAGAAGAAGAAGGTAAATAAGTATTTTGTAT

TATATAACAAACAAAGTAAGGAATACAGATTTATACAATAAATTGCCATACTAGTC

ACGTGAGATATCTCATCCATTCCCCAACTCCCAAGAAAATAAAAAAGTGAAAAATA

AAATCAAACCCAAAGATCAACCTCCCCATCATCATCGTCATCAAACCCCCAGCTCAA

TTCGCAATGGTTAGCACAAAAACATACACAGAAAGGGCATCAGCACACCCCTCCAA

GGTTGCCCAACGTTTATTAATTAAAGGCTAGGTGGAGGCTCAGTGATGATAAGTCTG

CGATGGTGGATGCATGTGTCATGGTCATAGCTGTTTCCTGTGTGAAATTGTTATCCGC

TCAGAGGGCACAATCCTATTCCGCGCTATCCGACAATCTCCAAGACATTAGGTGGAG

TTCAGTTCGGCGTATGGCATATGTCGCTGGAAAGAACATGTGAGCAAAAGGCCAGC

AAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGT

TCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAG

CTGGGCTGTGTGCACGAACCCCCCGTTCAGCCCGACCGCTGCGCCTTATCCGGTAAC
```

-continued

```
TATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTG
GTGGCCTAACTACGGCTACACTAGAAGAACAGTATTTGGTATCTGCGCTCTGCTGAA
GCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCTATTCAACAAAGCCG
CCGTCCCGTCAAGTCAGCGTAAATGGGTAGGGGGCTTCAAATCGTCCGCTCTGCCAG
TGTTACAACCAATTAACAAATTCTGATTAGAAAAACTCATCGAGCATCAAATGAAAC
TGCAATTTATTCATATCAGGATTATCAATACCATATTTTTGAAAAAGCCGTTTCTGTA
ATGAAGGAGAAAACTCACCGAGGCAGTTCCATAGGATGGCAAGATCCTGGTATCGG
TCTGCGATTCCGACTCGTCCAACATCAATACAACCTATTAATTTCCCCTCGTCAAAA
ATAAGGTTATCAAGTGAGAAATCACCATGAGTGACGACTGAATCCGGTGAGAATGG
CAAAAGCTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCGAG
ACGAAATACGCGATCGCTGTTAAAAGGACAATTACAAACAGGAATCGAATGCAACC
GGCGCAGGAACACTGCCAGCGCATCAACAATATTTTCACCTGAATCAGGATATTCTT
CTAATACCTGGAATGCTGTTTTCCCGGGGATCGCAGTGGTGAGTAACCATGCATCAT
CAGGAGTACGGATAAAATGCTTGATGGTCGGAAGAGGCATAAATTCCGTCAGCCAG
TTTAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGATT
GCCCGACATTATCGCGAGCCCATTTATACCCATATAAATCAGCATCCATGTTGGAAT
TTAATCGCGGCCTCGAGCAAGACGTTTCCCGTTGAATATGGCTCATAACACCCCTTG
TATTACTGTTTATGTAAGCAGACAGTTTTATTGTTCATGATGATATATTTTTATCTTGT
GCAATGTAACATCAGAGATTTTGAGACACAACGTGGCTTTCCCCCGCCGCTCTAGAA
CTAGTGGATCCAAATAAAACGAAAGGCTCAGTCGAAAGACTGGGCCTTTCGTTTTAT
CTGTTGTTTGTCGCATTATACGAGACGTCCAGGTTGGGATACCTGAAACAAAACCCA
TCGTACGGCCAAGGAAGTCTCCAATAACTGTGATCCACCACAAGCGCCAGGGTTTTC
CCAGTCACGACGTTGTAAAACGACGGCCAGTCATGCATAATCCGCACGCATCTGGA
ATAAGGAAGTGCCATTCCGCCTGACCT
``` pLD16

(SEQ ID NO: 161)
```
TTAATTAATTCCGCTTAATGGAGTCCAAAAAGACCAACCTCTGCGCCTCGATCGACG
TGACCACAACCGCCGAGTTCCTTTCGCTCATCGACAAGCTCGGTCCCCACATCTGTC
TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
```

```
GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGGAAAAAATTATAAATCTTTGG

ACTCAGTTGTGGCTAGTGACTTCATTGCACTTGGGATCACATCAGAAGTTGCTGAGA

CATTGCACGGACGCTTGGCAGAGATAGTTTGCAACTACGGCGCCGCAACACCTCAG

ACCTGGATTAACATCGCAAACCATATTCTAAGTCCAGATCTTCCATTTAGTCTCCATC

AGATGTTGTTCTACGGTTGTTATAAGGACTTTGGTCCAGCACCCCCAGCTTGGATAC

CAGACCCCGAAAAAGTAAAGTCCACGAACTTAGGTGCCTTGTTAGAAAAGCGGGGA

AAGGAGTTTCTAGGCGTTAAGTATAAGGACCCAATAAGTCTGTTTTCTCACTTCCAG

GAGTTTAGCGTTCGAAATCCGGAAGTCTACTGGCGGACGGTACTTATGGATGAAATG

AAGATACTGTTCAGCAAAGATCCCGAATGTATCCTCAGACGCGACGACATTAACAA

CCCAGGGGGCTCTGAGTGGCTACCAGGTGGATATCTCAACCTGGCCAAGAACTGTTT

GAATGTAAATAGTAACAAAAAACTTAACGACACTATGATAGTGTGGAGAGATGAAG

GAAATGACGATCTCCCATTGAATAAATTGACTCTTGATCAATTACGAAAACGAGTCT

GGTTGGTTGGATACGCCCTAGAAGAGATGGGCCTTGAGAAGGGATGTGCGATTGCA

ATTGACATGCCCATGCACGTAGATGCGGTTGTGATCTATTTAGCTATCGTCTTGGCA

GGCTACGTCGTTGTCTCCATTGCAGATTCATTCTCAGCACCGGAAATTTCCACAAGA

TTGCGTCTATCAAAGGCTAAGGCTATTTTTACACAAGATCATATCATCCGAGGGAAA

AAGCGTATACCTTTGTACCTGCGTGTCGTCGAGGCCAAGTCTCCGATGGCAATAGTT

ATCCCGTGTTCGGGTTCAAATATTGGTGCGGAATTGCGGGATGGTGATATTCTGTGG

GATTACTTCTTAGAACGCGCAAAGGAATTTAAGAACTGCGAATTTACAGCCCGTGAA

CAGCCAGTGGACGCGTACACAAATATTTTGTTCTCATCGGGAACCACCGGAGAGCC

AAAGGCGATACCATGGACTCAAGCTACGCCTCTCAAGGCGGCTGCTGATGGTTGGTC

ACACTTGGACATTAGAAAGGGTGACGTAATTGTATGGCCTACCAATTTGGGGTGGAT

GATGGGCCTTGGTTGGTCTATGCTTCACTCCTTAACGGGGCAAGCATCGCATTGTA

TAACGGATCTCCACTAGTGTCCGGCTTTGCCAAATTCGTTCAAGATGCGAAAGTTAC
```

```
TATGCTAGGAGTTGTCCCCTCCATCGTACGAAGCTGGAAAAGCACTAATTGCGTTAG

TGGGTACGATTGGTCTACAATCAGATGCTTCTCCTCATCGGGTGAGGCATCGAATGT

CGATGAATACTTATGGCTAATGGGAAGGGCTAACTACAAACCGGTCATCGAAATGT

GCGGTGGCACAGAGATCGGGGGTGCCTTCAGCGCCGGTTCGTTTTTACAAGCCCAAT

CTTTGAGTAGCTTCTCATCCCAATGTATGGGATGCACCTTGTACATTCTCGACAAGA

ATGGCTACCCGATGCCAAAGAACAAGCCGGGTATAGGTGAATTGGCCTTGGGACCC

GTGATGTTCGGTGCTTCCAAGACTTTACTTAACGGAAACCATCATGACGTTTATTTCA

AAGGCATGCCCACCTTGAACGGAGAAGTCTTGAGGAGACACGGAGATATCTTCGAA

CTCACTTCGAACGGCTATTATCACGCTCATGGTAGAGCAGATGACACGATGAATATC

GGGGGGATTAAAATTTCCTCAATCGAGATTGAAAGGGTGTGTAATGAAGTTGACGA

TAGAGTGTTTGAGACTACGGCCATTGGAGTGCCTCCATTGGGCGGAGGTCCAGAGC

AGCTCGTTATCTTTTTTGTTCTTAAGGACAGCAATGATACGACCATCGACCTAAACC

AATTGCGACTTAGTTTTAATCTTGGGTTACAAAAGAAATTGAACCCACTTTTTAAGG

TGACGAGGGTTGTGCCACTTTCGCTGTTGCCTAGGACAGCCACCAACAAAATAATGA

GAAGAGTGCTTAGACAGCAATTTAGTCATTTCGAGTGATAAGAGTGACTCTTTTGAT

AAGAGTCGCAAATTTGATTTCATAAGTATATATTCATTATGTAAAGTAGTAAATGGA

AAATTCATTAAAAAAAAAGCAAATTTCCGTTGTATGCATACTCCGAACACAAAACTA

GCCCCGGAAAAACCCTTAGTTGATAGTTGCGAATTTAGGTCGACCATATGCGACGGG

TACAACGAGAATTGTATTGAATTGATCAAGAACATGATCTTGGTGTTACAGAACATC

AAGTTCTTGGACCAGACTGAGAATGCACAGATATACAAGGCGTCATGTGATAAAAT

GGATGAGATTTATCCACAATTGAAGAAAGAGTTTATGGAAAGTGGTCAACCAGAAG

CTAAACAGGAAGAAGCAAACGAAGAGGTGAAACAAGAAGAAGAAGGTAAATAAGT

ATTTTGTATTATATAACAAACAAAGTAAGGAATACAGATTTATACAATAAATTGCCA

TACTAGTCACGTGAGATATCTCATCCATTCCCCAACTCCCAAGAAAATAAAAAAGTG

AAAAATAAAATCAAACCCAAAGATCAACCTCCCCATCATCATCGTCATCAAACCCC

CAGCTCAATTCGCAATGGTTAGCACAAAAACATACACAGAAAGGGCATCAGCACAC

CCCTCCAAGGTTGCCCAACGTTTATTAATTAAAGGCTAGGTGGAGGCTCAGTGATGA

TAAGTCTGCGATGGTGGATGCATGTGTCATGGTCATAGCTGTTTCCTGTGTGAAATT

GTTATCCGCTCAGAGGGCACAATCCTATTCCGCGCTATCCGACAATCTCCAAGACAT

TAGGTGGAGTTCAGTTCGGCGTATGGCATATGTCGCTGGAAAGAACATGTGAGCAA

AAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGG

AAGCGTGGCGCTTTCTCATAGCTCACGCTGTAGGTATCTCAGTTCGGTGTAGGTCGT

TCGCTCCAAGCTGGGCTGTGTGCACGAACCCCCCGTTCAGCCCGACCGCTGCGCCTT

ATCCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGAGT

TCTTGAAGTGGTGGCCTAACTACGGCTACACTAGAAGAACAGTATTTGGTATCTGCG

CTCTGCTGAAGCCAGTTACCTTCGGAAAAAGAGTTGGTAGCTCTTGATCCGGCAAAC
```

-continued

```
AAACCACCGCTGGTAGCGGTGGTTTTTTTGTTTGCAAGCAGCAGATTACGCGCAGAA

AAAAAGGATCTCAAGAAGATCCTTTGATCTTTTCTACGGGGTCTGACGCTCTATTCA

ACAAAGCCGCCGTCCCGTCAAGTCAGCGTAAATGGGTAGGGGGCTTCAAATCGTCC

GCTCTGCCAGTGTTACAACCAATTAACAAATTCTGATTAGAAAAACTCATCGAGCAT

CAAATGAAACTGCAATTTATTCATATCAGGATTATCAATACCATATTTTTGAAAAAG

CCGTTTCTGTAATGAAGGAGAAAACTCACCGAGGCAGTTCCATAGGATGGCAAGAT

CCTGGTATCGGTCTGCGATTCCGACTCGTCCAACATCAATACAACCTATTAATTTCCC

CTCGTCAAAAATAAGGTTATCAAGTGAGAAATCACCATGAGTGACGACTGAATCCG

GTGAGAATGGCAAAAGCTTATGCATTTCTTTCCAGACTTGTTCAACAGGCCAGCCAT

TACGCTCGTCATCAAAATCACTCGCATCAACCAAACCGTTATTCATTCGTGATTGCG

CCTGAGCGAGACGAAATACGCGATCGCTGTTAAAAGGACAATTACAAACAGGAATC

GAATGCAACCGGCGCAGGAACACTGCCAGCGCATCAACAATATTTTCACCTGAATC

AGGATATTCTTCTAATACCTGGAATGCTGTTTTCCCGGGGATCGCAGTGGTGAGTAA

CCATGCATCATCAGGAGTACGGATAAAATGCTTGATGGTCGGAAGAGGCATAAATT

CCGTCAGCCAGTTTAGTCTGACCATCTCATCTGTAACATCATTGGCAACGCTACCTTT

GCCATGTTTCAGAAACAACTCTGGCGCATCGGGCTTCCCATACAATCGATAGATTGT

CGCACCTGATTGCCCGACATTATCGCGAGCCCATTTATACCCATATAAATCAGCATC

CATGTTGGAATTTAATCGCGGCCTCGAGCAAGACGTTTCCCGTTGAATATGGCTCAT

AACACCCCTTGTATTACTGTTTATGTAAGCAGACAGTTTTATTGTTCATGATGATATA

TTTTTATCTTGTGCAATGTAACATCAGAGATTTTGAGACACAACGTGGCTTTCCCCCG

CCGCTCTAGAACTAGTGGATCCAAATAAAACGAAAGGCTCAGTCGAAAGACTGGGC

CTTTCGTTTTATCTGTTGTTTGTCGCATTATACGAGACGTCCAGGTTGGGATACCTGA

AACAAAACCCATCGTACGGCCAAGGAAGTCTCCAATAACTGTGATCCACCACAAGC

GCCAGGGTTTTCCCAGTCACGACGTTGTAAAACGACGGCCAGTCATGCATAATCCGC

ACGCATCTGGAATAAGGAAGTGCCATTCCGCCTGACCT
``` pLD20

(SEQ ID NO: 162)

```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA
```

```
CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAAGTGTTCTACGTTTAGTTTTTG

GTTTGTTTGTAAAATTATATTCTTCTTTTTTTCCTTCAACATTCAGACATCAATCGCCA

ACCCAAGGGAAAACTTCCTTAAGTGTTTTCTGCAGTACATCCCTAACAATGCAACAA

ACCTCAAGTTGGTGTACACTCAAAACAATCCACTCTATATGAGCGTGCTTAATAGCA

CAATCCACAACTTGCGCTTCACGTCAGATACTACGCCTAAGCCACTAGTGATCGTTA

CACCATCACACGTCAGCCATATTCAAGGAACGATCCTATGTCTGAAAAAGGTCGGGT

TGCAAATCAGGACTCGATCAGGAGGGCACGATAGTGAGGGAATGAGTTACATCTCG

CAAGTACCCTTCGTGATAGTTGACTTGCGAAATATGCGGTCTATTAAAATTGACGTA

CATAGCCAGACCGCCTGGGTTGAAGCAGGGGCAACCTTGGGTGAAGTTTATTACTG

GGTCAATGAAAAAAACGAAAACCTAAGTCTTGCTGCTGGATATTGCCCCACCGTTTG

CGCGGGTGGTCATTTTGGAGGCGGCGGATATGGTCCGTTGATGAGAAATTATGGACT

TGCAGCAGACAATATTATAGATGCCCACTTGGTGAACGTTCATGGAAAGGTCTTGGA

CCGTAAGTCCATGGGTGAAGATCTTTTCTGGGCCTTGAGAGGTGGTGGAGCGGAATC

GTTTGGCATCATCGTTGCCTGGAAAATTAGGTTGGTTGCGGTCCCGAAGAGTACAAT

GTTCTCCGTGAAGAAGATTATGGAAATACATGAGCTTGTCAAGTTAGTTAACAAGTG

GCAAAATATCGCTTATAAGTATGATAAAGACTTGCTTTTGATGACTCATTTTATTACG

CGAAACATAACCGATAACCAGGGCAAGAACAAGACTGCTATTCACACGTACTTCTC

CTCTGTATTTCTTGGAGGAGTAGACTCCTTAGTTGACTTGATGAACAAGAGTTTCCC

AGAATTGGGGATTAAGAAGACAGATTGCAGACAATTATCGTGGATAGATACAATCA

TATTCTATAGCGGTGTCGTCAATTACGATACTGATAATTTTAATAAAGAAATCCTCCT

AGATCGTTCAGCTGGGCAAAACGGGGCATTCAAAATTAAATTGGATTATGTGAAGA

AACCAATTCCAGAGCTGGTGTTTGTTCAGATATTGGAAAAACTTTACGAAGAAGACA

TTGGCGCAGGTATGTACGCTTTGTATCCATATGGAGGCATTATGGACGAGATCTCAG

AGCTGGCGATCCCCTTCCCGCACAGAGCTGGGATACTCTACGAGCTATGGTACATCT

GCTCTTGGGAGAAACAAGAAGACAACGAGAAACATCTCAATTGGATTCGGAACATA

TACAACTTTATGACCCCATACGTATCAAAAAACCCGCGCTTAGCATACTTGAATTAC

AGAGACTTAGATATCGGTATCAATGATCCTAAGAATCCTAACAATTACACCCAAGCC

CGTATTTGGGGTGAGAAATATTTCGGCAAGAATTTTGACAGATTAGTTAAGGTCAAA
```

-continued
ACACTCGTGGACCCCAACAACTTTTTCCGAAACGAGCAGTCGATTCCACCACTACCC

AGGCATAGACACTGATAAGAGTGACTCTTTTGATAAGAGTCGCAAATTTGATTTCAT

AAGTATATATTCATTATGTAAAGTAGTAAATGGAAAATTCATTAAAAAAAAAGCAA

ATTTCCGTTGTATGCATACTCCGAACACAAAACTAGCCCCGGAAAAACCCTTAGTTG

ATAGTTGCGAATTTAGGTCGACCATATGCGACGGGTACAACGAGAATTGTATTGAAT

TGATCAAGAACATGATCTTGGTGTTACAGAACATCAAGTTCTTGGACCAGACTGAGA

ATGCACAGATATACAAGGCGTCATGTGATAAAATGGATGAGATTTATCCACAATTG

AAGAAAGAGTTTATGGAAAGTGGTCAACCAGAAGCTAAACAGGAAGAAGCAAACG

AAGAGGTGAAACAAGAAGAAGAAGGTAAATAAGTATTTTGTATTATATAACAAACA

AAGTAAGGAATACAGATTTATACAATAAATTGCCATACTAGTCACGTGAGATATCTC

ATCCATTCCCCAACTCCCAAGAAAATAAAAAAGTGAAAAATAAAATCAAACCCAAA

GATCAACCTCCCCATCATCATCGTCATCAAACCCCCAGCTCAATTCGCAATGGTTAG

CACAAAAACATACACAGAAAGGGCATCAGCACACCCCTCCAAGGTTGCCCAACGTT

TATTAATTAAAGGCTAGGTGGAGGCTCAGTGATGATAAGTCTGCGATGGTGGATGC

ATGTGTCATGGTCATAGCTGTTTCCTGTGTGAAATTGTTATCCGCTCAGAGGGCACA

ATCCTATTCCGCGCTATCCGACAATCTCCAAGACATTAGGTGGAGTTCAGTTCGGCG

TATGGCATATGTCGCTGGAAAGAACATGTGAGCAAAAGGCCAGCAAAAGGCCAGGA

ACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTC

GGAAAAAGAGTTGGTAGCTCTTGATCCGGCAAACAAACCACCGCTGGTAGCGGTGG

TTTTTTTGTTTGCAAGCAGCAGATTACGCGCAGAAAAAAAGGATCTCAAGAAGATCC

TTTGATCTTTTCTACGGGGTCTGACGCTCTATTCAACAAAGCCGCCGTCCCGTCAAGT

CAGCGTAAATGGGTAGGGGGCTTCAAATCGTCCGCTCTGCCAGTGTTACAACCAATT

AACAAATTCTGATTAGAAAAACTCATCGAGCATCAAATGAAACTGCAATTTATTCAT

ATCAGGATTATCAATACCATATTTTTGAAAAAGCCGTTTCTGTAATGAAGGAGAAAA

CTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAG

TGAGAAATCACCATGAGTGACGACTGAATCCGGTGAGAATGGCAAAAGCTTATGCA

TTTCTTTCCAGACTTGTTCAACAGGCCAGCCATTACGCTCGTCATCAAAATCACTCGC

ATCAACCAAACCGTTATTCATTCGTGATTGCGCCTGAGCGAGACGAAATACGCGATC

GCTGTTAAAAGGACAATTACAAACAGGAATCGAATGCAACCGGCGCAGGAACACTG

CCAGCGCATCAACAATATTTTCACCTGAATCAGGATATTCTTCTAATACCTGGAATG

CTGTTTTCCCGGGGATCGCAGTGGTGAGTAACCATGCATCATCAGGAGTACGGATAA

AATGCTTGATGGTCGGAAGAGGCATAAATTCCGTCAGCCAGTTTAGTCTGACCATCT

-continued

CATCTGTAACATCATTGGCAACGCTACCTTTGCCATGTTTCAGAAACAACTCTGGCG

CATCGGGCTTCCCATACAATCGATAGATTGTCGCACCTGATTGCCCGACATTATCGC

GAGCCCATTTATACCCATATAAATCAGCATCCATGTTGGAATTTAATCGCGGCCTCG

AGCAAGACGTTTCCCGTTGAATATGGCTCATAACACCCCTTGTATTACTGTTTATGTA

AGCAGACAGTTTTATTGTTCATGATGATATATTTTTATCTTGTGCAATGTAACATCAG

AGATTTTGAGACACAACGTGGCTTTCCCCCGCCGCTCTAGAACTAGTGGATCCAAAT

AAAACGAAAGGCTCAGTCGAAAGACTGGGCCTTTCGTTTTATCTGTTGTTTGTCGCA

TTATACGAGACGTCCAGGTTGGGATACCTGAAACAAAACCCATCGTACGGCCAAGG

AAGTCTCCAATAACTGTGATCCACCACAAGCGCCAGGGTTTTCCCAGTCACGACGTT

GTAAAACGACGGCCAGTCATGCATAATCCGCACGCATCTGGAATAAGGAAGTGCCA

TTCCGCCTGACCT pLD22

(SEQ ID NO: 163)
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGACAGAAGTAGTAGATAGAGCAA

-continued

```
GTTCCCCAGCAAGTCCAGGATCTACGACCGCCGCCGCAGACGGTGCTAAGGTGGCG

GTGGAGCCACGCGTAGATGTAGCGGCCCTTGGCGAGCAGTTGCTAGGGCGATGGGC

TGACATCAGATTGCACGCACGAGACTTAGCAGGCCGCGAAGTGGTCCAAAAGGTTG

AAGGACTTACGCACACTGAGCATCGGAGTAGAGTCTTTGGACAGTTGAAGTACTTG

GTAGACAACAATGCTGTTCACAGAGCTTTTCCCTCCAGGCTAGGTGGATCAGATGAC

CATGGCGGTAATATAGCTGGATTCGAGGAATTAGTTACTGCTGATCCATCATTGCAA

ATAAAGGCCGGCGTTCAGTGGGGTTTGTTTGGTTCTGCAGTGATGCACTTGGGAACC

CGTGAACATCATGACAAGTGGTTGCCAGGTATTATGTCGTTAGAAATACCGGGGTGT

TTCGCGATGACAGAAACCGGGCACGGTAGCGACGTGGCCTCTATTGCTACAACAGC

AACTTATGATGAGGAAACCCAAGAGTTTGTTATTGATACCCCGTTCAGAGCCGCTTG

GAAAGATTATATCGGTAATGCAGCGAACGATGGTTTGGCGGCAGTTGTTTTCGCACA

ATTAATCACGAGGAAAGTGAACCATGGTGTACACGCCTTTTACGTGGATCTCAGAGA

TCCTGCGACTGGAGACTTCCTACCCGGAATAGGAGGAGAGGACGATGGAATCAAGG

GGGGATTGAATGGCATTGACAACGGTAGACTACATTTTACGAACGTACGCATTCCTA

GAACTAATCTTCTTAACAGATATGGCGATGTGGCGGTCGACGGCACATACCTGTCGA

CCATCGAATCACCAGGGCGCCGGTTCTTTACGATGCTTGGTACTCTAGTCCAGGGTA

GAGTTAGTCTCGATGGAGCAGCTGTCGCTGCACTGAAGGTCGCATTGCAAAGTGCA

ATTCACTACGCTGCGGAGAGGAGACAATTTAATGCGACTTCACCTACTGAAGAAGA

GGTCCTTCTTGATTATCAGAGGCATCAAAGGAGACTCTTTACACGACTTGCAACGAC

GTACGCCGCATCTTTCGCCCACGAGCAGCTATTGCAAAAGTTCGATGATGTCTTTTC

AGGGGCACATGATACCGACGCCGACCGGCAGGACTTGGAAACCCTAGCCGCCGCTT

TGAAGCCATTGAGCACATGGCATGCACTTGACACGTTACAAGAATGCAGAGAGGCC

TGTGGGGGGCCGGATTTTTGATAGAAAACCGTTTCGCGAGCTTGCGTGCTGACTTG

GACGTTTACGTCACATTCGAGGGTGATAACACAGTTTTATTGCAATTGGTTGCTAAA

CGGCTCTTGGCAGACTACGCAAAAGAGTTCAGAGGGGCCAACTTCGGCGTTCTTGCC

AGGTATGTGGTTGACCAAGCCGCGGGAGTGGCGCTCCACCGAACAGGACTAAGGCA

AGTCGCTCAATTTGTTGCAGACAGCGGGTCCGTTCAGAAGTCGGCTCTTGCGCTTCG

CGATGAAGAGGGTCAACGAACATTGTTAACGGACAGAGTACAGAGCATGGTTGCCG

AAGTGGGGGCTGCCTTGAAAGGCGCAGGCAAATTACCCCAACATCAAGCAGCTGCA

TTGTTCAACCAACACCAGAACGAACTTATTGAGGCTGCCCAGGCCCATGCAGAACTC

CTCCAATGGGAGGCATTTACAGAAGCTCTCGCTAAAGTCGACGATGCTGGTACAAA

GGAAGTGCTTACTCGATTGCGAGATCTCTTTGGTTTGTCCTTGATTGAAAAACACTTG

CTGTGGTATCTTATGAATGGACGTTTGTCCATGCAAAGAGGCAGGACAGTTGGAACT

TACATTAATCGTTTACTTGTCAAGATCCGTCCACACGCACTAGACTTGGTTGATGCCT

TCGGTTACGGCGCGGAGCATTTGCGTGCTGCTATCGCCACCGGAGCGGAAGCAACC

CGACAGGATGAAGCCCGAACGTATTTTAGACAACAACGGGCATCGGGACTGGCCCC

GGCCGATGAAAAGACCTTACTCGCTATCAAAGCTGGTAAATCAAGAGGGCGAAGGG

CAAAGCTATGATAAGAGTGACTCTTTTGATAAGAGTCGCAAATTTGATTTCATAAGT

ATATATTCATTATGTAAAGTAGTAAATGGAAAATTCATTAAAAAAAAAGCAAATTTC

CGTTGTATGCATACTCCGAACACAAAACTAGCCCCGGAAAAACCCTTAGTTGATAGT

TGCGAATTTAGGTCGACCATATGCGACGGGTACAACGAGAATTGTATTGAATTGATC
```

-continued

```
AAGAACATGATCTTGGTGTTACAGAACATCAAGTTCTTGGACCAGACTGAGAATGC

ACAGATATACAAGGCGTCATGTGATAAAATGGATGAGATTTATCCACAATTGAAGA

AAGAGTTTATGGAAAGTGGTCAACCAGAAGCTAAACAGGAAGAAGCAAACGAAGA

GGTGAAACAAGAAGAAGAAGGTAAATAAGTATTTTGTATTATATAACAAACAAAGT

AAGGAATACAGATTTATACAATAAATTGCCATACTAGTCACGTGAGATATCTCATCC

ATTCCCCAACTCCCAAGAAAATAAAAAAGTGAAAAATAAAATCAAACCCAAAGATC

AACCTCCCCATCATCATCGTCATCAAACCCCCAGCTCAATTCGCAATGGTTAGCACA

AAAACATACACAGAAAGGGCATCAGCACACCCCTCCAAGGTTGCCCAACGTTTATT

AATTAAAGGCTAGGTGGAGGCTCAGTGATGATAAGTCTGCGATGGTGGATGCATGT

GTCATGGTCATAGCTGTTTCCTGTGTGAAATTGTTATCCGCTCAGAGGGCACAATCC

TATTCCGCGCTATCCGACAATCTCCAAGACATTAGGTGGAGTTCAGTTCGGCGTATG

GCATATGTCGCTGGAAAGAACATGTGAGCAAAAGGCCAGCAAAAGGCCAGGAACC

GTAAAAAGGCCGCGTTGCTGGCGTTTTTCCATAGGCTCCGCCCCCTGACGAGCATC

ACAAAAATCGACGCTCAAGTCAGAGGTGGCGAAACCCGACAGGACTATAAAGATAC

CAGGCGTTTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAA

CCCGGTAAGACACGACTTATCGCCACTGGCAGCAGCCACTGGTAACAGGATTAGCA

GAGCGAGGTATGTAGGCGGTGCTACAGAGTTCTTGAAGTGGTGGCCTAACTACGGC

TACACTAGAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGGTGGTTTT

TTTGTTTGCAAGCAGCAGATTACGCGCAGAAAAAAAGGATCTCAAGAAGATCCTTT

GATCTTTTCTACGGGGTCTGACGCTCTATTCAACAAAGCCGCCGTCCCGTCAAGTCA

GCGTAAATGGGTAGGGGGCTTCAAATCGTCCGCTCTGCCAGTGTTACAACCAATTAA

CAAATTCTGATTAGAAAAACTCATCGAGCATCAAATGAAACTGCAATTTATTCATAT

CAGGATTATCAATACCATATTTTTGAAAAAGCCGTTTCTGTAATGAAGGAGAAAACT

CACCGAGGCAGTTCCATAGGATGGCAAGATCCTGGTATCGGTCTGCGATTCCGACTC

GTCCAACATCAATACAACCTATTAATTTCCCCTCGTCAAAAATAAGGTTATCAAGTG

AGAAATCACCATGAGTGACGACTGAATCCGGTGAGAATGGCAAAAGCTTATGCATT

TCTTTCCAGACTTGTTCAACAGGCCAGCCATTACGCTCGTCATCAAAATCACTCGCA

TCAACCAAACCGTTATTCATTCGTGATTGCGCCTGAGCGAGACGAAATACGCGATCG

CTGTTAAAAGGACAATTACAAACAGGAATCGAATGCAACCGGCGCAGGAACACTGC

CAGCGCATCAACAATATTTTCACCTGAATCAGGATATTCTTCTAATACCTGGAATGC

TGTTTTCCCGGGGATCGCAGTGGTGAGTAACCATGCATCATCAGGAGTACGGATAAA

ATGCTTGATGGTCGGAAGAGGCATAAATTCCGTCAGCCAGTTTAGTCTGACCATCTC

ATCTGTAACATCATTGGCAACGCTACCTTTGCCATGTTTCAGAAACAACTCTGGCGC

ATCGGGCTTCCCATACAATCGATAGATTGTCGCACCTGATTGCCCGACATTATCGCG

AGCCCATTTATACCCATATAAATCAGCATCCATGTTGGAATTTAATCGCGGCCTCGA

GCAAGACGTTTCCCGTTGAATATGGCTCATAACACCCCTTGTATTACTGTTTATGTAA
```

-continued

GCAGACAGTTTTATTGTTCATGATGATATATTTTTATCTTGTGCAATGTAACATCAGA

GATTTTGAGACACAACGTGGCTTTCCCCCGCCGCTCTAGAACTAGTGGATCCAAATA

AAACGAAAGGCTCAGTCGAAAGACTGGGCCTTTCGTTTTATCTGTTGTTTGTCGCAT

TATACGAGACGTCCAGGTTGGGATACCTGAAACAAAACCCATCGTACGGCCAAGGA

AGTCTCCAATAACTGTGATCCACCACAAGCGCCAGGGTTTTCCCAGTCACGACGTTG

TAAAACGACGGCCAGTCATGCATAATCCGCACGCATCTGGAATAAGGAAGTGCCAT

TCCGCCTGACCT pLD24

(SEQ ID NO: 164)
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATCATTTAAGAGCAGAAGGAC

CCGCATCAGTGTTAGCGATAGGTACAGCTAACCCAGAGAATATCTTAATCCAAGATG

AATTTCCTGACTACTATTTCCGTGTTACTAAATCGGAACATATGACTCAACTTAAAG

AGAAGTTCCGGAAAATCTGCGATAAATCCATGATCCGAAAGAGAAACTGTTTCCTTA

ACGAAGAACATCTCAAGCAAACCCGAGGTTGGTAGAGCACGAAATGCAGACCTTG

GATGCTAGGCAGGACATGTTGGTGGTCGAAGTGCCAAAACTCGGCAAGGACGCGTG

-continued

```
CGCTAAGGCAATCAAGGAGTGGGGTCAACCGAAGTCTAAAATCACGCATCTAATAT
TTACATCTGCACTGACAACCGACATGCCGGGTGCCGATTATCACTGCGCCAAGCTAC
TTGGATTGAGTCCACTGGTTAAGAGAGTTATGATGTATCAATTGGGGTGTTACGGAG
GGGGCACAGTCCTCAGAATTGCTAAGGATATTGCGGAAAATAACAAGGGCGCGAGG
GTCCTTGCTGTATGTTGTGATATTATGGCCTGTTTGTTTCGCGGGCCCTCGGATTCAG
ATTTGGAATTGCTTGTCGGACAGGCAATTTTTGGTGACGGGGCCGCAGCAGTCATAG
TGGGAGCCGAACCAGACGAAAGCGTGGGTGAAAGACCAATCTTTGAGTTGGTTCTG
ACCGGACAAACGATCTTACCTAACTCGGAAGGTACGATTGGAGGACATATTAGAGA
AGCCGGCCTAATTTTCGATCTTCACAAAGACGTTCCAATGTTAATCTCCAATAACAT
AGAAAAGTGCTTGATAGAAGCATTTACTCCCATTGGTATTAGTGACTGGAACAGCAT
TTTCTGGATCACCCACCCTGGAGGAAAAGCTATACTCGATAAGGTTGAAGAGAAAC
TCGACTTGAAAAAGGAGAAATTCGTTGACTCACGACATGTGTTATCAGAGCACGGG
AATATGAGTTCATCCACAGTCTTGTTCGTAATGGATGAATTGCGAAAACGCTCTCTT
GAGGAGGGAAAGAGCACAACCGGTGACGGGTTTGAGTGGGGCGTGCTATTCGGTTT
TGGCCCAGGTTTGACTGTCGAGCGGGTTGTTGTTCGTAGTGTACCAATTAAGTACGG
AAGAAGGGCAAAGTTGTGATAAGAGTGACTCTTTTGATAAGAGTCGCAAATTTGATT
TCATAAGTATATATTCATTATGTAAAGTAGTAAATGGAAAATTCATTAAAAAAAAAG
CAAATTTCCGTTGTATGCATACTCCGAACACAAAACTAGCCCCGGAAAAACCCTTAG
TTGATAGTTGCGAATTTAGGTCGACCATATGCGACGGGTACAACGAGAATTGTATTG
AATTGATCAAGAACATGATCTTGGTGTTACAGAACATCAAGTTCTTGGACCAGACTG
AGAATGCACAGATATACAAGGCGTCATGTGATAAAATGGATGAGATTTATCCACAA
TTGAAGAAAGAGTTTATGGAAAGTGGTCAACCAGAAGCTAAACAGGAAGAAGCAA
ACGAAGAGGTGAAACAAGAAGAAGAAGGTAAATAAGTATTTTGTATTATATAACAA
ACAAAGTAAGGAATACAGATTTATACAATAAATTGCCATACTAGTCACGTGAGATA
TCTCATCCATTCCCCAACTCCCAAGAAAATAAAAAAGTGAAAAATAAAATCAAACC
CAAAGATCAACCTCCCCATCATCATCGTCATCAAACCCCCAGCTCAATTCGCAATGG
TTAGCACAAAAACATACACAGAAAGGGCATCAGCACACCCCTCCAAGGTTGCCCAA
CGTTTATTAATTAAAGGCTAGGTGGAGGCTCAGTGATGATAAGTCTGCGATGGTGGA
TGCATGTGTCATGGTCATAGCTGTTTCCTGTGTGAAATTGTTATCCGCTCAGAGGGC
ACAATCCTATTCCGCGCTATCCGACAATCTCCAAGACATTAGGTGGAGTTCAGTTCG
GCGTATGGCATATGTCGCTGGAAAGAACATGTGAGCAAAAGGCCAGCAAAAGGCCA
GGAACCGTAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATA
GCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAA
CTACGGCTACACTAGAAGAACAGTATTTGGTATCTGCGCTCTGCTGAAGCCAGTTAC
```

-continued

CTTCGGAAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCTCAAGAA

GATCCTTTGATCTTTTCTACGGGGTCTGACGCTCTATTCAACAAAGCCGCCGTCCCGT

CAAGTCAGCGTAAATGGGTAGGGGGCTTCAAATCGTCCGCTCTGCCAGTGTTACAAC

CAATTAACAAATTCTGATTAGAAAAACTCATCGAGCATCAAATGAAACTGCAATTTA

TTCATATCAGGATTATCAATACCATATTTTTGAAAAAGCCGTTTCTGTAATGAAGGA

GAAAACTCACCGAGGCAGTTCCATAGGATGGCAAGATCCTGGTATCGGTCTGCGATT

CCGACTCGTCCAACATCAATACAACCTATTAATTTCCCCTCGTCAAAAATAAGGTTA

TCAAGTGAGAAATCACCATGAGTGACGACTGAATCCGGTGAGAATGGCAAAAGCTT

ATGCATTTCTTTCCAGACTTGTTCAACAGGCCAGCCATTACGCTCGTCATCAAAATC

ACTCGCATCAACCAAACCGTTATTCATTCGTGATTGCGCCTGAGCGAGACGAAATAC

GCGATCGCTGTTAAAAGGACAATTACAAACAGGAATCGAATGCAACCGGCGCAGGA

ACACTGCCAGCGCATCAACAATATTTTCACCTGAATCAGGATATTCTTCTAATACCT

GGAATGCTGTTTTCCCGGGGATCGCAGTGGTGAGTAACCATGCATCATCAGGAGTAC

GGATAAAATGCTTGATGGTCGGAAGAGGCATAAATTCCGTCAGCCAGTTTAGTCTGA

CCATCTCATCTGTAACATCATTGGCAACGCTACCTTTGCCATGTTTCAGAAACAACTC

TGGCGCATCGGGCTTCCCATACAATCGATAGATTGTCGCACCTGATTGCCCGACATT

ATCGCGAGCCCATTTATACCCATATAAATCAGCATCCATGTTGGAATTTAATCGCGG

CCTCGAGCAAGACGTTTCCCGTTGAATATGGCTCATAACACCCCTTGTATTACTGTTT

ATGTAAGCAGACAGTTTTATTGTTCATGATGATATATTTTTATCTTGTGCAATGTAAC

ATCAGAGATTTTGAGACACAACGTGGCTTTCCCCCGCCGCTCTAGAACTAGTGGATC

CAAATAAAACGAAAGGCTCAGTCGAAAGACTGGGCCTTTCGTTTTATCTGTTGTTTG

TCGCATTATACGAGACGTCCAGGTTGGGATACCTGAAACAAAACCCATCGTACGGC

CAAGGAAGTCTCCAATAACTGTGATCCACCACAAGCGCCAGGGTTTTCCCAGTCACG

ACGTTGTAAAACGACGGCCAGTCATGCATAATCCGCACGCATCTGGAATAAGGAAG

TGCCATTCCGCCTGACCT pLD56

(SEQ ID NO: 165)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

-continued

```
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCCGCGAAAGATAATCAAAATTA
CACTTGTGAATTTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACataATGGGGTTGTCCTTAGTTTGTACGTT
CAGTTTCCAAACTAACTACCACACACTACTAAATCCGCACAACAAAAACCCGAAAA
ATTCATTGCTCTCCTATCAGCACCCAAAAACACCCATTATCAAGTCTAGTTACGACA
ACTTTCCATCAAAATACTGTCTAACGAAAAACTTTCATTTGTTGGGCTTAAATTCTCA
TAATCGTATTTCCAGTCAGTCCCGATCGATCAGGGCCGGGAGTGACCAAATTGAAGG
TTCTCCACATCATGAAAGTGACAATTCAATTGCTACGAAGATTTTAAACTTTGGGCA
TACATGCTGGAAGCTACAGCGACCGTATGTAGTTAAGGGGATGATCAGCATTGCCTG
CGGCCTATTCGGAAGGGAACTCTTCAATAATAGACATCTTTTTTCTTGGGGTTTAATG
TGGAAAGCTTTTTTCGCTTTGGTTCCTATCCTTAGTTTTAACTTCTTCGCCGCTATTAT
GAATCAAATTTACGATGTTGACATCGACCGTATTAACAAACCCGATCTCCCCCTTGT
TTCAGGCGAGATGTCCATTGAAACGGCATGGATTTTGTCCATCATTGTTGCGCTTACT
GGCTTGATTGTTACCATTAAGCTTAAAAGCGCTCCCTTGTTCGTTTTTATATACATTT
TCGGCATTTTTGCCGGATTCGCATACAGTGTCCCGCCTATACGTTGGAAACAATATC
CATTCACGAACTTCTTGATCACGATCTCATCACATGTTGGATTGGCCTTTACGTCCTA
CAGTGCTACCACATCTGCCCTTGGATTGCCTTTCGTTTGGAGGCCTGCCTTCTCGTTT
ATCATTGCATTTATGACAGTGATGGGAATGACTATCGCATTTGCTAAAGATATCAGC
GACATAGAGGGCGATGCAAAATATGGGGTGAGTACTGTTGCGACGAAGTTGGGCGC
CCGAAATATGACCTTCGTTGTTTCCGGCGTTCTTTTACTTAACTATTTAGTATCGATT
AGCATCGGGATCATCTGGCCACAGGTGTTTAAATCAAATATTATGATCTTGTCGCAT
GCCATCCTAGCTTTCTGTCTTATATTTCAAACAAGAGAATTAGCCCTAGCGAACTAC
GCCTCAGCACCAAGTCGTCAGTTCTTCGAATTTATATGGCTACTCTACTACGCCGAA
TACTTCGTCTATGTCTTCATTTAGTAATAAGAGTGACTCTTTTGATAAGAGTCGCAAA
TTTGATTTCATAAGTATATATTCATTATGTAAAGTAGTAAATGGAAAATTCATTAAA
AAAAAAGCAAATTTCCGTTGTATGCATACTCCGAACACAAAACTAGCCCCGGAAAA
ACCCTTAGTTGATAGTTGCGAATTTAGGTCGACCATATGCGACGGGTACAACGAGAA
TTGTATTGAATTGATCAAGAACATGATCTTGGTGTTACAGAACATCAAGTTCTTGGA
CCAGACTGAGAATGCACAGATATACAAGGCGTCATGTGATAAAATGGATGAGATTT
```

-continued

```
ATCCACAATTGAAGAAAGAGTTTATGGAAAGTGGTCAACCAGAAGCTAAACAGGAA

GAAGCAAACGAAGAGGTGAAACAAGAAGAAGAAGGTAAATAAGTATTTTGTATTAT

ATAACAAACAAAGTAAGGAATACAGATTTATACAATAAATTGCCATACTAGTCACG

TGAGATATCTCATCCATTCCCCAACTCCCAAGAAAATAAAAAAGTGAAAAATAAAA

TCAAACCCAAAGATCAACCTCCCCATCATCATCGTCATCAAACCCCCAGCTCAATTC

GCAATGGTTAGCACAAAAACATACACAGAAAGGGCATCAGCACACCCCTCCAAGGT

TGCCCAACGTTTATTAATTAAAGGCTAGGTGGAGGCTCAGTGATGATAAGTCTGCGA

TGGTGGATGCATGTGTCATGGTCATAGCTGTTTCCTGTGTGAAATTGTTATCCGCTCA

GAGGGCACAATCCTATTCCGCGCTATCCGACAATCTCCAAGACATTAGGTGGAGTTC

AGTTCGGCGTATGGCATATGTCGCTGGAAAGAACATGTGAGCAAAAGGCCAGCAAA

AGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTCAA

GAAGATCCTTTGATCTTTTCTACGGGGTCTGACGCTCTATTCAACAAAGCCGCCGTC

CCGTCAAGTCAGCGTAAATGGGTAGGGGGCTTCAAATCGTCCGCTCTGCCAGTGTTA

CAACCAATTAACAAATTCTGATTAGAAAAACTCATCGAGCATCAAATGAAACTGCA

ATTTATTCATATCAGGATTATCAATACCATATTTTTGAAAAAGCCGTTTCTGTAATGA

AGGAGAAAACTCACCGAGGCAGTTCCATAGGATGGCAAGATCCTGGTATCGGTCTG

CGATTCCGACTCGTCCAACATCAATACAACCTATTAATTTCCCCTCGTCAAAAATAA

GGTTATCAAGTGAGAAATCACCATGAGTGACGACTGAATCCGGTGAGAATGGCAAA

AGCTTATGCATTTCTTTCCAGACTTGTTCAACAGGCCAGCCATTACGCTCGTCATCAA

AATCACTCGCATCAACCAAACCGTTATTCATTCGTGATTGCGCCTGAGCGAGACGAA

ATACGCGATCGCTGTTAAAAGGACAATTACAAACAGGAATCGAATGCAACCGGCGC

AGGAACACTGCCAGCGCATCAACAATATTTTCACCTGAATCAGGATATTCTTCTAAT

ACCTGGAATGCTGTTTTCCCGGGGATCGCAGTGGTGAGTAACCATGCATCATCAGGA

GTACGGATAAAATGCTTGATGGTCGGAAGAGGCATAAATTCCGTCAGCCAGTTTAGT

CTGACCATCTCATCTGTAACATCATTGGCAACGCTACCTTTGCCATGTTTCAGAAAC

AACTCTGGCGCATCGGGCTTCCCATACAATCGATAGATTGTCGCACCTGATTGCCCG

ACATTATCGCGAGCCCATTTATACCCATATAAATCAGCATCCATGTTGGAATTTAAT

CGCGGCCTCGAGCAAGACGTTTCCCGTTGAATATGGCTCATAACACCCCTTGTATTA

CTGTTTATGTAAGCAGACAGTTTTATTGTTCATGATGATATATTTTTATCTTGTGCAA

TGTAACATCAGAGATTTTGAGACACAACGTGGCTTTCCCCCGCCGCTCTAGAACTAG

TGGATCCAAATAAAACGAAAGGCTCAGTCGAAAGACTGGGCCTTTCGTTTTATCTGT
```

-continued

TGTTTGTCGCATTATACGAGACGTCCAGGTTGGGATACCTGAAACAAAACCCATCGT

ACGGCCAAGGAAGTCTCCAATAACTGTGATCCACCACAAGCGCCAGGGTTTTCCCA

GTCACGACGTTGTAAAACGACGGCCAGTCATGCATAATCCGCACGCATCTGGAATA

AGGAAGTGCCATTCCGCCTGACCT pLD87

(SEQ ID NO: 166)
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

```
CGTCCAGGTTGGGATACCTGAAACAAAACCCATCGTACGGCCAAGGAAGTCTCCAA
TAACTGTGATCCACCACAAGCGCCAGGGTTTTCCCAGTCACGACGTTGTAAAACGAC
GGCCAGTCATGCATAATCCGCACGCATCTGGAATAAGGAAGTGCCATTCCGCCTGA
CCTTTAATTAAGTCGACTTGATGTTTAGAGTGTCCAGATCCGCAAGATCGGCTCGCA
CTTGTGTTGTGTTGTTTCAAATCAGCCTGTCGTTTTGTGTCGTTTGAGATCATTCTGTC
TCACTCTTAGGCTCGCTTAGAACCGACAACGGAGAATCCGGGCTCGGTTTTTCGGTC
GGCCTTGATCTGGGCCTTGGACTTGTACTGGTCGGCCATCTCCACGTTGACCAGCTC
CTTGACCTTGTAGAGCTGACCGGCGATACCAGGAGACACCTTGTAGTACTTCTGGGA
GCCGACCTTGCCCAGACCGAGGGTCTTGAGCACGTCACGTGTTCTCCACGGCATTCG
CAGGATAGATCGGACCTGTGTGACTTTGTAGAACATGGCGTTTCAGGTGGTTGCGTG
AGTGTGTAAAATCGTGTCTTTCAGAAGTTACAAATTTCACCGCATTTAGAGTTTATG
CAGATGGGCGGTGTGTGGTGGGAGTTCGATTTCCGTGCGTGCATTTGATCTTGATG
AATTGGATTTGTACATGGGAATAGCACGTCAAGAACCGCCTACTGCAAACTCGTG
AATATTGAGATTATTGAGGAAATTCAAGGAAAATTCAGATCAGATTTGAGAGCAAA
GTCCAACAATACTACACAATCCCTTTCCTGTATTCTTCCACCATCGTCATCGTCGTCT
GTCTTCTCTTCAGCTTTTTAATTTCACTCCCCACAAACCCAAATTTAGCTGCATCATT
CATCAACCTCCAATTATAACTATACATCGCGACACGAACACGAAACACGAACCACG
AACCGCCGCTTTGTCGACGGAGTGAGACGGGAGAGAGACCATGGTCTCTCGCTCGT
CTCACGCTTAGCGGCCGCGTCGACATAACTTCGTATAGCATACATTATACGAAGTTA
TTTTCTAATTTGGACCGATAGCCGTATAGTCCAGTCTATCTATAAGTTCAACTAACTC
GTAACTATTACCATAACATATACTTCACTGCCCCAGATAAGGTTCCGATAAAAAGTT
GTGCAGACTAAATTTATTTCAGTCTCCTCTTCACCACCAAAATGCCCTCCTACGAAG
CGCGAGCTAACGTCCACAAGTCCGCCTTTGCCGCCCGAGTGCTCAAGCTCGTGGCAG
CCAAGAAAACCAACCTGTGTGCTTCTCTGGATGTTACCACCACCAAGGAGCTCATTG
AGCTTGCCGATAAGGTCGGACCTTATGTGTGCATGATCAAGACCCATATCGACATCA
TTGACGACTTCACCTACGCCGGAACTGTGCTCCCCCTCAAGGAACTTGCTCTTAAGC
ACGGTTTCTTCCTGTTCGAGGACAGAAAGTTCGCAGATATTGGCAACACTGTCAAGC
ACCAGTACAAGAACGGTGTCTACCGAATCGCCGAGTGGTCCGATATCACCAACGCC
CACGGTGTACCCGGAACCGGAATCATTGCTGGCCTGCGAGCTGGTGCCGAGGAAAC
TGTCTCTGAACAGAAGAAGGAGGATGTCTCTGACTACGAGAACTCCCAGTACAAGG
AGTTCCTGGTCCCCTCTCCCAACGAGAAGCTGGCCAGAGGTCTGCTCATGCTGGCCG
AGCTGTCTTGCAAGGGCTCTCTGGCCACTGGCGAGTACTCCAAGCAGACCATTGAGC
TTGCCCGATCCGACCCCGAGTTTGTGGTTGGCTTCATTGCCCAGAACCGACCTAAGG
GCGACTCTGAGGACTGGCTTATTCTGACCCCCGGGGTGGGTCTTGACGACAAGGGA
GATGCTCTCGGACAGCAGTACCGAACTGTTGAGGATGTCATGTCTACCGGAACGGAT
ATCATAATTGTCGGCCGAGGTCTGTACGGCCAGAACCGAGATCCTATTGAGGAGGC
CAAGCGATACCAGAAGGCTGGCTGGGAGGCTTACCAGAAGATTAACTGTTAGAGGT
TAGACTATGGATATGTCATTTAACTGTGTATATAGAGAGCGTGCAAGTATGGAGCGC
TTGTTCAGCTTGTATGATGGTCAGACGACCTGTCTGATCGAGTATGTATGATACTGC
ACAACCTGATAACTTCGTATAGCATACATTATACGAAGTTATCTCGAGGGATCCCTA
GGGAGGCACATCTAAACGAATAACGAATATTAATGATACCATCATATCTCAGAACA
```

-continued

TGTATGACTGCTGCTTCCAAACGATATGAGGATGAGTCCTCTTTCAGATTAAGATAG

AGTACAAATATATTATCTATATACTGGTGTCTGTGCGATGTCGTATGAGCGGTGAAT

CATGTGACTGTCACGTGGTTTGGCCCAAGTTACACCGTAGCTACGCCTTTCTTGACC

GACTCCATGGTCTTCTGGGCGGGTTGACAGTTTCCACTGGATGAGCGTCCGCCTCCT

GTTCCTGTCGTTGTCCCTGCAGCTCAGCCTCAATCTTCTGACCGAGCTCGGAGTCCA

GGGAAATGCCAACAGGTTGTCCAAGCAACATCATGGTTTGGTGGGCAGCCGTGATC

TCATCGTCGTTGGATACCATTCGGTACTTGGCCTCAATCTGCACAAAGTAGCGGTAC

CACTGGTTTCGAGCAAACCGCTCCAATTGAGCCTCTCCGTCGAGAGAGAGAGTAGGT

GATTGCTCCAACTTGCGGCCAAAATGAAGTTCTCGACTCACCTTTTTGAAGCGGTTC

TTCTTGCCCATCTTGGTGGCGAAAGTAGTGGCTAGTGGTGGATGACTTTGTATAATG

TACCGATGAAGAGGGTTGTATTTGCTCAGTAAGAAGTAGCGAGTGAAATCAGATCA

CTTAACGAGAGCAAAGGGCAATGGAATACCTGCTGCCTGATTAACAACAGCTTCTGT

GTCGTTTCTCTCTTGTGAATGAGTGTGTTGCTAGAGGTAGGTTGGCACTCCAATGTTA

CTTAATTAA pLD101

(SEQ ID NO: 167)
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGTCTGACGCTCTATTCAACAAAGCCGCCGTCCCGTCAAGTCAGCGTAAAT

GGGTAGGGGGCTTCAAATCGTCCTCGTGATACCAATTCGGAGCCTGCTTTTTTGTAC

AAACTTGTTGATAATGGCAATTCAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCA

GTGCTGCAATGATACCGCGAGAGCCACGCTCACCGGCTCCAGATTTATCAGCAATA

AACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGT

-continued

```
ATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGG

ATACATATTTGAATGTATTTAGAAAAATAAACAAATAGGGGTTCCGCGCACATTTCC

CCGAAAAGTGCCAGATACCTGAAACAAAACCCATCGTACGGCCAAGGAAGTCTCCA

ATAACTGTGATCCACCACAAGCGCCAGGGTTTTCCCAGTCACGACGTTGTAAAACGA

CGGCCAGTCATGCATAATCCGCACGCATCTGGAATAAGGAAGTGCCATTCCGCCTG

ACCTTTAATTAACGATCCGCGTAAATTCAGAGCAATGCCAAGATCCTTATTTCCGAT

AACAGCGAGATACACATCAGAAGAGGTGGAGACTCTGGCCCCGCACGACCACCACG

TCGTCACTCAAAGCAAAGTCACGATGTAGAAATCACAATCGTCCCCATAAGCACGT

GGATTCCCCTGGTTTTGTTTCGGCCTCGGCAGTGGCAATTCTGGGGTATATAAACCA

GCAAGGTTATGACCTGATTGACCTGCTTGTGGCCTGATAAACCGCCTGACTTTTGTG

ATAAGGTTGGGAGCATGCGGCTCGGGCCATTGTGAGCATTTTCGTCAAGGACTGGCC

AAGTCCAACTGGAAGAGACATGGGCAAAATGTCGACTTTACAGATGTACCCGAAAT

TGCTTCAATTGCTCTCAGCTGCCGGAACCGGATCTATCGGTGCAAGTATCGTACAGT

AGACATGTGCTATTGGTAACCCTCGGTATTGGCTAGGTTTCGTATCAGGGATACAGT

TCAACGCTGATCGCATATGGCATGATTCCGGCTCGACACAGCGACCAAGAACCAAG

CGTGTATGTCGTAGACTTGCAAATCATGTGGGGCTTATCCCCGGATTTCCCCAAGTC

ACGTTTTCACAAAGGCTGTCTCCCGAATGCATGAGCCGAGGCAGGCTAAACTGGTTT

GTTCATGTACCCCACACAACGTAAAGATGCACCCCATGTGCAGTGAAATACCACAA

GTATATATATACCGACCTACCCGAGATAGCAAATTGATTCTACACTTACACTACCAA

TTCTTACATCAAACCAAACCGCTTGAGACCATCCGGTCTCTGATCATCCTCGAGATA

ACTTCGTATAATGTATGCTATACGAAGTTATCAGGTTGTGCAGTATCATACATACTC

GATCAGACAGGTCGTCTGACCATCATACAAGCTGAACAAGCGCTCCATACTTGCAC

GCTCTCTATATACACAGTTAAATGACATATCCATAGTCTAACCTCTAACAGTTAATCT

TCTGGTAAGCCTCCCAGCCAGCCTTCTGGTATCGCTTGGCCTCCTCAATAGGATCTC

GGTTCTGGCCGTACAGACCTCGGCCGACAATTATGATATCCGTTCCGGTAGACATGA

CATCCTCAACAGTTCGGTACTGCTGTCCGAGAGCATCTCCCTTGTCGTCAAGACCCA

CCCCGGGGGTCAGAATAAGCCAGTCCTCAGAGTCGCCCTTAGGTCGGTTCTGGGCA

ATGAAGCCAACCACAAACTCGGGGTCGGATCGGGCAAGCTCAATGGTCTGCTTGGA

GTACTCGCCAGTGGCCAGAGAGCCCTTGCAAGACAGCTCGGCCAGCATGAGCAGAC

CTCTGGCCAGCTTCTCGTTGGGAGAGGGGACCAGGAACTCCTTGTACTGGGAGTTCT

CGTAGTCAGAGACATCCTCCTTCTTCTGTTCAGAGACAGTTTCCTCGGCACCAGCTC

GCAGGCCAGCAATGATTCCGGTTCCGGGTACACCGTGGGCGTTGGTGATATCGGACC
```

-continued

```
ACTCGGCGATTCGGTAGACACCGTTCTTGTACTGGTGCTTGACAGTGTTGCCAATAT
CTGCGAACTTTCTGTCCTCGAACAGGAAGAAACCGTGCTTAAGAGCAAGTTCCTTGA
GGGGGAGCACAGTTCCGGCGTAGGTGAAGTCGTCAATGATGTCGATATGGGTCTTG
ATCATGCACACATAAGGTCCGACCTTATCGGCAAGCTCAATGAGCTCCTTGGTGGTG
GTAACATCCAGAGAAGCACACAGGTTGGTTTTCTTGGCTGCCACGAGCTTGAGCACT
CGGGCGGCAAAGGCGGACTTGTGGACGTTAGCTCGCGCTTCGTAGGAGGGCATTTT
GGTGGTGAAGAGGAGACTGAAATAAATTTAGTCTGCACAACTTTTTATCGGAACCTT
ATCTGGGCAGTGAAGTATATGTTATGGTAATAGTTACGAGTTAGTTGAACTTATAG
ATAGACTGGACTATACGGCTATCGGTCCAAATTAGAAAATAACTTCGTATAATGTAT
GCTATACGAAGTTATGTCGACGCGGCCGCACAAGCACTACATGGACGAGGTCAAGG
CTGCCAACAACCCTCGTAACACCCATGCTCCTTACTACGAGACAAAGCTGCGACCCT
TCCTGTTCCGACCCGATGAGGACGAGGAGATTTGCGACCTGGACGAGTAGGTTGTTG
TAATACTATGATTTATTGTGTTTATATGTTATTGATACTATTGAAAGAGTTATTGTGT
AATTTTAGATGCTGTATGTTAACTAGAAGCTCAGATTCTACAAAGAGATCCTCAGAT
CTGAGGAATGATCTACGTTCTGCAATAGAAGGGACAACTGCAGCTCTGAATGACCA
CAAAAAGAATACACCACAAGCAGTTGTAACTGAGCTATTAGCCTTGCTTTCGCACCA
TTCGCTTTTCTGGATGGTAGCCCTTTACTACAAGTAGCTAATATGGAATGTACATTAC
CGTCTCATTACAATATGTATATGCAAGTTCATGGCACTTCATGCACACCAGCCCCTTC
GTTAAGTACCTTCCAAAAAGTGATCAATGATAAGTGATATATCTAATTTAGAGATCT
GGACACACGAACAAGTCGGGAACACAAATCCCGAGATGATTGCCTGCTCAGAGGAG
TCCAATTAGTCTTTACACCATTCGTGCTAATGAAGGGCACAGAATATTCCACTTTGA
AAGTTTAAGATTAAGCTCGGCTCGCAATTATGCATGAAAAATATGTAGGGAGAGAA
CGATCCCACGAGTTCTGTTTGGTTGCGAGAGTGTTCGGGTTTTCTCCTAAAAAGAAT
AGGGGAGGGAAAAATTATCGCCTAAGTCACCATTAATTAA
``` pLD102

(SEQ ID NO: 168)
```
AGGCTAGGTGGAGGCTCAGTGATGATAAGTCTGCGATGGTGGATGCATGTGTCATG
GTCATAGCTGTTTCCTGTGTGAAATTGTTATCCGCTCAGAGGGCACAATCCTATTCCG
CGCTATCCGACAATCTCCAAGACATTAGGTGGAGTTCAGTTCGGCGTATGGCATATG
TCGCTGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAG
AAGAACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTT
```

-continued

```
CTACGGGGTCTGACGCTCTATTCAACAAAGCCGCCGTCCCGTCAAGTCAGCGTAAAT

GGGTAGGGGGCTTCAAATCGTCCTCGTGATACCAATTCGGAGCCTGCTTTTTTGTAC

AAACTTGTTGATAATGGCAATTCAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCA

GTGCTGCAATGATACCGCGAGAGCCACGCTCACCGGCTCCAGATTTATCAGCAATA

AACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGT

ATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGG

ATACATATTTGAATGTATTTAGAAAAATAAACAAATAGGGGTTCCGCGCACATTTCC

CCGAAAAGTGCCAGATACCTGAAACAAAACCCATCGTACGGCCAAGGAAGTCTCCA

ATAACTGTGATCCACCACAAGCGCCAGGGTTTTCCCAGTCACGACGTTGTAAAACGA

CGGCCAGTCATGCATAATCCGCACGCATCTGGAATAAGGAAGTGCCATTCCGCCTG

ACCTTTAATTAATTGGCAAATTTTACTGTGGCCTTCAGAACGGTAAAAATAGACCAA

TCAGAATTCTGAAAAGCACATCTTGATCTCCTCATTGCGGGGAGTCCAACGGTGGTC

TTATTCCCCCGAATTTCCCGCTCAATCTCGTTCCAGACCGACCCGGACACAGTGCTT

AACGCCGTTCCGAAACTCTACCGCAGATATGCTCCAACGGACTGGGCTGCATAGAT

GTGATCCTCGGCTTGGAGAAATGGATAAAAGCCGGCCAAAAAAAAAGCGGAAAAA

AGCGGAAAAAAGAGAAAAAAAATCGCAAAATTTGAAAAATAGGGGGAAAAGACG

CAAAAACGCAAGGAGGGGGAGTATATGACACTGATAAGCAAGCTCACAACGGTTC

CTCTTATTTTTTCCTCATCTTCTGCCTAGGTTCCCAAAATCCCAGATGCTTCTCTCCA

GTGCCAAAAGTAAGTACCCCACAGGTTTTCGGCCGAAAATTCCACGTGCAGCAACG

TCGTGTGGGGTGTTAAAATGTGGGGCGGGGAACCAGGACAAGAGGCTCTTGTGGG

AGCCGAATGAGAGCACAAAGCGGGCGGGTGTGATAAGGGCATTTTTGCCCATTTTC

CCTTCTCCTGTCTCTCCGACGGTGATGGCGTTGTGCGTCCTCTATCTATTTCTTTTTAT

TTCTTTTTGTTTTATTTCTCTGACTACCGATTTGGCTTGATTTCCTCAACCCCACACAA

ATAAGCTCGGGCCGAGGAATATATATATACACGGACACAGTCGCCCTGTGGACAAC

ACGTCACTACCTCTACGACGCTTGAGACCATCCGGTCTCTGATCATCCTCGAGATAA

CTTCGTATAATGTATGCTATACGAAGTTATCAGGTTGTGCAGTATCATACATACTCG

ATCAGACAGGTCGTCTGACCATCATACAAGCTGAACAAGCGCTCCATACTTGCACGC
```

-continued

```
TCTCTATATACACAGTTAAATGACATATCCATAGTCTAACCTCTAACAGTTAATCTTC

TGGTAAGCCTCCCAGCCAGCCTTCTGGTATCGCTTGGCCTCCTCAATAGGATCTCGG

TTCTGGCCGTACAGACCTCGGCCGACAATTATGATATCCGTTCCGGTAGACATGACA

TCCTCAACAGTTCGGTACTGCTGTCCGAGAGCATCTCCCTTGTCGTCAAGACCCACC

CCGGGGGTCAGAATAAGCCAGTCCTCAGAGTCGCCCTTAGGTCGGTTCTGGGCAATG

AAGCCAACCACAAACTCGGGGTCGGATCGGGCAAGCTCAATGGTCTGCTTGGAGTA

CTCGCCAGTGGCCAGAGAGCCCTTGCAAGACAGCTCGGCCAGCATGAGCAGACCTC

TGGCCAGCTTCTCGTTGGGAGAGGGGACCAGGAACTCCTTGTACTGGGAGTTCTCGT

AGTCAGAGACATCCTCCTTCTTCTGTTCAGAGACAGTTTCCTCGGCACCAGCTCGCA

GGCCAGCAATGATTCCGGTTCCGGGTACACCGTGGGCGTTGGTGATATCGGACCACT

CGGCGATTCGGTAGACACCGTTCTTGTACTGGTGCTTGACAGTGTTGCCAATATCTG

CGAACTTTCTGTCCTCGAACAGGAAGAAACCGTGCTTAAGAGCAAGTTCCTTGAGGG

GGAGCACAGTTCCGGCGTAGGTGAAGTCGTCAATGATGTCGATATGGGTCTTGATCA

TGCACACATAAGGTCCGACCTTATCGGCAAGCTCAATGAGCTCCTTGGTGGTGGTAA

CATCCAGAGAAGCACACAGGTTGGTTTTCTTGGCTGCCACGAGCTTGAGCACTCGGG

CGGCAAAGGCGGACTTGTGGACGTTAGCTCGCGCTTCGTAGGAGGGCATTTTGGTGG

TGAAGAGGAGACTGAAATAAATTTAGTCTGCACAACTTTTTATCGGAACCTTATCTG

GGGCAGTGAAGTATATGTTATGGTAATAGTTACGAGTTAGTTGAACTTATAGATAGA

CTGGACTATACGGCTATCGGTCCAAATTAGAAAATAACTTCGTATAATGTATGCTAT

ACGAAGTTATGTCGACGCGGCCGCATGGAGCGTGTGTTCTGAGTCGATGTTTTCTAT

GGAGTTGTGAGTGTTAGTAGACATGATGGGTTTATATATGATGAATGAATAGATGTG

ATTTTGATTTGCACGATGGAATTGAGAACTTTGTAAACGTACATGGGAATGTATGAA

TGTGGGGGTTTTGTGACTGGATAACTGACGGTCAGTGGACGCCGTTGTTCAAATATC

CAAGAGATGCGAGAAACTTTGGGTCAAGTGAACATGTCCTCTCTGTTCAAGTAAACC

ATCAACTATGGGTAGTATATTTAGTAAGGACAAGAGTTGAGATTCTTTGGAGTCCTA

GAAACGTATTTTCGCGTTCCAAGATCAAATTAGTAGAGTAATACGGGCACGGGAAT

CCATTCATAGTCTCAATTTTCCCATAGGTGTGCTACAAGGTGTTGAGATGTGGTACA

GTACCACCATGATTCGAGGTAAAGAGCCCAGAAGTCATTGATGAGGTCAAGAAATA

CACAGATCTACAGCTCAATACAATGAATATCTTCTTTCATATTCTTCAGGTGACACC

AAGGGTGTCTATTTTCCCCAGAAATGCGTGAAAAGGCGCGTGTGTAGCGTGGAGTAT

GGGTTCGGTTGGCGTATCCTTCATATATCGACGAAATAGTAGGGCAAGAGATGACA

AAAAGTATCTATATGTAGACAGCGTAGAATATGGATTTGATTGGTATAAATTCATTT

ATTGCGTGTCTCACAAATACTCTCGATAAGTTGGGGTTAAACTGGAGATGGAACAAT

GTCGATATCTCGACATATTTTGATATTTGTTAATTAA
``` pLD111

(SEQ ID NO: 169)

```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG
```

-continued

```
GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATTGTTCAGCATTTAGTTTTTG

GTTTGTTTGTAAGATTATTTTCTTCTTTTTGTCATTTAACATTCAAATTTCAATTGCAA

ACCCACAAGAAAACTTTTTGAAGTGTTTTTCAGAATACATTCCAAACAATCCAGCTA

ACCCAAAGTTTATTTACACACAACATGATCAATTGTACATGTCAGTTTTGAACTCAA

CAATTCAAAACTTGAGATTTACATCAGATACCACACCAAAGCCATTGGTTATTGTTA

CACCATCAAACGTTTCCCATATTCAAGCATCAATCTTGTGTTCAAAGAAGGTTGGAT

TGCAAATTAGAACCAGATCAGGAGGACACGATGCAGAAGGAATGTCATACATTTCA

CAAGTTCCATTCGTTGTTGTTGATTTGAGAAACATGCACTCAATTAAGATTGATGTTC

ATTCACAAACAGCATGGGTTGAAGCAGGAGCAACATTGGGTGAAGTTTACTACTGG

ATTAACGAAAAGAACGAAAACTTCAGTTTTCCAGGAGGTTACTGTCCAACAGTTGG

AGTTGGAGGACATTTTTCAGGTGGAGGATACGGAGCATTGATGAGAAACTACGGAT

TGGCAGCAGATAACATTATTGATGCACACTTGGTTAACGTTGATGGAAAGGTTTTGG

ATAGAAAGTCAATGGGAGAAGATTTGTTTTGGGCAATTAGAGGAGGTGGTGGAGAG

AACTTTGGAATTATTGCAGCATGGAAGATCAAGTTGGTTGCAGTTCCATCAAAGTCA

ACAATCTTTTCAGTTAAGAAGAACATGGAAATTCATGGTTTGGTTAAGTTGTTTAAC

AAGTGGCAAAACATTGCATACAAGTACGATAAGGATTTGGTTTTGATGACACATTTT

ATTACAAAGAACATTACAGATAACCATGGAAAGAACAAGACAACAGTTCACGGATA

CTTTTCATCAATTTTTCACGGAGGAGTTGATTCATTGGTTGACTTGATGAACAAGTCA

TTTCCAGAATTGGGAATCAAGAAGACAGATTGTAAGGAATTTTCATGGATTGATACA
```

-continued

```
ACAATTTTCTACTCAGGAGTTGTTAACTTTAACACAGCAAACTTTAAGAAGGAAATT

TTGTTGGACAGATCAGCAGGAAAGAAGACCGCATTTTCCATTAAGTTGGATTACGTT

AAGAAACCAATTCCAGAAACAGCAATGGTTAAGATTTTGGAAAAGTTGTACGAAGA

AGATGTTGGTGTTGGAATGTACGTTTTGTACCCATACGGAGGAATTATGGAAGAAAT

CTCAGAATCAGCAATTCCATTTCCACATAGAGCAGGTATTATGTACGAATTGTGGTA

CACAGCATCATGGGAAAAGCAAGAAGATAATGAAAAGCATATTAACTGGGTTAGAT

CAGTTTACAACTTTACAACACCATACGTTTCACAAAACCCAAGATTGGCATACTTGA

ACTACAGAGATTTGGATTTGGGAAAGACAAACCCAGAATCACCAAACAACTATACA

CAAGCTAGAATTTGGGGAGAAAAGTACTTTGGTAAGAACTTCAACAGATTGGTTAA

AGTTAAGACAAAGGCAGATCCAAATAACTTCTTTAGAAACGAACAATCAATTCCAC

CATTGCCACCACATCATCATTAATAAGAGTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC

CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGCTTCAAATCGTCCGCTCTGCCAGTGTTACA

ACCAATTAACAAATTCTGATTAGAAAAACTCATCGAGCATCAAATGAAACTGCAATT
```

-continued

TATTCATATCAGGATTATCAATACCATATTTTTGAAAAAGCCGTTTCTGTAATGAAG

GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT pLD112

(SEQ ID NO: 170)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

-continued

```
CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATTGTAGCACTTTCTCATTCTG

GTTTGTTTGTAAGATTATTTTCTTTTTCTTGTCATTTAACATTCAAATTTCAATTGCAA

ACCCACAAGAGAACTTTTTGAAGTGTTTCTCAGAATACATTCCAAACAACCCAGCTA

ACCCAAAGTTTATTTACACCCAACACGATCAATTGTACATGTCAGTTTTGAACTCAA

CAATTCAAAACTTGAGATTTACATCAGATACAACACCAAAGCCATTGGTTATTGTTA

CACCATCAAACGTTAGTCATATTCAAGCATCAATCTTGTGTTCAAAGAAGGTTGGAT

TGCAAATTAGAACTAGATCAGGAGGACATGATGCAGAAGGATTGTCATACATTTCA

CAAGTTCCATTTGCAATTGTTGATTTGAGAAACATGCACACAGTTAAGGTTGATATT

CATTCACAAACAGCATGGGTTGAAGCAGGAGCAACATTGGGTGAAGTTTACTACTG

GATTAACGAAATGAACGAAAACTTCTCATTTCCAGGAGGATACTGTCCAACAGTTGG

TGTTGGAGGACACTTTTCAGGTGGTGGATACGGAGCATTGATGAGAAACTACGGATT

GGCAGCAGATAACATTATTGATGCACATTTGGTTAACGTTGATGGAAAGGTTTTGGA

TAGAAAGTCAATGGGAGAAGATTTGTTTTGGGCAATTAGAGGAGGTGGAGGAGAAA

ACTTTGGAATCATTGCAGCATGTAAGATCAAGTTGGTTGTTGTTCCATCAAAGGCAA

CAATCTTTTCAGTTAAGAAGAACATGGAAATCCATGGATTGGTTAAGTTGTTTAACA

AGTGGCAAAACATTGCATACAAGTACGATAAGGATTTGATGTTGACAACACATTTTA

GAACAAGAAACATTACAGATAACCACGGAAAGAATAAGACAACAGTTCATGGATAC

TTTTCATCAATTTTCTTGGGAGGAGTTGATTCATTGGTTGACTTGATGAACAAGAGTT

TTCCAGAATTGGGAATCAAGAAGACAGATTGTAAGGAATTGTCATGGATCGATACA

ACCATTTTCTACTCAGGAGTTGTTAACTACAACACAGCTAACTTTAAGAAGGAAATT

TTGTTGGACAGATCAGCAGGTAAAAAGACAGCATTTTCAATTAAGTTGGATTACGTT

AAGAAATTGATTCCAGAAACAGCAATGGTTAAGATTTTGGAAAAGTTGTACGAAGA

AGAAGTTGGAGTTGGAATGTACGTTTTGTACCCATACGGAGGAATTATGGATGAAAT

TTCAGAATCAGCAATTCCATTTCCACATAGAGCAGGTATTATGTACGAATTGTGGTA

CACAGCAACATGGGAAAAGCAAGAAGATAACGAAAAGCATATTAACTGGGTTAGAT

CAGTTTACAACTTTACAACCCCATACGTTTCACAAAACCCAAGATTGGCATACTTGA

ACTACAGAGATTTGGATTTGGGAAAGACAAACCCAGAATCACCAAATAACTACACA

CAAGCTAGAATTTGGGGAGAAAAGTACTTTGGTAAGAACTTTAACAGATTGGTGAA

GGTTAAGACAAAGGCAGACCCAAACAATTTCTTTAGAAACGAACAATCAATTCCAC

CATTGCCACCAAGACATCATTAATAAGAGTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC
```

-continued

```
CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGGCTTCAAATCGTCCGCTCTGCCAGTGTTACA

ACCAATTAACAAATTCTGATTAGAAAAACTCATCGAGCATCAAATGAAACTGCAATT

TATTCATATCAGGATTATCAATACCATATTTTTGAAAAAGCCGTTTCTGTAATGAAG

GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT
```

```
GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT
``` pLD113

(SEQ ID NO: 171)
```
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT
```

-continued

```
TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTAAATTATTGGCCCGAAAATTAATCAGTGTAGACTGGATCCTC

GAGAACCATTTAATTAACAAGTCGAGAACGTACCACTGTCCTCCACTACAAACACA

CCCAATCTGCTTCTTCCTAGTCAAGGTTGCTACACCGGTAAATTATAAATCATCATTTC

ATTAGCAGGGCTGGGCCCTTTTTATAGAGTCTTATACACTAGCGGACCCTGCCGGTA

GACCAACCCGCAGGCGCGTCAGTTTGCTCCTTCCATCAATGCGTCGTAGAAACGACT

TACTCCTTCTTGAGCAGCTCCTTGACCTTGTTGGCAACAAAGTCTCCGACCTCGGAG

GTGGAGGAGGAGCCTCCGATATCGGCGGTAGTGATACCAGCCTCGACGGACTCCTT

GACGGCAGCCTCAACAGCGTCACCGGCGGGCTTCATGTTAAGAGAGAACTTGAGCA

TCATGGCGGCAGACAGAATGGTGGCAATGGGGTTGACCTTCTGCTTGCCGAGATCG

GGGGCAGATCCGTGACAGGGCTCGTACAGACCGAACGCCTCGTTGGTGTCGGGCAG

AGAAGCCAGAGAGGCGGAGGGCAGCAGACCCAGAGAACCGGGGATGACGGAGGCC

TCGTCGGAGATGATATCGCCAAACATGTTGGTGGTGATGATGATACCATTCATCTTG

GAGGGCTGCTTGATGAGGATCATGGCGGCCGAGTCGATCAGCTGGTGGTTGAGCTC
```

-continued

```
CAGCTGGGGGAATTCGTCCTTGAGGACTCGGGTGACGGTCTTTCGCCAAAGTCGAGA

GGAGGCCAGCACGTTGGCCTTGTCAAGGGACCACACGGGAAGAGGGGGGTTGTGCT

GAAGGGCCAGGAAGGCGGCCATTCGGGCAATTCGCTCAACCTCAGGAACGGAGTAA

GTCTCAGTGTCGGAAGCGACGCCAGATCCGTCATCCTCCTTTCGCTCTCCAAAGTAG

ATACCTCCGACGAGCTCTCGGACAATGATGAAGTCGGTGCCCTCAACGTTTCGGATG

GGGGAGAGATCGGCGAGCTTGGGCGACAGCAGCTGGCAGGGTCGCAGGTTGGCGTA

CAGGTTCAGGTCCTTTCGCAGCTTGAGAAGACCCTGCTCGGGTCGCACGTCGGTTCG

TCCGTCGGGAGTGGTCCATACGGTGTTGGCAGCGCCTCCGACAGCACCGAGCATAA

TAGAGTCAGCCTTTCGGCAGATGTCGAGAGTAGCGTCGGTGATGGGCTCGCCCTCCT

TCTCAATGGCAGCTCCTCCAATGAGTCGGTCCTCAAACACAAACTCGGTGCCGGAGG

CCTCAGCAACAGACTTGAGCACCTTGACGGCCTCGGCAATCACCTCGGGGCCACAG

AAGTCGCCGCCGAGAAGAACAATCTTCTTGGAGTCAGTCTTGGTCTTCTTAGTTTCG

GGTTCCATTGTGGATGTGTGTGGTTGTATGTGTGATGTGGTGTGTGGAGTGAAAATC

TGTGGCTGGCAAACGCTCTTGTATATATACGCACTTTTGCCCGTGCTATGTGGAAGA

CTAAACCTCCGAAGATTGTGACTCAGGTAGTGCGGTATCGGCTAGGGACCCAAACCT

TGTCGATGCCGATAGCGCTATCGAACGTACCCCAGCCGGCCGGGAGTATGTCGGAG

GGGACATACGAGATCGTCAAGGGTTTGTGGCCAACTGGTAAATAAATGATGACTCA

GGCGACGACGGAATTCGACAGCAACTACTCCTTTCACCAACCATGTGCATTTTAGCT

CGAATAACATTCACAGGCTTGGTGATCTACATCCATGGTGTCTGGCCGATTACCGTG

GTGTTTTGGCAGTAACGAGAATATTGAGTGAACTCTTCCCATCACCAATAAAGACTC

ATACTACAATCACGAGCGCTTCAGCTGCCACTATAGTGTTGGTGACACAATACCCCT

CGATGCTGGGCATTACTGTAGCAAGAGATATTATTTCATGGCGCATTTTCCAGTCTA

CCTGACTTTTTAGTGTGATTTCTTCTCCACATTTTATGCTCAGTGTGAAAAGTTGGAG

TGCACACTTAATTATCGCCGGTTTTCGGAAAGTACTATGTGCTCAAGGTTGCACCCC

ACGTTACGTATGCAGCACATTGAGCAGCCTTTGGACCGTGGAGATAACGGTGTGGA

GATAGCAACGGGTAGTCTTCGTATTAATTCAATGCATTGTTAGTTTTATATGATATGG

TGTCGAGCGGCCGCGACCGGGTTGGCGGCGCATTTGTGTCCCAAAAAACAGCCCCA

ATTGCCCCAATTGACCCCAAATTGACCCAGTAGCGGGCCCAACCCCGGCGAGAGCC

CCCTTCTCCCCACATATCAAACCTCCCCCGGTTCCCACACTTGCCGTTAAGGGCGTA

GGGTACTGCAGTCTGGAATCTACGCTTGTTCAGACTTTGTACTAGTTTCTTTGTCTGG

CCATCCGGGTAACCCATGCCGGACGCAAAATAGACTACTGAAAATTTTTTTGCTTTG

TGGTTGGGACTTTAGCCAAGGGTATAAAAGACCACCGTCCCCGAATTACCTTTCCTC

TTCTTTTCTCTCTCCTTGTCAACTCACACCCGAAATCGTTAAGCATTTCCTTCTGAG

TATAAGAATCATTCAAAATGTCCAACCTCCTCACCGTCCACCAGAACCTTCCCGCCC

TTCCCGTGGACGCCACCTCCGACGAGGTCCGAAAGAACCTCATGGACATGTTCCGA

GATCGACAGGCCTTCTCCGAGCACACTTGGAAGATGCTCCTCTCCGTCTGCCGATCC

TGGGCCGCCTGGTGCAAGCTCAACAACCGAAAGTGGTTCCCCGCCGAGCCCGAGGA

CGTCCGAGACTACCTCCTTTACCTCCAGGCCCGAGGCCTCGCCGTCAAGACCATCCA

GCAGCACCTCGGCCAGCTCAACATGCTCCACCGACGATCCGGCCTCCCCCGACCCTC

CGACTCCAACGCCGTGTCCCTCGTCATGCGACGAATCCGAAAGGAGAACGTGGACG
```

-continued

```
CCGGCGAGCGAGCCAAGCAGGCCCTTGCCTTCGAGCGAACCGACTTCGACCAGGTC

CGATCCCTCATGGAGAACTCCGACCGATGCCAGGACATCCGAAACCTCGCCTTCCTT

GGCATCGCCTACAACACCCTCCTTCGAATCGCCGAGATCGCCCGAATCCGAGTCAAG

GACATCTCCCGAACCGACGGCGGCCGAATGCTCATCCACATCGGCCGAACCAAGAC

CCTCGTGTCCACCGCCGGCGTCGAGAAGGCCCTCTCCCTCGGCGTCACCAAGCTCGT

CGAGCGATGGATCTCCGTGTCCGGCGTCGCTGACGACCCCAACAACTACCTCTTCTG

CCGAGTCCGAAAGAACGGCGTCGCTGCTCCCTCCGCCACCTCCCAGCTCTCCACCCG

AGCCCTTGAGGGCATCTTCGAGGCCACCCACCGACTCATCTACGGCGCCAAGGACG

ACTCCGGCCAGCGATACCTCGCCTGGTCCGGCCACTCTGCTCGAGTCGGTGCCGCCC

GAGACATGGCCCGAGCCGGTGTCTCCATCCCCGAGATCATGCAGGCCGGCGGCTGG

ACCAACGTCAACATCGTCATGAACTACATCCGAAACCTCGACTCCGAGACTGGCGC

CATGGTCCGACTTCTTGAGGACGGCGACTGATGATCATATGATTACATTAATAGCTA

ATTACGTGTATCCGATATATATACTAATTACAATAGTACATATTAGAACATACAATA

GTTTTAATTAA
``` pLD125

(SEQ ID NO: 172)
```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT
```

```
CTTCTGCTTTTCCTTATTTTTGTTATATTTATTTACCATCCCTTATTTTGAATAGTTATT

CCCCACTAACATTGTTCAAATCTTCACGACATAATGTTCTTGAAACACATTTTTGTTG

CTCTCGCTTTTGCCTTGTTAGCTGACGCTACCCCAGCCCAGAAGAGATCTCCCGGCTT

CGTTGCTTTAGACTTTGACATCGTCAAGGTTCAAAAGAACGTGACTGCCAACGACGA

CGCCGCTGCCATTGTTGCCAAGAGACAGACCAACCCAAGGGAAAACTTCCTTAAGT

GTTTTCTGCAGTACATCCCTAACAATGCAACAAACCTCAAGTTGGTGTACACTCAAA

ACAATCCACTCTATATGAGCGTGCTTAATAGCACAATCCACAACTTGCGCTTCACGT

CAGATACTACGCCTAAGCCACTAGTGATCGTTACACCATCACACGTCAGCCATATTC

AAGGAACGATCCTATGTCTGAAAAAGGTCGGGTTGCAAATCAGGACTCGATCAGGA

GGGCACGATAGTGAGGGAATGAGTTACATCTCGCAAGTACCCTTCGTGATAGTTGAC

TTGCGAAATATGCGGTCTATTAAAATTGACGTACATAGCCAGACCGCCTGGGTTGAA

GCAGGGGCAACCTTGGGTGAAGTTTATTACTGGGTCAATGAAAAAAACGAAAACCT

AAGTCTTGCTGCTGGATATTGCCCCACCGTTTGCGCGGGTGGTCATTTTGGAGGCGG

CGGATATGGTCCGTTGATGAGAAATTATGGACTTGCAGCAGACAATATTATAGATGC

CCACTTGGTGAACGTTCATGGAAAGGTCTTGGACCGTAAGTCCATGGGTGAAGATCT

TTTCTGGGCCTTGAGAGGTGGTGGAGCGGAATCGTTTGGCATCATCGTTGCCTGGAA

AATTAGGTTGGTTGCGGTCCCGAAGAGTACAATGTTCTCCGTGAAGAAGATTATGGA

AATACATGAGCTTGTCAAGTTAGTTAACAAGTGGCAAAATATCGCTTATAAGTATGA

TAAAGACTTGCTTTTGATGACTCATTTTATTACGCGAAACATAACCGATAACCAGGG

CAAGAACAAGACTGCTATTCACACGTACTTCTCCTCTGTATTTCTTGGAGGAGTAGA

CTCCTTAGTTGACTTGATGAACAAGAGTTTCCCAGAATTGGGGATTAAGAAGACAGA

TTGCAGACAATTATCGTGGATAGATACAATCATATTCTATAGCGGTGTCGTCAATTA

CGATACTGATAATTTTAATAAAGAAATCCTCCTAGATCGTTCAGCTGGGCAAAACGG

GGCATTCAAAATTAAATTGGATTATGTGAAGAAACCAATTCCAGAGCTGGTGTTTGT

TCAGATATTGGAAAAACTTTACGAAGAAGACATTGGCGCAGGTATGTACGCTTTGTA

TCCATATGGAGGCATTATGGACGAGATCTCAGAGCTGGCGATCCCCTTCCCGCACAG

AGCTGGGATACTCTACGAGCTATGGTACATCTGCTCTTGGGAGAAACAAGAAGACA

ACGAGAAACATCTCAATTGGATTCGGAACATATACAACTTTATGACCCCATACGTAT

CAAAAAACCCGCGCTTAGCATACTTGAATTACAGAGACTTAGATATCGGTATCAATG

ATCCTAAGAATCCTAACAATTACACCCAAGCCCGTATTTGGGGTGAGAAATATTTCG

GCAAGAATTTTGACAGATTAGTTAAGGTCAAAACACTCGTGGACCCCAACAACTTTT

TCCGAAACGAGCAGTCGATTCCACCACTACCCAGGCATAGACACTGAGAGTGACTC

TTTTGATAAGAGTCGCAAATTTGATTTCATAAGTATATATTCATTATGTAAAGTAGTA

AATGGAAAATTCATTAAAAAAAAAGCAAATTTCCGTTGTATGCATACTCCGAACAC

AAAACTAGCCCCGGAAAAACCCTTAGTTGATAGTTGCGAATTTAGGTCGACCATATG

CGACGGGTACAACGAGAATTGTATTGAATTGATCAAGAACATGATCTTGGTGTTACA

GAACATCAAGTTCTTGGACCAGACTGAGAATGCACAGATATACAAGGCGTCATGTG

ATAAAATGGATGAGATTTATCCACAATTGAAGAAAGAGTTTATGGAAAGTGGTCAA

CCAGAAGCTAAACAGGAAGAAGCAAACGAAGAGGTGAAACAAGAAGAAGAAGGTA

AATAAGTATTTTGTATTATATAACAAACAAAGTAAGGAATACAGATTTATACAATAA
```

-continued

```
ATTGCCATACTAGTCACGTGAGATATCTCATCCATTCCCCAACTCCCAAGAAAATAA

AAAAGTGAAAAATAAAATCAAACCCAAAGATCAACCTCCCCATCATCATCGTCATC

AAACCCCCAGCTCAATTCGCAATGGTTAGCACAAAAACATACACAGAAAGGGCATC

AGCACACCCCTCCAAGGTTGCCCAACGTTTATTAATTAAAGGCTAGGTGGAGGCTCA

GTGATGATAAGTCTGCGATGGTGGATGCATGTGTCATGGTCATAGCTGTTTCCTGTG

TGAAATTGTTATCCGCTCAGAGGGCACAATCCTATTCCGCGCTATCCGACAATCTCC

AAGACATTAGGTGGAGTTCAGTTCGGCGTATGGCATATGTCGCTGGAAAGAACATG

TGAGCAAAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGCTG

CGCCTTATCCGGTAACTATCGTCTTGAGTCCAACCCGGTAAGACACGACTTATCGCC

ACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGAACAGTATTTGGTA

TCTGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCTGACGCTC

TATTCAACAAAGCCGCCGTCCCGTCAAGTCAGCGTAAATGGGTAGGGGGCTTCAAA

TCGTCCGCTCTGCCAGTGTTACAACCAATTAACAAATTCTGATTAGAAAAACTCATC

GAGCATCAAATGAAACTGCAATTTATTCATATCAGGATTATCAATACCATATTTTG

AAAAAGCCGTTTCTGTAATGAAGGAGAAAACTCACCGAGGCAGTTCCATAGGATGG

CAAGATCCTGGTATCGGTCTGCGATTCCGACTCGTCCAACATCAATACAACCTATTA

ATTTCCCCTCGTCAAAAATAAGGTTATCAAGTGAGAAATCACCATGAGTGACGACTG

AATCCGGTGAGAATGGCAAAAGCTTATGCATTTCTTTCCAGACTTGTTCAACAGGCC

AGCCATTACGCTCGTCATCAAAATCACTCGCATCAACCAAACCGTTATTCATTCGTG

ATTGCGCCTGAGCGAGACGAAATACGCGATCGCTGTTAAAAGGACAATTACAAACA

GGAATCGAATGCAACCGGCGCAGGAACACTGCCAGCGCATCAACAATATTTTCACC

TGAATCAGGATATTCTTCTAATACCTGGAATGCTGTTTTCCCGGGGATCGCAGTGGT

GAGTAACCATGCATCATCAGGAGTACGGATAAAATGCTTGATGGTCGGAAGAGGCA

TAAATTCCGTCAGCCAGTTTAGTCTGACCATCTCATCTGTAACATCATTGGCAACGCT

ACCTTTGCCATGTTTCAGAAACAACTCTGGCGCATCGGGCTTCCCATACAATCGATA

GATTGTCGCACCTGATTGCCCGACATTATCGCGAGCCCATTTATACCCATATAAATC

AGCATCCATGTTGGAATTTAATCGCGGCCTCGAGCAAGACGTTTCCCGTTGAATATG

GCTCATAACACCCCTTGTATTACTGTTTATGTAAGCAGACAGTTTTATTGTTCATGAT

GATATATTTTTATCTTGTGCAATGTAACATCAGAGATTTTGAGACACAACGTGGCTTT

CCCCCGCCGCTCTAGAACTAGTGGATCCAAATAAAACGAAAGGCTCAGTCGAAAGA

CTGGGCCTTTCGTTTTATCTGTTGTTTGTCGCATTATACGAGACGTCCAGGTTGGGAT
```

-continued

ACCTGAAACAAAACCCATCGTACGGCCAAGGAAGTCTCCAATAACTGTGATCCACC

ACAAGCGCCAGGGTTTTCCCAGTCACGACGTTGTAAAACGACGGCCAGTCATGCAT

AATCCGCACGCATCTGGAATAAGGAAGTGCCATTCCGCCTGACCT pLD127

(SEQ ID NO: 173)
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGCAATTGTCCTTGTCGGTTTTATC

AACCGTTGCCACGGCCTTGTTGTCCCTAACCACCGCCGTCGATGCTAAGTCCCACAA

CATCAAGTTGTCCAAGTTGTCCAACGAAGAAACATTGGACGCCTCCACATTCCAAGA

ATACACGAGCTCCTTGGCCAACAAGTACATGAACTTGTTCAACGCCGCTCACGGTAA

CCCAACCAGCTTTGGCTTGCAACACGTCTTGTCCAACCAAGAAGCTGAAGTCCCATT

CGTTACCCCACAAAAGGGTggcAACCCAAGGGAAAACTTCCTTAAGTGTTTTCTGCAG

TACATCCCTAACAATGCAACAAACCTCAAGTTGGTGTACACTCAAAACAATCCACTC

TATATGAGCGTGCTTAATAGCACAATCCACAACTTGCGCTTCACGTCAGATACTACG

CCTAAGCCACTAGTGATCGTTACACCATCACACGTCAGCCATATTCAAGGAACGATC

-continued

```
CTATGTCTGAAAAAGGTCGGGTTGCAAATCAGGACTCGATCAGGAGGGCACGATAG

TGAGGGAATGAGTTACATCTCGCAAGTACCCTTCGTGATAGTTGACTTGCGAAATAT

GCGGTCTATTAAAATTGACGTACATAGCCAGACCGCCTGGGTTGAAGCAGGGCAA

CCTTGGGTGAAGTTTATTACTGGGTCAATGAAAAAAACGAAAACCTAAGTCTTGCTG

CTGGATATTGCCCCACCGTTTGCGCGGGTGGTCATTTTGGAGGCGGCGGATATGGTC

CGTTGATGAGAAATTATGGACTTGCAGCAGACAATATTATAGATGCCCACTTGGTGA

ACGTTCATGGAAAGGTCTTGGACCGTAAGTCCATGGGTGAAGATCTTTTCTGGGCCT

TGAGAGGTGGTGGAGCGGAATCGTTTGGCATCATCGTTGCCTGGAAAATTAGGTTGG

TTGCGGTCCCGAAGAGTACAATGTTCTCCGTGAAGAAGATTATGGAAATACATGAG

CTTGTCAAGTTAGTTAACAAGTGGCAAAATATCGCTTATAAGTATGATAAAGACTTG

CTTTTGATGACTCATTTTATTACGCGAAACATAACCGATAACCAGGGCAAGAACAAG

ACTGCTATTCACACGTACTTCTCCTCTGTATTTCTTGGAGGAGTAGACTCCTTAGTTG

ACTTGATGAACAAGAGTTTCCCAGAATTGGGGATTAAGAAGACAGATTGCAGACAA

TTATCGTGGATAGATACAATCATATTCTATAGCGGTGTCGTCAATTACGATACTGAT

AATTTTAATAAAGAAATCCTCCTAGATCGTTCAGCTGGGCAAAACGGGGCATTCAAA

ATTAAATTGGATTATGTGAAGAAACCAATTCCAGAGCTGGTGTTTGTTCAGATATTG

GAAAAACTTTACGAAGAAGACATTGGCGCAGGTATGTACGCTTTGTATCCATATGGA

GGCATTATGGACGAGATCTCAGAGCTGGCGATCCCCTTCCCGCACAGAGCTGGGAT

ACTCTACGAGCTATGGTACATCTGCTCTTGGGAGAAACAAGAAGACAACGAGAAAC

ATCTCAATTGGATTCGGAACATATACAACTTTATGACCCCATACGTATCAAAAAACC

CGCGCTTAGCATACTTGAATTACAGAGACTTAGATATCGGTATCAATGATCCTAAGA

ATCCTAACAATTACACCCAAGCCCGTATTTGGGGTGAGAAATATTTCGGCAAGAATT

TTGACAGATTAGTTAAGGTCAAAACACTCGTGGACCCCAACAACTTTTTCCGAAACG

AGCAGTCGATTCCACCACTACCCAGGCATAGACACTGAGAGTGACTCTTTTGATAAG

AGTCGCAAATTTGATTTCATAAGTATATATTCATTATGTAAAGTAGTAAATGGAAAA

TTCATTAAAAAAAAAGCAAATTTCCGTTGTATGCATACTCCGAACACAAAACTAGCC

CCGGAAAAACCCTTAGTTGATAGTTGCGAATTTAGGTCGACCATATGCGACGGGTAC

AACGAGAATTGTATTGAATTGATCAAGAACATGATCTTGGTGTTACAGAACATCAAG

TTCTTGGACCAGACTGAGAATGCACAGATATACAAGGCGTCATGTGATAAAATGGA

TGAGATTTATCCACAATTGAAGAAAGAGTTTATGGAAAGTGGTCAACCAGAAGCTA

AACAGGAAGAAGCAAACGAAGAGGTGAAACAAGAAGAAGAAGGTAAATAAGTATT

TTGTATTATATAACAAACAAAGTAAGGAATACAGATTTATACAATAAATTGCCATAC

TAGTCACGTGAGATATCTCATCCATTCCCCAACTCCCAAGAAAATAAAAAAGTGAA

AAATAAAATCAAACCCAAAGATCAACCTCCCCATCATCATCGTCATCAAACCCCCA

GCTCAATTCGCAATGGTTAGCACAAAAACATACACAGAAAGGGCATCAGCACACCC

CTCCAAGGTTGCCCAACGTTTATTAATTAAAGGCTAGGTGGAGGCTCAGTGATGATA

AGTCTGCGATGGTGGATGCATGTGTCATGGTCATAGCTGTTTCCTGTGTGAAATTGTT

ATCCGCTCAGAGGGCACAATCCTATTCCGCGCTATCCGACAATCTCCAAGACATTAG

GTGGAGTTCAGTTCGGCGTATGGCATATGTCGCTGGAAAGAACATGTGAGCAAAAG

GCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAA
```

-continued

```
CCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTATCCG

GTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTG

AAGTGGTGGCCTAACTACGGCTACACTAGAAGAACAGTATTTGGTATCTGCGCTCTG

CTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCTATTCAACAA

AGCCGCCGTCCCGTCAAGTCAGCGTAAATGGGTAGGGGGCTTCAAATCGTCCGCTCT

GCCAGTGTTACAACCAATTAACAAATTCTGATTAGAAAAACTCATCGAGCATCAAAT

GAAACTGCAATTTATTCATATCAGGATTATCAATACCATATTTTTGAAAAAGCCGTT

TCTGTAATGAAGGAGAAAACTCACCGAGGCAGTTCCATAGGATGGCAAGATCCTGG

TATCGGTCTGCGATTCCGACTCGTCCAACATCAATACAACCTATTAATTTCCCCTCGT

CAAAAATAAGGTTATCAAGTGAGAAATCACCATGAGTGACGACTGAATCCGGTGAG

AATGGCAAAAGCTTATGCATTTCTTTCCAGACTTGTTCAACAGGCCAGCCATTACGC

TCGTCATCAAAATCACTCGCATCAACCAAACCGTTATTCATTCGTGATTGCGCCTGA

GCGAGACGAAATACGCGATCGCTGTTAAAAGGACAATTACAAACAGGAATCGAATG

CAACCGGCGCAGGAACACTGCCAGCGCATCAACAATATTTTCACCTGAATCAGGAT

ATTCTTCTAATACCTGGAATGCTGTTTTCCCGGGGATCGCAGTGGTGAGTAACCATG

CATCATCAGGAGTACGGATAAAATGCTTGATGGTCGGAAGAGGCATAAATTCCGTC

AGCCAGTTTAGTCTGACCATCTCATCTGTAACATCATTGGCAACGCTACCTTTGCCAT

GTTTCAGAAACAACTCTGGCGCATCGGGCTTCCCATACAATCGATAGATTGTCGCAC

CTGATTGCCCGACATTATCGCGAGCCCATTTATACCCATATAAATCAGCATCCATGT

TGGAATTTAATCGCGGCCTCGAGCAAGACGTTTCCCGTTGAATATGGCTCATAACAC

CCCTTGTATTACTGTTTATGTAAGCAGACAGTTTTATTGTTCATGATGATATATTTTT

ATCTTGTGCAATGTAACATCAGAGATTTTGAGACACAACGTGGCTTTCCCCCGCCGC

TCTAGAACTAGTGGATCCAAATAAAACGAAAGGCTCAGTCGAAAGACTGGGCCTTT

CGTTTTATCTGTTGTTTGTCGCATTATACGAGACGTCCAGGTTGGGATACCTGAAAC

AAAACCCATCGTACGGCCAAGGAAGTCTCCAATAACTGTGATCCACCACAAGCGCC

AGGGTTTTCCCAGTCACGACGTTGTAAAACGACGGCCAGTCATGCATAATCCGCACG

CATCTGGAATAAGGAAGTGCCATTCCGCCTGACCT
``` pLD131

(SEQ ID NO: 174)

```
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT
```

-continued

```
TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGATTGAATTTAAGCAAAAAATTAAATC

AAAATACCTTTATGTATCCAGCCCATGTAATAAACAAAAGGATTATATAACAAGAA
```

-continued

```
ATAAATATATACCTTTAATGGATCATTAGAATAAAAATAAATACGAGAAGCACACC
AGAGAAGCTTTTTGATTGCCACTATACCGCTACTTTGGTATATCTTATTATAATTGTT
GAATTTGCAAGATAGAATGTCATTCATTGGAGAGAAATCCAAGGAATATGTGGGAT
GAAATGACTAGAAGTATGAACAATGAGAATAGTACATACTTGTACCTGTATTTCTAG
AAGAGAGAAAGACAGTTGAGTGTGTGATTCTCGTCCAATAATAATCTCAATAGTAA
CGTGTGAATAGCTGTTCTTTGATAGTTGATATTTCTCGATGACTATTTATGTTGTACA
AGGGATTTTTTTCGTTGCTGTTGATTTCGAATTAGGCAATGCAGATATCATTTATGCT
ATCCATATTTAAGATTTCCCATACGCATTTATAACATTTATTCTACATAAATTGTTAA
ATGAACGAACTGCCATTATAAATTGTTTCCTAAATAGGAAGTGTTTTTCATAAAGCA
AGTAAGTTGTCTAATAATACTAAGTAATAAAAATAAGTTCATACAATATATTTTGAG
AACATCATTTGGAGGCGGTAGATGGAGTCTGTTTATTATTAAACAATGCGAGATGAC
CCCTTAAATATTGAGAACATCAGTTGGAGGCGGCAGATGGAGTCTGTCTATTTAGCA
ATGGGACATGACTGTCAGTATCATCATATGTATATATATAATACATATAATATTATA
TAACACGATTTTTTTAAATTATTGGCCCGAAAATTAATCAGTGTAGACTGGATCCTC
GAGAACCATTTAATTAAGATCGTCGACGATTCCGCCAAGTGAGACTGGCGATCGGG
AGAAGGGTTGGTGGTCATGGGGATAGAATTTGTACAAGTGGAAAAACCACTACGA
GTAGCGGATTTGATACCACAAGTAGCAGAGATATACAGCAATGGTGGGAGTGCAAG
TATCGGAATGTACTGTACCTCCTGTACTCGTACTCGTACGGCACTCGTAGAAACGGG
GCAATACGGGGAGAAGCGATCGCCCGTCTGTTCAATCGCCACAAGTCCGAGTAAT
GCTTGAGTATCGAAGTCTTGTACCTCCCTGTCAATCATGGCACCACTGGTCTTGACTT
GTCTATTCATACTGGACAAGCGCCAGAGTTAAGCTTGTAGCGAATTTCGCCCTCGGA
CATCACCCCATACGACGGACACACATGCCCGACAAACAGCCTCTCTTATTGTAGCTG
AAAGTATATTGAATGTGAACGTGTACAATATCAGGTACCAGCGGGAGGTTACGGCC
AAGGTGATACCGGAATAACCCTGGCTTGGAGATGGTCGGTCCATTGTACTGAAGTGT
CCGTGTCGTTTCCGTCACTGCCCCAATTGGACATGTTTGTTTTTCCGATCTTTCGGGC
GCCCTCTCCTTGTCTCCTTGTCTGTCTCCTGGACTGTTGCTACCCCATTTCTTTGGCCT
CCATTGGTTCCTCCCCGTCTTTCACGTCGTCTATGGTTGCATGGTTTCCCTTATACTTT
TCCCCACAGTCACATGTTATGGAGGGGTCTAGATGGAGGCCTAATTTTGACGTGCAA
GGGGCGAATTGGGGCGAGAAACACGTCGTGGACATGGTGCAAGGCCCGCAGGGTTG
ATTCGACGCTTTTCCGCGAAAAAAACAAGTCCAAATACCCCCGTTTATTCTCCCTCG
GCTCTCGGTATTTCACATGAAAACTATAACCTAGACTACACGGGCAACCTTAACCCC
AGAGTATACTTATATACCAAAGGGATGGGTCCTCAAAAATCACACAAGCAACGACG
CCATGGGCCTCTCTCTAGTATGTACCTTCTCTTTCCAGACCAACTATCACACTCTACT
GAACCCCCATAACAAGAACCCTAAAAATTCTCTTCTCAGTTACCAGCACCCCAAGAC
GCCTATCATTAAGTCCTCCTACGACAACTTTCCCTCAAGTACTGCCTGACCAAAAA
CTTCCATCTCCTGGGACTGAACTCTCATAACAGAATTAGTAGCCAGTCCCGATCTAT
CCGAGCTGGCTCTGACCAGATTGAGGGCTCCCCTCACCATGAATCCGACAACAGCAT
CGCTACCAAGATTTTGAATTTTGGTCACACATGCTGGAAGCTCCAGCGACCGTACGT
CGTGAAGGGTATGATCTCGATTGCCTGTGGACTGTTCGGACGTGAGCTTTTTAATAA
TCGACACTTGTTTTCATGGGGCCTCATGTGGAAGGCTTTTTTCGCCCTCGTGCCCATT
```

-continued
CTGTCTTTCAACTTCTTTGCCGCTATTATGAACCAAATCTACGACGTTGATATTGATA

GGATCAACAAGCCTGACCTGCCGCTCGTCTCGGGGGAGATGTCTATCGAGACAGCG

TGGATTCTTTCGATTATCGTCGCGCTGACTGGCCTTATCGTTACCATAAAGTTGAAGT

CTGCACCCCTCTTCGTGTTTATCTACATTTTCGGTATTTTTGCTGGATTCGCGTACTCC

GTTCCCCCTATCAGATGGAAGCAGTACCCCTTTACTAACTTTCTGATTACTATCAGCA

GCCACGTCGGTTTAGCCTTTACCTCATATTCGGCCACCACCAGTGCACTGGGCCTCC

CCTTCGTCTGGCGACCTGCATTTTCATTCATCATCGCCTTCATGACTGTGATGGGTAT

GACCATCGCTTTCGCTAAGGACATCTCCGACATCGAGGGTGATGCTAAATATGGAGT

GTCCACCGTGGCCACTAAGCTGGGAGCCCGGAACATGACGTTCGTCGTCTCTGGTGT

TCTGCTCCTTAACTACTTGGTTTCGATCTCCATTGGCATTATCTGGCCACAAGTCTTC

AAGTCCAACATTATGATTCTGTCCCACGCCATTCTTGCCTTTTGCCTGATCTTCCAGA

CACGCGAACTCGCTCTCGCTAACTACGCCTCCGCCCCATCGCGACAGTTCTTCGAGT

TCATCTGGCTGCTTTACTACGCCGAGTACTTCGTTTACGTGTTCATCTAATAAGAGTA

GGCAATTAACAGATAGTTTGCCGGTGATAATTCTCTTAACCTCCCACACTCCTTTGAC

ATAACGATTTATGTAACGAAACTGAAATTTGACCAGATATTGTTGTAAATAGAAAAT

CTGGCTTGTAGGTGGCAAAATGCGGCGTCTTTGTTCATCAATTCCCTCTGTGACTACT

CGTCATCCCTTTATGTTCGACTGTCGTATTTCTTATTTTCCATACATATGCAAGTGAG

ATGCCCGTGTCCGAATTCGCTATGGATCCATAGCGTCGACACCATATCATATAAAAC

TAACAATGCATTGAATTAATACGAAGACTACCCGTTGCTATCTCCACACCGTTATCT

CCACGGTCCAAAGGCTGCTCAATGTGCTGCATACGTAACGTGGGGTGCAACCTTGAG

CACATAGTACTTTCCGAAAACCGGCGATAATTAAGTGTGCACTCCAACTTTTCACAC

TGAGCATAAAATGTGGAGAAGAAATCACACTAAAAAGTCAGGTAGACTGGAAAATG

CGCCATGAAATAATATCTCTTGCTACAGTAATGCCCAGCATCGAGGGGTATTGTGTC

ACCAACACTATAGTGGCAGCTGAAGCGCTCGTGATTGTAGTATGAGTCTTTATTGGT

GATGGGAAGAGTTCACTCAATATTCTCGTTACTGCCAAAACACCACGGTAATCGGCC

AGACACCATGGATGTAGATCACCAAGCCTGTGAATGTTATTCGAGCTAAAATGCAC

ATGGTTGGTGAAAGGAGTAGTTGCTGTCGAATTCCGTCGTCGCCTGAGTCATCATTT

ATTTACCAGTTGGCCACAAACCCTTGACGATCTCGTATGTCCCCTCCGACATACTCC

CGGCCGGCTGGGGTACGTTCGATAGCGCTATCGGCATCGACAAGGTTTGGGTCCCTA

GCCGATACCGCACTACCTGAGTCACAATCTTCGGAGGTTTAGTCTTCCACATAGCAC

GGGCAAAAGTGCGTATATATACAAGAGCGTTTGCCAGCCACAGATTTTCACTCCACA

CACCACATCACACATACAACCACACACATCCACAATGGAACCCGAAACTAAGAAGA

CCAAGACTGACTCCAAGAAGATTGTTCTTCTCGGCGGCGACTTCTGTGGCCCCGAGG

TGATTGCCGAGGCCGTCAAGGTGCTCAAGTCTGTTGCTGAGGCCTCCGGCACCGAGT

TTGTGTTTGAGGACCGACTCATTGGAGGAGCTGCCATTGAGAAGGAGGGCGAGCCC

ATCACCGACGCTACTCTCGACATCTGCCGAAAGGCTGACTCTATTATGCTCGGTGCT

GTCGGAGGCGCTGCCAACACCGTATGGACCACTCCCGACGGACGAACCGACGTGCG

ACCCGAGCAGGGTCTTCTCAAGCTGCGAAAGGACCTGAACCTGTACGCCAACCTGC

GACCCTGCCAGCTGCTGTCGCCCAAGCTCGCCGATCTCTCCCCCATCCGAAACGTTG

AGGGCACCGACTTCATCATTGTCCGAGAGCTCGTCGGAGGTATCTACTTTGGAGAGC

GAAAGGAGGATGACGGATCTGGCGTCGCTTCCGACACTGAGACTTACTCCGTTCCTG

AGGTTGAGCGAATTGCCCGAATGGCCGCCTTCCTGGCCCTTCAGCACAACCCCCCTC

TTCCCGTGTGGTCCCTTGACAAGGCCAACGTGCTGGCCTCCTCTCGACTTTGGCGAA

AGACCGTCACCCGAGTCCTCAAGGACGAATTCCCCCAGCTGGAGCTCAACCACCAG

CTGATCGACTCGGCCGCCATGATCCTCATCAAGCAGCCCTCCAAGATGAATGGTATC

ATCATCACCACCAACATGTTTGGCGATATCATCTCCGACGAGGCCTCCGTCATCCCC

GGTTCTCTGGGTCTGCTGCCCTCCGCCTCTCTGGCTTCTCTGCCCGACACCAACGAGG

CGTTCGGTCTGTACGAGCCCTGTCACGGATCTGCCCCCGATCTCGGCAAGCAGAAGG

TCAACCCCATTGCCACCATTCTGTCTGCCGCCATGATGCTCAAGTTCTCTCTTAACAT

GAAGCCCGCCGGTGACGCTGTTGAGGCTGCCGTCAAGGAGTCCGTCGAGGCTGGTA

TCACTACCGCCGATATCGGAGGCTCCTCCTCCACCTCCGAGGTCGGAGACTTTGTTG

CCAACAAGGTCAAGGAGCTGCTCAAGAAGGAGTAAGTCGTTTCTACGACGCATTGA

TGGAAGGAGCAAACTGACGCGCCTGCGGGTTGGTCTACCGGCAGGGTCCGCTAGTG

TATAAGACTCTATAAAAGGGCCCAGCCCTGCTAATGAAATGATGATTTATAATTTA

CCGGTGTAGCAACCTTGACTAGAAGAAGCAGATTGGGTGTGTTTGTAGTGGAGGAC

AGTGGTACGTTTTAATTAA pLD132

(SEQ ID NO: 175)

TTAATTAAGATCGTCGACGATTCCGCCAAGTGAGACTGGCGATCGGGAGAAGGGTT

GGTGGTCATGGGGGATAGAATTTGTACAAGTGGAAAAACCACTACGAGTAGCGGAT

TTGATACCACAAGTAGCAGAGATATACAGCAATGGTGGGAGTGCAAGTATCGGAAT

GTACTGTACCTCCTGTACTCGTACTCGTACGGCACTCGTAGAAACGGGGCAATACGG

GGGAGAAGCGATCGCCCGTCTGTTCAATCGCCACAAGTCCGAGTAATGCTTGAGTAT

CGAAGTCTTGTACCTCCCTGTCAATCATGGCACCACTGGTCTTGACTTGTCTATTCAT

ACTGGACAAGCGCCAGAGTTAAGCTTGTAGCGAATTTCGCCCTCGGACATCACCCCA

TACGACGGACACACATGCCCGACAAACAGCCTCTCTTATTGTAGCTGAAAGTATATT

GAATGTGAACGTGTACAATATCAGGTACCAGCGGGAGGTTACGGCCAAGGTGATAC

CGGAATAACCCTGGCTTGGAGATGGTCGGTCCATTGTACTGAAGTGTCCGTGTCGTT

TCCGTCACTGCCCCAATTGGACATGTTTGTTTTTCCGATCTTTCGGGCGCCCTCTCCT

TGTCTCCTTGTCTGTCTCCTGGACTGTTGCTACCCCATTTCTTTGGCCTCCATTGGTTC

CTCCCCGTCTTTCACGTCGTCTATGGTTGCATGGTTTCCCTTATACTTTTCCCCACAGT

CACATGTTATGGAGGGGTCTAGATGGAGGCCTAATTTTGACGTGCAAGGGGCGAAT

TGGGGCGAGAAACACGTCGTGGACATGGTGCAAGGCCCGCAGGGTTGATTCGACGC

TTTTCCGCGAAAAAAACAAGTCCAAATACCCCCGTTTATTCTCCCTCGGCTCTCGGT

ATTTCACATGAAAACTATAACCTAGACTACACGGGCAACCTTAACCCCAGAGTATAC

TTATATACCAAAGGGATGGGTCCTCAAAAATCACACAAGCAACGACGCCATGAAGT

GTTCGACGTTTTCTTTTTGGTTTGTTTGTAAAATCATTTTCTTTTTCTTTTCTTTCAACA

TCCAAACGTCGATCGCAAACCCTAGAGAGAACTTTCTTAAGTGCTTCTCGCAGTACA

TCCCTAATAACGCTACCAACCTTAAGCTGGTGTACACCCAGAACAACCCTCTTTACA

TGTCTGTTCTAAACAGCACCATCCACAATCTTAGATTCACATCAGACACCACTCCCA

AGCCGCTCGTCATCGTGACCCCGAGTCATGTGTCCCATATCCAAGGCACTATCCTGT

GCTCTAAAAAGGTCGGTCTGCAGATTCGGACTCGCTCCGGTGGACATGATTCGGAGG

-continued

```
GCATGTCCTACATTAGCCAGGTCCCCTTTGTGATCGTGGACCTGAGGAACATGCGGT
CTATTAAGATTGATGTGCACTCACAGACCGCTTGGGTCGAGGCTGGTGCGACATTGG
GTGAGGTGTACTACTGGGTGAACGAGAAGAACGAGAACCTGAGCCTCGCCGCTGGC
TACTGTCCCACCGTTTGTGCCGGTGGACACTTCGGCGGAGGCGGATACGGTCCACTT
ATGCGAAACTACGGGCTCGCAGCTGATAATATCATCGACGCACACCTTGTTAACGTT
CACGGCAAGGTGCTGGACCGAAAAAGCATGGGTGAGGACCTATTTTGGGCCTTGCG
AGGCGGTGGTGCCGAATCCTTCGGAATTATCGTGGCCTGGAAGATCCGACTGGTCGC
TGTGCCAAAGTCCACTATGTTCTCCGTCAAGAAAATTATGGAGATCCACGAACTCGT
AAAGCTCGTCAATAAGTGGCAGAACATCGCCTACAAGTATGACAAGGATCTGCTGC
TCATGACTCACTTCATCACGCGAAACATTACAGACAACCAGGGAAAGAACAAGACC
GCTATCCATACCTACTTCTCCTCTGTCTTCCTTGGGGGTGTCGATTCCCTCGTTGATCT
CATGAACAAATCTTTTCCAGAGCTCGGAATCAAGAAGACCGACTGCCGACAGCTCT
CTTGGATCGACACCATTATTTTCTACTCAGGAGTCGTAAACTACGATACTGACAACT
TTAACAAGGAGATTCTGTTAGATCGATCGGCCGGCCAGAACGGTGCCTTCAAGATCA
AGCTCGACTATGTCAAAAAGCCCATTCCTGAATCCGTCTTCGTTCAAATTCTTGAAA
AGTTGTACGAGGAGGATATCGGCGCCGGAATGTACGCGCTGTACCCCTACGGTGGC
ATTATGGACGAGATTTCTGAAAGTGCTATTCCCTTCCCCCACCGTGCTGGCATTCTGT
ATGAGCTGTGGTACATTTGCTCCTGGGAAAAGCAGGAGGACAACGAGAAGCACTTG
AACTGGATACGAAACATTTACAATTTCATGACCCCCTATGTTTCGAAGAACCCTCGA
CTGGCCTACCTGAATTACCGCGACCTCGACATCGGAATTAACGACCCTAAGAACCCC
AATAACTATACTCAGGCCAGAATCTGGGGCGAGAAGTACTTCGGCAAGAACTTTGA
CCGTCTGGTTAAGGTCAAGACCCTCGTGGACCCTAACAACTTCTTCCGAAACGAGCA
GTCTATCCCCCCTCTGCCCCGACACCGGCATTAATAAGAGTAGGCAATTAACAGATA
GTTTGCCGGTGATAATTCTCTTAACCTCCCACACTCCTTTGACATAACGATTTATGTA
ACGAAACTGAAATTTGACCAGATATTGTTGTAAATAGAAAATCTGGCTTGTAGGTGG
CAAAATGCGGCGTCTTTGTTCATCAATTCCCTCTGTGACTACTCGTCATCCCTTTATG
TTCGACTGTCGTATTTCTTATTTTCCATACATATGCAAGTGAGATGCCCGTGTCCGAA
TTCGCTATGGATCCATAGCGCAGGTTGTGCAGTATCATACATACTCGATCAGACAGG
TCGTCTGACCATCATACAAGCTGAACAAGCGCTCCATACTTGCACGCTCTCTATATA
CACAGTTAAATGACATATCCATAGTCTAACCTCTAACAGTTAATCTTCTGGTAAGCC
TCCCAGCCAGCCTTCTGGTATCGCTTGGCCTCCTCAATAGGATCTCGGTTCTGGCCGT
ACAGACCTCGGCCGACAATTATGATATCCGTTCCGGTAGACATGACATCCTCAACAG
TTCGGTACTGCTGTCCGAGAGCATCTCCCTTGTCGTCAAGACCCACCCCGGGGGTCA
GAATAAGCCAGTCCTCAGAGTCGCCCTTAGGTCGGTTCTGGGCAATGAAGCCAACC
ACAAACTCGGGGTCGGATCGGGCAAGCTCAATGGTCTGCTTGGAGTACTCGCCAGT
GGCCAGAGAGCCCTTGCAAGACAGCTCGGCCAGCATGAGCAGACCTCTGGCCAGCT
TCTCGTTGGGAGAGGGGACCAGGAACTCCTTGTACTGGGAGTTCTCGTAGTCAGAGA
CATCCTCCTTCTTCTGTTCAGAGACAGTTTCCTCGGCACCAGCTCGCAGGCCAGCAA
TGATTCCGGTTCCGGGTACACCGTGGGCGTTGGTGATATCGGACCACTCGGCGATTC
GGTAGACACCGTTCTTGTACTGGTGCTTGACAGTGTTGCCAATATCTGCGAACTTTCT
GTCCTCGAACAGGAAGAAACCGTGCTTAAGAGCAAGTTCCTTGAGGGGGAGCACAG
```

-continued

```
TTCCGGCGTAGGTGAAGTCGTCAATGATGTCGATATGGGTCTTGATCATGCACACAT
AAGGTCCGACCTTATCGGCAAGCTCAATGAGCTCCTTGGTGGTGGTAACATCCAGAG
AAGCACACAGGTTGGTTTTCTTGGCTGCCACGAGCTTGAGCACTCGGGCGGCAAAG
GCGGACTTGTGGACGTTAGCTCGCGCTTCGTAGGAGGGCATTTTGGTGGTGAAGAGG
AGACTGAAATAAATTTAGTCTGCACAACTTTTTATCGGAACCTTATCTGGGGCAGTG
AAGTATATGTTATGGTAATAGTTACGAGTTAGTTGAACTTATAGATAGACTGGACTA
TACGGCTATCGGTCCAAATTAGAAATTAATTAAATGGTTCTCGAGGATCCAGTCTAC
ACTGATTAATTTTCGGGCCAATAATTTAAAAAAATCGTGTTATATAATATTATATGT
ATTATATATATACATATGATGATACTGACAGTCATGTCCCATTGCTAAATAGACAGA
CTCCATCTGCCGCCTCCAACTGATGTTCTCAATATTTAAGGGGTCATCTCGCATTGTT
TAATAATAAACAGACTCCATCTACCGCCTCCAAATGATGTTCTCAAAATATATTGTA
TGAACTTATTTTTATTACTTAGTATTATTAGACAACTTACTTGCTTTATGAAAAACAC
TTCCTATTTAGGAAACAATTTATAATGGCAGTTCGTTCATTTAACAATTTATGTAGAA
TAAATGTTATAAATGCGTATGGGAAATCTTAAATATGGATAGCATAAATGATATCTG
CATTGCCTAATTCGAAATCAACAGCAACGAAAAAAATCCCTTGTACAACATAAATA
GTCATCGAGAAATATCAACTATCAAAGAACAGCTATTCACACGTTACTATTGAGATT
ATTATTGGACGAGAATCACACACTCAACTGTCTTTCTCTCTTCTAGAAATACAGGTA
CAAGTATGTACTATTCTCATTGTTCATACTTCTAGTCATTTCATCCCACATATTCCTTG
GATTTCTCTCCAATGAATGACATTCTATCTTGCAAATTCAACAATTATAATAAGATAT
ACCAAAGTAGCGGTATAGTGGCAATCAAAAAGCTTCTCTGGTGTGCTTCTCGTATTT
ATTTTTATTCTAATGATCCATTAAAGGTATATATTTATTTCTTGTTATATAATCCTTTT
GTTTATTACATGGGCTGGATACATAAAGGTATTTTGATTTAATTTTTTGCTTAAATTC
AATCCCCCCTCGTTCAGTGTCAACTGTAATGGTAGGAAATTACCATACTTTTGAAGA
AGCAAAAAAATGAAAGAAATAAAAAATCGTATTTCCAGGTTAGACGTTCCGCAGA
ATCTAGAATGCGGTATGCGGTACATTGTTCTTCGAACGTAAAAGTTGCGCTCCCTGA
GATATTGTACATTTTTGCTTTTACAAGTACAAGTACATCGTACAACTATGTACTACTG
TTGATGCATCCACAACAGTTTGTTTTGTTTTTTTTGTTTTTTATTTTTCTAATGATTC
ATTACCGCTATGTATACCTACTTGTACTTGTAGTAAGCCGGGTTATTGGCGTTCAATT
AATCATAGACTTATGAATCTGCACGGTGTGCGCTGCGAGTTACTTTTAGCTTATGCA
TGCTACTTGGGTGTAATATTGGGATCAGGTCAGGCGGAATGGCACTTCCTTATTCCA
GATGCGTGCGGATTATGCATGACTGGCCGTCGTTTTACAACGTCGTGACTGGGAAAA
CCCTGGCGCTTGTGGTGGATCACAGTTATTGGAGACTTCCTTGGCCGTACGATGGGT
TTTGTTTCAGGTATCCCAACCTGGACGTCTCGTATAATGCGACAAACAACAGATAAA
ACGAAAGGCCCAGTCTTTCGACTGAGCCTTTCGTTTTATTTGGATCCACTAGTTCTAG
AGCGGCGGGGAAAGCCACGTTGTGTCTCAAAATCTCTGATGTTACATTGCACAAG
ATAAAAATATATCATCATGAACAATAAAACTGTCTGCTTACATAAACAGTAATACAA
GGGGTGTTATGAGCCATATTCAACGGGAAACGTCTTGCTCGAGGCCGCGATTAAATT
CCAACATGGATGCTGATTTATATGGGTATAAATGGGCTCGCGATAATGTCGGGCAAT
CAGGTGCGACAATCTATCGATTGTATGGGAAGCCCGATGCGCCAGAGTTGTTTCTGA
AACATGGCAAAGGTAGCGTTGCCAATGATGTTACAGATGAGATGGTCAGACTAAAC
```

-continued

```
TGGCTGACGGAATTTATGCCTCTTCCGACCATCAAGCATTTTATCCGTACTCCTGATG

ATGCATGGTTACTCACCACTGCGATCCCCGGGAAAACAGCATTCCAGGTATTAGAAG

AATATCCTGATTCAGGTGAAAATATTGTTGATGCGCTGGCAGTGTTCCTGCGCCGGT

TGCATTCGATTCCTGTTTGTAATTGTCCTTTTAACAGCGATCGCGTATTTCGTCTCGC

TCAGGCGCAATCACGAATGAATAACGGTTTGGTTGATGCGAGTGATTTTGATGACGA

GCGTAATGGCTGGCCTGTTGAACAAGTCTGGAAAGAAATGCATAAGCTTTTGCCATT

CTCACCGGATTCAGTCGTCACTCATGGTGATTTCTCACTTGATAACCTTATTTTTGAC

GAGGGGAAATTAATAGGTTGTATTGATGTTGGACGAGTCGGAATCGCAGACCGATA

CCAGGATCTTGCCATCCTATGGAACTGCCTCGGTGAGTTTTCTCCTTCATTACAGAAA

CGGCTTTTTCAAAAATATGGTATTGATAATCCTGATATGAATAAATTGCAGTTTCATT

TGATGCTCGATGAGTTTTTCTAATCAGAATTTGTTAATTGGTTGTAACACTGGCAGA

GCGGACGATTTGAAGCCCCCTACCCATTTACGCTGACTTGACGGGACGGCGGCTTTG

TTGAATAGAGCGTCAGACCCCGTAGAAAAGATCAAAGGATCTTCTTGAGATCCTTTT

TTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGA

GCGCAGATACCAAATACTGTTCTTCTAGTGTAGCCGTAGTTAGGCCACCACTTCAAG

AACTCTGTAGCACCGCCTACATACCTCGCTCTGCTAATCCTGTTACCAGTGGCTGCT

GCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCGAACTGAGATACCTACAGCGTGAGCTATGAGAAAGCGCCACGC

TTCCCGAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTCCTGTCG

GGTTTCGCCACCTCTGACTTGAGCGTCGATTTTTGTGATGCTCGTCAGGGGGCGGA

GCCTATGGAAAAACGCCAGCAACGCGGCCTTTTTACGGTTCCTGGCCTTTTGCTGGC

CTTTTGCTCACATGTTCTTTCCAGCGACATATGCCATACGCCGAACTGAACTCCACCT

AATGTCTTGGAGATTGTCGGATAGCGCGGAATAGGATTGTGCCCTCTGAGCGGATAA

CAATTTCACACAGGAAACAGCTATGACCATGACACATGCATCCACCATCGCAGACTT

ATCATCACTGAGCCTCCACCTAGCCT
``` pLD135

(SEQ ID NO: 176)
```
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG
```

-continued

```
AAGAACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTT
CTACGGGGTCTGACGCTCTATTCAACAAAGCCGCCGTCCCGTCAAGTCAGCGTAAAT
GGGTAGGGGGCTTCAAATCGTCCTCGTGATACCAATTCGGAGCCTGCTTTTTTGTAC
AAACTTGTTGATAATGGCAATTCAAGGATCTTCACCTAGATCCTTTTAAATTAAAAA
TGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCA
GTGCTGCAATGATACCGCGAGAGCCACGCTCACCGGCTCCAGATTTATCAGCAATA
AACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGT
ATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGC
CACATAGCAGAACTTTAAAAGTGCTCATCATTGGAAAACGTTCTTCGGGGCGAAAA
CTCTCAAGGATCTTACCGCTGTTGAGATCCAGTTCGATGTAACCCACTCGTGCACCC
AACTGATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCC
CCGAAAAGTGCCAGATACCTGAAACAAAACCCATCGTACGGCCAAGGAAGTCTCCA
ATAACTGTGATCCACCACAAGCGCCAGGGTTTTCCCAGTCACGACGTTGTAAAACGA
CGGCCAGTCATGCATAATCCGCACGCATCTGGAATAAGGAAGTGCCATTCCGCCTG
ACCTTTAATTAATTGGCAAATTTTACTGTGGCCTTCAGAACGGTAAAAATAGACCAA
TCAGAATTCTGAAAAGCACATCTTGATCTCCTCATTGCGGGGAGTCCAACGGTGGTC
TTATTCCCCCGAATTTCCCGCTCAATCTCGTTCCAGACCGACCCGGACACAGTGCTT
AACGCCGTTCCGAAACTCTACCGCAGATATGCTCCAACGGACTGGGCTGCATAGAT
GTGATCCTCGGCTTGGAGAAATGGATAAAAGCCGGCCAAAAAAAAAGCGGAAAAA
AGCGGAAAAAAAGAGAAAAAAAATCGCAAAATTTGAAAAATAGGGGAAAAGACG
CAAAAACGCAAGGAGGGGGAGTATATGACACTGATAAGCAAGCTCACAACGGTTC
CTCTTATTTTTTCCTCATCTTCTGCCTAGGTTCCCAAAATCCCAGATGCTTCTCTCCA
GTGCCAAAAGTAAGTACCCCACAGGTTTTCGGCCGAAAATTCCACGTGCAGCAACG
TCGTGTGGGTGTTAAAATGTGGGGCGGGGAACCAGGACAAGAGGCTCTTGTGGG
AGCCGAATGAGAGCACAAAGCGGGCGGGTGTGATAAGGGCATTTTTGCCCATTTTC
CCTTCTCCTGTCTCTCCGACGGTGATGGCGTTGTGCGTCCTCTATCTATTTCTTTTTAT
TTCTTTTTGTTTTATTTCTCTGACTACCGATTTGGCTTGATTTCCTCAACCCCACACAA
```

-continued
```
ATAAGCTCGGGCCGAGGAATATATATATACACGGACACAGTCGCCCTGTGGACAAC
ACGTCACTACCTCTACGACGCTATGGATCCATAGCGAATTCGGACACGGGCATCTCA
CTTGCATATGTATGGAAAATAAGAAATACGACAGTCGAACATAAAGGGATGACGAG
TAGTCACAGAGGGAATTGATGAACAAAGACGCCGCATTTTGCCACCTACAAGCCAG
ATTTTCTATTTACAACAATATCTGGTCAAATTTCAGTTTCGTTACATAAATCGTTATG
TCAAAGGAGTGTGGGAGGTTAAGAGAATTATCACCGGCAAACTATCTGTTAATTGCC
TACTCTTATTACAGTTTGGCTCGTCGTCCCCGAGACTTGCCGGCCTTGATAGCGAGG
AGTGTCTTCTCGTCAGCAGGGGCGCTACCGGAGGCTCGTTGCTGTCTGAAGTAGGTT
CGGGCCTCGTCCTGTCGGGTGGCCTCAGCGCCGGTGGCGATAGCGGCCCGAAGGTG
CTCGGCTCCGTAGCCGAAGGCATCAACCAGATCAAGTGCGTGTGGTCGGATCTTAAC
GAGAAGACGATTAATGTAAGTGCCGACCGTTCGGCCTCTCTGCATCGAGAGCCTACC
GTTCATCAGATACCAGCTGAGGTGCTTCTCGATAAGGGACAGACCAAAAAGGTCAC
GCAATCGGGTCAACACTTCCTTAGTGCCAGCGTCGTCCACCTTGGCCAAAGCCTCAG
TAAAGGCCTCCCACTGTAAAAGCTCAGCGTGGGCCTGGGCAGCCTCGATCAGTTCGT
TTTGATGCTGATTGAACAGTGCTGCCGCCTGGTGCTGGGGGAGCTTGCCCGCGCCTT
TGAGAGCAGCGCCAACCTCTGCAACCATGGACTGGACTCTGTCGGTCAGCAGAGTT
CGCTGACCTTCTTCGTCTCGGAGGGCAAGAGCAGATTTCTGGACAGATCCACTGTCG
GCCACGAACTGAGCGACCTGTCGCAGTCCGGTTCGGTGTAGCGCGACTCCGGCAGC
CTGGTCCACGACGTACCGCGCGAGCACGCCGAAGTTGGCACCTCGGAACTCCTTAG
CATAGTCAGCGAGCAGCCTCTTGGCCACCAACTGAAGAAGCACGGTGTTGTCTCCTT
CGAAGGTCACGTAGACGTCGAGATCGGCCCGGAGAGAAGCGAATCGGTTCTCAATC
AGAAAACCTGCACCCCCACACGCTTCTCGGCACTCTTGTAGGGTATCGAGAGCATGC
CAGGTAGAAAGGGGCTTCAGAGCAGCAGCCAGTGTCTCAAGGTCCTGACGGTCGGC
GTCAGTATCATGAGCACCCGAGAACACGTCGTCGAATTTCTGCAGCAGTTGCTCATG
GGCGAACGATGCGGCGTAGGTGGTGGCGAGTCGGGTAAAGAGGCGCCGCTGGTGTC
GCTGGTAATCCAGGAGCACCTCCTCCTCTGTGGGCGAAGTGGCGTTGAACTGTCTTC
GCTCAGCGGCGTAGTGGATGGCGGATTGCAGAGCAACCTTCGATGCAGCCACTGCA
GCACCGTCCAGGCTGACTCGGCCCTGGACCAGCGTACCTAGCATTGTAAAGAATCTT
CGCCCCGGAGATTCGATGGTTGAGCTGTAGGTGCCATCGACGGCAACATCGCCGTA
ACGGTTAAGCAGGTTGGTTCGGGGAATGCGAACATTGGTGAAATGGAGACGTCCGT
TATCAATTCCGTTTAGTCCCCCCTTAATACCGTCGTCCTCTCCACCAATACCAGGGAG
AAAGTCTCCGGTGGCGGGATCTCTCAGATCGACGTAGAAGGCGTGCACTCCATGGTT
AACCTTTCGAGTAATCAGTTGGGCAAACACGACAGCGGCCAAACCGTCGTTAGCGG
CGTTTCCAATGTAGTCCTTCCAGGCGGCTCGGAACGGGGTGTCAATAACGAACTCCT
GGGTTTCCTCATCATAGGTGGCCGTTGTAGCAATGGAAGCGACATCGGAGCCATGGC
CAGTCTCAGTCATGGCAAAGCAACCAGGGATTTCCAGAGACATGATGCCTGGGAGC
CACTTGTCGTGGTGCTCCCTAGTTCCCAAGTGCATAACAGCGGAGCCGAACAGTCCC
CACTGGACGCCGGCCTTGATCTGGAGGGAGGGGTCCGCCGTGACAAGCTCCTCAAA
ACCAGCGATGTTTCCGCCGTGGTCGTCACTACCACCCAGTCGAGAAGGAAAGGCTC
GGTGAACTGCGTTGTTATCGACCAAGTACTTGAGCTGGCCAAAGACGCGAGAGCGG
TGCTCTGTATGAGTCAGACCCTCCACCTTCTGAACTACCTCTCGTCCCGCAAGGTCCC
```

-continued

```
GGGCGTGGAGACGGATATCAGCCCATCGGCCCAGCAGCTGCTCTCCCAGCGCAGCC
ACATCTACTCGGGGCTCGACGGCCACCTTAGCACCGTCTGCGGCGGCCGTAGTTGAG
CCAGGGGATGCGGGGGATGAGGCTCTGTCAACTACTTCGGTCATGGCGTCGTTGCTT
GTGTGATTTTTGAGGACCCATCCCTTTGGTATATAAGTATACTCTGGGGTTAAGGTTG
CCCGTGTAGTCTAGGTTATAGTTTTCATGTGAAATACCGAGAGCCGAGGGAGAATAA
ACGGGGGTATTTGGACTTGTTTTTTTCGCGGAAAAGCGTCGAATCACCCCTGCGGGC
CTTGCACCATGTCCACGACGTGTTTCTCGCCCCAATTCGCCCCTTGCACGTCAAAATT
AGGCCTCCATCTAGACCCCTCCATAACATGTGACTGTGGGGAAAAGTATAAGGGAA
ACCATGCAACCATAGACGACGTGAAAGACGGGGAGGAACCAATGGAGGCCAAAGA
AATGGGGTAGCAACAGTCCAGGAGACAGACAAGGAGACAAGGAGAGGGCGCCCGA
AAGATCGGAAAAACAAACATGTCCAATTGGGGCAGTGACGGAAACGACACGGACA
CTTCAGTACAATGGACCGACCATCTCCAAGCCAGGGTTATTCCGGTATCACCTTGGC
CGTAACCTCCCGCTGGTACCTGATATTGTACACGTTCACATTCAATATACTTTCAGCT
ACAATAAGAGAGGCTGTTTGTCGGGCATGTGTGTCCGTCGTATGGGGTGATGTCCGA
GGGCGAAATTCGCTACAAGCTTAACTCTGGCGCTTGTCCAGTATGAATAGACAAGTC
AAGACCAGTGGTGCCATGATTGACAGGGAGGTACAAGACTTCGATACTCAAGCATT
ACTCGGACTTGTGGCGATTGAACAGACGGGCGATCGCTTCTCCCCCGTATTGCCCCG
TTTCTACGAGTGCCGTACGAGTACGAGTACAGGAGGTACAGTACATTCCGATACTTG
CACTCCCACCATTGCTGTATATCTCTGCTACTTGTGGTATCAAATCCGCTACTCGTAG
TGGTTTTTCCACTTGTACAAATTCTATCCCCCATGACCACCAACCCTTCTCCCGATCG
CCAGTCTCACTTGGCGGAATCGTCGACGATCATCCTCGAGATGCGGCCGCGTCGACA
TAACTTCGTATAGCATACATTATACGAAGTTATTTTCTAATTTGGACCGATAGCCGTA
TAGTCCAGTCTATCTATAAGTTCAACTAACTCGTAACTATTACCATAACATATACTTC
ACTGCCCCAGATAAGGTTCCGATAAAAAGTTGTGCAGACTAAATTTATTTCAGTCTC
CTCTTCACCACCAAAATGCCCTCCTACGAAGCGCGAGCTAACGTCCACAAGTCCGCC
TTTGCCGCCCGAGTGCTCAAGCTCGTGGCAGCCAAGAAAACCAACCTGTGTGCTTCT
CTGGATGTTACCACCACCAAGGAGCTCATTGAGCTTGCCGATAAGGTCGGACCTTAT
GTGTGCATGATCAAGACCCATATCGACATCATTGACGACTTCACCTACGCCGGAACT
GTGCTCCCCCTCAAGGAACTTGCTCTTAAGCACGGTTTCTTCCTGTTCGAGGACAGA
AAGTTCGCAGATATTGGCAACACTGTCAAGCACCAGTACAAGAACGGTGTCTACCG
AATCGCCGAGTGGTCCGATATCACCAACGCCCACGGTGTACCCGGAACCGGAATCA
TTGCTGGCCTGCGAGCTGGTGCCGAGGAAACTGTCTCTGAACAGAAGAAGGAGGAT
GTCTCTGACTACGAGAACTCCCAGTACAAGGAGTTCCTGGTCCCCTCTCCCAACGAG
AAGCTGGCCAGAGGTCTGCTCATGCTGGCCGAGCTGTCTTGCAAGGGCTCTCTGGCC
ACTGGCGAGTACTCCAAGCAGACCATTGAGCTTGCCCGATCCGACCCCGAGTTTGTG
GTTGGCTTCATTGCCCAGAACCGACCTAAGGGCGACTCTGAGGACTGGCTTATTCTG
ACCCCCGGGGTGGGTCTTGACGACAAGGGAGATGCTCTCGGACAGCAGTACCGAAC
TGTTGAGGATGTCATGTCTACCGGAACGGATATCATAATTGTCGGCCGAGGTCTGTA
CGGCCAGAACCGAGATCCTATTGAGGAGGCCAAGCGATACCAGAAGGCTGGCTGGG
AGGCTTACCAGAAGATTAACTGTTAGAGGTTAGACTATGGATATGTCATTTAACTGT
```

```
GTATATAGAGAGCGTGCAAGTATGGAGCGCTTGTTCAGCTTGTATGATGGTCAGACG

ACCTGTCTGATCGAGTATGTATGATACTGCACAACCTGATAACTTCGTATAGCATAC

ATTATACGAAGTTATCTCGAGGCGGCCGCATGGAGCGTGTGTTCTGAGTCGATGTTT

TCTATGGAGTTGTGAGTGTTAGTAGACATGATGGGTTTATATATGATGAATGAATAG

ATGTGATTTTGATTTGCACGATGGAATTGAGAACTTTGTAAACGTACATGGGAATGT

ATGAATGTGGGGGTTTTGTGACTGGATAACTGACGGTCAGTGGACGCCGTTGTTCAA

ATATCCAAGAGATGCGAGAAACTTTGGGTCAAGTGAACATGTCCTCTCTGTTCAAGT

AAACCATCAACTATGGGTAGTATATTTAGTAAGGACAAGAGTTGAGATTCTTTGGAG

TCCTAGAAACGTATTTTCGCGTTCCAAGATCAAATTAGTAGAGTAATACGGGCACGG

GAATCCATTCATAGTCTCAATTTTCCCATAGGTGTGCTACAAGGTGTTGAGATGTGG

TACAGTACCACCATGATTCGAGGTAAAGAGCCCAGAAGTCATTGATGAGGTCAAGA

AATACACAGATCTACAGCTCAATACAATGAATATCTTCTTTCATATTCTTCAGGTGA

CACCAAGGGTGTCTATTTTCCCCAGAAATGCGTGAAAAGGCGCGTGTGTAGCGTGG

AGTATGGGTTCGGTTGGCGTATCCTTCATATATCGACGAAATAGTAGGGCAAGAGAT

GACAAAAAGTATCTATATGTAGACAGCGTAGAATATGGATTTGATTGGTATAAATTC

ATTTATTGCGTGTCTCACAAATACTCTCGATAAGTTGGGGTTAAACTGGAGATGGAA

CAATGTCGATATCTCGACATATTTTGATATTTGTTAATTAA pLD137
                                               (SEQ ID NO: 177)
AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA
```

-continued

```
CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTAAATTATTGGCCCGAAAATTAATCAGTGTAGACTGGATCCTC

GAGAACCATTTAATTAAGATCAGAGACCGGATGGTCTCAAGCGTCGACACCATATC

ATATAAAACTAACAATGCATTGAATTAATACGAAGACTACCCGTTGCTATCTCCACA
```

-continued

CCGTTATCTCCACGGTCCAAAGGCTGCTCAATGTGCTGCATACGTAACGTGGGGTGC

AACCTTGAGCACATAGTACTTTCCGAAAACCGGCGATAATTAAGTGTGCACTCCAAC

TTTTCACACTGAGCATAAAATGTGGAGAAGAAATCACACTAAAAAGTCAGGTAGAC

TGGAAAATGCGCCATGAAATAATATCTCTTGCTACAGTAATGCCCAGCATCGAGGG

GTATTGTGTCACCAACACTATAGTGGCAGCTGAAGCGCTCGTGATTGTAGTATGAGT

CTTTATTGGTGATGGGAAGAGTTCACTCAATATTCTCGTTACTGCCAAAACACCACG

GTAATCGGCCAGACACCATGGATGTAGATCACCAAGCCTGTGAATGTTATTCGAGCT

AAAATGCACATGGTTGGTGAAAGGAGTAGTTGCTGTCGAATTCCGTCGTCGCCTGAG

TCATCATTTATTTACCAGTTGGCCACAAACCCTTGACGATCTCGTATGTCCCCTCCGA

CATACTCCCGGCCGGCTGGGGTACGTTCGATAGCGCTATCGGCATCGACAAGGTTTG

GGTCCCTAGCCGATACCGCACTACCTGAGTCACAATCTTCGGAGGTTTAGTCTTCCA

CATAGCACGGGCAAAAGTGCGTATATATACAAGAGCGTTTGCCAGCCACAGATTTTC

ACTCCACACACCACATCACACATACAACCACACACATCCACAATGGAACCCGAAAC

TAAGAAGACCAAGACTGACTCCAAGAAGATTGTTCTTCTCGGCGGCGACTTCTGTGG

CCCCGAGGTGATTGCCGAGGCCGTCAAGGTGCTCAAGTCTGTTGCTGAGGCCTCCGG

CACCGAGTTTGTGTTTGAGGACCGACTCATTGGAGGAGCTGCCATTGAGAAGGAGG

GCGAGCCCATCACCGACGCTACTCTCGACATCTGCCGAAAGGCTGACTCTATTATGC

TCGGTGCTGTCGGAGGCGCTGCCAACACCGTATGGACCACTCCCGACGGACGAACC

GACGTGCGACCCGAGCAGGGTCTTCTCAAGCTGCGAAAGGACCTGAACCTGTACGC

CAACCTGCGACCCTGCCAGCTGCTGTCGCCCAAGCTCGCCGATCTCTCCCCCATCCG

AAACGTTGAGGGCACCGACTTCATCATTGTCCGAGAGCTCGTCGGAGGTATCTACTT

TGGAGAGCGAAAGGAGGATGACGGATCTGGCGTCGCTTCCGACACTGAGACTTACT

CCGTTCCTGAGGTTGAGCGAATTGCCCGAATGGCCGCCTTCCTGGCCCTTCAGCACA

ACCCCCCTCTTCCCGTGTGGTCCCTTGACAAGGCCAACGTGCTGGCCTCCTCTCGACT

TTGGCGAAAGACCGTCACCCGAGTCCTCAAGGACGAATTCCCCCAGCTGGAGCTCA

ACCACCAGCTGATCGACTCGGCCGCCATGATCCTCATCAAGCAGCCCTCCAAGATGA

ATGGTATCATCATCACCACCAACATGTTTGGCGATATCATCTCCGACGAGGCCTCCG

TCATCCCCGGTTCTCTGGGTCTGCTGCCCTCCGCCTCTCTGGCTTCTCTGCCCGACAC

CAACGAGGCGTTCGGTCTGTACGAGCCCTGTCACGGATCTGCCCCCGATCTCGGCAA

GCAGAAGGTCAACCCCATTGCCACCATTCTGTCTGCCGCCATGATGCTCAAGTTCTC

TCTTAACATGAAGCCCGCCGGTGACGCTGTTGAGGCTGCCGTCAAGGAGTCCGTCGA

GGCTGGTATCACTACCGCCGATATCGGAGGCTCCTCCTCCACCTCCGAGGTCGGAGA

CTTTGTTGCCAACAAGGTCAAGGAGCTGCTCAAGAAGGAGTAAGTCGTTTCTACGAC

GCATTGATGGAAGGAGCAAACTGACGCGCCTGCGGGTTGGTCTACCGGCAGGGTCC

GCTAGTGTATAAGACTCTATAAAAAGGGCCCAGCCCTGCTAATGAAATGATGATTTA

TAATTTACCGGTGTAGCAACCTTGACTAGAAGAAGCAGATTGGGTGTGTTTGTAGTG

GAGGACAGTGGTACGTTTTAATTAA pLD138

(SEQ ID NO: 178)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

-continued

```
TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG
```

-continued

```
TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTAAATTATTGGCCCGAAAATTAATCAGTGTAGACTGGATCCTC

GAGAACCATTTAATTAATTTCTAATTTGGACCGATAGCCGTATAGTCCAGTCTATCT

ATAAGTTCAACTAACTCGTAACTATTACCATAACATATACTTCACTGCCCCAGATAA

GGTTCCGATAAAAAGTTGTGCAGACTAAATTTATTTCAGTCTCCTCTTCACCACCAA

AATGCCCTCCTACGAAGCGCGAGCTAACGTCCACAAGTCCGCCTTTGCCGCCCGAGT

GCTCAAGCTCGTGGCAGCCAAGAAAACCAACCTGTGTGCTTCTCTGGATGTTACCAC

CACCAAGGAGCTCATTGAGCTTGCCGATAAGGTCGGACCTTATGTGTGCATGATCAA

GACCCATATCGACATCATTGACGACTTCACCTACGCCGGAACTGTGCTCCCCCTCAA

GGAACTTGCTCTTAAGCACGGTTTCTTCCTGTTCGAGGACAGAAAGTTCGCAGATAT

TGGCAACACTGTCAAGCACCAGTACAAGAACGGTGTCTACCGAATCGCCGAGTGGT

CCGATATCACCAACGCCCACGGTGTACCCGGAACCGGAATCATTGCTGGCCTGCGA

GCTGGTGCCGAGGAAACTGTCTCTGAACAGAAGAAGGAGGATGTCTCTGACTACGA

GAACTCCCAGTACAAGGAGTTCCTGGTCCCCTCTCCCAACGAGAAGCTGGCCAGAG

GTCTGCTCATGCTGGCCGAGCTGTCTTGCAAGGGCTCTCTGGCCACTGGCGAGTACT

CCAAGCAGACCATTGAGCTTGCCCGATCCGACCCCGAGTTTGTGGTTGGCTTCATTG

CCCAGAACCGACCTAAGGGCGACTCTGAGGACTGGCTTATTCTGACCCCCGGGGTG

GGTCTTGACGACAAGGGAGATGCTCTCGGACAGCAGTACCGAACTGTTGAGGATGT

CATGTCTACCGGAACGGATATCATAATTGTCGGCCGAGGTCTGTACGGCCAGAACCG

AGATCCTATTGAGGAGGCCAAGCGATACCAGAAGGCTGGCTGGGAGGCTTACCAGA

AGATTAACTGTTAGAGGTTAGACTATGGATATGTCATTTAACTGTGTATATAGAGAG

CGTGCAAGTATGGAGCGCTTGTTCAGCTTGTATGATGGTCAGACGACCTGTCTGATC

GAGTATGTATGATACTGCACAACCTGCGCTTGAGACCATCCGGTCTCTGATCTTAAT

TAA
``` pLD139

(SEQ ID NO: 179)

```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACATAATGAACCCAAGGGAAAACTTCCTT

AAGTGTTTTCTGCAGTACATCCCTAACAATGCAACAAACCTCAAGTTGGTGTACACT

CAAAACAATCCACTCTATATGAGCGTGCTTAATAGCACAATCCACAACTTGCGCTTC

ACGTCAGATACTACGCCTAAGCCACTAGTGATCGTTACACCATCACACGTCAGCCAT

ATTCAAGGAACGATCCTATGTCTGAAAAAGGTCGGGTTGCAAATCAGGACTCGATC

AGGAGGGCACGATAGTGAGGGAATGAGTTACATCTCGCAAGTACCCTTCGTGATAG

TTGACTTGCGAAATATGCGGTCTATTAAAATTGACGTACATAGCCAGACCGCCTGGG

TTGAAGCAGGGCAACCTTGGGTGAAGTTTATTACTGGGTCAATGAAAAAAACGAA

AACCTAAGTCTTGCTGCTGGATATTGCCCCACCGTTTGCGCGGGTGGTCATTTTGGA

GGCGGCGGATATGGTCCGTTGATGAGAAATTATGGACTTGCAGCAGACAATATTAT

AGATGCCCACTTGGTGAACGTTCATGGAAAGGTCTTGGACCGTAAGTCCATGGGTGA

AGATCTTTTCTGGGCCTTGAGAGGTGGTGGAGCGGAATCGTTTGGCATCATCGTTGC
```

-continued

```
CTGGAAAATTAGGTTGGTTGCGGTCCCGAAGAGTACAATGTTCTCCGTGAAGAAGAT

TATGGAAATACATGAGCTTGTCAAGTTAGTTAACAAGTGGCAAAATATCGCTTATAA

GTATGATAAAGACTTGCTTTTGATGACTCATTTTATTACGCGAAACATAACCGATAA

CCAGGGCAAGAACAAGACTGCTATTCACACGTACTTCTCCTCTGTATTTCTTGGAGG

AGTAGACTCCTTAGTTGACTTGATGAACAAGAGTTTCCCAGAATTGGGGATTAAGAA

GACAGATTGCAGACAATTATCGTGGATAGATACAATCATATTCTATAGCGGTGTCGT

CAATTACGATACTGATAATTTTAATAAAGAAATCCTCCTAGATCGTTCAGCTGGGCA

AAACGGGGCATTCAAAATTAAATTGGATTATGTGAAGAAACCAATTCCAGAGCTGG

TGTTTGTTCAGATATTGGAAAAACTTTACGAAGAAGACATTGGCGCAGGTATGTACG

CTTTGTATCCATATGGAGGCATTATGGACGAGATCTCAGAGCTGGCGATCCCCTTCC

CGCACAGAGCTGGGATACTCTACGAGCTATGGTACATCTGCTCTTGGGAGAAACAA

GAAGACAACGAGAAACATCTCAATTGGATTCGGAACATATACAACTTTATGACCCC

ATACGTATCAAAAAACCCGCGCTTAGCATACTTGAATTACAGAGACTTAGATATCGG

TATCAATGATCCTAAGAATCCTAACAATTACACCCAAGCCCGTATTTGGGGTGAGAA

ATATTTCGGCAAGAATTTTGACAGATTAGTTAAGGTCAAAACACTCGTGGACCCCAA

CAACTTTTTCCGAAACGAGCAGTCGATTCCACCACTACCCAGGCATAGACACGGAA

GAAGGGCAAAGTTGTAAGAGTGACTCTTTTGATAAGAGTCGCAAATTTGATTTCATA

AGTATATATTCATTATGTAAAGTAGTAAATGGAAAATTCATTAAAAAAAAGCAAA

TTTCCGTTGTATGCATACTCCGAACACAAAACTAGCCCCGGAAAAACCCTTAGTTGA

TAGTTGCGAATTTAGGTCGACCATATGCGACGGGTACAACGAGAATTGTATTGAATT

GATCAAGAACATGATCTTGGTGTTACAGAACATCAAGTTCTTGGACCAGACTGAGA

ATGCACAGATATACAAGGCGTCATGTGATAAAATGGATGAGATTTATCCACAATTG

AAGAAAGAGTTTATGGAAAGTGGTCAACCAGAAGCTAAACAGGAAGAAGCAAACG

AAGAGGTGAAACAAGAAGAAGAAGGTAAATAAGTATTTTGTATTATATAACAAACA

AAGTAAGGAATACAGATTTATACAATAAATTGCCATACTAGTCACGTGAGATATCTC

ATCCATTCCCCAACTCCCAAGAAAATAAAAAAGTGAAAAATAAAATCAAACCCAAA

GATCAACCTCCCCATCATCATCGTCATCAAACCCCCAGCTCAATTCGCAATGGTTAG

CACAAAAACATACACAGAAAGGGCATCAGCACACCCCTCCAAGGTTGCCCAACGTT

TATTAATTAAAGGCTAGGTGGAGGCTCAGTGATGATAAGTCTGCGATGGTGGATGC

ATGTGTCATGGTCATAGCTGTTTCCTGTGTGAAATTGTTATCCGCTCAGAGGGCACA

ATCCTATTCCGCGCTATCCGACAATCTCCAAGACATTAGGTGGAGTTCAGTTCGGCG

TATGGCATATGTCGCTGGAAAGAACATGTGAGCAAAAGGCCAGCAAAAGGCCAGGA

ACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTC
```

-continued

```
GGAAAAAGAGTTGGTAGCTCTTGATCCGGCAAACAAACCACCGCTGGTAGCGGTGG

TTTTTTTGTTTGCAAGCAGCAGATTACGCGCAGAAAAAAAGGATCTCAAGAAGATCC

TTTGATCTTTTCTACGGGGTCTGACGCTCTATTCAACAAAGCCGCCGTCCCGTCAAGT

CAGCGTAAATGGGTAGGGGGCTTCAAATCGTCCGCTCTGCCAGTGTTACAACCAATT

AACAAATTCTGATTAGAAAAACTCATCGAGCATCAAATGAAACTGCAATTTATTCAT

ATCAGGATTATCAATACCATATTTTTGAAAAAGCCGTTTCTGTAATGAAGGAGAAAA

CTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAG

TGAGAAATCACCATGAGTGACGACTGAATCCGGTGAGAATGGCAAAAGCTTATGCA

TTTCTTTCCAGACTTGTTCAACAGGCCAGCCATTACGCTCGTCATCAAAATCACTCGC

ATCAACCAAACCGTTATTCATTCGTGATTGCGCCTGAGCGAGACGAAATACGCGATC

GCTGTTAAAGGACAATTACAAACAGGAATCGAATGCAACCGGCGCAGGAACACTG

CCAGCGCATCAACAATATTTTCACCTGAATCAGGATATTCTTCTAATACCTGGAATG

CTGTTTTCCCGGGGATCGCAGTGGTGAGTAACCATGCATCATCAGGAGTACGGATAA

AATGCTTGATGGTCGGAAGAGGCATAAATTCCGTCAGCCAGTTTAGTCTGACCATCT

CATCTGTAACATCATTGGCAACGCTACCTTTGCCATGTTTCAGAAACAACTCTGGCG

CATCGGGCTTCCCATACAATCGATAGATTGTCGCACCTGATTGCCCGACATTATCGC

GAGCCCATTTATACCCATATAAATCAGCATCCATGTTGGAATTTAATCGCGGCCTCG

AGCAAGACGTTTCCCGTTGAATATGGCTCATAACACCCCTTGTATTACTGTTTATGTA

AGCAGACAGTTTTATTGTTCATGATGATATATTTTTATCTTGTGCAATGTAACATCAG

AGATTTTGAGACACAACGTGGCTTTCCCCCGCCGCTCTAGAACTAGTGGATCCAAAT

AAAACGAAAGGCTCAGTCGAAAGACTGGGCCTTTCGTTTTATCTGTTGTTTGTCGCA

TTATACGAGACGTCCAGGTTGGGATACCTGAAACAAAACCCATCGTACGGCCAAGG

AAGTCTCCAATAACTGTGATCCACCACAAGCGCCAGGGTTTTCCCAGTCACGACGTT

GTAAAACGACGGCCAGTCATGCATAATCCGCACGCATCTGGAATAAGGAAGTGCCA

TTCCGCCTGACCT
``` pLD19

(SEQ ID NO: 180)
```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC
```

-continued
```
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCCGCGAAAGATAATCAAAATTA
CACTTGTGAATTTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACataATGGGTTTATCGTCAGTGTGCACTTT
TTCTTTTCAAACAAACTACCACACCCTCCTAAACCCTCACAATAATAACCCAAAAAC
CTCCTTGCTATGTTACAGACATCCAAAGACACCGATCAAGTATTCATACAACAATTT
TCCCAGTAAACATTGCTCAACGAAGTCCTTCCACTTGCAAAACAAATGCAGCGAATC
ATTGTCGATAGCTAAAAACTCGATACGTGCGGCAACCACTAACCAAACTGAGCCAC
CAGAGAGCGATAATCATTCAGTCGCCACCAAGATTTTGAACTTTGGAAAAGCCTGTT
GGAAACTTCAAAGGCCTTACACCATTATCGCATTTACCAGTTGCGCATGTGGTTTGT
TCGGGAAGGAATTATTACACAACACAAATTTGATCAGCTGGAGCCTAATGTTTAAGG
CATTTTTCTTCTTAGTTGCAATTTTGTGTATAGCTTCGTTTACAACGACCATTAATCA
GATTTACGACCTTCACATCGATCGGATCAATAAACCAGACTTGCCCCTTGCCTCTGG
GGAAATCTCTGTAAATACTGCATGGATCATGCTGATAATCGTGGCTTTGTTTGGATT
GATTATTACAATTAAGATGAAGGGGGGTCCATTATATATATTCGGGTACTGCTTCGG
CATTTTCGGTGGTATCGTTTACTCCGTCCCACCCTTTAGATGGAAACAGAACCCCAG
TACGGCCTTTCTACTCAATTTCTTGGCTCATATCATCACAAACTTCACATTCTATTAT
GCAAGCCGAGCGGCGCTTGGTTTGCCGTTCGAACTCAGACCGAGTTTTACATTTCTC
CTTGCCTTCATGAAACTGATGGGACTGGCCCTTGCATTGATCAAGGATGCGTCAGAT
GTCGAAGGCGACACTAAGTTCGGCATTCTGACGCTTGCTTCCAAGTATGGAAGTAGA
AATCTAACGCTTTTTTGTTCAGGAATAGTGCTACTTAGTTATGTTGCTGCTATACTCG
CTGGCATTATTTGGCCTCAGGCCTTCAACTCTAACGTAATGTTGTTATCCCATGCTAT
TTTGGCGTTCTGGTTGATCTTGCAAACGCGAGATTTTGCACTCACTAACTACGACCC
AGAGGCAGGAAGGCGCTTTTACGAGTTTATGTGGAAGTTGTATTATGCCGAATACTT
GGTTTATGTTTTCATTTGATAAgagTGACTCTTTTGATAAGAGTCGCAAATTTGATTTC
ATAAGTATATATTCATTATGTAAAGTAGTAAATGGAAAATTCATTAAAAAAAAAGC
AAATTTCCGTTGTATGCATACTCCGAACACAAAACTAGCCCCGGAAAAACCCTTAGT
TGATAGTTGCGAATTTAGGTCGACCATATGCGACGGGTACAACGAGAATTGTATTGA
ATTGATCAAGAACATGATCTTGGTGTTACAGAACATCAAGTTCTTGGACCAGACTGA
GAATGCACAGATATACAAGGCGTCATGTGATAAAATGGATGAGATTTATCCACAAT
```

-continued

```
TGAAGAAAGAGTTTATGGAAAGTGGTCAACCAGAAGCTAAACAGGAAGAAGCAAA

CGAAGAGGTGAAACAAGAAGAAGAAGGTAAATAAGTATTTTGTATTATATAACAA

CAAAGTAAGGAATACAGATTTATACAATAAATTGCCATACTAGTCACGTGAGATATC

TCATCCATTCCCCAACTCCCAAGAAAATAAAAAAGTGAAAAATAAAATCAAACCCA

AAGATCAACCTCCCCATCATCATCGTCATCAAACCCCCAGCTCAATTCGCAATGGTT

AGCACAAAAACATACACAGAAAGGGCATCAGCACACCCCTCCAAGGTTGCCCAACG

TTTATTAATTAAAGGCTAGGTGGAGGCTCAGTGATGATAAGTCTGCGATGGTGGATG

CATGTGTCATGGTCATAGCTGTTTCCTGTGTGAAATTGTTATCCGCTCAGAGGGCAC

AATCCTATTCCGCGCTATCCGACAATCTCCAAGACATTAGGTGGAGTTCAGTTCGGC

GTATGGCATATGTCGCTGGAAAGAACATGTGAGCAAAAGGCCAGCAAAAGGCCAGG

AACCGTAAAAAGGCCGCGTTGCTGGCGTTTTTCCATAGGCTCCGCCCCCCTGACGAG

CATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCT

CACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTA

CGGCTACACTAGAAGAACAGTATTTGGTATCTGCGCTCTGCTGAAGCCAGTTACCTT

CGGAAAAAGAGTTGGTAGCTCTTGATCCGGCAAACAAACCACCGCTGGTAGCGGTG

GTTTTTTTGTTTGCAAGCAGCAGATTACGCGCAGAAAAAAAGGATCTCAAGAAGATC

CTTTGATCTTTTCTACGGGGTCTGACGCTCTATTCAACAAAGCCGCCGTCCCGTCAAG

TCAGCGTAAATGGGTAGGGGGCTTCAAATCGTCCGCTCTGCCAGTGTTACAACCAAT

TAACAAATTCTGATTAGAAAAACTCATCGAGCATCAAATGAAACTGCAATTTATTCA

TATCAGGATTATCAATACCATATTTTTGAAAAAGCCGTTTCTGTAATGAAGGAGAAA

ACTCACCGAGGCAGTTCCATAGGATGGCAAGATCCTGGTATCGGTCTGCGATTCCGA

CTCGTCCAACATCAATACAACCTATTAATTTCCCCTCGTCAAAAATAAGGTTATCAA

GTGAGAAATCACCATGAGTGACGACTGAATCCGGTGAGAATGGCAAAAGCTTATGC

ATTTCTTTCCAGACTTGTTCAACAGGCCAGCCATTACGCTCGTCATCAAAATCACTCG

CATCAACCAAACCGTTATTCATTCGTGATTGCGCCTGAGCGAGACGAAATACGCGAT

CGCTGTTAAAAGGACAATTACAAACAGGAATCGAATGCAACCGGCGCAGGAACACT

GCCAGCGCATCAACAATATTTTCACCTGAATCAGGATATTCTTCTAATACCTGGAAT

GCTGTTTTCCCGGGGATCGCAGTGGTGAGTAACCATGCATCATCAGGAGTACGGATA

AAATGCTTGATGGTCGGAAGAGGCATAAATTCCGTCAGCCAGTTTAGTCTGACCATC

TCATCTGTAACATCATTGGCAACGCTACCTTTGCCATGTTTCAGAAACAACTCTGGC

GCATCGGGCTTCCCATACAATCGATAGATTGTCGCACCTGATTGCCCGACATTATCG

CGAGCCCATTTATACCCATATAAATCAGCATCCATGTTGGAATTTAATCGCGGCCTC

GAGCAAGACGTTTCCCGTTGAATATGGCTCATAACACCCCTTGTATTACTGTTTATGT

AAGCAGACAGTTTTATTGTTCATGATGATATATTTTTATCTTGTGCAATGTAACATCA

GAGATTTTGAGACACAACGTGGCTTTCCCCCGCCGCTCTAGAACTAGTGGATCCAAA
```

-continued

TAAAACGAAAGGCTCAGTCGAAAGACTGGGCCTTTCGTTTTATCTGTTGTTTGTCGC

ATTATACGAGACGTCCAGGTTGGGATACCTGAAACAAAACCCATCGTACGGCCAAG

GAAGTCTCCAATAACTGTGATCCACCACAAGCGCCAGGGTTTTCCCAGTCACGACGT

TGTAAAACGACGGCCAGTCATGCATAATCCGCACGCATCTGGAATAAGGAAGTGCC

ATTCCGCCTGACCT pLD26

(SEQ ID NO: 181)
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGCGGCAACCACTAACCAAACTG

AGCCACCAGAGAGCGATAATCATTCAGTCGCCACCAAGATTTTGAACTTTGGAAAA

GCCTGTTGGAAACTTCAAAGGCCTTACACCATTATCGCATTTACCAGTTGCGCATGT

GGTTTGTTCGGGAAGGAATTATTACACAACACAAATTTGATCAGCTGGAGCCTAATG

TTTAAGGCATTTTTCTTCTTAGTTGCAATTTTGTGTATAGCTTCGTTTACAACGACCA

TTAATCAGATTTACGACCTTCACATCGATCGGATCAATAAACCAGACTTGCCCCTTG

CCTCTGGGGAAATCTCTGTAAATACTGCATGGATCATGCTGATAATCGTGGCTTTGT

TTGGATTGATTATTACAATTAAGATGAAGGGGGGTCCATTATATATATTCGGGTACT

-continued

```
GCTTCGGCATTTTCGGTGGTATCGTTTACTCCGTCCCACCCTTTAGATGGAAACAGA

ACCCCAGTACGGCCTTTCTACTCAATTTCTTGGCTCATATCATCACAAACTTCACATT

CTATTATGCAAGCCGAGCGGCGCTTGGTTTGCCGTTCGAACTCAGACCGAGTTTTAC

ATTTCTCCTTGCCTTCATGAAACTGATGGGACTGGCCCTTGCATTGATCAAGGATGC

GTCAGATGTCGAAGGCGACACTAAGTTCGGCATTCTGACGCTTGCTTCCAAGTATGG

AAGTAGAAATCTAACGCTTTTTGTTCAGGAATAGTGCTACTTAGTTATGTTGCTGCT

ATACTCGCTGGCATTATTTGGCCTCAGGCCTTCAACTCTAACGTAATGTTGTTATCCC

ATGCTATTTTGGCGTTCTGGTTGATCTTGCAAACGCGAGATTTTGCACTCACTAACTA

CGACCCAGAGGCAGGAAGGCGCTTTTACGAGTTTATGTGGAAGTTGTATTATGCCGA

ATACTTGGTTTATGTTTTCATTTGATAAgagTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC

CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGGCTTCAAATCGTCCGCTCTGCCAGTGTTACA

ACCAATTAACAAATTCTGATTAGAAAAACTCATCGAGCATCAAATGAAACTGCAATT

TATTCATATCAGGATTATCAATACCATATTTTTGAAAAAGCCGTTTCTGTAATGAAG
```

```
                      -continued
GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT
```

References including disclosure related to compartmentalization of an enzyme through signal sequences include the following, each of which is incorporated by reference herein in its entirety: Agarwal et al. 2001 "Gene isolation and characterization of two acyl CoA oxidases from soybean with broad substrate specificities and enhanced expression in the growing seedling axis." Plant Mol Biol. 2001 November; 47(4):519-31; Alconado and Juarez 2006. "Acyl-CoA oxidase activity from *Beauveria bassiana*, an entomopathogenic fungus". J Basic Microbiol. 2006; 46(6):435-43; Aizpurua-Olaizola et al. "Identification and quantification of cannabinoids in *Cannabis sativa* L. plants by high performance liquid chromatography-mass spectrometry." Anal Bioanal Chem. 2014 November; 406(29):7549-60; Backer et al. "Innovative development and validation of an HPLC/DAD method for the qualitative and quantitative determination of major cannabinoids in *cannabis* plant material." J Chromatogr B Analyt Technol Biomed Life Sci. 2009 Dec. 15; 877(32):4115-24; Bakke et al. "N-ethylmaleimide-resistant acyl-coenzyme A oxidase from *Arthrobacter ureafaciens* NBRC 12140: molecular cloning, gene expression and characterization of the recombinant enzyme." Biochim Biophys Acta. 2007 January; 1774(1):65-71; Barth and Gaillardin. "Physiology and genetics of the dimorphic fungus *Yarrowia lipolytica*." FEMS Microbiol Rev. 1997 April; 19(4):219-37; Beggah et al. "Intra- and intermolecular events direct the propeptide-mediated maturation of the *Candida albicans* secreted aspartic proteinase Sap1p." Microbiology. 2000 November; 146 (Pt 11):2765-73; Brocard and Hartig. "Peroxisome targeting signal 1: is it really a simple tripeptide?" Biochim Biophys Acta. 2006 December; 1763(12):1565-73; Brown et al. "*Aspergillus* has distinct fatty acid synthases for primary and secondary metabolism.: Proc Natl Acad Sci USA. 1996 Dec. 10; 93(25): 14873-7; Carbalho et al. "Designing microorganisms for heterologous biosynthesis of cannabinoids." FEMS Yeast Res. 2017 Jun. 1; 17(4); Gagne et al. "Identification of olivetolic acid cyclase from *Cannabis sativa* reveals a unique catalytic route to plant polyketides." Proc Natl Acad Sci USA. 2012 Jul. 31; 109(31):12811-6; Gajewski et al. "Engineering fungal de novo fatty acid synthesis for short chain fatty acid production." Nat Commun. 2017 Mar. 10; 8:14650; Gao et al. "Iterative integration of multiple-copy pathway genes in *Yarrowia lipolytica* for heterologous β-carotene production". Metab Eng. 2017 May; 41:192-201; Gietz and Woods "Transformation of Yeast by Lithium Acetate/Single-Stranded Carrier DNA/Polyethylene Glycol Method". Methods Enzymol. 2002; 350:87-96.; Hong et al. "Engineering *Yarrowia lipolytica* to express secretory invertase with strong FBA1IN promoter". Yeast. 2012 February; 29(2):59-72; Hooks et al. "Long-chain acyl-CoA oxidases of *Arabidopsis*." Plant J. 1999 October; 20(1):1-13; Hunkova and Fenci. "Toxic effects of fatty acids on yeast cells: dependence of inhibitory effects on fatty acid concentration." Biotechnol Bioeng. 1977 November; 19(11):1623-41; Kistler and Boz "Cellular compartmentalization of secondary metabolism" Front. Microbiology February 2015; Klionsky et al. "Intracellular sorting and processing of a yeast vacuolar hydrolase: proteinase A propeptide contains vacuolar targeting information." Mol Cell Biol. 1988 May; 8(5):2105-16; Krink-Koutsoubelis et al." Engineered Production of Short-Chain Acyl-Coenzyme A Esters in *Saccharomyces cerevisiae*." ACS Synth Biol. 2018 Apr. 20; 7(4): 1105-1115; Lametschwandtner et al. "The difference in recognition of terminal tripeptides as peroxisomal targeting signal 1 between yeast and human is due to different affinities of their receptor Pex5p to the cognate signal and to residues adjacent to it." J Biol Chem. 1998 Dec. 11; 273 (50):33635-43; Ledesma-Amaro and Nicaud. "*Yarrowia lipolytica* as a biotechnological chassis to produce usual and unusual fatty acids." Prog Lipid Res. 2016 January; 61:40-50; Liang et al. "Structure, mechanism and function of prenyltransferase." Eur J Biochem. 2002 July; 269(14): 3339-54; Lui et al. "Membrane stress caused by octanoic acid in *Saccharomyces cerevisiae*" Appl Microbiol Biotechnol. 2013 April; 97(7):3239-51; Luo et. al 2002 "The acyl-CoA oxidases from the yeast *Yarrowia lipolytica*: characterization of Aox2p." Arch Biochem Biophys. November 1; 407(1):32-8; Luo et al 2019 "Complete biosynthesis of cannabinoids and their unnatural analogues in yeast." Nature. 2019 March; 567(7746):123-126; Pamplaniyi "Identification, isolation, and functional characterization of prenyltransferases in *Cannabis sativa*" Dissertation Dortmund 2016; Reiser et. al 2009 "AoxA is a major peroxisomal long chain fattyacyl-CoA oxidase required for beta-oxidation in *A. nidulans*". Curr Genet. 2010 April; 56(2): 139-50; Setoyama et. al 1995 "Functional expression of two forms of rat acyl-CoA oxidase and their substrate specificities" December 14; 217(2):482-7; Shimiu et al. "Type III Polyketide Synthases: Functional Classification and Phylogenomics. Chembiochem. 2017 Jan. 3; 18(1):50-65; Stout et al. "The hexanoyl-CoA precursor for cannabinoid biosynthesis is formed by an acyl-activating enzyme in *Cannabis sativa* trichomes." Plant J. 2012 August; 71(3):353-65; Tan et al. "Synthetic Pathway for the Production of Olivetolic Acid in *Escherichia coli*". ACS Synth Biol. 2018 Aug. 17; 7(8):1886-1896; Taura et al. "Characterization of olivetol synthase, a polyketide synthase putatively involved in cannabinoid biosynthetic pathway." FEBS Lett. 2009 Jun. 18; 583(12):2061-6; Zirpel et al. "Production of Δ9-tetrahydrocannabinolic acid from cannabigerolic acid by whole cells of *Pichia (Komagataella) pastoris* expressing Δ9-tetrahydrocannabinolic acid synthase from *Cannabis sativa* L." Biotechnol Lett. 2015 September; 37(9):1869-75; Zirpel et al. "Optimization of Δ9-tetrahydrocannabinolic acid synthase production in *Komagataella phaffii* via post-translational bottleneck identification." J Biotechnol. 2018 Apr. 20; 272-273:40-47; Zirpel "Recombinant Expression and Functional Characterization of Cannabinoid Producing Enzymes in *Komagataella phaffii*" Dissertation Dortmund 2018; Yang et al "Structural basis for olivetolic acid formation by a polyketide cyclase from *Cannabis sativa*." FEBS J. 2016 March; 283(6):1088-106; U.S. Pat. Nos. 7,851,199; 8,884, 100; 9,546,362; 9,611,460; 9,765,308; 9,822,384; 10,059, 971; 10,287,557; U.S. Pat. Publ. No. 2014/0228586 A1; U.S. Pat. Publ. No. 2016/0010126 A1; U.S. Pat. Publ. No. 2016/0298151 A1; U.S. Pat. Publ. No. 2017/0211049 A1; U.S. Pat. Publ. No. 2018/0073043 A1; U.S. Pat. Publ. No. 2018/0155748 A1; U.S. Pat. Publ. No. 2018/0334692A1; PCT Publ. No. WO2017139496A1; PCT Publ. No. WO2018200888A1; PCT Publ. No. WO2018219995A1; PCT Publ. No. WO2018148849A1; PCT Publ. No. WO2018148848A1; and PCT Publ. No. WO2019071000A1.

Exemplary Methods, Microorganisms, and Compositions (e.g., Polyketides)

Method 1: A method, comprising: providing a microorganism selected from the group consisting of a fungi and a yeast, wherein the microorganism has been modified to produce a polyketide in fermentation, wherein at least one of the enzymes that mediate the polyketide production have been targeted to at least one compartment within a secretory pathway resulting in an increase in secretion of the polyketide.

Method 2: Method 1, wherein the polyketide is a cannabinoid.

Method 3: Method 2, wherein the poleketide is a cannabinoid that is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 4: Method 1, wherein the polyketide is olivetolic acid.

Method 5: Method 1, wherein the microorganism is a yeast.

Method 6: Method 5, wherein the yeast is from a genus selected from the group consisting of *Candida, Arxula, Pichia, Scheffersomyces, Kluyveromyces, Saccharomyces, Yarrowia,* or *Schizosaccharomyces*.

Method 7: Method 5, wherein the yeast is a *Candida viswanathii*.

Method 8: Method 5, wherein the yeast is *Arxula adeninivorans*.

Method 9: Method 5, wherein the yeast is *Yarrowia lipolytica*.

Method 10: Method 1, wherein the microorganism is a fungi.

Method 11: Method 10, wherein the fungi is from a genus selected from the group consisting of *Aspergillus, Trichoderma* or *Myceliophthora*.

Method 12: Method 10, wherein the fungi is *Aspergillus niger*.

Method 13: Method 10, wherein the fungi is *Aspergillus terreus*.

Method 14: Method 10, wherein the fungi is *Trichoderma harzianum*.

Method 15: Method 10, wherein the fungi is *Myceliophthora thermophila*.

Method 16: Method 1, wherein the compartment within the secretory pathway is an endoplasmic reticulum.

Method 17: Method 1, wherein the compartment within the secretory pathway is a Golgi apparatus.

Method 18: Method 1, wherein the compartment within the secretory pathway is a vacuole.

Method 19: Method 1, wherein the compartment within the secretory pathway is an endosome.

Method 20: Method 1, wherein the enzyme is removed of its endogenous amino-terminal localization sequence and/or carboxyl-terminal localization sequence.

Method 21: Method 16, whereby the enzyme has been modified with the N-terminal addition of the N-terminal 24 amino acids (MMWKFLIAIGLIFSYCCNAQLLDS) from OST1 and a C-terminal addition of the amino acids FID L, to localize the enzyme to the endoplasmic reticulum.

Method 22: Method 18, whereby the enzyme has been modified by an N-terminal addition of N-terminal 73 amino acids (MGITENTQALLGGDSLSCLNKKKSNTKRNL-SYLLNIITVSIIAYLCFFATHNHHHDSGIPK VDPHKK-KNIIMM) of PHO8 to localize the enzyme to the vacuole.

Method 23: Method 18, whereby the enzyme has been modified with the N-terminal fusion with Sna4 to localize the enzyme to the vacuole.

Method 24: Method 18, whereby the enzyme has been modified with the N-terminal addition of N-terminal 92 amino acids (MQLSLSVLSTVATALLSLTTAVDAK-SHNIKLSKLSNEETLDASTFQEYTSSLANKYMNL FNAAHGNPTSFGLQHVLSNQEAEVPFVTPQKGG) from vacuolar aspartic protease to localize the enzyme to the vacuole.

Method 25: Method 19, whereby the enzyme has been modified with the N-terminal addition of N-terminal 305 amino acids from DOA4 (MTLLLKPTSELDATSRKIIER-IQSNSPTFQHLFDLLLNLLPFFDKTVSLLGSI-GYCDYEVA YVTYQTCI-QVVGLMKPKTNSLNQDIFKGVQLQTRKRASTFKAIL-SYFAEPETQEEDPLLN RFKSLSGGG-SKTKSSQDEVFHEWITSSELQRELSSKKVLLIDFR-PRKDYLNNHIKYKDLV HIEPTQLETLLDSASDQD-LETLVKKSAPTDQYHIFLERHKYDLIVVYNYNYGSE-STDRLL GIIDVVSKPNPFTKLITILMNNKYIS-SRLKVKPLFLSGGVLNWYKTFGIEYLERTLVQNGV AHT) to localize the enzyme to an endosomal compartment.

Method 26: Method 17, whereby the enzyme has been modified with the N-terminal addition of N-terminal 81 amino acids of beta-galactosyltransferase (MRLRE-PLLSGSAAMPGASLQRACRLLVAVCALHLGVTLVYY-LAGRDLSRLPQLVGVS TPLQGGSN-SAAAIGQSSGELRTGG) to localize the enzyme to a Golgi compartment.

Method 27: Method 17, whereby the enzyme has been modified with N-terminal 34 amino acids of rat liver alpha-2,6-sialyltransferase (MIHTNLKKKFSLFILVFLLFAV-ICVWKKGSDYEA) to localize the enzyme to a Golgi compartment.

Method 28: Method 16 whereby the enzyme has been modified the N-terminal addition of the N-terminal 31 amino acids (MKFGVLFSVFAAIVSALPLQEGPLNKRAYPS) from glucoamylase and a C-terminal addition of the amino acids HDEL to localize the enzyme to the endoplasmic reticulum.

Method 29: Method 1, wherein the fermentation uses a fatty acid and/or sugar as a carbon source.

Method 30: Method 1, wherein the fermentation uses dextrose or sucrose as a carbon source.

Method 31: Method 1, wherein the enzyme is prenyltransferase.

Method 32: Method 1, wherein the enzyme is cannabidiolic acid synthase.

Method 33: Method 32, wherein the microorganism has been modified to express the protein sequence SEQ. ID *53, 54, 55 or 56.

Method 34: Method 1, wherein the enzyme is tetrahydrocannabidiolic acid synthase.

Method 35: Method 34, wherein the microorganism has been modified to express the protein sequence SEQ. ID *58, 59, 60 or 61.

Method 36: Method 1, wherein the enzyme is cannabichromenic acid synthase.

Microorganism 37: A microorganism selected from the group consisting of a fungi and a yeast, wherein the microorganism has been modified to produce a polyketide in fermentation, wherein at least one of the enzymes that mediate the polyketide production have been targeted to at least one compartment within a secretory pathway resulting in an increase in secretion of the one polyketide.

Microorganism 38: Microorganism 37, wherein the microorganism is a yeast.

Microorganism 39: Microorganism 38, wherein the yeast is from a genus selected from the group consisting of Candida, Arxula, Pichia, Scheffersomyces, Kluyveromyces, Saccharomyces, Yarrowia, or Schizosaccharomyces.

Microorganism 40: Microorganism 38, wherein the yeast is a Candida viswanathii.

Microorganism 41: Microorganism 38, wherein the yeast is Arxula adeninivorans.

Microorganism 42: Microorganism 38, wherein the yeast is Yarrowia lipolytica.

Microorganism 43: Microorganism 37, wherein the microorganism is a fungi.

Microorganism 44: Microorganism 43, wherein the fungi is from a genus selected from the group consisting of Aspergillus, Trichoderma or Myceliophthora.

Microorganism 45: Microorganism 43, wherein the fungi is Aspergillus niger.

Microorganism 46: Microorganism 43, wherein the fungi is Aspergillus terreus.

Microorganism 47: Microorganism 43, wherein the fungi is Trichoderma harzianum.

Microorganism 48: Microorganism 43, wherein the fungi is Myceliophthora thermophila.

Microorganism 49: Microorganism 37, wherein the polyketide is a cannabinoid.

Microorganism 50: Microorganism 37, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Microorganism 51: Microorganism 37, wherein the polyketide is olivetolic acid.

Microorganism 52: Microorganism 37, wherein the compartment within the secretory pathway is an endoplasmic reticulum.

Microorganism 53: Microorganism 37, wherein the compartment within the secretory pathway is a Golgi apparatus.

Microorganism 54: Microorganism 37, wherein the compartment within the secretory pathway is a vacuole.

Microorganism 55: Microorganism 37, wherein the compartment within the secretory pathway is an endosome.

Microorganism 56: Microorganism 37, wherein the enzyme is removed of its endogenous amino-terminal localization sequence and/or carboxyl-terminal localization sequence.

Microorganism 57: Microorganism 52, whereby the enzyme has been modified with the N-terminal addition of the N-terminal 24 amino acids (MMWKFLIAIG-LIFSYCCNAQLLDS) from OST1 and a C-terminal addition of the amino acids HDEL to localize the enzyme to the endoplasmic reticulum.

Microorganism 58: Microorganism 54, whereby the enzyme has been modified by an IST-terminal addition of N-terminal 73 amino acids (MGITNETQALLGGD-SLSCLNKKKSNTKRNLSYLLNIITVSIIAYLCFFATH-NHHNDSGIPK VDPHKKKNIIMM) of PHO8 to localize the enzyme to the vacuole.

Microorganism 59: Microorganism 54, whereby the enzyme has been modified with the N-terminal fusion with Sna4 to localize the enzyme to the vacuole.

Microorganism 60: Microorganism 54, whereby the enzyme has been modified with the N-terminal addition of N-terminal 92 amino acids (MQLSLSVLSTVATALLSLT-TAVDAKSHNIKLSKLSNEETLDASTFQEYTSSLAN-KYMNL FNAAHGNPTSFGLQHVLSNQE-AEVPFVTPQKGG) from vacuolar aspartic protease to localize the enzyme to the vacuole.

Microorganism 61: Microorganism 55, whereby the enzyme has been modified with the N-terminal addition of N-terminal 305 amino acids from DOA4 (MTLLLKPTSEL- DATSRKIIER-
IQSNSPTFQHLFDLLLNLLPFFDKTVSLLGSI-
GYCDYEVA
YVTYQTCI-
QVVGLMKPKTNSLNQDIFKGVQLQTRKRASTFKAIL-
SYFAEPETQEEDPLLN RFKSLSGGG-
SKTKSSQDEVFHEWITSSELQRELSSKKVLLIDFRPK-
RKDYLNNHIKYKDLV HIEPTQLETLLDS-
ASDQDLEETLVKKSAPYDQYHIFLERHKYDLIV-
VYNYNYGSESTDRLL GIIDVVSKPNPFTKLIT-
ILMNNKYISSRLKVKPLFLSGGVLNWYKTFGIEYLE-
RTLVQNGV AHT) to localize the enzyme to an endosomal compartment.

Microorganism 62: Microorganism 53, whereby the enzyme has been modified with the N-terminal addition of N-terminal 81 amino acids of beta-galactosyltransferase (MRLRELLSGSAAMPGASLQRACRLLVA-
VCALHLGVTLVYYLAGRDLSRLPQLVGVS TPLQGG-
SNSAAAIGQSSGELRTGG) to localize the enzyme to a Golgi compartment.

Microorganism 63: Microorganism 53, whereby the enzyme has been modified with N-terminal 34 amino acids of rat liver alpha-2,6-sialyltransferase (MIHTNLKKKFSL-
FILVFLLFAVICVWKKGSDYEA) to localize the enzyme to a Golgi compartment.

Microorganism 64: Microorganism 52, whereby the enzyme has been modified the N-terminal addition of the N-terminal 31 amino acids (MKFGVLFSVFAAIVS-
ALPLQEGPLNKRAYPS) from glucoamylase and a C-terminal addition of the amino acids HDEL to localize the enzyme to the endoplasmic reticulum.

Microorganism 65: Microorganism 37, wherein the fermentation uses a fatty acid and/or sugar as a carbon source.

Microorganism 66: Microorganism 37, wherein the fermentation uses dextrose or sucrose as a carbon source.

Microorganism 67: Microorganism 37, wherein the enzyme is prenyltransferase.

Microorganism 68: Microorganism 37, wherein the enzyme is cannabidiolic acid synthase.

Microorganism 69: Microorganism 68, wherein the microorganism has been modified to express the protein sequence SEQ. ID *53, 54, 55 or 56.

Microorganism 70: Microorganism 37, wherein the enzyme is tetrahydrocannabidiolic acid synthase.

Microorganism 71: Microorganism 70, wherein the microorganism has been modified to express the protein sequence SEQ. ID *58, 59, 60 or 61.

Microorganism 72: Microorganism 37, wherein the enzyme is cannabichromenic acid synthase.

Polyketide 73: A polyketide produced by any one of Methods 1-36.

Polyketide 74: A polyketide produced by any one of Microorganisms 37-72.

Method 75: A method, comprising: providing as a feedstock at least one of a fatty acid, vegetable oil, or an alkane to a microorganism which has a modified beta-oxidation pathway, wherein the beta-oxidation pathway has been modified by a modification to produce a fatty acid or a fatty acid-CoA that is a substrate for an acyl-CoA synthase or a polyketide synthase, respectively, wherein the microorganism produces a polyketide.

Method 76: Method 75, wherein at least one of an acyl-coA oxidase, enoyl CoA hydratase, 3-hydroxyacyl-CoA dehydrogenase, B-ketothiolase or thiolase has been modified and/or replaced in the microorganism.

Method 77: Method 75, wherein the modification is one or more of a deletion, a mutation, a replacement, or an expression of one of acyl-coA oxidase, enoyl CoA hydratase, 3-hydroxyacyl-CoA dehydrogenase, B-ketoliase, or thiolase.

Method 78: Method 75, wherein the modification is of acyl-coA oxidase.

Method 79: Method 75, wherein the microorganism has been modified to include wherein the microorganism has been modified to express the protein sequence SEQ. ID 10.

Method 80: Method 75, wherein the feedstock is a fatty acid or a vegetable oil.

Method 81: Method 80, wherein the fatty acid is selected from the group consisting of oleic acid, palmitic acid, stearic acid, linoleic acid, alpha-linolenic acid, palmitoleic acid, tridecanoic acid, pentadecanoic acid, and nonanoic acid.

Method 82: Method 80, wherein the vegetable oil is selected from the group consisting of palm oil, soybean oil, corn oil, canola oil, coconut oil, sunflower oil, olive oil, palm kernel oil, lard, castor oil, peanut oil, sesame oil, grapeseed, avocado oil, and flaxseed oil.

Method 83: Method 75, wherein the fatty acid is in a form of a methyl ester or ethyl ester.

Method 84: Method 75, wherein the alkane is selected from the group consisting of octadecane, hetadecane, hexadecane, pentadecane, tetradecane, tridecane, dodecane, and undecane.

Method 85: Method 75, wherein the polyketide synthase is a tetraketyde synthase.

Method 86: Method 75, wherein the polyketide synthase is TKS1 or TKS1p.

Method 87: Method 75, wherein the polyketide synthase is targeted to the peroxisome.

Method 88: Method 75, wherein an olivetolic acid synthase is expressed.

Method 89: Method 88, wherein the olivetolic acid synthase is CsOAC1.

Method 90: Method 88, where the olivetolic acid synthase is targeted to the peroxisome.

Method 91: Method 75, wherein an endogenous acyl-coA oxidase has been mutated.

Method 92: Method 75, wherein an endogenous acyl-coA oxidase has been replaced with a non-native acyl-coA oxidase.

Method 93: Method 92, wherein the non-native acyl-coA oxidase is selected from the group consisting of ACO1P, ACO2, ACO3, ACO4, ACO5, ACO6, ACO7, ACO8, ACO9 and ACO10.

Method 94: Method 75, wherein the polyketide is a cannabinoid.

Method 95: Method 75, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 96: Method 75, wherein the polyketide is olivetolic acid.

Method 97: Method 75, wherein a polyketide synthase is expressed.

Method 98: Method 97, wherein the polyketide synthase is a tetraketyde synthase.

Method 99: Method 97, wherein the polyketide synthase is TKS1 or TKS1p

Method 100: Method 97, wherein the polyketide synthase is targeted to the peroxisome Method 101: Method 75, wherein an olivetolic acid synthase is expressed.

Method 102: Method 101, wherein the olivetolic acid synthase is CsOAC1

Method 103: Method 101, where the olivetolic acid synthase is targeted to the peroxisome.

Method 104: Method 75, wherein beta-oxidation has been modified.

Method 105: Method 104, wherein an endogenous acyl-coA oxidase has been mutated.

Method 106: Method 104, wherein an endogenous acyl-coA oxidase has been replaced with a non-native acyl-coA oxidase.

Method 107: Method 106, wherein the non-native acyl-coA oxidase is selected from the group consisting of ACO1P, ACO2, ACO3, ACO4, ACO5, ACO6, ACO7, ACO8, ACO9, and ACO10.

Method 108: Method 75, wherein the microorganism is a yeast.

Method 109: Method 108, wherein the yeast is from a genus selected from the group consisting of *Candida, Arxula, Pichia, Scheffersomyces, Kluyveromyces, Saccharomyces, Yarrowia,* or *Schizosaccharomyces.*

Method 110: Method 108, wherein the yeast is a *Candida viswanathii.*

Method 111: Method 108, wherein the yeast is *Arxula adeninivorans.*

Method 112: Method 108, wherein the yeast is *Yarrowia lipolytica.*

Method 113: Method 75, wherein the microorganism is a fungi.

Method 114: Method 113, wherein the fungi is from a genus selected from the group consisting of *Aspergillus, Trichoderma* or *Myceliophthora.*

Method 115: Method 113, wherein the fungi is *Aspergillus niger.*

Method 116: Method 113, wherein the fungi is *Aspergillus terreus.*

Method 117: Method 113, wherein the fungi is *Trichoderma harzianum.*

Method 118: Method 113, wherein the fungi is *Myceliophthora thermophila.*

Microorganism 119: A microorganism, wherein the microorganism is a yeast or a fungi having a modified beta-oxidation pathway, wherein the beta-oxidation pathway has been modified by a modification to produce a fatty acid or a fatty acid-CoA that is a substrate for an acyl-CoA synthase or a polyketide synthase, respectively, wherein the microorganism produces a polyketide Microorganism 120: Microorganism 119, wherein the microorganism is a yeast.

Microorganism 121: Microorganism 120, wherein the yeast is from a genus selected from the group consisting of *Candida, Arxula, Pichia, Scheffersomyces, Kluyveromyces, Saccharomyces, Yarrowia,* or *Schizosaccharomyces.*

Microorganism 122: Microorganism 120, wherein the yeast is a *Candida viswanathii.*

Microorganism 123: Microorganism 120, wherein the yeast is *Arxula adeninivorans.*

Microorganism 124: Microorganism 120, wherein the yeast is *Yarrowia lipolytica.*

Microorganism 125: Microorganism 119, wherein the microorganism is a fungi.

Microorganism 126: Microorganism 125, wherein the fungi is from a genus selected from the group consisting of *Aspergillus, Trichoderma* or *Myceliophthora.*

Microorganism 127: Microorganism 125, wherein the fungi is *Aspergillus niger.*

Microorganism 128: Microorganism 125, wherein the fungi is *Aspergillus terreus.*

Microorganism 129: Microorganism 125, wherein the fungi is *Trichoderma harzianum.*

Microorganism 130: Microorganism 125, wherein the fungi is *Myceliophthora thermophila.*

Microorganism 131: Microorganism 119, wherein at least one of an acyl-coA oxidase, enoyl CoA hydratase, 3-hydroxyacyl-CoA dehydrogenase, B-ketholiase or thiolase has been modified and/or replaced in the microorganism.

Microorganism 132: Microorganism 119, wherein the modification is one or more of a deletion, a mutation, a replacement, or an expression of one of acyl-coA oxidase, enoyl CoA hydratase, 3-hydroxyacyl-CoA dehydrogenase, B-ketholiase, or thiolase.

Microorganism 133: Microorganism 119, wherein the modification is of acyl-coA oxidase.

Microorganism 134: Microorganism 119, wherein the microorganism has been modified to include SEQ. ID 10.

Microorganism 135: Microorganism 119, wherein the polyketide synthase is a tetraketyde synthase.

Microorganism 136: Microorganism 119, wherein the polyketide synthase is TKS1 or TKS1p.

Microorganism 137: Microorganism 119, wherein the polyketide synthase is targeted to the peroxisome.

Microorganism 138: Microorganism 119, wherein an olivetolic acid synthase is expressed.

Microorganism 139: Microorganism 138, wherein the olivetolic acid synthase is CsOAC1.

Microorganism 140: Microorganism 119, where the olivetolic acid synthase is targeted to the peroxisome.

Microorganism 141: Microorganism 119, wherein an endogenous acyl-coA oxidase has been mutated.

Microorganism 142: Microorganism 119, wherein an endogenous acyl-coA oxidase has been replaced with a non-native acyl-coA oxidase.

Microorganism 143: Microorganism 142, wherein the non-native acyl-coA oxidase is selected from the group consisting of ACO1P, ACO2, ACO3, ACO4, ACO5, ACO6, ACO7, ACO8, ACO9, and ACO10.

Microorganism 144: Microorganism 119, wherein the polyketide is a cannabinoid.

Microorganism 145: Microorganism 119, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Microorganism 146: Microorganism 119, wherein the polyketide is olivetolic acid.

Polyketide 147: A polyketide produced by any one of Methods 75-118.

Polyketide 148: A polyketide produced by any one of Microorganisms 119-146.

Method 149: A method, comprising: providing a microorganism that has been modified to produce a polyketide; and providing the microorganism with a C5-11 fatty acid ester in fermentation to yield a corresponding C5-9 fatty acid, wherein the C5-9 fatty acid is activated by an Acyl-CoA synthase and is used as a substrate for a polyketide synthase, from which the polyketide is obtained.

Method 150: Method 149, wherein the microorganism has been genetically modified.

Method 151: Method 149, wherein the polyketide is a cannabinoid.

Method 152: Method 151, wherein the cannabinoid is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 153: Method 149, wherein the polyketide is olivetolic acid.

Method 154: Method 149, wherein the microorganism is a yeast.

Method 155: Method 154, wherein the yeast is from a genus selected from the group consisting of *Candida, Arxula, Pichia, Scheffersomyces, Kluyveromyces, Saccharomyces, Yarrowia*, or *Schizosaccharomyces*.

Method 156: Method 154, wherein the yeast is a *Candida viswanathii*.

Method 157: Method 154, wherein the yeast is *Arxula adeninivorans*.

Method 158: Method 154, wherein the yeast is *Yarrowia lipolytica*.

Method 159: Method 149, wherein the microorganism is a fungi.

Method 160: Method 159, wherein the fungi is from a genus selected from the group consisting of *Aspergillus, Trichoderma* or *Myceliophthora*.

Method 162: Method 159, wherein the fungi is *Aspergillus niger*.

Method 163: Method 159, wherein the fungi is *Aspergillus terreus*.

Method 164: Method 159, wherein the fungi is *Trichoderma harzianum*.

Method 164: Method 159, wherein the fungi is *Myceliophthora thermophila*.

Method 165: Method 159, wherein the $C_{5-11}$ fatty acid ester is a $C_6$ fatty acid ester.

Method 166: Method 159, wherein the $C_{5-11}$ fatty acid ester is an ester of an acid selected from the group consisting of pentanoic acid, hexanoic acid, heptanoic acid, octanoic acid, nonanoic acid, decanoic acid, and undecanoic acid.

Method 167: Method 159, wherein the $C_{5-11}$ fatty acid ester is an ester selected from the group consisting of methyl ester, ethyl ester, and genaryl ester.

Polyketide 168: A polyketide produced by any one of Methods 149-167.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and "one or more" to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of producing a polyketide in a peroxisome, the method comprising:
providing a fatty acid to a genetically modified microorganism, wherein the genetically modified microorganism is a yeast or a fungus, wherein the microorganism comprises a biosynthetic enzyme targeted to the peroxisome in the microorganism, wherein the biosynthetic enzyme is capable of catabolizing the fatty acid into the polyketide, wherein the biosynthetgic enzyme is an acyl-CoA oxidase, enoyl-CoA hydratase, 3-hydroxyacyl-CoA dehydrogenase, beta-ketothiolase, thiolase, acyl-CoA synthase, polyketide synthase, cannabidiolic acid synthase, tetrahydrocannabidiolic acid, olivetolic acid synthase, tetraketide synthase, TKS 1, or TKS 1 p;
culturing the microorganism under conditions sufficient to produce the polyketide in the peroxisome; and
isolating the polyketide.

2. The method of claim 1, wherein the polyketide is cannabigerolic acid, 49-tetrahydrocannabinolic acid, cannabidiolic acid, cannabichromenic acid, cannabigerovarinic acid, tetrahydrocannabivarin acid, cannabidivarinic acid, or cannabichromevarinic acid.

3. The method of claim 1, wherein the yeast is from a genus selected from the group consisting of *Candida, Arxula, Pichia, Scheffersomyces, Kluyveromyces, Saccharomyces, Yarrowia,* or *Schizosaccharomyces*.

4. The method of claim 1, wherein the biosynthetic enzyme comprises a peroxisomal targeting sequence.

5. The method of claim 4, wherein the peroxisomal targeting sequence has a consensus sequence of [S/A/H/C/E/P/Q/V]-[K/R/H/QHL/F] as set forth in SEQ ID NO: 7, or GRRAKL as set forth in SEQ ID NO: 6.

6. The method of claim 1, wherein the enzyme is removed of its endogenous amino-terminal localization sequence and/or carboxyl-terminal localization sequence.

7. A genetically modified microorganism, wherein the genetically modified microorganism is a yeast or a fungus, comprising a biosynthetic enzyme targeted to a peroxisome in the microorganism, wherein the biosynthetic enzyme is capable of catabolizing a fatty acid into a polyketide, wherein the biosynthetic enzyme is an acyl-CoA oxidase, enoyl-CoA hydratase, 3-hydroxyacyl-CoA dehydrogenase, beta-ketothiolase, thiolase, acyl-CoA synthase, polyketide synthase, cannabidiolic acid synthase, tetrahydrocannabidiolic acid, olivetolic acid synthase, tetraketide synthase, TKS1, or TKS 1p.

8. The genetically modified microorganism of claim 7, wherein the yeast is from a genus selected from the group consisting of *Candida, Arxula, Pichia, Scheffersomyces, Kluyveromyces, Saccharomyces, Yarrowia,* or *Schizosaccharomyces*.

9. The genetically modified microorganism of claim 7, wherein the biosynthetic enzyme comprises a peroxisomal targeting sequence.

10. The genetically modified microorganism of claim 9, wherein the peroxisomal targeting sequence has a consensus sequence of [S/A/H/C/E/P/Q/V]-[K/R/H/Q]-[L/F] as set forth in SEQ ID NO: 7, or GRRAKL as set forth in SEQ ID NO: 6.

11. The genetically modified microorganism of claim 7, wherein the microorganism is capable of producing in the peroxisome cannabigerolic acid, 49-tetrahydrocannabinolic acid, cannabidiolic acid, cannabichromenic acid, cannabigerovarinic acid, tetrahydrocannabivarin acid, cannabidivarinic acid, or cannabichromevarinic acid when cultured.

12. The genetically modified microorganism of claim 7, wherein the microorganism is capable of producing in the peroxisome a triacetic lactone (TAL).

13. A genetically modified microorganism, wherein the genetically modified microorganism is a yeast or a fungus, comprising a biosynthetic enzyme targeted to a peroxisome in the microorganism, wherein the biosynthetic enzyme is capable of catabolizing a fatty acid, vegetable oil, or an alkane into a polyketide, wherein the biosynthetic enzyme comprises a peroxisomal targeting sequence having a consensus sequence of [S/A/H/C/E/P/Q/V]-[K/R/H/QHL/F] as set forth in SEQ ID NO: 7, or GRRAKL as set forth in SEQ ID NO: 6.

14. The genetically modified microorganism of claim 13, wherein the biosynthetic enzyme is an acyl-CoA oxidase, enoyl-CoA hydratase, 3-hydroxyacyl-CoA dehydrogenase, beta-ketothiolase, thiolase, acyl-CoA synthase, polyketide synthase, cannabidiolic acid synthase, tetrahydrocannabidiolic acid, olivetolic acid synthase, tetraketide synthase, TKS1, or TKS1p.

15. The method of claim 1, wherein the microorganism is capable of producing in the peroxisome a triacetic lactone (TAL).

16. The method of claim 1, wherein the acyl-CoA oxidase comprises the protein sequence as set forth in SEQ ID NO: 10.

17. The method of claim 1, wherein the polyketide is olivetolic acid or hexanoic acid.

18. The genetically modified microorganism of claim 7, wherein the acyl-CoA oxidase comprises the protein sequence as set forth in SEQ ID NO: 10.

19. The genetically modified microorganism of claim 7, wherein the polyketide is olivetolic acid or hexanoic acid.

20. The genetically modified microorganism of claim 7, wherein the yeast is from a genus of *Candida*.

* * * * *

UNITED STATES PATENT AND TRADEMARK OFFICE
CERTIFICATE OF CORRECTION

PATENT NO. : 11,884,948 B2
APPLICATION NO. : 17/449847
DATED : January 30, 2024
INVENTOR(S) : Alexander Hutagalung It is certified that error appears in the above-identified patent and that said Letters Patent is hereby corrected as shown below:

On the Title Page

Page 2, Column 1 (Item (56) Other Publications), Line 9, Delete "entomopathgenic" and insert --entomopathogenic--.

Page 3, Column 1 (Item (56) Other Publications), Line 25, Delete "fattyacyl" and insert --fatty acyl--.

Page 3, Column 2 (Item (56) Other Publications), Line 31, Delete "phaffil"" and insert --phaffii"--.

In the Specification

Column 1, Line 16 (Approx.), Delete "filed, filed" and insert --filed--.

Column 2, Line 57, Delete "tetrahydrocannabidiolic" and insert --tetrahydrocannabinolic--.

Column 4, Line 63, Delete "dipoid," and insert --diploid,--.

Column 5, Line 10, Delete "pukherrima," and insert --pulcherrima,--.

Column 5, Line 15, Delete "pullans," and insert --pullulans,--.

Column 5, Line 15, Delete "T" and insert --T.--.

Column 5, Line 16-17, Delete "starkeyii," and insert --starkeyi,--.

Column 5, Line 19-20, Delete "Chrysosporuim, Chrysosporuim" and insert --Chrysosporium, Chrysosporium--.

Signed and Sealed this
Third Day of September, 2024

Katherine Kelly Vidal
*Director of the United States Patent and Trademark Office*

CERTIFICATE OF CORRECTION (continued)
U.S. Pat. No. 11,884,948 B2

Column 5, Line 20, Delete "Coccidiodes," and insert --Coccidioides,--.

Column 5, Line 22, Delete "Lssatchenkia," and insert --Issatchenkia,--.

Column 5, Line 33, Delete "lustitaniae," and insert --lusitaniae,--.

Column 5, Line 36, Delete "Chrysosporuim" and insert --Chrysosporium--.

Column 5, Line 37, Delete "Coccidiodes" and insert --Coccidioides--.

Column 5, Line 38, Delete "neofomans," and insert --neoformans,--.

Column 5, Line 41, Delete "Isstachenkia" and insert --Issatchenkia--.

Column 5, Line 43, Delete "hpoferus," and insert --lipoferus,--.

Column 5, Line 43-44, Delete "starkeyii," and insert --starkeyi,--.

Column 5, Line 51, Delete "pullans," and insert --pullulans,--.

Column 6, Line 1, Delete "lustitaniae," and insert --lusitaniae,--.

Column 6, Line 43, Delete "Norcardia baceteria," and insert --Nocardia bacteria,--.

Column 6, Line 48-49, Delete "marcessans)," and insert --marcescens),--.

Column 6, Line 53, Delete "Choroflexus" and insert --Chloroflexus--.

Column 6, Line 54, Delete "gigateum))," and insert --giganteum)),--.

Column 7, Line 5, Delete "Nicotania" and insert --Nicotiana--.

Column 7, Line 20, Delete "Ilavea," and insert --Llavea, --.

Column 8, Line 23, Delete "deshydrogenase" and insert --dehydrogenase--.

Column 8, Line 51, Delete "(3-" and insert --β- --.

Column 9, Line 1, Delete "PDX3" and insert --POX3--.

Column 10, Line 4, Delete "hexanoytriacetic" and insert --hexanoyltriacetic--.

Column 14, Line 23, Delete "(LN/" and insert --(L/V/--.

Column 15, Line 24, Delete "Anthrobacter)" and insert --Arthrobacter)--.

CERTIFICATE OF CORRECTION (continued)
U.S. Pat. No. 11,884,948 B2

Column 18, Line 39 (Approx.), Delete "Beuvaria" and insert --Beauveria--.

Column 48, Line 19, Delete "Terminato" and insert --Terminator--.

Column 52, Line 42, Delete "glycolsylase" and insert --glycosylase--.

Column 62, Line 29, Delete "hemaglutinin," and insert --hemagglutinin,--.

Column 62, Line 58, Delete "FlAsH™" and insert --FlAsH™--.

Column 66, Line 4, Delete "dicarboxylase." and insert --decarboxylase.--.

Column 66, Line 62, Delete "/710-021849%20_" and insert --/710_021849%20_--.

Column 75, Line 41, Delete "(3 SR" and insert --(3SR--.

Column 76, Line 14 (Approx.), Delete "herein" and insert --herein.--.

Column 82, Line 54-55, Delete "benzimdazolyl" and insert --benzimidazolyl--.

Column 122, Line 52, Delete "37 C" and insert --37° C.--.

Column 123, Line 3, Delete "30 C" and insert --30° C.--.

Column 123, Line 10 (Approx.), Delete "30 C" and insert --30° C.--.

Column 123, Line 22, Delete "30 C" and insert --30° C.--.

Column 123, Line 27, Delete "chorofom" and insert --chloroform--.

Column 123, Line 35, Delete "–20 C" and insert -- –20° C.--.

Column 126, Line 59 (Approx.), Delete "PDX5" and insert --POX5--.

Column 126, Line 62 (Approx.), Delete "PDX5" and insert --POX5--.

Column 127, Line 1, Delete "PDX5" and insert --POX5--.

Column 127, Line 11, Delete "PDX5" and insert --POX5--.

Column 127, Line 18, Delete "PDX4" and insert --POX4--.

Column 127, Line 20, Delete "PDX3" and insert --POX3--.

Column 129, Line 42, Delete "30 C" and insert --30° C.--.

CERTIFICATE OF CORRECTION (continued)
U.S. Pat. No. 11,884,948 B2

Column 129, Line 65, Delete "30 C" and insert --30° C.--.

Column 133, Line 11, Delete "StrainStrain" and insert --Strain--.

Column 138, Line 43, Delete "method" and insert --method.--

Column 138, Line 61, Delete "method" and insert --method.--.

Column 140, Line 5 (Approx.), Delete "method" and insert --method.--.

Column 271, Line 19, Delete "fattyacyl-" and insert --fatty acyl- --.

Column 272, Line 6, Delete "poleketide" and insert --polyketide--.

Column 272, Line 54, Delete "FID L," and insert --HDEL--.

Column 272, Line 58, Delete "ENT" and insert --NET--.

Column 272, Line 59, Delete "HHHDSGIPK VD" and insert --HHNDSGIPKVD--.

Column 273, Line 8, Delete "A Y" and insert --AY--.

Column 273, Line 10 (Approx.), Delete "N R" and insert --NR--.

Column 273, Line 12 (Approx.), Delete "V H" and insert --VH--.

Column 273, Line 13 (Approx.), Delete "PTD" and insert --PYD--.

Column 273, Line 14 (Approx.), Delete "L G" and insert --LG--.

Column 273, Line 15-16 (Approx.), Delete "V A" and insert --VA--.

Column 273, Line 22, Delete "S T" and insert --ST--.

Column 273, Line 48-49, Delete "tetrahydrocannabidiolic" and insert --tetrahydrocannabinolic--.

Column 274, Line 50, Delete "IST-terminal" and insert --N-terminal--.

Column 274, Line 53, Delete "K V" and insert --KV--.

Column 274, Line 62, Delete "L F" and insert --LF--.

Column 275, Line 3-4, Delete "A Y" and insert --AY--.

Column 275, Line 6, Delete "N R" and insert --NR--.

CERTIFICATE OF CORRECTION (continued)
U.S. Pat. No. 11,884,948 B2

Column 275, Line 7-8, Delete "RPKRK" and insert --RPRK--.

Column 275, Line 8, Delete "V H" and insert --VH--.

Column 275, Line 9, Delete "DLEE" and insert --DLE--.

Column 275, Line 10, Delete "L G" and insert --LG--.

Column 275, Line 12, Delete "V A" and insert --VA--.

Column 275, Line 17, Delete "RELL" and insert --REPLL--.

Column 275, Line 18, Delete "S T" and insert --ST--.

Column 275, Line 44, Delete "tetrahydrocannabidiolic" and insert --tetrahydrocannabinolic--.

Column 276, Line 2-3, Delete "B-ketholiase," and insert --B-ketothiolase,--.

Column 276, Line 24, Delete "hetadecane," and insert --heptadecane,--.

Column 278, Line 9, Delete "B-ketholiase" and insert --B-ketothiolase--.

Column 278, Line 15, Delete "B-ketholiase," and insert --B-ketothiolase,--.

Column 280, Line 14, Delete "including" and insert --'including--.

Column 280, Line 16, Delete "containing,'" and insert --'containing,'--.

Column 307, Line 9, Delete "Beuvaria" and insert --Beauveria--.

In the Claims

Column 641, Line 10, In Claim 1, delete "biosynthetgic" and insert --biosynthetic--.

Column 641, Line 14, In Claim 1, delete "tetrahydrocannabidiolic" and insert --tetrahydrocannabinolic--.

Column 641, Line 15-16, In Claim 1, delete "TKS 1, or TKS 1 p;" and insert --TKS1, or TKS1p;--.

Column 641, Line 21, In Claim 2, delete "49-" and insert --$\Delta$9- --.

Column 641, Line 33, In Claim 5, delete "/QHL/" and insert --/Q]-[L/--.

Column 641, Line 46-47, In Claim 7, delete "tetrahydrocannabidiolic" and insert --tetrahydrocannabinolic--.

Column 641, Line 48, In Claim 7, delete "TKS 1p." and insert --TKS1p.--.

Column 642, Line 11 (Approx.), In Claim 11, delete "49-" and insert --Δ9- --.

Column 642, Line 26, In Claim 13, delete "/QHL/F1" and insert --/Q]-[L/F]--.

Column 642, Line 33-34, In Claim 14, delete "tetrahydrocannabidiolic" and insert --tetrahydrocannabinolic--.